US008889142B2

(12) United States Patent
Theisen et al.

(10) Patent No.: US 8,889,142 B2

(45) Date of Patent: Nov. 18, 2014

(54) ***CHLAMYDIA TRACHOMATIS* ANTIGENS FOR VACCINE AND DIAGNOSTIC USE**

(75) Inventors: Michael Theisen, Frederiksberg (DK); Anja Olsen, Søborg (DK); Robert Leah, Birkerød (DK); Frank Follmann, Copenhagen (DK); Klaus Jensen, Copenhagen (DK); Peter Andersen, Brønshøj (DK)

(73) Assignee: Statens Serum Institut, Copenhagen (DK)

( * ) Notice: Subject to any disclaimer, the term of this patent is extended or adjusted under 35 U.S.C. 154(b) by 1649 days.

(21) Appl. No.: 11/577,868

(22) PCT Filed: Oct. 11, 2005

(86) PCT No.: PCT/DK2005/000651

§ 371 (c)(1), (2), (4) Date: Apr. 24, 2007

(87) PCT Pub. No.: WO2006/045308

PCT Pub. Date: May 4, 2006

(65) Prior Publication Data

US 2009/0304722 A1 Dec. 10, 2009

(30) Foreign Application Priority Data

Oct. 25, 2004 (DK) ................................ 2004 01633
Jul. 19, 2005 (DK) ................................ 2005 01069

(51) Int. Cl.

| | |
|---|---|
| ***A61K 39/00*** | (2006.01) |
| ***A61K 39/02*** | (2006.01) |
| ***A61K 39/38*** | (2006.01) |
| ***A61K 51/00*** | (2006.01) |
| ***C07K 14/295*** | (2006.01) |
| ***A61K 39/118*** | (2006.01) |

(52) U.S. Cl.

CPC ............ *C07K 14/295* (2013.01); *A61K 39/118* (2013.01)

USPC ... 424/192.1; 424/1.57; 424/1.69; 424/178.1; 424/184.1; 424/185.1; 424/190.1; 424/193.1; 424/197.11; 424/263.1

(58) Field of Classification Search

CPC ....... A61K 35/74; A61K 38/00; A61K 38/16; A61K 38/164; A61K 39/00; A61K 39/118; A61K 2300/00; A61K 2039/00; A61K 2039/02

See application file for complete search history.

(56) References Cited

FOREIGN PATENT DOCUMENTS

| | | | | |
|---|---|---|---|---|
| EP | 0 892 061 A2 | | 1/1999 | |
| WO | WO 99/27105 | * | 6/1995 | ............ C12N 15/31 |

(Continued)

OTHER PUBLICATIONS

Kalman et al., (1999. Nature Genetics vol. 21:385-389).*

(Continued)

*Primary Examiner* — Ja'na Hines

(74) *Attorney, Agent, or Firm* — Knobbe, Martens, Olson & Bear, LLP

(57) ABSTRACT

The present invention is related to antigen from *Chlamydia trachomatis* which are recognized by specific antibodies from individuals infected with *Chlamydia* or which can induce T cells from the same individuals to secrete gamma-interferon. The T cell reactive antigens are present in a whole-cell lysate and have apparent molecular weights of 5-12, 16-20, 25-35 and 58-74 kDa as determined by SDS-PAGE. The antigens of the invention are believed to be useful in vaccines but also as diagnostic compositions.

10 Claims, 25 Drawing Sheets

(56) References Cited

FOREIGN PATENT DOCUMENTS

Figure 1:
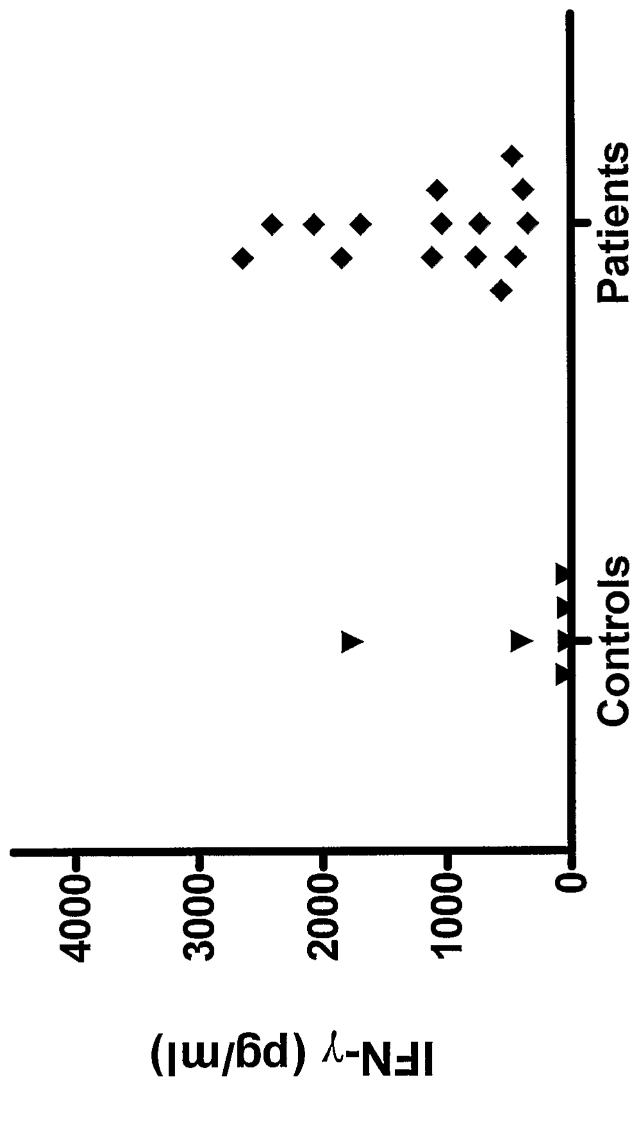

| | | | | | |
|---|---|---|---|---|---|
| WO | WO 98/28005 | * | 2/1998 | ............ | A61K 39/39 |
| WO | WO 99/28475 | * | 6/1999 | ............ | C12N 15/33 |
| WO | WO 99/28475 | A2 | 6/1999 | | |
| WO | WO 03/041560 | A2 | 11/2002 | | |
| WO | WO 03/040762 | A2 | 6/2003 | | |
| WO | WO 03/049762 | * | 6/2003 | ............ | A61K 31/70 |
| WO | WO 2004/074318 | A2 | 9/2004 | | |
| WO | WO 2005/002619 | A2 | 1/2005 | | |
| WO | WO 2006/050571 | A1 | 5/2006 | | |

OTHER PUBLICATIONS

Read et al (2000. Nucleic Acids Res. vol. 28:1397-406).*

Shirai et al., (2000. J. Infect. Dis. vol. 181(Suppl 3):S524-S527).*

Griffais, R. "*Chlamydia trachomatis* secreted protein" XP-002624761, Oct. 7, 1999.

Raczniak, Gregory et al., "A Single Amidotransferase Forms Asparaginyl-tRNA and Glutaminyl-tRNA in *Chlamydia trachomatis*" The Journal of Biological Chemistry, Dec. 7, 2001, pp. 45862-45867, vol. 276, No. 49.

Raczniak, Gregory et al., "Genomics-based identification of targets in pathogenic bacteria for potential therapeutic and diagnostic use" Toxicology, 2001, pp. 181-189, vol. 160.

Slepenkin, Anatoly et al., "Temporal Expression of Type III Secretion Genes of *Chlamydia pneumoniae*" Infection and Immunity, May 2003, pp. 2555-2562, vol. 71, No. 5.

Communication pursuant to Article 94(3)EPC, for Application No. EP 10 185 754.8, dated Jun. 18, 2012.

Cotter, T.W., Q. Meng, et al. (1995). "Protective efficacy of major outer membrane protein specific immunoglobulin A (IgA) and IgG Monoclonal antibodies in a murine model of *Chlamydia trachomatis* genital tract infection." *Infect. Immun* 63(12):4707-4714.

Fling, S.P., R.A. Sutherland, et al. (2001). "CD8+T cells recognize an inclusion membrane-associated protein from the vacuolar pathogen *Chlamydia trachomatis*." Proc.Natl.Acad.Sci.U.S.A 98(3): 1160-1165.

Goodall, J.C, G. Yeo, et al. (2001). "Identification of *Chlamydia trachomatis* antigens recognized by human CD4+ T lymphocytes by screening an expression library" *Eur.J.Immunol.* 31(:5)1513-1522.

Gu, L., W. M. Wenman, et al. (1995). "*Chlamydia trachomatis* RNA Polymerase alpha subunit: sequence and structural analysis"J. Bacteriol. 177(9): 2594-2601.

Hassell, A.B., D. J. Reynolds, et al. (1993). "Identification of T-cell stimulatory antigens of *Chlamydia trachomatis* using synovial fluid-derived T-cell clones," *Immunology* 79(4): 513-519.

Kubo, A. and R. S. Stephens (2000). "Characterization and functional analysis of PorB, a *Chlamydia porin* and neutralizing target." *Mol. Microbiol.* 38(4):772-780.

LaVerda, D., L N. Albanese, et al. (2000). Seroreactivity to *Chlamydia trachomatis* Hsp10 correlates with severity of human genital tract disease *Infect. Immun* 68(1): 303-309.

Mark J. Pallen, et al,: "Bioinformatics analysis of the locus for enterocyte effacement provides novel insights into type—III secretion" BMC Microbiology, vol. 5, No. 9, Mar. 9, 2005, pp. 1-21, XP002365884 figure 9.

Morrison, R. P. and H. D. Caldwell (2002). "Immunity to murine *Chlamydia* genital infection." *Infect. Immun* 70(5): 2741-51.

Morrison. S. G., H. Su, et al. (2002). "Immunity to murine *Chlamydia trachomatis* genital tract reinection involves B cells and CD4(+) T cells but not CD8(+) T cells." *Infect. Immun.* 68(12):6979-6987.

Oritz, L., K. P. Demick, et al. (1996), *Chlamydia trachomatis* major outer membrane protein (MOMP) epitopes that activate HLA class II-restricted T cells from infected humans. *J Immunol* 157(10): 4554-67.

Pal, S., I. Theodor, et al. (2001). Immunization with the *Chlamydia trachomatis* mouse pneumonitis major outer membrane protein can elicit a protective immune response against a genital challenge. *Infect Immun.* 69(10): 6240-6247.

Pal. S., K. M. Barnhart, et al. (1999). "Vaccination of mice with DNA plasmids coding for the *Chlamydia trachomatis* major outer membrane protein elicits an immune response but fails to protect againet a genital challenge." *Vaccine* 17(5): 459-465.

Schachter, J., J. Moncada, et al. (1988). 2 Nonculture methods for diagnosing chlamydial infection in patients with trachoma: a due to the pathogenesis of the disease?*J.Infect.Dis.* 158(6); 1347-1352.

Shaw, J., V, Grund, et al. (2002), "Dendritic cells pulsed with a recombinant chlamydial major outer membrane protein antigen elicit a CD4(+) type 2 rather than type 1 immune response that is not protective." *Infect Immun.* 70(3): 1097-1105.

Starnbach, M. N., W. P. Loomis, et al. (2003). "An inclusion membrane protein from *Chlamydia trachomatis* enters the MHC class I pathway and stimulates a CD8+T cell response." *J Immunol* 171(9): 4742-9.

Stephens, R. S., E. A. Wager., et al. (1988). "High resolution mapping of serovar-soecific and common antigenic determinants of the major outer membrane protein of *Chlamydia trachomatis*." *J.Exp.Med.* 167(3):817-831.

Stephens, R. S., S. Kalman, et al. (1998). "Genome sequence of an obligate intraceullular pathogen of humans: *Chlamydia trachomatis*." Science 282(5389): 754-759.

Stephens, R.S., et al.: "Hypothetical protein CT043"XP002368833 Database accession No. 084047, p. 98.

Su, H. and H. D. Caldwell (1995). "CD4+ T cells play a significant role in adoptive immunity to *Chlamydia trachomatis* infection of the mouse genital tract." *Infect Immun.* 63(9): 33302-3308.

Su, H. and H. D. Caldwell (1995). "Protective efficacy of a parenterally administerd MOMP-derived synthetic oligopeptide vaccine in a murine model of *Chlamydia trachomatis* genital tract infection: serum neutralizing IgG antibodies do not protect against chlamydial genital tract infection." *Vaccine* 13(11): 1023-1032.

Tipples, G. and G. McClarty (1995). "Cloning and expression of the *Chlamydia trachomatis* gene for CTP synthetase." *J. Biol. Chem.* 270(14): 7908-7914.

Zhang, D. J., X. Yang, et al. (1999). "Characterization of immune responses following intramuscular DNA immunization with the MOMP gene *Chlamydia trachomatis* mouse pneumonitis strain," *Immunology* 96(2): 314-321.

Zhang, Y., J. Tao, et al. (1997). Elongation factor Ts of *Chlamydia trachomatis*: structure of the gene and properties of the protein. *Arch. Biochem. Biophys.* 344(1): 43-52.

* cited by examiner

* P<0.05

Hydrosalpinx ratio (49 days post challenge)

Serum reactivity against whole Chlamydia EB

MoPn EB's

Sera:

Serovar D EB's

* Bands with correct size

Positive sera:
- Ct150
- Ct048
- Ct078

Ct184
Ct521High

Positive sera:
- Ct050
- Ct030
- Ct048

Ct078
Ct184
Ct521High

*CHLAMYDIA TRACHOMATIS* ANTIGENS FOR VACCINE AND DIAGNOSTIC USE

This application is the U.S. National Phase under 35 U.S.C. §371 of International Application No. PCT/DK2005/000651, filed Oct. 11, 2005, which claims priorities to Danish Patent Applications No. PA 2004 01633, filed Oct. 25, 2004, and No. PA 2005 01069, filed Jul. 19, 2005. The International Application was published in English under PCT Article 21(2).

FIELD OF INVENTION

The present invention discloses the use of immunogenic polypeptides and immunogenic compositions based on polypeptides and nucleic acid derived from *C. trachomatis* as vaccine and diagnostic agents.

GENERAL BACKGROUND

Chlamydial species cause a wide range of diseases in both animals and humans. Of particular concern is *C. trachomatis*, an obligatory intracellular bacterium, which infects and multiplies in epithelial cells. It is the most frequent cause of sexually transmitted disease (STD) in developed countries and it is the most common cause of ocular disease in developing countries (Schachter, Moncada et al. 1988). There is an estimated 92 million individuals who carry the infection globally (WHO, 1999).

The duration of untreated *Chlamydia* STD is prolonged, and complete clearance is often not reached within the first 12 months. The protective immunity induced during the infection is thought to be serovariant-specific and short-lived, thus allowing frequent re-infections (Katz, Batteiger et al. 1987). These circumstances, the prolonged course of infection and the possible re-infections may lead to the development of serious sequelae, including pelvic inflammatory disease, infertility and ectopic pregnancies (Brunham 1999).

The infection is effectively controlled by antibiotic therapy; however the high prevalence of asymptomatic cases suggests that sustainable *Chlamydia* control can only be envisaged if an effective *Chlamydia* vaccine is developed. While much effort has been devoted to a vaccine against *Chlamydia* infections over the last few decades, so far no vaccine has been developed.

This makes the development of a vaccine against *Chlamydia* an urgent matter. Many attempts to define protective chlamydial substances have been made, however, the demonstration of a specific long-term protective immune response has not yet been achieved. Over the last several decades much effort has been devoted into developing a vaccine against *Chlamydia* infections however, so far no vaccine has been developed. Some of the first efforts were focused on controlling trachoma, and whole viable or inactivated organisms were used as the antigen to immunize humans and monkeys (Wang, Grayston et al. 1967; Grayston and Wang 1978). Children vaccinated with an inactivated whole-cell vaccine initially resulted in protection but the protection was serovar specific and short-lived (Grayston and Wang 1978). Furthermore, reinfection of partially protected individuals resulted in clinical disease that was more sever than the disease occurring in non-vaccinated controls (Grayston and Wang 1978). The fact that the initial trials with inactivated whole organisms resulted in some cases of what appeared to be a hypersensitivity reaction prompted attempts to develop subunit vaccines.

*C. trachomatis* holds, as well as secretes, several proteins of potential relevance for the generation of a *chlamydia* vaccine. For a number of years, the search for candidate molecules has primarily focused on proteins associated with the surface of the infectious form the Elementary Body (EB). Despite the characterization of a large number of such proteins only a few of these have been demonstrated to elicit partial protection as subunit vaccines in animal models. The first immunogenic molecule described was the major outer membrane protein (MOMP), and this molecule has therefore been studied in great detail as a candidate vaccine. However, many attempts to immunize different animals with MOMP extracted from *C. trachomatis* or recombinant preparations gave variable results (Su, Parnell et al. 1995; Pal, Barnhart et al. 1999; Zhang, Yang et al. 1999; Pal, Theodor et al. 2001; Shaw, Grund et al. 2002). The reason for the relative ineffectiveness of MOMP as a vaccine is not known, but may result from inadequate adjuvants or delivery systems or from use of MOMP immunogens that do not mimic the native structure of the protein (Pal, Theodor et al. 2001)

More recently, several other immunogenic molecules have been identified (Hassell, Reynolds et al. 1993; Kubo and Stephens 2000; LaVerda, Albanese et al. 2000; Fling, Sutherland et al. 2001; Goodall, Yeo et al. 2001; Starnbach, Loomis et al. 2003). Immunity to *C. trachomatis* is characterized by some basic features; specifically sensitized T lymphocytes mediates protection (Su and Caldwell 1995; Morrison, Su et al. 2000; Morrison and Caldwell 2002), and the most important mediator molecule seems to be interferon gamma (IFNγ) (Morrison and Caldwell 2002). Additionally antibodies of the IgG, IgM, and IgA isotypes may also play a role (Cotter, Meng et al. 1995). In 1995 Tripples et al. (Tipples and McClarty 1995) isolated the gene for the CTP synthetase and Gu et al. (Gu, Wenman et al. 1995) cloned the region surrounding the gene for the alpha subunit of RNA polymerase. This region also contains genes for the proteins SecY, S13, S11, and L17, which are equivalent to *Escherichia coli* and *Bacillus subtilis* proteins. In 1997, the gene for elongation factor Ts was isolated (Zhang, Tao et al. 1997).

In 1998 Stevens et al published the complete genome sequence of *C. trachomatis* and predicted the presence of approximately 875 open reading frames. Among others, nucleotide sequences comprising CT442, CT460, CT509 CT579, CT587, CT713, CT812, or CT681 (MOMP) are described, and putative protein sequences for the above sequences are suggested. However importantly, this sequence information cannot be used to predict if the DNA is transcribed and translated into proteins in vivo.

More importantly, it is not possible on the basis of the sequences, to predict whether a given sequence will encode an immunogenic or an inactive protein. WO9928475 describes the complete genome sequence of *C. trachomatis* but has no evidence in support of any immunogenic effect whatsoever. Correspondingly WO9927105 describes the complete genome sequence of *C. pneumoniae.*

The only way to determine if a protein is recognized by the immune system during or after an infection with *C. trachomatis* is to produce the given protein and test it in an appropriate assay as described herein and possibly determine the fragment or epitope that has an immunogenic effect.

SUMMARY OF THE INVENTION

The invention is related to prevention, treatment and detection of infections caused by *Chlamydia* species (*C. trachomatis* ssp and *C. pneumonia*) by the use of a polypeptide comprising a *C. trachomatis* antigen or an immunogenic portion or other variant thereof, or by the use of a DNA sequence encoding a *C. trachomatis* antigen or an immunogenic portion or other variant thereof.

DETAILED DISCLOSURE OF THE INVENTION

The present invention discloses the use of the *Chlamydia* antigens (polypeptides or nucleic acids) ct043, ct511, ct521, ct616, ct803, ct067, ct679, ct583, ct603, ct026, ct093, ct357, ct659, ct111, ct509, ct587, ct023, ct025, ct078, ct082, ct118, ct174, ct003, ct005, ct027, ct032, ct008, ct016, ct028, ct035, ct141, ct643, ct414, ct874, ct456, ct681, ct123, ct125, ct126, ct133, ct150, ct175, ct376, ct083, ct089, ct155, ct168, ct175, ct184, ct124, ct082, ct336, ct342, ct842, ct323, ct080, ct084, ct110, ct119, ct541, ct443, ct795, ct396, ct283, ct051, ct002, ct009, ct015, ct030, ct048, ct061, ct063, ct068, ct071, ct051, ct080, ct115, ct119, ct678, ct561, ct538, ct582, ct875, ct322, ct112, ct315, ct610, ct147, ct228, ct232, ct614, ct098, ct265, ct375, ct004, ct038, ct040, ct052, ct053, ct201, ct245, ct246, ct405, ct420, ct426, ct507, ct512, ct513, ct514, ct516, ct316, ct439, ct492, ct520, ct523, ct526, ct611, ct613, ct626, ct630, ct647, ct649, ct725, ct734, ct779, ct801, ct833, ct835, ct836, ct845 or fragments (immunogenic portion, e.g. a T-cell or B-cell epitope) or homologs hereof for preparation of a pharmaceutical composition for preventing, treating or diagnosing infections caused by a bacteria from the *Chlamydia* species.

The invention also discloses the use of specific peptide fragments e.g. CT541-PF1 (aa pos. 111-243), CT443-PF1 (aa pos. 214-291), CT795-PF1 (aa pos. 1-163), CT396-PF1 (aa pos. 170-318), CT842-PF1 (aa pos. 433-515), CT283-PF1 (aa pos. 477-577), CT874-PF1 (aa pos. 330-426), CT051-PF1 (aa pos. 38-177), CT141-PF1 (aa pos. 17-126), CT643-PF1 (aa pos. 769-841), CT681-PF1 (aa pos. 156-391), CT681-PF2 (aa pos. 199-329), CT681-PF3 (aa pos. 294-349), CT414-PF1 (aa pos. 605-722), CT414-PF2 (aa pos. 463-530), CT456-PF1 (aa pos. 695-840), CT456-PF2 (aa pos. 137-229), CT456-PF3 (aa pos. 243-321), CT456-PF4 (aa pos. 209-291), CT456-PF5 (aa pos. 175-279), CT456-PF6 (aa pos. 567-730), CT456-PF7 (aa pos. 210-540), CT456-PF8 (aa pos. 190-279), CT521-PF1 (aa pos. 14-36), CT521-PF2 (aa pos. 40-62), CT521-PF3 (aa pos. 52-75), CT521-PF4 (aa pos. 66-88), CT521-PF5 (aa pos. 116-138), CT504-PF1 or the nucleic acid encoding these peptide fragments, for preparation of a pharmaceutical composition for preventing, treating or diagnosing infections caused by a bacteria from the *Chlamydia* species.

The present invention also discloses a pharmaceutical composition in the form of a vaccine or a diagnostic agent The polypeptide used for preparation of the pharmaceutical composition can be lipidated to allow a self-adjuvating effect or fused to a fusion partner where the fusion partner can be another polypeptide derived from *C. trachomatis*, including, but not limited to, one or more polypeptide fragments derived from CT812, CT579, CT587, Cap, CT713, CT442 or MOMP or at least one T-cell or B-cell epitope of any of the above mentioned. The invention also pertains to a fusion polypeptide comprising mutual fusions of two or more of the polypeptides (or immunogenic portions thereof) of the invention.

The vaccine disclosed by the invention can be used for preventing or treating an infection of the *Chlamydia* species, e.g. *C. trachomatis*.

The diagnostic agent disclosed by the invention (above mentioned antigen or an antibody against it) can be used for diagnosis of an infection of the *Chlamydia* species, e.g. *C. trachomatis*.

The diagnostic methods disclosed are based on cell mediated immunity, serology or a simple skin test. Diagnosis by cell mediated immunity of previous or ongoing infection with a bacterium from the *Chlamydia* species, comprises contacting a sample, e.g. a blood sample comprising mononuclear cells (e.g. T-lymphocytes), with the diagnostic reagent in order to detect a positive reaction, e.g. proliferation of the cells or release of cytokines such as IFNγ. Diagnosis by serology of previous or ongoing infection with a bacterium from the *Chlamydia* species said method comprising contacting a sample, e.g. a blood sample, with an antibody against the antigen in order to detect a positive reaction in case of infection or by contacting the antigen with a bodily fluid of the subject and when detecting binding of an antibody to said polypeptide, said binding being an indication that said subject is infected by a bacterium from the *Chlamydia* species. A skin test comprises intradermally injecting or applying to the skin, e.g. by a patch, the diagnostic reagent, a positive skin response at the location of injection or applying being indicative of an infection with a bacterium from the *Chlamydia* species.

The present invention also discloses a method for immunizing against an infection of a bacterium from the *Chlamydia* species, comprising administering the above mentioned vaccine of the invention to a mammal.

DEFINITIONS

Polypeptides

The word "polypeptide" in the present invention should have its usual meaning. That is an amino acid chain of any length, including a full-length protein, oligopeptides, short peptides and fragments thereof, wherein the amino acid residues are linked by covalent peptide bonds.

The polypeptide may be chemically modified by being glycosylated, by being lipidated (e.g. by chemical lipidation with palmitoyloxy succinimide as described by Mowat et al. 1991 or with dodecanoyl chloride as described by Lustig et al. 1976), by comprising prosthetic groups, or by containing additional amino acids such as e.g. a his-tag or a signal peptide.

Each polypeptide may thus be characterised by specific amino acids and be encoded by specific nucleic acid sequences. It will be understood that such sequences include analogues and variants produced by recombinant or synthetic methods wherein such polypeptide sequences have been modified by substitution, insertion, addition or deletion of one or more amino acid residues in the recombinant polypeptide and still be immunogenic in any of the biological assays described herein. Substitutions are preferably "conservative". These are defined according to the following table. Amino acids in the same block in the second column and preferably in the same line in the third column may be substituted for each other. The amino acids in the third column are indicated in one-letter code.

| | | |
|---|---|---|
| ALIPHATIC | Non-polar | GAP |
| | | ILV |
| | Polar-uncharged | CSTM |
| | | NQ |
| | Polar-charged | DE |
| | | KR |
| AROMATIC | | HFWY |

A preferred polypeptide within the present invention is an immunogenic antigen from *C. trachomatis*. Such antigen can for example be derived from the *C. trachomatis* cell and/or *C.*

*trachomatis* culture filtrate. Thus, a polypeptide comprising an immunogenic portion of one of the above antigens may consist entirely of the immunogenic portion, or may contain additional sequences. The additional sequences may be derived from the native *C. trachomatis* antigen or be heterologous and such sequences may, but need not, be immunogenic.

Each polypeptide is encoded by a specific nucleic acid sequence. It will be understood that such sequences include analogues and variants hereof wherein such nucleic acid sequences have been modified by substitution, insertion, addition or deletion of one or more nucleic acid. Substitutions are preferably silent substitutions in the codon usage which will not lead to any change in the amino acid sequence, but may be introduced to enhance the expression of the protein.

In the present context the term "substantially pure polypeptide fragment" means a polypeptide preparation which contains at most 5% by weight of other polypeptide material with which it is natively associated (lower percentages of other polypeptide material are preferred, e.g. at most 4%, at most 3%, at most 2%, at most 1%, and at most ½%). It is preferred that the substantially pure polypeptide is at least 96% pure, i.e. that the polypeptide constitutes at least 96% by weight of total polypeptide material present in the preparation, and higher percentages are preferred, such as at least 97%, at least 98%, at least 99%, at least 99.25%, at least 99.5%, and at least 99.75%. It is especially preferred that the polypeptide fragment is in "essentially pure form", i.e. that the polypeptide fragment is essentially free of any other antigen with which it is natively associated, i.e. free of any other antigen from bacteria belonging to the *Chlamydia* species. This can be accomplished by preparing the polypeptide fragment by means of recombinant methods in a non-chlamydia host cell as will be described in detail below, or by synthesizing the polypeptide fragment by the well-known methods of solid or liquid phase peptide synthesis, e.g. by the method described by Merrifield or variations thereof.

By the term "*Chlamydia* species" is understood a bacterium capable of causing the *Chlamydia* infection in an animal or in a human being. Examples are *C. trachomatis, C. pneumoniae* and *C. muridarum.*

The Major Outer Membrane Protein (MOMP) of *C. trachomatis*, is expressed during all phases of the developmental life cycle of *C. trachomatis* and constitute approximately 60% of the total protein content of the *chlamydia* outer membrane. MOMP can be divided into conserved domains interrupted by four highly variable domains (VD1-4) (Stephens, Wagar et al. 1988). In general T celle epitopes are located in the conserved regions (Ortiz, Demick et al. 1996) whereas the human antibody response is primarily directed against the variable domains. Based on the reactivity of specific mono clonal antibodies and detailed sequence analysis of the variable regions *C. trachomatis* can be divided into 15 different serovariants and of these serovariants A, B, Ba and C causes Trachoma, D-K causes sexually transmitted disease (STD), L1-L3 causes Lymphogranuloma venerum, and MoPn (*C. muridarum*) infects mice.

By "a *Chlamydia* patient" is understood an individual with culture or PCR proven infection with *Chlamydia* spp. Culture, microscopy and PCR diagnosis of *Chlamydia* are well known by any person skilled in the art.

By the term "delayed type hypersensitivity reaction" (DTH) is understood a T-cell mediated inflammatory response elicited after the injection of a polypeptide into, or application to, the skin, said inflammatory response appearing 72-96 hours after the polypeptide injection or application.

By the term "IFNγ" is understood interferon-gamma. The measurement of IFNγ is used as an indication of an immunological response.

By the terms "nucleic acid fragment" and "nucleic acid sequence" are understood any nucleic acid molecule including DNA, RNA, LNA (locked nucleic acids), PNA, RNA, dsRNA and RNA-DNA-hybrids. Also included are nucleic acid molecules comprising non-naturally occurring nucleosides. The term includes nucleic acid molecules of any length e.g. from 10 to 10000 nucleotides, depending on the use. When the nucleic acid molecule is for use as a pharmaceutical, e.g. in DNA therapy, or for use in a method for producing a polypeptide according to the invention, a molecule encoding at least one epitope is preferably used, having a length from about 18 to about 1000 nucleotides, the molecule being optionally inserted into a vector. When the nucleic acid molecule is used as a probe, as a primer or in antisense therapy, a molecule having a length of 10-100 is preferably used. According to the invention, other molecule lengths can be used, for instance a molecule having at least 12, 15, 21, 24, 27, 30, 33, 36, 39, 42, 50, 60, 70, 80, 90, 100, 200, 300, 400, 500 or 1000 nucleotides (or nucleotide derivatives), or a molecule having at most 10000, 5000, 4000, 3000, 2000, 1000, 700, 500, 400, 300, 200, 100, 50, 40, or 20 nucleotides (or nucleotide derivatives).

The term "stringent" when used in conjunction with hybridization conditions is as defined in the art, i.e. the hybridization is performed at a temperature not more than 15-20° C. under the melting point Tm, cf. Sambrook et al, 1989, pages 11.45-11.49. Preferably, the conditions are "highly stringent", i.e. 5-10° C. under the melting point Tm.

Throughout this specification, unless the context requires otherwise, the word "comprise", or variations thereof such as "comprises" or "comprising", will be understood to imply the inclusion of a stated element or integer or group of elements or integers but not the exclusion of any other element or integer or group of elements or integers.

Sequence Identity

The term "sequence identity" indicates a quantitative measure of the degree of homology between two amino acid sequences of equal length or between two nucleotide sequences of equal length. The two sequences to be compared must be aligned to best possible fit possible with the insertion of gaps or alternatively, truncation at the ends of the protein sequences. The sequence identity can be calculated as $$\frac{(N_{ref} - N_{dif})100}{N_{ref}},$$

wherein $N_{dif}$ is the total number of non-identical residues in the two sequences when aligned and wherein $N_{ref}$ is the number of residues in one of the sequences. Hence, the DNA sequence AGTCAGTC will have a sequence identity of 75% with the sequence AATCAATC ($N_{dif}$=2 and $N_{ref}$=8). A gap is counted as non-identity of the specific residue(s), i.e. the DNA sequence AGTGTC will have a sequence identity of 75% with the DNA sequence AGTCAGTC ($N_{dif}$=2 and $N_{ref}$=8). Sequence identity can alternatively be calculated by the BLAST program e.g. the BLASTP program (Pearson and Lipman 1988) (www.ncbi.nlm.nih.gov/cgi-bin/BLAST). In one aspect of the invention, alignment is performed with the sequence alignment method ClustalW with default parameters as described by Thompson J., et al 1994, available at http://www2.ebi.ac.uk/clustalw/.

A preferred minimum percentage of sequence identity is at least 80%, such as at least 85%, at least 90%, at least 91%, at least 92%, at least 93%, at least 94%, at least 95%, at least 96%, at least 97%, at least 98%, at least 99%, and at least 99.5%.

Immunogenic Portion

In a preferred embodiment of the invention, the polypeptide comprises an immunogenic portion of the polypeptide, such as an epitope for a B-cell or T-cell.

The immunogenic portion of a polypeptide is a part of the polypeptide, which elicits an immune response in an animal or a human being, and/or in a biological sample determined by any of the biological assays described herein. The immunogenic portion of a polypeptide may be a T-cell epitope or a B-cell epitope. Immunogenic portions can be related to one or a few relatively small parts of the polypeptide, they can be scattered throughout the polypeptide sequence or be situated in specific parts of the polypeptide. For a few polypeptides epitopes have even been demonstrated to be scattered throughout the polypeptide covering the full sequence (Ravn, Demissie et al. 1999).

In order to identify relevant T-cell epitopes which are recognised during an immune response, it is possible to use a "brute force" method: Since T-cell epitopes are linear, deletion mutants of the polypeptide will, if constructed systematically, reveal what regions of the polypeptide are essential in immune recognition, e.g. by subjecting these deletion mutants e.g. to the IFNγ assay described herein. Another method utilises overlapping oligopeptides for the detection of MHC class II epitopes, preferably synthetic, having a length of e.g. 20 amino acid residues derived from the polypeptide. These peptides can be tested in biological assays (e.g. the IFNγ assay as described herein) and some of these will give a positive response (and thereby be immunogenic) as evidence for the presence of a T cell epitope in the peptide. For the detection of MHC class I epitopes it is possible to predict peptides that will bind (Stryhn, Pedersen et al. 1996) and hereafter produce these peptides synthetic and test them in relevant biological assays e.g. the IFNγ assay as described herein. The peptides preferably having a length of e.g. 8 to 11 amino acid residues derived from the polypeptide. B-cell epitopes can be determined by analysing the B cell recognition to overlapping peptides covering the polypeptide of interest as e.g. described in Harboe et al (Harboe, Oettinger et al. 1996).

Although the minimum length of a T-cell epitope has been shown to be at least 6 amino acids, it is normal that such epitopes are constituted of longer stretches of amino acids. Hence, it is preferred that the polypeptide fragment of the invention has a length of at least 7 amino acid residues, such as at least 8, at least 9, at least 10, at least 12, at least 14, at least 16, at least 18, at least 20, at least 22, at least 24, and at least 30 amino acid residues. Hence, in important embodiments of the inventive method, it is preferred that the polypeptide fragment has a length of at most 50 amino acid residues, such as at most 40, 35, 30, 25, and 20 amino acid residues. It is expected that the peptides having a length of between 10 and 20 amino acid residues will prove to be most efficient as MCH class II epitopes and therefore especially preferred lengths of the polypeptide fragment used in the inventive method are 18, such as 15, 14, 13, 12 and even 11 amino acid residues. It is expected that the peptides having a length of between 7 and 12 amino acid residues will prove to be most efficient as MCH class I epitopes and therefore especially preferred lengths of the polypeptide fragment used in the inventive method are 11, such as 10, 9, 8 and even 7 amino acid residues.

Immunogenic portions of polypeptides may be recognised by a broad part (high frequency) or by a minor part (low frequency) of the genetically heterogenic human population. In addition some immunogenic portions induce high immunological responses (dominant), whereas others induce lower, but still significant, responses (subdominant). High frequency> <low frequency can be related to the immunogenic portion binding to widely distributed MHC molecules (HLA type) or even by multiple MHC molecules (Kilgus, Jardetzky et al. 1991) (Sinigaglia, Guttinger et al. 1988).

In the context of providing candidate molecules for a new vaccine against *Chlamydia* infection, the subdominat epitopes are however as relevant as are the dominat epitopes since it has been show that such epitopes can induce protection regardless of being subdominant.

Variants

A common feature of the polypeptides of the invention is their capability to induce an immunological response as illustrated in the examples. It is understood that a variant of a polypeptide of the invention produced by substitution, insertion, addition or deletion is also immunogenic determined by any of the assays described herein.

Immune Individual

An immune individual is defined as a person or an animal, which has cleared or controlled an infection with *chlamydia*.

Immunogenic

An immunogenic polypeptide is defined as a polypeptide that induces an immune response in a biological sample or an individual currently or previously infected with a *chlamydia*. The immune response may be monitored by one of the following methods:

An in vitro cellular response is determined by release of a relevant cytokine such as IFNγ, from lymphocytes withdrawn from an animal or human being currently or previously infected with *chlamydia*, or by detection of proliferation of these T cells. The induction being performed by the addition of the polypeptide or the immunogenic portion to a suspension comprising from $1\times10^5$ cells to $3\times10^5$ cells per well. The cells being isolated from either the blood, the spleen, the liver or the lung and the addition of the polypeptide or the immunogenic portion resulting in a concentration of not more than 20 μg per ml suspension and the stimulation being performed from two to five days. For monitoring cell proliferation the cells are pulsed with radioactive labeled Thymidine and after 16-22 hours of incubation detecting the proliferation by liquid scintillation counting. A positive response being a response more than background plus two standard deviations. The release of IFNγ can be determined by the ELISA method, which is well known to a person skilled in the art. A positive response being a response more than background plus two standard deviations. Other cytokines than IFNγ could be relevant when monitoring the immunological response to the polypeptide, such as IL-12, TNF-α, IL-4, IL-5, IL-10, IL-6, TGF-β. Another and more sensitive method for determining the presence of a cytokine (e.g. IFNγ) is the ELISPOT method where the cells isolated from either the blood, the spleen, the liver or the lung are diluted to a concentration of preferable of 1 to $4\times10^6$ cells/ml and incubated for 18-22 hrs in the presence of the polypeptide or the immunogenic portion resulting in a concentration of not more than 20 μg per ml. The cell suspensions are hereafter diluted to 1 to $2\times10^6$/ml and transferred to Maxisorp plates coated with anti-IFNγ and incubated for preferably 4 to 16 hours. The IFNγ producing cells are determined by the use of labelled secondary anti-IFNγ antibody and a relevant substrate giving rise to spots, which can be enumerated using a dissection microscope. It is also a possibility to determine the presence of mRNA coding for the relevant cytokine by the use of the PCR technique. Usually one or more cytokines will be measured utilizing for example the PCR, ELISPOT or ELISA. It will be appreciated by a person skilled in the art that a significant increase or decrease in the amount of any of these cytokines induced by a specific polypeptide can be used in evaluation of the immunological activity of the polypeptide.

An in vitro cellular response may also be determined by the use of T cell lines derived from an immune individual or a *C. trachomatis* infected person where the T cell lines have been driven with either live *chlamydia* or extracts from the bacterial cell for 10 to 20 days with the addition of IL-2. The induction being performed by addition of not more than 20 μg polypeptide per ml suspension to the T cell lines containing from $1\times10^5$ cells to $3\times10^5$ cells per well and incubation being performed from two to six days. The induction of IFNγ or release of another relevant cytokine is detected by ELISA. The stimulation of T cells can also be monitored by detecting cell proliferation using radioactively labeled Thymidine as described above. For both assays a positive response being a response more than background plus two standard deviations.

An in vivo cellular response which may be determined as a positive DTH response after intradermal injection or local application patch of at most 100 μg of the polypeptide or the immunogenic portion to an individual who is clinically or subclinically infected with *chlamydia*, a positive response having a diameter of at least 5 mm 72-96 hours after the injection or application.

An in vitro humoral response is determined by a specific antibody response in an immune or infected individual. The presence of antibodies may be determined by an ELISA technique or a Western blot where the polypeptide or the immunogenic portion is absorbed to either a nitrocellulose membrane or a polystyrene surface. The serum is preferably diluted in PBS from 1:10 to 1:100 and added to the absorbed polypeptide and the incubation being performed from 1 to 12 hours. By the use of labeled secondary antibodies the presence of specific antibodies can be determined by measuring the OD e.g. by ELISA where a positive response is a response of more than background plus two standard deviations or alternatively a visual response in a Western blot.

Another relevant parameter is measurement of the protection in animal models induced after vaccination with the polypeptide in an adjuvant or after DNA vaccination. Suitable animal models include primates, guinea pigs or mice, which are challenged with an infection of *chlamydia*. Readout for induced protection could be decrease of the bacterial load in target organs compared to non-vaccinated animals, prolonged survival times compared to non-vaccinated animals and diminished weight loss compared to non-vaccinated animals.

Preparation Methods

In general, *C. trachomatis* antigens, and DNA sequences encoding such antigens, may be prepared using any one of a variety of procedures.

They may be purified as native proteins from the *C. trachomatis* cell by procedures such as those described above. Immunogenic antigens may also be produced recombinantly using a DNA sequence encoding the antigen, which has been inserted into an expression vector and expressed in an appropriate host. Examples of host cells are *E. coli*. The polypeptides or immunogenic portion hereof can also be produced synthetically having fewer than about 100 amino acids, and generally fewer than 50 amino acids and may be generated using techniques well known to those ordinarily skilled in the art, such as commercially available solid-phase techniques where amino acids are sequentially added to a growing amino acid chain.

In the construction and preparation of plasmid DNA encoding the polypeptide as defined for DNA vaccination a host strain such as *E. coli* can be used. Plasmid DNA can then be prepared from overnight cultures of the host strain carrying the plasmid of interest, and purified using e.g. the Qiagen Giga-Plasmid column kit (Qiagen, Santa Clarita, Calif., USA) including an endotoxin removal step. It is essential that plasmid DNA used for DNA vaccination is endotoxin free.

Fusion Proteins

The immunogenic polypeptides may also be produced as fusion proteins, by which methods superior characteristics of the polypeptide of the invention can be achieved. For instance, fusion partners that facilitate export of the polypeptide when produced recombinantly, fusion partners that facilitate purification of the polypeptide, and fusion partners which enhance the immunogenicity of the polypeptide fragment of the invention are all interesting possibilities. Therefore, the invention also pertains to a fusion polypeptide comprising at least one polypeptide or immunogenic portion defined above and at least one fusion partner. The fusion partner can, in order to enhance immunogenicity, be another polypeptide derived from *C. trachomatis*, such as a polypeptide fragment derived from *Chlamydia* species, such as CT812, CT579, CT587 (Goodall, Yeo et al. 2001), Cap (Fling, Sutherland et al. 2001), CT713 (Kubo and Stephens 2000), CT442 (Starnbach, Loomis et al. 2003), or MOMP (Stephens, Wagar et al. 1988) or at least one T-cell epitope or B cell epitope of any of the above mentioned. The invention also pertains to a fusion polypeptide comprising mutual fusions of two or more of the polypeptides (or immunogenic portions thereof) of the invention.

Other fusion partners, which could enhance the immunogenicity of the product, are lymphokines such as IFNγ, IL-2 and IL-12. In order to facilitate expression and/or purification, the fusion partner can e.g. be a bacterial fimbrial protein, e.g. the pilus components pilin and papA; protein A; the ZZ-peptide (ZZ-fusions are marketed by Pharmacia in Sweden); the maltose binding protein; gluthatione S-transferase; β-galactosidase; or poly-histidine. Fusion proteins can be produced recombinantly in a host cell, which could be *E. coli*, and it is a possibility to induce a linker region between the different fusion partners.

Other interesting fusion partners are polypeptides, which are lipidated so that the immunogenic polypeptide is presented in a suitable manner to the immune system. This effect is e.g. known from vaccines based on the *Borrelia burgdorferi* OspA polypeptide as described in e.g. WO 96/40718 A or vaccines based on the *Pseudomonas aeruginosa* OprI lipoprotein (Cote-Sierra, Jongert et al. 1998). Another possibility is N-terminal fusion of a known signal sequence and an N-terminal cystein to the immunogenic polypeptide. Such a fusion results in lipidation of the immunogenic polypeptide at the N-terminal cystein, when produced in a suitable production host.

Pharmaceutical Composition

A pharmaceutical composition is defined as any vaccine (both therapeutic and prophylactic) or any diagnostic reagent as described in the following.

Vaccine, Protein

Another part of the invention pertains to a vaccine composition comprising a polypeptide (or at least one immunogenic portion thereof) or fusion polypeptide according to the invention. In order to ensure optimum performance of such a vaccine composition it is preferred that it comprises an immunologically and pharmaceutically acceptable carrier, vehicle or adjuvant.

An effective vaccine, wherein a polypeptide of the invention is recognized by the animal, will in an animal model be able to decrease bacterial load in target organs, prolong survival times and/or diminish weight loss after challenge with virulent *Chlamydia*, compared to non-vaccinated animals Suitable carriers are selected from the group consisting of a polymer to which the polypeptide(s) is/are bound by hydrophobic non-covalent interaction, such as a plastic, e.g. polystyrene, or a polymer to which the polypeptide(s) is/are covalently bound, such as a polysaccharide, or a polypeptide, e.g. bovine serum albumin, ovalbumin or keyhole limpet haemocyanin. Suitable vehicles are selected from the group consisting of a diluent and a suspending agent. The adjuvant is preferably selected from the group consisting of dimethyldioctadecylammonium bromide (DDA), Quil A, poly I:C, aluminium hydroxide, Freund's incomplete adjuvant, IFNγ, IL-2, IL-12, monophosphoryl lipid A (MPL), Treholose Dimycolate (TDM), Trehalose Dibehenate (TDB) and muramyl dipeptide (MDP).

Preparation of vaccines which contain peptide sequences as active ingredients is generally well understood in the art, as exemplified by U.S. Pat. Nos. 4,608,251; 4,601,903; 4,599,231 and 4,599,230, all incorporated herein by reference.

Other methods of achieving adjuvant effect for the vaccine include use of agents such as aluminum hydroxide or phosphate (alum), synthetic polymers of sugars (Carbopol), aggregation of the protein in the vaccine by heat treatment, aggregation by reactivating with pepsin treated (Fab) antibodies to albumin, mixture with bacterial cells such as *C. parvum* or endotoxins or lipopolysaccharide components of gram-negative bacteria, emulsion in physiologically acceptable oil vehicles such as mannide mono-oleate (Aracel A) or emulsion with 20 percent solution of a perfluorocarbon (Fluosol-DA) used as a block substitute may also be employed. Other possibilities involve the use of immune modulating substances such as cytokines or synthetic IFNγ inducers such as poly I:C in combination with the above-mentioned adjuvants.

Another interesting possibility for achieving adjuvant effect is to employ the technique described in (Gosselin, Wardwell et al. 1992)(which is hereby incorporated by reference herein). In brief, a relevant antigen such as an antigen of the present invention can be conjugated to an antibody (or antigen binding antibody fragment) against the Fcγ receptors on monocytes/macrophages.

The vaccines are administered in a manner compatible with the dosage formulation, and in such amount as will be therapeutically effective and immunogenic. The quantity to be administered depends on the subject to be treated, including, e.g., the capacity of the individual's immune system to mount an immune response, and the degree of protection desired. Suitable dosage ranges are of the order of several hundred micrograms active ingredient per vaccination with a preferred range from about 0.1 μg to 1000 μg, such as in the range from about 1 μg to 300 μg, and especially in the range from about 10 μg to 50 μg. Suitable regimens for initial administration and booster shots are also variable but are typified by an initial administration followed by subsequent inoculations or other administrations.

The manner of application may be varied widely. Any of the conventional methods for administration of a vaccine are applicable. These are believed to include oral application on a solid physiologically acceptable base or in a physiologically acceptable dispersion, parenterally, by injection or the like. The dosage of the vaccine will depend on the route of administration and will vary according to the age of the person to be vaccinated and, to a lesser degree, the size of the person to be vaccinated.

The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides; such suppositories may be formed from mixtures containing the active ingredient in the range of 0.5% to 10%, preferably 1-2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and advantageously contain 10-95% of active ingredient, preferably 25-70%.

In many instances, it will be necessary to have multiple administrations of the vaccine. Especially, vaccines can be administered to prevent an infection with *chlamydia* and/or to treat established *chlamydia* infection. When administered to prevent an infection, the vaccine is given prophylactically, before definitive clinical signs or symptoms of an infection are present.

Due to genetic variation, different individuals may react with immune responses of varying strength to the same polypeptide. Therefore, the vaccine according to the invention may comprise several different polypeptides in order to increase the immune response. The vaccine may comprise two or more polypeptides or immunogenic portions, where all of the polypeptides are as defined above, or some but not all of the peptides may be derived from one or more of the other *chlamydia* serovariants. In the latter example, the polypeptides not necessarily fulfilling the criteria set forth above for polypeptides may either act due to their own immunogenicity or merely act as adjuvants.

The vaccine may comprise 1-20, such as 2-20 or even 3-20 different polypeptides or fusion polypeptides, such as 3-10 different polypeptides or fusion polypeptides.

The invention also pertains to a method for immunising an animal, including a human being, against *Chlamydia* infection caused by a *Chlamydia* species, comprising administering to the animal the polypeptide of the invention, or a vaccine composition of the invention as described above, or a living vaccine described above.

The invention also pertains to a method for producing an immunologic composition according to the invention, the method comprising preparing, synthesising or isolating a polypeptide according to the invention, and solubilizing or dispersing the polypeptide in a medium for a vaccine, and optionally adding other *C. trachomatis* antigens and/or a carrier, vehicle and/or adjuvant substance.

Vaccine DNA.

The nucleic acid fragments of the invention may be used for effecting in vivo expression of antigens, i.e. the nucleic acid fragments may be used in so-called DNA vaccines as reviewed in (Ulmer, Donnelly et al. 1993), which is included by reference.

Hence, the invention also relates to a vaccine comprising a nucleic acid fragment according to the invention, the vaccine effecting in vivo expression of antigen by an animal, including a human being, to whom the vaccine has been administered, the amount of expressed antigen being effective to confer substantially increased resistance to infections caused by virulent *chlamydia* in an animal, including a human being.

The efficacy of such a DNA vaccine can possibly be enhanced by administering the gene encoding the expression product together with a DNA fragment encoding a polypeptide which has the capability of modulating an immune response.

Live Recombinant Vaccines

One possibility for effectively activating a cellular immune response for a vaccine can be achieved by expressing the relevant antigen in a vaccine in a non-pathogenic microorganism or virus. Well-known examples of such microorganisms are *Mycobacterium bovis* BCG, *Salmonella* and *Pseudomonas* and examples of viruses are Vaccinia Virus and Adenovirus.

Another possibility is to integrate the DNA encoding the polypeptide according to the invention in an attenuated virus such as the vaccinia virus or Adenovirus (Rolph and Ramshaw 1997). The recombinant vaccinia virus is able to replicate within the cytoplasma of the infected host cell and the polypeptide of interest can therefore induce an immune response, which is envisioned to induce protection against *Chlamydia.*

Therapeutic Vaccine.

The invention also relates to the use of a polypeptide or nucleic acid of the invention for use as therapeutic vaccines as have been described in the literature exemplified by D. Lowry (Lowry et al 1999). Antigens with therapeutic properties may be identified based on their ability to diminish the severity of *C. trachomatis* infection in experimental animals or prevent reactivation of previous infection, when administered as a vaccine. The composition used for therapeutic vaccines can be prepared as described above for vaccines.

Diagnostic Protein

The invention also relates to a method of diagnosing *Chlamydia* infection caused by a *chlamydia* in an animal, including a human being, comprising intradermally injecting, in the animal, a polypeptide according to the invention, a positive skin response at the location of injection being indicative of the animal having a *Chlamydia* infection, and a negative skin response at the location of injection being indicative of the animal not having an infection.

When diagnosis of previous or ongoing infection with virulent *chlamydia* is the aim, a blood sample comprising mononuclear cells (i.e. T-lymphocytes) from a patient could be contacted with a sample of one or more polypeptides of the invention. This contacting can be performed in vitro and a positive reaction could e.g. be proliferation of the T-cells or release of cytokines such as IFNγ into the extracellular phase. It is also conceivable to contact a serum sample from a subject with a polypeptide of the invention, the demonstration of a binding between antibodies in the serum sample and the polypeptide being indicative of previous or ongoing infection.

The invention therefore also relates to an in vitro method for diagnosing ongoing or previous sensitisation in an animal or a human being with a *Chlamydia* species, the method comprising providing a blood sample from the animal or human being, and contacting the sample from the animal with the polypeptide of the invention, a significant release into the extracellular phase of at least one cytokine by mononuclear cells in the blood sample being indicative of the animal being sensitised. A positive response being a response more than release from a blood sample derived from a patient without the *chlamydia* diagnosis plus two standard deviations. The invention also relates to the in vitro method for diagnosing ongoing or previous sensitisation in an animal or a human being with *chlamydia*, the method comprising providing a blood sample from the animal or human being, and by contacting the sample from the animal with the polypeptide of the invention demonstrating the presence of antibodies recognizing the polypeptide of the invention in the serum sample. The immunogenic composition used for diagnosing may comprise 1-20, such as 2-20 or even 3-20 different polypeptides or fusion polypeptides, such as 3-10 different polypeptides or fusion polypeptides.

Diagnostic DNA

The nucleic acid probes encoding the polypeptide of the invention can be used in a variety of diagnostic assays for detecting the presence of pathogenic organisms in a given sample. A method of determining the presence of chlamydial nucleic acids in an animal, including a human being, or in a sample, comprising administering a nucleic acid fragment of the invention to the animal or incubating the sample with the nucleic acid fragment of the invention or a nucleic acid fragment complementary thereto, and detecting the presence of hybridised nucleic acids resulting from the incubation (by using the hybridisation assays which are well-known in the art), is also included in the invention. Such a method of diagnosing *Chlamydia* infection might involve the use of a composition comprising at least a part of a nucleotide sequence as defined above and detecting the presence of nucleotide sequences in a sample from the animal or human being to be tested which hybridise with the nucleic acid fragment (or a complementary fragment) by the use of PCR technique.

Antibodies

A monoclonal or polyclonal antibody, which is specifically reacting with a polypeptide of the invention in an immuno assay, or a specific binding fragment of said antibody, is also a part of the invention. The antibodies can be produced by methods known to the person skilled in the art. Polyclonal antibodies can be raised in a mammal, for example, by one or more injections of a polypeptide according to the present invention and, if desired, an adjuvant. The monoclonal antibodies according to the present invention may, for example, be produced by the hybridoma method first described by Kohler and Milstein (1975), or may be produced by recombinant DNA methods such as described in U.S. Pat. No. 4,816,567. The monoclonal antibodies may also be isolated from phage libraries generated using the techniques described by (McCafferty, Griffiths et al. 1990), for example. Methods for producing antibodies are described in the literature, e.g. in U.S. Pat. No. 6,136,958.

A sample of a potentially infected organ may be contacted with such an antibody recognizing a polypeptide of the invention. The demonstration of the reaction by means of methods well known in the art between the sample and the antibody will be indicative of an ongoing infection. It is of course also a possibility to demonstrate the presence of anti-chlamydial antibodies in serum by contacting a serum sample from a subject with at least one of the polypeptide fragments of the invention and using well-known methods for visualising the reaction between the antibody and antigen.

In diagnostics, an antibody, a nucleic acid fragment and/or a polypeptide of the invention can be used either alone, or as a constituent in a composition. Such compositions are known in the art, and comprise compositions in which the antibody, the nucleic acid fragment or the polypeptide of the invention is coupled, preferably covalently, to at least one other molecule, e.g. a label (e.g. radioactive or fluorescent) or a carrier molecule.

The present invention discloses antigenic components of *C. trachomatis* which have:

1) the capacity to stimulate T cells from patients with a urogenital *Chlamydia* infection to secrete INFγ, or
2) the capacity to stimulate T cells from patients with a urogenital *Chlamydia* infection to secrete cytokines which inhibit *Chlamydia* growth in vitro, or
3) is recognized by serum IgG, and/or IgM, and/or IgA, antibodies from patients with a urogenital *chlamydia* infection, or
4) is recognized by T cells and/or antibodies from mice experimentally infected with *Chlamydia muridarum* and/or *C. trachomatis*, or
5) is able by administration to induce an immune response in mice which recognize the *C. trachomatis* bacterial antigen, or
6) is able by vaccination to provide at least partial immunity against an experimental challenge infection with *Chlamydia muridarum* and/or *C. trachomatis*.

Figure 2:
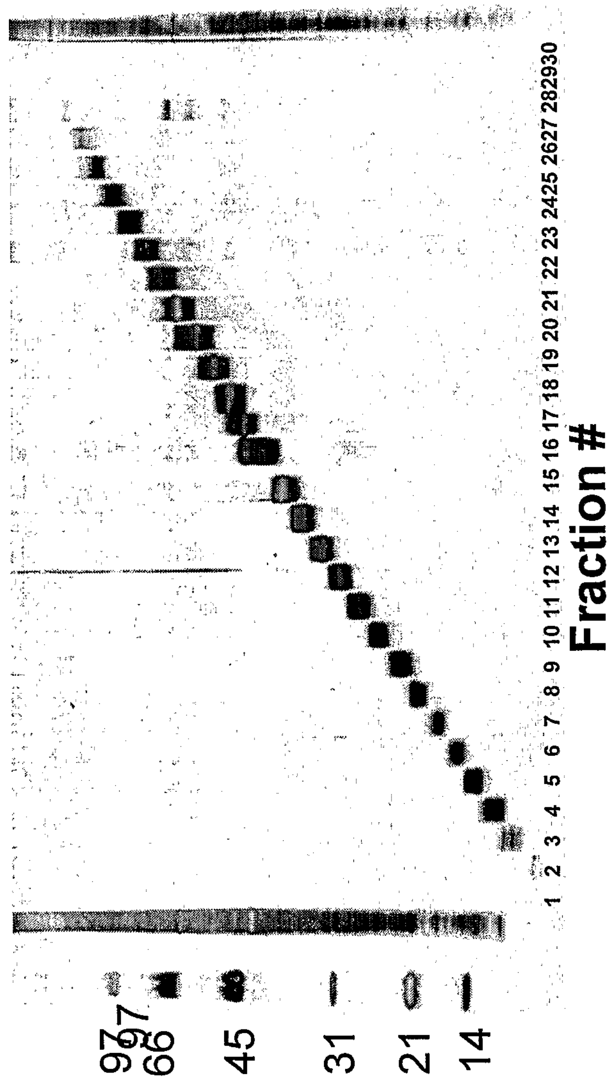
Figure 3:
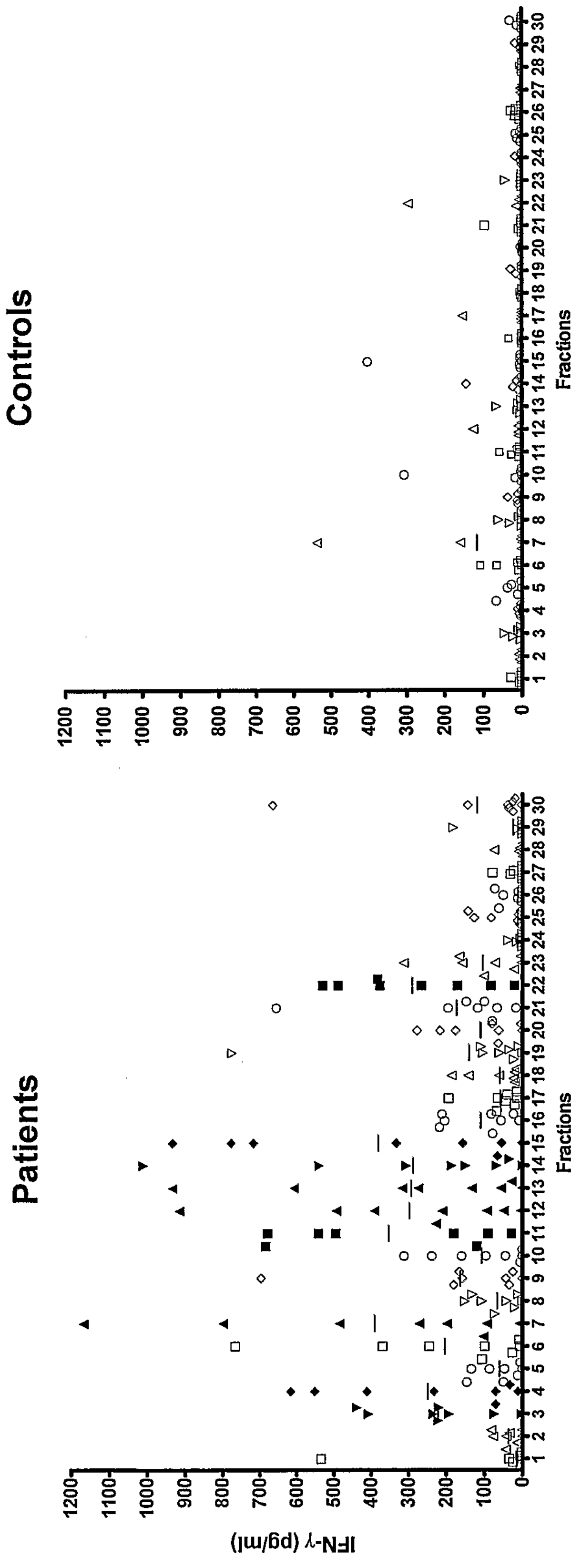

Firstly, in order to identify the molecular targets of protective T cells among proteins from *C. trachomatis*, a protein lysate of *C. trachomatis* serovar D (strain UW-3/Cx, ATCC No: VR-885) was fractionated by the multi-elution technique (Andersen and Heron 1993). This technique separates proteins in a complex protein mixture according to their molecular weight into narrow fractions which are then used to stimulate Peripheral Blood Mononuclear Cells (PBMCs) in vitro. After several days of incubation the release of INFγ is monitored by ELISA (FIG. 1). The responses of *Chlamydia* patients were compared to the responses of normal blood donors with no previous diagnosis of *Chlamydia* infection. This comparison allows identification of *C. trachomatis* proteins which have the capacity to trigger effector T cells to release INFγ during the first phases of the human infection. Using this approach it was demonstrated that the targets for these protective T cells are proteins or fragments of proteins with apparent molecular weights of 5-12, 16-20, 25-35 and 58-74 kDa (FIGS. 2 and 3). The precise identity of bacterial proteins within each stimulatory region was determined by mass spectrometry.

Figure 4:
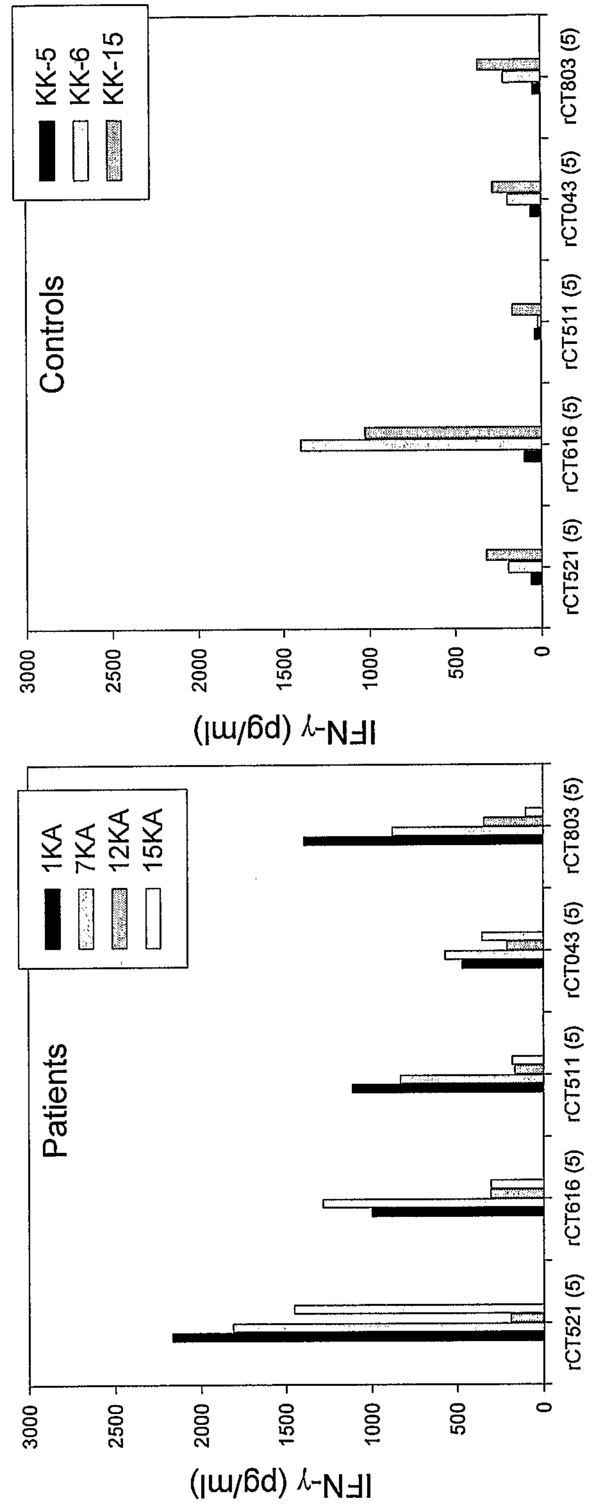

To further identify and characterise the stimulating antigens, each specific *C. trachomatis* antigens may be a) purified antigens from *C. trachomatis* extracts as exemplified in Example 1, b) antigens produced and purified from *E. coli* as exemplified in Example 1, c) overlapping synthetic peptides as exemplified in Example 1, or d) transduction of target patient PBMC directly with recombinant Adenovirus constructs as exemplified by Example 5. This method enabled the identification of single antigens and peptides derived thereof within each stimulatory region with exceedingly stimulating capacity measured by the release of INFγ as exemplified in FIG. 4.

Secondly, a directed expression-library was constructed by amplifying full-length *C. trachomatis* genes by polymerase chain reaction (PCR) using gene-specific oligonucleotides containing a Kozak sequence in the 5'-primer and a stop codon in the 3'-primer. Genomic DNA from *C. trachomatis* serovar D was used as template for the PCR reactions and a newly developed UNIX program was used for automated primer design including primer position within the gene of interest and Tm. Amplicons were first inserted by recombination into the Gateway “entry vector” (Invitrogen) and then transferred by recombination into the pDEST17 expression vector (Invitrogen), which contains a $His_6$-tag and the same recombination sequences as the entry vector. Individual clones were screened for the expression of *C. trachomatis* antigens by the colony blot method (French maul and maul 1986) using a pool of human serum samples with high levels of *C. trachomatis* specific IgG, IgM, or IgA antibodies. The nitrocellulose filters used for the colony lift had been presoaked in 1% arabinose solution in order to induce transcription originating for the plasmid encoded promoter prior to cell lysis. Positive clones which bind to serum IgG, IgM, or IgA antibodies from *chlamydia* patients were selected for further analysis by western blotting using the same pool of serum samples as used for the initial screening. This method led to the identification of clones encoding immunoreactive *C. trachomatis* proteins of vaccine and diagnostic relevance.

Thirdly, a genomic expression library was constructed in *E. coli* phage lambda gt11 (λgt11). High-molecular-weight chromosomal DNA of *C. trachomatis* serovar D was extracted from elementary bodies in a lysis buffer containing SDS (1%) and Proteinase K (100 ug/ml) followed by phenol extraction and ethanol precipitation. DNA was partially degraded by sonication and DNA fragments of 0.2-0.8 kb in size were ligated into λgt11. The ligation mixture was packaged in vitro and the recombinant phages were plated on *E. coli* Y1090r− yielding a genomic expression library containing approximately $3.4\times10^5$ primary lambda phages. This primary library was amplified to resulting in a genome random expression library with $6.7\times10^9$ PFU/ml. In a first experiment, this library was screened by a plaque-lift method using the same pool of human serum samples as used above for the screening of the full-length expression library. Eighty-eight immuno reactive plaques binding to *C. trachomatis*-specific IgG, IgM, or IgA antibodies were identified. These plaques were pooled into eight pools (two pools of IgA reactive plaques, five pools of IgG reactive plaques and one pool of IgM reactive plaques) and rescreened with the same serum-pool (primary antibody) as used in the initial screening. Individual sero reactive phage plaques were isolated and the sequences of the DNA inserts of individually sero reactive phages were determined. This method identified a several clones encoding specific *C. trachomatis* immunoreactive peptides of vaccine and diagnostic relevance.

Lastly, animal models of the disease have been established in small rodent in order to identify antigens which are recognized by the murine immunesystem during an experimental *Chlamydia* infection or provides at least partial immunity against a challenge infection. Different *chlamydia* species exhibit a high degree of specificity towards their natural host. Thus, *C. trachomatis* serovar D used in the different screening strategies described above is a human pathogen, which does not cause pathological changes in mice as normally associated with the human infection. On the other hand, mice can be experimentally infected with the closely related *Chlamydia muridarum* MoPn strain, and several researchers have previously demonstrated induction of partial immunity against experimental MoPn infection. A genital infection model has therefore been established and validated in C57 mice. The protective efficacy of different antigens was studied in this model by evaluating 1) bacterial counts by cervical swaps, 2) pathological changes in the genital tract, and 3) cellular in vitro assays for immune reactive cells.

TABLE 1

| *Chlamydia* antigen | Protein sequence | DNA sequence |
|---|---|---|
| CT043 | SEQ ID NO. 1 | SEQ ID NO. 2 |
| CT511 | SEQ ID NO. 3 | SEQ ID NO. 4 |
| CT521 | SEQ ID NO. 5 | SEQ ID NO. 6 |
| CT616 | SEQ ID NO. 7 | SEQ ID NO. 8 |
| CT803 | SEQ ID NO. 9 | SEQ ID NO. 10 |
| CT067 | SEQ ID NO. 11 | SEQ ID NO. 12 |
| CT679 | SEQ ID NO. 13 | SEQ ID NO. 14 |
| CT583 | SEQ ID NO. 15 | SEQ ID NO. 16 |
| CT603 | SEQ ID NO. 17 | SEQ ID NO. 18 |
| CT026 | SEQ ID NO. 19 | SEQ ID NO. 20 |
| CT093 | SEQ ID NO. 21 | SEQ ID NO. 22 |
| CT357 | SEQ ID NO. 23 | SEQ ID NO. 24 |
| CT659 | SEQ ID NO. 25 | SEQ ID NO. 26 |
| CT111 | SEQ ID NO. 27 | SEQ ID NO. 28 |
| CT509 | SEQ ID NO. 29 | SEQ ID NO. 30 |
| CT587 | SEQ ID NO. 31 | SEQ ID NO. 32 |
| CT023 | SEQ ID NO. 33 | SEQ ID NO. 34 |
| CT025 | SEQ ID NO. 35 | SEQ ID NO. 36 |
| CT078 | SEQ ID NO. 37 | SEQ ID NO. 38 |
| CT082 | SEQ ID NO. 39 | SEQ ID NO. 40 |
| CT118 | SEQ ID NO. 41 | SEQ ID NO. 42 |
| CT174 | SEQ ID NO. 43 | SEQ ID NO. 44 |
| CT003 | SEQ ID NO. 45 | SEQ ID NO. 46 |
| CT005 | SEQ ID NO. 47 | SEQ ID NO. 48 |
| CT027 | SEQ ID NO. 49 | SEQ ID NO. 50 |
| CT032 | SEQ ID NO. 51 | SEQ ID NO. 52 |
| CT008 | SEQ ID NO. 53 | SEQ ID NO. 54 |
| CT016 | SEQ ID NO. 55 | SEQ ID NO. 56 |
| CT028 | SEQ ID NO. 57 | SEQ ID NO. 58 |
| CT035 | SEQ ID NO. 59 | SEQ ID NO. 60 |
| CT141 | SEQ ID NO. 61 | SEQ ID NO. 62 |
| CT643 | SEQ ID NO. 63 | SEQ ID NO. 64 |
| CT414 | SEQ ID NO. 65 | SEQ ID NO. 66 |
| CT874 | SEQ ID NO. 67 | SEQ ID NO. 68 |
| CT456 | SEQ ID NO. 69 | SEQ ID NO. 70 |
| CT681 | SEQ ID NO. 71 | SEQ ID NO. 72 |
| CT123 | SEQ ID NO. 73 | SEQ ID NO. 74 |
| CT125 | SEQ ID NO. 75 | SEQ ID NO. 76 |
| CT126 | SEQ ID NO. 77 | SEQ ID NO. 78 |
| CT133 | SEQ ID NO. 79 | SEQ ID NO. 80 |
| CT150 | SEQ ID NO. 81 | SEQ ID NO. 82 |
| CT175 | SEQ ID NO. 83 | SEQ ID NO. 84 |
| CT376 | SEQ ID NO. 85 | SEQ ID NO. 86 |
| CT083 | SEQ ID NO. 87 | SEQ ID NO. 88 |
| CT089 | SEQ ID NO. 89 | SEQ ID NO. 90 |
| CT155 | SEQ ID NO. 91 | SEQ ID NO. 92 |
| CT168 | SEQ ID NO. 93 | SEQ ID NO. 94 |
| CT184 | SEQ ID NO. 95 | SEQ ID NO. 96 |
| CT124 | SEQ ID NO. 97 | SEQ ID NO. 98 |
| CT336 | SEQ ID NO. 99 | SEQ ID NO. 100 |
| CT342 | SEQ ID NO. 101 | SEQ ID NO. 102 |
| CT842 | SEQ ID NO. 103 | SEQ ID NO. 104 |
| CT323 | SEQ ID NO. 105 | SEQ ID NO. 106 |
| CT080 | SEQ ID NO. 107 | SEQ ID NO. 108 |
| CT084 | SEQ ID NO. 109 | SEQ ID NO. 110 |
| CT110 | SEQ ID NO. 111 | SEQ ID NO. 112 |
| CT119 | SEQ ID NO. 113 | SEQ ID NO. 114 |
| CT541 | SEQ ID NO. 115 | SEQ ID NO. 116 |
| CT443 | SEQ ID NO. 117 | SEQ ID NO. 118 |
| CT795 | SEQ ID NO. 119 | SEQ ID NO. 120 |
| CT396 | SEQ ID NO. 121 | SEQ ID NO. 122 |
| CT283 | SEQ ID NO. 123 | SEQ ID NO. 124 |
| CT051 | SEQ ID NO. 125 | SEQ ID NO. 126 |
| CT002 | SEQ ID NO. 185 | SEQ ID NO. 186 |
| CT009 | SEQ ID NO. 187 | SEQ ID NO. 188 |
| CT015 | SEQ ID NO. 189 | SEQ ID NO. 190 |
| CT030 | SEQ ID NO. 191 | SEQ ID NO. 192 |
| CT048 | SEQ ID NO. 193 | SEQ ID NO. 194 |
| CT061 | SEQ ID NO. 195 | SEQ ID NO. 196 |
| CT063 | SEQ ID NO. 197 | SEQ ID NO. 198 |
| CT068 | SEQ ID NO. 199 | SEQ ID NO. 200 |
| CT071 | SEQ ID NO. 201 | SEQ ID NO. 202 |
| CT115 | SEQ ID NO. 203 | SEQ ID NO. 204 |
| CT678 | SEQ ID NO. 205 | SEQ ID NO. 206 |
| CT561 | SEQ ID NO. 207 | SEQ ID NO. 208 |
| CT538 | SEQ ID NO. 209 | SEQ ID NO. 210 |
| CT582 | SEQ ID NO. 211 | SEQ ID NO. 212 |
| CT875 | SEQ ID NO. 213 | SEQ ID NO. 214 |
| CT322 | SEQ ID NO. 215 | SEQ ID NO. 216 |
| CT112 | SEQ ID NO. 217 | SEQ ID NO. 218 |
| CT315 | SEQ ID NO. 219 | SEQ ID NO. 220 |
| CT610 | SEQ ID NO. 221 | SEQ ID NO. 222 |
| CT147 | SEQ ID NO. 223 | SEQ ID NO. 224 |
| CT228 | SEQ ID NO. 225 | SEQ ID NO. 226 |
| CT232 | SEQ ID NO. 227 | SEQ ID NO. 228 |
| CT614 | SEQ ID NO. 229 | SEQ ID NO. 230 |
| CT098 | SEQ ID NO. 231 | SEQ ID NO. 232 |
| CT265 | SEQ ID NO. 233 | SEQ ID NO. 234 |
| CT375 | SEQ ID NO. 235 | SEQ ID NO. 236 |
| CT004 | SEQ ID NO. 237 | SEQ ID NO. 238 |
| CT038 | SEQ ID NO. 239 | SEQ ID NO. 240 |
| CT040 | SEQ ID NO. 241 | SEQ ID NO. 242 |
| CT052 | SEQ ID NO. 243 | SEQ ID NO. 244 |
| CT053 | SEQ ID NO. 245 | SEQ ID NO. 246 |
| CT201 | SEQ ID NO. 247 | SEQ ID NO. 248 |
| CT245 | SEQ ID NO. 249 | SEQ ID NO. 250 |
| CT246 | SEQ ID NO. 251 | SEQ ID NO. 252 |
| CT405 | SEQ ID NO. 253 | SEQ ID NO. 254 |
| CT420 | SEQ ID NO. 255 | SEQ ID NO. 256 |
| CT426 | SEQ ID NO. 257 | SEQ ID NO. 258 |
| CT507 | SEQ ID NO. 259 | SEQ ID NO. 260 |
| CT512 | SEQ ID NO. 261 | SEQ ID NO. 262 |
| CT513 | SEQ ID NO. 263 | SEQ ID NO. 264 |
| CT514 | SEQ ID NO. 265 | SEQ ID NO. 266 |
| CT516 | SEQ ID NO. 267 | SEQ ID NO. 268 |
| CT316 | SEQ ID NO. 269 | SEQ ID NO. 270 |
| CT439 | SEQ ID NO. 271 | SEQ ID NO. 272 |
| CT492 | SEQ ID NO. 273 | SEQ ID NO. 274 |
| CT520 | SEQ ID NO. 275 | SEQ ID NO. 276 |
| CT523 | SEQ ID NO. 277 | SEQ ID NO. 278 |
| CT526 | SEQ ID NO. 279 | SEQ ID NO. 280 |
| CT611 | SEQ ID NO. 281 | SEQ ID NO. 282 |
| CT613 | SEQ ID NO. 283 | SEQ ID NO. 284 |
| CT626 | SEQ ID NO. 285 | SEQ ID NO. 286 |
| CT630 | SEQ ID NO. 287 | SEQ ID NO. 288 |
| CT647 | SEQ ID NO. 289 | SEQ ID NO. 290 |
| CT649 | SEQ ID NO. 291 | SEQ ID NO. 292 |
| CT725 | SEQ ID NO. 293 | SEQ ID NO. 294 |
| CT734 | SEQ ID NO. 295 | SEQ ID NO. 296 |
| CT779 | SEQ ID NO. 297 | SEQ ID NO. 298 |
| CT801 | SEQ ID NO. 299 | SEQ ID NO. 300 |
| CT833 | SEQ ID NO. 301 | SEQ ID NO. 302 |
| CT835 | SEQ ID NO. 303 | SEQ ID NO. 304 |
| CT836 | SEQ ID NO. 305 | SEQ ID NO. 306 |
| CT845 | SEQ ID NO. 307 | SEQ ID NO. 308 |

*Chlamydia* antigens

TABLE 2

*Chlamydia* antigenic fragments

| Peptide fragment | Amino acid sequence | DNA sequence |
|---|---|---|
| CT541-PF1 (aa pos. 111-243) | SEQ ID NO. 127 | SEQ ID NO. 128 |
| CT443-PF1 (aa pos. 214-291) | SEQ ID NO. 129 | SEQ ID NO. 130 |
| CT795-PF1 (aa pos. 1-163) | SEQ ID NO. 131 | SEQ ID NO. 132 |
| CT396-PF1 (aa pos. 170-318) | SEQ ID NO. 133 | SEQ ID NO. 134 |
| CT842-PF1 (aa pos. 433-515) | SEQ ID NO. 135 | SEQ ID NO. 136 |
| CT283-PF1 (aa pos. 477-577) | SEQ ID NO. 137 | SEQ ID NO. 138 |
| CT874-PF1 (aa pos. 330-426) | SEQ ID NO. 139 | SEQ ID NO. 140 |
| CT051-PF1 (aa pos. 38-177) | SEQ ID NO. 141 | SEQ ID NO. 142 |
| CT141-PF1 (aa pos. 17-126) | SEQ ID NO. 143 | SEQ ID NO. 144 |
| CT643-PF1 (aa pos. 769-841) | SEQ ID NO. 145 | SEQ ID NO. 146 |
| CT681-PF1 (aa pos. 156-391) | SEQ ID NO. 147 | SEQ ID NO. 148 |
| CT681-PF2 (aa pos. 199-329) | SEQ ID NO. 149 | SEQ ID NO. 150 |
| CT681-PF3 (aa pos. 294-349) | SEQ ID NO. 151 | SEQ ID NO. 152 |
| CT414-PF1 (aa pos. 605-722) | SEQ ID NO. 153 | SEQ ID NO. 154 |
| CT414-PF2 (aa pos. 463-530) | SEQ ID NO. 155 | SEQ ID NO. 156 |
| CT456-PF1 (aa pos. 695-840) | SEQ ID NO. 157 | SEQ ID NO. 158 |
| CT456-PF2 (aa pos. 137-229) | SEQ ID NO. 159 | SEQ ID NO. 160 |

TABLE 2-continued

| *Chlamydia* antigenic fragments | | |
|---|---|---|
| Peptide fragment | Amino acid sequence | DNA sequence |
| CT456-PF3 (aa pos. 243-321) | SEQ ID NO. 161 | SEQ ID NO. 162 |
| CT456-PF4 (aa pos. 209-291) | SEQ ID NO. 163 | SEQ ID NO. 164 |
| CT456-PF5 (aa pos. 175-279) | SEQ ID NO. 165 | SEQ ID NO. 166 |
| CT456-PF6 (aa pos. 567-730) | SEQ ID NO. 167 | SEQ ID NO. 168 |
| CT456-PF7 (aa pos. 210-540) | SEQ ID NO. 169 | SEQ ID NO. 170 |
| CT456-PF8 (aa pos. 190-279) | SEQ ID NO. 171 | SEQ ID NO. 172 |
| CT521-PF1 (aa pos. 14-36) | SEQ ID NO. 173 | SEQ ID NO. 174 |
| CT521-PF2 (aa pos. 40-62) | SEQ ID NO. 175 | SEQ ID NO. 176 |
| CT521-PF3 (aa pos. 52-75) | SEQ ID NO. 177 | SEQ ID NO. 178 |
| CT521-PF4 (aa pos. 66-88) | SEQ ID NO. 179 | SEQ ID NO. 180 |
| CT521-PF5 (aa pos. 116-138) | SEQ ID NO. 181 | SEQ ID NO. 182 |
| CT504-PF1 (reverse) | SEQ ID NO. 183 | SEQ ID NO. 184 |

FIGURE LEGENDS

FIG. 1

Cellular reactivity to a *C. trachomatis* serovar D lysate. IFNγ responses of PBMC's isolated from 6 control donors and 15 patients. PBMC's were stimulated with 5 μg/ml of a *C. Trachomatis* lysate and IFNγ release was determined 5 days later in the supernatants.

FIG. 2

Protein fractions of *C. trachomatis* serovar D. A lysate from the bacteria was separated into narrow-molecular fractions by the multielution technique. The fractions were analysed by SDS-PAGE and silver staining. The migration of molecular weight markers is shown at the right (lane 1) in kilodaltons. The lysate is shown in the third and last lanes.

FIG. 3

Human T cell recognition of *C. trachomatis* serovar D protein fractions. PBMC's isolated from 8 *Chlamydia* patients (responding to the whole lysate >1000 pg/ml) and 6 control donors were stimulated with 2 μg/ml of the individual fractions. The release of IFNγ were measured in the supernatants 5 days later. Short line indicates the mean IFNγ release.

FIG. 4

T cell responses to recombinant proteins in 4 patients and 3 controls. PBMC's were stimulated with 5 μg/ml of rCT521, rCT511, rCT616, r CT043 and rCT803. Values shown means of IFNγ for triplicate cultures.

FIG. 5

The recognition of rCT521 in 41 *chlamydia* patients (all responding to a *C. trachomatis* serovar D lysate with more than 1500 pg/ml of IFNγ and 11 control donors responding with less than 1500 pg/ml of IFNγ to the lysate. PBMC's were stimulated with rCT521 (5 μg/ml) and a pool of overlapping CT521 peptides (10 ug/ml each) and the level of INFγ were measured in the supernatants. C: Control wells without antigen. Short Lines indicate the mean INFγ (pg/ml).

FIG. 6

INFγ release stimulated with CT521 peptides (10 ug/ml). Short lines indicate the mean INFγ release for each peptide. Cut off is set to 200 pg/ml INFγ (line).

FIG. 7

INFγ release by PBMC transduced with different recombinant Adenovirus encoding *C. trachomatis* antigens. Patient PBMC were tranduced with indicated Adenovirus at a multiplicity of infection of 1, and INF□ release was determined at day two. AdVaMock indicates activity of a transduced Adenovirus without insert.

FIG. 8

Inclusion Forming Units at PID7 and PID14

FIG. 9

Hydrosalpinx scores at PID49

FIG. 10

T cell responses to *C. Trachomatis* proteins (FIG. 10*a*-10*i*). The proteins were testet in 10 patients (●) and 5 controls (□). C, cell cultures without antigen. Values shown are median and 75 and 25% percentiles.

FIG. 11

T cell responses to *C. Trachomatis* proteins where 5 or more patients responds with a level of IFN-γ above all controls. The proteins were testet in 10 patients (●) and 5 controls (□). C, cell cultures without antigen. Values shown are median and 75 and 25% percentiles.

FIG. 12

Antigen specific responses by blood lymphocytes 1 week after the last immunization. The IFN-γ response were measured in cell cultures pooled from 10 animals. Each bar represents the means of triplicate calues+/−standard deviation.

FIG. 13

Inclusion forming units 7, 14 and 21 days post infection in C3H/HeN mice. The values are shown as log 10 IFU/ml. All values represents the mean of 10 animals+/−Standard error of the mean.

FIG. 14.

Serum reactivity against immunogen measured by ELISA measured as dilution at OD=1.0. Each point represents a mean of 4 animals+/−standard error of the mean.

FIG. 15:

Specific serum reactivity against whole elementary bodies lysates from either *Chlamydia muridarum* (MoPn EB's) or *Chlamydia trachomatis* (Serovar D EB's). Positives are marked by a red dot. Positives are bands with size in agreement with theoretical size.

FIG. 16

Antigen specific responses by splenocytes 3 weeks after the last immunization. The IFN-g response were measured in cell cultures from 4 individual animals. Each bar represents the means of triplicate calues+/−standard deviation.

EXAMPLES

Example 1

Identification of Human T Cell Antigens of *C. trachomatis* Serovar D

Introduction

We have analysed the human T cell responses to *C. trachomatis* proteins using narrow molecular weight fractions derived from complex protein mixtures separated by SDS-PAGE followed by electroelution. This technique enable direct analysis of the immune response and making comparison of stimulatory protein fractions possible. This has led to the identification of a number of stimulatory protein fractions and identification of T cell targets. Further evaluation of these T cell targets have been done using recombinant technologies and overlapping peptides spanning the entire sequence of the protein.

Materials and Methods

Microorganism and cultivation *C. Trachomatis* serovar D (strain UW-3/Cx) was propagated in Hela 229 cells (ATCC, Rockville, Md., USA). The cells were cultivated in passage medium RPMI 1640 (Gibco BRL, Grand Island, N.Y., USA)

containing 5% fetal calf serum (Gibco BRL; heat inactivated), 1% v/v Hepes, 1% v/v L-glutamine, 1% v/v pyrovate and 10 μg/ml gentamycine.

Semiconfluent monolayers of Hela 229 cells in 175 $cm^2$ flasks were pre-treated for 15 minutes at RT with DEAE-dextran (45 μg/ml in HBSS) and infected with one inclusion forming unit per cell of *C. trachomatis* serovar D in 3 ml HBSS. The flasks were incubated on a plate rocker for 2 h at 37° C. After 2 h 50 ml passage medium RPMI 1640 supplemented with 5% glucose and 1 μg/ml cycloheximid were added pr. flask and the cells were further incubated for 72 h in an athmosphere of 5% $CO_2$ in humidified air.

Harvesting of *C. trachomatis*

Chlamydiae were harvested 72 h post infection. The cells were dislodged from the flasks with a cell scraper and centrifuged 30 minutes at 35,000 g and 4° C. The pellets were resuspended in 5 ml HBSS per flask, sonicated on ice and centrifuged at 500 g and 4° C. for 15 minutes. The supernatant was collected and saved on ice and the pellet was resuspended to same volume as before and sonication and centrifugation were repeated. The two supernatants were pooled and centrifuged 30 minutes at 30000 g and 4° C. and the pellet resuspended with a needle and syringe in a SPG buffer (3 ml/T175). After a brief sonication the suspension was gently layered over a 30% Diatrizoate solution (50 g Meglumine diatrizoate, 7.7 g Sodium diatrizoate in 76 ml $H_2O$) and centrifuged at 40,000 g for 30 min. After centrifugation the pellet were resuspended in SPG buffer and stored at −70° C.

Preparation of *C. trachomatis* Lysate for Fractionation

A quantity of 6-8 mg of *C. trachomatis* was centrifuged 30000 g for 30 minutes and the pellet was resuspended 1:1 in WFI and samplebuffer/DTT and boiled for 5 minutes. After 2×12 sec. of sonication the suspension was centrifuged 30000 g for 30 minutes. The supernatant was stored at −70° C. until use.

Fractionation of *C. trachomatis* Lysate

*C. trachomatis* lysate was fractionated as described by Andersen and Heron (1993). Briefly, *C. trachomatis* lysate in a quantity of around 6-8 mg of protein was separated by SDS-page (10 to 20% gel) overnight (11-cm-wide center well, 0.75-mm gel). Gels preequilibrated in elution buffer (ammonia Caps buffer pH 10.2) were transferred to a Multi-Eluter and electroeluted for 20 min. The protein fractions were aspirated and analysed by separation on SDS 10-20% polyacrylamide gels followed by silver staining (Blum and Gross 1987). The protein concentration in the fractions was estimated by the Micro BCA method (Pierce, Oud-beijerland, The Netherlands). 0.5 ml of all fractions were stabilized by 0.5% human AB serum and kept frozen at −70° C. until use. The rest was stored at −70° C. without serum in order to be used for mass spectrometry analysis Mass Spectometry Analysis Samples for peptide mass mapping were cut out of a silver stained SDS-PAGE gel. The band was washed, dried, reduced and alkylated with iodoacetamide before being digested overnight by modified trypsin essentially as described by Shevchenko et al, 1998.

Donors

Patients diagnosed with *Chlamydia* at Bispebjerg hospital, Denmark were asked to participate in the study and to give a blood sample before initiation of antibiotic therapy. Control subjects with no records of *Chlamydia* infections were also asked to participated in the study. Samples from individual patients were annotated with a unique identifiable annotation by assigning a running number, either M or K for male or female, and optionally A, B, C . . . for $1^{st}$, $2^{nd}$, $3^{rd}$, . . . sample collected from the particular patient. In all cases, the A sample were collected before any treatment was initiated. For example, 12 MB denotes the second sample taken from the male patient number 12. Control samples were annotated KK-xx.

Lymphocyte Preparation and Cell Culture

Peripheral blood mononuclear cells (PBMC's) were separated from whole blood by lymphoprep (Nycomed A/S, Oslo, Norway) density gradient centrifugation and frozen in liquid nitrogen until use. PBMC were thrawed and resuspended in RPMI 1640, supplemented with 1% penicillin/streptomycin, 1% nonessential amino acids, 1% glutamine (Gibco), 1% pyrovat, 1% heepes and 10% human AB Serum (local blood bank, Rigshospitalet, Copenhagen). The viability and number of cells were determined by Nigrosin staining. The cells were cultured in triplicates in round-bottom microtiter plates (Nunc, Roskilde, Denmark) at $1.25\times10^5$ cells/well in a total volume of 100 μl. On the basis of initial dose-response studies, antigens were added in the following concentrations: SvD lysate: 2 μg/ml, SvD fractions 2 μg/ml, rCT521 5 μg/ml, CT521 overlapping peptides 10 μg/ml. Phytohemagglutinin (PHA, 2 μg/ml) was used as a positive control an cell cultures without antigen were included as a negative control. After 5 days of incubation at 37° C. in humidified air (5% $CO_2$ and 95% air), the supernatants were harvested.

IFNγ Assay

The amount of IFNγ in the supernatants were determined by ELISA with commercially available antibodies (Endogen) and used according to the manufacturer's instructions. Recombinant IFNγ was used as a standard (Endogen).

Overlapping Peptides 10 synthetic 22-23 mer peptides (9-12 aa overlap) covering the complete primary sequence of CT521 were synthesized by solid phase methods (Schafer-N).

Production of *C. trachomatis* Antigens in *E. coli.*

The CT genes encoding antigens identified by mass-spectrometry were cloned in frame with the $NH_2$-terminal $(His)_6$ sequence of the pDEST17 vector according to the Gateway Cloning Technology Manual (Invitrogen). For production of the recombinant *C. trachomatis* antigens, the plasmid vectors were cloned in the BL21-AI *E. coli* strain (Invitrogen) facilitating high-level recombinant protein production in the presence of arabinose.

Mini-Scale Purification of Recombinant *C. trachomatis* Antigens.

Bacterial cell pellets were suspended in 10 mM Imidazole, 20 mM $NaH_2PO_4$, 500 mM NaCl, 8M Urea, subjected to cell disruption by BeadBeater according to manufacturer's instructions (BioSpec Products, Inc.), following incubation with gentle shaking at room temperature for 1 h. The cleared supernatant was applied on a HisTrap column (Pharmacia Biotech), washed and eluted with 0.5M Imidazol, 20 mM $NaH_2PO_4$, 500 mM NaCl, 8M Urea. The eluted sample was separated by electrophoresis on a preparative SDS-PAGE. The recombinant polypeptide of interest was identified by Coomassie-Blue stain, cut out and electro eluted from the gel piece using the Model 422 Electro-Eluter according to Instruction manual (BioRad). The electro eluted recombinant antigen was precipitated in 80%-95% Acetone (Aldrich HPLC grade), washed in 95% Ethanol, and resuspended in a minimal volumen of 10 mM Imidazole, 20 mM $NaH_2PO_4$, 500 mM NaCl, 8M Urea. The sample was finally dialysed to 50 mM Tris pH 7.5; 150 mM NaCl, 40% glycerol and stored at −20° C.

Results:

T Cell Response to a *Chlamydia* Lysate

*Chlamydia* patients were screened for their T cell recognition of a *C. Trachomatis* serovar D lysate harvested 72 h post infection of Hela cells. The lysate represents a mixture of all the components of the bacteria and cover the whole antigen repertoire of the bacteria. This preparation was used to stimulate PBMCs from 15 *Chlamydia* patients and 6 control donors (FIG. 1). The response to the lysate was associated with a pronounced level of IFNγ (>1000 pg/ml) in 8 out of 15 patients. Only one control donor responded to the lysate with more than 1000 pg/ml of IFNγ.

*Chlamydia* Patients Recognize Multiple Antigens

The specificity of the T cell response was investigated by stimulating PBMCs with protein fractions obtained by the multielution technique. The technique was used on the lysate and resulted in narrow fractions with a minimal overlap between neighbouring fractions (FIG. 2). The numbers of polypeptides in each fraction are estimated to be 10 to 30. Such a panel of fractions was used to screen the antigen recognition patterns of the 8 patients responding to the whole lysate and the 6 control donors (FIG. 3). The cellular response to the fractions showed that the response was directed to multiple antigens. Peak production of IFNγ was however observed in the molecular mass regions 5-12, 16-20, 25-35 and 58-74 KDa.

Recognition of Recombinant Proteins by *Chlamydia* Patients

An SDS page was run with fraction 7 and the neighbouring fractions 6 and 8 covering the molecular mass region 16-20 (FIG. 2), the gel was silverstained and the areas containing the fractions were cut out of the gel, placed in Milli Q water and sent to mass-spectrometry for protein identification. Six hits were identified: CT521, CT043, CT511, CT616, CT315 and CT803. Further more fraction 10, 11, 12, 13, 14 and 15 covering the molecular mass region 25-35 were sent to mass-spectrometry. Ten hits were identified: CT603, CT678, CT561, CT610, CT538, CT582, CT583, CT679, CT067, CT681. Fraction 22 covering the molecular mass region 58-74 was sent to mass-spectrometry. Three hits were identified CT875, CT110, CT112. Finally a fraction 18 was sent to mass spectrometry and 2 hits were identified: CT587 and CT322.

The recombinant proteins, rCT043, rCT511, rCT521, rCT616, rCT803, were purified from *E. coli* and the immunological activities of the 5 *C. trachomatis* proteins were investigated in 4 patients 1KA, 15KA, 7KA and 12KA (FIG. 4). rCT521 was the most promising antigen out of the 4 tested. Three out of 4 patients (1KA, 7KA and 15KA) responded strongly (>1000 pg/m) to rCT521 compared to the control donors. rCT803, rCT511 and rCT616 induced high levels of IFNγ in two (1KA, 7KA) out of four patients whereas rCT043 induced low levels of IFNγ in all patients. The recombinant proteins CT043, CT511, CT603, CT561, CT610, CT583, CT679, CT067, CT681 CT875, CT110, CT112 CT587 and CT322 were produced in E-coli and testet for T cell recognition in 10 patient and 5 controls (Example 8)

CT521 Recognition by *Chlamydia* Patients

Figure 5:
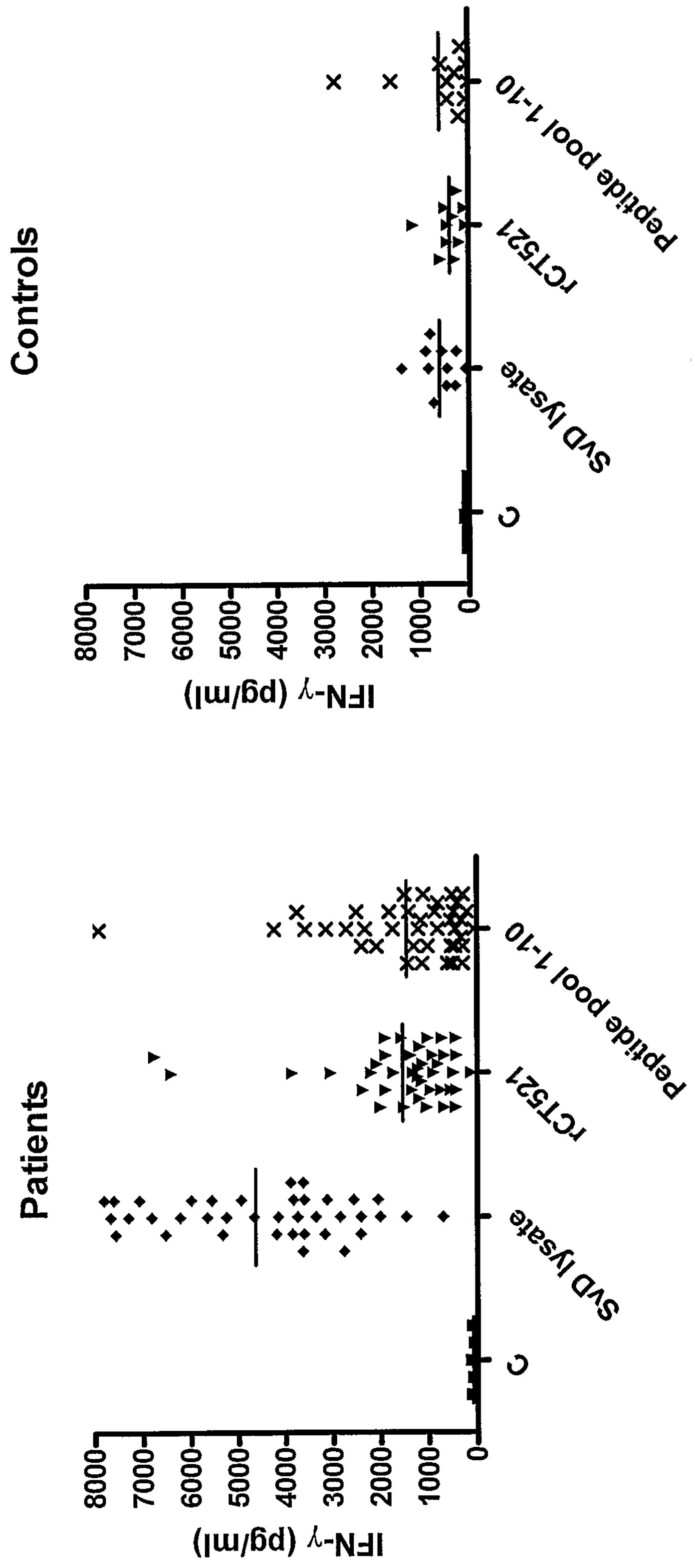

The recognition of CT521 by *Chlamydia* infected patients were tested in a larger panel of donors. A total of 41 *chlamydia* patients all responding to a *Chlamydia* lysate with more than 1500 pg/ml of IFNγ were tested for recognition of CT521. In addition 11 control donors responding with less than 1500 pg/ml of IFNγ to the lysate were included (FIG. 5). Patients could be divided into CT521 positive and CT521 negative on the basis of IFNγ responses exceeding 500 pg/ml. 34 out of the 41 patients were CT521 positive (82.9%) whereas only two out of 11 controls responded to CT521 (18.2%). These results demonstrate that CT521 is frequently recognized by *Chlamydia* patients responding to the whole *Chlamydia* lysate.

Fine Specificity of the T Cell Response to CT521 Mapped by Synthetic Peptides

Figure 6:
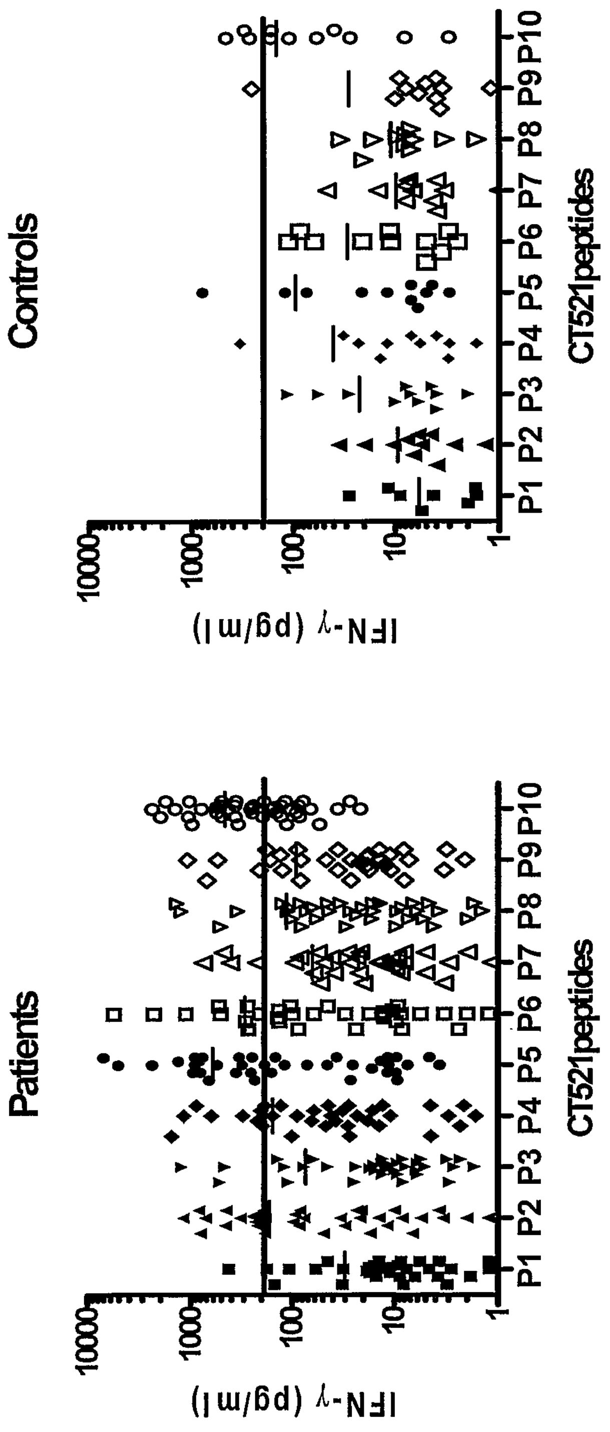

The fine specificity of the T cell responses to CT521 was mapped by screening a panel of overlapping peptides covering the complete CT521 sequence. The peptides were synthetized as 22-23 mers with 9-12 amino acid overlap and were used to stimulate PBMC from 41 *Chlamydia* patients and 11 controls (FIG. 6). Even though the response was highly heterogeneous certain hierarchy existed with certain regions being strong targets for the response. Epitopes present in the N-terminal part of the protein (aa14 to aa36), the central part (aa40 to aa88), and in the C-terminal part (aa116 to aa138) of the protein were more strongly or more frequently recognized than the others.

Example 2

Directed Library Strategy (Screening for Antibody Targets)

Introduction

A High Throughput approach was taken to test for serum reactive antigens in the *C. trachomatis* serovar D genome. A full length library was constructed of the first 200 Open Reading Frames (ORFs). This library was designed to express the antigens recombinantly in *Escherichia coli*. For screening of this library, we used a pool of serum from 5 high responding patients which were selected based on their reactivity towards a whole *C. trachomatis* Elementary Body (EB) extract by Western blot analysis.

Materials and Methods

Construction of Full Length Library

The genome of *C. trachomatis* serovar D is publicly available and the primary annotation was used as defined by Stephens et. al. (Stephens, Kalman et al. 1998). Genes Ct001 to Ct200 was selected for cloning. 5' and 3' primers for amplification of the specific genes was designed by a “in house” software. The full length sequences of the 200 specific *C. trachomatis* genes were cloned into the Entry Vector, pDONR201 (Invitrogen), which enable to clone the genes of interest into different destination vectors of the Gateway cloning system (Invitrogen). The pDEST17 destination vector was used for expression of the recombinant *C. trachomatis* protein in *E. coli* with a 6× Histidine affinity tag. The bacterial host was BL21-AI™ for production of the recombinant *C. trachomatis* proteins by induction with arabinose.

Expression

2*96 Deep Well plates containing 1 ml cultures of were grown over night at 37° C. The culture was diluted to $OD_{600}$=0.1 and incubated at 37° C. with shaking (180 rpm) until $OD_{600}$=0.5 was reached then the culture was induced by adding L-arabinose to a final concentration of 0.2%. After 4 hours of induction the cultures were put on ice and the bacterial pellet was collected by centrifugation (3.000 g/20 min.). Pellets were kept in the fridge until results from the colony blot was obtained.

Patient Serum

Serum from five positive *C. trachomatis* patients, 3KA, 11KA, 12KA, 13KA, and 17KA, was selected for preparing a patient serum pool to be used in the library screening. These patient sera were selected by their specific and high reactivity against *C. trachomatis* serovar D elementary body extract in Western blot analyses using alkaline phosphatase conjugated rabbit anti-human-IgA, -IgG, and -IgM, respectively, as secondary detection marker (DakoCytomation, Denmark).

The patient serum pool (diluted 10 times) was pre-treated with total *E. coli* protein extract at 2 mg/ml for 3 h at room temperature. The working patient pool serum was 1:200 in 10 mM Tris-HCl, pH 8, 150 mM NaCl, 0.05% Tween20 (TBST).

Colony Blot

Screening of the full length *E. coli* expression library was basically performed according to French et al. (1986). Bacterial cultures (1 ml) encoding the Ct001-Ct200 and selected genes throughout the genome were grown over night at 37° C. in two 96 Deep Well plates. Using a (6×8) gripper tool, the bacterial cultures were transferred to Petri dishes containing LB-agar (containing 100 ug/ml ampicillin). The colonies were left over night at 30° C. The colonies were replicated onto a nitrocellulose membrane presoaked in 1% L-arabinose and transferred to new LB-agar plates (with 100 ug/ml ampicillin and 0.2% L-arabinose) with the colony side down. The plates were incubated at 37° C. for 4 hours and finally the membranes were transferred to an empty Petri dish with colony side up for 15 min over a filter paper presoaked in chloroform, thereby exposing the bacteria to chloroform vapor. The membranes were incubated over night in lysis buffer containing lysozyme and DNase. After repeated washing steps the membranes were incubated with primary antibody (working patient pool serum) for 2 hours at room temperature. The membranes were washed repeatedly (4 times with excess 1×TBST) before incubating in secondary antibody for 1 h. The second antibody was either:

A. Rabbit anti human IgG (D0336) DakoCytomation

B. Rabbit anti human IgA (D0338) DakoCytomation

C. Rabbit anti human IgM (D0337) DakoCytomation or

D. A pool of Rabbit anti human IgG (D0336) and Rabbit anti human IgA (D0338)

All conjugated to alkaline phosphatase.

After a second washing in 1×TBST, the membranes were developed by BCIP/NBT substrate (Sigma Fast).

Positive clones were selected in all categories (IgG, IgA and IgM).

Western Blot of Clones Positive in Colony Blot

Bacterial pellets from the 1 ml cultures were resuspended in 200 μl SDS-PAGE sample buffer and heated to 95° C. for 5 min, electrophoresed by SDS-PAGE and transferred to nitrocellulose by standard Western blotting method. The membranes were incubated with the same patient serum pool and a pool of the secondary antibodies (A-C) as described above. As a control for protein induction a replicate membrane was incubated with anti Penta-His antibody and processed according to the manufacturer's instructions (Qiagen). Two colonies that did not react in the colony blot were included as controls.

Results:

The identity of the CT antigens recognized by patient serum in the bacterial colony screening approach is:

| Antigen | IgG | IgA | IgM | Western Blot |
|---|---|---|---|---|
| Ct080 | | + | | ++ |
| Ct084 | | | +++ | + |
| Ct089 | ++ | | | ++ |
| Ct110 | +++ | ++ | | + |
| Ct115 | ++ | ++ | | + |
| Ct118 | ++ | | | + |
| Ct119 | ++ | | | +++ |
| Ct125 | | + | ++ | ++ |
| Ct147 | | + | | ++ |
| Ct155 | +++ | +++ | | − |
| Ct168 | | + | | + |
| Ct174 | | ++ | | ++ |
| Ct184 | | + | | ++ |
| Ct228 | | + | | ++ |
| Ct232 | + | | | + |
| Ct614 | | + | | + |
| Ct795 | +++ | +++ | | +++ |

-continued where +, ++, +++, and −, indicate relative "visual intensity of reactivity" when analysed on colony blot or by Western blot.

Example 3

Random Library Strategy

Introduction

In order to screen for serum reactive antigen in the *C. trachomatis* serovar D genome, a random expression library was constructed in the expression vector λgt11. This library was designed to express randomly *C. trachomatis* peptide fragments of 100-400 amino acid residues fused in frame with the β-galactosidase. The library was screened with serum from patients which were selected based on their reactivity towards a whole *C. trachomatis* Elementary Body (EB) extract by Western blot analysis.

Materials and Methods

Isolation of High Molecular Weight *C. trachomatis* Serovar D Genomic DNA.

A crude *C. trachomatis* serovar D elementary body preparation containing ~$8.6\times10^9$ IFU (infectious units) was further purified by 44-54% Diatrizoate solution step density gradient ultracentrifugation at 40.000×g for 60 min. The elementary bodies banded at the 54% interface were collected, diluted in 10 volumes SPG buffer (250 mM Sucrose; 10 mM $Na_2HPO_4$; 5 mM L-Glutamic acid), and precipitated by centrifugation at 30.000×g for 30 min. The elementary body pellet was resuspended in 5 ml TENS buffer (50 mM Tris pH 9; 100 mM EDTA; 200 mM NaCl; 1% SDS) and incubated with 100 ug/ml Proteinase K at 37° C. for 60 min. The sample was diluted once in TENS buffer and the nucleic acids were purified by phenol/chloroform extraction and ethanol precipitation (Maniatis et al., 1987). RNA was removed by treatment with 25 U/ml RNaseT1 and RNaseA cocktail (Stratagene) at 37° C. for 60 min followed by another phenol/chloroform extraction and ethanol precipitation. The *C. trachomatis* serovar D genomic DNA preparation was resuspended in TE at 0.4 ug/ul and an aliquot was tested by agarose gel electrophoresis and shown to contain high molecular weight DNA>>50 kb.

Construction of Whole-*C. trachomatis-Genome* Random Expression Library.

The generation of random *C. trachomatis* genomic DNA fragments by sonication was performed by placing a microcentrifuge tube containing 50 ug of DNA in 175 ul TM buffer (10 mM Tris pH8; 10 mM $MgCl_2$) into an ice-water bath placed in Soniprep150 sonicator (MSE). The microtip (⅛" Ø) was placed ~2 mm below the sample surface and sonication was performed continue sly for 80 min at 15 microns amplitude. Under these conditions the genomic DNA was randomly fractionated to fragment size ranges of 0.05 to 1 kb when analysed by agarose gel electrophoresis. During the subsequent preparation of the sonicated CT genomic DNA phenol/chloroform extraction and ethanol precipitation steps are included when appropriate. End-repair and phosphorylation of ~10 ug sonicated DNA fragments were performed in a combined incubation with T4 DNA polymerase, Klenow DNA polymerase and T4 polynucleotid kinase. Furthermore, the random fragmented CT genome DNA was subjected to EcoRI Methylase treatment prior to linker ligation with 50-fold molar excess phosphorylated EcoRI linker (12-mer, BioLabs). The DNA was treated with EcoRI and the final DNA preparation was size fractionated on a 6% acrylamide gel and fragments of 0.2-0.8 kb in size were eluted from the gel piece by incubation in 500 ul GES buffer (0.5M $NH_4$Acetate; 10 mM MgAcetate; 0.1 mM EDTA; 0.1% SDS) at 42° C. over night. The cleared supernatant was ethanol precipitated twice, and the final pellet was resuspended in 10 ul TE. The DNA was ligated to EcoRI digested and dephosphorylated λgt11 phage vector arms (Stratagene). The ligation mix was packaged in vitro with Gigapack III Gold extracts according to the manufacturer's instructions (Stratagene). Recombinant phages were plated on *E. coli* Y1090r– and a total of ~340.000 primary lambda phages were generated of which ~60% were true recombinant phages as jugded by the blue/white color selection assay upon plating phages in the presence of IPTG and X-gal. The primary phage expression library was amplified at densities of approximately $3\times10^4$ PFU/135 mm Ø plate, collected and stored in aliquots in 7% v/v DMSO at –80° C. The titer of the amplified whole-*C. trachomatis*-genome random expression library was $6.7\times10^9$ PFU/ml.

Patient Serum

The patient pool serum used in the screening of the random expression library was identical to the previously described in Example 2.

Screening the Whole-*C. trachomatis-Genome* Random Expression Library

The amplified λgt11 expression library was absorbed to *E. coli* Y1090r– cells and plated at $5\times10^4$-$1\times10^5$ PFU per 135 mm agar plate and incubated at 42° C. for 3½ h. Plates are overlayed with dried nitrocellulose membrane filters (BioTrace NT, Pall Corporation) pre-saturated with 10 mM IPTG in $H_2O$ and further incubated at 37° C. for additional 3½ h. The filters were transferred to TBST containing 1.5% BSA and incubated at RT for 30 min, following incubation with 1:200 diluted patient pool serum at RT for 30 min. Excess patient serum is removed by 3 washings in TBST for 10 min each, following incubation with either alkaline phosohatase conjugated rabbit anti-human-IgA, -IgG, or -IgM at RT for 30 min. After final 3 washings in TBST for 10 min each, the filters were developed by BCIP/NBT substrate (Sigma Fast).

Positive immunoreactive plaque areas are collected in pools of 10 areas, titered, and rescreened at plating densities of $2.5$–$5\times10^3$ PFU per 135 mm agar plate for identification of individual positive plaques.

DNA Sequencing and Sequence Analysis.

The individual positive selected phage plaques were picked by pouncing the plaque area, suspended in 20 ul $H_2O$, vortexed for 10 sec and incubated at 37° C. for 15 min. The suspension was centrifuged in microfuge at maximum speed for 30 sec, and 4.5 ul of the cleared supernatant was used for PCR amplification using 2.5 pmol each of Forward primer, 5'-ccagccatcgccatctgctgcacg-3', and λgt11 EcoRI Reverse Primer (BioLabs) and one volume of Hot StarTaq Master Mix (Qiagen). The remaining phage suspension was diluted in 100 ul SM buffer and stored as phage stock at 4° C. with 25 ul $CHCl_3$.

The PCR amplification was performed in a Gene Amp PCR System 9700 thermocycler (Applied Biosystem) at 95° C. for 15 min, and then 30 cycles at 95° C. for 1 min, 60° C. for 1 min, and 72° C. for 1 min. Four ul were tested by agarose gel electrophoresis. For sequencing the amplified DNA, the remaining 6 ul of PCR reaction is diluted five-fold and purified by Micro Spin S-300 HR columns according to the manufacturer's instructions (Amersham Biosciences). The sequencing was performed by the dideoxy chain termination method (contracted by MWG-BIOTECH, Germany) using either the sequencing primer, 5'-CACCAGACCAACTGG-TAATG-3', priming 28 bases downstream the EcoRI cloning site in the LacZ gene, or the 5'-GCCATCGCCATCTGCTG-CACG-3', priming 85 bases upstream the EcoRI cloning site in the LacZ gene. Sequences were analysed with Vector NTI Suite software package (InforMax).

Results:

Identification of *C. trachomatis* Sero-Reactive Antigens by Expression Library Screening.

The first screening of the *C. trachomatis* λgt11 expression library using the pooled patient serum as primary antibody identified several immunoreactive plaques areas when using either anti-human IgA, -IgG, or IgM as secondary detection antibodies, respectively. In summary, 88 positive plaques areas were picked and pooled:

No. of Plaque Areas Picked for Rescreening:

| Seroreactive Class | # plaque hits | # pools for screeening |
|---|---|---|
| IgA | 24 | 2 pools á 12 plaque areas |
| IgG | 50 | 5 pools á 10 plaque areas |
| IgM | 14 | 1 pool á 14 plaque areas |
| Total | 88 | 8 pools |

The generated phage pools were rescreened using the same screening conditions as at the initial screening except that the plating density was much lower in order to enable identification of individual positive phage plaques. In summary, a total of 129 individual positive plaques were picked, annotated and used for direct sequence analyses and generation of phage stocks, respectively:

No. of Individual Picked Positive Plaques:

| Sero reactive Class | # Individual plaques |
|---|---|
| IgA | 41 |
| IgG | 79 |
| IgM | 9 |
| Total | 129 |

The identity of the insert expressed as β-galactosidase fusion in the individual isolated positive phages was identified by sequencing and Blast analysis (EMBL-EBI).

The identity of CT antigens were identified by screening the random expression library.

The sequences of a total of 103 individual plaques were determined and grouped in 22 unique sequence identities (PF=peptide fragment):

CT541-PF1 (aa pos. 111-243)
CT443-PF1 (aa pos. 214-291)
CT795-PF1 (aa pos. 1-163)
CT396-PF1 (aa pos. 170-318)
CT842-PF1 (aa pos. 433-515)
CT283-PF1 (aa pos. 477-577)
CT874-PF1 (aa pos. 330-426)
CT051-PF1 (aa pos. 38-177)
CT141-PF1 (aa pos. 17-126)
CT643-PF1 (aa pos. 769-841)
CT681-PF1 (aa pos. 156-391)
CT681-PF2 (aa pos. 199-329)
CT681-PF3 (aa pos. 294-349)
CT414-PF1 (aa pos. 605-722)
CT414-PF2 (aa pos. 463-530)

CT456-PF1 (aa pos. 695-840)
CT456-PF2 (aa pos. 137-229)
CT456-PF3 (aa pos. 243-321)
CT456-PF4 (aa pos. 209-291)
CT456-PF5 (aa pos. 175-279)
CT456-PF6 (aa pos. 567-730)
CT456-PF7 (aa pos. 71-180)
CT456-PF8 (aa pos. 190-279)
CT504-PF1

Example 5

Generation of Recombinant Adenovirus Encoding *C. trachomatis* Antigens

Introduction

In order to explore an alternative delivery route of *C. trachomatis* antigens to target cells for screening for T-cell reactivity, we constructed and tested recombinant Adenovirus encoding the antigens by direct transduction of patient PBMC.

Materials and Methods.

Construction of Recombinant Adenovirus Stocks.

Recombinant adenovirus encoding selected *C. trachomatis* antigens were generated essential by using the ViraPower Adenoviral Gateway Expression System (Invitrogen) introducing the CT genes in frame with an ATG initiation codon in the context of the Kozak sequence, ACCATGG, into the pAd/CMV/V5-DEST vector (Invitrogen). Stop codons were introduced just ownstream the CT gene ORF's. Viable recombinant adenovirus are produced in transfected 293A cells according to the manufacturer's instructions (Invitrogen). Primary recombinant adenoviral stocks are prepared by the freeze-thaw method and stored in aliquots at −80° C. The titers measured as $TCID_{50}$ in 293A cells of the recombinant adenovirus stocks were determined by the Endpoint Method.

Results:

Preparation of Adenovirus Stocks

Full length *C. trachomatis* antigens were cloned in Adenovirus for direct transduction and expression of the CT antigens in the PBMC target cell assays.

The following CT antigens available as Adenovirus stocks: CT460, CT529, CT579, CT587, CT681, CT509, CT713, CT043, CT511, CT521, CT616.

T Cell Response to Adenoviral Transduced *C. trachomatis* Antigens.

Figure 7:
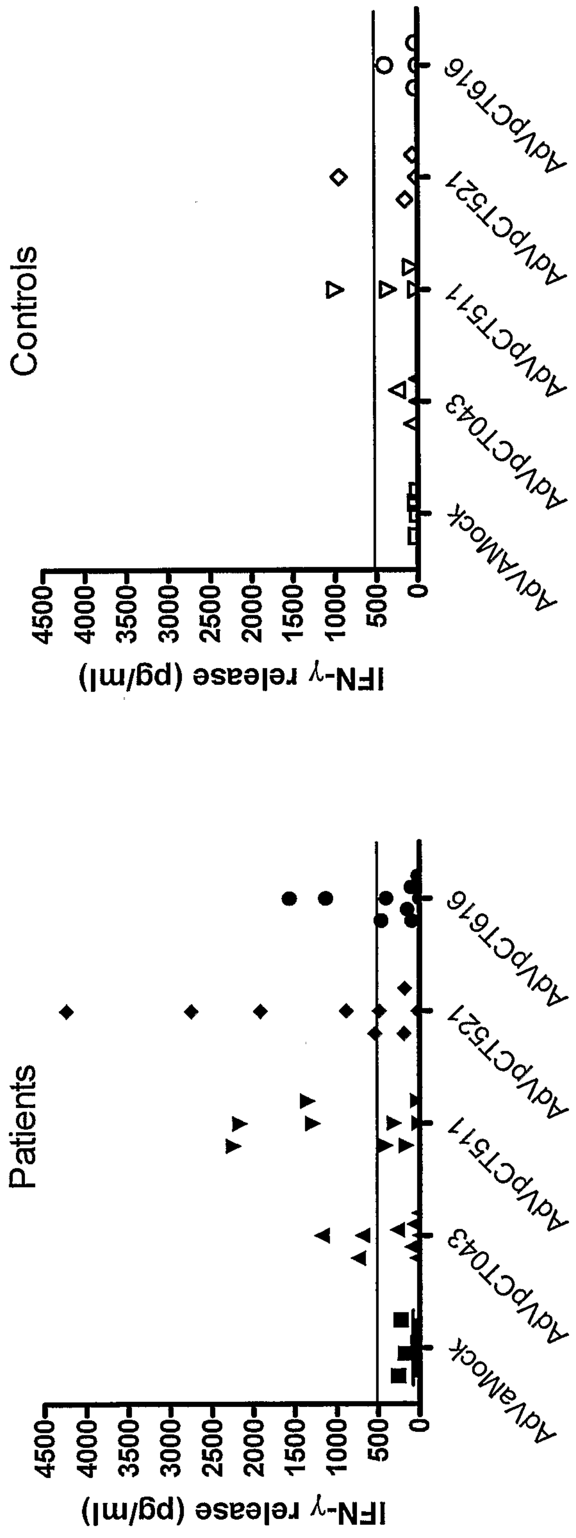

The immunological activities of four Adenovirus constructs (AdVpCT043, AdVpCT511, AdVpCT521 and AdVpCT616) were investigated in 9 patients and 4 controls (FIG. 7). AdVpCT521 induced a strong IFN□ response (>500 pg/ml) in 6 out of 9 patients. AdVpCT511 were recognized with levels of IFN-γ exceeding 500 pg/ml in 4 out of 9 patients whereas AdVpCT616 and AdVpCT043 only stimulated a response in 2 and 3 patients respectively. In the control group one donor responded to AdVpCT511 and AdVpCT521.

Example 6

Rodent Protection Strategy

Introduction

The rodent protection strategy is used to evaluate the efficacy of *Chlamydia* antigens. Briefly, animals immunized with antigens will be infected with a vaginal challenge of *C. muridarum*. The protective capability of the immunizing antigen will be evaluated by quantitation of vaginal Chlamydial load and by scoring the chronic pathological changes. The pre-challenge immuneresponse to the vaccine antigen will be accessed by quantitation of INFg after restimulation of spleen cells. and by assessing the serum antibody reactivity against a *C. trachomatis* EB lysate and the ELISA-reactivity against the immunogen. The antigens checked in this model are: Ct015, Ct025, Ct026, Ct030, Ct048, Ct063, Ct078, Ct080, Ct184, Ct521, Ct051, Ct089, Ct175, Ct443, Ct456, Ct511, Ct541, Ct583 & Ct603

Materials and Methods.

Animals

Female C57BL/6J, mice, 8-12 weeks of age, were obtained from Harlan Laboratories. Animals were housed under standard environmental conditions and provided standard food and water ad libitum The use of mice is guided by the regulations set forward by the Danish ministry of justice (Lov om dyreforsøg, jvf lovbekendelser nr. 726 of 9. September 1993), and Animal protection committees. A detailed description of the proposed experiments has been submitted to and approved by the regional ethical review board (2003/561-786) held by the applicant.

*Chlamydia muridarum*

*C. muridarum* was propagated in HeLa 229 cells (ATCC, Rockville, Md., USA). The HeLa cells were grown in complete media (RPMI-1640 (Gibco BRL); 5% heat inactivated Fetal Bovine Serum (Cambrex bioscience); 1% v/v Hepes, 1% v/v L-glutamine, 1% v/v pyrovate and 10 μg/ml gentamycine. Subconfluent monolayers of HeLa 229 cells plated in 175 $cm^2$ flasks were pre-treated for 15 minutes at RT with 45 μg/ml DEAE-dextran in Hanks buffered salt solution (HBSS) and infected at an 1 MOI (i.e. one inclusion forming unit (IFU) of *C. muridarum* per HeLa cell) in 3 ml HBSS. After 2 h of incubation at 37° C., 50 ml complete media supplemented with 5% glucose and 1 μg/ml cycloheximid were added and the infected cells were further incubated for 42-44 hours in a humidified incubator containing 5% $CO_2$. After microscopically confirming the presence of inclusions within a proper amount of target cells the monolayer were dislodged from the flasks with a cell scraper and centrifuged 30 min at 35.000 g and 4° C. The pellets were resuspended in 5 ml HBSS per flask, sonicated on ice at 2×1000 joule and centrifuged at 500 g for 15 min 4° C. The supernatants were collected and stored on ice. The pellets were resuspended in 5 ml HBSS and sonicated and centrifuged as in the last step. The supernatants were pooled and centrifuged for 30 min at 30.000 g, 4° C. and the pellets resuspended SPG buffer (250 mM Sucrose; 10 mM $Na_2HPO_4$; 5 mM L-Glutamic acid). After a brief sonication the suspension was gently layered over a 30% Diatrizoate solution and centrifuged at 40,000 g for 30 min. After centrifugation the pellet were resuspended in SPG buffer and stored at −70° C.

Infectivity of the *C. muridarum* preparation was quantitated by titration on McCoy cells followed by enumeration of inclusions in immunofluorescence assay. Briefly, 90-95% subconfluent HeLa 229 monolayers were centrifuged for 1 hour at 750 g at RT with titrated inoculum followed by incubation at for 2 h at 35° C. The inoculum was replaced by complete medium supplemented with 5% glucose and 1 μg/ml cycloheximide and further incubated for 42-44 h at 37° C. For staining the cells were fixed in 99% icecold ethanol for 15 min. The fixed cells were incubatied with a rabbit polyclonal anti-Chlamydia MOMP antibody for 1 h followed by secondary staining with a FITC labelled swine-anti rabbit Ig antibody. The cells were counterstained with Propidium iodine. The inclusion positive cells in 20 high-power (40×)

fields were enumerated with a fluorescence microscope to quantitate the infectivity of the *C. muridarum* stock (expressed in IFU/ul).

Infection of Mice

Mice were infected by the intra vaginal route by $10^5$ to $10^7$ IFU's (100-10.000 $ID_{50}$). The infection was monitored at day 7 and day 14 after inoculation by obtaining cervicovaginal swabs followed by fluorescent staining and enumeration of infectious units in the specimen.

Immunization

Mice were immunized subcutaneously (sc) three times with 2 weeks interval at the base of the tail. The vaccines consisted of 1-5 ug of peptide (see above) emulsified in 250 ug DDA and 100 ug TDB. As a negative control, DDA/TDB alone, without peptide were injected. As a positive control, mice were infected intra nasally for 55-75 days with $10^5$ IFU *C. muridarum*. The nasal infection leaves the animals almost completely protected, comparable to the protection induced by the vaginal infection.

Lymphocyte Cultures, Serum Antibodies and Evaluation of Immuneinducing Potential For evaluation of ability to induce a strong immuneresponse, spleens were taken at 21 days after last immunization and spleen lymphocytes were obtained by rubbing the tissue through a metal mesh to a single cell suspension, washed once in RPMI-1640 at 800 g at RT and resuspended in re-stimulation media. (RPMI-1640, Gibo, 10% heat-inactivated Fetal Bovine Serum, Biochrom AG, Berlin, Penicillin G 100 U/ml, streptomycin 100 ug/ml, 10 mM Hepes, 2 mM L-glutamine, 1 mM pyrovate).

Figure 16:
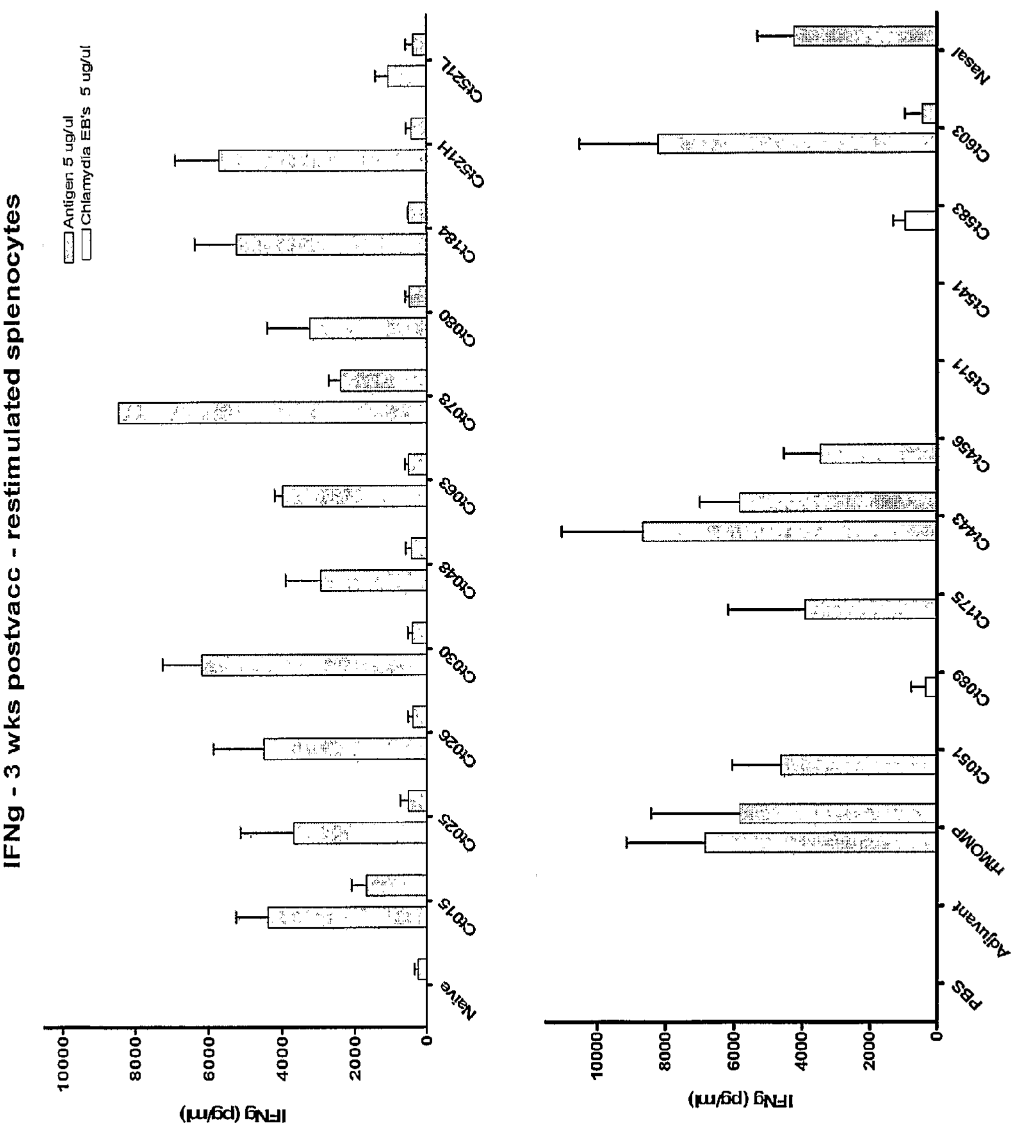

The isolated cells were cultured in triplicates in round-bottom 96-well plates at $2\times10^5$ cells per well in 200 ul re-stimulation media. Peptides were added in concentrations ranging from 0.08 to 5 ug/ml. and incubated for 72 h. Negative and positive controls (either media or 5 ug/ml ConA) were included in all experiments as necessary. After restimulation the supernatants were harvested and IFN-γ quantitated by enzyme-linked immunosorbent assay (Brandt, Elhay et al. 2000). Vaccine candidates giving high levels of critical IFNg above 2000 pg/ul was: Ct015, Ct025, Ct026, Ct030, Ct048, Ct063, Ct078, Ct080, Ct184, Ct521, native *C. Muridarum* MOMP, Ct051, Ct175, Cy443, Ct456 & Ct603, (FIG. 16).

Figure 15:
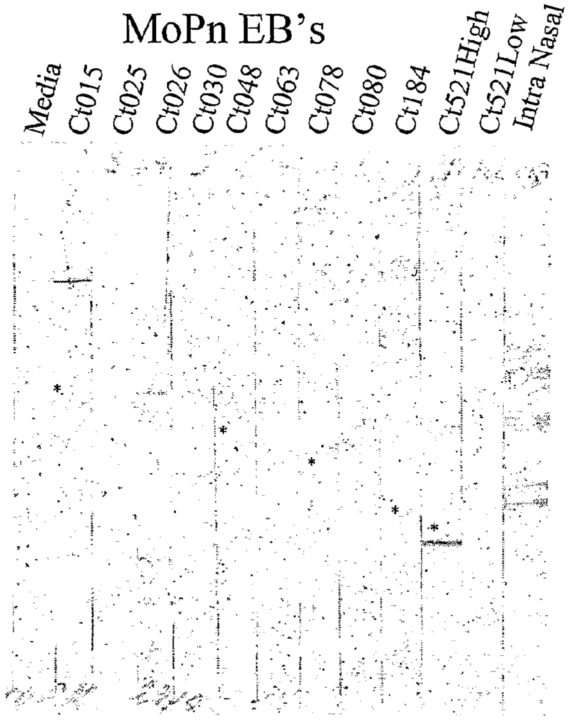
Figure 15:
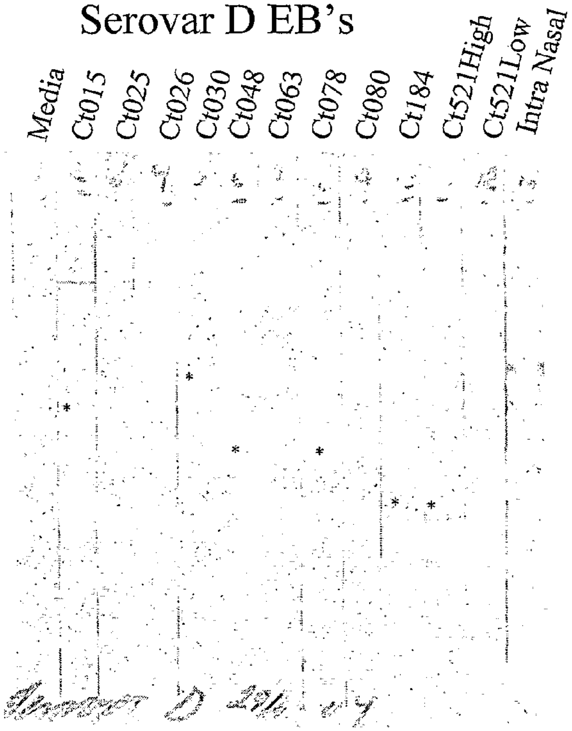

At the same timepoint, blood samples were drawn from the eye sinus and serum prepared. Serum was tested for reactivity against *Chlamydia trachomatis* SvD and *Chlamydia muridarum* elementary bodies by western blot analysis (Theisen, Soe et al. 2004). Briefly, density gradient purified elementarybodies were electrophorezed on a 4-12% polyacrylamid gel, electro blotted onto nitrocellulose and blocked in skimmed milk in a Mesh buffer. Pools of sera (4 animals from each vaccine group) were diluted 1:100 and incubated with the blot for 1 hr, washed and further incubated with a secondary alkaline phosphatase coupled antibody for 1 hr. Reactions were visualized by incubation with BCIP/NBT (Sigma) substrate. Bands were evaluated as positives when obsevered size were in agreement with theoretical size. Positives were: Ct015, Ct030, Ct048, Ct078, Ct184 & Ct521 (FIG. 15)

Figure 14:
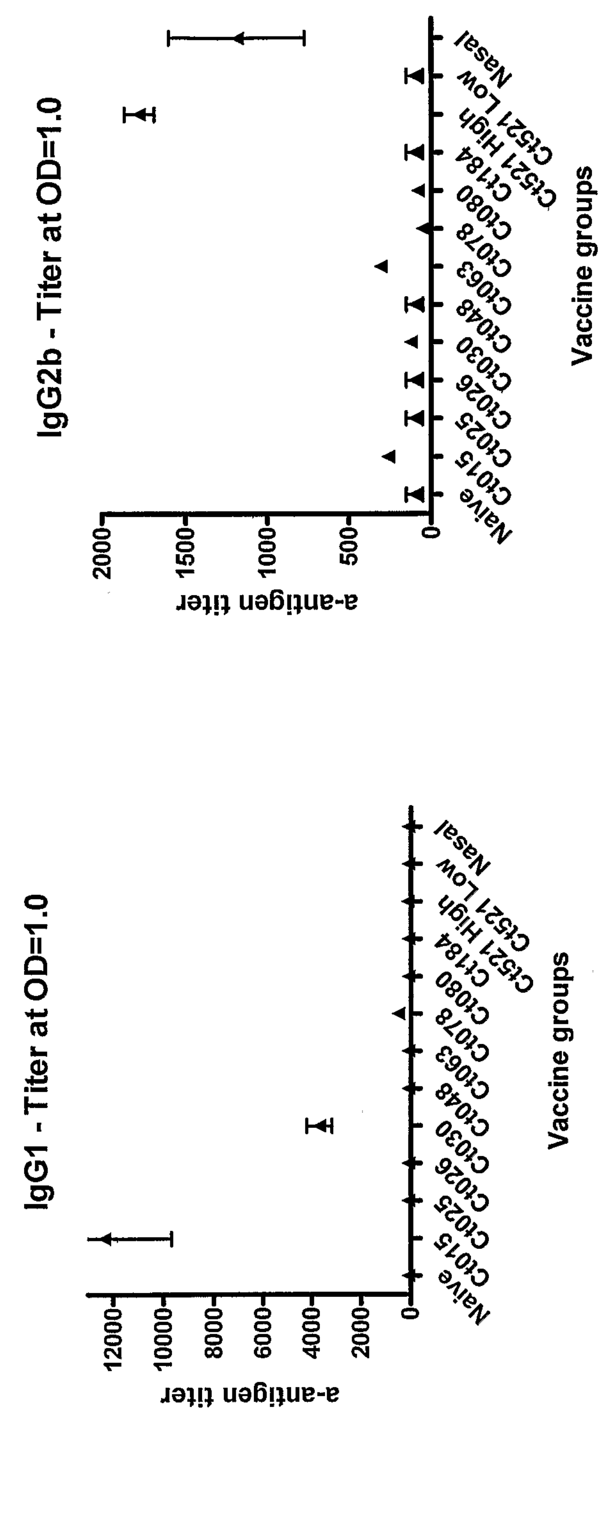

Serum was tested by ELISA (Rosenkrands, Agger et al. 2005) for reactivity against the recombinant protein used for immunization and against heat-inactivated *Chlamydia muridarum* elementary bodies, Briefly, plates were coated with antigen (0.5 ug/ml) in carbonate buffer o/n, blocked with BSA and washed. The plates were incubated with pre-diluted samples for 2 hrs at room temperature, washed and incubated with a peroxidase conjugated secondary antibody for 1 hr. Reactions were visualized by incubation with TMB substrate and the reaction stopped with sulphuric acid and read at 450 nm. Titers at OD=1.0 were calculated after applying four-parameter fit.on the data (FIG. 14). Antigen high in IgG1 were: Ct015 &Ct030. Antigens high in IgG2b were: Ct063, Ct521High.

Evaluation of the Protective Efficacy

For evaluation of vaccine efficacy, mice were challenged 8-12 weeks after the first immunization by intra vaginal infection by $10^5$ to $10^7$ IFU's (100-10.000 $ID_{50}$). The protective efficacy of the vaccine candidates was monitored by pathological evaluation and by enumeration of infectious units obtained by cervicovaginal swabs.

Figure 8A:
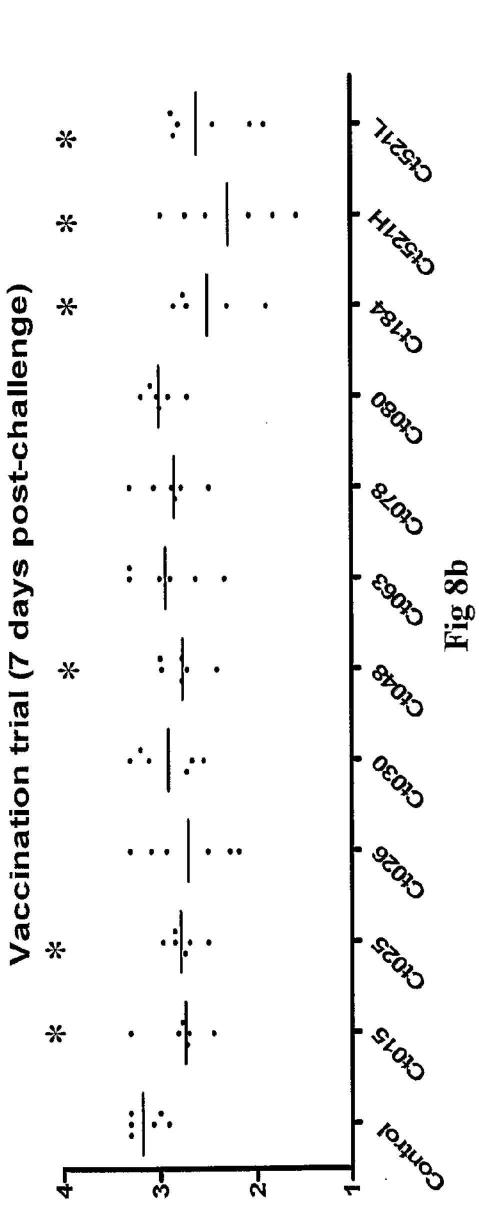
Figure 8B:
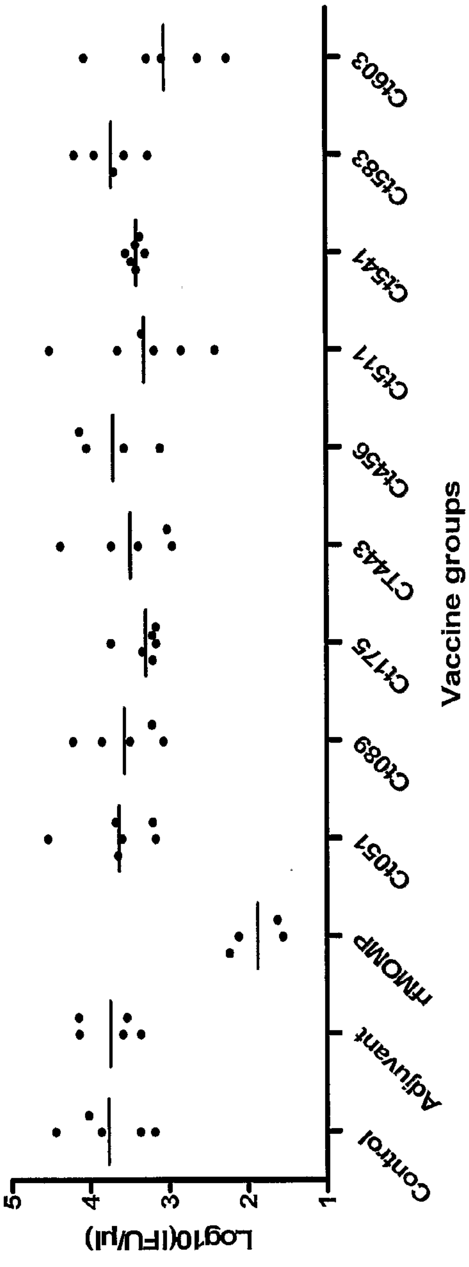
Figure 8C:
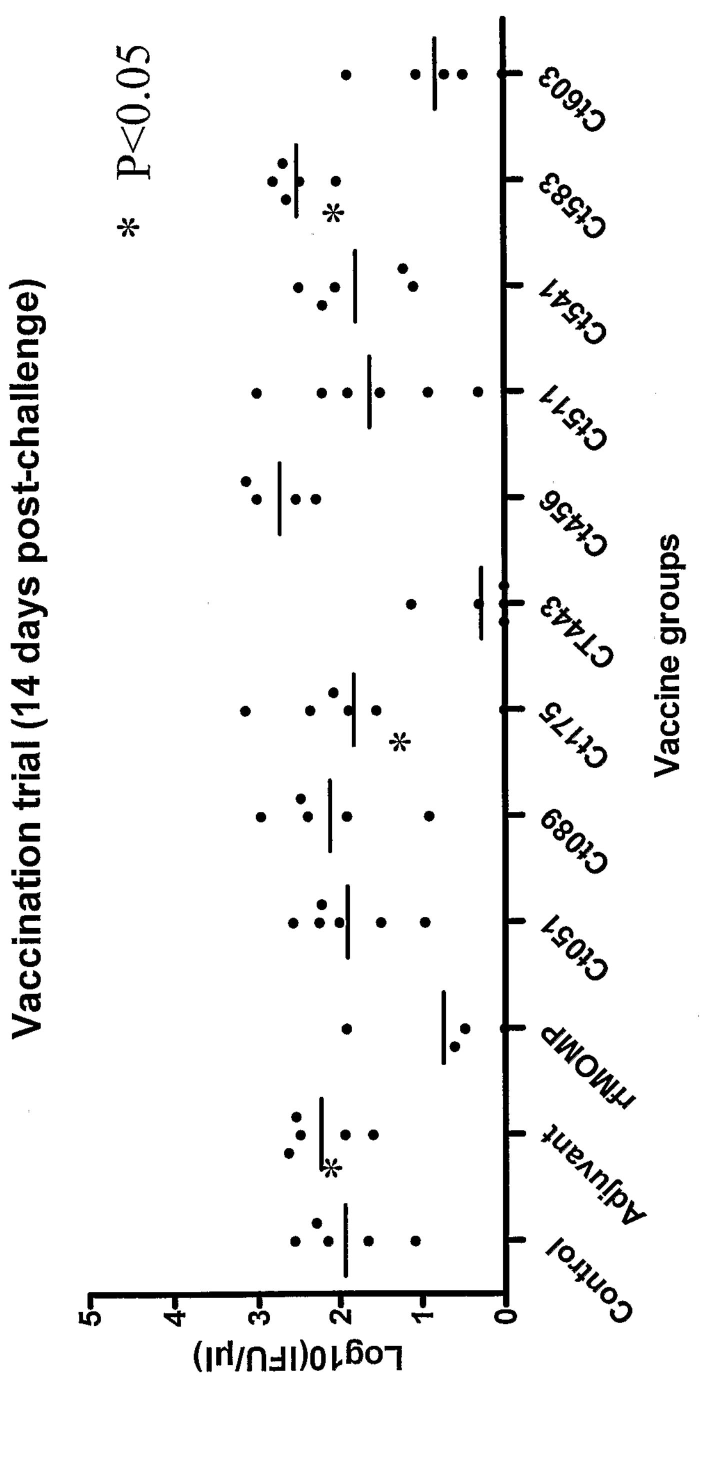

The bacterial load was determined by cervicocvaginal swabs obtained at 7, 14 and/or 21 days after challenge. The swabs were submerged in 1 ml SPG buffer at 4° C. until prepared. At the same day, *C. muridarum* EB's were mechanically shaken off of the swab by vortexing the specimen for 30 s at full speed in the presence of mm glass beads. The buffer was transferred to eppendorf tubes and stored at −80° C. until analyzed. Infectious EB's were quantitated by enumeration of inclusions in subconfluent McCoy cells in immunofluorescence assay as described above. (FIG. 8) Antigens inducing protection after enumeration of swap-IFU's at PID7 are: Ct015, Ct025, Ct048, Ct184, Ct521, Ct443, Ct603 and native *C. muridarum* MOMP.

Figure 9:
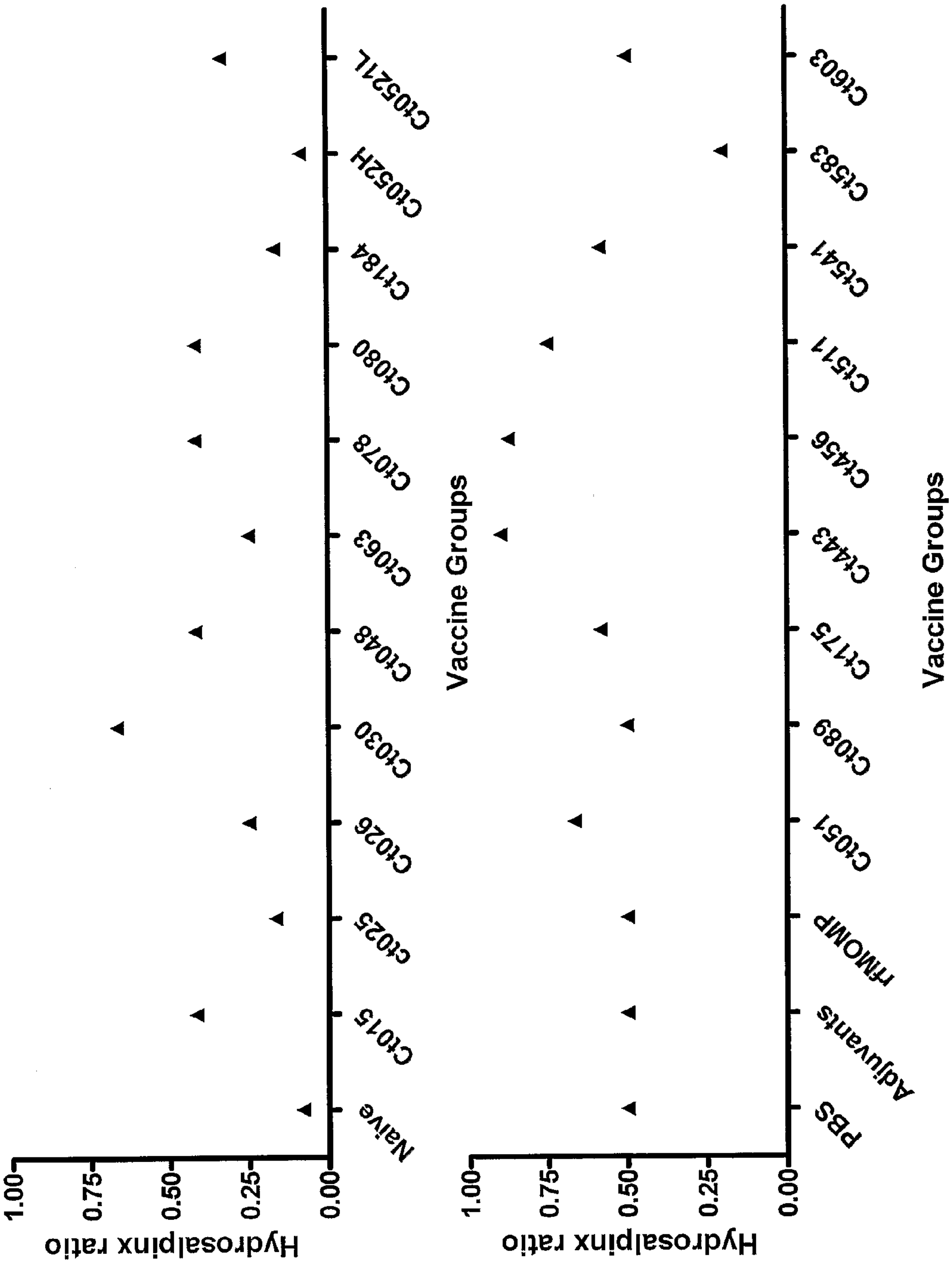
Figure 10A:
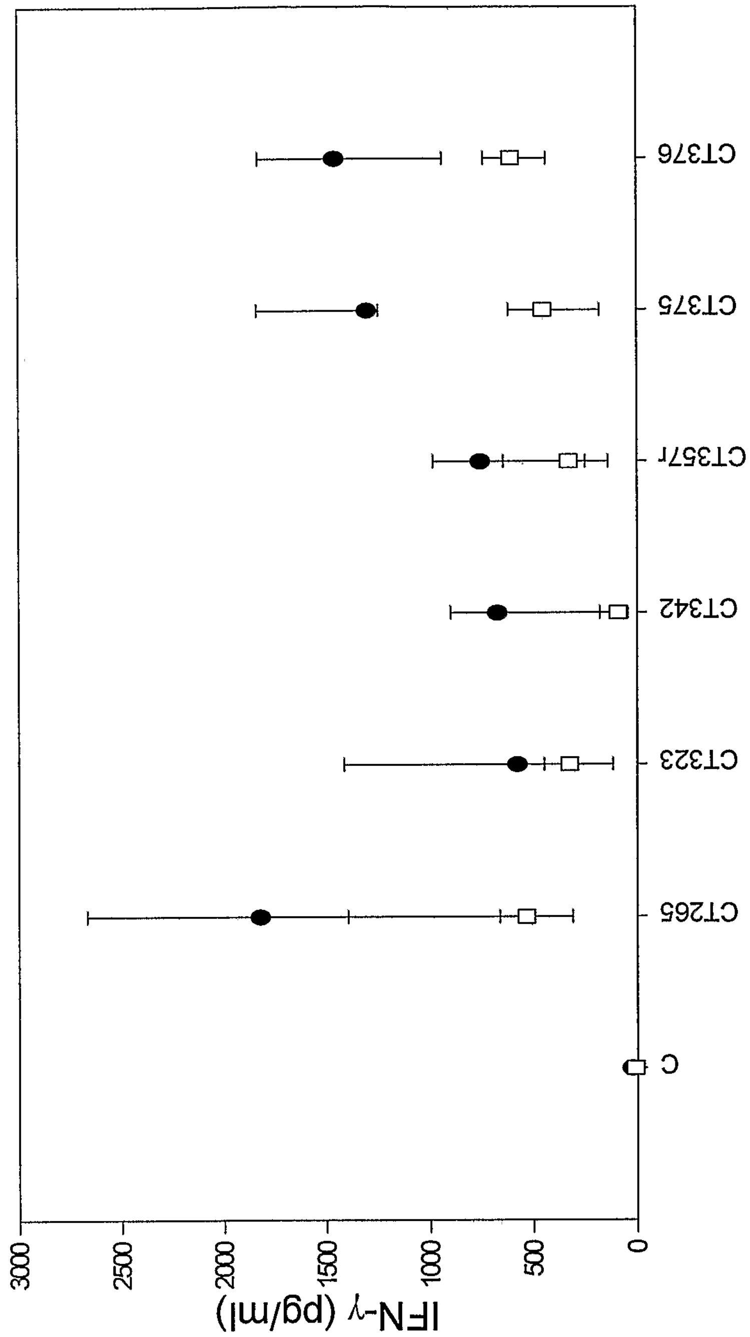
Figure 10B:
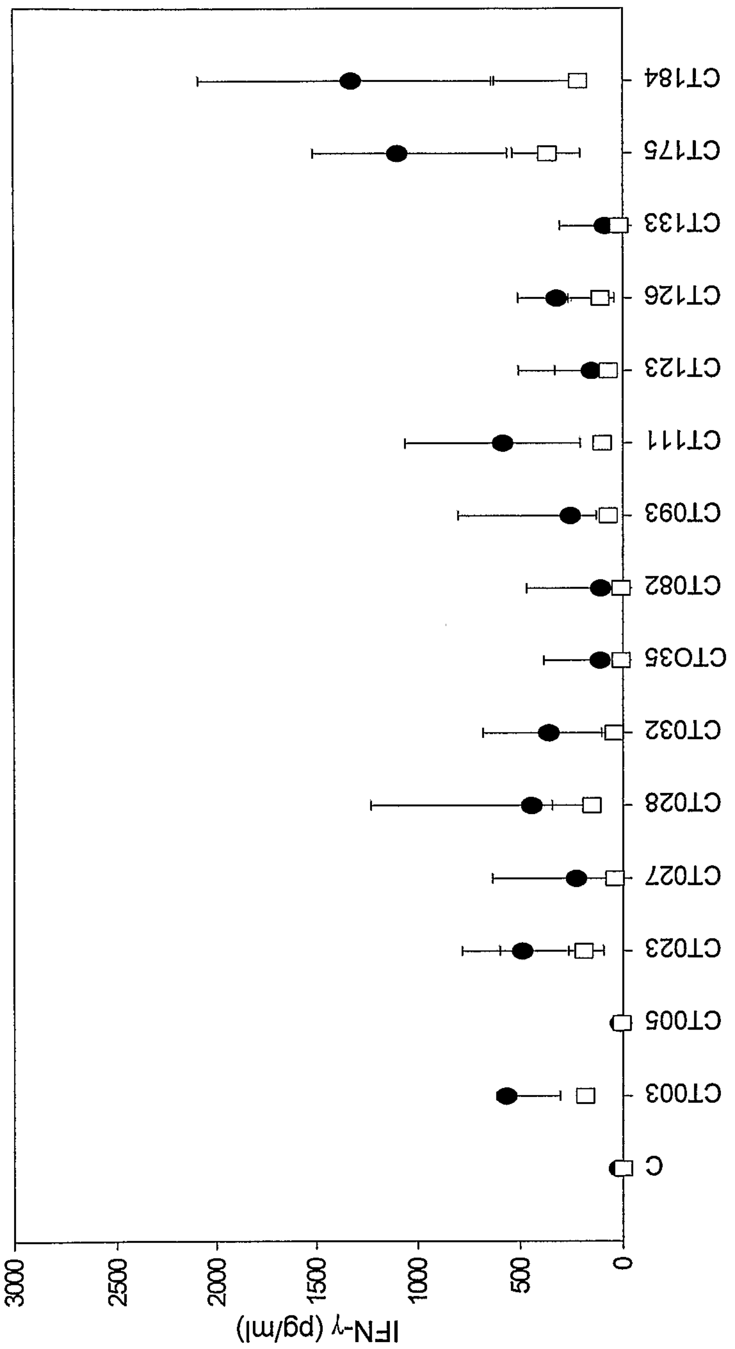
Figure 10C:
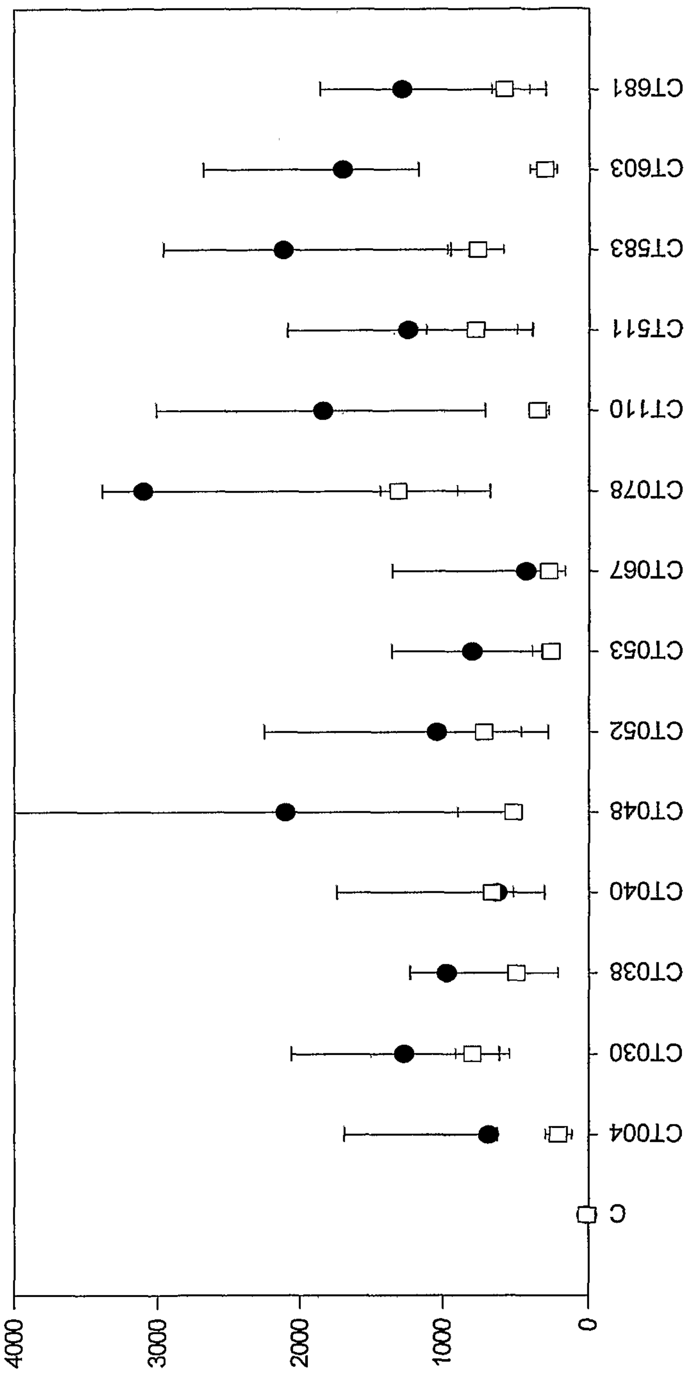
Figure 10D:
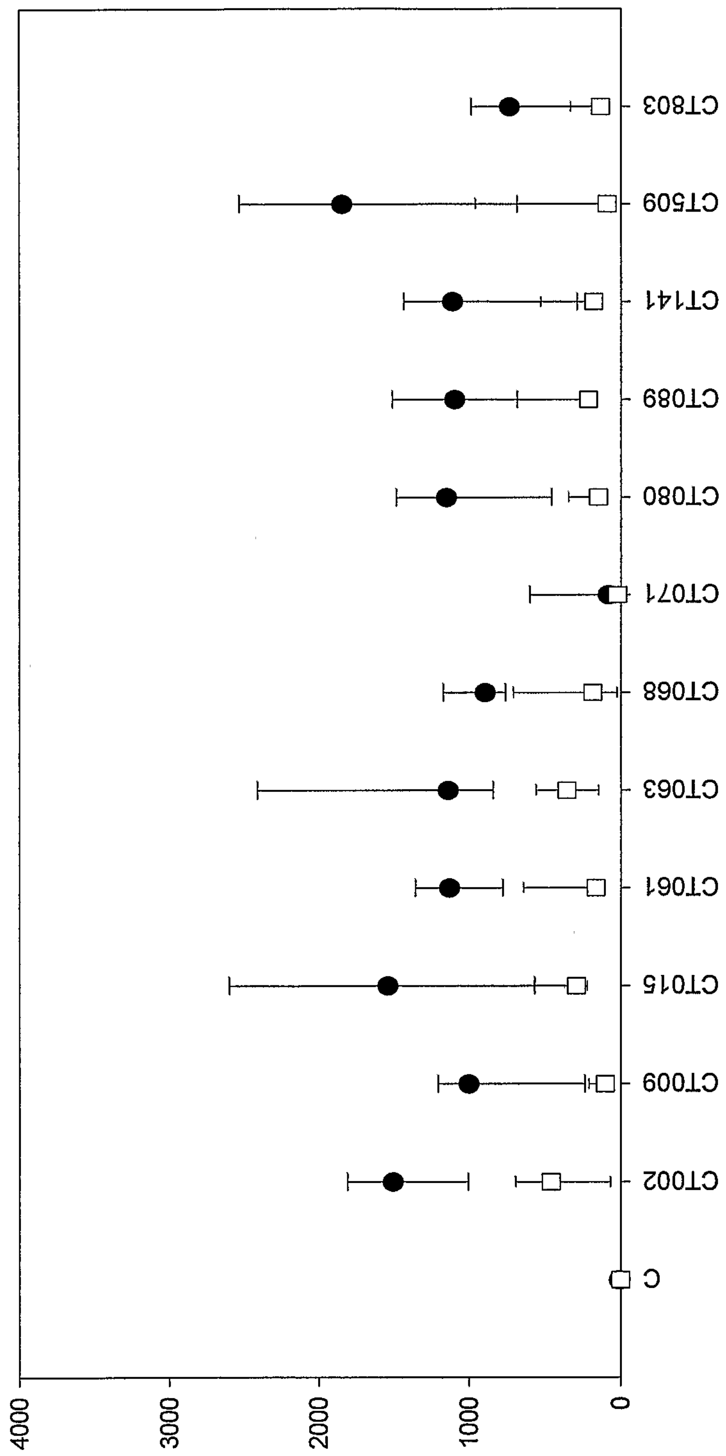
Figure 10E:
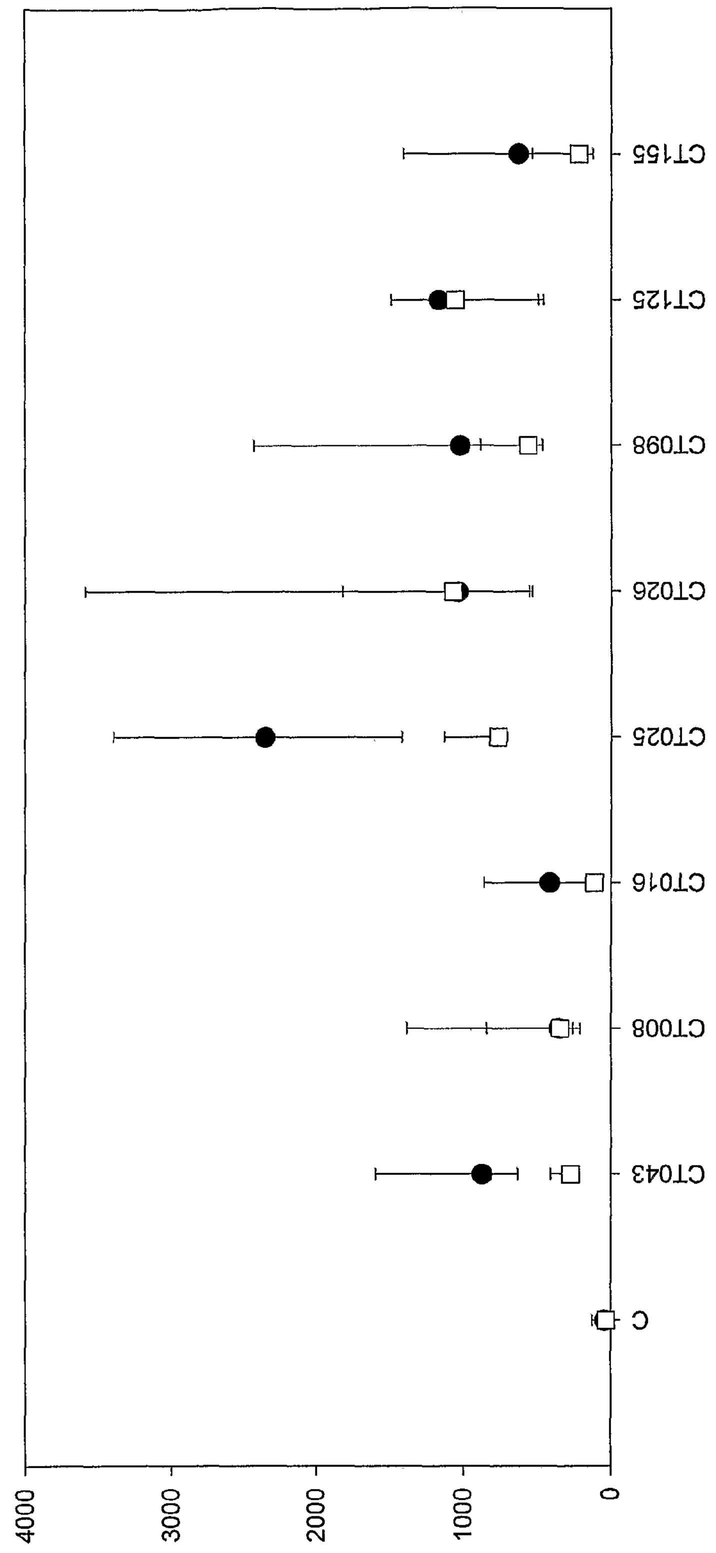
Figure 10F:
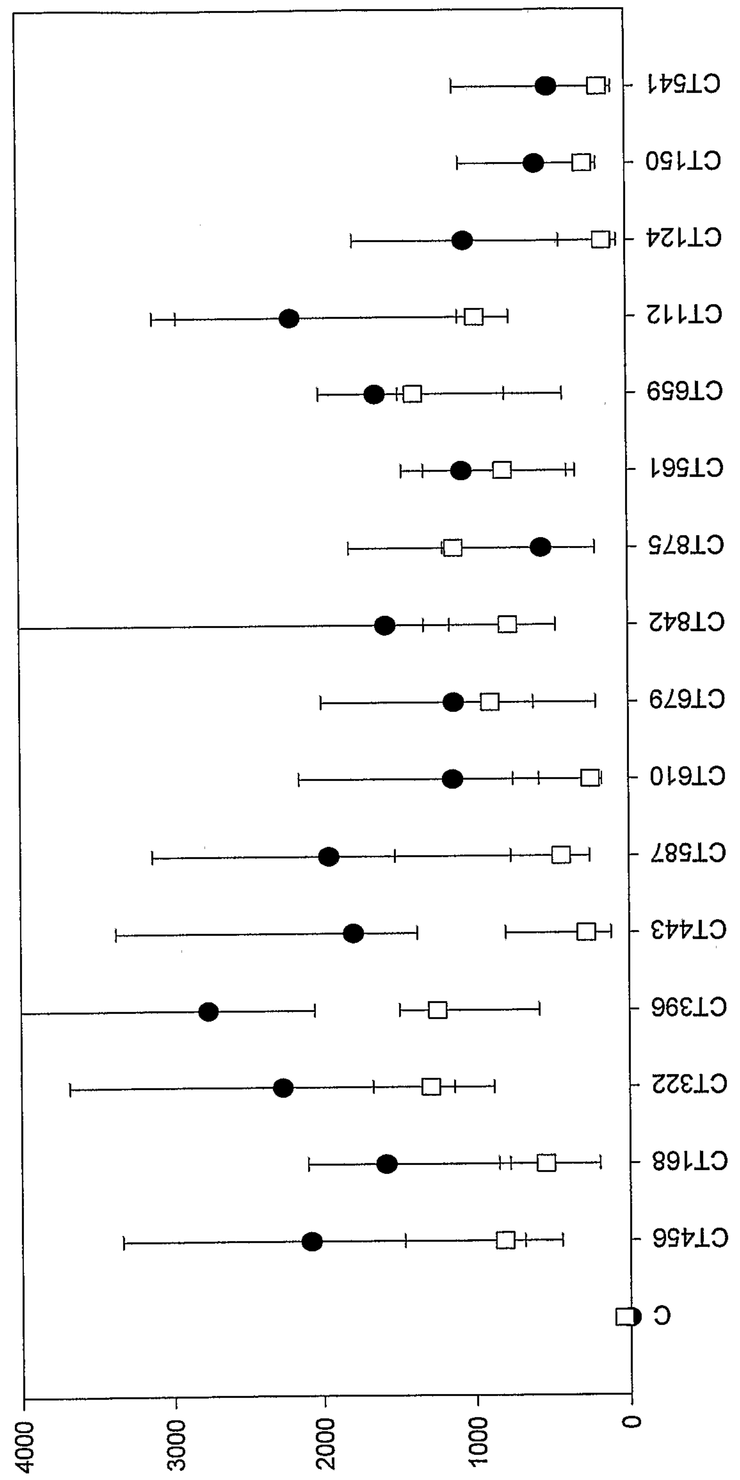
Figure 10G:
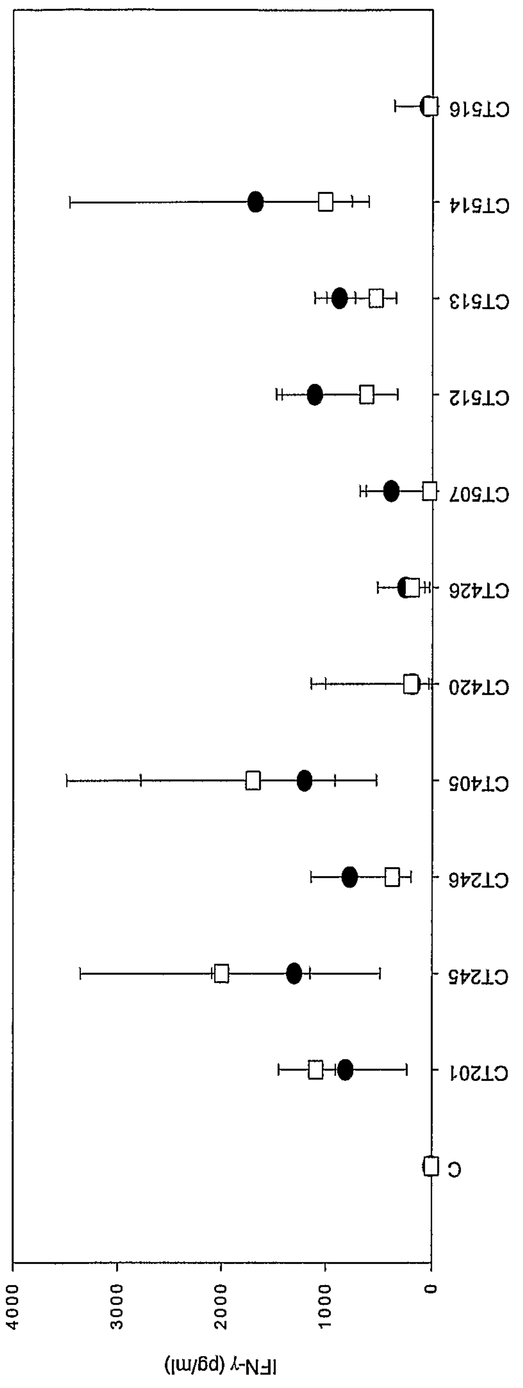
Figure 10H:
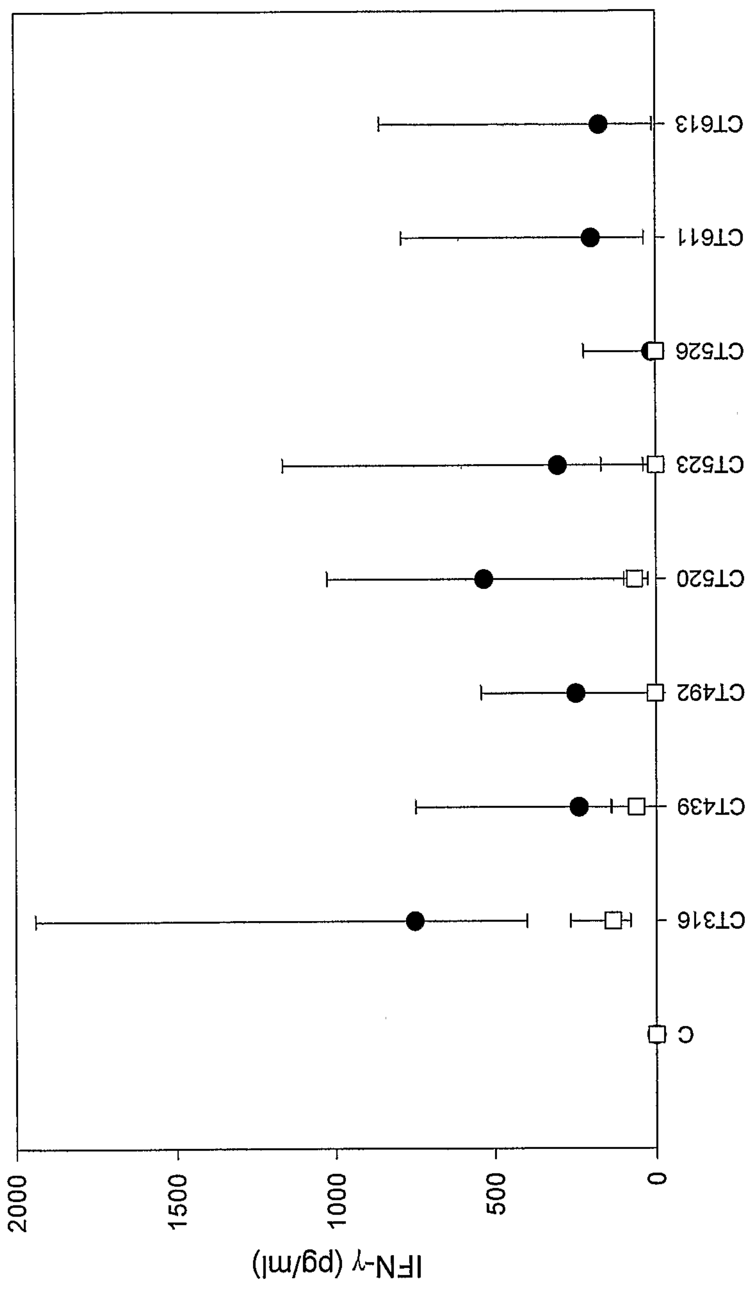
Figure 10I:
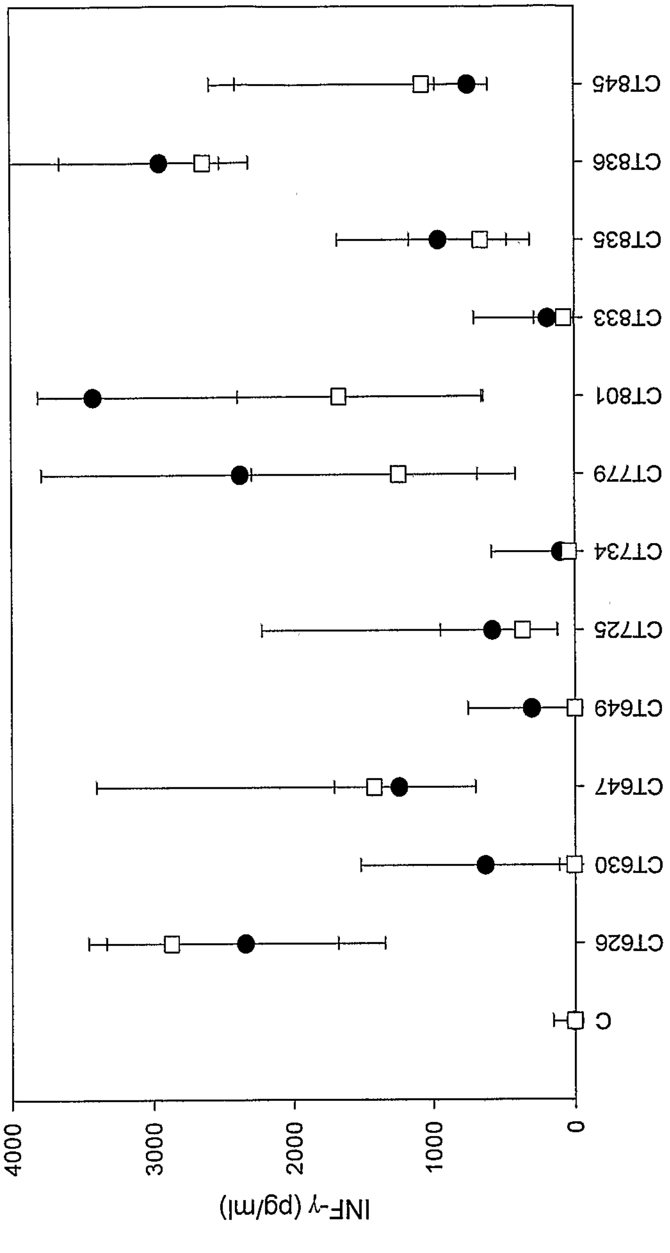

For pathology whole genital tracts were evaluated macroscopically for signs of acute and chronic pathology at PID49. From the gross pathological evaluation a hydrosalpinx-score were calculated. The score is calculated as the ratio of hydrosalpinges over total number of fallopian tubes in the individual vaccine group (FIG. 9). Antigens inducing a fair protection at PID42 are Ct025, Ct063, Ct184, Ct521.

Based on the available material, Ct184 and Ct521 are the antigens performing best in the challenge model. Formulated in Lipovacc, they are inducing the least pathology and the best protection against viginal *Chlamydia*.

Example 7

Screening for *C. trachomatis* Specific T-Cell Epitope Targets Using the Whole-Genome Random Expression Library Introduction The whole-genome random expression library was used for directly screening for potential *C. trachomatis* specific antigen targets that stimulate T-cell proliferation in patient PBMC's. Pools of bacteria expressing random selected λgt11 phages expressing recombinant polypeptides in fusion with β-galactosidase in the lysogen host bacteria Y1089r− (facilitating lysogen phage growth) are directly administered to patient PBMC cells. Following incubation, where the patient PBMC's are activated, possibly through specific effector T-cells due to the bacterial expressed *C. trachomatis* antigen exposure, the mixture is cleared for further bacterial growth by adding antibiotics, and further incubated 2 to 4 days essentially as described in Example 1. The read out may be INFγ and/or specific T-cell proliferation.

In theory, a whole-genome random expression library containing individual random expressed *C. trachomatis* gene sequences of 0.4-0.8 kb in size covers any gene sequence (in correct orientation and in reading frame with the fusion partner, β-galactosidase), in about 1:10.000 individual lambda clones. Thus, screening of 10 to 20 pools each containing 500 to 1000 of randomly selected bacterial clones covers the whole *C. trachomatis* genome. Data by Alderson et al (2000) have shown that as much as adding $10^6$ control bacteria/well containing as little as $10^4$ T cells result in low level of unspecific INFγ and proliferation. Significant and specific INFγ release as well as specific T-cell proliferation was found by adding as little as $10^3$ antigen specific bacteria/well containing as little as $10^4$ T-cells. Thus, a pool with $10^6$ bacteria containing 500 different individual clones added to $10^5$ PBMC cells/well may expose the T-cell population in each well with 2000 bacteria specifically expressing a particular recombinant fusion.

Materials and Methods

Construction of the λgt11 Phage Clone Expressing β-Galactosidase/CT521 Fusion.

A λgt11-βgal/CT521 was constructed for use as positive T-cell epitope target control. The full length sequence encoding the CT521 was amplified by PCR using *C. trachomatis* serovar D genomic DNA as template and the specific forward primer, 5'-TATAGAATTCATGTTAATGCCTAAACGAACAAAA-3', and reverse primer, 5'-TATAGAATTCTTATACCCTTTCCACACGCTTAACAAATCG-3', containing EcoRI sites for cloning into the EcoRI cloning site of the λgt11 exprssion vector in frame with β-galactosidase open rading frame. The cloned recombinant phage construct was verified for correct orientation and sequence by direct sequencing individual phage plaques (see example 3).

Preparation of Whole-*Chlamydia trachomatis-Genome* Random Expression Library as λgt11 Lysogen Library.

The lysogen bacterial stock of the whole-*C. trachomatis*-genome random expression library in Y1089r– is essentially constructed by the method described by Singh et al (1989).

Example 8

PBMC from 10 *Chlamydia* patients and 5 controls were isolated and cultivated as described previously (Example 1). Cell cultures were established in triplicate cultures of 1.25×$10^5$ PBMCs and stimulated with 5 μg of protein. Cell cultures without antigen were included as negative controls (C), and PHA (2 μg/ml) was used as a mitogenic positive control (result not shown). The following antigens were tested: CT043, CT008 CT016 CT025 CT026, CT048, CT098, CT110, CT125, CT155, CT003, CT005, CT023, CT027, CT028, CT032, CT035, CT078, CT082, CT093, CT111, CT123, CT126, CT133, CT175, CT184, CT002, CT009, CT015, CT061, CT063, CT068, CT071, CT080; CT089, CT141, CT509, CT803, CT004, CT030, CT038, CT040, CT052, CT053, CT067, CT511, CT583, CT603, CT681, CT265, CT323, CT322, CT342, CT357r, CT375, CT376, CT456, CT213, CT168, CT396, CT443, CT587, CT610, CT679, CT842, CT875, CT561, CT659, CT112, CT124, CT150, CT201, CT245, CT246, CT405, CT420, CT426, CT507, CT512, CT513, CT514, CT516, CT316, CT439, CT492, CT520, CT523, CT526, CT611, CT613, CT626, CT630, CT647, CT649, CT725, CT734, CT779, CT 801, CT833, CT835, CT836, CT845 and CT541 (FIG. 10).

Figure 11:
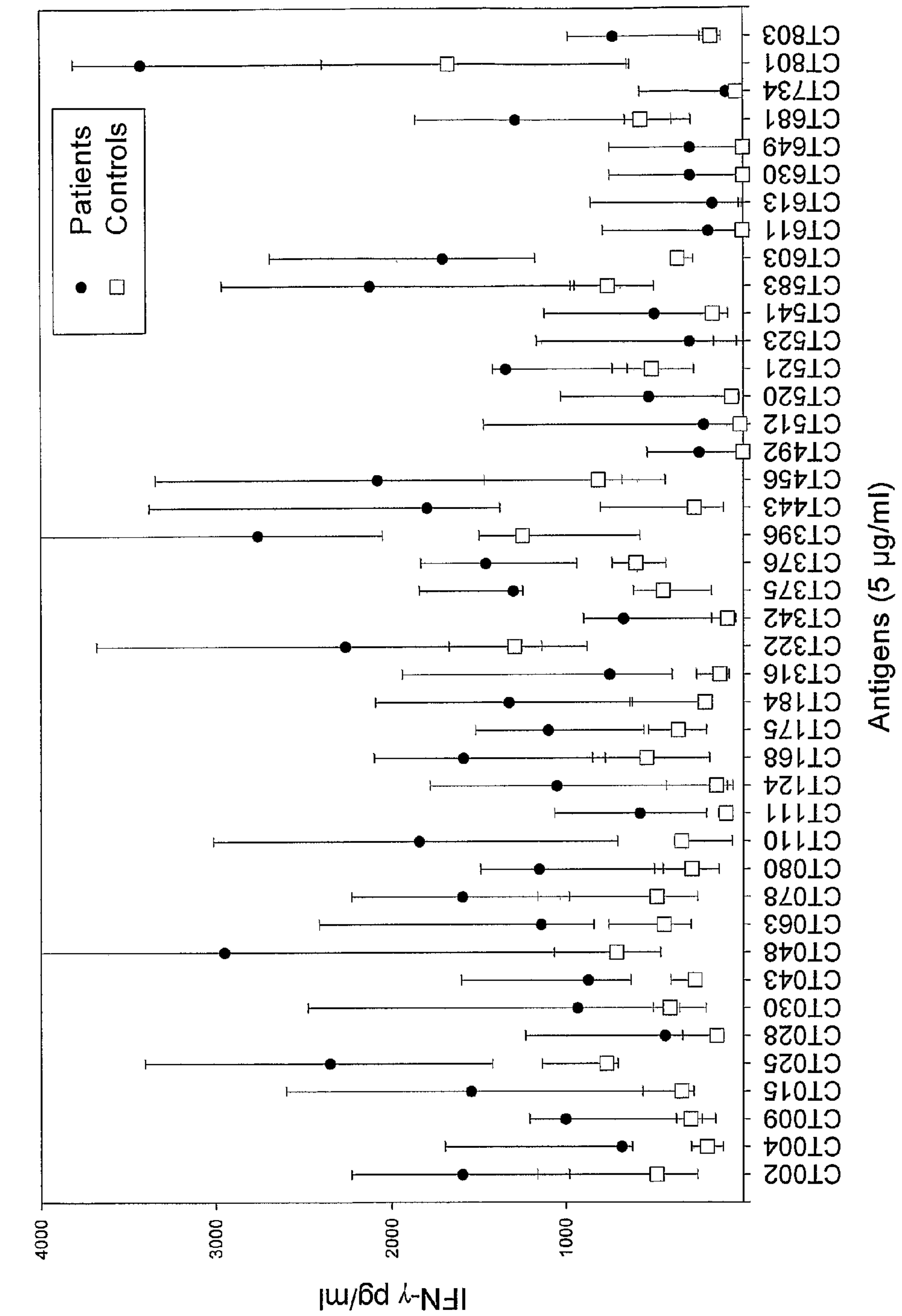

As seen in FIG. 10 the degree of human recognition varies. Some are strongly and frequently recognized—more than 5 patients responding with a level of IFN-γ above all controls. These includes CT375, CT376, CT004, CT048, CT078, CT110, CT583, CT603, CT681, CT184, CT175, CT025, CT002, CT015, CT063, CT456, CT168, CT396, CT443, CT124, CT028, CT030, CT43, CT048, CT080, CT111, CT316, CT322, CT342, CT375, CT492, CT512, CT520, CT521, CT523, CT541, CT611, CT613, CT630, CT649, CT734, CT801, CT803 (FIG. 11) whereas others are not recognized at all (ex. CT071, CT133, CT005).

Example 9

Mapia Testing of Antibody Targets—Essentially as Described in Lyashchenko et. al. (2000)

Briefly, antigens from example 2 and 3 were purified as described in example 1. Antigens were printed on nitrocellulose membrane and tested for reaction against a panel of patient sera and control sera (20 of each). Controls were used for defining the visual cut-off. Patient sera with a clear reaction over the visual cut-off are regarded as positive and are ranked from 1 to 20 positives.

| Antigen | Number of Positve |
|---|---|
| Ct051 | 4 |
| Ct080 | 0 |
| Ct089 | 10 |
| Ct110 | 18 |
| Ct115 | 1 |
| Ct118 | 6 |
| Ct119 | 9 |
| Ct125 | 8 |
| Ct141 | 0 |
| Ct155 | 0 |
| Ct168 | 7 |
| Ct174 | 0 |
| Ct184 | 1 |
| Ct283 | 1 |
| Ct396 | 5 |
| Ct443 | 19 |
| Ct456 | 8 |
| Ct541 | 9 |
| Ct643 | 0 |
| Ct681 | 19 |
| Ct842 | 2 |
| Ct874 | 4 |

Example 10

Protection Strategy in C3H/HeN Mice

The antigens examined in this model are: CT521, TC0052 (muridarum major outer membrane protein) and the combination of the two proteins.

Materials and Methods.

Animals

Female C3H/HeN mice, 8-12 weeks of age, were obtained from Harlan Laboratory. Animals were housed under standard environmental conditions and provided standard food and water ad libitum

*Chlamydia muridarum*

*C. muridarum* was propagated in HeLa 229 cells and harvested as described in Example 6.

Infection of Mice

Mice were infected by the intravaginal route by $10^5$ IFU's. The infection was monitored at day 7 day 14 and day 21 after inoculation by obtaining cervicovaginal swabs followed by fluorescent staining and enumeration of infectious units in the specimen as described in example 6.

Immunization

Mice were immunized subcutaneously (sc) three times with 2 weeks interval at the base of the tail. The vaccines consisted of either 5 μg rCT521, 5 μg rTC0052 or the combination (5 μg rCT521+5 μg rTC0052) emulsified in 250 ug DDA and 100 ug TDB. As a negative control, DDA/TDB alone, without protein was injected.

Lymphocyte Cultures and Evaluation of Immuneinducing Potential

For evaluation of ability to induce a strong immune response, blood samples were drawn from the eye sinus 7 days after the last immunization, pooled in groups (10 mice) and the blood lymphocytes purified on density gradient and resuspended in re-stimulation media (RPMI-1640, Gibo, 10% heat-inactivated Fetal Bovine Serum, Biochrom AG, Berlin, Penicillin G 100 U/ml, streptomycin 100 ug/ml, 10 mM Hepes, 2 mM L-glutamine, 1 mM pyrovate).

Figure 12:
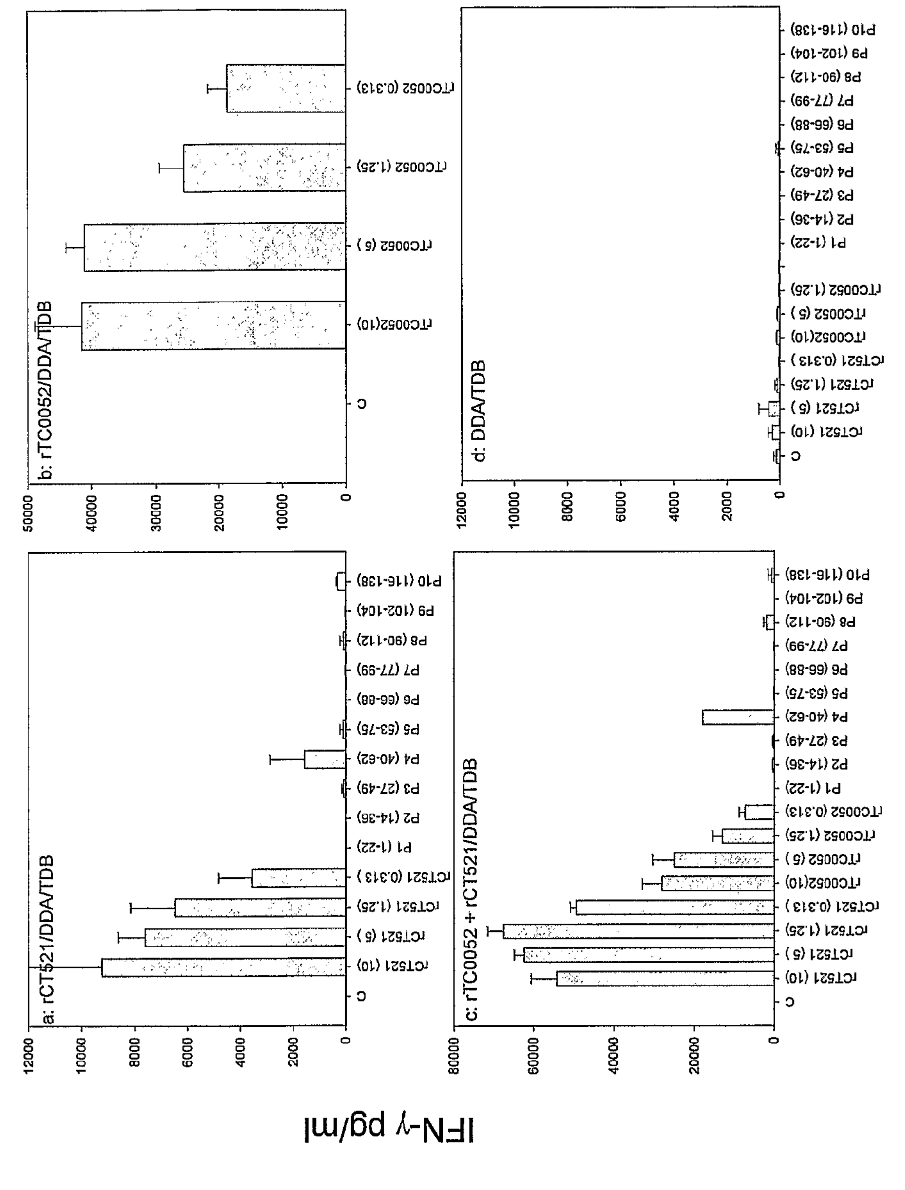

The isolated cells were cultured in triplicates in round-bottom 96-well plates at $2\times10^5$ cells per well in 200 ul re-stimulation media. Proteins were added in concentrations ranging from 0.31 ug/ml to 10 μg/ml and incubated for 72 h. Negative and positive controls (either media or 5 ug/ml ConA) were included. After restimulation the supernatants were harvested and IFN-γ quantitated by enzyme-linked immunosorbent assay (Brandt et al., 2000) (FIG. 12). Immunization with rCT521 induced a strong IFN-γ release in response to restimulation with rCT521 and an epitope mapping (peptides described in example 1) of CT521 revealed P4 (aa 40-62) as the dominant epitope (FIG. 12*a*). Likewise immunization with rTC0052 also induced a strong release of IFN-γ in response to the homologous protein (FIG. 12*b*). Interestingly the mixture of rCT521 and rTC0052 very efficiently enhanced the response to rCT521 compared to immunization with rCT521 alone (FIG. 12*c*).

Evaluation of the Protective Efficacy

Figure 13:
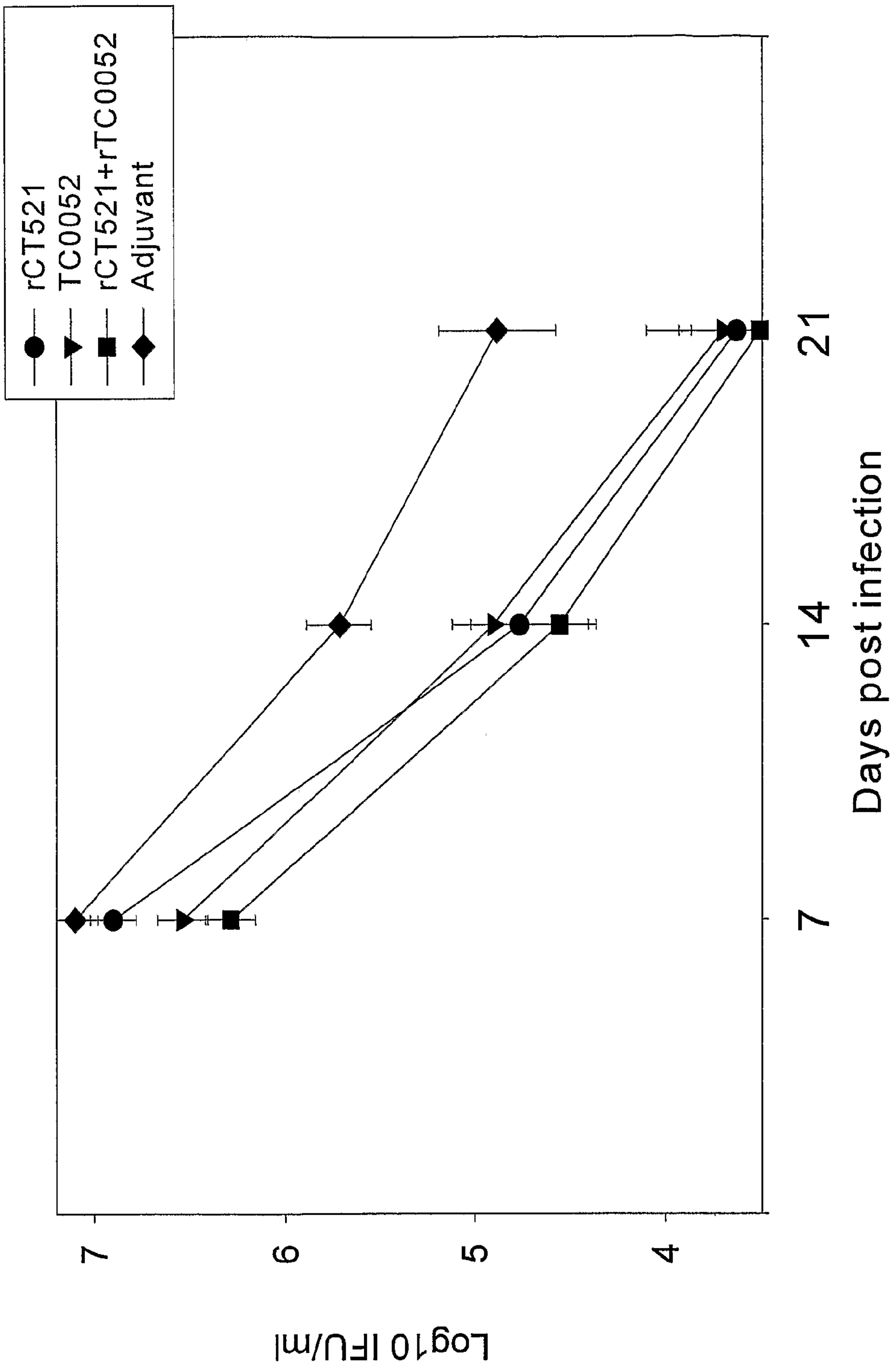

For evaluation of vaccine efficacy, mice were challenged 10 weeks after the first immunization by intravaginal infection with $10^5$ IFU's. The protective efficacy of the vaccine candidates was monitored by enumeration of infectious units obtained by cervicovaginal swabs as described in example 6. Both rCT521 and rTC0052 induced high levels of protection and the combination of the two proteins had a positive additive effect on protection (FIG. 13). Protection experiments with rCT521 have been repeated in the C3H/HeN mice with similar results and high levels of protection after immunisation with rCT521 has also been found in BALB/c×C57BL/6j F1 mice (results not shown).

REFERENCES

Alderson, M. R., Bement, T., Day, C. H., Zhu, L., Molesh, D., Sleiky, Y. A. W., Coler, R., Lewinsohn, D. M., Reed, S. G., and Dillon, D. C. (2000). "Wxpression cloning of an immunodominant family of *Mycobacterium tuberculosos* antigen using human CD4+ T cells." J. Exp. Med. 191(3): 551-9.

Andersen, P. and I. Heron (1993). "Simultaneous electroelution of whole SDS-polyacrylamide gels for the direct cellular analysis of complex protein mixtures." *J Immunol Methods* 161(1): 29-39.

Brandt, L., M. Elhay, et al. (2000). "ESAT-6 subunit vaccination against *Mycobacterium tuberculosis*." Infect Immun 68(2): 791-5.

Brunham, R. C. (1999). Human immunity to *Chlamydia. Chlamydia Intracellular biology, Pathogenesis, and Immunity*. R. S. Stephens. Washington, D.C., ASM Press: 211-238.

Cote-Sierra, J., E. Jongert, et al. (1998). "A new membrane-bound Oprl lipoprotein expression vector. High production of heterologous fusion proteins in gram (−) bacteria and the implications for oral vaccination." *Gene* 221(1): 25-34.

Cotter, T. W., Q. Meng, et al. (1995). "Protective efficacy of major outer membrane protein-specific immunoglobulin A (IgA) and IgG monoclonal antibodies in a murine model of *Chlamydia trachomatis* genital tract infection." *Infect. Immun.* 63(12): 4704-4714.

Fling, S. P., R. A. Sutherland, et al. (2001). "CD8+ T cells recognize an inclusion membrane-associated protein from the vacuolar pathogen *Chlamydia trachomatis*." *Proc. Natl. Acad. Sci. U.S.A* 98(3): 1160-1165.

Goodall, J. C., G. Yeo, et al. (2001). "Identification of *Chlamydia trachomatis* antigens recognized by human CD4+ T lymphocytes by screening an expression library." *Eur. J. Immunol.* 31(5): 1513-1522.

Gosselin, E. J., K. Wardwell, et al. (1992). "Enhanced antigen presentation using human Fc gamma receptor (monocyte/macrophage)-specific immunogens." *J Immunol* 149(11): 3477-81.

Grayston, J. T. and S. P. Wang (1978). "The potential for vaccine against infection of the genital tract with *Chlamydia trachomatis*." *Sex Transm. Dis.* 5: 73-77.

Gu, L., W. M. Wenman, et al. (1995). "*Chlamydia trachomatis* RNA polymerase alpha subunit: sequence and structural analysis." *J. Bacteriol.* 177(9): 2594-2601.

Harboe, M., T. Oettinger, et al. (1996). "Evidence for occurrence of the ESAT-6 protein in *Mycobacterium tuberculosis* and virulent *Mycobacterium bovis* and for its absence in *Mycobacterium bovis* BCG." *Infect Immun* 64(1): 16-22.

Hassell, A. B., D. J. Reynolds, et al. (1993). "Identification of T-cell stimulatory antigens of *Chlamydia trachomatis* using synovial fluid-derived T-cell clones." *Immunology* 79(4):513-519.

Katz, B. P., B. E. Batteiger, et al. (1987). "Effect of prior sexually transmitted disease on the isolation of *Chlamydia trachomatis*." *Sex Transm. Dis.* 14(3): 160-164.

Kilgus, J., T. Jardetzky, et al. (1991). "Analysis of the permissive association of a malaria T cell epitope with DR molecules." *J Immunol* 146(1): 307-15.

Kubo, A. and R. S. Stephens (2000). "Characterization and functional analysis of PorB, a *Chlamydia* porin and neutralizing target." *Mol. Microbiol.* 38(4): 772-780.

LaVerda, D., L. N. Albanese, et al. (2000). "Seroreactivity to *Chlamydia trachomatis Hsp*10 correlates with severity of human genital tract disease." *Infect. Immun.* 68(1): 303-309.

McCafferty, J., A. D. Griffiths, et al. (1990). "Phage antibodies: filamentous phage displaying antibody variable domains." *Nature* 348(6301): 552-4.

Morrison, R. P. and H. D. Caldwell (2002). "Immunity to murine chlamydial genital infection." *Infect Immun* 70(6): 2741-51.

Morrison, S. G., H. Su, et al. (2000). "Immunity to murine *Chlamydia trachomatis* genital tract reinfection involves B cells and CD4(+) T cells but not CD8(+) T cells." *Infect. Immun.* 68(12): 6979-6987.

Ortiz, L., K. P. Demick, et al. (1996). "*Chlamydia trachomatis* major outer membrane protein (MOMP) epitopes that activate HLA class II-restricted T cells from infected humans." *J Immunol* 157(10): 4554-67.

Pal, S., K. M. Barnhart, et al. (1999). "Vaccination of mice with DNA plasmids coding for the *Chlamydia trachomatis* major outer membrane protein elicits an immune response but fails to protect against a genital challenge." *Vaccine* 17(5): 459-465.

Pal, S., I. Theodor, et al. (2001). "Immunization with the *Chlamydia trachomatis* mouse pneumonitis major outer membrane protein can elicit a protective immune response against a genital challenge." *Infect. Immun.* 69(10): 6240-6247.

Pearson, W. R. and D. J. Lipman (1988). "Improved tools for biological sequence comparison." *Proc Natl Acad Sci USA* 85(8): 2444-8.

Ravn, P., A. Demissie, et al. (1999). "Human T cell responses to the ESAT-6 antigen from *Mycobacterium tuberculosis.*" *J Infect Dis* 179(3): 637-45.

Rolph, M. S, and I. A. Ramshaw (1997). "Recombinant viruses as vaccines and immunological tools." *Curr Opin Immunol* 9(4): 517-24.

Rosenkrands, I., E. M. Agger, et al. (2005). "Cationic liposomes containing mycobacterial lipids: a new powerful Th1 adjuvant system." *Infect Immun* 73(9): 5817-26.

Schachter, J., J. Moncada, et al. (1988). "Nonculture methods for diagnosing chlamydial infection in patients with trachoma: a clue to the pathogenesis of the disease?" *J. Infect. Dis.* 158(6): 1347-1352.

Shaw, J., V. Grund, et al. (2002). "Dendritic cells pulsed with a recombinant chlamydial major outer membrane protein antigen elicit a CD4(+) type 2 rather than type 1 immune response that is not protective." *Infect. Immun.* 70(3): 1097-1105.

Sinigaglia, F., M. Guttinger, et al. (1988). "A malaria T-cell epitope recognized in association with most mouse and human MHC class II molecules." *Nature* 336(6201): 778-80.

Stambach, M. N., W. P. Loomis, et al. (2003). "An inclusion membrane protein from *Chlamydia trachomatis* enters the MHC class I pathway and stimulates a CD8+ T cell response." *J Immunol* 171(9): 4742-9.

Stephens, R. S., S. Kalman, et al. (1998). "Genome sequence of an obligate intracellular pathogen of humans: *Chlamydia trachomatis." Science* 282(5389): 754-759.

Stephens, R. S., E. A. Wagar, et al. (1988). "High-resolution mapping of serovar-specific and common antigenic determinants of the major outer membrane protein of *Chlamydia trachomatis." J. Exp. Med.* 167(3): 817-831.

Stryhn, A., L. O. Pedersen, et al. (1996). "Peptide binding specificity of major histocompatibility complex class I resolved into an array of apparently independent subspecificities: quantitation by peptide libraries and improved prediction of binding." *Eur J Immunol* 26(8): 1911-8.

Su, H. and H. D. Caldwell (1995). "CD4+ T cells play a significant role in adoptive immunity to *Chlamydia trachomatis* infection of the mouse genital tract." *Infect. Immun.* 63(9): 3302-3308.

Su, H., M. Parnell, et al. (1995). "Protective efficacy of a parenterally administered MOMP-derived synthetic oligopeptide vaccine in a murine model of *Chlamydia trachomatis* genital tract infection: serum neutralizing IgG antibodies do not protect against chlamydial genital tract infection." *Vaccine* 13(11): 1023-1032.

Theisen, M., S. Soe, et al. (2004). "A *Plasmodium falciparum* GLURP-MSP3 chimeric protein; expression in *Lactococcus* lactis, immunogenicity and induction of biologically active antibodies." *Vaccine* 22(9-10): 1188-98.

Tipples, G. and G. McClarty (1995). "Cloning and expression of the *Chlamydia trachomatis* gene for CTP synthetase." *J. Biol. Chem.* 270(14): 7908-7914.

Ulmer, J. B., J. J. Donnelly, et al. (1993). "Heterologous protection against influenza by injection of DNA encoding a viral protein." *Science* 259(5102): 1745-9.

Wang, S. P., J. T. Grayston, et al. (1967). "Trachoma vaccine studies in monkeys." *Am. J. Ophthalmol.* 63(5): Suppl-30.

Zhang, D. J., X. Yang, et al. (1999). "Characterization of immune responses following intramuscular DNA immunization with the MOMP gene of *Chlamydia trachomatis* mouse pneumonitis strain." *Immunology* 96(2): 314-321.

Zhang, Y., J. Tao, et al. (1997). "Elongation factor Ts of *Chlamydia trachomatis*: structure of the gene and properties of the protein." *Arch. Biochem. Biophys.* 344(1): 43-52.

The invention claimed is:

1. A pharmaceutical composition comprising a *Chlamydia trachomatis* fusion protein, which comprises a fusion partner joined to a *Chlamydia trachomatis* polypeptide, wherein said fusion partner is a *Chlamydia trachomatis* antigen and, wherein said *Chlamydia trachomatis* polypeptide comprises an immunogenic polypeptide encoded by an amino acid sequence having at least 95% sequence identity to SEQ. ID. NO. 1.

2. The pharmaceutical composition according to claim 1, wherein the fusion partner comprises a CT812, CT579, CT587, Cap, CT713, CT442, CT561 or Major Outer Membrane Protein (MOMP) polypeptide.

3. The pharmaceutical composition according to claim 1, wherein said fusion protein is formulated for vaccination.

4. The pharmaceutical composition according to claim 1, wherein said fusion protein is formulated for delivery to a subject not infected with *Chlamydia trachomatis*.

5. A method for immunizing a subject against an infection of *Chlamydia trachomatis*, comprising administering the pharmaceutical composition according to claim 4 to said subject, at a dosage of 0.1 to 1000 μg of said fusion protein per immunization.

6. The method of claim 5, wherein the fusion partner comprises a CT812, CT579, CT587, Cap, CT713, CT442, CT561 or Major Outer Membrane Protein (MOMP) polypeptide.

7. A method for immunizing a subject against an infection of *Chlamydia trachomatis*, comprising administering the pharmaceutical composition according to claim 3 to said subject, at a dosage of 0.1 to 1000 μg of said fusion protein per immunization.

8. The method of claim 7, wherein the fusion partner comprises a CT812, CT579, CT587, Cap, CT713, CT442, CT561 or Major Outer Membrane Protein (MOMP) polypeptide.

9. A method for immunizing a subject against an infection of *Chlamydia trachomatis*, comprising administering the pharmaceutical composition according to claim 1 to said subject, at a dosage of 0.1 to 1000 μg of said fusion protein per immunization.

10. The method of claim 9, wherein the fusion partner comprises a CT812, CT579, CT587, Cap, CT713, CT442, CT561 or Major Outer Membrane Protein (MOMP) polypeptide.

* * * * *

SEQUENCE LISTING

```
<160> NUMBER OF SEQ ID NOS: 308

<210> SEQ ID NO 1
<211> LENGTH: 167
<212> TYPE: PRT
<213> ORGANISM: Chlamydia trachomatis

<400> SEQUENCE: 1

Met Ser Arg Gln Asn Ala Glu Glu Asn Leu Lys Asn Phe Ala Lys Glu
1               5                   10                  15

Leu Lys Leu Pro Asp Val Ala Phe Asp Gln Asn Asn Thr Cys Ile Leu
            20                  25                  30

Phe Val Asp Gly Glu Phe Ser Leu His Leu Thr Tyr Glu Glu His Ser
        35                  40                  45

Asp Arg Leu Tyr Val Tyr Ala Pro Leu Leu Asp Gly Leu Pro Asp Asn
    50                  55                  60

Pro Gln Arg Arg Leu Ala Leu Tyr Glu Lys Leu Leu Glu Gly Ser Met
65                  70                  75                  80

Leu Gly Gly Gln Met Ala Gly Gly Gly Val Gly Val Ala Thr Lys Glu
                85                  90                  95

Gln Leu Ile Leu Met His Cys Val Leu Asp Met Lys Tyr Ala Glu Thr
            100                 105                 110

Asn Leu Leu Lys Ala Phe Ala Gln Leu Phe Ile Glu Thr Val Val Lys
        115                 120                 125
```

-continued

```
Trp Arg Thr Val Cys Ser Asp Ile Ser Ala Gly Arg Glu Pro Thr Val
    130                 135                 140

Asp Thr Met Pro Gln Met Pro Gln Gly Gly Gly Gly Gly Ile Gln Pro
145                 150                 155                 160

Pro Pro Ala Gly Ile Arg Ala
                165
```

```
<210> SEQ ID NO 2
<211> LENGTH: 501
<212> TYPE: DNA
<213> ORGANISM: Chlamydia trachomatis

<400> SEQUENCE: 2

atgtccaggc agaatgctga ggaaaatcta aaaaattttg ctaaagagct taaactcccc      60

gacgtggcct tcgatcagaa taatacgtgc attttgtttg ttgatggaga gttttctctt     120

cacctgacct acgaagaaca ctctgatcgc ctttatgttt acgcacctct tcttgacgga     180

ctgccagaca atccgcaaag aaggttagct ctatatgaga agttgttaga aggctctatg     240

ctcggaggcc aaatggctgg tggaggggta ggagtcgcta ctaaggaaca gttgatctta     300

atgcactgcg tgttagacat gaagtatgca gagaccaacc tactcaaagc ttttgcacag     360

ctttttattg aaaccgttgt gaaatggcga actgtttgtt ctgatatcag cgctggacga     420

gaacccactg ttgataccat gccacaaatg cctcaagggg gtggcggagg aattcaacct     480

cctccagcag gaatccgtgc a                                               501
```

```
<210> SEQ ID NO 3
<211> LENGTH: 144
<212> TYPE: PRT
<213> ORGANISM: Chlamydia trachomatis

<400> SEQUENCE: 3

Met Ile Lys Leu Glu Cys Leu Gln Asp Pro Ser Pro Arg Lys Arg Arg
1               5                   10                  15

Thr Lys Leu Leu Gly Arg Gly Pro Ser Ser Gly His Gly Lys Thr Ser
            20                  25                  30

Gly Arg Gly His Lys Gly Asp Gly Ser Arg Ser Gly Tyr Lys Arg Arg
        35                  40                  45

Phe Gly Tyr Glu Gly Gly Gly Val Pro Leu Tyr Arg Arg Val Pro Thr
    50                  55                  60

Arg Gly Phe Ser His Thr Arg Phe Asp Lys Cys Val Glu Glu Ile Thr
65                  70                  75                  80

Thr Gln Arg Leu Asn Glu Ile Phe Asp Asn Gly Ala Glu Val Ser Leu
                85                  90                  95

Glu Ala Leu Lys Glu Arg Lys Val Ile His Arg Glu Thr Ser Arg Val
            100                 105                 110

Lys Val Ile Leu Lys Gly Ala Leu Asp Lys Lys Leu Val Trp Lys Asp
        115                 120                 125

Ala Ala Ile Val Leu Ser Glu Gly Val Lys Ser Leu Ile Glu Ala Val
    130                 135                 140
```

```
<210> SEQ ID NO 4
<211> LENGTH: 432
<212> TYPE: DNA
<213> ORGANISM: Chlamydia trachomatis

<400> SEQUENCE: 4

atgattaagt tagagtgttt acaagatcct tcgcctcgta agcgaagaac gaaactcttg      60
```

```
ggccgaggac cttcttctgg tcacgggaaa acaagtggtc gaggacacaa aggagacggt    120

agccgttctg gatacaagag acgtttcgga tatgaagggg gaggcgtacc tttatacaga    180

agagttccta cacgaggatt ttctcataca cgctttgata aatgtgttga agaaatcaca    240

acacaacgtt tgaatgagat tttgacaat ggcgcagaag tatctttgga agctttaaaa    300

gaaagaaaag ttatccatag agagacttct cgtgttaaag taatccttaa aggagctctg    360

gataagaaat tagtctggaa agatgctgca atagtgctgt cagaaggagt aaaaagtctt    420

atcgaggctg tt                                                        432


<210> SEQ ID NO 5
<211> LENGTH: 138
<212> TYPE: PRT
<213> ORGANISM: Chlamydia trachomatis

<400> SEQUENCE: 5

Met Leu Met Pro Lys Arg Thr Lys Phe Arg Lys Gln Gln Lys Gly Gln
1               5                   10                  15

Phe Ala Gly Leu Ser Lys Gly Ala Thr Phe Val Asp Phe Gly Glu Phe
            20                  25                  30

Gly Met Gln Thr Leu Glu Arg Gly Trp Ile Thr Ser Arg Gln Ile Glu
        35                  40                  45

Ala Cys Arg Val Ala Ile Asn Arg Tyr Leu Lys Arg Lys Gly Lys Val
    50                  55                  60

Trp Ile Arg Val Phe Pro Asp Lys Ser Val Thr Lys Lys Pro Ala Glu
65                  70                  75                  80

Thr Arg Met Gly Lys Gly Lys Gly Ala Pro Asp His Trp Val Val Val
                85                  90                  95

Val Arg Pro Gly Arg Ile Leu Phe Glu Val Ala Asn Val Ser Lys Glu
            100                 105                 110

Asp Ala Gln Asp Ala Leu Arg Arg Ala Ala Ala Lys Leu Gly Ile Arg
        115                 120                 125

Thr Arg Phe Val Lys Arg Val Glu Arg Val
    130                 135


<210> SEQ ID NO 6
<211> LENGTH: 414
<212> TYPE: DNA
<213> ORGANISM: Chlamydia trachomatis

<400> SEQUENCE: 6

atgttaatgc ctaaacgaac aaaatttcgc aagcagcaga aaggtcagtt tgctggattg     60

agtaagggag caacgtttgt tgacttcggc gaatttggaa tgcagactct ggaaagagga    120

tggattacca gccgccaaat tgaggcatgc agggttgcta tcaacagata tttaaaacgt    180

aaagggaaag tttggattcg agttttccca gataagagtg taacgaaaaa acctgctgaa    240

actcgaatgg gtaaaggtaa gggagctcct gatcactggg tagttgttgt ccgtcccgga    300

cgtattttat tcgaagtggc aaacgtttcg aaagaagatg ctcaggatgc tttgagaaga    360

gctgctgcaa agttaggaat tagaacacga tttgttaagc gtgtggaaag ggta          414


<210> SEQ ID NO 7
<211> LENGTH: 429
<212> TYPE: PRT
<213> ORGANISM: Chlamydia trachomatis

<400> SEQUENCE: 7
```

-continued

```
Met Gln Tyr Val Met Gly Arg Thr Asn Ser Met Thr Arg Gly Phe Leu
1               5                   10                  15

Asn Lys Arg Arg Val Leu Glu Lys Cys Arg Thr Ala Lys Gln Lys Ile
            20                  25                  30

His Tyr Cys Ile Ser Arg Tyr Phe His Tyr Leu Pro Pro Val Leu Ala
        35                  40                  45

Ile Leu Leu Pro Ile Gly Ser Trp Pro Phe Leu Ser Glu Gln Gln Trp
    50                  55                  60

Trp Tyr Gly Ser Phe Leu Phe Pro Val Val Ser Ser Leu Gly Trp Leu
65                  70                  75                  80

Phe Ala Ile Gly Arg Arg Glu Arg Gln Leu Arg Ala Ala Ala Gly Gln
                85                  90                  95

Leu Leu Glu Ala Lys Ile Arg Lys Leu Thr Glu Gln Asp Glu Gly Leu
            100                 105                 110

Lys Asn Ile Arg Glu Thr Ile Glu Lys Arg Gln Lys Glu Thr Asp Arg
        115                 120                 125

Leu Lys Leu His Asn Asp Lys Leu Val Glu Gln Leu Gly Gln Ala Arg
    130                 135                 140

Glu Val Phe Ile Gln Ala Lys Gly Arg Tyr Asp His Met Glu Glu Leu
145                 150                 155                 160

Ser Arg Arg Leu Lys Glu Glu Asn Gln Gln Leu Gln Ile Gln Leu Glu
                165                 170                 175

Ala Ala Val Arg Glu Arg Asn Glu Lys Ile Leu Glu Asn Gln Glu Leu
            180                 185                 190

Leu Gln Glu Leu Lys Glu Thr Leu Ala Tyr Gln Gln Glu Leu His Asp
        195                 200                 205

Glu Tyr Gln Ala Thr Phe Val Glu Gln His Ser Met Leu Asp Lys Arg
    210                 215                 220

Gln Ala Tyr Ile Gly Asn Leu Glu Ala Lys Val Gln Asp Leu Met Cys
225                 230                 235                 240

Glu Leu Arg Asn Leu Leu Gln Leu Glu Met Gly Ala Lys Thr Asn Leu
                245                 250                 255

Pro Gly Lys Pro Val Ala Ser Arg Asp Val Val Ala Gln Leu Val Leu
            260                 265                 270

Glu Phe Arg Lys Ile Val Phe Arg Val Glu Thr Thr Glu Ala Ala Asp
        275                 280                 285

Ser Leu Thr Ala Leu Arg Tyr Thr Arg Thr Asp Pro Ser Ala His Asn
    290                 295                 300

Tyr Ser Leu Ala Cys Arg Gln Leu Phe Asp Gly Leu Arg Glu Glu Asn
305                 310                 315                 320

Leu Gly Met Leu Phe Ile Tyr Ala Pro Phe Ala Gln Arg Val Leu Phe
                325                 330                 335

Ala Asn Ala Leu Phe Asn Asp Trp Thr Gly Tyr Gly Leu Glu Asp Phe
            340                 345                 350

Leu Asn Arg Glu Ser Asp Val Val Leu Glu Gly Phe Ala Gln Trp Glu
        355                 360                 365

Arg Asp Leu Leu Thr Glu Ser Arg Val Glu Arg Ser Gly Lys Ile Val
    370                 375                 380

Ile Lys Thr Lys Ala Phe Gly Ala Thr Pro Phe Tyr Tyr Cys Val Val
385                 390                 395                 400

Thr Leu Asp Lys Gly Pro Phe Ala Gln His Ile Leu Gly Val Leu Tyr
                405                 410                 415
```

-continued

```
Pro Ala Lys Ala Ser Phe Phe Thr Asn Leu Ser Tyr Ile
            420                 425


<210> SEQ ID NO 8
<211> LENGTH: 1287
<212> TYPE: DNA
<213> ORGANISM: Chlamydia trachomatis

<400> SEQUENCE: 8

atgcagtatg tgatgggaag gaccaatagt atgacaaggg gtttttttgaa taagcgaaga      60

gttctagaga aatgtaggac tgccaaacaa aaaatacact attgtatttc gcgatacttt     120

cattacctcc cacccgtttt ggcgattctc ctgcctatag ggagttggcc tttttttgtcc     180

gagcagcaat ggtggtatgg ttcctttctc ttccctgttg tttcttcttt agggtggttg     240

ttcgcgattg ggaggcgaga gcggcagttg cgtgccgccg ctgggcagct ccttgaagca     300

aagattcgta agcttacaga gcaagacgaa ggattaaaaa atatacgaga gactattgaa     360

aagcgtcaaa aagaaacgga tcgtttaaaa ttgcacaatg ataagttggt ggagcaattg     420

ggacaagctc gagaagtctt tattcaagcc aaagggcgtt acgaccatat ggaggagttg     480

tcccgaagat tgaaagagga aaaccagcaa ttacaaatac agttggaagc tgccgttcgt     540

gaacgtaatg agaaaatttt agaaaatcaa gaattgcttc aggagctcaa agaaacgctt     600

gcttatcagc aagagctgca tgatgaatat caagcaacct ttgtggagca gcatagcatg     660

ctggataaga gacaggctta tattggtaat ttggaagcaa aagtacaaga cctcatgtgc     720

gaactacgta atctattgca attggaaatg ggggctaaga cgaatttacc aggaaagcca     780

gtagcttctc gagatgtagt ggctcagctg gtattagagt ttcgtaaaat tgtttttcgt     840

gtagagacaa cggaagcggc ggattctttg acagctttgc ggtatacaag aacagatccg     900

tctgcccata actactcctt agcttgtcgg caattattcg atgggttgag agaagaaaat     960

ctagggatgc tatttattta tgctcccttt gcgcaaagag tcctttttgc caatgctttg    1020

tttaatgatt ggacgggata cggattagaa gatttttttaa acagagagag cgatgttgtt    1080

cttgagggat tcgcgcaatg ggagcgggat cttttaacag aatctagagt agaacgttct    1140

ggtaaaattg ttattaaaac aaaagctttt ggggcgactc ccttctatta ttgtgtagtc    1200

acgttagata agggtccttt tgctcaacat atactagggg ttttgtaccc tgcaaaagcc    1260

agttttttta caaatctttc ctatatt                                        1287


<210> SEQ ID NO 9
<211> LENGTH: 167
<212> TYPE: PRT
<213> ORGANISM: Chlamydia trachomatis

<400> SEQUENCE: 9

Met Lys Pro Gln Leu Leu Leu Leu Glu Asp Val Asp Gly Leu Gly Arg
1               5                   10                  15

Ser Gly Asp Leu Val Val Ala Lys Pro Gly Tyr Val Arg Asn Tyr Leu
            20                  25                  30

Leu Pro Lys Gly Lys Ala Val Val Ala Ser Ala Gly Thr Leu Arg Leu
        35                  40                  45

Gln Ala Lys Leu Gln Glu Gln Arg Leu Leu Gln Ala Ala Ala Asp Lys
    50                  55                  60

Glu Glu Ser Leu Arg Leu Ala Glu Met Leu Arg Ser Ile Val Leu Asp
65                  70                  75                  80

Phe Gln Val Arg Val Asp Ser Glu Asn Asn Met Tyr Gly Ser Val Thr
```

```
                85                  90                  95

Val Asn Asp Met Ile Ser Ala Ala Glu Gln Gln Gly Val Val Leu Thr
            100                 105                 110

Arg Lys Asn Phe Pro Arg Ser His Ser Gly Ile Lys Asn Leu Gly Arg
        115                 120                 125

His Val Val Gly Leu Lys Leu Lys Glu Gly Val Thr Ala Asp Leu His
    130                 135                 140

Leu Glu Val Arg Ala Asp His Glu Ile Ile Glu Gln Lys Glu Leu Gln
145                 150                 155                 160

Ser Ala Glu Glu Gln Glu Gly
                165


<210> SEQ ID NO 10
<211> LENGTH: 501
<212> TYPE: DNA
<213> ORGANISM: Chlamydia trachomatis

<400> SEQUENCE: 10

atgaaaccac aattactttt attagaggat gtcgatggct tagggcgttc cggcgatctt     60

gttgtcgcta agcccggata cgttagaaac tacctgctcc ctaaagggaa ggcagtggtt    120

gctagcgctg gaactctccg tttgcaagca aagttgcaag agcagcgttt gctgcaagct    180

gcggccgata aagaagagtc tcttcgtttg gcagagatgc ttagaagcat cgttttggat    240

ttccaagttc gtgtagattc tgagaataat atgtacggtt ccgtaaccgt gaatgatatg    300

attagtgctg ctgagcaaca aggtgttgtt cttacacgta agaatttccc tcgctctcat    360

agcggtatta agaatctcgg aagacacgta gttggactga aattaaaaga aggcgtgact    420

gcggatcttc atttggaagt tcgtgctgat cacgaaatca ttgaacaaaa agaactccaa    480

agcgcagaag aacaagaagg t                                              501


<210> SEQ ID NO 11
<211> LENGTH: 326
<212> TYPE: PRT
<213> ORGANISM: Chlamydia trachomatis

<400> SEQUENCE: 11

Met Ser Phe Phe His Thr Arg Lys Tyr Lys Leu Ile Leu Arg Gly Leu
1               5                   10                  15

Leu Cys Leu Ala Gly Cys Phe Leu Met Asn Ser Cys Ser Ser Ser Arg
            20                  25                  30

Gly Asn Gln Pro Ala Asp Glu Ser Ile Tyr Val Leu Ser Met Asn Arg
        35                  40                  45

Met Ile Cys Asp Cys Val Ser Arg Ile Thr Gly Asp Arg Val Lys Asn
    50                  55                  60

Ile Val Leu Ile Asp Gly Ala Ile Asp Pro His Ser Tyr Glu Met Val
65                  70                  75                  80

Lys Gly Asp Glu Asp Arg Met Ala Met Ser Gln Leu Ile Phe Cys Asn
                85                  90                  95

Gly Leu Gly Leu Glu His Ser Ala Ser Leu Arg Lys His Leu Glu Gly
            100                 105                 110

Asn Pro Lys Val Val Asp Leu Gly Gln Arg Leu Leu Asn Lys Asn Cys
        115                 120                 125

Phe Asp Leu Leu Ser Glu Glu Gly Phe Pro Asp Pro His Ile Trp Thr
    130                 135                 140

Asp Met Arg Val Trp Gly Ala Ala Val Lys Glu Met Ala Ala Ala Leu
```

```
145                 150                 155                 160

Ile Gln Gln Phe Pro Gln Tyr Glu Glu Asp Phe Gln Lys Asn Ala Asp
                165                 170                 175

Gln Ile Leu Ser Glu Met Glu Glu Leu Asp Arg Trp Ala Ala Arg Ser
            180                 185                 190

Leu Ser Thr Ile Pro Glu Lys Asn Arg Tyr Leu Val Thr Gly His Asn
        195                 200                 205

Ala Phe Ser Tyr Phe Thr Arg Arg Tyr Leu Ser Ser Asp Ala Glu Arg
    210                 215                 220

Val Ser Gly Glu Trp Arg Ser Arg Cys Ile Ser Pro Glu Gly Leu Ser
225                 230                 235                 240

Pro Glu Ala Gln Ile Ser Ile Arg Asp Ile Met Arg Val Val Glu Tyr
                245                 250                 255

Ile Ser Ala Asn Asp Val Glu Val Val Phe Leu Glu Asp Thr Leu Asn
            260                 265                 270

Gln Asp Ala Leu Arg Lys Ile Val Ser Cys Ser Lys Ser Gly Gln Lys
        275                 280                 285

Ile Arg Leu Ala Lys Ser Pro Leu Tyr Ser Asp Asn Val Cys Asp Asn
    290                 295                 300

Tyr Phe Ser Thr Phe Gln His Asn Val Arg Thr Ile Thr Glu Glu Leu
305                 310                 315                 320

Gly Gly Thr Val Leu Glu
                325


<210> SEQ ID NO 12
<211> LENGTH: 978
<212> TYPE: DNA
<213> ORGANISM: Chlamydia trachomatis

<400> SEQUENCE: 12

atgtcttttt ttcatactag aaaatataag cttatcctca gaggactctt gtgtttagca      60

ggctgtttct taatgaacag ctgttcctct agtcgaggaa atcaacccgc tgatgaaagc     120

atctatgtct tgtctatgaa tcgcatgatt tgtgattgcg tgtctcgcat aactggggat     180

cgagtcaaga atattgttct gattgatgga gcgattgatc ctcattcata tgagatggtg     240

aagggggatg aagaccgaat ggctatgagc cagctgattt tttgcaatgg tttaggttta     300

gagcattcag ctagtttacg taaacattta gagggtaacc caaaagtcgt tgatttaggt     360

caacgtttgc ttaacaaaaa ctgttttgat cttctgagtg aagaaggatt ccctgaccca     420

catatttgga cggatatgag agtatggggt gctgctgtaa aagagatggc tgcggcatta     480

attcaacaat ttcctcaata tgaagaagat tttcaaaaga atgcggatca gatcttatca     540

gagatggagg aacttgatcg ttgggcagcg cgttctctct ctacgattcc tgaaaaaaat     600

cgctatttag tcacaggcca caatgcgttc agttacttta ctcgtcggta tctatcctct     660

gatgcggaga gagtgtctgg ggagtggaga tcgcgttgca tttctccaga agggttgtct     720

cctgaggctc agattagtat ccgagatatt atgcgtgtag tggagtatat ctctgcaaac     780

gatgtagaag ttgtcttttt agaggatacc ttaaatcaag atgctttgag aaagattgtt     840

tcttgctcta agagcggaca aaagattcgt ctcgctaagt ctcctttata tagcgataat     900

gtctgtgata actattttag cacgttccag cacaatgttc gcacaattac agaagaattg     960

ggagggactg ttcttgaa                                                  978


<210> SEQ ID NO 13
```

<211> LENGTH: 282
<212> TYPE: PRT
<213> ORGANISM: Chlamydia trachomatis

<400> SEQUENCE: 13

```
Met Ser Asp Phe Ser Met Glu Thr Leu Lys Asn Leu Arg Gln Gln Thr
1               5                   10                  15

Gly Val Gly Leu Thr Lys Cys Lys Glu Ala Leu Glu His Ala Lys Gly
            20                  25                  30

Asn Leu Glu Asp Ala Val Val Tyr Leu Arg Lys Leu Gly Leu Ala Ser
        35                  40                  45

Ala Gly Lys Lys Glu His Arg Glu Thr Lys Glu Gly Val Ile Ala Ala
    50                  55                  60

Arg Val Asp Glu Arg Gly Ala Ala Leu Val Glu Val Asn Val Glu Thr
65                  70                  75                  80

Asp Phe Val Ala Asn Asn Asn Val Phe Arg Ala Phe Val Thr Ser Leu
                85                  90                  95

Leu Ser Asp Leu Leu Asp His Glu Leu Ser Asp Val Asp Ala Leu Ala
            100                 105                 110

Leu Val Met Ser Ser Gln Glu Pro Ser Leu Ser Val Glu Glu Leu Lys
        115                 120                 125

Ala Val Thr Met Gln Thr Val Gly Glu Asn Ile Arg Ile Ser Arg Ala
    130                 135                 140

Phe Tyr Thr Pro Val Asn Ser Gly Gln Ser Val Gly Ile Tyr Ser His
145                 150                 155                 160

Gly Asn Gly Lys Ala Val Ala Ile Ala Phe Leu Ser Gly Ser Glu Asn
                165                 170                 175

Gln Glu Ala Leu Ala Lys Asp Ile Ala Met His Ile Val Ala Ser Gln
            180                 185                 190

Pro Gln Phe Leu Ser Lys Glu Ser Val Pro Gln Glu Val Leu Glu Arg
        195                 200                 205

Glu Arg Glu Val Phe Ser Ser Gln Val Ala Gly Lys Pro Gln Glu Val
    210                 215                 220

Val Glu Lys Ile Thr Gln Gly Lys Phe Arg Ala Phe Phe Gln Glu Ala
225                 230                 235                 240

Cys Leu Leu Glu Gln Ala Phe Ile Lys Asp Pro Glu Val Thr Ile Gln
                245                 250                 255

Gly Leu Ile Asp Arg Ala Ala Lys Ala Ser Gly Glu Pro Leu Lys Val
            260                 265                 270

Glu His Phe Val Phe Trp Lys Met Gly Ala
        275                 280
```

<210> SEQ ID NO 14
<211> LENGTH: 846
<212> TYPE: DNA
<213> ORGANISM: Chlamydia trachomatis

<400> SEQUENCE: 14

```
atgagcgact tctccatgga aacattgaaa aatttaagac agcagacagg tgtaggcctg      60

actaaatgta aagaagctct tgagcacgcc aagggcaatt tagaggatgc ggttgtttat     120

ttacgtaagc tcgggcttgc ctctgcaggc aaaaaagagc accgagaaac aaaagagggc     180

gtgattgctg cacgagttga tgaacgtggt gcagcgcttg ttgaagttaa cgttgaaacc     240

gattttgttg ctaacaacaa cgtatttcga gcattcgtta cgagtttatt gtccgatctt     300

cttgaccacg agcttagcga tgttgatgct ttggctctcg taatgtcctc tcaagagcct     360
```

-continued

```
tccttatctg tggaagagct taaagctgtc acgatgcaaa cggttggaga gaatatccgc    420

attagccgag ctttctacac gcctgttaac tctggtcaaa gtgtagggat ttattctcat    480

ggaaatggaa aagctgtggc tatagctttc ctttctgggt ctgagaatca agaggctttg    540

gctaaagaca ttgctatgca tattgtcgca agtcagccgc agttcttaag taaagaaagc    600

gttcctcaag aagttctaga aagagaacga gaagtatttt cttcccaagt ggctgggaaa    660

ccccaagaag tagttgagaa aattactcaa gggaaattta gggccttttt ccaagaggct    720

tgtttgttag aacaagcctt tattaaagac cctgaagtca caattcaagg tctgattgat    780

agagctgcaa aagctagtgg cgagccactc aaagttgagc actttgtctt ctggaaaatg    840

ggcgca                                                               846
```

```
<210> SEQ ID NO 15
<211> LENGTH: 263
<212> TYPE: PRT
<213> ORGANISM: Chlamydia trachomatis

<400> SEQUENCE: 15

Met Gly Asn Ile Lys Thr Leu Leu Glu Asn Arg Phe Lys Lys Pro Thr
1               5                   10                  15

Pro Asp Lys Met Glu Ser Leu Ala Lys Lys Arg Leu Glu Gly Glu Leu
            20                  25                  30

Ser Pro Phe Leu Asn Gly Phe Thr Asn Pro Lys Leu Ser Ser Gln Glu
        35                  40                  45

Glu Ala Arg Phe Arg Gln Leu Leu Glu Glu Tyr Ser Phe Ser Lys Glu
    50                  55                  60

Ile Ser His Asn Asp Leu Gln Gln Leu Cys His Leu Ser Ala Gln Val
65                  70                  75                  80

Lys Gln Ile His His Gln Ala Ile Leu Leu His Gly Glu Arg Ile Lys
                85                  90                  95

Lys Val Arg Glu Leu Leu Lys Thr Tyr Arg Glu Gly Val Phe Ser Ala
            100                 105                 110

Trp Leu Leu Leu Thr Tyr Gly Asn Arg Gln Thr Pro Tyr Asn Phe Leu
        115                 120                 125

Val Tyr Tyr Glu Leu Phe Ser Ala Leu Pro Asp Thr Leu Lys Leu Glu
    130                 135                 140

Leu Glu Arg Leu Pro Arg Gln Ala Val Tyr Thr Leu Ala Ser Arg Glu
145                 150                 155                 160

Gly Ser Gln Glu Lys Lys Glu Glu Ile Ile Arg Asn Tyr Gln Gly Glu
                165                 170                 175

Thr Arg Gly Glu Leu Leu Glu Ile Ile Arg Arg Glu Phe Pro Leu Leu
            180                 185                 190

Pro Thr Asp Arg Arg Gln Ser Ser Leu Ala Gln Gln Ala Phe Ser Phe
        195                 200                 205

Phe Ala Lys Gly Thr Lys Leu Leu Gln Arg Cys Thr Asp Ile Ser Gln
    210                 215                 220

Glu Glu Leu Leu Ser Leu Glu Lys Leu Ile Lys Lys Leu Gln Lys Val
225                 230                 235                 240

Thr Thr Asn Leu Leu Ser Asn Thr Lys Val Ser Leu Asn Asp Asp Glu
                245                 250                 255

Thr Gln Asn Ser Arg Asn Arg
            260
```

<210> SEQ ID NO 16
<211> LENGTH: 789
<212> TYPE: DNA
<213> ORGANISM: Chlamydia trachomatis

<400> SEQUENCE: 16
atgggaaata ttaaaaccct tttagagaat cgctttaaga aacctacacc cgataaaatg 60
gaatccctcg ctaaaaagcg tttagaagga gagctttctc cttttctaaa tgggtttact 120
aatcctaaac tctcttcgca agaggaagct agattccgtc aattactaga agagtactcc 180
ttttctaagg aaatctccca taacgatctc caacaactgt gtcacttatc tgctcaggtt 240
aaacagattc atcatcaagc tatccttctc catggtgagc gaatcaagaa agttcgtgaa 300
ttattaaaaa cctatcgaga aggagttttt tcagcttggc tcttactcac ctatgggaat 360
cggcagacac cttataattt tcttgtttat tacgagctat tctcagctct tccagacact 420
cttaaactcg agttagaaag actgcctcga caagcagtgt atacactagc ttctcgagaa 480
ggctcgcaag agaaaaaaga ggaaattatc cgtaactatc aaggtgaaac tcgtggagaa 540
ctcctagaaa ttatccgtag agaatttccg ctacttccta ccgatcgacg tcaatcatcc 600
cttgcccaac aagccttttc tttttttgca aaaggaacaa aattattaca gcgatgtaca 660
gacatttctc aagaagagct cctctccctg gaaaaattga ttaaaaagtt acaaaaagtt 720
acaactaacc ttctttctaa cactaaggta tcccttaatg acgacgaaac ccaaaactct 780
agaaatcga 789

<210> SEQ ID NO 17
<211> LENGTH: 195
<212> TYPE: PRT
<213> ORGANISM: Chlamydia trachomatis

<400> SEQUENCE: 17

Met Gly Ser Leu Val Gly Arg Gln Ala Pro Asp Phe Ser Gly Lys Ala
1 5 10 15

Val Val Cys Gly Glu Glu Lys Glu Ile Ser Leu Ala Asp Phe Arg Gly
20 25 30

Lys Tyr Val Val Leu Phe Phe Tyr Pro Lys Asp Phe Thr Tyr Val Cys
35 40 45

Pro Thr Glu Leu His Ala Phe Gln Asp Arg Leu Val Asp Phe Glu Glu
50 55 60

Arg Gly Ala Val Val Leu Gly Cys Ser Val Asp Asp Ile Glu Thr His
65 70 75 80

Ser Arg Trp Leu Ala Val Ala Arg Asn Ala Gly Gly Ile Glu Gly Thr
85 90 95

Glu Tyr Pro Leu Leu Ala Asp Pro Ser Phe Lys Ile Ser Glu Ala Phe
100 105 110

Gly Val Leu Asn Pro Glu Gly Ser Leu Ala Leu Arg Ala Thr Phe Leu
115 120 125

Ile Asp Lys Tyr Gly Val Val Arg His Ala Val Ile Asn Asp Leu Pro
130 135 140

Leu Gly Arg Ser Ile Asp Glu Glu Leu Arg Ile Leu Asp Ser Leu Ile
145 150 155 160

Phe Phe Glu Asn His Gly Met Val Cys Pro Ala Asn Trp Arg Ser Gly
165 170 175

Glu Arg Gly Met Val Pro Ser Glu Glu Gly Leu Lys Glu Tyr Phe Gln
180 185 190

```
Thr Met Asp
        195


<210> SEQ ID NO 18
<211> LENGTH: 585
<212> TYPE: DNA
<213> ORGANISM: Chlamydia trachomatis

<400> SEQUENCE: 18

atgggatcac tagttggaag acaggctccg gatttttctg gtaaagccgt tgtttgtgga      60

gaagagaaag aaatctctct agcagacttt cgtggtaagt atgtagtgct cttcttttat     120

cctaaagatt ttacctatgt ttgtcctaca gaattgcatg cttttcaaga tagattggta     180

gattttgaag agcgaggtgc agtcgtgctt ggttgctccg ttgacgacat tgagacacat     240

tctcgttggc tcgctgtagc gagaaatgca ggaggaatag agggaacaga atatcctctg     300

ttagcagacc cttcttttaa aatatcagaa gcttttggtg ttttgaatcc tgaaggatcg     360

ctcgctttaa gagcgacttt ccttatcgat aaatatgggg ttgttcgtca tgcggttatc     420

aatgatcttc ctttagggcg ttccattgac gaggaattgc gtattttaga ttcattgatc     480

ttctttgaga accacggaat ggtttgtcca gctaactggc gttctggaga gcgtggaatg     540

gtgccttctg aagagggatt aaaagaatat ttccagacga tggat                     585


<210> SEQ ID NO 19
<211> LENGTH: 116
<212> TYPE: PRT
<213> ORGANISM: Chlamydia trachomatis

<400> SEQUENCE: 19

Val Ala Leu Lys Ile Arg Leu Arg Gln Gln Gly Arg Lys Asn His Val
1               5                   10                  15

Val Tyr Arg Leu Val Leu Ala Asp Val Glu Ser Pro Arg Asp Gly Lys
            20                  25                  30

Tyr Ile Glu Leu Leu Gly Trp Tyr Asp Pro His Ser Glu Gln Asn Tyr
        35                  40                  45

Gln Leu Lys Ser Glu Arg Ile Phe Tyr Trp Leu Asn Gln Gly Ala Glu
    50                  55                  60

Leu Thr Glu Lys Ala Gly Ala Leu Val Lys Gln Gly Ala Pro Gly Val
65                  70                  75                  80

Tyr Ala Glu Leu Met Ala Lys Lys Val Ala Arg Arg Ala Val Val Arg
                85                  90                  95

Gln Lys Arg Arg Ala Tyr Arg Gln Arg Leu Ala Ala Arg Lys Ala Glu
            100                 105                 110

Ala Ala Ala Lys
        115


<210> SEQ ID NO 20
<211> LENGTH: 348
<212> TYPE: DNA
<213> ORGANISM: Chlamydia trachomatis

<400> SEQUENCE: 20

gtggcgttaa aaattcgttt aagacaacaa ggacgtaaga accatgttgt atatagatta      60

gtactagctg atgtggagtc tcctagagat ggtaaatata ttgagctgtt gggatggtac     120

gatcctcata gcgagcagaa ttatcagctg aaaagcgaac ggatttttta ttggttgaat     180

caaggagctg agcttacaga gaaggctggg gctttagtga aacaaggagc tcctggggtt     240
```

-continued

```
tatgctgaac taatggctaa aaaagttgct cgtagagcag tcgttagaca aaaaagacga    300

gcttatcgtc agcgtcttgc tgcaagaaag gctgaagcag ctgctaag                348


<210> SEQ ID NO 21
<211> LENGTH: 301
<212> TYPE: PRT
<213> ORGANISM: Chlamydia trachomatis

<400> SEQUENCE: 21

Val Met Gln Met Asp Leu Phe Tyr Ser Leu Leu Pro Ser Ser Asn Pro
1               5                   10                  15

Val Glu Ser Val Thr Ile Gly Phe Phe Asp Gly Cys His Leu Gly His
            20                  25                  30

Gln Ala Leu Leu Ser Phe Leu Thr Lys Phe Pro Ser Lys Ser Gly Val
        35                  40                  45

Ile Thr Phe Ser Gln His Pro Glu His Thr Leu Ser Asn Ser Pro Pro
    50                  55                  60

Glu Thr Ile Thr Ser Leu Glu Glu Arg Val Gln Leu Leu Ala Gly Cys
65                  70                  75                  80

Gly Ile Asp Tyr Leu Ala Val Leu Pro Phe Asn Gln Glu Ile Ala Asn
                85                  90                  95

Gln Glu Ala Glu Pro Phe Ile Gln Ser Ile Tyr Lys Thr Leu Arg Pro
            100                 105                 110

Ser Arg Ile Val Leu Gly Tyr Asp Ser Arg Leu Gly Lys Gly Gly Leu
        115                 120                 125

Gly Thr Ala Gln Thr Leu Arg Pro Phe Ala Ala Ser Leu Gly Ile Ser
    130                 135                 140

Leu Glu Glu Val Pro Pro Leu Gln Ile Glu Gly Thr Ile Val Ser Ser
145                 150                 155                 160

Arg Lys Ile Arg Gln Phe Leu Arg Lys Lys Asp Leu Cys Ser Ala Glu
                165                 170                 175

Lys Phe Leu Gly Arg Pro Phe Ser Tyr Thr Gly Lys Val Ala His Gly
            180                 185                 190

Arg Gly Ile Gly Ala Ser Phe Gly Tyr Ala Thr Ile Asn Leu Pro Leu
        195                 200                 205

Thr His Ser Leu Leu Pro Leu Gly Val Tyr Thr Cys Thr Ile Val Ile
    210                 215                 220

Glu Gly Phe Ser Tyr Ala Gly Val Met Asn Leu Gly Met Ala Pro Thr
225                 230                 235                 240

Met Gln Arg His Gln Leu Cys Leu Glu Ala His Ile Leu Asp Phe Ser
                245                 250                 255

Glu Asp Leu Tyr Asp Lys Ser Ile Thr Val Ile Pro Glu Gln Phe Leu
            260                 265                 270

Arg Glu Glu Lys Leu Phe Ser Ser Lys Asp Glu Leu Val Leu Ala Ile
        275                 280                 285

Gln Glu Asp Ile Arg Gln Ala Arg Leu Asn Lys Asn Arg
    290                 295                 300


<210> SEQ ID NO 22
<211> LENGTH: 903
<212> TYPE: DNA
<213> ORGANISM: Chlamydia trachomatis

<400> SEQUENCE: 22

gtgatgcaaa tggacttatt ctacagcctg ctcccgtcct ctaatcctgt agaatctgtt     60
```

-continued

```
actataggtt ttttcgatgg gtgtcattta ggacaccaag ctttgctttc ttttttaacg    120

aagtttccta gcaaatctgg agtaattacg ttcagccagc atcctgagca tactttgtct    180

aactctcctc cagaaactat tacctctctt gaggagcgtg ttcagcttct ggctggctgc    240

ggcattgatt atctagccgt tctccctttt aaccaggaaa tagctaatca agaggcagag    300

ccatttatcc agtctattta caagactcta cgtccatcaa gaattgtctt gggttacgat    360

tctagacttg ggaagggtgg tttaggaaca gcacaaacgt taaggccttt tgctgcctct    420

ttagggatat ctctagaaga agtccctccc ctacagattg aaggtactat tgtatctagc    480

agaaaaattc gacaatttct tagaaagaaa gatttgtgct ctgcagaaaa gtttcttggg    540

agaccttttt cttatacagg aaaggttgct catggacgag gaattggggc atcttttgga    600

tatgcaacaa tcaatcttcc ccttacccat tctctacttc ctttaggggt atatacttgt    660

actatcgtta ttgaagggtt cagctatgca ggtgttatga atttaggtat ggcgcccaca    720

atgcaaagac accaactatg cctagaggca catatccttg atttttcaga agatctctac    780

gataagagta ttactgtgat tcctgagcaa tttctcaggg aagaaaagct cttttcttct    840

aaagacgagc ttgtccttgc cattcaagaa gatatccgcc aagcccgtct caataaaaat    900

aga                                                                  903
```

<210> SEQ ID NO 23
<211> LENGTH: 112
<212> TYPE: PRT
<213> ORGANISM: Chlamydia trachomatis

<400> SEQUENCE: 23

```
Lys His Met Pro Val Val Gln Lys Pro Ser Val Leu Glu Tyr Ala Pro
1               5                   10                  15

Val Ser Pro Ser Thr Thr Ser Asp Ser Lys Ile Pro Asn His Arg Ser
            20                  25                  30

Gly Ala Ser Cys Ile Lys Ile Ser Met Ile Leu Ala Cys Ser Leu Leu
        35                  40                  45

Ala Val Gly Ile Ile Leu Ala Ile Ala Leu Leu Ala Ser Pro Gly Ser
    50                  55                  60

Leu Ala Tyr Val Leu Val Ala Gly Ile Leu Ala Leu His Ala Val Leu
65                  70                  75                  80

Ala Leu Ala Leu Gly Leu Trp Ile Ser Ser Ser Thr Lys His Ala Leu
                85                  90                  95

Leu Ser Glu Asn Ser Gly Thr Glu Leu Ile Thr Ile Lys Lys Gln Gln
            100                 105                 110
```

<210> SEQ ID NO 24
<211> LENGTH: 339
<212> TYPE: DNA
<213> ORGANISM: Chlamydia trachomatis

<400> SEQUENCE: 24

```
aaacatatgc ctgtagtaca gaaaccttca gttttggagt acgctcctgt ttctccttct     60

acgacttctg attcaaaaat accaaaccac cgatctggag cctcttgtat caagatctcc    120

atgattttgg catgttctct tctagcggtc ggcattattc tcgcaatagc cttgcttgct    180

tcccctggaa gtcttgccta tgtcttagta gctggtatat tagctcttca tgccgtttta    240

gcccttgctt taggattatg gatctcctca tcaaccaagc atgcactact gagtgaaaac    300

tccggtaccg agctgattac aataaagaaa caacaataa                           339
```

<210> SEQ ID NO 25
<211> LENGTH: 82
<212> TYPE: PRT
<213> ORGANISM: Chlamydia trachomatis

<400> SEQUENCE: 25

```
Asp Leu Leu Arg Met Lys Glu Phe Leu Ala Tyr Ile Val Lys Asn Leu
1               5                   10                  15

Val Asp Lys Pro Glu Glu Val His Leu Lys Glu Val Gln Gly Thr Asn
            20                  25                  30

Thr Ile Ile Tyr Glu Leu Thr Val Ala Lys Gly Asp Ile Gly Lys Ile
        35                  40                  45

Ile Gly Lys Glu Gly Arg Thr Ile Lys Ala Ile Arg Thr Leu Leu Val
    50                  55                  60

Ser Val Ala Ser Arg Asp Asn Val Lys Val Ser Leu Glu Ile Met Glu
65                  70                  75                  80

Glu Arg
```

<210> SEQ ID NO 26
<211> LENGTH: 249
<212> TYPE: DNA
<213> ORGANISM: Chlamydia trachomatis

<400> SEQUENCE: 26

```
gatttgcttc gcatgaaaga gtttttagcg tacattgtaa aaaatcttgt tgataagcca      60

gaggaagtgc atctgaaaga ggtgcaggga accaatacga ttatctacga attgactgtt     120

gctaagggag atatcggtaa aattatcggt aaagaaggac gcactattaa ggctatccgt     180

actttattgg tttccgtagc aagtcgagat aatgtgaaag tcagcctaga aattatggaa     240

gagcggtaa                                                             249
```

<210> SEQ ID NO 27
<211> LENGTH: 102
<212> TYPE: PRT
<213> ORGANISM: Chlamydia trachomatis

<400> SEQUENCE: 27

```
Met Ser Asp Gln Ala Thr Thr Leu Lys Ile Lys Pro Leu Gly Asp Arg
1               5                   10                  15

Ile Leu Val Lys Arg Glu Glu Glu Ala Ser Thr Ala Arg Gly Gly Ile
            20                  25                  30

Ile Leu Pro Asp Thr Ala Lys Lys Lys Gln Asp Arg Ala Glu Val Leu
        35                  40                  45

Ala Leu Gly Thr Gly Lys Lys Asp Asp Lys Gly Gln Gln Leu Pro Phe
    50                  55                  60

Glu Val Gln Val Gly Asn Ile Val Leu Ile Asp Lys Tyr Ser Gly Gln
65                  70                  75                  80

Glu Leu Thr Val Glu Gly Glu Glu Tyr Val Ile Val Gln Met Ser Glu
                85                  90                  95

Val Ile Ala Val Leu Gln
            100
```

<210> SEQ ID NO 28
<211> LENGTH: 306
<212> TYPE: DNA
<213> ORGANISM: Chlamydia trachomatis

<400> SEQUENCE: 28

-continued

```
atgtcagatc aagcaacgac cctcaagatt aaacctttgg gagatagaat tttagttaaa      60

agagaagaag aagcttccac tgcaagaggc ggaatcattc ttcctgacac tgccaaaaaa     120

aagcaagata gagctgaagt tttagctcta ggaacaggca aaaaagatga taaagggcag     180

caacttcctt ttgaagttca ggttggtaac atcgttttaa ttgataaata ttctggccaa     240

gaacttactg tcgaaggtga agagtacgtc atcgttcaaa tgagcgaagt tatcgcagtt     300

ctgcaa                                                                306
```

<210> SEQ ID NO 29
<211> LENGTH: 122
<212> TYPE: PRT
<213> ORGANISM: Chlamydia trachomatis

<400> SEQUENCE: 29

```
Met Pro Arg Ile Ile Gly Ile Asp Ile Pro Ala Lys Lys Lys Leu Lys
1               5                   10                  15

Ile Ser Leu Thr Tyr Ile Tyr Gly Ile Gly Pro Ala Leu Ser Lys Glu
            20                  25                  30

Ile Ile Ala Arg Leu Gln Leu Asn Pro Glu Ala Arg Ala Ala Glu Leu
        35                  40                  45

Thr Glu Glu Glu Val Gly Arg Leu Asn Ala Leu Leu Gln Ser Asp Tyr
    50                  55                  60

Val Val Glu Gly Asp Leu Arg Arg Arg Val Gln Ser Asp Ile Lys Arg
65                  70                  75                  80

Leu Ile Thr Ile His Ala Tyr Arg Gly Gln Arg His Arg Leu Ser Leu
                85                  90                  95

Pro Val Arg Gly Gln Arg Thr Lys Thr Asn Ser Arg Thr Arg Lys Gly
            100                 105                 110

Lys Arg Lys Thr Val Ala Gly Lys Lys Lys
        115                 120
```

<210> SEQ ID NO 30
<211> LENGTH: 366
<212> TYPE: DNA
<213> ORGANISM: Chlamydia trachomatis

<400> SEQUENCE: 30

```
atgccacgca tcattggaat agatattcct gcgaaaaaga aattaaaaat aagtcttaca      60

tatatttatg gaatagggcc agctctttct aaagagatca ttgctagatt gcagttgaat     120

cccgaagcta gagctgcaga gttgactgag gaagaggttg gtcgactaaa cgctctttta     180

cagtcggatt acgttgttga aggggatttg cgccgtcgtg tgcaatctga tatcaaacgt     240

ctgattacta tccatgctta tcgtggacaa agacatagac tttctttgcc tgttcgtggt     300

cagagaacaa aaacaaattc tcgcacgcgt aagggtaaac gtaaaactgt tgcaggtaag     360

aagaaa                                                                366
```

<210> SEQ ID NO 31
<211> LENGTH: 424
<212> TYPE: PRT
<213> ORGANISM: Chlamydia trachomatis

<400> SEQUENCE: 31

```
Met Phe Asp Val Val Ile Ser Asp Ile Glu Ala Arg Glu Ile Leu Asp
1               5                   10                  15

Ser Arg Gly Tyr Pro Thr Leu Cys Val Lys Val Ile Thr Asn Thr Gly
```

```
            20                  25                  30

Thr Phe Gly Glu Ala Cys Val Pro Ser Gly Ala Ser Thr Gly Ile Lys
        35                  40                  45

Glu Ala Leu Glu Leu Arg Asp Lys Asp Pro Lys Arg Tyr Gln Gly Lys
    50                  55                  60

Gly Val Leu Gln Ala Ile Ser Asn Val Glu Lys Val Leu Met Pro Ala
65                  70                  75                  80

Leu Gln Gly Phe Ser Val Phe Asp Gln Ile Thr Ala Asp Ala Ile Met
                85                  90                  95

Ile Asp Ala Asp Gly Thr Pro Asn Lys Glu Lys Leu Gly Ala Asn Ala
            100                 105                 110

Ile Leu Gly Val Ser Leu Ala Leu Ala Lys Ala Ala Ala Asn Thr Leu
        115                 120                 125

Gln Arg Pro Leu Tyr Arg Tyr Leu Gly Gly Ser Phe Ser His Val Leu
    130                 135                 140

Pro Cys Pro Met Met Asn Leu Ile Asn Gly Gly Met His Ala Thr Asn
145                 150                 155                 160

Gly Leu Gln Phe Gln Glu Phe Met Ile Arg Pro Ile Ser Ala Pro Ser
                165                 170                 175

Leu Thr Glu Ala Val Arg Met Gly Ala Glu Val Phe Asn Ala Leu Lys
            180                 185                 190

Lys Ile Leu Gln Asn Arg Gln Leu Ala Thr Gly Val Gly Asp Glu Gly
        195                 200                 205

Gly Phe Ala Pro Asn Leu Ala Ser Asn Ala Glu Ala Leu Asp Leu Leu
    210                 215                 220

Leu Thr Ala Ile Glu Thr Ala Gly Phe Thr Pro Arg Glu Asp Ile Ser
225                 230                 235                 240

Leu Ala Leu Asp Cys Ala Ala Ser Ser Phe Tyr Asn Thr Gln Asp Lys
                245                 250                 255

Thr Tyr Asp Gly Lys Ser Tyr Ala Asp Gln Val Gly Ile Leu Ala Glu
            260                 265                 270

Leu Cys Glu His Tyr Pro Ile Asp Ser Ile Glu Asp Gly Leu Ala Glu
        275                 280                 285

Glu Asp Phe Glu Gly Trp Lys Leu Leu Ser Glu Thr Leu Gly Asp Arg
    290                 295                 300

Val Gln Leu Val Gly Asp Asp Leu Phe Val Thr Asn Ser Ala Leu Ile
305                 310                 315                 320

Ala Glu Gly Ile Ala Gln Gly Leu Ala Asn Ala Val Leu Ile Lys Pro
                325                 330                 335

Asn Gln Ile Gly Thr Leu Thr Glu Thr Ala Glu Ala Ile Arg Leu Ala
            340                 345                 350

Thr Ile Gln Gly Tyr Ala Thr Ile Leu Ser His Arg Ser Gly Glu Thr
        355                 360                 365

Glu Asp Thr Thr Ile Ala Asp Leu Ala Val Ala Phe Asn Thr Gly Gln
    370                 375                 380

Ile Lys Thr Gly Ser Leu Ser Arg Ser Glu Arg Ile Ala Lys Tyr Asn
385                 390                 395                 400

Arg Leu Met Ala Ile Glu Glu Glu Met Gly Pro Glu Ala Leu Phe Gln
                405                 410                 415

Asp Ser Asn Pro Phe Ser Lys Ala
            420
```

<210> SEQ ID NO 32

```
<211> LENGTH: 1272
<212> TYPE: DNA
<213> ORGANISM: Chlamydia trachomatis

<400> SEQUENCE: 32

atgtttgatg tcgtcatctc cgatatagaa gcgagagaaa ttttagattc tcgaggctat     60

cccacattat gtgttaaagt catcactaat acaggaacct ttggtgaagc gtgcgttcct    120

tctggagcat ctacaggcat caaggaagct ttggaactgc gtgacaaaga tcctaaacgt    180

taccaaggga aaggggtctt acaagccatt tctaatgtcg aaaaagtgct gatgcccgct    240

ttacaaggat tcagcgtatt tgaccaaatt acagctgatg cgattatgat tgatgctgat    300

ggaactccga acaaagaaaa gttaggagct aatgcgattc ttggagtctc cctagcatta    360

gcaaaagctg ctgcaaatac tttacagaga cctttatatc ggtatcttgg tggatctttc    420

tcgcatgtgc ttccttgccc tatgatgaat cttatcaatg gcggtatgca tgctacaaat    480

ggtctccaat tccaagaatt tatgattcgt ccaattagcg ctccttctct aacagaggct    540

gtgcggatgg gagcagaagt cttcaacgcc ttaaaaaaaa tcttacagaa tcgacagctg    600

gctacaggtg ttggtgatga aggcggattt gctcctaatc ttgcctctaa tgccgaagct    660

ctggatctac tcttaacagc aatcgaaact gcaggattca cacctagaga agatatttct    720

ttagctctcg actgcgctgc ttcttctttc tataataccc aagataaaac ctatgatggg    780

aaatcgtatg cagatcaagt gggtatactt gcagaactct gtgagcacta tcctatagat    840

tctatcgaag atgggctagc cgaagaagat tttgagggct ggaaactcct atccgagact    900

ttaggagatc gtgtgcaact agttggagac gacctatttg tgacgaattc tgcattgatt    960

gctgaaggaa tcgctcaagg acttgccaat gccgttctca tcaaaccaaa ccaaattgga   1020

acacttacag aaactgcaga agctattcgt ttagcaacta tacaaggcta cgctaccatt   1080

ctttcgcata gatcaggaga aacagaagat actaccatag cagaccttgc tgtcgctttt   1140

aatacaggtc agattaaaac agggtctctt tcccgttctg agcgtatcgc taagtataac   1200

cgtctaatgg caattgaaga agagatgggt ccagaagctc tattccaaga ttcaaatccc   1260

ttttctaaag ca                                                       1272


<210> SEQ ID NO 33
<211> LENGTH: 359
<212> TYPE: PRT
<213> ORGANISM: Chlamydia trachomatis

<400> SEQUENCE: 33

Met Glu Ile Lys Val Leu Glu Cys Leu Lys Arg Leu Glu Glu Val Glu
1               5                   10                  15

Lys Gln Ile Ser Asp Pro Asn Ile Phe Ser Asn Pro Lys Glu Tyr Ser
            20                  25                  30

Ser Leu Ser Lys Glu His Ala Arg Leu Ser Glu Ile Lys Asn Ala His
        35                  40                  45

Glu Ser Leu Val Ala Thr Lys Lys Ile Leu Gln Asp Asp Lys Leu Ala
    50                  55                  60

Leu Ser Thr Glu Lys Asp Pro Glu Ile Val Ala Met Leu Glu Glu Gly
65                  70                  75                  80

Val Leu Val Gly Glu Glu Ala Val Glu Arg Leu Ser Lys Gln Leu Glu
                85                  90                  95

Asn Leu Leu Ile Pro Pro Asp Pro Asp Asp Asp Leu Ser Val Ile Met
            100                 105                 110
```

```
Glu Leu Arg Ala Gly Thr Gly Gly Asp Glu Ala Ala Leu Phe Val Gly
        115                 120                 125

Asp Cys Val Arg Met Tyr His Leu Tyr Ala Ala Ser Lys Gly Trp Gln
    130                 135                 140

Cys Glu Val Leu Ser Thr Ser Glu Ser Asp Leu Gly Gly Tyr Lys Glu
145                 150                 155                 160

Tyr Val Met Gly Ile Ser Gly Ala Ser Val Lys Arg Phe Leu Gln Tyr
                165                 170                 175

Glu Ala Gly Thr His Arg Val Gln Arg Val Pro Glu Thr Glu Thr Gln
            180                 185                 190

Gly Arg Val His Thr Ser Ala Val Thr Val Ala Val Leu Pro Glu Pro
        195                 200                 205

Ala Glu Asp Asp Glu Glu Val Phe Ile Asp Glu Lys Asp Leu Arg Ile
    210                 215                 220

Asp Thr Phe Arg Ser Ser Gly Ala Gly Gly Gln His Val Asn Val Thr
225                 230                 235                 240

Asp Ser Ala Val Arg Ile Thr His Ile Pro Ser Gly Val Val Val Thr
                245                 250                 255

Cys Gln Asp Glu Arg Ser Gln His Lys Asn Lys Ala Lys Ala Met Arg
            260                 265                 270

Val Leu Lys Ala Arg Ile Arg Asp Ala Glu Val Gln Lys Arg Ala Gln
        275                 280                 285

Glu Ala Ser Ala Met Arg Ser Ala Gln Val Gly Ser Gly Asp Arg Ser
    290                 295                 300

Glu Arg Ile Arg Thr Tyr Asn Phe Pro Gln Asn Arg Val Thr Asp His
305                 310                 315                 320

Arg Ile Gly Leu Thr Leu Tyr Asn Leu Asp Arg Val Met Glu Gly Glu
                325                 330                 335

Leu Asp Met Ile Thr Thr Ala Leu Val Thr His Val His Arg Gln Leu
            340                 345                 350

Phe Gly His Glu Glu Thr Ala
        355
```

<210> SEQ ID NO 34
<211> LENGTH: 1077
<212> TYPE: DNA
<213> ORGANISM: Chlamydia trachomatis

<400> SEQUENCE: 34

```
atggaaataa aagttttaga gtgtttaaag cgccttgaag aagttgaaaa gcagatatcc      60

gatccgaata tctttagtaa tcctaaagaa tatagttcgc tgagcaagga gcatgcgcgt     120

ctttctgaga ttaaaaatgc tcatgagtca ttggttgcga caaagaaaat tcttcaggac     180

gataaactcg ctttatcaac agagaaggat ccagaaatag tagctatgct agaagaagga     240

gttcttgtag gggaagaggc tgtagaacgt ctatcgaagc agttagaaaa cctgcttatt     300

ccacctgatc cagatgatga tctcagtgtg attatggagt tgcgagcagg aacgggagga     360

gatgaagcgg ctctttttgt aggggactgt gtgcgcatgt atcaccttta tgcagcaagt     420

aaggggtggc aatgcgaagt tctctctaca tcggagtcag atctcggagg ctacaaagaa     480

tatgttatgg ggatttctgg ggcttctgtg aaacgtttct tgcagtatga agcaggaaca     540

catcgtgtgc aaagggtccc agaaacagag actcagggta gggtacatac gtctgcggta     600

acggtagctg ttcttccaga accagcagaa gatgacgaag aagttttcat tgatgagaag     660

gatttacgta ttgatacctt ccgttcttct ggagccggag gccagcacgt caacgttaca     720
```

-continued

```
gattccgctg tgcgtattac tcatattcct tctggcgttg tcgttacgtg ccaagatgaa    780

cgcagtcagc ataaaaataa agctaaggct atgcgcgtgc taaaagctcg tattcgcgat    840

gcagaagtgc agaagcgcgc gcaagaagcc tctgctatgc gttctgctca ggtaggaagc    900

ggagatcgtt cggagcgaat tcgaacctat aattttcctc aaaaccgtgt gaccgatcac    960

cgaattggct taactttata taacttagat cgtgtaatgg aaggagagtt ggatatgatt   1020

acgacagctc ttgtaaccca cgtacatcgg cagctattcg gtcatgaaga aactgct      1077
```

<210> SEQ ID NO 35
<211> LENGTH: 448
<212> TYPE: PRT
<213> ORGANISM: Chlamydia trachomatis

<400> SEQUENCE: 35

```
Met Ile Ser Ser Leu Ser Gln Lys Leu Ser Asn Ile Phe Ser Ser Leu
1               5                   10                  15

Phe Thr Ala Lys Arg Val Thr Glu Glu Ser Ile Ser Asp Ser Ile Arg
            20                  25                  30

Glu Val Arg Leu Ala Leu Leu Asp Ala Asp Val Asn Tyr Gln Ala Val
        35                  40                  45

Lys Asp Phe Ile Ala Lys Val Lys Gln Lys Val Val Gly Glu Glu Val
    50                  55                  60

Trp Lys His Val Ser Pro Gly Gln Gln Phe Ile Lys Cys Leu His Glu
65                  70                  75                  80

Glu Leu Ser Ser Ser Leu Ala Ser Glu Gln Thr Ala Val Ser Leu Arg
                85                  90                  95

Gly Cys Pro Ala Val Ile Leu Leu Cys Gly Leu Gln Gly Ala Gly Lys
            100                 105                 110

Thr Thr Thr Cys Ala Lys Leu Ala Asp Tyr Phe Leu Arg Glu Lys Lys
        115                 120                 125

Ala Lys Lys Val Leu Val Ala Ser Cys Asp Leu Lys Arg Phe Ser Ala
    130                 135                 140

Val Glu Gln Leu Glu Gly Leu Val Lys Gln Thr Gly Ala Asp Phe Phe
145                 150                 155                 160

Arg Arg Glu Gly Asn Asp Pro Val Asp Met Ala Ala Glu Ala Val Gln
                165                 170                 175

His Ala Lys Ser Gln Gly Tyr Asp Leu Val Leu Val Asp Thr Ala Gly
            180                 185                 190

Arg Leu His Val Asp Asp Ala Leu Met Asp Glu Leu Val Ala Ile Ala
        195                 200                 205

Arg Val Thr Thr Pro Cys Glu Thr Leu Phe Val Met Asn Leu Ala Met
    210                 215                 220

Gly Gln Asp Ala Val Val Thr Ala Lys Ala Phe Asp Glu Arg Leu Gly
225                 230                 235                 240

Leu Thr Gly Val Val Val Ser Met Ala Asp Gly Asp Ala Arg Ala Gly
                245                 250                 255

Ala Val Leu Ser Val Lys Ser Leu Leu Asn Lys Pro Ile Lys Phe Glu
            260                 265                 270

Gly Cys Gly Glu Lys Ile Lys Asp Leu Arg Pro Phe Asn Ala Gln Ser
        275                 280                 285

Met Ala Glu Arg Ile Leu Gly Met Gly Asp Thr Ile Ser Leu Val Asp
    290                 295                 300

Lys Met Arg Glu Cys Ile Ser Glu Glu Glu Asn Lys Glu Leu Glu Glu
```

-continued 305 310 315 320

Lys Leu Thr Lys Ala Thr Phe Thr Tyr Glu Asp Phe His Lys Gln Ile
325 330 335

Leu Ala Phe Arg Arg Leu Gly Pro Leu Arg Lys Ile Met Asn Met Met
340 345 350

Pro Ser Phe Gly Gly Ala Lys Pro Ser Asp Lys Asp Leu Glu Glu Ser
355 360 365

Glu Lys Gln Met Lys Arg Asn Glu Ala Ile Ile Leu Ser Met Thr Pro
370 375 380

Glu Glu Arg Lys Glu Leu Val Glu Leu Ser Met Ser Arg Met Lys Arg
385 390 395 400

Ile Ala Ala Gly Cys Gly Leu Thr Leu Gly Asp Val Asn Gln Phe Arg
405 410 415

Lys Gln Met Met Gln Ser Lys Lys Phe Phe Lys Gly Met Thr Arg Glu
420 425 430

Lys Met Glu Gln Met Gly Lys Lys Met Ser Gly Gly Asn Leu Trp Arg
435 440 445

<210> SEQ ID NO 36
<211> LENGTH: 1344
<212> TYPE: DNA
<213> ORGANISM: Chlamydia trachomatis

<400> SEQUENCE: 36
atgattagtt ctttatcgca aaaattatct aatattttct cctcactttt taccgcaaag 60
agggtgacag aggagagtat ttccgactcc attagagagg ttcgcttagc tcttctagat 120
gccgatgtga attatcaggc ggtgaaggat tttattgcta aagtgaagca gaaagttgtt 180
ggggaagaag tttggaaaca tgtctctcct gggcaacagt ttatcaagtg tttgcatgaa 240
gagctttcat cttctcttgc ttcagagcag accgctgttt cgttacgggg atgcccagct 300
gttattttac tctgcgggtt acagggagcg gggaaaacga ctacttgtgc taagcttgct 360
gactattttc ttcgagaaaa gaaggcaaag aaagtgctgg tagcctcctg tgatttgaaa 420
cgtttttcgg ctgtagaaca gttagaaggt ttagtaaaac aaacaggagc agatttttc 480 cgaagggaag gaaatgatcc tgtggacatg gcggcggagg cggttcagca tgcgaaaagc 540
caaggatatg atttagtcct tgtagatacc gctggacggc ttcatgtgga tgatgcgttg 600
atggatgagt tagtagctat tgctcgtgta acgaccccgt gcgaaacctt gttcgttatg 660
aacttagcga tgggacaaga tgcggttgtt actgcaaaag cttttgacga gcgcttaggc 720
ttaacaggtg tggttgtgtc tatggcagac ggtgatgctc gagctggagc ggtgttgtct 780
gtgaagtcct tgcttaataa gccaattaaa tttgaagggt gtggagagaa gataaaggat 840
ctacgtcctt ttaacgcaca gtcgatggca gaacgtattc ttggaatggg agatacgatc 900
agtctagtgg acaagatgcg agagtgtatc tctgaagaag agaataaaga gttagaagaa 960
aagttaacaa aagcaacgtt cacttatgag gattttcata agcagatact tgcttttcgt 1020
cgtttagggc ctttgcgtaa gatcatgaat atgatgccaa gttttggtgg tgcaaaacct 1080
agcgataagg atttggaaga atccgagaaa caaatgaaaa gaaatgaagc gattattctg 1140
tctatgactc cagaggaacg aaaggagtta gtggaattga gtatgagccg gatgaaaaga 1200
atcgctgcgg gctgtggatt gacgctaggt gatgtcaatc agttccgtaa gcaaatgatg 1260
caatctaaga agtttttaa gggaatgacc cgagagaaaa tggaacagat gggtaaaaaa 1320
atgtctggag ggaatctgtg gcgt 1344

<210> SEQ ID NO 37
<211> LENGTH: 287
<212> TYPE: PRT
<213> ORGANISM: Chlamydia trachomatis

<400> SEQUENCE: 37

```
Met Leu Leu Lys Gly Ala Pro Ala Ala Asp His Ile Leu Ala Thr Ile
1               5                   10                  15

Lys Glu Asn Ile Arg Ala Cys Ser Lys Ala Pro Gly Leu Ala Val Val
            20                  25                  30

Leu Ile Gly Asn Asn Pro Ala Ser Glu Ile Tyr Val Asn Met Lys Ile
        35                  40                  45

Lys Arg Ala Thr Asp Leu Gly Met Val Ser Lys Ser Tyr Arg Lys Pro
    50                  55                  60

Ser Asp Ala Thr Leu Ser Asp Ile Leu Ala Leu Ile His Gln Leu Asn
65                  70                  75                  80

Asn Asp Glu Asn Ile His Gly Ile Leu Val Gln Leu Pro Leu Pro Lys
                85                  90                  95

His Leu Asp Ala Gln Ala Ile Leu Ser Thr Ile Thr Pro Asp Lys Asp
            100                 105                 110

Val Asp Gly Leu His Pro Val Asn Val Gly Lys Leu Leu Leu Gly Glu
        115                 120                 125

Thr Asp Gly Phe Ile Pro Cys Thr Pro Ala Gly Ile Val Glu Leu Cys
    130                 135                 140

Lys Tyr Tyr Glu Ile Pro Leu His Gly Lys His Val Val Ile Leu Gly
145                 150                 155                 160

Arg Ser Asn Ile Val Gly Lys Pro Leu Ala Ala Leu Leu Met Gln Arg
                165                 170                 175

His Ala Asp Thr Asn Ala Ser Val Thr Leu Leu His Ser Gln Ser Glu
            180                 185                 190

His Leu Thr Glu Ile Thr Arg Thr Ala Asp Ile Leu Ile Ser Ala Ile
        195                 200                 205

Gly Val Pro Leu Phe Val Asn Lys Glu Met Ile Ala Glu Lys Thr Val
    210                 215                 220

Ile Met Asp Val Gly Thr Ser Arg Ile Pro Ala Ala Asn Pro Lys Gly
225                 230                 235                 240

Tyr Ile Leu Val Gly Asp Val Asp Phe Asn Asn Val Val Pro Val Cys
                245                 250                 255

Arg Ala Ile Thr Pro Val Pro Gly Gly Val Gly Pro Met Thr Val Ala
            260                 265                 270

Met Leu Met Arg Asn Thr Trp Glu Ser Phe Leu Arg His Thr Ser
        275                 280                 285
```

<210> SEQ ID NO 38
<211> LENGTH: 861
<212> TYPE: DNA
<213> ORGANISM: Chlamydia trachomatis

<400> SEQUENCE: 38

```
atgttattaa agggtgcgcc agcagctgac catattttag caacaatcaa ggaaaatatc      60

cgagcctgct ccaaagctcc tggtcttgct gttgtgttga taggaaataa tccggcctca     120

gaaatctatg tgaatatgaa aatcaagcgt gctacggatt tggggatggt gtctaaatcc     180

tatcgcaagc cctcggatgc cacactatcc gacattttag cgctcatcca ccaactcaat     240
```

-continued

```
aatgatgaga acatccacgg aatccttgtt caactccccc tacccaaaca tttagacgct    300

caagctattc tttccactat cacccctgac aaagacgtcg atggactaca ccctgtcaat    360

gtagggaaac tacttcttgg agaaacagat ggatttatcc catgcactcc tgctggaatt    420

gtggaactgt gcaaatatta tgagatccct ctccatggaa agcacgttgt tatcttagga    480

cgtagcaata tcgtaggtaa acctttagcg gccttactta tgcaaagaca tgcagatact    540

aatgctagtg tcactctcct tcatagccaa tctgagcatc ttaccgagat cactaggact    600

gcagatattc tcatttcagc tattggagta ccgctctttg taaataaaga gatgattgca    660

gaaaaaacgg tgatcatgga tgtcggtacc tcaagaatcc ctgcagcgaa tcctaaaggt    720

tatatccttg taggagatgt cgattttaac aatgttgtac ctgtttgccg agccattact    780

cctgtccctg gtggagtcgg cccaatgacc gtcgctatgc taatgagaaa tacatgggaa    840

agtttttgc gtcatacctc c                                               861


<210> SEQ ID NO 39
<211> LENGTH: 560
<212> TYPE: PRT
<213> ORGANISM: Chlamydia trachomatis

<400> SEQUENCE: 39

Met Ser Ile Ser Gly Ser Gly Asn Val Ser Pro Ala Thr Pro Asp Phe
1               5                   10                  15

Asp Pro Ser Ile Leu Met Gly Arg Gln Ala Ala Ser Ala His Ala Ala
            20                  25                  30

Lys Glu Ala Ser Gly Ala Ser Lys Ala Thr Glu Thr Ser Ala Ala Glu
        35                  40                  45

Gln Gln Ala Leu Ile Ser Ser Gly Thr Glu Leu Asp Tyr Val Thr Asp
    50                  55                  60

Leu Gln Gln Ser Glu Gly Lys Tyr Lys Lys Thr Leu Asp Lys Thr Ser
65                  70                  75                  80

Lys Ser Pro Lys Thr Lys Leu Lys Gly Asn Phe Ser Lys Val Arg Ala
                85                  90                  95

Gly Thr Lys Gly Phe Leu Thr Gly Phe Gly Thr Arg Ala Ser Arg Ile
            100                 105                 110

Ser Ala Arg Lys Ala Glu Asn Asn Gly Glu Gly Met Ser Met Ile Pro
        115                 120                 125

Ser Gln Met Glu Tyr Val Lys Lys Lys Gly Asn Arg Val Ser Pro Glu
    130                 135                 140

Met Gln Asn Phe Tyr Leu Gly Ala Ser Gly Leu Trp Ser Pro Thr Ser
145                 150                 155                 160

Asp Val Ser Ser Ile Thr Glu Asn Cys Leu Gly Ala Thr Ala Leu Ser
                165                 170                 175

Thr Thr Pro Leu Leu Thr Thr Met Gln Asp Pro Val Ser Ile Glu His
            180                 185                 190

Leu Ser Ser Gly Glu Ile Thr Ala Leu Ala Ser Phe Asn Pro Asn Val
        195                 200                 205

Arg Thr Ala Ser Leu Asn Glu Gln Thr Ile Asn Ala Trp Thr Glu Ala
    210                 215                 220

Arg Leu Gly Gly Glu Met Val Ser Thr Leu Leu Asp Pro Asn Ile Glu
225                 230                 235                 240

Thr Ser Ser Leu Leu Arg Arg Ala Pro Thr Val Ser Asn Glu Gly Met
                245                 250                 255

Val Asp Val Ser Asp Met Gly Asn Gln Thr Thr Ser Leu Ser Met Glu
```

-continued

```
            260                 265                 270

Gly Leu Val Asn Thr Val Val Asp Asp Pro Ala Ser Ala Glu Glu Glu
        275                 280                 285

Lys Lys Thr Gly Glu Leu Ser Leu Glu Glu Met Ala Ala Met Ala Lys
    290                 295                 300

Met Met Ala Ala Leu Leu Ser Ser Gly Gln Gly Met Ala Val Phe Ile
305                 310                 315                 320

Ala Ser Ser Thr Pro Ser Ser Gly Leu Thr Gln Phe Pro Glu Pro Lys
                325                 330                 335

Phe Ser Gly Thr Ile Pro His His Phe Ser Lys Lys Glu Asp Asn Glu
            340                 345                 350

Thr Ile Trp Gly Leu Asp Ser Gln Ile Gly Ser Ile Ala Phe Asp Thr
        355                 360                 365

Arg Arg Glu Asn Asn Ala Ser Pro Leu Pro Thr Thr Ser Leu His Glu
    370                 375                 380

Glu Ala Ser Tyr Arg Phe Pro Val Gly Glu Ala Pro Leu Asp Val Asn
385                 390                 395                 400

Glu Ile Pro Phe Ala Val Gln His Ser Thr Val Phe Ser Lys Glu Thr
                405                 410                 415

Ala Asn Thr Glu Gln Ala Leu Ile Gln Asn Glu Ser Leu Gly Glu Ile
            420                 425                 430

Pro Val Ser Ala Glu Val Val Gly Gln Asp Thr Val Ser Ser Ala Tyr
        435                 440                 445

Gln Phe Pro Ser His Leu Gly Met Ala Val Leu Ala Ser Val Pro Leu
    450                 455                 460

Ser Thr Glu Asp Tyr Lys Thr Ala Val Glu His Arg Lys Gly Pro Gly
465                 470                 475                 480

Gly Pro Pro Asp Pro Leu Ile Tyr Gln Tyr Arg Asn Val Ala Val Asp
                485                 490                 495

Pro Ala Ile Ile Phe Gln Ser Pro Ser Pro Phe Ser Val Ser Ser Arg
            500                 505                 510

Phe Ser Val Gln Gly Lys Pro Glu Ala Val Ala Val Tyr Asn Asp Asp
        515                 520                 525

Gln Glu Glu Ala Ala Gly Gly Asn Arg Asp Ser Asp Glu Gly Lys Asp
    530                 535                 540

Gln Glu Gln Asp Lys Thr Arg Glu Thr Glu Asp Ala Gly Gly Asp Ser
545                 550                 555                 560


<210> SEQ ID NO 40
<211> LENGTH: 1680
<212> TYPE: DNA
<213> ORGANISM: Chlamydia trachomatis

<400> SEQUENCE: 40

atgtcaattt ctggaagtgg taatgtatct cctgcaactc ctgattttga cccatccatc      60

ttgatgggaa gacaggcggc atcagctcat gcagccaaag aggcctccgg agcatccaag     120

gctacggaaa cgtctgctgc agaacaacaa gcgttaatta gttctggaac ggaactagac     180

tatgtcacgg atttgcagca aagcgagggt aaatacaaaa agaccctcga taagacttcg     240

aaatctccta aaacaaaatt aaaagggaat ttttccaaag tacgtgcagg tactaaagga     300

ttccttacag gatttggaac gcgagcttct cgtatttctg ctcgtaaggc agaaaataat     360

ggagaaggga tgtctatgat ccctagccag atggaatatg tgaagaaaaa agggaatcgg     420

gtttctcctg aaatgcaaaa tttttatctt ggagcttcag gattatggag tccaacgtct     480
```

-continued gatgtttctt ctataacgga aaattgtttg ggagctactg ccctgtcaac aaccccttta 540
ttgacgacta tgcaagatcc tgtgtctata gagcatctat catctggaga aatcactgca 600
ttagcttcgt ttaatcctaa tgttcgtaca gcttctttga atgagcagac aattaatgct 660
tggacagaag ctaggttggg aggagaaatg gtttccactc tcttagaccc caatattgag 720
acgtcttctc ttctacgtcg agctcctacc gtaagtaacg aagggatggt cgatgtttcg 780
gatatgggaa accagactac aagtttatcc atggaaggat tagtaaatac tgttgttgat 840
gatccagctt ctgcagaaga agaaaaaaag actggagagc tctctttgga agagatggca 900
gccatggcaa aaatgatggc agcgctatta agctctggtc aagggatggc agtttttata 960
gcttcttcca ctcctagttc aggcttaaca caatttcctg aacctaagtt ctcaggaact 1020
atcccacatc atttttctaa aaaggaagat aacgaaacca tttggggatt ggattctcag 1080
ataggaagca tagcatttga tacacggaga gaaaataatg cgtccccttt accgacaaca 1140
agcttgcacg aggaggcttc ttataggttc cctgtaggag aagctccttt ggatgttaat 1200
gaaatccctt ttgctgttca acatagtacg gtattttcaa aggagactgc gaatacagaa 1260
caagctctta ttcagaatga gagtttggga gagataccag tttctgctga ggtagtagga 1320
caagatacgg ttagttcggc ttaccagttt ccttcccatt tagggatggc cgtgttagcc 1380
tcggttcctc tttctacaga ggattataag actgcagtag aacatcgtaa aggtcctgga 1440
ggacctccag acccattgat ttatcaatac cgaaatgtgg ctgttgatcc cgccattatt 1500
tttcaatcac cgtctccatt cagtgtttct tcgcgttttt ccgtgcaagg taagccggaa 1560
gctgtagctg tatacaatga tgatcaagaa gaagctgcag gtggaaatcg agatagtgat 1620
gaagggaaag accaagagca ggataaaacg agagaaacag aggatgcagg aggcgattca 1680

<210> SEQ ID NO 41
<211> LENGTH: 167
<212> TYPE: PRT
<213> ORGANISM: Chlamydia trachomatis

<400> SEQUENCE: 41

Met Ile Cys Cys Asp Lys Val Leu Ser Ser Val Gln Ser Met Pro Val
1               5                   10                  15

Ile Asp Lys Cys Ser Val Thr Lys Cys Leu Gln Thr Ala Lys Gln Ala
            20                  25                  30

Ala Val Leu Ala Leu Ser Leu Phe Ala Val Phe Ala Ser Gly Ser Leu
        35                  40                  45

Ser Ile Leu Ser Ala Ala Val Leu Phe Ser Gly Thr Ala Ala Val Leu
    50                  55                  60

Pro Tyr Leu Leu Ile Leu Thr Thr Ala Leu Leu Gly Phe Val Cys Ala
65                  70                  75                  80

Val Ile Val Leu Leu Arg Asn Leu Ser Ala Val Val Gln Ser Cys Lys
                85                  90                  95

Lys Arg Ser Pro Glu Glu Ile Glu Gly Ala Ala Arg Pro Ser Asp Gln
            100                 105                 110

Gln Glu Ser Gly Gly Arg Leu Ser Glu Glu Ser Ala Ser Pro Gln Ala
        115                 120                 125

Ser Pro Thr Ser Ser Thr Phe Gly Leu Glu Ser Ala Leu Arg Ser Ile
    130                 135                 140

Gly Asp Ser Val Ser Gly Ala Phe Asp Asp Ile Asn Lys Asp Asn Ser
145                 150                 155                 160

-continued

```
Arg Ser Arg Ser His Ser Phe
                165


<210> SEQ ID NO 42
<211> LENGTH: 501
<212> TYPE: DNA
<213> ORGANISM: Chlamydia trachomatis

<400> SEQUENCE: 42

atgatctgct gtgacaaagt cttgtcgagc gtacaatcaa tgcctgttat agataaatgc      60

tctgtaacga aatgcttaca aacggctaag caagcagctg ttcttgcgtt gtctttgttt     120

gcggtgtttg cttcaggaag tttatccata ttatcagcgg cggtactgtt tagtggcact     180

gctgctgttc ttccatatct gctgatatta acaacagctc ttctaggatt tgtttgtgct     240

gttattgtgc ttttaagaaa tttatcagca gttgttcaga gttgtaaaaa gagatcacct     300

gaagaaattg aaggggctgc tcgtccctct gatcagcagg aatcaggagg acgtttgtcc     360

gaggagagcg cttcaccaca agcatctcct acttcgtcta cttttggtct tgaatccgct     420

ttgcgctcaa taggagatag tgtttctggg gcattcgatg atataaataa ggacaacagc     480

cgttctcgat cacactcctt c                                               501


<210> SEQ ID NO 43
<211> LENGTH: 151
<212> TYPE: PRT
<213> ORGANISM: Chlamydia trachomatis

<400> SEQUENCE: 43

Met Leu Ile Phe Phe Asp Lys Ser Gln Ser Gly Ala Leu Pro Asp Arg
1               5                   10                  15

Leu Glu Arg Ala Gly Asn Leu Leu Arg Phe Ala Val Asn Arg Gly Met
            20                  25                  30

Ala Ser Gln Ile Lys Val Thr Ser Ala Gln Ser Gly His Ile Phe Phe
        35                  40                  45

Ser Glu Lys Met Ile Ser Val Cys Lys Arg Ile Ala Cys Ile Val Leu
    50                  55                  60

Cys Ile Val Leu Ala Pro Phe Cys Leu Leu Gly Ala Leu Ile Gly Thr
65                  70                  75                  80

Ile Ala Tyr Lys Leu Ser Asn Ser Tyr Gln Asn Ala Leu Tyr Leu Phe
                85                  90                  95

Arg Glu His Arg Asn Met Cys Ser Glu Val Glu Lys Ala Met Lys Gly
            100                 105                 110

Lys Asn Lys Gln Ile Thr Arg Leu Gln Arg Asn Phe Arg Lys Val Leu
        115                 120                 125

Glu Lys Lys His Ile Ala Asp Val Lys Lys Gln Lys Glu Tyr Gln Glu
    130                 135                 140

Met Cys Arg Gln Ser Glu Ser
145                 150


<210> SEQ ID NO 44
<211> LENGTH: 453
<212> TYPE: DNA
<213> ORGANISM: Chlamydia trachomatis

<400> SEQUENCE: 44

atgcttattt ttttcgataa atcacaatca ggtgcgctac ctgatagact agaacgcgct      60

gggaatcttc tgagatttgc tgtaaatagg gggatggcct ctcaaataaa agtaacttct     120
```

-continued

```
gctcagtctg ggcatatttt cttttctgag aagatgatct ctgtatgcaa acgtattgct    180

tgtattgttt tatgtattgt acttgctcca ttttgtttgt taggagcttt gataggaacc    240

attgcttaca aactatcaaa ttcctatcag aatgctcttt acctcttccg cgagcatcga    300

aatatgtgtt cggaagtaga aaaagctatg aaagggaaaa acaaacaaat tactcgttta    360

caaagaaact ttcgaaaagt tttagaaaaa aaacatattg cagatgttaa gaaacaaaaa    420

gaataccagg agatgtgtcg tcaatcagaa agt                                 453
```

<210> SEQ ID NO 45
<211> LENGTH: 491
<212> TYPE: PRT
<213> ORGANISM: Chlamydia trachomatis

<400> SEQUENCE: 45

```
Met Tyr Arg Lys Ser Ala Leu Glu Leu Arg Asp Ala Val Val Asn Arg
1               5                   10                  15

Glu Leu Ser Val Thr Ala Ile Thr Glu Tyr Phe Tyr His Arg Ile Glu
            20                  25                  30

Ser His Asp Glu Gln Ile Gly Ala Phe Leu Ser Leu Cys Lys Glu Arg
        35                  40                  45

Ala Leu Leu Arg Ala Ser Arg Ile Asp Asp Lys Leu Ala Lys Gly Asp
    50                  55                  60

Pro Ile Gly Leu Leu Ala Gly Ile Pro Ile Gly Val Lys Asp Asn Ile
65                  70                  75                  80

His Ile Thr Gly Val Lys Thr Thr Cys Ala Ser Lys Met Leu Glu Asn
                85                  90                  95

Phe Val Ala Pro Phe Asp Ser Thr Val Val Arg Arg Ile Glu Met Glu
            100                 105                 110

Asp Gly Ile Leu Leu Gly Lys Leu Asn Met Asp Glu Phe Ala Met Gly
        115                 120                 125

Ser Thr Thr Arg Tyr Ser Ala Phe His Pro Thr Asn Asn Pro Trp Asp
    130                 135                 140

Leu Glu Arg Val Pro Gly Gly Ser Ser Gly Gly Ser Ala Ala Ala Val
145                 150                 155                 160

Ser Ala Arg Phe Cys Pro Ile Ala Leu Gly Ser Asp Thr Gly Gly Ser
                165                 170                 175

Ile Arg Gln Pro Ala Ala Phe Cys Gly Val Val Gly Phe Lys Pro Ser
            180                 185                 190

Tyr Gly Ala Val Ser Arg Tyr Gly Leu Val Ala Phe Gly Ser Ser Leu
        195                 200                 205

Asp Gln Ile Gly Pro Leu Thr Thr Val Val Glu Asp Val Ala Leu Ala
    210                 215                 220

Met Asp Ala Phe Ala Gly Arg Asp Pro Lys Asp Ser Thr Thr Arg Asp
225                 230                 235                 240

Phe Phe Lys Gly Thr Phe Ser Gln Ala Leu Ser Leu Glu Val Pro Lys
                245                 250                 255

Leu Ile Gly Val Pro Arg Gly Phe Leu Asp Gly Leu Gln Glu Asp Cys
            260                 265                 270

Lys Glu Asn Phe Phe Glu Ala Leu Ala Val Met Glu Arg Glu Gly Ser
        275                 280                 285

Arg Ile Ile Asp Val Asp Leu Ser Val Leu Lys His Ala Val Pro Val
    290                 295                 300

Tyr Tyr Ile Val Ala Ser Ala Glu Ala Ala Thr Asn Leu Ala Arg Phe
305                 310                 315                 320
```

```
Asp Gly Val Arg Tyr Gly His Arg Cys Ala Gln Ala Asp Asn Met His
                325                 330                 335

Glu Met Tyr Ala Arg Ser Arg Lys Glu Gly Phe Gly Lys Glu Val Thr
            340                 345                 350

Arg Arg Ile Leu Leu Gly Asn Tyr Val Leu Ser Ala Glu Arg Gln Asn
        355                 360                 365

Ile Phe Tyr Lys Lys Gly Met Ala Val Arg Ala Arg Leu Ile Asp Ala
    370                 375                 380

Phe Gln Ala Ala Phe Glu Arg Cys Asp Val Ile Ala Met Pro Val Cys
385                 390                 395                 400

Ala Thr Pro Ala Ile Arg Asp Gln Asp Val Leu Asp Pro Val Ser Leu
                405                 410                 415

Tyr Leu Gln Asp Val Tyr Thr Val Ala Val Asn Leu Ala Tyr Leu Pro
            420                 425                 430

Ala Ile Ser Val Pro Ser Gly Leu Ser Lys Glu Gly Leu Pro Leu Gly
        435                 440                 445

Val Gln Phe Ile Gly Glu Arg Gly Ser Asp Gln Gln Ile Cys Gln Val
    450                 455                 460

Gly Tyr Ser Phe Gln Glu His Ser Gln Ile Lys Gln Leu Tyr Pro Lys
465                 470                 475                 480

Ala Val Asn Gly Leu Phe Asp Gly Gly Ile Glu
                485                 490


<210> SEQ ID NO 46
<211> LENGTH: 1473
<212> TYPE: DNA
<213> ORGANISM: Chlamydia trachomatis

<400> SEQUENCE: 46

atgtatcgta agagtgcttt agaattaaga gatgctgtag tgaacagaga gctttcagtt      60

acagcgatta cagaatattt ttatcatcgt atagaaagtc atgacgaaca gattggagct     120

tttctttctc tttgtaaaga gcgggctttg cttagagctt cacgtataga tgacaaacta     180

gcaaaaggag atccaatagg gttactagca ggaatcccta tcggagttaa agataatatt     240

catatcacag gagtgaaaac aacctgtgct tcgaaaatgt tggaaaactt cgtggctccc     300

tttgattcca cggtggtgag acgtatagag atggaagacg ggattttact gggtaagttg     360

aacatggatg agtttgccat gggatccaca actcggtatt ccgcttttca tcctaccaat     420

aatccttggg atttagaacg agttccaggg ggttcttcag gtggatccgc ggcagcagtt     480

tcggcgaggt tctgtcctat cgcgttagga tcggataccg gaggatcgat tcgtcaacca     540

gcagcatttt gtggagttgt tggatttaaa ccttcctatg gagcagtttc tcgctacgga     600

ttagtcgctt ttggatcctc tttagatcag attggaccat tgacaacggt ggtagaggat     660

gtcgctctgg caatggatgc ctttgctggt cgtgatccca aagattccac tacgagagac     720

ttttttaaag ggacgttttc gcaagccttg tcattggaag ttcctaagtt aatcggagtt     780

cctagaggat tcctagacgg actgcaagaa gattgtaaag aaaacttttt cgaagctctt     840

gctgttatgg aacgtgaagg cagtcgcatt attgatgtag atctcagtgt tttgaaacat     900

gcggtacctg tttactatat tgttgcttct gcagaagctg ccacaaactt agcccgtttt     960

gatggtgttc ggtatggtca tcgttgtgcg caggctgata acatgcatga aatgtatgcg    1020

cgttctcgta aagaaggctt tggaaaagaa gtaactcgta gaattctttt agggaattat    1080

gtgctttcag cagaaagaca aaacatcttt tataagaaag gaatggcagt tcgtgctcgc    1140
```

-continued

```
ttaatagacg cttttcaagc tgcttttgag cgctgtgatg tgatcgctat gcctgtatgc   1200

gcaacgcctg ccatcagaga tcaggatgtt ttggatccgg tttctctata tctacaggat   1260

gtttataccg tagcggtaaa cttggcctat ttacctgcca tttccgttcc ttccggactg   1320

tctaaagaag gtctcccatt aggtgttcaa tttattgggg aaagaggttc ggatcagcag   1380

atttgtcaag taggatacag cttccaggaa cactcgcaaa tcaaacaatt atatcctaaa   1440

gcagtgaatg gactttttga cggaggaata gaa                               1473
```

<210> SEQ ID NO 47
<211> LENGTH: 363
<212> TYPE: PRT
<213> ORGANISM: Chlamydia trachomatis

<400> SEQUENCE: 47

```
Met Thr Pro Val Thr Pro Val Pro Pro Gln Ser Pro Gln Gln Val Lys
1               5                   10                  15

Gly Leu Leu Ser Arg Phe Leu Thr Ala Pro Asp Arg His Pro Lys Leu
            20                  25                  30

Arg Tyr Val Tyr Asp Ile Ala Leu Ile Ala Ile Ser Ile Leu Cys Ile
        35                  40                  45

Val Ser Ile Ile Leu Trp Thr Gln Gly Ser Gly Leu Ala Leu Phe Ala
    50                  55                  60

Ile Ala Pro Ala Leu Ala Ile Gly Ala Leu Gly Val Thr Leu Leu Val
65                  70                  75                  80

Ser Asp Leu Ala Glu Ser Gln Lys Ser Lys Glu Ile Ala Asp Thr Val
                85                  90                  95

Ala Ala Val Ser Leu Pro Phe Ile Leu Thr Gly Thr Ala Ala Gly Leu
            100                 105                 110

Met Phe Ser Ala Ile Ala Val Gly Gly Gly Ala Val Ile Leu Ala Asn
        115                 120                 125

Pro Leu Phe Leu Met Gly Ser Met Thr Leu Gly Phe Ala Leu Met Ser
    130                 135                 140

Leu His Arg Val Thr Tyr Gln Tyr Leu Ser Asn Arg Glu Gln Trp Lys
145                 150                 155                 160

Gln Gln Lys Lys Leu Glu Gln Val Glu Leu Ala Ala Trp Glu Ser His
                165                 170                 175

Leu Pro Lys Glu Ser Lys Ser Ser Ala Leu Glu Glu Val Arg Tyr Ser
            180                 185                 190

Pro Arg Leu Met Lys Arg Gly Lys Thr Trp Arg Lys Arg Ala Ile Arg
        195                 200                 205

Arg Lys Asn Tyr Thr Pro Ile Pro Leu Val Asp Lys Thr Leu Gln Thr
    210                 215                 220

Met Gln Pro Asp Ala Leu Phe Ser Ser Thr Thr Thr His Ser Thr Asp
225                 230                 235                 240

Ser Glu Gln Ile Leu Thr Ser Val Ser Pro Gln Ser Ser Asp Thr Glu
                245                 250                 255

Ser Ser Ser Ser Ser Ser Phe His Thr Pro Pro Asn Ser Asp Lys Glu
            260                 265                 270

Leu Ser Asp Ser Asn Ser Ser Asp Ser Ser Ser Ser Glu Tyr Met
        275                 280                 285

Asp Ala Leu Glu Thr Val Ala Ala Gly Asp Val Ser Gly Ile Thr Pro
    290                 295                 300

Pro Ser Lys Pro Ser Ser Ser Pro Lys Thr Thr Arg Arg Val Val Lys
```

-continued

```
305                 310                 315                 320

Leu Ser Arg Ser Glu Arg Asn Ala Gln His His Arg Asn Lys Asp Gln
                325                 330                 335

Glu Gln Arg Gln Asp Ser Ser Glu Ser Ser Glu Glu Asp Ser Ser Ser
            340                 345                 350

Asp Ser Ser Gln Lys Lys Lys Pro Ser Arg Lys
        355                 360
```

<210> SEQ ID NO 48
<211> LENGTH: 1089
<212> TYPE: DNA
<213> ORGANISM: Chlamydia trachomatis

<400> SEQUENCE: 48

```
atgactccag taacaccagt ccctccccaa tctccccaac aggtaaaagg gcttttatcc     60

aggtttctga cggcacccga tcgtcacccc aaactacgct atgtttacga tattgctctt    120

atagctatta gtattctctg tattgtgagt atcattctct ggacacaagg gtctggactc    180

gctttatttg caatcgctcc agccttagct attggagccc taggagtcac tctgctagtc    240

tcagatcttg ccgaatccca gaaaagtaaa gagattgctg ataccgttgc ggcagtctct    300

cttcctttta tcctaacagg gacagctgct ggattgatgt ttctgctat tgccgtaggc     360

ggaggcgctg taatcttagc gaatcctcta ttcctaatgg gctctatgac tctcggcttt    420

gctctgatgt ctctgcatag agtgacctat caatatctca gcaatcgcga gcaatggaaa    480

cagcagaaga agctcgaaca agttgagtta gctgcctggg agagccatct tcctaaagaa    540

agcaaatcct ccgctctgga agaggttcgc tattcccctc gtttgatgaa aagagggaag    600

acttggcgaa aacgggcaat cagaagaaaa aactatacac ctattccgtt ggtcgacaaa    660

acattgcaaa ccatgcaacc ggatgcactc ttctcctcta caaccacaca ttctacagat    720

agtgagcaga ttctaacttc tgtcagtcct caaagctcag ataccgaatc ctcctcttct    780

tctagcttcc acactccacc aaatagcgat aaagaactgt ccgactcgaa ttcttctgac    840

agcagctctt cttctgaata tatggatgct cttgaaaccg tagctgcagg agatgtctca    900

ggaataaccc ctccatccaa accctcttct tctccgaaaa cgacacgccg cgtcgtaaag    960

ctctctcgca gcgagagaaa tgctcagcat catcgtaata aagaccaaga gcaaagacaa   1020

gacagcagcg aatcttcgga agaggattcc tcatccgatt catctcaaaa gaagaaaccc   1080

tctcgtaaa                                                           1089
```

<210> SEQ ID NO 49
<211> LENGTH: 352
<212> TYPE: PRT
<213> ORGANISM: Chlamydia trachomatis

<400> SEQUENCE: 49

```
Met Glu Ile Asp Ile Leu Ser Leu Phe Pro Asp Tyr Phe Ala Ser Pro
1               5                   10                  15

Leu Gln Ala Thr Ile Leu Gly Arg Ala Ile Lys Gln Gly Ala Leu Ser
            20                  25                  30

Val Arg Ser Arg Asp Ile Arg Glu Phe Gly Leu Gly Lys Trp Lys Gln
        35                  40                  45

Val Asp Asp Ser Pro Tyr Asn Gly Glu Gly Met Leu Leu Met Ala Glu
    50                  55                  60

Pro Val Val Gln Ala Ile Arg Ser Ile Arg Arg Lys Lys Ser Lys Val
65                  70                  75                  80
```

```
Ile Tyr Leu Ser Pro Gln Gly Gln Leu Leu Ser Ala Lys Lys Ser Arg
                85                  90                  95

Glu Leu Ala Ser Cys Ser His Leu Val Leu Leu Cys Gly His Tyr Glu
            100                 105                 110

Gly Ile Asp Glu Arg Ala Leu Thr Ala Glu Val Asp Glu Glu Ile Ser
        115                 120                 125

Ile Gly Asp Tyr Val Leu Thr Asn Gly Cys Ala Ala Ala Leu Val Leu
    130                 135                 140

Val Asp Ala Leu Ala Arg Phe Ile Pro Gly Val Leu Gly Asn Gln Glu
145                 150                 155                 160

Ser Ala Glu Tyr Asp Ser Leu Glu Asn Gly Leu Leu Glu Gly Pro Gln
                165                 170                 175

Tyr Thr Arg Pro Arg Val Phe Glu Gly Glu Ser Val Pro Glu Val Leu
            180                 185                 190

Leu Cys Gly Asp His Gln Lys Ile Ala Asp Trp Arg Lys Gln Val Ser
        195                 200                 205

Leu Glu Arg Thr Arg Glu Arg Arg Pro Asp Leu Tyr Leu Gln Tyr Phe
    210                 215                 220

Tyr Gly Asn Ser Ala Cys Leu Ser Thr Gln Glu Asp Leu Pro Arg Ile
225                 230                 235                 240

Glu Val Val Ser Pro Lys Thr Phe Ser Val Val Leu Glu Val Gln Asp
                245                 250                 255

Leu Arg Lys Ala Lys Lys Phe Tyr Ser Arg Met Phe Gly Lys Glu Cys
            260                 265                 270

Trp Asp Gly Asp Lys Leu Phe Leu Leu Gly Lys Thr Ser Leu Tyr Leu
        275                 280                 285

Gln Gln Thr Lys Glu Thr Arg Gly Pro Thr Thr Val Phe Ile Glu Leu
    290                 295                 300

Glu Thr Asp His Asp Phe Val Arg Phe Leu Lys Arg Trp Glu Ile Leu
305                 310                 315                 320

Gly Gly Glu Leu Gly Glu Gln Gly Thr Gly Gly Phe Pro Leu Arg Gln
                325                 330                 335

Val Phe Asp Leu Asp Gly His Ile Trp Val Val Ser Cys Val Gln Lys
            340                 345                 350
```

<210> SEQ ID NO 50
<211> LENGTH: 1056
<212> TYPE: DNA
<213> ORGANISM: Chlamydia trachomatis

<400> SEQUENCE: 50

```
atggagatag atattctctc tttattcccg gactattttg ctagtccttt acaggcgact      60

attttgggcc gagcaattaa acagggagct ttatctgttc gctcccgaga tattcgagag     120

ttcggcttag ggaaatggaa gcaggtagat gactctccct ataatggaga ggggatgctt     180

ttgatggcag agcctgtggt acaggctatt agaagcataa gaagaaagaa gtccaaggtc     240

atatacttat ctccgcaggg acaacttctt tccgcaaaga aaagtcgtga actggcgtcg     300

tgttcgcatt tggtattgtt atgtggacac tatgagggaa ttgatgaaag ggcgttgact     360

gccgaagtgg atgaggagat aagtattggt gattacgttc tcaccaatgg gtgcgcggcg     420

gctttagttc tcgtagatgc tcttgcgcgc ttcattccgg gagttttagg gaaccaagaa     480

agtgcagagt acgactctct tgaaaatgga ttgttagaag gtcctcagta cactcgtcca     540

cgggtttttg agggtgagtc ggtccctgaa gtgttgctct gtggagacca tcagaagatt     600
```

```
gcagattgga gaaaacaggt tagtctagag agaactagag aacgtcgacc agatctgtat    660

ctgcagtatt tttatggtaa cagtgcttgt ttaagtactc aagaggatct ccctaggata    720

gaggtagttt ctcccaaaac cttttctgta gttttagaag ttcaagatct tcgaaaagct    780

aagaagttct attccaggat gtttggaaaa gagtgttggg acggagataa attattcctt    840

ttagggaaga cgagtttgta cctgcaacag acaaaagaaa caagaggccc gaccacagta    900

tttatagagc tggagaccga tcatgatttt gttcgttttt taaaacgatg ggaaatactc    960

ggaggggagc ttggtgaaca agggacggga gggtttcctt taagacaggt ttttgattta   1020

gatggccata tttgggttgt ctcttgtgta cagaaa                             1056
```

```
<210> SEQ ID NO 51
<211> LENGTH: 550
<212> TYPE: PRT
<213> ORGANISM: Chlamydia trachomatis

<400> SEQUENCE: 51

Val Glu Ser Ser Arg Ile Leu Ile Thr Ser Ala Leu Pro Tyr Ala Asn
1               5                   10                  15

Gly Pro Leu His Phe Gly His Ile Thr Gly Ala Tyr Leu Pro Ala Asp
            20                  25                  30

Val Tyr Ala Arg Phe Gln Arg Leu Gln Gly Lys Glu Val Leu Tyr Ile
        35                  40                  45

Cys Gly Ser Asp Glu Tyr Gly Ile Ala Ile Thr Leu Asn Ala Glu Leu
    50                  55                  60

Ala Gly Met Gly Tyr Gln Glu Tyr Val Asp Met Tyr His Lys Leu His
65                  70                  75                  80

Lys Asp Thr Phe Lys Lys Leu Gly Ile Ser Val Asp Phe Phe Ser Arg
                85                  90                  95

Thr Thr Asn Thr Tyr His Pro Ala Ile Val Gln Asp Phe Tyr Arg Asn
            100                 105                 110

Leu Gln Glu Arg Gly Leu Val Glu Asn Gln Val Thr Glu Gln Leu Tyr
        115                 120                 125

Ser Glu Glu Glu Gly Lys Phe Leu Ala Asp Arg Tyr Val Val Gly Thr
    130                 135                 140

Cys Pro Lys Cys Gly Phe Asp Arg Ala Arg Gly Asp Glu Cys Gln Gln
145                 150                 155                 160

Cys Gly Ala Asp Tyr Glu Ala Arg Asp Leu Lys Glu Pro Arg Ser Lys
                165                 170                 175

Leu Thr Gly Ala Ala Leu Ser Leu Arg Asp Thr Glu His Ala Tyr Leu
            180                 185                 190

His Leu Glu Arg Met Lys Glu Asp Leu Leu Ala Phe Val Gln Gly Ile
        195                 200                 205

Tyr Leu Arg Pro His Met Arg Asn Phe Val Thr Asp Tyr Ile Glu His
    210                 215                 220

Leu Arg Pro Arg Ala Val Thr Arg Asp Leu Ser Trp Gly Ile Pro Val
225                 230                 235                 240

Pro Asp Leu Glu Asn Lys Val Phe Tyr Val Trp Phe Asp Ala Pro Ile
                245                 250                 255

Gly Tyr Ile Ser Gly Thr Met Asp Trp Ala Ala Ser Ile Gly Asp Pro
            260                 265                 270

Glu Ala Trp Lys Lys Phe Trp Leu Asp Asp Thr Val Thr Tyr Ala Gln
        275                 280                 285
```

-continued

```
Phe Ile Gly Lys Asp Asn Thr Ser Phe His Ala Ala Ile Phe Pro Ala
    290                 295                 300

Met Glu Ile Gly Gln Ser Leu Pro Tyr Lys Lys Val Asp Ala Leu Val
305                 310                 315                 320

Thr Ser Glu Phe Leu Leu Leu Glu Gly Phe Gln Phe Ser Lys Ser Asp
                325                 330                 335

Gly Asn Phe Ile Asp Met Asp Ala Phe Leu Glu Thr Tyr Ser Leu Asp
            340                 345                 350

Lys Leu Arg Tyr Val Leu Ala Ala Ile Ala Pro Glu Thr Ser Asp Ser
        355                 360                 365

Glu Phe Ser Phe Gln Glu Phe Lys Thr Arg Cys Asn Ser Glu Leu Val
    370                 375                 380

Gly Lys Tyr Gly Asn Phe Val Asn Arg Val Leu Ala Phe Ala Val Lys
385                 390                 395                 400

Asn Gly Cys Thr Glu Leu Ser Ser Pro Gln Leu Glu Gln Lys Asp Leu
                405                 410                 415

Asp Phe Ile Ser Lys Ser Gln Lys Leu Ala Lys Asp Ala Ala Glu His
            420                 425                 430

Tyr Ala Gln Tyr Ser Leu Arg Lys Ala Cys Ser Thr Ile Met Glu Leu
        435                 440                 445

Ala Ala Leu Gly Asn Gly Tyr Phe Asn Asp Glu Ala Pro Trp Lys Leu
    450                 455                 460

Ala Lys Glu Gly Asn Trp Asn Arg Val Arg Ala Ile Leu Phe Cys Ala
465                 470                 475                 480

Cys Tyr Cys Gln Lys Leu Leu Ala Leu Ile Ser Tyr Pro Ile Met Pro
                485                 490                 495

Glu Thr Ala Leu Lys Ile Leu Glu Met Ile Ala Pro His Ser Leu Asp
            500                 505                 510

Leu Gly Ser Gln Asp Pro Asp Arg Leu Gln Ser Leu Trp Thr Asp Ser
        515                 520                 525

Phe Phe Asp Tyr Ser Glu Glu Lys Phe Ser Leu Lys Glu Pro Glu Leu
    530                 535                 540

Leu Phe Thr Met Val Glu
545                 550
```

<210> SEQ ID NO 52
<211> LENGTH: 1650
<212> TYPE: DNA
<213> ORGANISM: Chlamydia trachomatis

<400> SEQUENCE: 52

```
gtggaatctt cccgtattct tattacttct gcgttgcctt acgcaaatgg tcctttgcat      60

tttggacata ttaccggtgc ttatttgcct gcagatgttt atgcgcgttt tcagagacta     120

caaggcaaag aggtcttgta tatttgtggt tctgatgaat acggaatcgc aattaccctt     180

aatgcagagt tggcaggcat ggggtatcaa gaatatgtcg acatgtatca taagcttcat     240

aaagatacct tcaagaaatt gggaatttct gtagatttct tttccagaac tacgaacact     300

tatcatcctg ctattgtgca agatttctat cgaaacttgc aggaacgcgg actggtagag     360

aatcaggtga ccgaacagct gtattctgag gaagaaggga agtttctagc ggaccgttat     420

gttgtaggta cttgtcccaa gtgtgggttc gatcgagctc gaggagatga gtgtcagcag     480

tgcggtgccg attacgaagc tagagatctg aaagagcctc gttctaaatt aacgggggca     540

gctttatctt tacgtgatac ggaacatgct tacttgcatt tggagcgcat gaaagaagat     600
```

-continued

```
ttgcttgctt tcgtgcaagg tatttatcta cgtcctcata tgcgtaattt cgttacggat     660

tacatcgagc atttacgtcc tcgagcagtg actcgagatt tgtcttgggg aatacccgtt     720

cctgatttgg aaaataaggt attctatgta tggttcgatg ctccaattgg ttacataagt     780

ggaactatgg attgggcagc atcgattgga gaccctgaag cttggaagaa gttttggttg     840

gacgatactg tgacctacgc acagtttata ggtaaagata atacttcttt ccatgcggct     900

attttccctg ctatggaaat aggacaatct cttccctata agaaagtgga tgctcttgta     960

acatcagaat ttttattgtt agaaggtttc cagttcagta aatcggatgg gaattttata    1020

gacatggatg cgtttttaga aacgtattcc ttggataaac tgcgttatgt gttggcagcg    1080

attgctccag agacttcgga tagcgaattc tctttccaag agttcaagac gcgatgcaat    1140

tctgagcttg tagggaagta tggaaatttt gtgaatcgag ttctagcttt tgctgttaag    1200

aatggatgca cagagctttc ttctcctcaa ttagagcaaa aggatttgga ttttatctca    1260

aaatctcaaa aacttgctaa ggatgcagcc gaacattacg cacaatacag tttgcgtaag    1320

gcgtgttcca cgattatgga attagctgct ttagggaatg gctatttcaa tgatgaagct    1380

ccatggaaat tggctaaaga gggtaactgg aatcgggtac gcgctattct attctgtgct    1440

tgttactgcc agaagttgct agctctcatt tcctatccta ttatgcctga aacagcattg    1500

aagattttgg aaatgatagc tccacattcc ttagatctag gttcccaaga tccagataga    1560

ttacaatctc tttggacaga ttcctttttt gattactcgg aagagaaatt ttctctgaaa    1620

gagcctgaat tattgttcac aatggtagag                                     1650
```

<210> SEQ ID NO 53
<211> LENGTH: 300
<212> TYPE: PRT
<213> ORGANISM: Chlamydia trachomatis

<400> SEQUENCE: 53

```
Met Pro Ser Ser Phe Val Ser Gln Leu Ser Pro Ser Leu Phe Ser Ile
1               5                   10                  15

Leu Arg Glu Gln Leu Glu Lys Lys Gly Phe Thr Ile Ser Ile Pro Pro
            20                  25                  30

His Thr Val Phe Gln Gly Arg Ser Pro Thr Val Ser Cys Thr Val Tyr
        35                  40                  45

Gln Ser Gly Lys Ile Val Val Gln Gly Lys Gly Thr Gln Glu Phe Val
    50                  55                  60

Glu Phe Phe Leu Glu Pro Glu Ile Leu Gln Thr Phe Ser Ser Gln Asn
65                  70                  75                  80

Val Gln Gln Asp Leu Arg Ser Arg Ile Gly Val Asp Glu Ser Gly Lys
                85                  90                  95

Gly Asp Phe Phe Gly Pro Leu Cys Thr Ala Gly Val Tyr Ala Ser Ser
            100                 105                 110

Pro Gln Ala Ile Glu Ala Leu Tyr Lys Thr Ser Ile Cys Asp Ser Lys
        115                 120                 125

Leu Ile Pro Asp Ala Lys Ile Leu Ser Leu Ala Gln Asn Ile Arg Ser
    130                 135                 140

Leu Cys Ala Cys Lys Val Ile Thr Leu Phe Pro Glu Lys Tyr Asn Ala
145                 150                 155                 160

Leu Tyr Ala Asn Phe Gln Asn Leu Asn Ser Leu Leu Ala Trp Thr His
                165                 170                 175

Ala Thr Ile Ile Asp Asn Leu Ala Pro His Pro Ala Gly Ala Val Phe
            180                 185                 190
```

```
Ala Ile Ser Asp Gln Phe Ala Ser Ser Glu Arg Val Leu Leu Gln Ala
        195                 200                 205

Val Arg Lys Lys Cys Ser Asp Ile Glu Leu Ile Gln Arg His Arg Ala
    210                 215                 220

Glu Gln Asp Val Val Val Ala Ala Ala Ser Ile Leu Ala Arg Glu Ala
225                 230                 235                 240

Phe Leu Ser Ser Ile His Ala Leu Glu Ser Gln Tyr Gln Ile Arg Leu
                245                 250                 255

Leu Lys Gly Ala Ser Gly Lys Val Lys Gln Arg Ala Lys Glu Ile Leu
            260                 265                 270

His Asn Lys Gly Gln Val Val Leu Glu Lys Val Cys Lys Thr His Phe
        275                 280                 285

Lys Thr Phe Asn Glu Val Leu Gly Ser Gly Asn Gln
    290                 295                 300


<210> SEQ ID NO 54
<211> LENGTH: 900
<212> TYPE: DNA
<213> ORGANISM: Chlamydia trachomatis

<400> SEQUENCE: 54

atgccctcct ctttcgtttc gcaactgtct ccttctttat tttctatact tcgagaacaa      60

ctagaaaaga aagggttcac catctctatc cccccccaca ctgtatttca aggaagatct     120

ccgaccgtta gctgcactgt atatcaatct gggaaaattg tagtacaggg taaaggaact     180

caagaatttg tagaattttt ccttgagcca gagattctac aaacgttctc ctcacagaac     240

gtacaacagg atttacgttc tcgcattggt gtggatgaat ctggaaaagg agattttttt     300

gggcctctgt gcactgctgg agtatatgct tcttccccac aagctataga agctctttat     360

aaaaccagca tttgtgattc taagctcatt cctgatgcta aatcctttc tttagcccaa      420

aacattcgct cgctttgtgc gtgtaaagtc attaccttgt tcccagaaaa atataacgca     480

ctatatgcca atttccagaa tttaaactcc ctcctagctt ggacacacgc cactattatc     540

gataatttgg ctcctcatcc tgcaggagca gtctttgcta tttcagacca attcgcctct     600

tcagagagag tccttctaca ggctgttcgc aagaagtgct cggatattga attaatccag     660

cgtcatcgtg cagaacaaga cgtggtggta gctgcagctt ctatcttagc tcgtgaagct     720

tttctctctt ccatacacgc cctagaatct caataccaaa tccgccttct aaaaggagct     780

tctgggaaag tcaagcaacg agccaaagag attcttcata acaaaggaca ggttgtatta     840

gaaaaagtct gtaaaacaca tttcaaaaca ttcaatgagg tgcttggttc gggcaatcaa     900


<210> SEQ ID NO 55
<211> LENGTH: 242
<212> TYPE: PRT
<213> ORGANISM: Chlamydia trachomatis

<400> SEQUENCE: 55

Met Lys Val Lys Ile Asn Asp Gln Phe Ile Cys Ile Ser Pro Tyr Ile
1               5                   10                  15

Ser Ala Arg Trp Asn Gln Ile Ala Phe Ile Glu Ser Cys Asp Gly Gly
            20                  25                  30

Thr Glu Gly Gly Ile Thr Leu Lys Leu His Leu Ile Asp Gly Glu Thr
        35                  40                  45

Val Ser Ile Pro Asn Leu Gly Gln Ala Ile Val Asp Glu Val Phe Gln
    50                  55                  60
```

Glu His Leu Leu Tyr Leu Glu Ser Thr Ala Pro Gln Lys Asn Lys Glu
65 70 75 80

Glu Glu Lys Ile Ser Ser Leu Leu Gly Ala Val Gln Gln Met Ala Lys
85 90 95

Gly Cys Glu Val Gln Val Phe Ser Gln Lys Gly Leu Val Ser Met Leu
100 105 110

Leu Gly Gly Ala Gly Ser Ile Asn Val Leu Leu Gln His Ser Pro Glu
115 120 125

His Lys Asp His Pro Asp Leu Pro Thr Asp Leu Leu Glu Arg Ile Ala
130 135 140

Gln Met Met Arg Ser Leu Ser Ile Gly Pro Thr Ser Ile Leu Ala Lys
145 150 155 160

Pro Glu Pro His Cys Asn Cys Leu His Cys Gln Ile Gly Arg Ala Thr
165 170 175

Val Glu Glu Glu Asp Ala Gly Val Ser Asp Glu Asp Leu Thr Phe Arg
180 185 190

Ser Trp Asp Ile Ser Gln Ser Gly Glu Lys Met Tyr Thr Val Thr Asp
195 200 205

Pro Leu Asn Pro Glu Glu Gln Phe Asn Val Tyr Leu Gly Thr Pro Ile
210 215 220

Gly Cys Thr Cys Gly Gln Pro Tyr Cys Glu His Val Lys Ala Val Leu
225 230 235 240

Tyr Thr

<210> SEQ ID NO 56
<211> LENGTH: 726
<212> TYPE: DNA
<213> ORGANISM: Chlamydia trachomatis

<400> SEQUENCE: 56
atgaaagtta aaattaatga tcagttcatt tgtatttccc catacatttc tgctcgatgg 60
aatcagatag ctttcataga gtcttgtgat ggagggacgg aagggggtat tactttgaaa 120
ctccatttaa ttgatggaga gacagtctct atacctaatc taggacaagc gattgttgat 180
gaggtgttcc aagagcactt gctatattta gagtccacag ctcctcagaa aaacaaggaa 240
gaggaaaaaa ttagctcttt gttaggagct gttcaacaaa tggctaaagg atgcgaagta 300
caggtttttt ctcaaaaggg cttggtttct atgttactag gaggagctgg ttcgattaat 360
gtgttgttgc aacattctcc agaacataag gatcatcctg atcttcctac cgatttactg 420
gagaggatag cgcaaatgat gcgttcatta tctataggac caacttctat tttagctaag 480
ccagagcctc attgcaactg tttgcattgt caaattggac gagctacagt ggaagaagag 540
gatgccggag tatcggatga ggatcttact tttcgttcat gggatatctc tcaaagtgga 600
gaaaagatgt acactgttac agatcctttg aatccagaag agcagtttaa tgtgtattta 660
ggaacgccga ttggatgcac atgtgggcag ccatactgtg aacacgtgaa agctgttctt 720
tatact 726

<210> SEQ ID NO 57
<211> LENGTH: 121
<212> TYPE: PRT
<213> ORGANISM: Chlamydia trachomatis

<400> SEQUENCE: 57

Met Gly Asn Leu Ile Lys Glu Leu Gln Asp Glu Gln Cys Arg Thr Asp

```
1               5                   10                  15

Leu Ala Asp Phe Cys Val Gly Asp Thr Ile Arg Val Ala Thr Asn Ile
            20                  25                  30

Ser Glu Gly Gly Lys Glu Arg Val Gln Val Phe Gln Gly Thr Val Met
        35                  40                  45

Ala Arg Lys Gly Gly Gly Ala Gly Glu Thr Val Ser Leu His Arg Val
    50                  55                  60

Ala Tyr Gly Glu Gly Met Glu Lys Ser Phe Leu Leu Asn Ser Pro Lys
65                  70                  75                  80

Ile Val Ser Ile Glu Val Val Lys Arg Gly Lys Val Ser Arg Ala Arg
                85                  90                  95

Leu Phe Tyr Leu Arg Gly Lys Thr Gly Lys Ala Ala Lys Val Lys Glu
            100                 105                 110

Leu Ile Gly Ser Arg Ala Ala Lys Lys
        115                 120


<210> SEQ ID NO 58
<211> LENGTH: 363
<212> TYPE: DNA
<213> ORGANISM: Chlamydia trachomatis

<400> SEQUENCE: 58

atggggaact taatcaagga attgcaagac gagcagtgca gaactgatct cgctgatttc      60

tgtgttggtg acacgattcg tgtggctaca aacatttcag aaggagggaa ggagcgggtt     120

caggtattcc aaggaacagt catggcccgt aaaggcggtg gtgcaggaga aacagtttct     180

cttcatagag ttgcttacgg tgaagggatg gagaagagct ttctactgaa tagccctaag     240

atcgtaagta ttgaagttgt aaaacgcgga aaagtatcgc gtgcacgcct cttctatttg     300

agaggaaaaa ctggtaaggc tgctaaagtt aaagagctta tcggttctcg ggctgctaag     360

aaa                                                                   363


<210> SEQ ID NO 59
<211> LENGTH: 257
<212> TYPE: PRT
<213> ORGANISM: Chlamydia trachomatis

<400> SEQUENCE: 59

Met Lys Arg Ile Leu Val Tyr Ser Asp Arg Gly Val Ser Pro Tyr Tyr
1               5                   10                  15

Leu Arg His Thr Val Arg Trp Leu Lys Gln Val Ala Ala Pro Phe Gln
            20                  25                  30

Met Glu Val Cys Arg Val Asn Gly Arg Phe Leu Ile His Glu Pro Leu
        35                  40                  45

Trp Glu Glu Thr Thr Gln Leu Leu Val Ile Pro Gly Gly Ala Asp Val
    50                  55                  60

Pro Tyr His Asn Val Leu His Gly Leu Gly Thr Ala Arg Ile Asp Asn
65                  70                  75                  80

Tyr Val Arg Glu Gly Gly Cys Tyr Leu Gly Ile Cys Ala Gly Ala Tyr
                85                  90                  95

Phe Gly Cys Ala Gln Phe Glu Phe Leu Glu Pro Thr Gly Ser Leu Phe
            100                 105                 110

Val Ala Lys Arg Asp Leu Gly Phe Phe Pro Gly Ala Ala Asn Gly Pro
        115                 120                 125

Val Tyr Glu Ser Ala Phe Ser Tyr Thr Ser Ser Ser Gly Val Leu Ala
    130                 135                 140
```

Ala Pro Leu Val Phe Ala Asp Phe Pro Gly Glu Ser Phe Ser Leu Phe
145 150 155 160

Asn Gly Gly Cys Cys Phe Glu Asn Ala Glu His Phe Pro Glu Ile Cys
165 170 175

Ile Glu Ala Arg Tyr Asn Asn Leu Leu Gly Lys Pro Ala Ala Ile Val
180 185 190

Ser Arg Arg Leu Asp Lys Gly Leu Val Val Leu Ser Gly Pro His Ile
195 200 205

Glu Tyr Leu Pro Glu Phe Cys Ser Leu Gln Glu Asp Asn Val Ile Gln
210 215 220

Ala Arg Glu Gln Ile Ala Ala His Ser Ser Ser Leu Glu Glu Tyr Lys
225 230 235 240

Gln Phe Leu Ile His Arg Leu Leu Ser Asn Val Val Glu His Val Leu
245 250 255

Tyr

<210> SEQ ID NO 60
<211> LENGTH: 771
<212> TYPE: DNA
<213> ORGANISM: Chlamydia trachomatis

<400> SEQUENCE: 60
atgaagcgta tcttagtgta ttcggataga ggagtttctc cttactattt gcgccatact 60
gttcgctggt tgaagcaggt agctgctcca ttccagatgg aggtatgtcg cgtgaatgga 120
cgtttcttga ttcatgagcc tctttgggaa gaaacaaccc agcttcttgt aattccagga 180
ggtgctgatg taccttatca taatgtgttg catggactgg ggacagcgcg tatcgataac 240
tacgtaagag agggaggctg ttacctaggt atttgcgcag gagcttattt tggttgcgcg 300
cagtttgaat ttctagagcc tacaggatct ttatttgttg ctaagcgaga tttaggtttt 360
ttcccgggag ctgctaatgg tcctgtttat gaaagcgcct ttcttatac aagttcctct 420 ggagttttag ccgctccact agttttcgct gattttcctg gagagagttt ctctcttttt 480
aatgggggat gctgtttcga aaatgcggaa catttccccg aaatatgcat cgaggcgcgc 540
tataataatc ttcttggaaa acctgcagct attgtctcca gacgcctcga taaggggcta 600
gtcgtgcttt ctggtcctca tatagagtac ctcccagagt tttgctcctt gcaagaagat 660
aatgttattc aggcgagaga gcaaattgca gcgcattctt cgagtctaga ggagtacaag 720
cagttcttaa tccatcgcct attgagtaat gtcgtcgagc acgttttgta t 771

<210> SEQ ID NO 61
<211> LENGTH: 148
<212> TYPE: PRT
<213> ORGANISM: Chlamydia trachomatis

<400> SEQUENCE: 61

Met Leu Lys Lys Pro Asn Arg Asn Asp Pro Cys Pro Cys Gly Ser Gly
1 5 10 15

Lys Lys Tyr Lys Gln Cys Cys Leu Lys Ser Gln Ala Leu Thr Ala Arg
20 25 30

His Thr Pro Glu Gly Lys Phe Lys Phe Ser Ile Thr Ala Ser Pro Ala
35 40 45

Ala Gly Ala Ser Thr Glu Gly Phe Thr Lys Leu Phe Arg Gln Ser Val
50 55 60

Asp Ser Tyr Thr Ser Glu Gln Lys Glu Gly Met Ser Arg Phe Leu Ile 65 70 75 80

Thr Lys Asn Lys Glu Pro Ile Gly Lys Arg Ala Ile Arg Lys Ala Lys
85 90 95

Ala Lys Glu Glu Arg Ile Ile Ser Glu Lys Leu Ser Gln His Glu Phe
100 105 110

Gln Val Met Asp Thr Glu Val Ser Gly Glu Asp Ile Gln Ser Ser Leu
115 120 125

Asp Tyr Glu Gln Phe Leu Pro Thr Glu Glu Asp Tyr Arg Val Gln Lys
130 135 140

Glu Glu Asp Ser
145

<210> SEQ ID NO 62
<211> LENGTH: 444
<212> TYPE: DNA
<213> ORGANISM: Chlamydia trachomatis

<400> SEQUENCE: 62
atgttgaaaa agcctaatag aaacgatcct tgtccttgtg ggtctgggaa gaagtataag 60
cagtgttgtt tgaaatcaca agctctaact gctcgccata ctcctgaagg gaagtttaag 120
ttttctataa cagcttcgcc tgccgcaggc gcttccacgg aaggtttcac aaaactgttt 180
cgccaatcag tggattctta tacctcagaa caaaaagagg ggatgagtcg gtttcttatt 240
actaaaaata aggaacctat agggaaacgc gcgattcgca aggctaaggc aaaagaagag 300
cgcatcattt cagagaaact aagccagcac gaatttcaag tgatggatac agaagtatcg 360
ggagaagata tacagtcttc actagattat gaacagtttc ttcctacaga agaagactac 420
cgtgtgcaga aagaggaaga ttca 444

<210> SEQ ID NO 63
<211> LENGTH: 857
<212> TYPE: PRT
<213> ORGANISM: Chlamydia trachomatis

<400> SEQUENCE: 63

Met Lys Lys Ser Leu Ile Ile Val Glu Ser Pro Ala Lys Ile Lys Thr
1 5 10 15

Leu Arg Lys Leu Leu Gly Glu Gly Phe Ile Phe Asp Ser Ser Leu Gly
20 25 30

His Ile Val Asp Leu Pro Ala Lys Gly Phe Gly Ile Asp Ile Glu Asn
35 40 45

Gly Phe Val Pro Asp Tyr Gln Ile Leu Glu Gly Lys Lys Glu Val Ile
50 55 60

Arg Lys Ile Cys Ala Glu Ala Lys Lys Cys Asp Val Val Tyr Leu Ala
65 70 75 80

Pro Asp Pro Asp Arg Glu Gly Glu Ala Ile Ala Trp His Ile Ala Asn
85 90 95

Gln Leu Pro Lys Asp Thr Lys Ile Gln Arg Ile Ser Phe Asn Ala Ile
100 105 110

Thr Lys Gly Ala Val Thr Glu Ala Leu Lys His Pro Arg Glu Ile Asp
115 120 125

Met Ala Leu Val Asn Ala Gln Gln Ala Arg Arg Phe Leu Asp Arg Ile
130 135 140

Val Gly Tyr Lys Ile Ser Pro Ile Leu Gly Arg Lys Leu Gln Arg Trp
145 150 155 160

-continued

```
Ser Gly Val Ser Ala Gly Arg Val Gln Ser Val Ala Leu Lys Leu Val
                165                 170                 175

Val Asp Arg Glu Tyr Ala Ile Glu Arg Phe Val Pro Val Glu Phe Trp
            180                 185                 190

Asn Ile Arg Val His Leu Lys Asp Pro Gln Thr Gln Lys Thr Phe Trp
        195                 200                 205

Ala His Leu His Ser Val Asn Gly Lys Lys Trp Glu Lys Glu Ile Pro
    210                 215                 220

Glu Gly Lys Thr Ser Asp Glu Val Ile Leu Ile Asp Ser Lys Glu Lys
225                 230                 235                 240

Ala Asp Glu Ile Val Ala Leu Leu Glu Ser Ala Thr Tyr Val Val Asp
                245                 250                 255

Arg Val Glu Ser Lys Glu Lys Lys Arg His Ala Tyr Pro Pro Phe Ile
            260                 265                 270

Thr Ser Thr Leu Gln Gln Glu Ala Ser Arg His Tyr Arg Phe Ser Ser
        275                 280                 285

Ser Arg Thr Met Asn Ile Ala Gln Thr Leu Tyr Glu Gly Val Asp Leu
    290                 295                 300

Asp Ser Gln Gly Ala Val Gly Leu Ile Thr Tyr Met Arg Thr Asp Ser
305                 310                 315                 320

Val Arg Thr Asp Pro Glu Ala Val Lys Gln Val Arg Lys Tyr Ile Glu
                325                 330                 335

Gly His Phe Gly Lys Glu Phe Val Pro Ser Ser Pro Asn Val Tyr Ala
            340                 345                 350

Thr Lys Lys Met Ala Gln Asp Ala His Glu Ala Ile Arg Pro Thr Asp
        355                 360                 365

Val Thr Ile Thr Pro Glu Ser Ile Arg Ser Lys Leu Thr Glu Asp Gln
    370                 375                 380

Tyr Lys Leu Tyr Ser Leu Ile Trp Lys Arg Phe Val Ala Ser Gln Met
385                 390                 395                 400

Ile Ser Ala Ile Tyr Asp Thr Leu Ala Ile Arg Ile Thr Thr Asn Lys
                405                 410                 415

Gly Ile Asp Leu Arg Ala Thr Gly Ser Cys Leu Lys Phe Lys Gly Phe
            420                 425                 430

Leu Ala Val Tyr Glu Glu Lys Arg Asp Glu Glu Gly Asp Glu Glu Glu
        435                 440                 445

Asn Ile His Leu Pro Lys Leu Asn Glu Arg Asp Val Leu Thr Lys Glu
    450                 455                 460

Glu Leu Glu Ala Glu Gln Ser His Thr Lys Pro Leu Pro Arg Phe Thr
465                 470                 475                 480

Glu Ala Ser Leu Val Lys Glu Leu Glu Lys Ser Gly Ile Gly Arg Pro
                485                 490                 495

Ser Thr Tyr Ala Thr Ile Met Asn Lys Ile Gln Ser Arg Glu Tyr Thr
            500                 505                 510

Leu Lys Glu Gly Gln Arg Leu Arg Pro Thr Glu Leu Gly Lys Val Val
        515                 520                 525

Cys Gln Phe Leu Glu Thr Asn Phe Pro Arg Ile Met Asp Ile Gly Phe
    530                 535                 540

Thr Ala Gly Met Glu Asp Glu Leu Glu Leu Ile Ala Asp Asn Lys Lys
545                 550                 555                 560

Pro Trp Lys Gln Leu Leu Gln Glu Phe Cys Glu Leu Phe Leu Pro Phe
                565                 570                 575

Val Val Thr Ala Glu Lys Glu Ala Phe Ile Pro Arg Ile Val Thr Glu
```

-continued 580 585 590

Ile Asp Cys Pro Lys Cys His Lys Gly Lys Leu Val Lys Ile Trp Ala
595 600 605

Lys Asn Arg Tyr Phe Phe Gly Cys Ser Glu Tyr Pro Thr Cys Asp Tyr
610 615 620

Lys Thr Ser Glu Glu Glu Leu Thr Phe Asp Lys Asn Glu Tyr Ala Glu
625 630 635 640

Asp Thr Pro Trp Asp Ala Pro Cys Ala Leu Cys Gly Gly Glu Met Lys
645 650 655

Val Arg His Gly Lys Phe Gly Ser Phe Leu Gly Cys Glu Asn Tyr Pro
660 665 670

Lys Cys His Tyr Ile Val Asn Leu Phe Lys Lys Gly Glu Ala Gly Ala
675 680 685

Glu Pro Glu Ala Thr Val His Cys Pro Ala Glu Gly Cys Thr Gly His
690 695 700

Leu Val Lys Arg Arg Ser Arg Phe Asn Lys Met Phe Tyr Ser Cys Ser
705 710 715 720

Glu Tyr Pro Ala Cys Ser Val Ile Gly Asn Ser Val Asp Ala Val Ile
725 730 735

Glu Lys Tyr Ala Gly Thr Pro Lys Thr Pro Tyr Glu Lys Lys Pro Lys
740 745 750

Ala Lys Lys Ser Ile Ala Ser Thr Lys Gly Lys Ala Ala Lys Thr Val
755 760 765

Lys Lys Ser Ser Ala Thr Thr Lys Lys Arg Ala Thr Lys Ala Tyr Thr
770 775 780

Pro Ser Ala Ala Leu Ala Ala Val Ile Gly Ala Asp Pro Val Gly Arg
785 790 795 800

Pro Glu Ala Thr Lys Lys Leu Trp Glu Tyr Ile Lys Glu Lys Gly Leu
805 810 815

Gln Ser Pro Gln Asn Lys Lys Ile Ile Ile Pro Asp Ser Lys Leu Gln
820 825 830

Gly Val Ile Gly Ala Asp Pro Ile Asp Met Phe Ala Leu Ser Lys Lys
835 840 845

Leu Ser Ala His Leu Ile Lys Glu Glu
850 855

<210> SEQ ID NO 64
<211> LENGTH: 2571
<212> TYPE: DNA
<213> ORGANISM: Chlamydia trachomatis

<400> SEQUENCE: 64
atgaaaaaat ccttaatcat cgttgaatcc ccagccaaga ttaaaacttt gcgtaagttg 60
ttaggagaag ggtttatttt tgactcttcc ttggggcata ttgttgatct tcctgcaaaa 120
gggtttggta ttgatattga aaatggattt gttccggact accaaatttt agaagggaag 180
aaagaggtta ttcggaaaat ttgcgccgaa gcgaaaaaat gtgatgtagt ttatctcgct 240
cccgatccag accgagaagg agaggctata gcatggcata tcgcgaatca gctgcctaag 300
gatactaaaa ttcaacgtat ttcattcaat gccattacta aaggagctgt taccgaagct 360
ttgaagcatc ctagggaaat tgatatggcg ttggtcaatg cacagcaggc acgacgcttt 420
ctagatcgca ttgtgggata caagatctct ccgatcctag gtcgcaagct gcaacgttgg 480
tctggggttt ctgcaggaag agtgcagtct gtagctctta aattagtagt agatcgggaa 540

-continued

```
tatgctatag aacgatttgt tcccgtcgaa ttttggaata tccgagtgca tcttaaagat    600
cctcaaaccc aaaagacatt ctgggctcat ttgcattccg tgaatgggaa gaaatgggaa    660
aaagaaattc ctgaagggaa gacttctgat gaagtgattt taattgattc taaagagaag    720
gcagatgaga ttgtcgctct attagaatca gctacatatg ttgtagatcg tgtagagtct    780
aaagagaaaa aacgtcacgc ctatcctccg tttattactt ctacgttgca gcaagaagct    840
agtcgtcatt accgcttttc ctcttccaga acgatgaaca tagcgcagac tttatatgaa    900
ggggtagatt tagatagtca aggtgctgtg ggattgatca catacatgcg aaccgattcc    960
gtacgtacgg atcctgaagc tgtaaaacag gtgcgcaaat atatcgaagg tcattttggt   1020
aaggaattcg ttccttcttc tccgaacgtg tatgccacga aaaaaatggc acaggatgca   1080
cacgaagcta tacgtcctac agatgttaca atcactccgg aatcgatacg cagtaagtta   1140
acggaagatc agtacaagct gtattctttg atatggaagc gttttgttgc atcacaaatg   1200
atatccgcaa tttacgatac actcgcgatt cgtattacga cgaataaagg tatcgatctg   1260
cgtgctacag gctcttgttt gaaatttaaa gggttcttag ctgtttacga agagaaaaga   1320
gatgaagaag gggatgaaga ggaaaacatt catcttccga agcttaatga gcgagatgtt   1380
ctaacaaagg aagagttaga agcagaacaa tcgcatacca agcctttgcc gcgatttaca   1440
gaagcttctt tagtgaaaga actcgagaag tcaggaatag ggagaccttc tacctatgcc   1500
actatcatga ataaaatcca gagtcgggaa tatacgttga aagaagggca aaggctacgt   1560
cctactgaat taggaaaagt agtttgtcag tttttagaaa cgaattttcc tcgtattatg   1620
gatattggtt ttaccgctgg catggaagat gagttagaac tgattgctga taataaaaaa   1680
ccttggaagc agctattaca agaattttgt gaactctttc ttccttttgt agtcacggca   1740
gaaaaagaag cctttatccc tcgtattgtg acagaaatag actgtccaaa atgtcataaa   1800
gggaaattag taaaaatttg ggctaaaaat cgctatttct ttggttgctc cgaatatcct   1860
acttgcgact ataaaacttc ggaagaggag ctgacgttcg acaaaaacga gtatgctgaa   1920
gacactcctt gggacgcacc ctgtgctctg tgcggaggag aaatgaaagt ccggcatggg   1980
aaatttggaa gtttccttgg ctgcgagaac tatccgaagt gtcactacat tgttaatctt   2040
ttcaaaaagg gagaagctgg ggctgagcct gaagcgacag tgcattgtcc tgcagaagga   2100
tgtacaggac accttgtgaa aagacgctca cgatttaata aaatgtttta ttcttgctcc   2160
gaatatcctg catgtagcgt gattggtaac tctgtagatg ctgtaattga aaagtatgca   2220
ggaacgccta aaactcctta tgagaagaaa ccaaaagcga aaaaatcaat agcctctacc   2280
aagggaaagg ctgcaaaaac agtgaaaaaa agctcagcaa caacaaaaaa acgagctacc   2340
aaagcgtaca caccttctgc tgctttagca gcggtgattg gtgcggatcc tgtagggcgt   2400
cccgaagcca ctaagaagct atgggagtat attaaggaaa aaggattgca atcccctcaa   2460
aataaaaaaa tcattattcc tgatagtaaa ttgcagggag tgataggagc tgatccaatc   2520
gacatgttcg cgctatctaa aaaattaagc gcgcacttaa tcaaggaaga g            2571
```

<210> SEQ ID NO 65
<211> LENGTH: 1770
<212> TYPE: PRT
<213> ORGANISM: Chlamydia trachomatis

<400> SEQUENCE: 65

```
Met Lys Phe Met Ser Ala Thr Ala Val Phe Ala Ala Ala Leu Ser Ser
1               5                   10                  15
```

```
Val Thr Glu Ala Ser Ser Ile Gln Asp Gln Ile Lys Asn Thr Asp Cys
            20                  25                  30

Asn Val Ser Lys Leu Gly Tyr Ser Thr Ser Gln Ala Phe Thr Asp Met
        35                  40                  45

Met Leu Ala Asp Asn Thr Glu Tyr Arg Ala Ala Asp Ser Val Ser Phe
    50                  55                  60

Tyr Asp Phe Ser Thr Ser Ser Arg Leu Pro Arg Lys His Leu Ser Ser
65                  70                  75                  80

Ser Ser Glu Ala Ser Pro Thr Thr Glu Gly Val Ser Ser Ser Ser Ser
                85                  90                  95

Gly Glu Thr Asp Glu Lys Thr Glu Glu Glu Leu Asp Asn Gly Gly Ile
            100                 105                 110

Ile Tyr Ala Arg Glu Lys Leu Thr Ile Ser Glu Ser Gln Asp Ser Leu
        115                 120                 125

Ser Asn Gln Ser Ile Glu Leu His Asp Asn Ser Ile Phe Phe Gly Glu
    130                 135                 140

Gly Glu Val Ile Phe Asp His Arg Val Ala Leu Lys Asn Gly Gly Ala
145                 150                 155                 160

Ile Tyr Gly Glu Lys Glu Val Val Phe Glu Asn Ile Lys Ser Leu Leu
                165                 170                 175

Val Glu Val Asn Ile Ala Val Glu Lys Gly Gly Ser Val Tyr Ala Lys
            180                 185                 190

Glu Arg Val Ser Leu Glu Asn Val Thr Glu Ala Thr Phe Ser Ser Asn
        195                 200                 205

Gly Gly Glu Gln Gly Gly Gly Gly Ile Tyr Ser Glu Gln Asp Met Leu
    210                 215                 220

Ile Ser Asp Cys Asn Asn Val His Phe Gln Gly Asn Ala Ala Gly Ala
225                 230                 235                 240

Thr Ala Val Lys Gln Cys Leu Asp Glu Glu Met Ile Val Leu Leu Ala
                245                 250                 255

Glu Cys Val Asp Ser Leu Ser Glu Asp Thr Leu Asp Ser Thr Pro Glu
            260                 265                 270

Thr Glu Gln Thr Glu Ser Asn Gly Asn Gln Asp Gly Ser Ser Glu Thr
        275                 280                 285

Glu Asp Thr Gln Val Ser Glu Ser Pro Glu Ser Thr Pro Ser Pro Asp
    290                 295                 300

Asp Val Leu Gly Lys Gly Gly Gly Ile Tyr Thr Glu Lys Ser Leu Thr
305                 310                 315                 320

Ile Thr Gly Ile Thr Gly Thr Ile Asp Phe Val Ser Asn Ile Ala Thr
                325                 330                 335

Asp Ser Gly Ala Gly Val Phe Thr Lys Glu Asn Leu Ser Cys Thr Asn
            340                 345                 350

Thr Asn Ser Leu Gln Phe Leu Lys Asn Ser Ala Gly Gln His Gly Gly
        355                 360                 365

Gly Ala Tyr Val Thr Gln Thr Met Ser Val Thr Asn Thr Thr Ser Glu
    370                 375                 380

Ser Ile Thr Thr Pro Pro Leu Ile Gly Glu Val Ile Phe Ser Glu Asn
385                 390                 395                 400

Thr Ala Lys Gly His Gly Gly Gly Ile Cys Thr Asn Lys Leu Ser Leu
                405                 410                 415

Ser Asn Leu Lys Thr Val Thr Leu Thr Lys Asn Ser Ala Lys Glu Ser
            420                 425                 430

Gly Gly Ala Ile Phe Thr Asp Leu Ala Ser Ile Pro Ile Thr Asp Thr
```

-continued

```
        435                 440                 445

Pro Glu Ser Ser Thr Pro Ser Ser Ser Ser Pro Ala Ser Thr Pro Glu
    450                 455                 460

Val Val Ala Ser Ala Lys Ile Asn Arg Phe Phe Ala Ser Thr Ala Lys
465                 470                 475                 480

Pro Ala Ala Pro Ser Leu Thr Glu Ala Glu Ser Asp Gln Thr Asp Gln
                485                 490                 495

Thr Glu Thr Ser Asp Thr Asn Ser Asp Ile Asp Val Ser Ile Glu Asn
            500                 505                 510

Ile Leu Asn Val Ala Ile Asn Gln Asn Thr Ser Ala Lys Lys Gly Gly
        515                 520                 525

Ala Ile Tyr Gly Lys Lys Ala Lys Leu Ser Arg Ile Asn Asn Leu Glu
    530                 535                 540

Leu Ser Gly Asn Ser Ser Gln Asp Val Gly Gly Gly Leu Cys Leu Thr
545                 550                 555                 560

Glu Ser Val Glu Phe Asp Ala Ile Gly Ser Leu Leu Ser His Tyr Asn
                565                 570                 575

Ser Ala Ala Lys Glu Gly Gly Ala Ile His Ser Lys Thr Val Thr Leu
            580                 585                 590

Ser Asn Leu Lys Ser Thr Phe Thr Phe Ala Asp Asn Thr Val Lys Ala
        595                 600                 605

Ile Val Glu Ser Thr Pro Glu Ala Pro Glu Glu Ile Pro Pro Val Glu
    610                 615                 620

Gly Glu Glu Ser Thr Ala Thr Glu Asp Pro Asn Ser Asn Thr Glu Gly
625                 630                 635                 640

Ser Ser Ala Asn Thr Asn Leu Glu Gly Ser Gln Gly Asp Thr Ala Asp
                645                 650                 655

Thr Gly Thr Gly Asp Val Asn Asn Glu Ser Gln Asp Thr Ser Asp Thr
            660                 665                 670

Gly Asn Ala Glu Ser Glu Glu Gln Leu Gln Asp Ser Thr Gln Ser Asn
        675                 680                 685

Glu Glu Asn Thr Leu Pro Asn Ser Asn Ile Asp Gln Ser Asn Glu Asn
    690                 695                 700

Thr Asp Glu Ser Ser Asp Ser His Thr Glu Glu Ile Thr Asp Glu Ser
705                 710                 715                 720

Val Ser Ser Ser Ser Glu Ser Gly Ser Ser Thr Pro Gln Asp Gly Gly
                725                 730                 735

Ala Ala Ser Ser Gly Ala Pro Ser Gly Asp Gln Ser Ile Ser Ala Asn
            740                 745                 750

Ala Cys Leu Ala Lys Ser Tyr Ala Ala Ser Thr Asp Ser Ser Pro Val
        755                 760                 765

Ser Asn Ser Ser Gly Ser Glu Glu Pro Val Thr Ser Ser Ser Asp Ser
    770                 775                 780

Asp Val Thr Ala Ser Ser Asp Asn Pro Asp Ser Ser Ser Ser Gly Asp
785                 790                 795                 800

Ser Ala Gly Asp Ser Glu Glu Pro Thr Glu Pro Glu Ala Gly Ser Thr
                805                 810                 815

Thr Glu Thr Leu Thr Leu Ile Gly Gly Gly Ala Ile Tyr Gly Glu Thr
            820                 825                 830

Val Lys Ile Glu Asn Phe Ser Gly Gln Gly Ile Phe Ser Gly Asn Lys
        835                 840                 845

Ala Ile Asp Asn Thr Thr Glu Gly Ser Ser Ser Lys Ser Asp Val Leu
    850                 855                 860
```

```
Gly Gly Ala Val Tyr Ala Lys Thr Leu Phe Asn Leu Asp Ser Gly Ser
865                 870                 875                 880

Ser Arg Arg Thr Val Thr Phe Ser Gly Asn Thr Val Ser Ser Gln Ser
                885                 890                 895

Thr Thr Gly Gln Val Ala Gly Gly Ala Ile Tyr Ser Pro Thr Val Thr
            900                 905                 910

Ile Ala Thr Pro Val Val Phe Ser Lys Asn Ser Ala Thr Asn Asn Ala
        915                 920                 925

Asn Asn Thr Thr Asp Thr Gln Arg Lys Asp Thr Phe Gly Gly Ala Ile
    930                 935                 940

Gly Ala Thr Ser Ala Val Ser Leu Ser Gly Gly Ala His Phe Leu Glu
945                 950                 955                 960

Asn Val Ala Asp Leu Gly Ser Ala Ile Gly Leu Val Pro Gly Thr Gln
                965                 970                 975

Asn Thr Glu Thr Val Lys Leu Glu Ser Gly Ser Tyr Tyr Phe Glu Lys
            980                 985                 990

Asn Lys Ala Leu Lys Arg Ala Thr  Ile Tyr Ala Pro Val  Val Ser Ile
        995                 1000                 1005

Lys Ala  Tyr Thr Ala Thr Phe  Asn Gln Asn Arg Ser  Leu Glu Glu
    1010                 1015                 1020

Gly Ser  Ala Ile Tyr Phe Thr  Lys Glu Ala Ser Ile  Glu Ser Leu
    1025                 1030                 1035

Gly Ser  Val Leu Phe Thr Gly  Asn Leu Val Thr Leu  Thr Leu Ser
    1040                 1045                 1050

Thr Thr  Thr Glu Gly Thr Pro  Ala Thr Thr Ser Gly  Asp Val Thr
    1055                 1060                 1065

Lys Tyr  Gly Ala Ala Ile Phe  Gly Gln Ile Ala Ser  Ser Asn Gly
    1070                 1075                 1080

Ser Gln  Thr Asp Asn Leu Pro  Leu Lys Leu Ile Ala  Ser Gly Gly
    1085                 1090                 1095

Asn Ile  Cys Phe Arg Asn Asn  Glu Tyr Arg Pro Thr  Ser Ser Asp
    1100                 1105                 1110

Thr Gly  Thr Ser Thr Phe Cys  Ser Ile Ala Gly Asp  Val Lys Leu
    1115                 1120                 1125

Thr Met  Gln Ala Ala Lys Gly  Lys Thr Ile Ser Phe  Phe Asp Ala
    1130                 1135                 1140

Ile Arg  Thr Ser Thr Lys Lys  Thr Gly Thr Gln Ala  Thr Ala Tyr
    1145                 1150                 1155

Asp Thr  Leu Asp Ile Asn Lys  Ser Glu Asp Ser Glu  Thr Val Asn
    1160                 1165                 1170

Ser Ala  Phe Thr Gly Thr Ile  Leu Phe Ser Ser Glu  Leu His Glu
    1175                 1180                 1185

Asn Lys  Ser Tyr Ile Pro Gln  Asn Val Val Leu His  Ser Gly Ser
    1190                 1195                 1200

Leu Val  Leu Lys Pro Asn Thr  Glu Leu His Val Ile  Ser Phe Glu
    1205                 1210                 1215

Gln Lys  Glu Gly Ser Ser Leu  Val Met Thr Pro Gly  Ser Val Leu
    1220                 1225                 1230

Ser Asn  Gln Thr Val Ala Asp  Gly Ala Leu Val Ile  Asn Asn Met
    1235                 1240                 1245

Thr Ile  Asp Leu Ser Ser Val  Glu Lys Asn Gly Ile  Ala Glu Gly
    1250                 1255                 1260
```

-continued

```
Asn Ile  Phe Thr Pro Pro Glu  Leu Arg Ile Ile Asp  Thr Thr Thr
    1265                 1270                 1275

Gly Gly  Ser Gly Gly Thr Pro  Ser Thr Asp Ser Glu  Ser Asn Gln
    1280                 1285                 1290

Asn Ser  Asp Asp Thr Glu Glu  Gln Asn Asn Asn Asp  Ala Ser Asn
    1295                 1300                 1305

Gln Gly  Glu Ser Ala Asn Gly  Ser Ser Ser Pro Ala  Val Ala Ala
    1310                 1315                 1320

Ala His  Thr Ser Arg Thr Arg  Asn Phe Ala Ala Ala  Ala Thr Ala
    1325                 1330                 1335

Thr Pro  Thr Thr Thr Pro Thr  Ala Thr Thr Thr Thr  Ser Asn Gln
    1340                 1345                 1350

Val Ile  Leu Gly Gly Glu Ile  Lys Leu Ile Asp Pro  Asn Gly Thr
    1355                 1360                 1365

Phe Phe  Gln Asn Pro Ala Leu  Arg Ser Asp Gln Gln  Ile Ser Leu
    1370                 1375                 1380

Leu Val  Leu Pro Thr Asp Ser  Ser Lys Met Gln Ala  Gln Lys Ile
    1385                 1390                 1395

Val Leu  Thr Gly Asp Ile Ala  Pro Gln Lys Gly Tyr  Thr Gly Thr
    1400                 1405                 1410

Leu Thr  Leu Asp Pro Asp Gln  Leu Gln Asn Gly Thr  Ile Ser Val
    1415                 1420                 1425

Leu Trp  Lys Phe Asp Ser Tyr  Arg Gln Trp Ala Tyr  Val Pro Arg
    1430                 1435                 1440

Asp Asn  His Phe Tyr Ala Asn  Ser Ile Leu Gly Ser  Gln Met Leu
    1445                 1450                 1455

Met Val  Thr Val Lys Gln Gly  Leu Leu Asn Asp Lys  Met Asn Leu
    1460                 1465                 1470

Ala Arg  Phe Glu Glu Val Ser  Tyr Asn Asn Leu Trp  Ile Ser Gly
    1475                 1480                 1485

Leu Gly  Thr Met Leu Ser Gln  Val Gly Thr Pro Thr  Ser Glu Glu
    1490                 1495                 1500

Phe Thr  Tyr Tyr Ser Arg Gly  Ala Ser Val Ala Leu  Asp Ala Lys
    1505                 1510                 1515

Pro Ala  His Asp Val Ile Val  Gly Ala Ala Phe Ser  Lys Met Ile
    1520                 1525                 1530

Gly Lys  Thr Lys Ser Leu Lys  Arg Glu Asn Asn Tyr  Thr His Lys
    1535                 1540                 1545

Gly Ser  Glu Tyr Ser Tyr Gln  Ala Ser Val Tyr Gly  Gly Lys Pro
    1550                 1555                 1560

Phe His  Phe Val Ile Asn Lys  Lys Thr Glu Lys Ser  Leu Pro Leu
    1565                 1570                 1575

Leu Leu  Gln Gly Val Ile Ser  Tyr Gly Tyr Ile Lys  His Asp Thr
    1580                 1585                 1590

Val Thr  His Tyr Pro Thr Ile  Arg Glu Arg Asn Lys  Gly Glu Trp
    1595                 1600                 1605

Glu Asp  Leu Gly Trp Leu Thr  Ala Leu Arg Val Ser  Ser Val Leu
    1610                 1615                 1620

Arg Thr  Pro Ala Gln Gly Asp  Thr Lys Arg Ile Thr  Val Tyr Gly
    1625                 1630                 1635

Glu Leu  Glu Tyr Ser Ser Ile  Arg Gln Lys Gln Phe  Thr Glu Thr
    1640                 1645                 1650

Glu Tyr  Asp Pro Arg Tyr Phe  Asp Asn Cys Thr Tyr  Arg Asn Leu
```

-continued

```
    1655                1660                1665

Ala Ile  Pro Met Gly Leu Ala  Phe Glu Gly Glu Leu  Ser Gly Asn
    1670                1675                1680

Asp Ile  Leu Met Tyr Asn Arg  Phe Ser Val Ala Tyr  Met Leu Ser
    1685                1690                1695

Ile Tyr  Arg Asn Ser Pro Thr  Cys Lys Tyr Gln Val  Leu Ser Ser
    1700                1705                1710

Gly Glu  Gly Gly Glu Ile Ile  Cys Gly Val Pro Thr  Arg Asn Ser
    1715                1720                1725

Ala Arg  Gly Glu Tyr Ser Thr  Gln Leu Tyr Leu Gly  Pro Leu Trp
    1730                1735                1740

Thr Leu  Tyr Gly Ser Tyr Thr  Ile Glu Ala Asp Ala  His Thr Leu
    1745                1750                1755

Ala His  Met Met Asn Cys Gly  Ala Arg Met Thr Phe
    1760                1765                1770


<210> SEQ ID NO 66
<211> LENGTH: 5310
<212> TYPE: DNA
<213> ORGANISM: Chlamydia trachomatis

<400> SEQUENCE: 66

atgaaattta tgtcagctac tgctgtattt gctgcagcac tctcctccgt tactgaggcg     60

agctcgatcc aagatcaaat aaagaatacc gactgcaatg ttagcaaatt aggatattca    120

acttctcaag catttactga tatgatgcta gcagacaaca cagagtatcg agctgctgat    180

agtgtttcat tctatgactt ttcgacatct tccagattac ctagaaaaca tcttagtagt    240

agtagtgaag cttctccaac gacagaagga gtgtcttcat cttcatctgg agaaactgat    300

gagaaaacag aagaagaact agacaatggc ggaatcattt atgctagaga gaaactaact    360

atctcagaat ctcaggactc tctctctaat caaagcatag aactccatga caatagtatt    420

ttcttcggag aaggtgaagt tatctttgat cacagagttg ccctcaaaaa cggaggagct    480

atttatggag agaaagaggt agtctttgaa aacataaaat ctctactagt agaagtaaat    540

atcgcggtcg agaaaggggg tagcgtctat gcaaaagaac gagtatcttt agaaaatgtt    600

accgaagcaa ccttctcctc caatggtggg gaacaaggtg gtggtggaat ctattcagaa    660

caggatatgt taatcagtga ttgcaacaat gtacatttcc aagggaatgc tgcaggagca    720

acagcagtaa aacaatgtct ggatgaagaa atgatcgtat tgctcgcaga atgcgttgat    780

agcttatccg aagatacact ggatagcact ccagaaacgg aacagactga gtcaaatgga    840

aatcaagacg gttcgtctga aacagaagat acacaagtat cagaatcacc agaatcaact    900

cctagccccg acgatgtttt aggtaaaggt ggtggtatct atacagaaaa atctttgacc    960

atcactggaa ttacagggac tatagatttt gtcagtaaca tagctaccga ttctggagca   1020

ggtgtattca ctaaagaaaa cttgtcttgc accaacacga atagcctaca gtttttgaaa   1080

aactcggcag gtcaacatgg aggaggagcc tacgttactc aaaccatgtc tgttactaat   1140

acaactagtg aaagtataac tactcccccct ctcataggag aagtgatttt ctctgaaaat   1200

acagctaaag ggcacggtgg tggtatctgc actaacaaac tttctttatc taatttaaaa   1260

acggtgactc tcactaaaaa ctctgcaaag gagtctggag gagctatttt tacagatctg   1320

gcgtctatac caataacaga taccccagaa tcttctaccc cctcttcctc ctcgcctgca   1380

agcactcctg aagtagttgc ttctgctaaa ataaatcgat tctttgcctc tacggcaaaa   1440
```

-continued

```
ccggcagccc cttctctaac agaggctgag tctgatcaaa cggatcaaac agaaacttct   1500
gatactaata gcgatataga cgtgtcgatt gagaacattt tgaatgtcgc tatcaatcaa   1560
aacacttctg cgaaaaaagg aggggctatt tacgggaaaa aagctaaact ttcccgtatt   1620
aacaatcttg aactttcagg gaattcatcc caggatgtag gaggaggtct ctgtttaact   1680
gaaagcgtag aatttgatgc aattggatcg ctcttatccc actataactc tgctgctaaa   1740
gaaggtgggg ctattcattc taaaacggtt actctatcta acctcaagtc taccttcact   1800
tttgcagata acactgttaa agcaatagta gaaagcactc ctgaagctcc agaagagatt   1860
cctccagtag aaggagaaga gtctacagca acagaagatc caaattctaa tacagaagga   1920
agttcggcta acactaacct tgaaggatct caaggggata ctgctgatac agggactggt   1980
gatgttaaca atgagtctca agacacatca gatactggaa acgctgaatc tgaagaacaa   2040
ctacaagatt ctacacaatc taatgaagaa aatacccttc ccaatagtaa tattgatcaa   2100
tctaacgaaa acacagacga atcatctgat agccacactg aggaaataac tgacgagagt   2160
gtctcatcgt cctctgaaag tggatcatct actcctcaag atggaggagc agcttcttca   2220
ggggctccct caggagatca atctatctct gcaaacgctt gtttagctaa aagctatgct   2280
gcgagtactg atagctcccc cgtatctaat tcttcaggtt cagaagagcc tgtcacttct   2340
tcttcagatt cagacgttac tgcatcttct gataatccag actcttcctc atctggagat   2400
agcgctggag actctgaaga accgactgag ccagaagctg gttctacaac agaaactctt   2460
actttaatag gaggaggtgc tatctatgga gaaactgtta agattgagaa cttctctggc   2520
caaggaatat tttctggaaa caaagctatc gataacacca cagaaggctc ctcttccaaa   2580
tctgacgtcc tcggaggtgc ggtctatgct aaaacattgt ttaatctcga tagcgggagc   2640
tctagacgaa ctgtcacctt ctccgggaat actgtctctt ctcaatctac aacaggtcag   2700
gttgctggag gagctatcta ctctcctact gtaaccattg ctactcctgt agtatttttct   2760
aaaaactctg caacaaacaa tgctaataac actacagata ctcagagaaa agacaccttt   2820
ggaggagcta tcggagctac ttctgctgtt tctctatcag gaggggctca tttcttagaa   2880
aacgttgctg acctcggatc tgctattggg ttggtgccag gcacacaaaa tacagaaaca   2940
gtgaaattag agtctggctc ctactacttt gaaaaaaata aagctttaaa acgagctact   3000
atttacgcac ctgtcgtttc cattaaagcc tatactgcga catttaacca aaacagatct   3060
ctagaagaag gaagcgcgat ttactttaca aaagaagcat ctattgagtc tttaggctct   3120
gttctcttca caggaaactt agtaacccta acgctaagca caactacaga aggcacacca   3180
gccacaacct caggagatgt aacaaaatat ggtgctgcta tctttggaca aatagcaagc   3240
tcaaacggat ctcagacgga taaccttccc ctgaaactca ttgcttcagg aggaaatatt   3300
tgtttccgaa acaatgaata ccgtcctact tcttctgata ccggaacctc tactttctgt   3360
agtattgcgg gagatgttaa attaaccatg caagctgcaa aagggaaaac gatcagtttc   3420
tttgatgcaa tccggacctc tactaagaaa acaggtacac aggcaactgc ctacgatact   3480
ctcgatatta ataaatctga ggattcagaa actgtaaact ctgcgtttac aggaacgatt   3540
ctgttctcct ctgaattaca tgaaaataaa tcctatattc cacaaaacgt agttctacac   3600
agtggatctc ttgtattgaa gccaaatacc gagcttcatg ttatttcttt tgagcagaaa   3660
gaaggctctt ctctcgttat gacacctgga tctgttcttt cgaaccagac tgttgctgat   3720
ggagctttgg tcataaataa catgaccatt gatttatcca gcgtagagaa aaatggtatt   3780
gctgaaggaa atatctttac tcctccagaa ttgagaatca tagacactac tacaggtgga   3840
```

```
agcggtggaa ccccatctac agatagtgaa agtaaccaga atagtgatga taccgaggag   3900
caaaataata atgacgcctc gaatcaagga gaaagcgcga atggatcgtc ttctcctgca   3960
gtagctgctg cacacacatc tcgtacaaga aactttgccg ctgcagctac agccacacct   4020
acgacaacac caacggctac aactacaaca agcaaccaag taatcctagg aggagaaatt   4080
aaactcatcg atcctaatgg gaccttcttc cagaaccctg cattaagatc cgaccaacaa   4140
atctccttgt tagtgctccc tacagactca tcaaaaatgc aagctcagaa aatagtactg   4200
acgggtgata ttgctcctca gaaaggatat acaggaacac tcactctgga tcctgatcaa   4260
ctacaaaatg gaacgatctc agtgctctgg aaatttgact cttatagaca atgggcttat   4320
gtacctagag acaatcattt ctatgcgaac tcgattctgg gatctcaaat gttaatggtc   4380
acagtcaaac aaggcttgct caacgataaa atgaatctag ctcgctttga ggaagttagc   4440
tataacaacc tgtggatatc aggactagga acgatgctat cgcaagtagg aacacctact   4500
tctgaagaat tcacttatta cagcagagga gcttctgttg ccttagatgc taaaccagcc   4560
catgatgtga ttgttggagc tgcatttagt aagatgatcg ggaaaacaaa atccttgaaa   4620
agagagaata actacactca caaaggatcc gaatattctt accaagcatc ggtatacgga   4680
ggcaaaccat tccactttgt aatcaataaa aaaacggaaa aatcgctacc gctattgtta   4740
caaggagtca tctcttacgg atatatcaaa catgatacag tgactcacta tccaacgatc   4800
cgtgaacgaa acaaaggaga atgggaagac ttaggatggc tgacagctct ccgtgtctcc   4860
tctgtcttaa gaactcctgc acaaggggat actaaacgta tcactgttta cggagaattg   4920
gaatactcca gtatccgtca gaaacaattc acagaaacag aatacgatcc tcgttacttc   4980
gacaactgca cctatagaaa cttagcaatt cctatggggt tagcattcga aggagagctc   5040
tctggtaacg atattttgat gtacaacaga ttctctgtag catacatgct atcaatctat   5100
cgaaattctc caacatgcaa ataccaagtg ctctcttcag gagaaggcgg agaaattatt   5160
tgtggagtac cgacaagaaa ctcagctcgc ggagaataca gcacgcagct gtacctggga   5220
cctttgtgga ctctgtatgg atcctacacg atagaagcag acgcacatac actagctcat   5280
atgatgaact gcggtgctcg tatgacattc                                    5310
```

<210> SEQ ID NO 67
<211> LENGTH: 878
<212> TYPE: PRT
<213> ORGANISM: Chlamydia trachomatis

<400> SEQUENCE: 67

```
Met Arg Pro Asp His Met Asn Phe Cys Cys Leu Cys Ala Ala Ile Leu
1               5                   10                  15

Ser Ser Thr Ala Val Leu Phe Gly Gln Asp Pro Leu Gly Glu Thr Ala
            20                  25                  30

Leu Leu Thr Lys Asn Pro Asn His Val Val Cys Thr Phe Phe Glu Asp
        35                  40                  45

Cys Thr Met Glu Ser Leu Phe Pro Ala Leu Cys Ala His Ala Ser Gln
    50                  55                  60

Asp Asp Pro Leu Tyr Val Leu Gly Asn Ser Tyr Cys Trp Phe Val Ser
65                  70                  75                  80

Lys Leu His Ile Thr Asp Pro Lys Glu Ala Leu Phe Lys Glu Lys Gly
                85                  90                  95

Asp Leu Ser Ile Gln Asn Phe Arg Phe Leu Ser Phe Thr Asp Cys Ser
            100                 105                 110
```

```
Ser Lys Glu Ser Ser Pro Ser Ile Ile His Gln Lys Asn Gly Gln Leu
        115                 120                 125

Ser Leu Arg Asn Asn Gly Ser Met Ser Phe Cys Arg Asn His Ala Glu
    130                 135                 140

Gly Ser Gly Gly Ala Ile Ser Ala Asp Ala Phe Ser Leu Gln His Asn
145                 150                 155                 160

Tyr Leu Phe Thr Ala Phe Glu Glu Asn Ser Ser Lys Gly Asn Gly Gly
                165                 170                 175

Ala Ile Gln Ala Gln Thr Phe Ser Leu Ser Arg Asn Val Ser Pro Ile
            180                 185                 190

Ser Phe Ala Arg Asn Arg Ala Asp Leu Asn Gly Gly Ala Ile Cys Cys
        195                 200                 205

Ser Asn Leu Ile Cys Ser Gly Asn Val Asn Pro Leu Phe Phe Thr Gly
    210                 215                 220

Asn Ser Ala Thr Asn Gly Gly Ala Ile Cys Cys Ile Ser Asp Leu Asn
225                 230                 235                 240

Thr Ser Glu Lys Gly Ser Leu Ser Leu Ala Cys Asn Gln Glu Thr Leu
                245                 250                 255

Phe Ala Ser Asn Ser Ala Lys Glu Lys Gly Gly Ala Ile Tyr Ala Lys
            260                 265                 270

His Met Val Leu Arg Tyr Asn Gly Pro Val Ser Phe Ile Asn Asn Ser
        275                 280                 285

Ala Lys Ile Gly Gly Ala Ile Ala Ile Gln Ser Gly Gly Ser Leu Ser
    290                 295                 300

Ile Leu Ala Gly Glu Gly Ser Val Leu Phe Gln Asn Asn Ser Gln Arg
305                 310                 315                 320

Thr Ser Asp Gln Gly Leu Val Arg Asn Ala Ile Tyr Leu Glu Lys Asp
                325                 330                 335

Ala Ile Leu Ser Ser Leu Glu Ala Arg Asn Gly Asp Ile Leu Phe Phe
            340                 345                 350

Asp Pro Ile Val Gln Glu Ser Ser Ser Lys Glu Ser Pro Leu Pro Ser
        355                 360                 365

Ser Leu Gln Ala Ser Val Thr Ser Pro Thr Pro Ala Thr Ala Ser Pro
    370                 375                 380

Leu Val Ile Gln Thr Ser Ala Asn Arg Ser Val Ile Phe Ser Ser Glu
385                 390                 395                 400

Arg Leu Ser Glu Glu Glu Lys Thr Pro Asp Asn Leu Thr Ser Gln Leu
                405                 410                 415

Gln Gln Pro Ile Glu Leu Lys Ser Gly Arg Leu Val Leu Lys Asp Arg
            420                 425                 430

Ala Val Leu Ser Ala Pro Ser Leu Ser Gln Asp Pro Gln Ala Leu Leu
        435                 440                 445

Ile Met Glu Ala Gly Thr Ser Leu Lys Thr Ser Ser Asp Leu Lys Leu
    450                 455                 460

Ala Thr Leu Ser Ile Pro Leu His Ser Leu Asp Thr Glu Lys Ser Val
465                 470                 475                 480

Thr Ile His Ala Pro Asn Leu Ser Ile Gln Lys Ile Phe Leu Ser Asn
                485                 490                 495

Ser Gly Asp Glu Asn Phe Tyr Glu Asn Val Glu Leu Leu Ser Lys Glu
            500                 505                 510

Gln Asn Asn Ile Pro Leu Leu Thr Leu Ser Lys Glu Gln Ser His Leu
        515                 520                 525
```

```
His Leu Pro Asp Gly Asn Leu Ser Ser His Phe Gly Tyr Gln Gly Asp
    530                 535                 540

Trp Thr Phe Ser Trp Lys Asp Ser Asp Glu Gly His Ser Leu Ile Ala
545                 550                 555                 560

Asn Trp Thr Pro Lys Asn Tyr Val Pro His Pro Glu Arg Gln Ser Thr
                565                 570                 575

Leu Val Ala Asn Thr Leu Trp Asn Thr Tyr Ser Asp Met Gln Ala Val
            580                 585                 590

Gln Ser Met Ile Asn Thr Ile Ala His Gly Gly Ala Tyr Leu Phe Gly
        595                 600                 605

Thr Trp Gly Ser Ala Val Ser Asn Leu Phe Tyr Ala His Asp Ser Ser
    610                 615                 620

Gly Lys Pro Ile Asp Asn Trp His His Arg Ser Leu Gly Tyr Leu Phe
625                 630                 635                 640

Gly Ile Ser Thr His Ser Leu Asp Asp His Ser Phe Cys Leu Ala Ala
                645                 650                 655

Gly Gln Leu Leu Gly Lys Ser Ser Asp Ser Phe Ile Thr Ser Thr Glu
            660                 665                 670

Thr Thr Ser Tyr Ile Ala Thr Val Gln Ala Gln Leu Ala Thr Pro Leu
        675                 680                 685

Met Lys Ile Ser Ala Gln Ala Cys Tyr Asn Glu Ser Ile His Glu Leu
    690                 695                 700

Lys Thr Lys Tyr Arg Ser Phe Ser Lys Glu Gly Phe Gly Ser Trp His
705                 710                 715                 720

Ser Val Ala Val Ser Gly Glu Val Cys Ala Ser Ile Pro Ile Val Ser
                725                 730                 735

Asn Gly Ser Gly Leu Phe Ser Ser Phe Ser Ile Phe Ser Lys Leu Gln
            740                 745                 750

Gly Phe Ser Gly Thr Gln Asp Gly Phe Glu Glu Ser Ser Gly Glu Ile
        755                 760                 765

Arg Ser Phe Ser Ala Ser Ser Phe Arg Asn Ile Ser Leu Pro Met Gly
    770                 775                 780

Ile Thr Phe Glu Lys Lys Ser Gln Lys Thr Arg Asn Tyr Tyr Tyr Phe
785                 790                 795                 800

Leu Gly Ala Tyr Ile Gln Asp Leu Lys Arg Asp Val Glu Ser Gly Pro
                805                 810                 815

Val Val Leu Leu Lys Asn Ala Val Ser Trp Asp Ala Pro Met Ala Asn
            820                 825                 830

Leu Asp Ser Arg Ala Tyr Met Phe Arg Leu Thr Asn Gln Arg Ala Leu
        835                 840                 845

His Arg Leu Gln Thr Leu Leu Asn Val Ser Tyr Val Leu Arg Gly Gln
    850                 855                 860

Ser His Ser Tyr Ser Leu Asp Leu Gly Thr Thr Tyr Arg Phe
865                 870                 875
```

<210> SEQ ID NO 68
<211> LENGTH: 2634
<212> TYPE: DNA
<213> ORGANISM: Chlamydia trachomatis

<400> SEQUENCE: 68

```
atgcgacctg atcatatgaa cttctgttgt ctatgtgctg ctattttgtc atccacagcg      60

gtcctctttg gccaggatcc cttaggtgaa accgccctcc tcactaaaaa tcctaatcat     120

gtcgtctgta catttttga ggactgtacc atggagagcc tctttcctgc tctttgtgct     180
```

-continued

```
catgcatcac aagatgatcc tttgtatgta cttggaaatt cctactgttg gttcgtatct    240
aaactccata tcacggaccc caaagaggct ctttttaaag aaaaaggaga tctttccatt    300
caaaatttc gcttcctttc cttcacagat tgctcttcca aggaaagctc tccttctatt    360
attcatcaaa agaatggtca gttatccttg cgcaataatg gtagcatgag tttctgtcga    420
aatcatgctg aaggctctgg aggagccatc tctgcggatg ccttttctct acaacacaac    480
tatcttttca cagcttttga agagaattct tctaaaggaa atggcggagc cattcaggct    540
caaaccttct ctttatctag aaatgtgtcg cctatttctt tcgcccgtaa tcgtgcggat    600
ttaaatggcg gcgctatttg ctgtagtaat cttatttgtt cagggaatgt aaaccctctc    660
tttttcactg gaaactccgc cacgaatgga ggcgctattt gttgtatcag cgatctaaac    720
acctcagaaa aaggctctct ctctcttgct tgtaaccaag aaacgctatt tgcaagcaat    780
tctgctaaag aaaaaggcgg ggctatttat gccaagcaca tggtattgcg ttataacggt    840
cctgtttcct tcattaacaa cagcgctaaa ataggtggag ctatcgccat ccagtccgga    900
gggagtctct ctatccttgc aggtgaagga tctgttctgt tccagaataa ctcccaacgc    960
acctccgacc aaggtctagt aagaaacgcc atctacttag agaaagatgc gattctttct   1020
tccttagaag ctcgcaacgg agatattctt ttctttgatc ctattgtaca agaaagtagc   1080
agcaaagaat cgcctcttcc ctcctctttg caagccagcg tgacttctcc caccccagcc   1140
accgcatctc ctttagttat tcagacaagt gcaaaccgtt cagtgatttt ctcgagcgaa   1200
cgtctttctg aagaagaaaa aactcctgat aacctcactt cccaactaca gcagcctatc   1260
gaactgaaat ccggacgctt agttttaaaa gatcgcgctg tcctttccgc gccttctctc   1320
tctcaggatc ctcaagctct cctcattatg gaagcgggaa cttctttaaa aacttcctct   1380
gatttgaagt tagctacgct aagtattccc cttcattcct tagatactga aaaaagcgta   1440
actatccacg cccctaacct ttctatccaa aagatcttcc tctctaattc tggagatgag   1500
aatttttatg aaaatgtaga gcttctcagt aaagagcaaa acaatattcc tctccttact   1560
ctctctaaag agcaatctca tttacatctt cctgatggga acctctcttc tcactttgga   1620
tatcaaggag attggacttt ttcttggaaa gattctgatg aagggcattc tctgattgct   1680
aattggacgc ctaaaaacta tgtgcctcat ccagaacgtc aatctacact cgttgcgaac   1740
actctttgga acacctattc cgatatgcaa gctgtgcagt cgatgattaa tacaatagcg   1800
cacggaggag cctatctatt tggaacgtgg ggatctgctg tttctaattt attctatgct   1860
cacgacagct ctgggaaacc tatcgataat tggcatcata gaagccttgg ctacctattc   1920
ggtatcagta ctcacagttt agatgaccat tctttctgct tggctgcagg acaattactc   1980
gggaaatcgt ccgattcctt tattacgtct acagaaacga cctcctatat agctactgta   2040
caagcgcaac tcgctacccc tctaatgaaa atctctgcac aggcatgcta taatgaaagt   2100
atccatgagc taaaaacaaa atatcgctcc ttctctaaag aaggattcgg atcctggcat   2160
agcgttgcag tatccggaga agtgtgcgca tcgattccta ttgtatccaa tggttccgga   2220
ctgttcagct ccttctctat tttctctaaa ctgcaaggat tttcaggaac acaggacggt   2280
tttgaggaga gttcgggaga gattcggtcc ttttctgcca gctctttcag aaatatttca   2340
cttcctatgg gaataacatt tgaaaaaaaa tcccaaaaaa cacgaaacta ctattacttt   2400
ctgggagcct acatccaaga cctaaaacgt gatgtggaat cgggacctgt agtgttactc   2460
aaaaatgccg tctcctggga tgctcctatg gcgaacttgg attcgcgagc ctacatgttc   2520
```

aggcttacga atcaaagagc tctgcataga cttcagacgc tgttaaatgt gtcttacgta 2580
ctgcgcgggc aaagccatag ttactccctg gatctgggga ccacttacag gttc 2634

<210> SEQ ID NO 69
<211> LENGTH: 1005
<212> TYPE: PRT
<213> ORGANISM: Chlamydia trachomatis

<400> SEQUENCE: 69

Met Thr Asn Ser Ile Ser Gly Tyr Gln Pro Thr Val Thr Thr Ser Thr
1 5 10 15

Ser Ser Thr Thr Ser Ala Ser Gly Ala Ser Gly Ser Leu Gly Ala Ser
20 25 30

Ser Val Ser Thr Thr Ala Asn Ala Thr Val Thr Gln Thr Ala Asn Ala
35 40 45

Thr Asn Ser Ala Ala Thr Ser Ser Ile Gln Thr Thr Gly Glu Thr Val
50 55 60

Val Asn Tyr Thr Asn Ser Ala Ser Ala Pro Asn Val Thr Val Ser Thr
65 70 75 80

Ser Ser Ser Ser Thr Gln Ala Thr Ala Thr Ser Asn Lys Thr Ser Gln
85 90 95

Ala Val Ala Gly Lys Ile Thr Ser Pro Asp Thr Ser Glu Ser Ser Glu
100 105 110

Thr Ser Ser Thr Ser Ser Ser Asp His Ile Pro Ser Asp Tyr Asp Asp
115 120 125

Val Gly Ser Asn Ser Gly Asp Ile Ser Asn Asn Tyr Asp Asp Val Gly
130 135 140

Ser Asn Asn Gly Asp Ile Ser Ser Asn Tyr Asp Asp Ala Ala Ala Asp
145 150 155 160

Tyr Glu Pro Ile Arg Thr Thr Glu Asn Ile Tyr Glu Ser Ile Gly Gly
165 170 175

Ser Arg Thr Ser Gly Pro Glu Asn Thr Ser Gly Gly Ala Ala Ala Ala
180 185 190

Leu Asn Ser Leu Arg Gly Ser Ser Tyr Ser Asn Tyr Asp Asp Ala Ala
195 200 205

Ala Asp Tyr Glu Pro Ile Arg Thr Thr Glu Asn Ile Tyr Glu Ser Ile
210 215 220

Gly Gly Ser Arg Thr Ser Gly Pro Glu Asn Thr Ser Gly Gly Ala Ala
225 230 235 240

Ala Ala Leu Asn Ser Leu Arg Gly Ser Ser Tyr Ser Asn Tyr Asp Asp
245 250 255

Ala Ala Ala Asp Tyr Glu Pro Ile Arg Thr Thr Glu Asn Ile Tyr Glu
260 265 270

Ser Ile Gly Gly Ser Arg Thr Ser Gly Pro Glu Asn Thr Ser Asp Gly
275 280 285

Ala Ala Ala Ala Ala Leu Asn Ser Leu Arg Gly Ser Ser Tyr Thr Thr
290 295 300

Gly Pro Arg Asn Glu Gly Val Phe Gly Pro Gly Pro Glu Gly Leu Pro
305 310 315 320

Asp Met Ser Leu Pro Ser Tyr Asp Pro Thr Asn Lys Thr Ser Leu Leu
325 330 335

Thr Phe Leu Ser Asn Pro His Val Lys Ser Lys Met Leu Glu Asn Ser
340 345 350

Gly His Phe Val Phe Ile Asp Thr Asp Arg Ser Ser Phe Ile Leu Val

-continued

```
        355                 360                 365

Pro Asn Gly Asn Trp Asp Gln Val Cys Ser Ile Lys Val Gln Asn Gly
    370                 375                 380

Lys Thr Lys Glu Asp Leu Asp Ile Lys Asp Leu Glu Asn Met Cys Ala
385                 390                 395                 400

Lys Phe Cys Thr Gly Phe Ser Lys Phe Ser Gly Asp Trp Asp Ser Leu
                405                 410                 415

Val Glu Pro Met Val Ser Ala Lys Ala Gly Val Ala Ser Gly Gly Asn
            420                 425                 430

Leu Pro Asn Thr Val Ile Ile Asn Asn Lys Phe Lys Thr Cys Val Ala
        435                 440                 445

Tyr Gly Pro Trp Asn Ser Gln Glu Ala Ser Ser Gly Tyr Thr Pro Ser
    450                 455                 460

Ala Trp Arg Arg Gly His Arg Val Asp Phe Gly Gly Ile Phe Glu Lys
465                 470                 475                 480

Ala Asn Asp Phe Asn Lys Ile Asn Trp Gly Thr Gln Ala Gly Pro Ser
                485                 490                 495

Ser Glu Asp Asp Gly Ile Ser Phe Ser Asn Glu Thr Pro Gly Ala Gly
            500                 505                 510

Pro Ala Ala Ala Pro Ser Pro Thr Pro Ser Ser Ile Pro Ile Ile Asn
        515                 520                 525

Val Asn Val Asn Val Gly Gly Thr Asn Val Asn Ile Gly Asp Thr Asn
    530                 535                 540

Val Asn Thr Thr Asn Thr Thr Pro Thr Thr Gln Ser Thr Asp Ala Ser
545                 550                 555                 560

Thr Asp Thr Ser Asp Ile Asp Asp Ile Asn Thr Asn Asn Gln Thr Asp
                565                 570                 575

Asp Ile Asn Thr Thr Asp Lys Asp Ser Asp Gly Ala Gly Gly Val Asn
            580                 585                 590

Gly Asp Ile Ser Glu Thr Glu Ser Ser Ser Gly Asp Asp Ser Gly Ser
        595                 600                 605

Val Ser Ser Ser Glu Ser Asp Lys Asn Ala Ser Val Gly Asn Asp Gly
    610                 615                 620

Pro Ala Met Lys Asp Ile Leu Ser Ala Val Arg Lys His Leu Asp Val
625                 630                 635                 640

Val Tyr Pro Gly Glu Asn Gly Gly Ser Thr Glu Gly Pro Leu Pro Ala
                645                 650                 655

Asn Gln Thr Leu Gly Asp Val Ile Ser Asp Val Glu Asn Lys Gly Ser
            660                 665                 670

Ala Gln Asp Thr Lys Leu Ser Gly Asn Thr Gly Ala Gly Asp Asp Asp
        675                 680                 685

Pro Thr Thr Thr Ala Ala Val Gly Asn Gly Ala Glu Glu Ile Thr Leu
    690                 695                 700

Ser Asp Thr Asp Ser Gly Ile Gly Asp Asp Val Ser Asp Thr Ala Ser
705                 710                 715                 720

Ser Ser Gly Asp Glu Ser Gly Gly Val Ser Ser Pro Ser Ser Glu Ser
                725                 730                 735

Asn Lys Asn Thr Ala Val Gly Asn Asp Gly Pro Ser Gly Leu Asp Ile
            740                 745                 750

Leu Ala Ala Val Arg Lys His Leu Asp Lys Val Tyr Pro Gly Asp Asn
        755                 760                 765

Gly Gly Ser Thr Glu Gly Pro Leu Gln Ala Asn Gln Thr Leu Gly Asp
    770                 775                 780
```

```
Ile Val Gln Asp Met Glu Thr Thr Gly Thr Ser Gln Glu Thr Val Val
785                 790                 795                 800

Ser Pro Trp Lys Gly Ser Thr Ser Ser Thr Glu Ser Ala Gly Gly Ser
                805                 810                 815

Gly Ser Val Gln Thr Leu Leu Pro Ser Pro Pro Pro Thr Pro Ser Thr
            820                 825                 830

Thr Thr Leu Arg Thr Gly Thr Gly Ala Thr Thr Thr Ser Leu Met Met
        835                 840                 845

Gly Gly Pro Ile Lys Ala Asp Ile Ile Thr Thr Gly Gly Gly Gly Arg
    850                 855                 860

Ile Pro Gly Gly Gly Thr Leu Glu Lys Leu Leu Pro Arg Ile Arg Ala
865                 870                 875                 880

His Leu Asp Ile Ser Phe Asp Ala Gln Gly Asp Leu Val Ser Thr Glu
                885                 890                 895

Glu Pro Gln Leu Gly Ser Ile Val Asn Lys Phe Arg Gln Glu Thr Gly
            900                 905                 910

Ser Arg Gly Ile Leu Ala Phe Val Glu Ser Ala Pro Gly Lys Pro Gly
        915                 920                 925

Ser Ala Gln Val Leu Thr Gly Thr Gly Gly Asp Lys Gly Asn Leu Phe
    930                 935                 940

Gln Ala Ala Ala Ala Val Thr Gln Ala Leu Gly Asn Val Ala Gly Lys
945                 950                 955                 960

Val Asn Leu Ala Ile Gln Gly Gln Lys Leu Ser Ser Leu Val Asn Asp
                965                 970                 975

Asp Gly Lys Gly Ser Val Gly Arg Asp Leu Phe Gln Ala Ala Ala Gln
            980                 985                 990

Thr Thr Gln Val Leu Ser Ala Leu  Ile Asp Thr Val Gly
        995                 1000                 1005
```

<210> SEQ ID NO 70
<211> LENGTH: 3015
<212> TYPE: DNA
<213> ORGANISM: Chlamydia trachomatis

<400> SEQUENCE: 70

```
atgacgaatt ctatatcagg ttatcaacct actgttacaa cttctacatc atcaaccact     60

tcggcatcag gtgcttccgg atctctggga gcttcttctg tatctactac cgcaaacgct    120

acagttacac aaacagcaaa cgcaacaaat tcagcggcta catcttctat ccaaacgact    180

ggagagactg tagtaaacta tacgaattca gcctccgccc ccaatgtaac tgtatcgacc    240

tcctcttctt ccacacaagc cacagccact tcgaataaaa cttcccaagc cgttgctgga    300

aaaatcactt ctccagatac ttcagaaagc tcagaaacta gctctacctc atcaagcgat    360

catatcccta gcgattacga tgacgttggt agcaatagtg gagatattag caacaactac    420

gatgacgtag gtagtaacaa cggagatatc agtagcaatt atgacgatgc tgctgctgat    480

tacgagccga taagaactac tgaaaatatt tatgagagta ttggtggctc tagaacaagt    540

ggcccagaaa atacaagtgg tggtgcagca gcagcactca attctctaag aggctcctcc    600

tacagcaatt atgacgatgc tgctgctgat tacgagccga taagaactac tgaaaatatt    660

tatgagagta ttggtggctc tagaacaagt ggcccagaaa atacgagtgg tggtgcagca    720

gcagcactca attctctaag aggctcctcc tacagcaatt atgacgatgc tgctgctgat    780

tacgagccga taagaactac tgaaaatatt tatgagagta ttggtggctc tagaacaagt    840
```

ggcccagaaa atacgagtga tggtgcagca gcagcagcac tcaattctct aagaggctcc 900
tcctacacaa cagggcctcg taacgagggt gtattcggcc ctggaccgga aggactacca 960
gacatgtctc ttccttcata cgatcctaca aataaaacct cgttattgac tttcctctcc 1020
aaccctcatg taaagtcgaa aatgcttgaa aactcggggc atttcgtctt cattgataca 1080
gatagaagta gtttcattct tgttcctaac ggaaattggg accaagtctg ttcaattaaa 1140
gttcaaaatg gaaagaccaa agaagatctc gacatcaaag acttggaaaa catgtgtgca 1200
aaattctgta cagggtttag caaattctct ggtgactggg acagtcttgt agaacctatg 1260
gtgtcagcca aagctggagt ggccagcgga ggcaatcttc ccaatacagt gattatcaat 1320
aataaattca aaacttgcgt tgcttatggt ccttggaata gccaggaagc aagttctggt 1380
tatacacctt ctgcttggag acgtggtcat cgagtagatt ttggaggaat ttttgagaaa 1440
gccaacgact ttaataaaat caactgggga actcaagccg ggcctagtag cgaagacgat 1500
ggcatttcct tctccaatga aactcctgga gctggtcctg cagctgctcc atcaccaacg 1560
ccatcctcta ttcctatcat caatgtcaat gtcaatgttg gcggaactaa tgtgaatatt 1620
ggagatacga atgtcaacac gactaacacc acaccaacaa ctcaatctac agacgcctct 1680
acagatacaa gcgatatcga tgacataaat accaacaacc aaactgatga tatcaatacg 1740
acagacaaag actctgacgg agctggtgga gtcaatggcg atatatccga aacagaatcc 1800
tcttctggag atgattcagg aagtgtctct tcctcagaat cagacaagaa tgcctctgtc 1860
ggaaatgacg gacctgctat gaaagatatc ctttctgccg tgcgtaaaca cctagacgtc 1920
gtttaccctg gcgaaaatgg cggttctaca gaagggcctc tcccagctaa ccaaactctc 1980
ggagacgtaa tctctgatgt agagaataaa ggctccgctc aggatacaaa attgtcagga 2040
aatacaggag ctggggatga cgatccaaca accacagctg ctgtaggtaa tggagcggaa 2100
gagatcactc tttccgacac agattctggt atcggagatg atgtatccga tacagcgtct 2160
tcatctgggg atgaatccgg aggagtctcc tctccctctt cagaatccaa taaaaatact 2220
gccgttggaa atgacggacc ttctggacta gatatcctcg ctgccgtacg taaacattta 2280
gataaggttt accctggcga caatggtggt tctacagaag ggcctctcca agctaaccaa 2340
actcttggag atatcgtcca ggatatggaa acaacaggga catcccaaga aaccgttgta 2400
tccccatgga aaggaagcac ttcttcaacg gaatcagcag gaggaagtgg tagcgtacaa 2460
acactactgc cttcaccacc tccaaccccg tcaactacaa cattaagaac gggcacagga 2520
gctaccacca catccttgat gatgggagga ccaatcaaag ctgacataat aacaactggt 2580
ggcggaggac gaattcctgg aggaggaacg ttagaaaagc tgctccctcg tatacgtgcg 2640
cacttagaca tatcctttga tgcgcaaggc gatctcgtaa gtactgaaga gcctcagctt 2700
ggctcgattg taaacaaatt ccgccaagaa actggttcaa gaggaatctt agctttcgtt 2760
gagagtgctc caggcaagcc gggatctgca caggtcttaa cgggtacagg gggagataaa 2820
ggcaacctat tccaagcagc tgccgcagtc acccaagcct taggaaatgt tgcagggaaa 2880
gtcaaccttg cgatacaagg ccaaaaacta tcatccctag tcaatgacga cgggaagggg 2940
tctgttggaa gagatttatt ccaagcagca gcccaaacaa ctcaagtgct aagcgcactg 3000
attgataccg tagga 3015

<210> SEQ ID NO 71
<211> LENGTH: 393
<212> TYPE: PRT
<213> ORGANISM: Chlamydia trachomatis

```
<400> SEQUENCE: 71

Met Lys Lys Leu Leu Lys Ser Val Leu Val Phe Ala Ala Leu Ser Ser
1               5                   10                  15

Ala Ser Ser Leu Gln Ala Leu Pro Val Gly Asn Pro Ala Glu Pro Ser
            20                  25                  30

Leu Met Ile Asp Gly Ile Leu Trp Glu Gly Phe Gly Gly Asp Pro Cys
        35                  40                  45

Asp Pro Cys Ala Thr Trp Cys Asp Ala Ile Ser Met Arg Val Gly Tyr
    50                  55                  60

Tyr Gly Asp Phe Val Phe Asp Arg Val Leu Lys Thr Asp Val Asn Lys
65                  70                  75                  80

Glu Phe Gln Met Gly Ala Lys Pro Thr Thr Asp Thr Gly Asn Ser Ala
                85                  90                  95

Ala Pro Ser Thr Leu Thr Ala Arg Glu Asn Pro Ala Tyr Gly Arg His
            100                 105                 110

Met Gln Asp Ala Glu Met Phe Thr Asn Ala Ala Cys Met Ala Leu Asn
        115                 120                 125

Ile Trp Asp Arg Phe Asp Val Phe Cys Thr Leu Gly Ala Thr Ser Gly
    130                 135                 140

Tyr Leu Lys Gly Asn Ser Ala Ser Phe Asn Leu Val Gly Leu Phe Gly
145                 150                 155                 160

Asp Asn Glu Asn Gln Lys Thr Val Lys Ala Glu Ser Val Pro Asn Met
                165                 170                 175

Ser Phe Asp Gln Ser Val Val Glu Leu Tyr Thr Asp Thr Thr Phe Ala
            180                 185                 190

Trp Ser Val Gly Ala Arg Ala Ala Leu Trp Glu Cys Gly Cys Ala Thr
        195                 200                 205

Leu Gly Ala Ser Phe Gln Tyr Ala Gln Ser Lys Pro Lys Val Glu Glu
    210                 215                 220

Leu Asn Val Leu Cys Asn Ala Ala Glu Phe Thr Ile Asn Lys Pro Lys
225                 230                 235                 240

Gly Tyr Val Gly Lys Glu Phe Pro Leu Asp Leu Thr Ala Gly Thr Asp
                245                 250                 255

Ala Ala Thr Gly Thr Lys Asp Ala Ser Ile Asp Tyr His Glu Trp Gln
            260                 265                 270

Ala Ser Leu Ala Leu Ser Tyr Arg Leu Asn Met Phe Thr Pro Tyr Ile
        275                 280                 285

Gly Val Lys Trp Ser Arg Ala Ser Phe Asp Ala Asp Thr Ile Arg Ile
    290                 295                 300

Ala Gln Pro Lys Ser Ala Thr Ala Ile Phe Asp Thr Thr Thr Leu Asn
305                 310                 315                 320

Pro Thr Ile Ala Gly Ala Gly Asp Val Lys Thr Gly Ala Glu Gly Gln
                325                 330                 335

Leu Gly Asp Thr Met Gln Ile Val Ser Leu Gln Leu Asn Lys Met Lys
            340                 345                 350

Ser Arg Lys Ser Cys Gly Ile Ala Val Gly Thr Thr Ile Val Asp Ala
        355                 360                 365

Asp Lys Tyr Ala Val Thr Val Glu Thr Arg Leu Ile Asp Glu Arg Ala
    370                 375                 380

Ala His Val Asn Ala Gln Phe Arg Phe
385                 390
```

<210> SEQ ID NO 72
<211> LENGTH: 1179
<212> TYPE: DNA
<213> ORGANISM: Chlamydia trachomatis

<400> SEQUENCE: 72

```
atgaaaaaac tcttgaaatc ggtattagta tttgccgctt tgagttctgc ttcctccttg     60
caagctctgc ctgtggggaa tcctgctgaa ccaagcctta tgatcgacgg aattctgtgg    120
gaaggtttcg gcggagatcc ttgcgatcct tgcgccactt ggtgtgacgc tatcagcatg    180
cgtgttggtt actacggaga ctttgttttc gaccgtgttt tgaaaactga tgtgaataaa    240
gaatttcaga tgggtgccaa gcctacaact gatacaggca atagtgcagc tccatccact    300
cttacagcaa gagagaatcc tgcttacggc cgacatatgc aggatgctga gatgtttaca    360
aatgccgctt gcatggcatt gaatatttgg gatcgttttg atgtattctg tacattagga    420
gccaccagtg gatatcttaa aggaaactct gcttctttca atttagttgg attgtttgga    480
gataatgaaa atcaaaaaac ggtcaaagcg gagtctgtac caaatatgag ctttgatcaa    540
tctgttgttg agttgtatac agatactact tttgcgtgga gcgtcggcgc tcgcgcagct    600
ttgtgggaat gtggatgtgc aactttagga gcttcattcc aatatgctca atctaaacct    660
aaagtagaag aattaaacgt tctctgcaat gcagcagagt ttactattaa taaacctaaa    720
gggtatgtag gtaaggagtt tcctcttgat cttacagcag gaacagatgc tgcgacagga    780
actaaggatg cctctattga ttaccatgaa tggcaagcaa gtttagctct ctcttacaga    840
ctgaatatgt tcactcccta cattggagtt aaatggtctc gagcaagctt tgatgccgat    900
acgattcgta tagcccagcc aaaatcagct acagctattt ttgatactac cacgcttaac    960
ccaactattg ctggagctgg cgatgtgaaa actggcgcag agggtcagct cggagacaca   1020
atgcaaatcg tttccttgca attgaacaag atgaaatcta gaaaatcttg cggtattgca   1080
gtaggaacaa ctattgtgga tgcagacaaa tacgcagtta cagttgagac tcgcttgatc   1140
gatgagagag cagctcacgt aaatgcacaa ttccgcttc                          1179
```

<210> SEQ ID NO 73
<211> LENGTH: 164
<212> TYPE: PRT
<213> ORGANISM: Chlamydia trachomatis

<400> SEQUENCE: 73

```
Met Asp Leu Lys Gln Ile Glu Lys Leu Met Ile Ala Met Gly Arg Asn
1               5                   10                  15

Lys Met Lys Arg Ile Val Ile Lys Arg Glu Gly Leu Glu Leu Glu Leu
            20                  25                  30

Glu Arg Asp Thr Val Pro Ser Ile Gln Glu Pro Val Phe Tyr Asp Asn
        35                  40                  45

Arg Leu Phe Ala Gly Phe Ser Gln Glu Arg Pro Ile Pro Thr Asp Gln
    50                  55                  60

Asn Leu Gly Asn Pro Ile Val Lys Glu Ser Ile Glu Lys Lys Glu Ser
65                  70                  75                  80

Glu Ala Pro Ala Gln Gly Asp Phe Ile Val Ser Pro Leu Val Gly Thr
                85                  90                  95

Phe Tyr Gly Ser Pro Ser Pro Glu Ala Pro Ala Phe Ile Lys Pro Gly
            100                 105                 110

Asp Thr Val Ser Glu Asp Thr Val Val Cys Ile Val Glu Ala Met Lys
        115                 120                 125
```

```
Val Met Asn Glu Val Lys Ala Gly Met Ser Gly Arg Val Glu Glu Ile
    130                 135                 140

Leu Ile Thr Asn Gly Asp Pro Val Gln Phe Gly Ser Lys Leu Phe Arg
145                 150                 155                 160

Ile Val Lys Ala
```

<210> SEQ ID NO 74
<211> LENGTH: 492
<212> TYPE: DNA
<213> ORGANISM: Chlamydia trachomatis

<400> SEQUENCE: 74

```
atggatttaa agcagataga aaagctcatg attgctatgg gccgtaataa aatgaagcgc      60

attgttatca agcgtgaagg tttggagtta gagttagaaa gggatacagt cccaagtatt     120

caggagccag tcttttatga taacagactg tttgctggat tttcccaaga aagacctatt     180

cctacagatc aaaaccttgg gaatcctatt gttaaagaga gtatcgagaa gaaagaaagt     240

gaggcgcctg ctcagggaga ttttattgtt tctccgctgg taggcacttt ttatggctct     300

ccttcgccag aggctccagc atttattaag cctggggata ctgtttcaga ggataccgtt     360

gtttgtatcg tggaagctat gaaggtaatg aacgaggtaa aggcaggaat gtctggtcgc     420

gtagaagaaa tattgattac taatggtgat ccagtccagt ttggttctaa gttattccgt     480

atagttaagg ct                                                         492
```

<210> SEQ ID NO 75
<211> LENGTH: 150
<212> TYPE: PRT
<213> ORGANISM: Chlamydia trachomatis

<400> SEQUENCE: 75

```
Met Glu Lys Arg Lys Asp Thr Lys Thr Thr Leu Ala Lys Ala Ser Asp
1               5                   10                  15

Asp Arg Asn Lys Ala Trp Tyr Val Val Asn Ala Glu Gly Lys Thr Leu
            20                  25                  30

Gly Arg Leu Ser Ser Glu Val Ala Lys Ile Leu Arg Gly Lys His Lys
        35                  40                  45

Val Thr Phe Thr Pro His Val Ala Met Gly Asp Gly Val Ile Val Ile
    50                  55                  60

Asn Ala Glu Lys Val Arg Leu Thr Gly Ala Lys Arg Ala Gln Lys Val
65                  70                  75                  80

Tyr His Tyr Tyr Thr Gly Phe Ile Ser Gly Met Arg Glu Val Pro Phe
                85                  90                  95

Glu Asn Met Ile Ala Arg Lys Pro Ala Tyr Val Ile Glu His Ala Val
            100                 105                 110

Lys Gly Met Leu Pro Lys Thr Lys Leu Gly Arg Arg Gln Met Lys Ser
        115                 120                 125

Leu Arg Val Leu Lys Gly Ser Ser Tyr Ala Gln Tyr Glu Ala Ile Lys
    130                 135                 140

Pro Ile Val Leu Asp Ala
145                 150
```

<210> SEQ ID NO 76
<211> LENGTH: 450
<212> TYPE: DNA
<213> ORGANISM: Chlamydia trachomatis

<400> SEQUENCE: 76

-continued atggaaaaaa gaaaagatac gaaaacgacc ctagctaagg cttcggacga tcgaaacaaa 60
gcctggtatg tagttaatgc tgaagggaag accttaggga gattatcttc agaagttgcg 120
aagatcctga gaggtaagca taaggtgact tttactcctc acgtagcgat gggagatggt 180
gtcattgtga tcaatgctga gaaagtgcgt ttgactggcg caaaaagagc tcagaaagtg 240
tatcactatt acacaggctt tatttctggg atgcgagaag ttccttttga aaacatgatt 300
gcgcgaaagc ctgcttatgt tatcgagcat gctgttaaag gaatgttgcc taaaacaaaa 360
cttggaagac gtcaaatgaa atctttaaga gttttgaaag gtagttctta cgcacagtat 420
gaagctatca aaccaattgt tttagacgcg 450

<210> SEQ ID NO 77
<211> LENGTH: 129
<212> TYPE: PRT
<213> ORGANISM: Chlamydia trachomatis

<400> SEQUENCE: 77

Met Ile Gln Glu Ser Val Ala Thr Gly Arg Arg Lys Gln Ala Val Ser
1 5 10 15

Ser Val Arg Leu Arg Ser Gly Asn Gly Lys Ile Asp Val Asn Gly Lys
20 25 30

Thr Leu Glu Gln Tyr Phe Pro Leu Glu Val Gln Arg Ala Thr Ile Leu
35 40 45

Ala Pro Leu Arg Met Leu Gly Asp Val Asn Ser Phe Asp Leu Ile Ile
50 55 60

Arg Val Ser Gly Gly Gly Val Gln Gly Gln Val Ile Ala Thr Arg Leu
65 70 75 80

Gly Leu Ala Arg Ala Val Leu Gln Glu Lys Glu Asp Met Lys Gln Glu
85 90 95

Leu Lys Ala Gln Gly Phe Leu Thr Arg Asp Pro Arg Lys Lys Glu Arg
100 105 110

Lys Lys Tyr Gly Arg Lys Lys Ala Arg Lys Ser Phe Gln Phe Ser Lys
115 120 125

Arg

<210> SEQ ID NO 78
<211> LENGTH: 387
<212> TYPE: DNA
<213> ORGANISM: Chlamydia trachomatis

<400> SEQUENCE: 78
atgatacaag agtctgttgc aacaggcaga agaaagcagg ctgtttctag cgttcgtctt 60
cgttctggaa atggaaaaat tgacgtaaat ggaaagactt tagagcaata tttccctctt 120
gaagttcaaa gagcaaccat cttagctccg ctcagaatgc tcggtgatgt caacagtttc 180
gatttgatta tccgagtaag tggaggaggg gttcaaggtc aggttattgc tactcgattg 240
ggtttagcta gagctgttct gcaagagaaa gaagacatga agcaagaatt gaaggctcaa 300
ggcttcttga ctcgagatcc tcgtaagaaa gagcgtaaaa aatacggtcg taagaaagct 360
cgtaagagtt tccaattctc caaacga 387

<210> SEQ ID NO 79
<211> LENGTH: 267
<212> TYPE: PRT
<213> ORGANISM: Chlamydia trachomatis

<400> SEQUENCE: 79

```
Met Ser Arg Lys Pro Ala Ser Asn Ser Ser Arg Asn Thr Lys Arg Ser
1               5                   10                  15

Ser Asp Thr Ser Trp Glu Val Ile Ala Gln Asp Tyr Asn Lys Ala Val
            20                  25                  30

Asp Arg Asp Gly His Phe Tyr His Lys Glu Val Ile Leu Pro Asn Leu
        35                  40                  45

Leu Ser Lys Leu His Ile Ser Arg Ser Ser Ser Leu Val Asp Val Gly
    50                  55                  60

Cys Gly Gln Gly Ile Leu Glu Lys His Leu Pro Lys His Leu Pro Tyr
65                  70                  75                  80

Leu Gly Ile Asp Leu Ser Pro Ser Leu Leu Arg Phe Ala Lys Lys Ser
                85                  90                  95

Ala Ser Ser Lys Ser Arg Arg Phe Leu His His Asp Met Thr Gln Pro
            100                 105                 110

Val Pro Ala Asp His His Glu Gln Phe Ser His Ala Thr Ala Ile Leu
        115                 120                 125

Ser Leu Gln Asn Met Glu Ser Pro Glu Gln Ala Ile Ala His Thr Ala
    130                 135                 140

Asn Leu Leu Ala Pro Gln Gly Arg Leu Phe Ile Val Leu Asn His Pro
145                 150                 155                 160

Cys Phe Arg Ile Pro Arg Leu Ser Ser Trp Leu Tyr Asp Glu Pro Lys
                165                 170                 175

Lys Leu Leu Ser Arg Lys Ile Asp Arg Tyr Leu Ser Pro Val Ala Val
            180                 185                 190

Pro Ile Val Val His Pro Gly Glu Lys His Ser Glu Thr Thr Tyr Ser
        195                 200                 205

Phe His Phe Pro Leu Ser Tyr Trp Val Gln Ala Leu Ser Asn His Asn
    210                 215                 220

Leu Leu Ile Asp Ser Met Glu Glu Trp Ile Ser Pro Lys Lys Ser Ser
225                 230                 235                 240

Gly Lys Arg Ala Arg Ala Glu Asn Leu Cys Arg Lys Glu Phe Pro Leu
                245                 250                 255

Phe Leu Phe Ile Ser Ala Leu Lys Ile Ser Lys
            260                 265
```

<210> SEQ ID NO 80
<211> LENGTH: 801
<212> TYPE: DNA
<213> ORGANISM: Chlamydia trachomatis

<400> SEQUENCE: 80

```
atgtccagaa aaccggcttc taactcatcc cggaacacca aacggtcctc agacacttcc      60

tgggaagtca ttgcccaaga ttataataaa gccgttgatc gcgatggaca tttctatcat     120

aaggaagtga ttctccctaa tctcctttct aagctacata tttcccgctc atcgtctctg     180

gttgatgtag gatgtggtca agggattttg gagaagcatt tacccaaaca tctcccttat     240

ctaggaatcg atctttcccc tagtctgctg cgttttgcaa agaaaagcgc ttcctcaaaa     300

tcacgtcgct ttcttcatca cgatatgacg caaccggtac cagcagatca tcatgagcag     360

ttttcccatg ctacagcaat cctttctctt cagaatatgg aatctccaga acaagctatc     420

gcacacacag cgaatctttt ggctcctcaa ggtaggttgt ttattgttct caaccatcca     480

tgctttcgca tccctaggct ttcttcatgg ctttatgatg agcctaaaaa actcttatct     540
```

-continued

```
agaaaaatag accgctatct ctctcctgtg gcggttccta tcgttgtgca tcctggagaa    600

aaacattctg agacgacata ttctttccat ttccccttaa gctattgggt acaagcttta    660

tctaatcaca atcttctgat tgatagtatg gaagaatgga tctcccctaa aaaatcctca    720

gggaagaggg ctcgagcaga aaatctttgt cgcaaggagt ttccgctttt cttgtttatc    780

tcagcattaa aaatatcaaa a                                              801
```

<210> SEQ ID NO 81
<211> LENGTH: 52
<212> TYPE: PRT
<213> ORGANISM: Chlamydia trachomatis

<400> SEQUENCE: 81

```
Met Ala Ser Lys Asn Arg Glu Ile Ile Lys Leu Lys Ser Thr Glu Ser
1               5                   10                  15

Ser Glu Met Tyr Trp Thr Val Lys Asn Lys Arg Lys Thr Ser Gly Arg
            20                  25                  30

Leu Glu Leu Lys Lys Tyr Asp Arg Lys Leu Arg Lys His Val Ile Phe
        35                  40                  45

Lys Glu Ala Lys
    50
```

<210> SEQ ID NO 82
<211> LENGTH: 156
<212> TYPE: DNA
<213> ORGANISM: Chlamydia trachomatis

<400> SEQUENCE: 82

```
atggccagca aaaaccgcga aattatcaaa ttgaaaagta ccgaaagttc tgaaatgtat     60

tggactgtta aaaataaaag aaaaacaagc ggtcgactag aacttaaaaa gtatgataga    120

aagctgcgta agcacgttat cttcaaagaa gctaag                              156
```

<210> SEQ ID NO 83
<211> LENGTH: 529
<212> TYPE: PRT
<213> ORGANISM: Chlamydia trachomatis

<400> SEQUENCE: 83

```
Met His His Arg Lys Phe Leu Ala Val Ser Ile Ala Phe Val Ser Leu
1               5                   10                  15

Ala Phe Gly Leu Thr Ser Cys Tyr His Lys Lys Glu Glu Pro Lys Asp
            20                  25                  30

Val Leu Arg Ile Ala Ile Cys His Asp Pro Met Ser Leu Asp Pro Arg
        35                  40                  45

Gln Val Phe Leu Ser Lys Asp Val Ser Ile Val Lys Ala Leu Tyr Glu
    50                  55                  60

Gly Leu Val Arg Glu Lys Glu Ala Ala Phe Gln Leu Ala Leu Ala Glu
65                  70                  75                  80

Arg Tyr His Gln Ser Asp Asp Gly Cys Val Tyr Thr Phe Phe Leu Lys
                85                  90                  95

Asn Thr Phe Trp Ser Asn Gly Asp Val Val Thr Ala Tyr Asp Phe Glu
            100                 105                 110

Glu Ser Ile Lys Gln Ile Tyr Phe Arg Glu Ile Asp Asn Pro Ser Leu
        115                 120                 125

Arg Ser Leu Ala Leu Ile Lys Asn Ser His Ala Val Leu Thr Gly Ala
    130                 135                 140
```

```
Leu Pro Val Glu Asp Leu Gly Val Arg Ala Leu Asn Ala Lys Thr Leu
145                 150                 155                 160

Glu Ile Val Leu Glu Asn Pro Phe Pro Tyr Phe Leu Glu Ile Leu Ala
                165                 170                 175

His Pro Val Phe Tyr Pro Val His Thr Ser Leu Arg Glu Tyr Tyr Lys
            180                 185                 190

Asp Lys Arg Asn Lys Arg Val Phe Pro Ile Ile Ser Asn Gly Pro Phe
        195                 200                 205

Ala Ile Gln Cys Tyr Glu Pro Gln Arg Tyr Leu Leu Ile Asn Lys Asn
    210                 215                 220

Pro Leu Tyr His Ala Lys His Asp Val Leu Leu Asn Ser Val Cys Leu
225                 230                 235                 240

Gln Ile Val Pro Asp Ile His Thr Ala Met Gln Leu Phe Gln Lys Asn
                245                 250                 255

His Ile Asp Leu Val Gly Leu Pro Trp Ser Ser Ser Phe Ser Leu Glu
            260                 265                 270

Glu Gln Arg Asn Leu Pro Arg Glu Lys Leu Phe Asp Tyr Pro Val Leu
        275                 280                 285

Ser Cys Ser Val Leu Phe Cys Asn Ile His Gln Thr Pro Leu Asn Asn
    290                 295                 300

Pro Ser Leu Arg Thr Ala Leu Ser Leu Ala Ile Asn Arg Glu Thr Leu
305                 310                 315                 320

Leu Lys Leu Ala Gly Lys Gly Cys Ser Ala Thr Ser Phe Val His Pro
                325                 330                 335

Gln Leu Ser Gln Ile Pro Ala Thr Thr Leu Ser Gln Asp Glu Arg Ile
            340                 345                 350

Ala Leu Ala Lys Gly Tyr Leu Thr Glu Ala Leu Lys Thr Leu Ser Gln
        355                 360                 365

Glu Asp Leu Glu Lys Ile Thr Leu Ile Tyr Pro Ile Glu Ser Val Cys
    370                 375                 380

Leu Arg Ala Val Val Gln Glu Ile Arg Gln Gln Leu Phe Asp Val Leu
385                 390                 395                 400

Gly Phe Lys Ile Ser Thr Leu Gly Leu Glu Tyr His Cys Phe Leu Asp
                405                 410                 415

Lys Arg Ser Arg Gly Glu Phe Ser Leu Ala Thr Gly Asn Trp Ile Ala
            420                 425                 430

Asp Tyr His Gln Ala Ser Ala Phe Leu Ser Val Leu Gly Asn Gly Thr
        435                 440                 445

Arg Tyr Lys Asp Phe Gln Leu Ile Asn Trp Gln Asn Gln Lys Tyr Thr
    450                 455                 460

Asn Ile Val Ala Gln Leu Leu Ile Gln Glu Ser Ser Asp Leu Gln Leu
465                 470                 475                 480

Met Ala Glu Gln Leu Leu Leu Lys Glu Ser Pro Leu Ile Pro Leu Tyr
                485                 490                 495

His Leu Asp Tyr Val Tyr Ala Lys Gln Pro Arg Val Ser Asp Leu Gln
            500                 505                 510

Thr Ser Ser Arg Gly Glu Ile Asp Leu Lys Arg Val Ser Leu Ala Glu
        515                 520                 525

Gly
```

<210> SEQ ID NO 84
<211> LENGTH: 1587
<212> TYPE: DNA
<213> ORGANISM: Chlamydia trachomatis

<400> SEQUENCE: 84

```
atgcatcaca ggaagttttt agcagtttcc attgctttcg taagtttagc ttttgggcta     60
acatcttgtt atcataaaaa agaagaacca aaagatgttt tgcggattgc gatctgtcat    120
gatccaatgt ctttagatcc gcgtcaggtt tttttaagca aagatgtttc tattgtaaaa    180
gctctctatg aagggttagt ccgggaaaaa gaagctgcgt tccagctagc tttggcagaa    240
agatatcatc aatctgatga tggttgtgtt tatacttttt ttctaaaaaa tacattctgg    300
agcaacggag atgttgtaac agcatatgat tttgaagagt ctattaaaca aatttatttc    360
cgagaaattg ataacccttc gttacgctct cttgcattaa ttaaaaattc tcatgctgtt    420
ttaacaggag ctctccctgt tgaagattta ggtgttagag ctttgaatgc gaaaactcta    480
gaaattgttt tagaaaaccc gtttccttat tttctagaga tattggcgca cccggttttt    540
tatccggtgc acacctcttt acgagaatat tacaaagata agcgtaacaa acgcgttttc    600
ccgataattt ctaatggtcc ttttgcgatt caatgttatg agccgcaaag atatttacta    660
atcaacaaaa accctctgta tcatgccaag cacgatgttc tgttaaattc ggtatgtttg    720
cagatagttc ctgatatcca tacagctatg cagttattcc aaaaaaatca tatcgattta    780
gttgggttac cctggagctc ctccttttct ttagaagaac aaagaaatct ccctagagaa    840
aaattatttg attatcctgt attgagttgc tctgttttat tctgtaacat tcatcaaaca    900
cctttaaata atccctcgct gagaacagcc ctctctttag caatcaatcg agaaacttta    960
ttaaaactag caggtaaagg ctgtagcgct acgagctttg ttcacccaca attatctcag   1020
atacctgcta ctactttgtc tcaagatgag cggattgctt tagcaaaagg ctacttgacc   1080
gaagctttaa agactttatc tcaagaagat ttagaaaaaa ttacattaat ttatcctata   1140
gaatctgttt gcttacgagc cgttgttcaa gaaattcgcc aacaattatt tgatgtactg   1200
ggatttaaaa tttctacatt aggattagaa tatcattgtt ttttagacaa acgttccaga   1260
ggagaattct ccttagcaac tggtaattgg attgcagact atcatcaagc tagtgctttc   1320
ctgtctgtcc taggtaatgg gacaagatat aaagactttc aattgattaa ctggcagaac   1380
caaaagtaca caaatatagt tgctcaactt ctgattcaag aatcaagcga cctacagctt   1440
atggcagagc agttgttgct taaagaaagt cctcttattc ctctatacca cctcgattat   1500
gtgtatgcga aacagcctcg ggtgtctgat ctccaaacct cttctcgtgg agaaattgat   1560
ttaaaaagag tttcattagc tgaagga                                        1587
```

<210> SEQ ID NO 85
<211> LENGTH: 339
<212> TYPE: PRT
<213> ORGANISM: Chlamydia trachomatis

<400> SEQUENCE: 85

```
Glu Tyr Val Arg Phe Val Lys Val Lys Arg Gly Trp Leu Met Val Ser
1               5                   10                  15

Gln Thr Val Ser Val Ala Val Thr Gly Gly Thr Gly Gln Ile Ala Tyr
            20                  25                  30

Ser Phe Leu Phe Ser Leu Ala His Gly Asp Val Phe Gly Leu Asp Cys
        35                  40                  45

Gly Ile Asp Leu Arg Ile Tyr Asp Ile Pro Gly Thr Glu Arg Ala Leu
    50                  55                  60

Ser Gly Val Arg Met Glu Leu Asp Asp Gly Ala Phe Pro Leu Leu Gln
65                  70                  75                  80
```

-continued

```
Arg Val Gln Val Thr Thr Ser Leu His Asp Ala Phe Asp Gly Ile Asp
                85                  90                  95

Ala Ala Phe Leu Ile Gly Ser Val Pro Arg Gly Pro Gly Met Glu Arg
            100                 105                 110

Arg Asp Leu Leu Lys Lys Asn Gly Glu Ile Phe Ala Thr Gln Gly Lys
        115                 120                 125

Ala Leu Asn Thr Thr Ala Lys Arg Asp Ala Lys Ile Phe Val Val Gly
    130                 135                 140

Asn Pro Val Asn Thr Asn Cys Trp Ile Ala Met Asn His Ala Pro Arg
145                 150                 155                 160

Leu Leu Arg Lys Asn Phe His Ala Met Leu Arg Leu Asp Gln Asn Arg
                165                 170                 175

Met His Ser Met Leu Ser His Arg Ala Glu Val Pro Leu Ser Ala Val
            180                 185                 190

Ser Gln Val Val Val Trp Gly Asn His Ser Ala Lys Gln Val Pro Asp
        195                 200                 205

Phe Thr Gln Ala Leu Ile Asn Asp Arg Pro Ile Ala Glu Thr Ile Ala
    210                 215                 220

Asp Arg Asp Trp Leu Glu Asn Ile Met Val Pro Ser Val Gln Ser Arg
225                 230                 235                 240

Gly Ser Ala Val Ile Glu Ala Arg Gly Lys Ser Ser Ala Ala Ser Ala
                245                 250                 255

Ala Arg Ala Leu Ala Glu Ala Ala Arg Ser Ile Tyr Gln Pro Lys Glu
            260                 265                 270

Gly Glu Trp Phe Ser Ser Gly Val Cys Ser Asp His Asn Pro Tyr Gly
        275                 280                 285

Leu Pro Glu Asp Leu Ile Phe Gly Phe Pro Cys Arg Met Leu Ala Thr
    290                 295                 300

Gly Glu Tyr Glu Val Ile Pro Arg Leu Pro Trp Asp Ala Phe Ile Arg
305                 310                 315                 320

Gly Lys Met Gln Ile Ser Leu Asp Glu Ile Leu Gln Glu Lys Ala Ser
                325                 330                 335

Val Ser Leu
```

<210> SEQ ID NO 86
<211> LENGTH: 1020
<212> TYPE: DNA
<213> ORGANISM: Chlamydia trachomatis

<400> SEQUENCE: 86

```
ttacaaagat acgctagctt tttcctgaag aatctcatca agagatattt gcattttccc      60

acggataaag gcatcccaag gaagccttgg aatcacttca tattctcccg ttgctagcat     120

tcgacaaggg aaaccaaaga ttaaatcttc cggtaatcca tagggattgt ggtccgaaca     180

cactccggaa gaaaaccatt ctccttcttt tggctgatat attgatcgag cagcctctgc     240

taaagctcgt gctgcagaag ctgccgaaga cttccctcgt gcttcgatta ctgcactacc     300

acgactctgt acagaaggca ccataatatt ctctaaccaa tcacgatccg ctatcgtctc     360

tgcgatagga cggtcattaa tcagagcttg cgtaaaatca ggcacttgtt tggcggagtg     420

atttccccaa accacaactt gtgatacagc cgataaaggt acttctgctc tatgcgataa     480

catgctatgc atacgattct ggtccaatcg tagcatcgca tgaaagttct ttctcaataa     540

tctgggagca tgattcattg ctatccagca attggtattc acagggttcc caacaacaaa     600
```

-continued

```
aatctttgca tcccgcttgg ctgttgtgtt caaagctttt ccttgcgtag caaaaatctc    660

cccatttttc tttagaagat ctcttctctc cattcctggg cctctaggaa ctgaccctat    720

aaggaatgcc gcatcaatgc catcaaaagc atcatgcaat gatgtcgtta cctgcacacg    780

ctgtaataaa gggaaagcac catcatctag ctccatgcgc acaccagata aagccctttc    840

tgttccagga atatcgtaga tacgcagatc gatgccacaa tcaaggccaa aaacatctcc    900

atgagccaga gaaaatagaa agctataggc tatttgccct gttcctcctg ttactgctac    960

actcactgtt tgagaaacca taagccaccc tctctttact tttacaaaac gcacatactc   1020
```

<210> SEQ ID NO 87
<211> LENGTH: 160
<212> TYPE: PRT
<213> ORGANISM: Chlamydia trachomatis

<400> SEQUENCE: 87

```
Met Arg Ile Ile Pro Phe Asp Pro Tyr Gly Ser Met Ala Phe Gln Ala
1               5                   10                  15

Ile Ala Lys Asp Pro Gln Glu Arg Lys Asn Gly Ser Ile Ser Glu Lys
            20                  25                  30

Ile Ser Glu Glu Ile Ala Arg Asn Glu Ala Leu Arg Met Ala Leu Leu
        35                  40                  45

Ala Ile Ala Asp Gln Glu Asp Lys Glu Lys Lys Gln Lys His Arg Phe
    50                  55                  60

Lys Ile Leu Thr Lys Lys Gln Thr Arg Ile Leu Leu Gly Gln Leu Arg
65                  70                  75                  80

His Phe Arg Leu Asp Phe Gln Lys Leu Gln Ala Gly Val Val Ile Glu
                85                  90                  95

Trp Ser Trp Asp Asp Lys Ser Glu Arg Ser Lys Ser Leu Gly Ser Arg
            100                 105                 110

Ile Thr Arg Lys Ser Lys Lys Thr Ile Cys Ile Ser Ala Ala Ala Ala
        115                 120                 125

Gln Ala Ile Ala His Ala Ala Glu Ala Trp Val Ile Ala Arg Asn Glu
    130                 135                 140

Gly Ile Leu Glu Met Thr Leu Ser Leu Phe Gln His Lys Asp Asn Glu
145                 150                 155                 160
```

<210> SEQ ID NO 88
<211> LENGTH: 480
<212> TYPE: DNA
<213> ORGANISM: Chlamydia trachomatis

<400> SEQUENCE: 88

```
atgagaataa tccctttttga tccttatgga tccatggctt ttcaagcgat agcgaaagat     60

cctcaagagc gaaagaatgg gagcatatca gagaaaattt cagaagagat tgctcgtaat    120

gaagctttac gcatggcttt attggctatt gccgatcaag aagataaaga aaaaaaacaa    180

aagcatcggt tcaaaatctt aaccaaaaaa caaaccagga tattgcttgg tcagctacgt    240

catttccgat tggatttcca aaaactgcaa gcaggagttg tcatcgagtg gtcttgggat    300

gataaatccg agcgctctaa gtcattagga tctcggatta ccagaaaatc taagaaaacg    360

atctgtatta gcgctgctgc agcacaagct attgctcatg ccgcagaggc ttgggtgatt    420

gcccgcaatg aaggaatctt ggagatgacg ttgtcactat tccaacataa agacaacgaa    480
```

<210> SEQ ID NO 89
<211> LENGTH: 421

```
<212> TYPE: PRT
<213> ORGANISM: Chlamydia trachomatis

<400> SEQUENCE: 89

Met Thr Ala Ser Gly Gly Ala Gly Gly Leu Gly Ser Thr Gln Thr Val
1               5                   10                  15

Asp Val Ala Arg Ala Gln Ala Ala Ala Ala Thr Gln Asp Ala Gln Glu
            20                  25                  30

Val Ile Gly Ser Gln Glu Ala Ser Glu Ala Ser Met Leu Lys Gly Cys
        35                  40                  45

Glu Asp Leu Ile Asn Pro Ala Ala Ala Thr Arg Ile Lys Lys Lys Gly
    50                  55                  60

Glu Lys Phe Glu Ser Leu Glu Ala Arg Arg Lys Pro Thr Ala Asp Lys
65                  70                  75                  80

Ala Glu Lys Lys Ser Glu Ser Thr Glu Glu Lys Gly Asp Thr Pro Leu
                85                  90                  95

Glu Asp Arg Phe Thr Glu Asp Leu Ser Glu Val Ser Gly Glu Asp Phe
            100                 105                 110

Arg Gly Leu Lys Asn Ser Phe Asp Asp Asp Ser Ser Pro Asp Glu Ile
        115                 120                 125

Leu Asp Ala Leu Thr Ser Lys Phe Ser Asp Pro Thr Ile Lys Asp Leu
    130                 135                 140

Ala Leu Asp Tyr Leu Ile Gln Thr Ala Pro Ser Asp Gly Lys Leu Lys
145                 150                 155                 160

Ser Thr Leu Ile Gln Ala Lys His Gln Leu Met Ser Gln Asn Pro Gln
                165                 170                 175

Ala Ile Val Gly Gly Arg Asn Val Leu Leu Ala Ser Glu Thr Phe Ala
            180                 185                 190

Ser Arg Ala Asn Thr Ser Pro Ser Ser Leu Arg Ser Leu Tyr Phe Gln
        195                 200                 205

Val Thr Ser Ser Pro Ser Asn Cys Ala Asn Leu His Gln Met Leu Ala
    210                 215                 220

Ser Tyr Leu Pro Ser Glu Lys Thr Ala Val Met Glu Phe Leu Val Asn
225                 230                 235                 240

Gly Met Val Ala Asp Leu Lys Ser Glu Gly Pro Ser Ile Pro Pro Ala
                245                 250                 255

Lys Leu Gln Val Tyr Met Thr Glu Leu Ser Asn Leu Gln Ala Leu His
            260                 265                 270

Ser Val Asn Ser Phe Phe Asp Arg Asn Ile Gly Asn Leu Glu Asn Ser
        275                 280                 285

Leu Lys His Glu Gly His Ala Pro Ile Pro Ser Leu Thr Thr Gly Asn
    290                 295                 300

Leu Thr Lys Thr Phe Leu Gln Leu Val Glu Asp Lys Phe Pro Ser Ser
305                 310                 315                 320

Ser Lys Ala Gln Lys Ala Leu Asn Glu Leu Val Gly Pro Asp Thr Gly
                325                 330                 335

Pro Gln Thr Glu Val Leu Asn Leu Phe Phe Arg Ala Leu Asn Gly Cys
            340                 345                 350

Ser Pro Arg Ile Phe Ser Gly Ala Glu Lys Lys Gln Gln Leu Ala Ser
        355                 360                 365

Val Ile Thr Asn Thr Leu Asp Ala Ile Asn Ala Asp Asn Glu Asp Tyr
    370                 375                 380

Pro Lys Pro Gly Asp Phe Pro Arg Ser Ser Phe Ser Ser Thr Pro Pro
385                 390                 395                 400
```

His Ala Pro Val Pro Gln Ser Glu Ile Pro Thr Ser Pro Thr Ser Thr
405 410 415

Gln Pro Pro Ser Pro
420

<210> SEQ ID NO 90
<211> LENGTH: 1263
<212> TYPE: DNA
<213> ORGANISM: Chlamydia trachomatis

<400> SEQUENCE: 90
atgactgcat caggaggagc tggagggcta ggcagcaccc aaacagtaga cgttgcgcga 60
gcacaagctg ctgcagctac tcaagatgca caagaggtta tcggctctca ggaagcttct 120
gaggcaagta tgctcaaagg atgtgaggat ctcataaatc ctgcagctgc aacccgaatc 180
aaaaaaaaag gagagaagtt tgaatcatta gaagctcgtc gcaaaccaac agcggataaa 240
gcagaaaaga aatccgagag cacagaggaa aaaggcgata ctcctcttga agatcgtttc 300
acagaagatc tttccgaagt ctccggagaa gattttcgag gattgaaaaa ttcgttcgat 360
gatgattctt ctcctgacga aattctcgat gcgctcacaa gtaaattttc tgatcccaca 420
ataaaggatc tagctcttga ttatctaatt caaacagctc cctctgatgg gaaacttaag 480
tccactctca ttcaggcaaa gcatcaactg atgagccaga atcctcaggc gattgttgga 540
ggacgcaatg ttctgttagc ttcagaaacc tttgcttcca gagcaaatac atctccttca 600
tcgcttcgct ccttatattt ccaagtaacc tcatccccct ctaattgcgc taatttacat 660
caaatgcttg cttcttactt gccatcagag aaaaccgctg ttatggagtt tctagtaaat 720
ggcatggtag cagatttaaa atcggagggc ccttccattc ctcctgcaaa attgcaagta 780
tatatgacgg aactaagcaa tctccaagcc ttacactctg taaatagctt ttttgataga 840
aatattggga acttggaaaa tagcttaaag catgaaggac atgcccctat tccatcctta 900
acgacaggaa atttaactaa aaccttctta caattagtag aagataaatt cccttcctct 960
tccaaagctc aaaaggcatt aaatgaactg gtaggcccag atactggtcc tcaaactgaa 1020
gttttaaact tattcttccg cgctcttaat ggctgttcgc ctagaatatt ctctggagct 1080
gaaaaaaaac agcagctggc atcggttatc acaaatacgc tagatgcgat aaatgcggat 1140
aatgaggatt atcctaaacc aggtgacttc ccacgatctt ccttctctag tacgcctcct 1200
catgctccag tacctcaatc tgagattcca acgtcaccta cctcaacaca gcctccatca 1260
ccc 1263

<210> SEQ ID NO 91
<211> LENGTH: 313
<212> TYPE: PRT
<213> ORGANISM: Chlamydia trachomatis

<400> SEQUENCE: 91

Met Leu Ala Gly Ser Lys Arg Lys His Lys Thr Pro Glu Asp Thr Ser
1 5 10 15

Ser Ser Ser Ser Lys Arg Ala Arg Ser Ser Ser Ser Gln Val Val Pro
20 25 30

Arg Leu Leu Gln His His Glu Leu Ile Gln Leu Tyr Ser Ala His Gln
35 40 45

Gln Arg Asn Asn Glu Pro Val Lys Met Ile Cys Glu Thr Ile Leu Gln
50 55 60

Ala Lys Arg Ser Val Leu Leu Lys Ile Phe Asn Ile Gly Ser Pro Arg
65 70 75 80

Ile Leu Ala Ala Leu Ala Glu Ala Ser Asn Arg Ala Pro Val Ser Val
85 90 95

His Tyr Gln Met Gly Pro Phe Ser Lys His Cys Thr Glu Gly Asn Val
100 105 110

Gln Phe Arg Pro Arg Arg Gly Cys Ser Leu Leu His Arg Lys Thr Leu
115 120 125

Leu Ile Asp Asn Asn Ile Val Val Thr Gly Thr Ala Asn Tyr Thr Glu
130 135 140

Ala Ser Leu Glu Lys Asp Val Asn Leu Thr Ala Lys Ile Phe Ser Glu
145 150 155 160

His Leu Tyr Arg Trp Ala Phe Arg His Asp Arg Gly Glu Val Arg Val
165 170 175

Gly Ser Gln Gln Val Ser Tyr Tyr Ser Leu Ser Gln Ile Arg Arg Asp
180 185 190

Leu Cys Val Lys Ala Ile Leu Glu Ala Asn Gly Ile Val Leu Arg Glu
195 200 205

Arg Thr Cys Glu Gly Ile Leu His Thr Lys Val Cys Cys Ile Asp Ser
210 215 220

Ser Thr Leu Ile Ile Gly Ser Val Asn Trp Ser Arg Gly Gly Leu Thr
225 230 235 240

Leu Asn Leu Glu Glu Phe Leu Ile Ile Asn Pro Leu Thr Glu Thr Gln
245 250 255

Leu Glu Cys Tyr Asn Glu Leu Trp Ala His Ile Glu Thr Asn Ser Arg
260 265 270

Leu Met Thr Lys Glu Leu Ile Gln Leu His Glu Lys Arg Lys Lys Ser
275 280 285

Ile Thr Asp Pro Lys Gln Ile Ser Ser Ser Thr Gln Asp Glu Glu Asn
290 295 300

Ala Ser Thr Ser Ala Glu Gln Gln Phe
305 310

<210> SEQ ID NO 92
<211> LENGTH: 939
<212> TYPE: DNA
<213> ORGANISM: Chlamydia trachomatis

<400> SEQUENCE: 92
atgctcgccg gatccaagag aaaacacaag actcccgaag acacttcttc ttcctcctct 60
aaacgagccc gatcttcttc gagccaagtc gtacctagac tcttacagca tcacgaactg 120
atccaactct actctgctca tcagcaaaga aataacgaac ctgtgaaaat gatttgtgaa 180
acaattctac aagctaagcg cagcgttcta ttaaaaatat ttaatatcgg atcccccaga 240
attcttgcag ccttagctga ggcttctaat agagcgcctg tctccgtaca ctatcaaatg 300
gggccttttt caaaacactg tactgaagga aatgtgcagt ttagacctcg aagagggtgt 360
tctcttttac atagaaaaac ccttcttata gacaataata ttgtcgttac gggaacagca 420
aactatacag aggcctctct tgaaaaagat gtgaacttaa cggctaaaat atttagcgaa 480
cacctatatc gctgggcttt ccgacacgat cgaggagagg tgcgagtagg ctcgcaacaa 540
gtatcctact attcgctaag tcaaatacga agagacttgt gcgtcaaagc tatcctcgaa 600
gctaacggca ttgtcctacg agaacgtaca tgcgaaggca ttctgcatac caaagtctgc 660
tgtattgata gctcgacact cattatagga tccgtcaact ggagtagagg aggtcttaca 720

```
ttaaatctgg aagagttctt gattatcaat ccgcttacag agacacaact cgaatgctat    780

aacgagcttt gggcacatat agaaacaaac agtagattga tgactaaaga gctgattcag    840

ttacatgaga agagaaaaaa atccataaca gaccctaagc aaatctcttc ttctactcaa    900

gacgaagaga atgcttccac atcagcagaa cagcagttc                           939


<210> SEQ ID NO 93
<211> LENGTH: 100
<212> TYPE: PRT
<213> ORGANISM: Chlamydia trachomatis

<400> SEQUENCE: 93

Val Ser Leu Ile Thr Thr Gln Thr Gly Tyr Phe Ala Arg Gln Asn Arg
1               5                   10                  15

Arg Gly Gly Phe Gln Val Phe Tyr Ser Ile Tyr Gly Leu Glu Gly Lys
            20                  25                  30

Val Gln Pro His Gln Ala Pro Gly Asp Met Leu Cys Asp Ile Thr Glu
        35                  40                  45

Asp Val Val Leu Thr Val Lys Asp Val Asp Glu Ser Asp Tyr Gln Gln
    50                  55                  60

Lys Arg Ile Tyr Val Val Leu Asp Leu Ala Thr Glu Glu Glu Arg Arg
65                  70                  75                  80

Leu Arg Ala Asp Lys Asn Val Ile Leu Ile Pro Arg Gly Glu Asn Ser
                85                  90                  95

Lys Lys Arg Lys
            100


<210> SEQ ID NO 94
<211> LENGTH: 300
<212> TYPE: DNA
<213> ORGANISM: Chlamydia trachomatis

<400> SEQUENCE: 94

gtgtcgttga ttacaacgca aacaggatac tttgctcggc agaacagacg aggagggttc     60

caagtcttct atagtattta cggattagaa gggaaagtgc aaccacacca agctcctgga    120

gatatgctat gcgacattac tgaagacgta gtgttaacgg tcaaagatgt ggatgaaagc    180

gactaccaac agaaacgaat ttatgtggtt ttagatttag cgacggaaga agagcgtagg    240

ttgcgagcag ataagaacgt gatccttatt cctagagggg agaattctaa gaaaagaaaa    300


<210> SEQ ID NO 95
<211> LENGTH: 148
<212> TYPE: PRT
<213> ORGANISM: Chlamydia trachomatis

<400> SEQUENCE: 95

Met Asn Ile Ala Lys Gln Gln Gln Ala Phe Leu Gly Ile Asp Tyr Gly
1               5                   10                  15

Lys Lys Arg Ile Gly Leu Ala Phe Ala Ser Ser Pro Leu Leu Ile Pro
            20                  25                  30

Leu Pro Ile Gly Asn Val Glu Ala Arg Ser Ser Leu Thr Leu Thr Ala
        35                  40                  45

Gln Ala Leu Val Ser Ile Ile Lys Glu Arg Ala Val Thr Thr Val Val
    50                  55                  60

Phe Gly Asn Pro Leu Pro Met Gln Lys Ala Tyr Ala Ser Ser Val Gln
65                  70                  75                  80
```

-continued

```
Ser Glu Ile Gln Glu Leu Ala Ala Leu Ile Gln Glu Met Thr Ala Ile
                85                  90                  95

Glu Val Ile Leu Trp Asp Glu Arg Leu Ser Ser Ala Gln Ala Glu Arg
            100                 105                 110

Met Leu Lys Ser Asp Cys Gly Leu Asn Arg Lys Gln Arg Lys Asn Pro
        115                 120                 125

Ser Asp Ser Leu Ala Ala Thr Leu Ile Leu Ser Ser Phe Leu Asp Ser
    130                 135                 140

Arg Lys Leu Tyr
145
```

```
<210> SEQ ID NO 96
<211> LENGTH: 444
<212> TYPE: DNA
<213> ORGANISM: Chlamydia trachomatis

<400> SEQUENCE: 96

atgaacatcg ctaagcaaca acaagctttt ttagggatcg attatgggaa aaaacgtatt      60

ggcctagctt ttgccagttc ccctcttctg atccctttgc ctatagggaa tgtagaagcc     120

cgttcctctc ttactttgac agctcaagcg ctcgtctcta ttatcaaaga gcgtgctgtt     180

acgacagtag ttttcgggaa tccattacct atgcaaaaag cttatgcttc aagcgtgcaa     240

tcagaaattc aagaactagc cgcactcatc caagaaatga ctgctataga agtcattctt     300

tgggatgagc ggctatcttc agcacaagca gaacgcatgt taaaaagcga ttgtgggctt     360

aatcgaaaac agcggaaaaa tccttcggat agtctagctg ccactttaat cctttctagc     420

tttttagatt ctcgaaaact atac                                            444
```

```
<210> SEQ ID NO 97
<211> LENGTH: 571
<212> TYPE: PRT
<213> ORGANISM: Chlamydia trachomatis

<400> SEQUENCE: 97

Met Ser Val Thr Gly Gln Asp Asn Lys Glu Leu Gln Gln Glu Phe Val
1               5                   10                  15

Ile Val Gly Glu Pro Ile Val Pro Gly Ile Gly Leu Gly Lys Ala Leu
            20                  25                  30

Leu Leu Gly Lys Ser Ser Leu Arg Ile Arg Glu Leu Thr Leu Pro Gln
        35                  40                  45

Glu Glu Val Glu His Glu Ile Ser Arg Tyr Tyr Lys Ala Leu Lys Arg
    50                  55                  60

Ser Arg Ser Asp Leu Ala Ala Leu Glu Lys Glu Ala Lys Gly Lys Gln
65                  70                  75                  80

Gly Tyr Gln Glu Ile Ala Ser Ile Leu Gln Ala His Leu Glu Ile Ile
                85                  90                  95

Lys Asp Pro Leu Leu Thr Glu Glu Val Val Lys Thr Ile Arg Lys Asp
            100                 105                 110

Arg Lys Asn Ala Glu Phe Val Phe Ser Ser Val Met Gly Glu Ile Glu
        115                 120                 125

Lys Ser Leu Cys Ala Val Gln Lys Thr Thr Ala Thr Arg Val Asp Arg
    130                 135                 140

Val Gln Asp Ile His Asp Ile Ser Asn Arg Val Ile Gly His Leu Cys
145                 150                 155                 160

Cys Gln His Lys Ser Ser Leu Gly Glu Phe Asp Gln Asn Leu Ile Val
                165                 170                 175
```

```
Phe Ser Glu Glu Leu Thr Pro Ser Glu Ala Ala Asn Ala Asn Pro Glu
            180                 185                 190

Tyr Ile Arg Gly Phe Val Ser Leu Glu Gly Ala Lys Thr Ser His Thr
        195                 200                 205

Ala Ile Val Ser Leu Ala Lys Asn Ile Pro Tyr Val Ala Asn Phe Thr
    210                 215                 220

Thr Glu Leu Trp Asp Thr Ile Lys Glu Phe Ser Gly Thr Leu Val Leu
225                 230                 235                 240

Ile Asn Gly Asp Lys Gly Glu Ile Thr Phe Asn Pro Gln Leu Ser Thr
                245                 250                 255

Ile Gln Thr Tyr Tyr Arg Lys Gln Ala Ser Val Ser Val Thr Val Pro
            260                 265                 270

Val Gln Val Gln Thr Gly Lys Asn Leu Pro Leu Ile Ser Leu Ser Ala
        275                 280                 285

Gln Ile Val Ser Thr Glu Glu Leu Pro Met Ile Glu Arg Glu Ser Pro
    290                 295                 300

Gly Thr Ser Val Gly Leu Phe Arg Ser Glu Phe Met Ala Phe Ser Leu
305                 310                 315                 320

Gly Arg Leu Pro Cys Val Glu Glu Gln Ala Asp Gln Tyr Ala Gln Leu
                325                 330                 335

Val Gln Phe Gln Cys Ser Asp Ile His Val Leu Arg Leu Phe Asp Phe
            340                 345                 350

Gly Glu Asp Lys Glu Cys Pro Cys Ile Ser Ser Ser His Arg Ser Val
        355                 360                 365

Arg Trp Leu Leu Glu Gln Glu Lys Val Leu Lys Glu Gln Leu Gln Ala
    370                 375                 380

Ile Ala Ile Val Ser Arg Ile Gly Arg Leu Lys Val Leu Ile Pro Gly
385                 390                 395                 400

Val Ile Asp Ala Ser Glu Ile Ala Leu Val Lys Arg Leu Phe Gln Glu
                405                 410                 415

Glu Ile Arg Leu Leu Lys Gly Ile Ser Glu Asn Ile Leu Trp Gly Ser
            420                 425                 430

Met Ile Glu Ile Pro Ser Ala Val Trp Met Ile Glu Glu Ile Leu Gln
        435                 440                 445

Glu Ser Ser Phe Val Ala Leu Gly Thr Asn Asp Leu Ala Gln Tyr Thr
    450                 455                 460

Leu Gly Thr Ser Arg Glu Arg Ser Leu Leu Gly Glu Arg Ser Arg Val
465                 470                 475                 480

Pro His Pro Ser Val Ile Arg Met Ile His His Val Val Glu Gln Ala
                485                 490                 495

Lys Gln Lys Asn Val Pro Val Ser Val Cys Gly Glu Met Ala Gly Asp
            500                 505                 510

Pro Ala Leu Leu Pro Met Phe Leu Gly Leu Gly Val Lys Glu Leu Ser
        515                 520                 525

Ala Val Ile Pro Ala Ile Asn Ser Leu Lys Met Arg Leu Leu Asp Leu
    530                 535                 540

Asn Ser Arg Glu Cys Ser Arg Leu Thr Lys Gln Leu Leu Arg Ala Lys
545                 550                 555                 560

Thr Tyr Glu Glu Val His Gln Leu Leu Tyr Val
                565                 570
```

<210> SEQ ID NO 98
<211> LENGTH: 1713

<212> TYPE: DNA
<213> ORGANISM: Chlamydia trachomatis

<400> SEQUENCE: 98

```
atgagcgtta cgggtcaaga taataaggag ttgcaacagg agtttgttat tgtaggggag      60
cctatagtcc ctggaatagg gctagggaaa gctttattgt tgggcaaatc ttctttgcgg     120
atacgagagc taactcttcc tcaagaagaa gtggaacatg agatcagtcg ctactacaag     180
gctttgaaga gatctcgttc agatctagct gctttagaaa aagaagcaaa gggaaagcag     240
ggatatcaag agatagcttc cattttgcag gcacatctag aaattataaa agaccctctt     300
ctcacggaag aggtggttaa aacaattaga aaagatcgaa agaatgcgga gtttgttttt     360
tcttctgtca tgggagagat agagaaatct ctatgtgctg tacagaagac gactgctacc     420
agagtagatc gagttcagga tatccatgat atttctaatc gagtgattgg ccatctttgt     480
tgtcagcata agagttcttt aggggagttt gatcagaatc ttattgtctt ttcggaagag     540
cttactccct cggaagccgc aaatgctaat cccgagtaca tcaggggctt tgtatcttta     600
gagggcgcaa aaacttcgca taccgcgatt gtatctttgg ctaaaaatat tccttatgtt     660
gccaatttta ctacagagtt atgggatact attaaagagt ttagtgggac attagttctc     720
attaatgggg ataagggaga gattacgttt aatcctcagc taagtacgat acaaacttat     780
tatcgtaagc aagcgtctgt ttctgtcact gttccagtgc aggtgcagac agggaaaaat     840
ctgcctctta tctctctctc agcacagata gtaagtacag aagaattgcc catgattgaa     900
agggagtctc cagggacaag tgttgggctc ttccgttcag aatttatggc tttttctttg     960
ggacgcttac cctgtgttga agaacaagct gatcaatatg ctcaattagt tcagtttcag    1020
tgttcagata ttcatgtatt gcgtttgttt gattttggag aggataaaga gtgtccttgt    1080
atttcctctt ctcatcggtc agtacggtgg ttattagaac aagaaaaagt attgaaggag    1140
cagttgcagg ctattgctat tgtttctaga ataggacgac ttaaggtatt gattcctggg    1200
gtgatagatg cttcagaaat tgctttagta aagcggcttt ttcaagaaga aattcggcta    1260
ttgaaaggga tcagtgaaaa tatcttatgg ggaagcatga tagagatccc ttctgcagtt    1320
tggatgatag aggaaatttt acaagagagt tcttttgtag ctttaggtac taatgatctt    1380
gctcagtata ctttaggcac ttctagagag cgttccttac ttggggagcg gagtagagtg    1440
ccgcatcctt ctgttattag aatgattcat catgttgtag agcaggctaa acagaagaat    1500
gttcccgtat ctgtatgtgg agagatggca ggagaccctg ctcttctgcc tatgttttta    1560
ggactagggg taaaggagtt atcagctgtc atcccagcaa taaattcttt gaaaatgcga    1620
ttattagatt tgaactcaag ggagtgctct cgtttaacga agcagttatt gcgggcgaaa    1680
acatacgaag aggttcatca actcctgtat gtg                                 1713
```

<210> SEQ ID NO 99
<211> LENGTH: 90
<212> TYPE: PRT
<213> ORGANISM: Chlamydia trachomatis

<400> SEQUENCE: 99

```
Ser Leu Asn Lys Ser Gly Val Thr Ile Pro Gly Leu Leu Cys Val Arg
1               5                   10                  15

Ala Arg Arg Ala Leu Leu Asn Lys Thr Asn Tyr Val Leu Arg Leu Phe
            20                  25                  30

Met Pro Ser Val Lys Val Arg Val Gly Glu Pro Ile Asp Arg Ala Leu
        35                  40                  45
```

```
Arg Ile Leu Lys Lys Lys Ile Asp Lys Glu Gly Ile Leu Lys Thr Ser
    50                  55                  60

Lys Ser His Arg Phe Tyr Asp Lys Pro Ser Val Lys Lys Arg Ala Lys
65                  70                  75                  80

Ser Lys Ala Ala Ala Lys Tyr Arg Gly Arg
                85                  90


<210> SEQ ID NO 100
<211> LENGTH: 273
<212> TYPE: DNA
<213> ORGANISM: Chlamydia trachomatis

<400> SEQUENCE: 100

ctaacgacca cgatatttgg ctgcagcctt ggattttgct cgttttttta cagaaggttt      60

gtcgtagaat ctatgagact tagaagtttt caaaattcct tctttgtcga tttttttctt     120

taaaattctt agagctcgat ctataggctc tccaactctg actttaacac tgggcatgaa     180

taaccttaat acgtaattgg ttttatttaa taacgcgcgc ctagctcgaa cgcacaagag     240

accggggatt gtaacaccac ttttatttag gct                                  273


<210> SEQ ID NO 101
<211> LENGTH: 695
<212> TYPE: PRT
<213> ORGANISM: Chlamydia trachomatis

<400> SEQUENCE: 101

Met Ala Phe Glu Thr Phe Ser Val Ala Leu Asp Lys Asp Lys Thr Leu
1               5                   10                  15

Ile Phe Glu Thr Gly Lys Ile Ala Arg Gln Ala Ser Gly Ala Val Leu
            20                  25                  30

Val Lys Met Asn Glu Thr Trp Val Phe Ser Ser Ala Cys Ala Ala Ser
        35                  40                  45

Leu Ser Glu Ala Val Asp Phe Leu Pro Phe Arg Val Asp Tyr Gln Glu
    50                  55                  60

Lys Phe Ser Ser Ala Gly Arg Thr Ser Gly Gly Phe Leu Lys Arg Glu
65                  70                  75                  80

Gly Arg Pro Ser Glu Arg Glu Ile Leu Val Ser Arg Leu Met Asp Arg
                85                  90                  95

Ser Leu Arg Pro Ser Phe Pro Asn Arg Leu Met Gln Asp Ile Gln Val
            100                 105                 110

Leu Ser Tyr Val Trp Ser Tyr Asp Gly Lys Thr Leu Pro Asp Pro Leu
        115                 120                 125

Ala Ile Cys Gly Ala Ser Ala Ala Leu Ala Ile Ser Glu Val Pro Gln
    130                 135                 140

Asn Cys Ile Val Ala Gly Val Arg Val Gly Leu Val Gly Gly Lys Trp
145                 150                 155                 160

Val Ile Asn Pro Thr Arg Asp Glu Leu Ser Ala Ser Lys Leu Asp Leu
                165                 170                 175

Val Met Ala Gly Thr Ala Ser Ala Val Leu Met Ile Glu Gly His Cys
            180                 185                 190

Asp Phe Leu Thr Glu Glu Gln Val Leu Glu Ala Ile Ala Phe Gly Gln
        195                 200                 205

Thr Tyr Ile Ala Lys Ile Cys Asp Ala Ile Glu Ala Trp Gln Lys Ala
    210                 215                 220

Ile Gly Lys Gln Lys Asn Phe Ser Ala Val Leu Asp Met Pro Glu Asp
```

-continued

```
225                 230                 235                 240

Val Gln Asn Val Val Ser Asp Phe Ile Arg Glu Lys Phe Glu Lys Ala
                245                 250                 255

Leu Ser Phe Arg Asp Lys Glu Ala Leu Glu Gln Ala Ser Lys Glu Leu
            260                 265                 270

Glu Glu Ser Val Ile Ala Asn Leu Val Gln Glu Glu Asn Ser Asp Phe
        275                 280                 285

Ser Leu Leu Asn Val Lys Ala Ala Phe Lys Thr Ala Lys Ser Asn Gln
    290                 295                 300

Met Arg Ala Leu Ile Gln Asp Leu Gly Ile Arg Val Asp Gly Arg Thr
305                 310                 315                 320

Thr Thr Glu Ile Arg Pro Ile Ser Ile Glu Thr Pro Phe Leu Pro Arg
                325                 330                 335

Thr His Gly Ser Cys Leu Phe Thr Arg Gly Glu Thr Gln Ser Met Ala
            340                 345                 350

Val Cys Thr Leu Gly Gly Glu Asn Met Ala Gln Arg Phe Glu Asp Leu
        355                 360                 365

Asn Gly Asp Gly Ala Ala Arg Phe Tyr Leu Gln Tyr Phe Phe Pro Pro
    370                 375                 380

Phe Ser Val Gly Glu Val Gly Arg Ile Gly Ser Pro Gly Arg Arg Glu
385                 390                 395                 400

Ile Gly His Gly Lys Leu Ala Glu Lys Ala Leu Ser His Val Leu Pro
                405                 410                 415

Glu Thr Ser Arg Phe Pro Tyr Ile Ile Arg Leu Glu Ser Asn Ile Thr
            420                 425                 430

Glu Ser Asn Gly Ser Ser Ser Met Ala Ser Val Cys Gly Gly Cys Leu
        435                 440                 445

Ala Leu Met Asp Ala Gly Val Pro Ile Lys Ala Pro Val Ala Gly Ile
    450                 455                 460

Ala Met Gly Leu Ile Leu Asp Arg Asp Gln Ala Ile Ile Leu Ser Asp
465                 470                 475                 480

Ile Ser Gly Ile Glu Asp His Leu Gly Asp Met Asp Phe Lys Val Ala
                485                 490                 495

Gly Thr Ala Lys Gly Ile Thr Ala Phe Gln Met Asp Ile Lys Ile Glu
            500                 505                 510

Gly Ile Thr His Lys Ile Met Glu Gln Ala Leu Ala Gln Ala Lys Gln
        515                 520                 525

Gly Arg Ser His Ile Leu Asn Leu Met Thr Gln Val Leu Ala Ser Pro
    530                 535                 540

Lys Gly Thr Val Ser Lys Tyr Ala Pro Arg Ile Glu Thr Met Gln Ile
545                 550                 555                 560

Asn Thr Ser Lys Ile Ala Thr Val Ile Gly Pro Gly Gly Lys Gln Ile
                565                 570                 575

Arg Gln Ile Ile Glu Arg Ser Gly Ala Gln Val Asp Ile Asn Asp Asp
            580                 585                 590

Gly Val Ile Asn Ile Ala Ala Ser Thr Gln Glu Ser Ile Asn Lys Ala
        595                 600                 605

Lys Glu Leu Ile Glu Gly Leu Thr Gly Glu Val Glu Val Gly Lys Val
    610                 615                 620

Tyr Asn Gly Arg Val Thr Ser Ile Ala Thr Phe Gly Val Phe Val Glu
625                 630                 635                 640

Val Leu Pro Gly Lys Glu Gly Leu Cys His Ile Ser Glu Leu Ser Lys
                645                 650                 655
```

```
Gln Lys Val Asp Asn Ile Ser Asp Phe Val Lys Glu Gly Asp Lys Leu
            660                 665                 670

Ala Val Lys Leu Leu Ser Ile Asn Glu Lys Gly Gln Leu Lys Leu Ser
        675                 680                 685

His Lys Ala Thr Leu Glu Asp
    690                 695


<210> SEQ ID NO 102
<211> LENGTH: 2085
<212> TYPE: DNA
<213> ORGANISM: Chlamydia trachomatis

<400> SEQUENCE: 102

atggcttttg agactttttc tgttgcgtta gacaaagata aaacattaat tttcgagaca     60

gggaaaatag ctcgccaggc cagtggggct gttctcgtca aaatgaacga gacttgggtt    120

ttttcttcag cgtgtgcagc ctccttgtca gaggctgtcg attttctgcc tttcagagta    180

gactatcaag agaagttttc ctccgcagga agaacctctg gaggatttct aaaacgtgaa    240

ggacggcctt ccgagagaga aattcttgtt tctcggctaa tggatcgctc tttgcgtccg    300

tcgtttccta atagactcat gcaagatatt caagtcttgt cctacgtttg gtcttacgac    360

gggaaaactt tacctgatcc tctagctatt tgcggagctt ctgccgcttt agctatctca    420

gaggttcctc aaaattgtat cgttgcgggt gtacgcgttg ggctcgtcgg aggaaagtgg    480

gtcattaacc caaccagaga tgagttaagt gcctccaagc tggatctcgt catggcagga    540

acagcttctg cagttttaat gattgaagga cattgcgact ttttaacaga agagcaagtt    600

ctagaagcca ttgcttttgg gcaaacctat atagctaaaa tatgcgatgc tattgaagca    660

tggcagaaag ctatcggcaa acaaaagaat ttctctgccg ttcttgatat gccagaagac    720

gtacaaaatg tagtttcaga ttttattaga gaaaaattcg aaaaagcatt gtcttttaga    780

gataaagaag ctctagagca agcctcgaaa gaattagagg aatccgttat tgctaacttg    840

gttcaagaag aaaacagtga tttttctttg ttgaacgtta aggctgcatt taagacagca    900

aaatccaatc aaatgcgagc tcttatccaa gatcttggta ttcgtgtaga tggacgaacc    960

accacagaga ttcgccccat ttccatagag actccttttc ttccaagaac acacggaagt   1020

tgcttattta ctcgcggaga gacgcaaagc atggccgtat gtacgcttgg aggcgaaaat   1080

atggcgcagc gattcgaaga tctgaatgga gatggagccg ctcgcttcta tctacagtat   1140

ttcttccctc ctttctccgt aggagaagtt ggcagaattg gttccccagg aagacgtgaa   1200

attggacatg ggaaattagc tgagaaagct ttaagtcatg ttcttcctga gacatcacga   1260

ttcccttata tcattcgcct agaatctaat attactgagt ctaatggatc ttcctccatg   1320

gcatccgtat gtggaggctg tcttgcactc atggatgctg gagttcctat caaagctccc   1380

gtggcaggta ttgctatggg cttaatctta gatcgagatc aagccatcat cttgtctgat   1440

atttccggta tagaagatca tctaggagat atggacttta aagtagccgg aacagctaaa   1500

ggtattacag ctttccaaat ggatatcaag atagagggaa tcactcataa gattatggag   1560

caagctctag cgcaagctaa acaagggcgt agtcatatcc ttaatcttat gacacaggtt   1620

ctggcctccc ctaagggaac tgtttctaaa tatgctccgc gcattgaaac tatgcagatc   1680

aatacctcaa aaatcgcaac ggtcattggt cccggaggaa aacaaatccg tcaaattatc   1740

gagcgttctg gtgcgcaagt tgacatcaat gatgacggcg tcattaacat agctgcaagc   1800

acccaagaat cgattaacaa agctaaagaa cttatcgaag gattaactgg agaagttgaa   1860
```

gtcggtaaag tttataatgg ccgtgttaca tctatcgcaa catttggggt attcgtagaa 1920
gtcctcccag gaaaagaagg gctctgtcat atttctgaat tgtctaaaca aaaagtagac 1980
aatatctctg actttgtcaa agaaggagac aagcttgctg ttaaactcct tagcattaac 2040
gaaaaaggcc agttgaagct gagccataag gcaacgctgg aagat 2085

<210> SEQ ID NO 103
<211> LENGTH: 77
<212> TYPE: PRT
<213> ORGANISM: Chlamydia trachomatis

<400> SEQUENCE: 103

Val Phe Leu Gly Met Ala Lys Lys Glu Asp Thr Ile Val Leu Glu Gly
1 5 10 15

Arg Val Glu Glu Leu Leu Pro Gly Met His Phe Arg Val Met Leu Glu
20 25 30

Asn Gly Val Pro Ile Thr Ala His Leu Cys Gly Lys Met Arg Met Ser
35 40 45

Asn Ile Arg Leu Leu Val Gly Asp Arg Val Thr Val Glu Met Ser Thr
50 55 60

Tyr Asp Leu Thr Lys Ala Arg Val Val Tyr Arg His Arg
65 70 75

<210> SEQ ID NO 104
<211> LENGTH: 234
<212> TYPE: DNA
<213> ORGANISM: Chlamydia trachomatis

<400> SEQUENCE: 104
ttaacgatgt ctgtagacaa cacgagcctt cgtcaaatca taagtagaca tttcgacggt 60
cacgcgatct ccaacgagca agcggatatt actcatacgc attttaccgc acagatgcgc 120
tgtaatggga accccattct ctaacatcac cctaaaatgc atgccgggca acaactcttc 180
cactctacct tctagaacga tcgtatcttc tttttttgcc attcctaaaa aaac 234

<210> SEQ ID NO 105
<211> LENGTH: 97
<212> TYPE: PRT
<213> ORGANISM: Chlamydia trachomatis

<400> SEQUENCE: 105

Met Lys Lys Arg Ser Ser Arg Lys Leu Ala Gln Val Ile Gly Arg Lys
1 5 10 15

Thr Gly Asn Tyr Phe Pro Ala Ser Ile Glu Gly Glu Thr Lys Lys Glu
20 25 30

His Lys His His Tyr Ser Thr Ala Ser Lys Glu Lys Glu Ser Leu Arg
35 40 45

Lys Arg Ala Lys Glu Phe Asp Val Leu Val His Ser Leu Leu Asp Lys
50 55 60

His Val Pro Gln Asn Ser Asp Gln Val Leu Ile Phe Thr Tyr Gln Asn
65 70 75 80

Gly Phe Val Glu Thr Asp Phe His Asn Phe Gly Arg Tyr Ser Val Lys
85 90 95

Leu

<210> SEQ ID NO 106
<211> LENGTH: 291

```
<212> TYPE: DNA
<213> ORGANISM: Chlamydia trachomatis

<400> SEQUENCE: 106

atgaaaaaaa gaagcagtcg caagctagct caagtgattg ggcgtaagac gggaaactat      60

ttcccagctt ctattgaagg cgaaaccaag aaagagcaca aacatcatta cagcacagcc     120

tcaaaagaaa aagagtctct acgaaaaaga gcgaaagagt tcgatgtgct agtacattcg     180

ttattagata aacacgttcc tcaaaattct gaccaagttt tgatttttac gtaccagaat     240

ggctttgtgg agacagactt tcataatttt gggcgatatt ctgtgaaact g              291


<210> SEQ ID NO 107
<211> LENGTH: 361
<212> TYPE: PRT
<213> ORGANISM: Chlamydia trachomatis

<400> SEQUENCE: 107

Met Lys Lys Thr Lys His Leu Ile Ser Lys Ile Met Phe Ser Leu Val
1               5                   10                  15

Ser Leu Phe Val Gly Gly Phe Leu Leu Lys Ala Pro Ala Pro Thr Gln
            20                  25                  30

Ser Ala Asp Thr Phe Gln Thr Leu Ile Glu Ser Lys Glu Pro Val Ile
        35                  40                  45

Phe Thr Lys Gln Cys Gly Asp Asn Val Thr Gln Ile Leu Cys Asp Ala
    50                  55                  60

Ile Asp Ser Ala Lys Lys Asp Ile Phe Leu Ser Ile Tyr Asp Leu Ser
65                  70                  75                  80

Ala Pro Ala Ile Thr Thr Ser Leu Lys Lys Gln Val Ser Ala Arg Ile
                85                  90                  95

Pro Val Cys Ile His Tyr Gln Arg Ile Ser Lys Asn Ala Glu Phe Ser
            100                 105                 110

Gln Ser Pro Tyr Leu Thr Leu Gly Glu His Pro Pro Met His Arg Lys
        115                 120                 125

Leu Met His Gln Lys Thr Met Ala Ile Asp Gly Glu Leu Ala Trp Ile
    130                 135                 140

Gly Ser Ala Asn Phe Thr Leu Ala Ser Leu Glu Lys Ser Ala Asn Leu
145                 150                 155                 160

Ile Ile Gly Leu Lys Ser Ala Glu Ile Cys His Phe Ile Lys Thr Gln
                165                 170                 175

Thr Ser Gly Arg Cys Phe Ile Asn Asn Gln Leu Ile Glu Tyr Phe Ser
            180                 185                 190

Phe Asp Gly Gly Ser Ser Ala Ala Leu Glu Thr Val Leu His His Ile
        195                 200                 205

Arg Ser Ala Lys Glu Ser Ile Gln Val Gly Met Phe Ala Leu Thr Leu
    210                 215                 220

Pro Gln Ile Ile Ala Glu Leu Asn Ala Ala Gln Asn Cys Gly Val Asp
225                 230                 235                 240

Val Val Ile Leu Val Asp Lys Gly Tyr Lys Ser Phe Thr Val Gln Gln
                245                 250                 255

Ile Lys Gln Leu Glu His Pro Ser Leu Ser Ile Tyr Glu Lys Val Thr
            260                 265                 270

Pro Tyr Gln Leu His His Lys Phe Gly Ile Phe Asp Lys Lys Thr Leu
        275                 280                 285

Ile Thr Gly Ser Val Asn Trp Ser Glu Asn Gly Phe Leu Ile Asn Thr
    290                 295                 300
```

Glu Asp Met Ile Val Ile Glu Asn Leu Thr Glu Lys Gln Gln Ser Lys
305 310 315 320

Ile Gln Ala Ile Trp Glu Gly Leu Val Arg Glu Cys Ala Leu Tyr Tyr
325 330 335

Ser Pro Asp Gln Glu Glu Lys Glu Lys Asp Pro Leu Ile Ile Pro Phe
340 345 350

Pro Pro Ser Glu Lys Lys Gln Ala Ala
355 360

<210> SEQ ID NO 108
<211> LENGTH: 1083
<212> TYPE: DNA
<213> ORGANISM: Chlamydia trachomatis

<400> SEQUENCE: 108
atgaaaaaaa caaaacacct tatttccaaa ataatgttca gcttagtttc ccttttttgtt 60 ggaggatttt tactaaaagc cccagccccg actcaatctg ctgatacctt ccaaacgctt 120
attgaatcca aggaacctgt tatcttcacc aaacagtgtg gagacaatgt aacgcaaata 180
ctatgtgatg cgatagactc tgcaaaaaaa gatatttttc tcagtattta tgacctatct 240
gctcccgcta tcacgacaag tttgaaaaaa caagtgtccg ctcgcattcc tgtatgtatt 300
cattaccaac gtatctctaa aaatgcggag ttctctcagt ctccctatct taccttggga 360
gaacatcctc ccatgcacag aaaactcatg catcaaaaaa ctatggcaat agatggagaa 420
ctcgcttgga tcggatctgc taattttaca ttagcttcgt tagagaagag cgctaaccta 480
ataattggat taaaaagcgc agaaatttgt cattttatta aaacgcaaac ctctggtcgg 540
tgctttatta acaatcaact catcgagtat ttttcctttg atggggggag ttctgctgct 600
ctagaaacag ttcttcacca tattcgatca gcgaaagaat ccatccaagt aggtatgttt 660
gctctcactt tacctcagat tattgctgaa ttgaatgccg cacaaaactg tggtgttgat 720
gtagtgatcc tcgtcgacaa aggatacaaa tcctttaccg tacagcaaat taagcaattg 780
gaacatccta gtctctctat ttatgaaaag gtaaccccgt accaactaca tcataaattt 840
ggcattttcg ataaaaagac gctaattaca ggatctgtca attggtctga gaatggcttc 900
cttattaata cagaagacat gattgtcatt gaaaatctga cagaaaaaca gcaaagcaaa 960
atacaggcga tatgggaagg attagtaaga gagtgtgctt tgtattactc cccagatcaa 1020
gaggaaaaag aaaaagatcc tttaatcatt ccgttccctc ctagcgaaaa aaaacaagct 1080
gct 1083

<210> SEQ ID NO 109
<211> LENGTH: 458
<212> TYPE: PRT
<213> ORGANISM: Chlamydia trachomatis

<400> SEQUENCE: 109

Leu Met Lys Lys Val Leu Ile Ala Asn Arg Gly Glu Ile Ala Ile Arg
1 5 10 15

Ile Ile Arg Ala Cys His Asp Leu Gly Leu Ala Thr Val Ala Val Tyr
20 25 30

Ser Met Ala Asp Gln Glu Ala Leu His Val Leu Leu Ala Asp Glu Ala
35 40 45

Val Cys Ile Gly Glu Ala Gln Ala Ala Lys Ser Tyr Leu Lys Ile Ala
50 55 60

-continued

Asn Ile Leu Ala Ala Cys Glu Ile Thr Gly Val Asp Ala Val His Pro
65 70 75 80

Gly Tyr Gly Phe Leu Ser Glu Asn Ala Asn Phe Ala Ser Ile Cys Glu
85 90 95

Ser Cys Gly Leu Thr Phe Ile Gly Pro Ser Ala Glu Ser Ile Ala Thr
100 105 110

Met Gly Asp Lys Val Ala Ala Lys Gln Leu Ala Lys Lys Ile Lys Cys
115 120 125

Pro Val Ile Pro Gly Ser Glu Gly Val Val Lys Asp Glu Val Glu Gly
130 135 140

Ile Arg Ile Ala Glu Lys Ile Gly Phe Pro Ile Val Ile Lys Ala Val
145 150 155 160

Ala Gly Gly Gly Gly Arg Gly Ile Arg Ile Val Arg Glu Lys Asp Glu
165 170 175

Phe Tyr Arg Ala Phe Thr Ala Ala Arg Ala Glu Ala Glu Ala Gly Phe
180 185 190

Asn Asn Pro Asp Val Tyr Ile Glu Lys Phe Ile Glu Asn Pro Arg His
195 200 205

Leu Glu Val Gln Val Ile Gly Asp Lys His Gly Asn Tyr Val Tyr Leu
210 215 220

Gly Glu Arg Asp Cys Thr Val Gln Arg Arg Arg Gln Lys Leu Ile Glu
225 230 235 240

Glu Thr Pro Ser Pro Ile Leu Thr Pro Glu Met Arg Ala Lys Val Gly
245 250 255

Lys Val Ala Val Asp Leu Ala Arg Ser Ala Gly Tyr Phe Ser Val Gly
260 265 270

Thr Val Glu Phe Leu Leu Asp Lys Glu Lys Arg Phe Tyr Phe Met Glu
275 280 285

Met Asn Thr Arg Ile Gln Val Glu His Thr Ile Thr Glu Glu Val Thr
290 295 300

Gly Ile Asp Leu Leu Lys Ala Gln Ile Ser Val Ala Lys Gly Glu Lys
305 310 315 320

Leu Pro Trp Lys Gln Lys Asn Ile Lys Phe Lys Gly His Val Ile Gln
325 330 335

Cys Arg Ile Asn Ala Glu Asp Pro Ile Asn Asn Phe Thr Pro Ser Pro
340 345 350

Gly Arg Leu Asp Tyr Tyr Leu Pro Pro Ala Gly Pro Ala Val Arg Val
355 360 365

Asp Gly Ala Cys Tyr Ser Gly Tyr Ala Ile Pro Pro Tyr Tyr Asp Ser
370 375 380

Met Ile Ala Lys Val Ile Thr Lys Gly Lys Asn Arg Glu Glu Ala Ile
385 390 395 400

Ala Ile Met Lys Arg Ala Leu Lys Glu Phe His Ile Gly Gly Val His
405 410 415

Ser Thr Ile Pro Phe His Gln Phe Met Leu Asp Asn Pro Lys Phe Leu
420 425 430

Leu Ser Asp Tyr Asp Ile Asn Tyr Val Asp Gln Leu Leu Ala Ser Gly
435 440 445

Ser Thr Phe Leu Asn Leu Ala Asp Gly Ser
450 455

<210> SEQ ID NO 110
<211> LENGTH: 1377
<212> TYPE: DNA

<213> ORGANISM: Chlamydia trachomatis

<400> SEQUENCE: 110

```
ttaatgaaga aagtattgat tgcaaataga ggcgagatag ctattcggat tattcgagca     60
tgtcatgatc taggattagc tactgttgct gtatattcta tggcggatca agaagctttg    120
catgtgcttc ttgctgacga agctgtttgt attggagaag ctcaggcagc aaaatcctac    180
ctaaagatcg ccaatatttt agctgcttgt gagattactg ggtagatgc tgtgcatcct     240
ggttatggtt tcttaagtga aaatgcaaac tttgcttcta tttgtgaaag ttgtgggctc    300
acatttatcg gtcctagtgc tgagtcgata gcgactatgg gagataaagt cgcagctaag    360
cagttggcta aaaagattaa gtgccctgta atccctggat ctgaaggtgt agtgaaggat    420
gaggtggaag ggattagaat tgcagaaaag atcggattcc ccatcgtcat caaagctgtt    480
gctggaggcg gtggacgagg aatacggatt gttagagaaa aagacgaatt ctacagggct    540
tttactgccg ctcgggctga agcagaagcg ggatttaata atcctgacgt gtatattgaa    600
aaatttattg aaaatccaag acatttagaa gttcaagtaa ttggagataa gcacggaaat    660
tacgtgtatc ttggagaacg agattgtaca gtacaaaggc gtcggcaaaa attaatagaa    720
gagactccaa gtcctatttt aactccagaa atgcgagcta aagttggaaa agtagcagtg    780
gatttagctc ggagtgccgg gtatttctct gttggaacag tagaatttct gttagataag    840
gagaagcgtt tttatttcat ggagatgaat acgcgtatcc aagtggaaca tactattacg    900
gaagaagtga cagggatcga tttgttaaag gctcagatta gtgtcgctaa gggagaaaaa    960
ctgccttgga agcaaaagaa tataaagttt aaagggcacg tgattcaatg ccgaatcaat   1020
gcagaggatc caattaataa ctttactcct tcccctggta gattagatta ttatctccct   1080
cctgcaggtc ctgctgtgcg agtagacggg gcttgctaca gtggttatgc gatacctcct   1140
tattatgatt ccatgattgc taaggtaatc acaaaaggaa agaatcgaga ggaagcgata   1200
gccattatga aaagagcttt aaaagagttc catattggtg gggtgcattc tacaattcct   1260
tttcatcagt tcatgttgga taatccgaag tttcttcttt ctgattatga tattaattac   1320
gtggaccagc ttttagcgtc tggtagcacc tttttaaatt tagctgatgg cagctaa      1377
```

<210> SEQ ID NO 111
<211> LENGTH: 544
<212> TYPE: PRT
<213> ORGANISM: Chlamydia trachomatis

<400> SEQUENCE: 111

```
Met Val Ala Lys Asn Ile Lys Tyr Asn Glu Glu Ala Arg Lys Lys Ile
1               5                   10                  15

Gln Lys Gly Val Lys Thr Leu Ala Glu Ala Val Lys Val Thr Leu Gly
            20                  25                  30

Pro Lys Gly Arg His Val Val Ile Asp Lys Ser Phe Gly Ser Pro Gln
        35                  40                  45

Val Thr Lys Asp Gly Val Thr Val Ala Lys Glu Val Glu Leu Ala Asp
    50                  55                  60

Lys His Glu Asn Met Gly Ala Gln Met Val Lys Glu Val Ala Ser Lys
65                  70                  75                  80

Thr Ala Asp Lys Ala Gly Asp Gly Thr Thr Thr Ala Thr Val Leu Ala
                85                  90                  95

Glu Ala Ile Tyr Thr Glu Gly Leu Arg Asn Val Thr Ala Gly Ala Asn
            100                 105                 110
```

```
Pro Met Asp Leu Lys Arg Gly Ile Asp Lys Ala Val Lys Val Val Val
        115                 120                 125

Asp Gln Ile Arg Lys Ile Ser Lys Pro Val Gln His His Lys Glu Ile
    130                 135                 140

Ala Gln Val Ala Thr Ile Ser Ala Asn Asn Asp Ala Glu Ile Gly Asn
145                 150                 155                 160

Leu Ile Ala Glu Ala Met Glu Lys Val Gly Lys Asn Gly Ser Ile Thr
                165                 170                 175

Val Glu Glu Ala Lys Gly Phe Glu Thr Val Leu Asp Ile Val Glu Gly
            180                 185                 190

Met Asn Phe Asn Arg Gly Tyr Leu Ser Ser Tyr Phe Ala Thr Asn Pro
        195                 200                 205

Glu Thr Gln Glu Cys Val Leu Glu Asp Ala Leu Val Leu Ile Tyr Asp
    210                 215                 220

Lys Lys Ile Ser Gly Ile Lys Asp Phe Leu Pro Val Leu Gln Gln Val
225                 230                 235                 240

Ala Glu Ser Gly Arg Pro Leu Leu Ile Ile Ala Glu Asp Ile Glu Gly
                245                 250                 255

Glu Ala Leu Ala Thr Leu Val Val Asn Arg Ile Arg Gly Gly Phe Arg
            260                 265                 270

Val Cys Ala Val Lys Ala Pro Gly Phe Gly Asp Arg Arg Lys Ala Met
        275                 280                 285

Leu Glu Asp Ile Ala Ile Leu Thr Gly Gly Gln Leu Ile Ser Glu Glu
    290                 295                 300

Leu Gly Met Lys Leu Glu Asn Ala Asn Leu Ala Met Leu Gly Lys Ala
305                 310                 315                 320

Lys Lys Val Ile Val Ser Lys Glu Asp Thr Thr Ile Val Glu Gly Met
                325                 330                 335

Gly Glu Lys Glu Ala Leu Glu Ala Arg Cys Glu Ser Ile Lys Lys Gln
            340                 345                 350

Ile Glu Asp Ser Ser Ser Asp Tyr Asp Lys Glu Lys Leu Gln Glu Arg
        355                 360                 365

Leu Ala Lys Leu Ser Gly Gly Val Ala Val Ile Arg Val Gly Ala Ala
    370                 375                 380

Thr Glu Ile Glu Met Lys Glu Lys Lys Asp Arg Val Asp Asp Ala Gln
385                 390                 395                 400

His Ala Thr Ile Ala Ala Val Glu Glu Gly Ile Leu Pro Gly Gly Gly
                405                 410                 415

Thr Ala Leu Ile Arg Cys Ile Pro Thr Leu Glu Ala Phe Leu Pro Met
            420                 425                 430

Leu Thr Asn Glu Asp Glu Gln Ile Gly Ala Arg Ile Val Leu Lys Ala
        435                 440                 445

Leu Ser Ala Pro Leu Lys Gln Ile Ala Ala Asn Ala Gly Lys Glu Gly
    450                 455                 460

Ala Ile Ile Phe Gln Gln Val Met Ser Arg Ser Ala Asn Glu Gly Tyr
465                 470                 475                 480

Asp Ala Leu Arg Asp Ala Tyr Thr Asp Met Leu Glu Ala Gly Ile Leu
                485                 490                 495

Asp Pro Ala Lys Val Thr Arg Ser Ala Leu Glu Ser Ala Ala Ser Val
            500                 505                 510

Ala Gly Leu Leu Leu Thr Thr Glu Ala Leu Ile Ala Glu Ile Pro Glu
        515                 520                 525

Glu Lys Pro Ala Ala Ala Pro Ala Met Pro Gly Ala Gly Met Asp Tyr
```

-continued 530 535 540

<210> SEQ ID NO 112
<211> LENGTH: 1632
<212> TYPE: DNA
<213> ORGANISM: Chlamydia trachomatis

<400> SEQUENCE: 112
atggtcgcta aaaacattaa atacaacgaa gaagccagaa agaaaattca aaaaggagtt 60
aagactttag ctgaagctgt aaaagtcact ctagggccta aaggacgaca tgttgtcata 120
gataaaagct tcggatcccc tcaagtaact aaagatggtg ttaccgttgc gaaagaagtt 180
gagcttgccg acaaacatga aaatatgggc gctcaaatgg tcaaagaagt cgccagcaaa 240
actgctgaca aagctggaga cggaactaca acagctactg ttcttgctga agctatctat 300
acagaaggat tacgcaatgt aacagctgga gcaaatccaa tggacctcaa acgaggtatt 360
gataaagctg ttaaggttgt tgttgatcaa atcagaaaaa tcagcaaacc tgttcagcat 420
cataaagaaa ttgctcaagt tgcaacaatt tctgctaata atgatgcaga aatcgggaat 480
ctgattgctg aagcaatgga gaaagttggt aaaaacggct ctatcactgt tgaagaagca 540
aaaggatttg aaaccgtttt ggatattgtt gaaggaatga atttcaatag aggttacctc 600
tctagctact tcgcaacaaa tccagaaact caagaatgtg tattagaaga cgctttggtt 660
ctaatctacg ataagaaaat ttctgggatc aaagatttcc ttcctgtttt acaacaagtt 720
gctgaatccg gccgtcctct tcttattata gcagaagaca ttgaaggcga agctttagct 780
actttggtcg tgaacagaat tcgtggagga ttccgggttt gcgcagttaa agctccaggc 840
tttggagata gaagaaaagc tatgttagaa gacatcgcta tcttaactgg cggtcaactc 900
attagcgaag agttgggcat gaaattagaa aacgctaact tagctatgtt aggtaaagct 960
aaaaaagtta tcgtttctaa agaagacacg accatcgtcg aaggaatggg tgaaaaagaa 1020
gctttagaag ctcgttgcga aagcatcaaa aaacaaattg aagacagctc ttctgattac 1080
gataaagaaa aactccaaga gcgtcttgct aagctctctg gtggagtagc agtcattcgc 1140
gttggagctg caacagagat tgagatgaaa gagaaaaaag atcgtgtaga cgatgctcaa 1200
catgctacaa tcgctgctgt tgaagaagga attcttcctg gtggaggaac ggcattaatc 1260
cgttgtatcc ctactcttga agccttcttg ccaatgttga ctaatgaaga tgagcaaatt 1320
ggagctcgca ttgttttgaa agctctttcc gctcctttga aacaaattgc tgcaaacgca 1380
ggaaaagaag gtgctatcat cttccaacaa gttatgtccc gttctgcgaa cgaaggatat 1440
gatgcattgc gtgatgcata cacagatatg cttgaagctg gtattttaga tcctgctaaa 1500
gtaacccgtt ctgctttaga aagcgcggct tccgtagctg gattactttt gacaacagaa 1560
gctctcattg cagagattcc agaagaaaaa cctgctgcag ctccagcaat gcctggcgca 1620
ggaatggact at 1632

<210> SEQ ID NO 113
<211> LENGTH: 273
<212> TYPE: PRT
<213> ORGANISM: Chlamydia trachomatis

<400> SEQUENCE: 113

Met Thr Thr Pro Thr Leu Ile Val Thr Pro Pro Ser Pro Pro Ala Pro
1 5 10 15

Ser Tyr Ser Ala Asn Arg Val Pro Gln Pro Ser Leu Met Asp Lys Ile
20 25 30

```
Lys Lys Ile Ala Ala Ile Ala Ser Leu Ile Leu Ile Gly Thr Ile Gly
        35                  40                  45

Phe Leu Ala Leu Leu Gly His Leu Val Gly Phe Leu Ile Ala Pro Gln
    50                  55                  60

Ile Thr Ile Val Leu Leu Ala Leu Phe Ile Ile Ser Leu Ala Gly Asn
65                  70                  75                  80

Ala Leu Tyr Leu Gln Lys Thr Ala Asn Leu His Leu Tyr Gln Asp Leu
                85                  90                  95

Gln Arg Glu Val Gly Ser Leu Lys Glu Ile Asn Phe Met Leu Ser Val
            100                 105                 110

Leu Gln Lys Glu Phe Leu His Leu Ser Lys Glu Phe Ala Thr Thr Ser
        115                 120                 125

Lys Asp Leu Ser Ala Val Ser Gln Asp Phe Tyr Ser Cys Leu Gln Gly
    130                 135                 140

Phe Arg Asp Asn Tyr Lys Gly Phe Glu Ser Leu Leu Asp Glu Tyr Lys
145                 150                 155                 160

Asn Ser Thr Glu Glu Met Arg Lys Leu Phe Ser Gln Glu Ile Ile Ala
                165                 170                 175

Asp Leu Lys Gly Ser Val Ala Ser Leu Arg Glu Glu Ile Arg Phe Leu
            180                 185                 190

Thr Pro Leu Ala Glu Glu Val Arg Arg Leu Ala His Asn Gln Gln Ser
        195                 200                 205

Leu Thr Val Val Ile Glu Glu Leu Lys Thr Ile Arg Asp Ser Leu Arg
    210                 215                 220

Asp Glu Ile Gly Gln Leu Ser Gln Leu Ser Lys Thr Leu Thr Ser Gln
225                 230                 235                 240

Ile Ala Leu Gln Arg Lys Glu Ser Ser Asp Leu Cys Ser Gln Ile Arg
                245                 250                 255

Glu Thr Leu Ser Ser Pro Arg Lys Ser Ala Ser Pro Ser Thr Lys Ser
            260                 265                 270

Ser
```

<210> SEQ ID NO 114
<211> LENGTH: 819
<212> TYPE: DNA
<213> ORGANISM: Chlamydia trachomatis

<400> SEQUENCE: 114

```
atgacaacgc ctactctaat cgtgacccct ccatctcccc ctgcaccttc ctactcagcc      60

aatcgcgtac ctcaaccttc tttgatggac aaaattaaga aaatagcagc cattgcctcc     120

ctaattctta taggcacaat aggcttttta gctcttttgg gacatcttgt tggctttctg     180

atcgctccac aaatcactat tgttcttctt gccctattca ttatctcatt agcagggaat     240

gctctttatc tacagaaaac cgctaatcta catctatacc aggatctgca aagagaagtt     300

gggtctctaa aagaaattaa tttcatgctg agcgttctac agaaagaatt tcttcattta     360

tctaaagaat ttgcaacgac atctaaagac ctctctgctg tatctcaaga tttttattct     420

tgtttgcaag gatttagaga taactataaa ggttttgaat ctcttttgga tgagtataaa     480

aactctacag aagaaatgcg caaacttttt tcgcaagaaa tcatagcaga tcttaaaggc     540

tctgttgcct cattaagaga ggaaatccga ttcctaaccc cattagcaga agaagttcgc     600

cgattagcgc ataaccagca atcattaaca gtggttattg aagaattaaa aacaattcgt     660

gatagcttac gagatgaaat tggacaactt tcacaacttt ctaaaactct taccagtcaa     720
```

attgcattac aacgaaaaga gagctcagat ctgtgttccc agataagaga gacgctctcc 780
tcccccagaa agtctgcatc accctctaca aaaagctcc 819

<210> SEQ ID NO 115
<211> LENGTH: 243
<212> TYPE: PRT
<213> ORGANISM: Chlamydia trachomatis

<400> SEQUENCE: 115

Met Lys Asn Ile Leu Ser Trp Met Leu Met Phe Ala Val Ala Leu Pro
1 5 10 15

Ile Val Gly Cys Asp Asn Gly Gly Gly Ser Gln Thr Ser Ala Thr Glu
20 25 30

Lys Ser Met Val Glu Asp Ser Ala Leu Thr Asp Asn Gln Lys Leu Ser
35 40 45

Arg Thr Phe Gly His Leu Leu Ser Arg Gln Leu Ser Arg Thr Glu Asp
50 55 60

Phe Ser Leu Asp Leu Val Glu Val Ile Lys Gly Met Gln Ser Glu Ile
65 70 75 80

Asp Gly Gln Ser Ala Pro Leu Thr Asp Thr Glu Tyr Glu Lys Gln Met
85 90 95

Ala Glu Val Gln Lys Ala Ser Phe Glu Ala Lys Cys Ser Glu Asn Leu
100 105 110

Ala Ser Ala Glu Lys Phe Leu Lys Glu Asn Lys Glu Lys Ala Gly Val
115 120 125

Ile Glu Leu Glu Pro Asn Lys Leu Gln Tyr Arg Val Val Lys Glu Gly
130 135 140

Thr Gly Arg Val Leu Ser Gly Lys Pro Thr Ala Leu Leu His Tyr Thr
145 150 155 160

Gly Ser Phe Ile Asp Gly Lys Val Phe Asp Ser Ser Glu Lys Asn Lys
165 170 175

Glu Pro Ile Leu Leu Pro Leu Thr Lys Val Ile Pro Gly Phe Ser Gln
180 185 190

Gly Met Gln Gly Met Lys Glu Gly Glu Val Arg Val Leu Tyr Ile His
195 200 205

Pro Asp Leu Ala Tyr Gly Thr Ala Gly Gln Leu Pro Pro Asn Ser Leu
210 215 220

Leu Ile Phe Glu Val Lys Leu Ile Glu Ala Asn Asp Asp Asn Val Ser
225 230 235 240

Val Thr Glu

<210> SEQ ID NO 116
<211> LENGTH: 729
<212> TYPE: DNA
<213> ORGANISM: Chlamydia trachomatis

<400> SEQUENCE: 116
atgaagaata tattaagttg gatgcttatg tttgcagtcg ctctgcctat cgtaggatgt 60
gataacggag gcggttcgca aacatcggct acggagaaaa gcatggtaga agactctgca 120
ttgacagaca atcaaaagtt atcaagaact tttgggcatt tattgtctcg tcagttgagc 180
cgaacggaag atttttcgtt agatcttgtt gaagtgatta aagggatgca atctgaaata 240
gatggacaga gtgctccttt aacagacaca gaatatgaaa aacaaatggc agaagtacaa 300
aaagctagtt tcgaagcaaa atgctcggaa aatttagctt ctgcagaaaa attcttaaaa 360

```
gaaaataaag agaaggctgg ggttattgag ttagagccta ataagttaca gtaccgtgtt    420

gtgaaagagg gtacaggacg ggttctttct gggaagccta cagctttgct tcactataca    480

gggagcttca tcgatgggaa ggtttttgat tcttcagaga agaataaaga gcccatttta    540

ctgcctttga ccaaagtaat tcctggattt tcccaaggta tgcaaggtat gaaagaagga    600

gaggttcgag ttctttacat acatccagat ttagcttacg gaacagctgg acaattacct    660

ccaaactctc tactcatttt tgaagtgaag ttaattgaag caaacgacga taatgtatct    720

gttacagaa                                                            729


<210> SEQ ID NO 117
<211> LENGTH: 553
<212> TYPE: PRT
<213> ORGANISM: Chlamydia trachomatis

<400> SEQUENCE: 117

Met Arg Ile Gly Asp Pro Met Asn Lys Leu Ile Arg Arg Ala Val Thr
1               5                   10                  15

Ile Phe Ala Val Thr Ser Val Ala Ser Leu Phe Ala Ser Gly Val Leu
            20                  25                  30

Glu Thr Ser Met Ala Glu Ser Leu Ser Thr Asn Val Ile Ser Leu Ala
        35                  40                  45

Asp Thr Lys Ala Lys Asp Asn Thr Ser His Lys Ser Lys Lys Ala Arg
    50                  55                  60

Lys Asn His Ser Lys Glu Thr Pro Val Asp Arg Lys Glu Val Ala Pro
65                  70                  75                  80

Val His Glu Ser Lys Ala Thr Gly Pro Lys Gln Asp Ser Cys Phe Gly
                85                  90                  95

Arg Met Tyr Thr Val Lys Val Asn Asp Asp Arg Asn Val Glu Ile Thr
            100                 105                 110

Gln Ala Val Pro Glu Tyr Ala Thr Val Gly Ser Pro Tyr Pro Ile Glu
        115                 120                 125

Ile Thr Ala Thr Gly Lys Arg Asp Cys Val Asp Val Ile Ile Thr Gln
    130                 135                 140

Gln Leu Pro Cys Glu Ala Glu Phe Val Arg Ser Asp Pro Ala Thr Thr
145                 150                 155                 160

Pro Thr Ala Asp Gly Lys Leu Val Trp Lys Ile Asp Arg Leu Gly Gln
                165                 170                 175

Gly Glu Lys Ser Lys Ile Thr Val Trp Val Lys Pro Leu Lys Glu Gly
            180                 185                 190

Cys Cys Phe Thr Ala Ala Thr Val Cys Ala Cys Pro Glu Ile Arg Ser
        195                 200                 205

Val Thr Lys Cys Gly Gln Pro Ala Ile Cys Val Lys Gln Glu Gly Pro
    210                 215                 220

Glu Asn Ala Cys Leu Arg Cys Pro Val Val Tyr Lys Ile Asn Ile Val
225                 230                 235                 240

Asn Gln Gly Thr Ala Thr Ala Arg Asn Val Val Val Glu Asn Pro Val
                245                 250                 255

Pro Asp Gly Tyr Ala His Ser Ser Gly Gln Arg Val Leu Thr Phe Thr
            260                 265                 270

Leu Gly Asp Met Gln Pro Gly Glu His Arg Thr Ile Thr Val Glu Phe
        275                 280                 285

Cys Pro Leu Lys Arg Gly Arg Ala Thr Asn Ile Ala Thr Val Ser Tyr
    290                 295                 300
```

-continued

Cys Gly Gly His Lys Asn Thr Ala Ser Val Thr Thr Val Ile Asn Glu
305 310 315 320

Pro Cys Val Gln Val Ser Ile Ala Gly Ala Asp Trp Ser Tyr Val Cys
325 330 335

Lys Pro Val Glu Tyr Val Ile Ser Val Ser Asn Pro Gly Asp Leu Val
340 345 350

Leu Arg Asp Val Val Val Glu Asp Thr Leu Ser Pro Gly Val Thr Val
355 360 365

Leu Glu Ala Ala Gly Ala Gln Ile Ser Cys Asn Lys Val Val Trp Thr
370 375 380

Val Lys Glu Leu Asn Pro Gly Glu Ser Leu Gln Tyr Lys Val Leu Val
385 390 395 400

Arg Ala Gln Thr Pro Gly Gln Phe Thr Asn Asn Val Val Val Lys Ser
405 410 415

Cys Ser Asp Cys Gly Thr Cys Thr Ser Cys Ala Glu Ala Thr Thr Tyr
420 425 430

Trp Lys Gly Val Ala Ala Thr His Met Cys Val Val Asp Thr Cys Asp
435 440 445

Pro Val Cys Val Gly Glu Asn Thr Val Tyr Arg Ile Cys Val Thr Asn
450 455 460

Arg Gly Ser Ala Glu Asp Thr Asn Val Ser Leu Met Leu Lys Phe Ser
465 470 475 480

Lys Glu Leu Gln Pro Val Ser Phe Ser Gly Pro Thr Lys Gly Thr Ile
485 490 495

Thr Gly Asn Thr Val Val Phe Asp Ser Leu Pro Arg Leu Gly Ser Lys
500 505 510

Glu Thr Val Glu Phe Ser Val Thr Leu Lys Ala Val Ser Ala Gly Asp
515 520 525

Ala Arg Gly Glu Ala Ile Leu Ser Ser Asp Thr Leu Thr Val Pro Val
530 535 540

Ser Asp Thr Glu Asn Thr His Ile Tyr
545 550

<210> SEQ ID NO 118
<211> LENGTH: 1659
<212> TYPE: DNA
<213> ORGANISM: Chlamydia trachomatis

<400> SEQUENCE: 118
atgcgaatag gagatcctat gaacaaactc atcagacgag cagtgacgat cttcgcggtg 60
actagtgtgg cgagtttatt tgctagcggg gtgttagaga cctctatggc agagtctctc 120
tctacaaacg ttattagctt agctgacacc aaagcgaaag acaacacttc tcataaaagc 180
aaaaaagcaa gaaaaaacca cagcaaagag actcccgtag accgtaaaga ggttgctccg 240
gttcatgagt ctaaagctac aggacctaaa caggattctt gctttggcag aatgtataca 300
gtcaaagtta atgatgatcg caatgttgaa atcacacaag ctgttcctga atatgctacg 360
gtaggatctc cctatcctat tgaaattact gctacaggta aaagggattg tgttgatgtt 420
atcattactc agcaattacc atgtgaagca gagttcgtac gcagtgatcc agcgacaact 480
cctactgctg atggtaagct agtttggaaa attgaccgct taggacaagg cgaaaagagt 540
aaaattactg tatgggtaaa acctcttaaa gaaggttgct gctttacagc tgcaacagta 600
tgcgcttgtc cagagatccg ttcggttaca aaatgtggac aacctgctat ctgtgttaaa 660

-continued caagaaggcc cagagaatgc ttgtttgcgt tgcccagtag tttacaaaat taatatagtg 720
aaccaaggaa cagcaacagc tcgtaacgtt gttgttgaaa atcctgttcc agatggttac 780
gctcattctt ctggacagcg tgtactgacg tttactcttg gagatatgca acctggagag 840
cacagaacaa ttactgtaga gttttgtccg cttaaacgtg gtcgtgctac caatatagca 900
acggtttctt actgtggagg acataaaaat acagcaagcg taacaactgt gatcaacgag 960
ccttgcgtac aagtaagtat tgcaggagca gattggtctt atgtttgtaa gcctgtagaa 1020
tatgtgatct ccgtttccaa tcctggagat cttgtgttgc gagatgtcgt cgttgaagac 1080
actctttctc ccggagtcac agttcttgaa gctgcaggag ctcaaatttc ttgtaataaa 1140
gtagtttgga ctgtgaaaga actgaatcct ggagagtctc tacagtataa agttctagta 1200
agagcacaaa ctcctggaca attcacaaat aatgttgttg tgaagagctg ctctgactgt 1260
ggtacttgta cttcttgcgc agaagcgaca acttactgga aaggagttgc tgctactcat 1320
atgtgcgtag tagatacttg tgaccctgtt tgtgtaggag aaaatactgt ttaccgtatt 1380
tgtgtcacca acagaggttc tgcagaagat acaaatgttt ctttaatgct taaattctct 1440
aaagaactgc aacctgtatc cttctctgga ccaactaaag gaacgattac aggcaataca 1500
gtagtattcg attcgttacc tagattaggt tctaaagaaa ctgtagagtt ttctgtaaca 1560
ttgaaagcag tatcagctgg agatgctcgt ggggaagcga ttctttcttc cgatacattg 1620
actgttccag tttctgatac agagaataca cacatctat 1659

<210> SEQ ID NO 119
<211> LENGTH: 163
<212> TYPE: PRT
<213> ORGANISM: Chlamydia trachomatis

<400> SEQUENCE: 119

Met Arg Phe Leu Leu Ala Leu Phe Ser Leu Ile Leu Val Leu Pro Ala
1 5 10 15

Thr Glu Ala Phe Ser Thr Glu Asp Lys Gln Cys Gln Gln Glu Ala Glu
20 25 30

Glu Asp Cys Ser Gln Val Ala Asp Thr Cys Val Phe Tyr Ser Tyr Ala
35 40 45

Glu Gly Leu Glu His Ala Arg Asp Glu Gly Lys Leu Thr Leu Val Val
50 55 60

Leu Leu Asp Thr Ser Gly Tyr Ser Phe Glu Thr Leu Ala Asp Ala Ala
65 70 75 80

His Ala Met Glu Ser Ser Leu Leu Ser Thr Phe Ala Asp Phe Val Val
85 90 95

Leu Ser Arg Arg Glu Ala Val Pro Leu Ile Tyr Pro Pro Val Pro Asp
100 105 110

Pro Met Val Gly Glu Ile Ala Leu Phe Leu Glu Ala Phe Ser Asp Gln
115 120 125

Thr Phe Pro Ser Gln Pro Val Ile Val Thr Leu Ala Ile Gly Ala Ser
130 135 140

Ser Ala Glu Ile Met Asp Ile Thr Glu Ile Pro Ser Ile Asn Pro Glu
145 150 155 160

Phe Val Glu

<210> SEQ ID NO 120
<211> LENGTH: 489
<212> TYPE: DNA
<213> ORGANISM: Chlamydia trachomatis

<400> SEQUENCE: 120

```
atgagattct tgttagcttt attctcactg atactagttc ttcctgcgac tgaggcattc     60
tcaacagagg ataagcagtg tcaacaagaa gcagaggaag actgtagtca ggtagcggac    120
acctgcgtat tttatagcta tgcagagggt ttagaacacg caagggacga agggaaactc    180
accttagtag tattgttaga tacttctggg tattccttcg agactcttgc tgatgcagcc    240
catgctatgg aaagttcgtt gctatccaca tttgctgatt ttgtggttct ttctaggagg    300
gaagcagttc cactgattta tcctccggtt ccagatccta tggttggcga gatagcgttg    360
ttcttagaag ctttctcaga tcaaacattt ccatcacagc ctgtgattgt taccttagct    420
attggggctt cttctgcaga gatcatggat attaccgaga ttccgtcaat aaatcctgaa    480
tttgttgag                                                            489
```

<210> SEQ ID NO 121
<211> LENGTH: 660
<212> TYPE: PRT
<213> ORGANISM: Chlamydia trachomatis

<400> SEQUENCE: 121

```
Met Ser Glu Lys Arg Lys Ser Asn Lys Ile Ile Gly Ile Asp Leu Gly
1               5                   10                  15

Thr Thr Asn Ser Cys Val Ser Val Met Glu Gly Gly Gln Pro Lys Val
            20                  25                  30

Ile Ala Ser Ser Glu Gly Thr Arg Thr Thr Pro Ser Ile Val Ala Phe
        35                  40                  45

Lys Gly Gly Glu Thr Leu Val Gly Ile Pro Ala Lys Arg Gln Ala Val
    50                  55                  60

Thr Asn Pro Glu Lys Thr Leu Ala Ser Thr Lys Arg Phe Ile Gly Arg
65                  70                  75                  80

Lys Phe Ser Glu Val Glu Ser Glu Ile Lys Thr Val Pro Tyr Lys Val
                85                  90                  95

Ala Pro Asn Ser Lys Gly Asp Ala Val Phe Asp Val Glu Gln Lys Leu
            100                 105                 110

Tyr Thr Pro Glu Glu Ile Gly Ala Gln Ile Leu Met Lys Met Lys Glu
        115                 120                 125

Thr Ala Glu Ala Tyr Leu Gly Glu Thr Val Thr Glu Ala Val Ile Thr
    130                 135                 140

Val Pro Ala Tyr Phe Asn Asp Ser Gln Arg Ala Ser Thr Lys Asp Ala
145                 150                 155                 160

Gly Arg Ile Ala Gly Leu Asp Val Lys Arg Ile Ile Pro Glu Pro Thr
                165                 170                 175

Ala Ala Ala Leu Ala Tyr Gly Ile Asp Lys Glu Gly Asp Lys Lys Ile
            180                 185                 190

Ala Val Phe Asp Leu Gly Gly Gly Thr Phe Asp Ile Ser Ile Leu Glu
        195                 200                 205

Ile Gly Asp Gly Val Phe Glu Val Leu Ser Thr Asn Gly Asp Thr His
    210                 215                 220

Leu Gly Gly Asp Asp Phe Asp Gly Val Ile Ile Asn Trp Met Leu Asp
225                 230                 235                 240

Glu Phe Lys Lys Gln Glu Gly Ile Asp Leu Ser Lys Asp Asn Met Ala
                245                 250                 255

Leu Gln Arg Leu Lys Asp Ala Ala Glu Lys Ala Lys Ile Glu Leu Ser
            260                 265                 270
```

Gly Val Ser Ser Thr Glu Ile Asn Gln Pro Phe Ile Thr Ile Asp Ala
275 280 285

Asn Gly Pro Lys His Leu Ala Leu Thr Leu Thr Arg Ala Gln Phe Glu
290 295 300

His Leu Ala Ser Ser Leu Ile Glu Arg Thr Lys Gln Pro Cys Ala Gln
305 310 315 320

Ala Leu Lys Asp Ala Lys Leu Ser Ala Ser Asp Ile Asp Asp Val Leu
325 330 335

Leu Val Gly Gly Met Ser Arg Met Pro Ala Val Gln Ala Val Val Lys
340 345 350

Glu Ile Phe Gly Lys Glu Pro Asn Lys Gly Val Asn Pro Asp Glu Val
355 360 365

Val Ala Ile Gly Ala Ala Ile Gln Gly Gly Val Leu Gly Gly Glu Val
370 375 380

Lys Asp Val Leu Leu Leu Asp Val Ile Pro Leu Ser Leu Gly Ile Glu
385 390 395 400

Thr Leu Gly Gly Val Met Thr Pro Leu Val Glu Arg Asn Thr Thr Ile
405 410 415

Pro Thr Gln Lys Lys Gln Ile Phe Ser Thr Ala Ala Asp Asn Gln Pro
420 425 430

Ala Val Thr Ile Val Val Leu Gln Gly Glu Arg Pro Met Ala Lys Asp
435 440 445

Asn Lys Glu Ile Gly Arg Phe Asp Leu Thr Asp Ile Pro Pro Ala Pro
450 455 460

Arg Gly His Pro Gln Ile Glu Val Thr Phe Asp Ile Asp Ala Asn Gly
465 470 475 480

Ile Leu His Val Ser Ala Lys Asp Ala Ala Ser Gly Arg Glu Gln Lys
485 490 495

Ile Arg Ile Glu Ala Ser Ser Gly Leu Lys Glu Asp Glu Ile Gln Gln
500 505 510

Met Ile Arg Asp Ala Glu Leu His Lys Glu Glu Asp Lys Gln Arg Lys
515 520 525

Glu Ala Ser Asp Val Lys Asn Glu Ala Asp Gly Met Ile Phe Arg Ala
530 535 540

Glu Lys Ala Val Lys Asp Tyr His Asp Lys Ile Pro Ala Glu Leu Val
545 550 555 560

Lys Glu Ile Glu Glu His Ile Glu Lys Val Arg Gln Ala Ile Lys Glu
565 570 575

Asp Ala Ser Thr Thr Ala Ile Lys Ala Ala Ser Asp Glu Leu Ser Thr
580 585 590

His Met Gln Lys Ile Gly Glu Ala Met Gln Ala Gln Ser Ala Ser Ala
595 600 605

Ala Ala Ser Ser Ala Ala Asn Ala Gln Gly Gly Pro Asn Ile Asn Ser
610 615 620

Glu Asp Leu Lys Lys His Ser Phe Ser Thr Arg Pro Pro Ala Gly Gly
625 630 635 640

Ser Ala Ser Ser Thr Asp Asn Ile Glu Asp Ala Asp Val Glu Ile Val
645 650 655

Asp Lys Pro Glu
660

<210> SEQ ID NO 122
<211> LENGTH: 1980

<212> TYPE: DNA
<213> ORGANISM: Chlamydia trachomatis

<400> SEQUENCE: 122
atgagcgaaa aaagaaagtc taacaaaatt attggtatcg acctagggac gaccaactct 60
tgcgtctctg ttatggaagg tggccaacct aaagttattg cctcttctga aggaactcgt 120
actactcctt ctatcgttgc ttttaaaggt ggcgaaactc ttgttggaat tcctgcaaaa 180
cgtcaggcag taaccaatcc tgaaaaaaca ttggcttcta ctaagcgatt catcggtaga 240
aaattctctg aagtcgaatc tgaaattaaa acagtcccct acaaagttgc tcctaactcg 300
aaaggagatg cggtctttga tgtggaacaa aaactgtaca ctccagaaga aatcggcgct 360
cagatcctca tgaagatgaa ggaaactgct gaggcttatc tcggagaaac agtaacggaa 420
gcagtcatta ccgtaccagc ttactttaac gattctcaaa gagcttctac aaaagatgct 480
ggacgtatcg caggattaga tgttaaacgc attattcctg aaccaacagc ggccgctctt 540
gcttatggta ttgataagga aggagataaa aaaatcgccg tcttcgactt aggaggagga 600
actttcgata tttctatctt ggaaatcggt gacggagttt ttgaagttct ctcaaccaac 660
ggggatactc acttgggagg agacgacttc gatggagtca tcatcaactg gatgcttgat 720
gaattcaaaa aacaagaagg cattgatcta agcaaagata acatggcttt gcaaagattg 780
aaagatgctg ctgaaaaagc aaaaatagaa ttgtctggtg tatcgtctac tgaaatcaat 840
cagccattca tcactatcga cgctaatgga cctaaacatt tggctttaac tctaactcgc 900
gctcaattcg aacacctagc ttcctctctc attgagcgaa ccaaacaacc ttgtgctcag 960
gctttaaaag atgctaaatt gtccgcttct gacattgatg atgttcttct agttggcgga 1020
atgtccagaa tgcctgcggt acaagcagtt gtaaaagaga tctttggtaa agagcctaat 1080
aaaggcgtca atccagatga agttgtagcg attggagctg ctattcaggg tggtgtcctc 1140
ggcggagaag tgaaagacgt tctgttgttg gatgtgattc ccctctcttt aggaattgag 1200
actctaggtg gggtcatgac tcctttggta gagagaaaca ctacaatccc tactcagaag 1260
aagcaaatct tctctacagc cgctgacaat cagccagcag tgactatcgt cgttcttcaa 1320
ggtgaacggc ctatggcgaa agacaataag gaaattggaa gatttgatct aacagacatt 1380
cctcctgctc ctcgcggcca tccacaaatt gaggtaacct tcgatattga tgccaacgga 1440
attttacacg tttctgctaa agatgctgct agtggacgcg aacaaaaaat ccgtattgaa 1500
gcaagctctg gattaaaaga agatgaaatt caacaaatga tccgcgatgc agagcttcat 1560
aaagaggaag acaaacaacg aaaagaagct tctgatgtga aaaatgaagc cgatggaatg 1620
atctttagag ccgaaaaagc tgtgaaagat taccacgaca aaattcctgc agaacttgtt 1680
aaagaaattg aagagcatat tgagaaagta cgccaagcaa tcaaagaaga tgcttccaca 1740
acagctatca aagcagcttc tgatgagttg agtactcata tgcaaaaaat cggagaagct 1800
atgcaggctc aatccgcatc cgcagcagca tcttctgcag cgaatgctca aggagggcca 1860
aacattaact ccgaagatct gaaaaaacat agtttcagca cacgacctcc agcaggagga 1920
agcgcctctt ctacagacaa cattgaagat gctgatgttg aaattgttga taaacctgag 1980

<210> SEQ ID NO 123
<211> LENGTH: 698
<212> TYPE: PRT
<213> ORGANISM: Chlamydia trachomatis

<400> SEQUENCE: 123

-continued

```
Leu Phe Ser Lys Lys Lys Gly Leu Leu Leu Ala Phe Phe Asn Lys His
1               5                   10                  15

Gln Lys Lys Phe Ile Gly Leu Val Ile Ala Gly Val Cys Leu Ser Gly
            20                  25                  30

Val Gly Val Gly Val Gly Gln Thr Val Lys Lys Thr Asn Lys Leu Gly
        35                  40                  45

Ser Gly Lys Thr Val Tyr Arg Thr Pro Leu Gly Arg Lys Tyr Ser Glu
    50                  55                  60

Lys Glu Phe Leu Leu Leu Lys His Phe Leu Ser Asn Glu Ala Tyr Pro
65                  70                  75                  80

Phe Thr Gly Asn Pro Arg Glu Trp Asn Phe Leu Asn Glu Gly Leu Leu
                85                  90                  95

Thr Glu Arg Phe Leu Thr Asn Lys Leu Gly Glu Lys Ile Phe Leu Ser
            100                 105                 110

Ile Tyr Lys Ser Gly Phe Pro Ala Phe Asp Lys Glu Arg Ser Tyr Glu
        115                 120                 125

Gly Tyr Arg Arg Phe Asp Ala Pro Phe Ile Ser Ser Glu Glu Val Trp
    130                 135                 140

Lys Ser Ser Ala Pro Gln Leu Arg Glu Ala Phe His Ile Phe Gln Gln
145                 150                 155                 160

Leu Thr Asp Pro Val Ser Pro Glu Gly Phe Ala Ala Arg Val Arg Leu
                165                 170                 175

Phe Leu Glu Glu Lys Lys Phe Pro His Tyr Val Leu Arg Gln Met Leu
            180                 185                 190

Glu Tyr Arg Arg Gln Met Phe Asn Leu Pro Val Asp Asn Ser Leu Val
        195                 200                 205

Gln Gly Arg Asp Leu Arg Leu Phe Gly Tyr Lys Asn Val Lys Asp Trp
    210                 215                 220

Phe Gly Asp Lys Tyr Ile Ser Ser Val Thr Glu Ala Met Leu Cys Phe
225                 230                 235                 240

Ile Asp Glu Gln Lys Lys Lys Val Gly Met Pro Ser Leu Lys Glu Ala
                245                 250                 255

Arg Gln Asp Phe Tyr Asp Lys Ala Gln His Ala Phe Ala Arg Leu Ser
            260                 265                 270

Lys His Ala Glu Phe Asn Leu Thr Phe Glu Gln Leu Val Ala Ser Phe
        275                 280                 285

Tyr Ala Phe Met Gly Val Glu Glu Ser Asp Phe Leu Ser Met Tyr Arg
    290                 295                 300

Glu Ile Leu Leu Tyr Lys Lys Ala Leu Leu Ser Leu Glu Gly Ala Val
305                 310                 315                 320

Ser Phe Asp Tyr Tyr Pro Leu Gln Lys Phe Phe Ser Met Gly Lys Asp
                325                 330                 335

Ser Val Ser Val Glu Leu Phe His Leu Pro Asp Ser Leu Val Phe Lys
            340                 345                 350

Asp Lys Glu Asp Leu Glu Ala Phe Glu Thr Tyr Leu His Leu Thr Ala
        355                 360                 365

Phe Pro Ser Ala His Val Leu Asp Val Pro Thr Lys Ala Phe Pro Ile
    370                 375                 380

Glu Arg Val Arg Arg Lys Ala Glu Cys Leu Val Gly Lys Arg Phe Ala
385                 390                 395                 400

Val Ser Tyr Gln Ser Val Lys Leu Ser Asp Leu Glu Lys Tyr Val Pro
                405                 410                 415

Met Ser Gln Val Tyr Gln Trp Tyr Gln Asn Pro Glu Asn Phe Glu Glu
```

```
            420                 425                 430

Ile Val Leu Glu Phe Pro Glu Leu Glu Thr Ser Ser Ser Leu Arg Asp
        435                 440                 445

Ile Leu Asn Leu Arg Pro Ala Ile Val Glu Lys Ala His Ser Tyr Val
    450                 455                 460

Arg Lys Ala Ile Leu Arg Ala Asp Pro Glu Arg Ile Gln Ser Glu Leu
465                 470                 475                 480

Ala Lys Lys Glu Arg Gln Glu Glu Glu Leu Phe Leu Ser Ile Gly Lys
                485                 490                 495

Asp His Val Leu Pro Gly Ile Gln Asn Gly Val Arg Leu Ala Asn Val
            500                 505                 510

Leu Met Gln Gln Asp Ser Val Asp Ser Tyr Thr Gln Asp Asn Glu His
        515                 520                 525

Phe Tyr Ser Ile Ser Val Ile Ser Arg Ala Asp Lys Asp Glu Val Leu
    530                 535                 540

Pro Tyr Lys Glu Val Leu Arg Lys Gly Leu Lys Lys Val Leu Leu Glu
545                 550                 555                 560

Lys Tyr Lys Ala Glu Glu Arg Ile Ser Arg Val Leu Thr His Leu Gln
                565                 570                 575

Glu Ala Phe Pro Asn Ser Gln Gly Gln Asp Leu Tyr Gln Arg Arg Leu
            580                 585                 590

Val Arg Phe Val Lys Ala Phe Gln Thr Gly Lys Leu Ala Gln Gly Asp
        595                 600                 605

Leu Phe Gly Gly Leu Glu Lys Thr Met Lys Thr Phe Ser Arg Gly Asp
    610                 615                 620

Gln Gly Ala Pro Gln Glu Phe Glu Asp Met Phe Ala Leu Lys Glu Gly
625                 630                 635                 640

Gln Val Ser Asp Val Leu Phe Asp Leu Asp Lys Gly Pro Phe Tyr Tyr
                645                 650                 655

Thr Ala Ile Ser Lys Ser Cys Cys Asp Tyr Pro Val Ser Leu Asp Lys
            660                 665                 670

Leu Leu Phe Ala Lys Ser His Leu Asn Glu Glu Phe Leu Arg Pro Tyr
        675                 680                 685

Leu Glu Glu Val Phe Phe His Asn Pro Ser
    690                 695
```

<210> SEQ ID NO 124
<211> LENGTH: 2094
<212> TYPE: DNA
<213> ORGANISM: Chlamydia trachomatis

<400> SEQUENCE: 124

```
ttgttctcaa aaaagaaggg tctcttgtta gcatttttta acaagcatca aaagaagttt      60

atcggactag ttatcgctgg cgtttgttta tctggagttg gcgtaggcgt tggtcaaacc     120

gttaagaaaa caaacaaatt aggatctggt aaaacagtct atagaactcc tttgggtagg     180

aaatattctg aaaaagaatt ccttcttttg aaacattttt tatccaatga agcctatcct     240

tttacaggga atcctaggga gtggaatttt cttaatgagg gtttgttaac cgagcgtttc     300

ctaacgaata agttagggga aaagatcttc ctgagtatat acaagtctgg atttccagct     360

tttgataaag agaggagtta cgaagggtat cggcgattcg atgctccttt tatttcttca     420

gaagaagttt ggaaatcttc cgcgcctcaa ttacgagagg ctttccatat attccagcaa     480

ttgactgatc cagtctctcc agaagggttt gctgctcgag taaggctgtt cttagaagaa     540
```

aaaaaattcc ctcactacgt tcttagacaa atgctggaat atcgtcgtca gatgttcaat 600
cttccagtcg acaattcttt ggttcaaggt cgtgatttac gtctattcgg atataaaaat 660
gtgaaagatt ggtttgggga taagtacatt tcttctgtta cagaggcaat gttatgtttt 720
atagatgagc aaaaaaagaa ggttgggatg ccttccttaa aagaagctcg ccaagatttt 780
tatgataagg cgcaacatgc atttgctaga ctgagtaaac atgctgagtt caatttaaca 840
ttcgagcagc tagtggcctc tttttatgct tttatggggg tagaagagtc tgattttctc 900
agtatgtatc gagaaatttt gttatataag aaagctcttt tatctctaga aggggctgtg 960
agtttcgatt actatccttt gcagaagttc ttttctatgg ggaaagattc ggtatctgtg 1020
gagttattcc atttaccgga tagtttagtt ttcaaggaca aagaagattt agaagctttt 1080
gagacctacc tccatttaac agcttttcct tccgctcacg ttttagatgt tcccacaaaa 1140
gcctttccaa tagaaagggt acgacgtaaa gccgagtgtc tggttgggaa acgtttcgct 1200
gtttcttatc agagcgtaaa actatcggat ctagaaaaat atgtgccgat gtctcaagtc 1260
taccagtggt atcaaaatcc tgaaaacttt gaagaaattg tattagaatt tccagagtta 1320
gaaaccagtt cttctctacg cgatatctta aatttgagac cagctattgt agagaaagcc 1380
cattcctatg taagaaaagc aattcttcgt gcagatccag agcggattca atctgaatta 1440
gctaagaaag agcggcaaga ggaagaactt ttcttgtcta taggtaagga tcatgtgtta 1500
ccaggtattc agaacggtgt tcgtttagct aatgtgctga tgcaacaaga ttctgtagat 1560
agctatactc aagataatga acatttctat tccattagtg taatcagtcg cgcagataag 1620
gatgaggttt tgccgtataa agaagttttg cgcaaagggc taaagaaagt tctattagag 1680
aaatacaaag cagaagagcg cattagtcgt gttttgacgc atctgcaaga agcttttcca 1740
aatagtcagg gccaggattt atatcagaga cgtttagtta gatttgtcaa agctttccaa 1800
acaggaaaat tagcgcaggg agatcttttt gggggactag agaaaactat gaagacgttt 1860
tctagaggtg atcagggggc ccctcaagag ttcgaagata tgtttgcctt aaaagaaggt 1920
caagtatccg atgtgttatt cgatttggat aaaggccctt tctattacac tgctatttcc 1980
aagtcttgtt gtgattatcc agtaagccta gataagctat tatttgctaa aagtcacttg 2040
aatgaggaat ttttaagacc ctatttggaa gaagtttttt ttcacaaccc tagt 2094

<210> SEQ ID NO 125
<211> LENGTH: 520
<212> TYPE: PRT
<213> ORGANISM: Chlamydia trachomatis

<400> SEQUENCE: 125

Met Asn Lys Lys Glu Arg Ile Asn Lys Lys Asn Ala Ser Thr Lys Phe
1 5 10 15

Gln Arg Ser Thr Pro Thr Arg Ala Leu Leu Ser Ile Gly Ser Gln Gln
20 25 30

Leu Ser Ser Phe Thr Lys Leu Ser Phe Asp Gly Gln Ala Lys Leu Thr
35 40 45

Gly Val Ala Thr Pro Thr Arg Asp Thr Asp Val Val Pro Leu Gln Tyr
50 55 60

Leu Gln Ala Arg Tyr Leu Ser Lys Asn Asp Pro Asn Pro Gly Tyr Leu
65 70 75 80

Pro Ile His Gly Gly Asn Met Thr Gly Asn Ile Asn Met Gly Thr His
85 90 95

Ser Val Phe Asn Leu Lys Gln Pro Glu Lys Pro Lys Ile Glu Leu Pro

-continued

```
            100                 105                 110

Ser Glu Thr Asp Lys Pro Lys Asp Pro Arg Glu Glu Asp Gly Phe Ala
        115                 120                 125

Glu Lys Thr Ala Glu Glu Gln Glu Gln Glu Ile Lys Glu Tyr Asn Thr
    130                 135                 140

Lys Leu Ala Glu Tyr Gln Lys Lys Ile Asp Asp Tyr Asn Ala Ala Trp
145                 150                 155                 160

Glu Ala Phe Tyr Ser Glu Ala Ala Thr Val Lys Tyr Val Lys Gly Ile
                165                 170                 175

Val Asp Lys Ile Leu Asn Asn Asp Lys Leu Ser Thr Ala Leu Asn Ser
            180                 185                 190

Ala Thr Glu Val Glu Lys Lys Ile Ala Leu Ala Gln Lys Ala Leu Gly
        195                 200                 205

Ile Glu Ile Thr Ile Asn Pro Asp Ala Asp Thr Asn Pro Asp Thr Asp
    210                 215                 220

Gln Glu Thr Pro Asp Pro Ala Pro Val Ala Asp Thr Glu Glu Lys Glu
225                 230                 235                 240

Ser Pro Pro Leu Ser Tyr Asn Asp Leu Pro Ser Val Ile Lys Asn Ser
                245                 250                 255

Gln Phe Val Val Thr Gln Ser Gln Asn Lys Ile Thr Gly Asp Leu Lys
            260                 265                 270

Met Thr Asn Ala Gln Ile Ala Asn Ile Lys Thr Pro Asp Thr Gly Asp
        275                 280                 285

Ser Asn Tyr Ala Ala Asn Val Thr Tyr Leu Glu Ser Lys Leu Lys Gln
    290                 295                 300

Pro Gln Arg Ala Phe Leu Ser Asn Thr Leu Pro Thr Glu Ser Ser Ser
305                 310                 315                 320

Ser Ile Ser Leu Asn Gly His Ile Pro Trp Leu Ser Thr Thr Asn Gly
                325                 330                 335

Ser Ser Ser Pro Ala Glu Pro Asp Phe Lys Ser Lys Leu Ala Asp Gln
            340                 345                 350

Cys Phe Asp Thr Ser Ser Gln Glu Asn Leu Lys Val Lys Thr Ala Gly
        355                 360                 365

Leu Leu Val Leu Ser Val Arg Gly Thr Trp Ser Pro Thr Thr Ser Pro
    370                 375                 380

Ile Thr Asn Gly Ser Thr Pro Thr Pro Thr Thr Ile Ser Val Asn Leu
385                 390                 395                 400

Thr Val Thr Pro Asp Asn Ser Ser Arg Thr Asn Thr Ser Ser Ser Gly
                405                 410                 415

Ser Asp Ser Ser Gly Asp Ala Ser Ala Thr Thr Leu Thr Ile Pro Leu
            420                 425                 430

Thr Leu Tyr Ser Gly Glu Ser Val Gln Leu Gln Leu Pro Ile Thr Thr
        435                 440                 445

Thr Ser Ser Val Lys Ile Ala Thr Thr Thr Ser Gln Thr Ser Asn Gly
    450                 455                 460

Gly Ser Asp Thr Ser Ser Gln Ile Thr Leu Ser Ser Trp Ser Trp Glu
465                 470                 475                 480

Ala Ala Leu Tyr Pro Thr Asp Val Thr Val Thr Asn Lys Thr Thr Pro
                485                 490                 495

Pro Thr Thr Glu Thr Pro Ser Ser Pro Ser Pro Ser Ser Pro Asn Ser
            500                 505                 510

Glu Ser Thr Glu Gly Gln Thr Pro
        515                 520
```

<210> SEQ ID NO 126
<211> LENGTH: 1560
<212> TYPE: DNA
<213> ORGANISM: Chlamydia trachomatis

<400> SEQUENCE: 126
atgaataaaa aagaacgaat taataaaaaa aacgcatcta cgaaatttca acgaagtaca 60
cccactagag ctttactgag tattggttca caacagctct cttcattcac taagttaagc 120
tttgatggac aagctaagtt aaccggagta gctactccga ctcgtgatac ggatgttgtg 180
ccactacaat accttcaagc acgctatcta tctaaaaatg acccaaatcc aggttatctt 240
cccattcatg gagggaacat gactgggaac attaatatgg gaacgcattc cgtatttaat 300
ttgaagcagc cagagaaacc taagatagag cttccttccg aaaccgacaa accaaaagac 360
ccgcgagaag aagacggttt tgcagaaaaa acagccgagg aacaagaaca agagatcaaa 420
gagtacaaca caaagctggc agaataccag aaaaaaatcg atgattacaa tgcagcatgg 480
gaagcttttt actcagaagc agctactgtg aaatatgtca aaggtattgt tgataagatt 540
ttgaacaatg acaaactaag cacagctcta aattctgcta ctgaagtaga aaaaaaaatc 600
gcattggctc aaaaagctct cggcattgaa attacgatca accccgacgc tgatactaat 660
cccgatactg accaagaaac acctgatcca gctcctgtcg cagatacaga agaaaaggaa 720
tcccctcctt tatcttataa cgatctccct tcggtaatta agaattctca gtttgtggtg 780
acacaatctc agaataagat tacaggggat ctaaagatga ctaatgcaca gatcgccaat 840
atcaaaactc cggatactgg tgacagtaat tatgcagcca atgtaaccta cctggagtcc 900
aaactcaaac aacctcagag agcttttctt tctaatactc ttccaactga aagctcttca 960
tctatatctc ttaatgggca tattccttgg ctcagcacaa caaacggatc ttcctctcct 1020
gcagaacctg attttaagag caaactagct gatcaatgct tcgacacctc atcacaagaa 1080
aatctaaaag taaaaacggc aggcctactg gttttatctg taagagggac gtggagtcct 1140
acaacttccc caataactaa tggaagcaca ccgacaccca cgactatatc cgtgaaccta 1200
acagtcactc cagacaattc tagtagaacc aatacctcta gtagcggatc agactcttct 1260
ggagacgctt cagcaactac acttactatc cctctgacac tatactctgg ggaatctgta 1320
caactacaac ttcctattac gactacatct agtgtaaaaa tagctacaac tacctcccaa 1380
acttctaatg gaggaagtga tacctcatca caaataacac tatcatcttg gtcttgggaa 1440
gcagctctat atccaacgga tgttaccgta accaataaaa caactcctcc aacaacagaa 1500
acaccttcgt ctccatcacc atcatcacct aattcagagt caacagaagg acaaacacct 1560

<210> SEQ ID NO 127
<211> LENGTH: 133
<212> TYPE: PRT
<213> ORGANISM: Chlamydia trachomatis

<400> SEQUENCE: 127

Asn Leu Ala Ser Ala Glu Lys Phe Leu Lys Glu Asn Lys Glu Lys Ala
1               5                   10                  15

Gly Val Ile Glu Leu Glu Pro Asn Lys Leu Gln Tyr Arg Val Val Lys
            20                  25                  30

Glu Gly Thr Gly Arg Val Leu Ser Gly Lys Pro Thr Ala Leu Leu His
        35                  40                  45

Tyr Thr Gly Ser Phe Ile Asp Gly Lys Val Phe Asp Ser Ser Glu Lys

```
    50                  55                  60

Asn Lys Glu Pro Ile Leu Leu Pro Leu Thr Lys Val Ile Pro Gly Phe
65                  70                  75                  80

Ser Gln Gly Met Gln Gly Met Lys Glu Gly Glu Val Arg Val Leu Tyr
                85                  90                  95

Ile His Pro Asp Leu Ala Tyr Gly Thr Ala Gly Gln Leu Pro Pro Asn
            100                 105                 110

Ser Leu Leu Ile Phe Glu Val Lys Leu Ile Glu Ala Asn Asp Asp Asn
        115                 120                 125

Val Ser Val Thr Glu
    130


<210> SEQ ID NO 128
<211> LENGTH: 399
<212> TYPE: DNA
<213> ORGANISM: Chlamydia trachomatis

<400> SEQUENCE: 128

aatttagctt ctgcagaaaa attcttaaaa gaaaataaag agaaggctgg ggttattgag     60

ttagagccta ataagttaca gtaccgtgtt gtgaaagagg gtacaggacg ggttctttct    120

gggaagccta cagctttgct tcactataca gggagcttca tcgatgggaa ggtttttgat    180

tcttcagaga agaataaaga gcccatttta ctgcctttga ccaaagtaat tcctggattt    240

tcccaaggta tgcaaggtat gaaagaagga gaggttcgag ttctttacat acatccagat    300

ttagcttacg gaacagctgg acaattacct ccaaactctc tactcatttt tgaagtgaag    360

ttaattgaag caaacgacga taatgtatct gttacagaa                           399


<210> SEQ ID NO 129
<211> LENGTH: 77
<212> TYPE: PRT
<213> ORGANISM: Chlamydia trachomatis

<400> SEQUENCE: 129

Pro Ala Ile Cys Val Lys Gln Glu Gly Pro Glu Asn Ala Cys Leu Arg
1               5                   10                  15

Cys Pro Val Val Tyr Lys Ile Asn Ile Val Asn Gln Gly Thr Ala Thr
            20                  25                  30

Ala Arg Asn Val Val Val Glu Asn Pro Val Pro Asp Gly Tyr Ala His
        35                  40                  45

Ser Ser Gly Gln Arg Val Leu Thr Phe Thr Leu Gly Asp Met Gln Pro
    50                  55                  60

Gly Glu His Arg Thr Ile Thr Val Glu Phe Cys Pro Leu
65                  70                  75


<210> SEQ ID NO 130
<211> LENGTH: 231
<212> TYPE: DNA
<213> ORGANISM: Chlamydia trachomatis

<400> SEQUENCE: 130

cctgctatct gtgttaaaca agaaggccca gagaatgctt gtttgcgttg cccagtagtt     60

tacaaaatta atatagtgaa ccaaggaaca gcaacagctc gtaacgttgt tgttgaaaat    120

cctgttccag atggttacgc tcattcttct ggacagcgtg tactgacgtt tactcttgga    180

gatatgcaac ctggagagca cagaacaatt actgtagagt tttgtccgct t             231
```

<210> SEQ ID NO 131
<211> LENGTH: 163
<212> TYPE: PRT
<213> ORGANISM: Chlamydia trachomatis

<400> SEQUENCE: 131

Met Arg Phe Leu Leu Ala Leu Phe Ser Leu Ile Leu Val Leu Pro Ala
1 5 10 15

Thr Glu Ala Phe Ser Thr Glu Asp Lys Gln Cys Gln Gln Glu Ala Glu
20 25 30

Glu Asp Cys Ser Gln Val Ala Asp Thr Cys Val Phe Tyr Ser Tyr Ala
35 40 45

Glu Gly Leu Glu His Ala Arg Asp Glu Gly Lys Leu Thr Leu Val Val
50 55 60

Leu Leu Asp Thr Ser Gly Tyr Ser Phe Glu Thr Leu Ala Asp Ala Ala
65 70 75 80

His Ala Met Glu Ser Ser Leu Leu Ser Thr Phe Ala Asp Phe Val Val
85 90 95

Leu Ser Arg Arg Glu Ala Val Pro Leu Ile Tyr Pro Pro Val Pro Asp
100 105 110

Pro Met Val Gly Glu Ile Ala Leu Phe Leu Glu Ala Phe Ser Asp Gln
115 120 125

Thr Phe Pro Ser Gln Pro Val Ile Val Thr Leu Ala Ile Gly Ala Ser
130 135 140

Ser Ala Glu Ile Met Asp Ile Thr Glu Ile Pro Ser Ile Asn Pro Glu
145 150 155 160

Phe Val Glu

<210> SEQ ID NO 132
<211> LENGTH: 514
<212> TYPE: DNA
<213> ORGANISM: Chlamydia trachomatis

<400> SEQUENCE: 132
attttagtag aagaggagtt ctctcatgag attcttgtta gctttattct cactgatact 60
agttcttcct gcgactgagg cattctcaac agaggataag cagtgtcaac aagaagcaga 120
ggaagactgt agtcaggtag cggacacctg cgtattttat agctatgcag agggtttaga 180
acacgcaagg gacgaaggga aactcacctt agtagtattg ttagatactt ctgggtattc 240
cttcgagact cttgctgatg cagcccatgc tatggaaagt tcgttgctat ccacatttgc 300
tgattttgtg gttctttcta ggagggaagc agttccactg atttatcctc cggttccaga 360
tcctatggtt ggcgagatag cgttgttctt agaagctttc tcagatcaaa catttccatc 420
acagcctgtg attgttacct tagctattgg ggcttcttct gcagagatca tggatattac 480
cgagattccg tcaataaatc ctgaatttgt tgag 514

<210> SEQ ID NO 133
<211> LENGTH: 149
<212> TYPE: PRT
<213> ORGANISM: Chlamydia trachomatis

<400> SEQUENCE: 133

Arg Ile Ile Pro Glu Pro Thr Ala Ala Ala Leu Ala Tyr Gly Ile Asp
1 5 10 15

Lys Glu Gly Asp Lys Lys Ile Ala Val Phe Asp Leu Gly Gly Gly Thr
20 25 30

-continued

Phe Asp Ile Ser Ile Leu Glu Ile Gly Asp Gly Val Phe Glu Val Leu
        35                  40                  45

Ser Thr Asn Gly Asp Thr His Leu Gly Gly Asp Asp Phe Asp Gly Val
    50                  55                  60

Ile Ile Asn Trp Met Leu Asp Glu Phe Lys Lys Gln Glu Gly Ile Asp
65                  70                  75                  80

Leu Ser Lys Asp Asn Met Ala Leu Gln Arg Leu Lys Asp Ala Ala Glu
                85                  90                  95

Lys Ala Lys Ile Glu Leu Ser Gly Val Ser Ser Thr Glu Ile Asn Gln
            100                 105                 110

Pro Phe Ile Thr Ile Asp Ala Asn Gly Pro Lys His Leu Ala Leu Thr
        115                 120                 125

Leu Thr Arg Ala Gln Phe Glu His Leu Ala Ser Ser Leu Ile Glu Arg
    130                 135                 140

Thr Lys Gln Pro Cys
145

<210> SEQ ID NO 134
<211> LENGTH: 447
<212> TYPE: DNA
<213> ORGANISM: Chlamydia trachomatis

<400> SEQUENCE: 134
cgcattattc ctgaaccaac agcggccgct cttgcttatg gtattgataa ggaaggagat 60
aaaaaaatcg ccgtcttcga cttaggagga ggaactttcg atatttctat cttggaaatc 120
ggtgacggag tttttgaagt tctctcaacc aacggggata ctcacttggg aggagacgac 180
ttcgatggag tcatcatcaa ctggatgctt gatgaattca aaaaacaaga aggcattgat 240
ctaagcaaag ataacatggc tttgcaaaga ttgaaagatg ctgctgaaaa agcaaaaata 300
gaattgtctg gtgtatcgtc tactgaaatc aatcagccat tcatcactat cgacgctaat 360
ggacctaaac atttggcttt aactctaact cgcgctcaat tcgaacacct agcttcctct 420
ctcattgagc gaaccaaaca accttgc 447

<210> SEQ ID NO 135
<211> LENGTH: 82
<212> TYPE: PRT
<213> ORGANISM: Chlamydia trachomatis

<400> SEQUENCE: 135

Ser Asn Gly Ser Ser Ser Met Ala Ser Val Cys Gly Gly Cys Leu Ala
1               5                   10                  15

Leu Met Asp Ala Gly Val Pro Ile Lys Ala Pro Val Ala Gly Ile Ala
            20                  25                  30

Met Gly Leu Ile Leu Asp Arg Asp Gln Ala Ile Ile Leu Ser Asp Ile
        35                  40                  45

Ser Gly Ile Glu Asp His Leu Gly Asp Met Asp Phe Lys Val Ala Gly
    50                  55                  60

Thr Ala Lys Gly Ile Thr Ala Phe Gln Met Asp Ile Lys Ile Glu Gly
65                  70                  75                  80

Ile Thr

<210> SEQ ID NO 136
<211> LENGTH: 246
<212> TYPE: DNA
<213> ORGANISM: Chlamydia trachomatis

<400> SEQUENCE: 136
tctaatggat cttcctccat ggcatccgta tgtggaggct gtcttgcact catggatgct 60
ggagttccta tcaaagctcc cgtggcaggt attgctatgg gcttaatctt agatcgagat 120
caagccatca tcttgtctga tatttccggt atagaagatc atctaggaga tatggacttt 180
aaagtagccg gaacagctaa aggtattaca gctttccaaa tggatatcaa gatagaggga 240
atcact 246

<210> SEQ ID NO 137
<211> LENGTH: 101
<212> TYPE: PRT
<213> ORGANISM: Chlamydia trachomatis

<400> SEQUENCE: 137

Gln Ser Glu Leu Ala Lys Lys Glu Arg Gln Glu Glu Glu Leu Phe Leu
1 5 10 15

Ser Ile Gly Lys Asp His Val Leu Pro Gly Ile Gln Asn Gly Val Arg
20 25 30

Leu Ala Asn Val Leu Met Gln Gln Asp Ser Val Asp Ser Tyr Thr Gln
35 40 45

Asp Asn Glu His Phe Tyr Ser Ile Ser Val Ile Ser Arg Ala Asp Lys
50 55 60

Asp Glu Val Leu Pro Tyr Lys Glu Val Leu Arg Lys Gly Leu Lys Lys
65 70 75 80

Val Leu Leu Glu Lys Tyr Lys Ala Glu Glu Arg Ile Ser Arg Val Leu
85 90 95

Thr His Leu Gln Glu
100

<210> SEQ ID NO 138
<211> LENGTH: 303
<212> TYPE: DNA
<213> ORGANISM: Chlamydia trachomatis

<400> SEQUENCE: 138
caatctgaat tagctaagaa agagcggcaa gaggaagaac ttttcttgtc tataggtaag 60
gatcatgtgt taccaggtat tcagaacggt gttcgtttag ctaatgtgct gatgcaacaa 120
gattctgtag atagctatac tcaagataat gaacatttct attccattag tgtaatcagt 180
cgcgcagata aggatgaggt tttgccgtat aaagaagttt tgcgcaaagg gctaaagaaa 240
gttctattag agaaatacaa agcagaagag cgcattagtc gtgttttgac gcatctgcaa 300
gaa 303

<210> SEQ ID NO 139
<211> LENGTH: 97
<212> TYPE: PRT
<213> ORGANISM: Chlamydia trachomatis

<400> SEQUENCE: 139

Ala Ile Tyr Leu Glu Lys Asp Ala Ile Leu Ser Ser Leu Glu Ala Arg
1 5 10 15

Asn Gly Asp Ile Leu Phe Phe Asp Pro Ile Val Gln Glu Ser Ser Ser
20 25 30

Lys Glu Ser Pro Leu Pro Ser Ser Leu Gln Ala Ser Val Thr Ser Pro
35 40 45

Thr Pro Ala Thr Ala Ser Pro Leu Val Ile Gln Thr Ser Ala Asn Arg 50 55 60

Ser Val Ile Phe Ser Ser Glu Arg Leu Ser Glu Glu Glu Lys Thr Pro
65 70 75 80

Asp Asn Leu Thr Ser Gln Leu Gln Gln Pro Ile Glu Leu Lys Ser Gly
85 90 95

Arg

<210> SEQ ID NO 140
<211> LENGTH: 291
<212> TYPE: DNA
<213> ORGANISM: Chlamydia trachomatis

<400> SEQUENCE: 140
gccatctact tagagaaaga tgcgattctt tcttccttag aagctcgcaa cggagatatt 60
cttttctttg atcctattgt acaagaaagt agcagcaaag aatcgcctct tccctcctct 120
ttgcaagcca gcgtgacttc tcccacccca gccaccgcat ctcctttagt tattcagaca 180
agtgcaaacc gttcagtgat tttctcgagc gaacgtcttt ctgaagaaga aaaaactcct 240
gataacctca cttcccaact acagcagcct atcgaactga aatccggccg g 291

<210> SEQ ID NO 141
<211> LENGTH: 141
<212> TYPE: PRT
<213> ORGANISM: Chlamydia trachomatis

<400> SEQUENCE: 141

Lys Leu Ser Phe Asp Gly Gln Ala Lys Leu Thr Gly Val Ala Thr Pro
1 5 10 15

Thr Arg Asp Thr Asp Val Val Pro Leu Gln Tyr Leu Gln Ala Arg Tyr
20 25 30

Leu Ser Lys Asn Asp Pro Asn Pro Gly Tyr Leu Pro Ile His Gly Gly
35 40 45

Asn Met Thr Gly Asn Ile Asn Met Gly Thr His Ser Val Phe Asn Leu
50 55 60

Lys Gln Pro Glu Lys Pro Lys Ile Glu Leu Pro Ser Glu Thr Asp Lys
65 70 75 80

Pro Lys Asp Pro Arg Glu Glu Asp Gly Phe Ala Glu Lys Thr Ala Glu
85 90 95

Glu Gln Glu Gln Glu Ile Lys Glu Tyr Asn Thr Lys Leu Ala Glu Tyr
100 105 110

Gln Lys Lys Ile Asp Asp Tyr Asn Ala Ala Trp Glu Ala Phe Tyr Ser
115 120 125

Glu Ala Ala Thr Val Lys Tyr Val Lys Gly Ile Val Asp
130 135 140

<210> SEQ ID NO 142
<211> LENGTH: 423
<212> TYPE: DNA
<213> ORGANISM: Chlamydia trachomatis

<400> SEQUENCE: 142
aagttaagct ttgatggaca agctaagtta accggagtag ctactccgac tcgtgatacg 60
gatgttgtgc cactacaata ccttcaagca cgctatctat ctaaaaatga cccaaatcca 120
ggttatcttc ccattcatgg agggaacatg actgggaaca ttaatatggg aacgcattcc 180
gtatttaatt tgaagcagcc agagaaacct aagatagagc ttccttccga aaccgacaaa 240

```
ccaaaagacc cgcgagaaga agacggtttt gcagaaaaaa cagccgagga acaagaacaa    300

gagatcaaag agtacaacac aaagctggca gaataccaga aaaaaatcga tgattacaat    360

gcagcatggg aagcttttta ctcagaagca gctactgtga aatatgtcaa aggtattgtt    420

gat                                                                  423
```

<210> SEQ ID NO 143
<211> LENGTH: 110
<212> TYPE: PRT
<213> ORGANISM: Chlamydia trachomatis

<400> SEQUENCE: 143

```
Lys Lys Tyr Lys Gln Cys Cys Leu Lys Ser Gln Ala Leu Thr Ala Arg
1               5                   10                  15

His Thr Pro Glu Gly Lys Phe Lys Phe Ser Ile Thr Ala Ser Pro Ala
            20                  25                  30

Ala Gly Ala Ser Thr Glu Gly Phe Thr Lys Leu Phe Arg Gln Ser Val
        35                  40                  45

Asp Ser Tyr Thr Ser Glu Gln Lys Glu Gly Met Ser Arg Phe Leu Ile
    50                  55                  60

Thr Lys Asn Lys Glu Pro Ile Gly Lys Arg Ala Ile Arg Lys Ala Lys
65                  70                  75                  80

Ala Lys Glu Glu Arg Ile Ile Ser Glu Lys Leu Ser Gln His Glu Phe
                85                  90                  95

Gln Val Met Asp Thr Glu Val Ser Gly Glu Asp Ile Gln Ser
            100                 105                 110
```

<210> SEQ ID NO 144
<211> LENGTH: 330
<212> TYPE: DNA
<213> ORGANISM: Chlamydia trachomatis

<400> SEQUENCE: 144

```
aagaagtata agcagtgttg tttgaaatca caagctctaa ctgctcgcca tactcctgaa     60

gggaagttta agttttctat aacagcttcg cctgccgcag gcgcttccac ggaaggtttc    120

acaaaactgt ttcgccaatc agtggattct tatacctcag aacaaaaaga ggggatgagt    180

cggtttctta ttactaaaaa taaggaacct atagggaaac gcgcgattcg caaggctaag    240

gcaaaagaag agcgcatcat ttcagagaaa ctaagccagc acgaatttca agtgatggat    300

acagaagtat cgggagaaga tatacagtct                                     330
```

<210> SEQ ID NO 145
<211> LENGTH: 73
<212> TYPE: PRT
<213> ORGANISM: Chlamydia trachomatis

<400> SEQUENCE: 145

```
Lys Lys Ser Ser Ala Thr Thr Lys Lys Arg Ala Thr Lys Ala Tyr Thr
1               5                   10                  15

Pro Ser Ala Ala Leu Ala Ala Val Ile Gly Ala Asp Pro Val Gly Arg
            20                  25                  30

Pro Glu Ala Thr Lys Lys Leu Trp Glu Tyr Ile Lys Glu Lys Gly Leu
        35                  40                  45

Gln Ser Pro Gln Asn Lys Lys Ile Ile Ile Pro Asp Ser Lys Leu Gln
    50                  55                  60

Gly Val Ile Gly Ala Asp Pro Ile Asp
65                  70
```

<210> SEQ ID NO 146
<211> LENGTH: 219
<212> TYPE: DNA
<213> ORGANISM: Chlamydia trachomatis

<400> SEQUENCE: 146
aaaaaaagct cagcaacaac aaaaaaacga gctaccaaag cgtacacacc ttctgctgct 60
ttagcagcgg tgattggtgc ggatcctgta gggcgtcccg aagccactaa gaagctatgg 120
gagtatatta aggaaaaagg attgcaatcc cctcaaaata aaaaaatcat tattcctgat 180
agtaaattgc agggagtgat aggagctgat ccaatcgac 219

<210> SEQ ID NO 147
<211> LENGTH: 236
<212> TYPE: PRT
<213> ORGANISM: Chlamydia trachomatis

<400> SEQUENCE: 147

Val Gly Leu Phe Gly Asp Asn Glu Asn Gln Lys Thr Val Lys Ala Glu
1               5                   10                  15

Ser Val Pro Asn Met Ser Phe Asp Gln Ser Val Val Glu Leu Tyr Thr
            20                  25                  30

Asp Thr Thr Phe Ala Trp Ser Val Gly Ala Arg Ala Ala Leu Trp Glu
        35                  40                  45

Cys Gly Cys Ala Thr Leu Gly Ala Ser Phe Gln Tyr Ala Gln Ser Lys
    50                  55                  60

Pro Lys Val Glu Glu Leu Asn Val Leu Cys Asn Ala Ala Glu Phe Thr
65                  70                  75                  80

Ile Asn Lys Pro Lys Gly Tyr Val Gly Lys Glu Phe Pro Leu Asp Leu
                85                  90                  95

Thr Ala Gly Thr Asp Ala Ala Thr Gly Thr Lys Asp Ala Ser Ile Asp
            100                 105                 110

Tyr His Glu Trp Gln Ala Ser Leu Ala Leu Ser Tyr Arg Leu Asn Met
        115                 120                 125

Phe Thr Pro Tyr Ile Gly Val Lys Trp Ser Arg Ala Ser Phe Asp Ala
    130                 135                 140

Asp Thr Ile Arg Ile Ala Gln Pro Lys Ser Ala Thr Ala Ile Phe Asp
145                 150                 155                 160

Thr Thr Thr Leu Asn Pro Thr Ile Ala Gly Ala Gly Asp Val Lys Thr
                165                 170                 175

Gly Ala Glu Gly Gln Leu Gly Asp Thr Met Gln Ile Val Ser Leu Gln
            180                 185                 190

Leu Asn Lys Met Lys Ser Arg Lys Ser Cys Gly Ile Ala Val Gly Thr
        195                 200                 205

Thr Ile Val Asp Ala Asp Lys Tyr Ala Val Thr Val Glu Thr Arg Leu
    210                 215                 220

Ile Asp Glu Arg Ala Ala His Val Asn Ala Gln Phe
225                 230                 235

<210> SEQ ID NO 148
<211> LENGTH: 708
<212> TYPE: DNA
<213> ORGANISM: Chlamydia trachomatis

<400> SEQUENCE: 148
gttggattgt ttggagataa tgaaaatcaa aaaacggtca aagcggagtc tgtaccaaat 60

```
atgagctttg atcaatctgt tgttgagttg tatacagata ctacttttgc gtggagcgtc    120

ggcgctcgcg cagctttgtg ggaatgtgga tgtgcaactt taggagcttc attccaatat    180

gctcaatcta aacctaaagt agaagaatta aacgttctct gcaatgcagc agagtttact    240

attaataaac ctaaagggta tgtaggtaag gagtttcctc ttgatcttac agcaggaaca    300

gatgctgcga caggaactaa ggatgcctct attgattacc atgaatggca agcaagttta    360

gctctctctt acagactgaa tatgttcact ccctacattg gagttaaatg gtctcgagca    420

agctttgatg ccgatacgat tcgtatagcc cagccaaaat cagctacagc tatttttgat    480

actaccacgc ttaacccaac tattgctgga gctggcgatg tgaaaactgg cgcagagggt    540

cagctcggag acacaatgca aatcgtttcc ttgcaattga acaagatgaa atctagaaaa    600

tcttgcggta ttgcagtagg aacaactatt gtggatgcag acaaatacgc agttacagtt    660

gagactcgct tgatcgatga gagagcagct cacgtaaatg cacaattc                 708


<210> SEQ ID NO 149
<211> LENGTH: 131
<212> TYPE: PRT
<213> ORGANISM: Chlamydia trachomatis

<400> SEQUENCE: 149

Ala Ala Leu Trp Glu Cys Gly Cys Ala Thr Leu Gly Ala Ser Phe Gln
1               5                   10                  15

Tyr Ala Gln Ser Lys Pro Lys Val Glu Glu Leu Asn Val Leu Cys Asn
            20                  25                  30

Ala Ala Glu Phe Thr Ile Asn Lys Pro Lys Gly Tyr Val Gly Lys Glu
        35                  40                  45

Phe Pro Leu Asp Leu Thr Ala Gly Thr Asp Ala Ala Thr Gly Thr Lys
    50                  55                  60

Asp Ala Ser Ile Asp Tyr His Glu Trp Gln Ala Ser Leu Ala Leu Ser
65                  70                  75                  80

Tyr Arg Leu Asn Met Phe Thr Pro Tyr Ile Gly Val Lys Trp Ser Arg
                85                  90                  95

Ala Ser Phe Asp Ala Asp Thr Ile Arg Ile Ala Gln Pro Lys Ser Ala
            100                 105                 110

Thr Ala Ile Phe Asp Thr Thr Thr Leu Asn Pro Thr Ile Ala Gly Ala
        115                 120                 125

Gly Asp Val
    130


<210> SEQ ID NO 150
<211> LENGTH: 393
<212> TYPE: DNA
<213> ORGANISM: Chlamydia trachomatis

<400> SEQUENCE: 150

gcagctttgt gggaatgtgg atgtgcaact ttaggagctt cattccaata tgctcaatct     60

aaacctaaag tagaagaatt aaacgttctc tgcaatgcag cagagtttac tattaataaa    120

cctaaagggt atgtaggtaa ggagtttcct cttgatctta cagcaggaac agatgctgcg    180

acaggaacta aggatgcctc tattgattac catgaatggc aagcaagttt agctctctct    240

tacagactga atatgttcac tccctacatt ggagttaaat ggtctcgagc aagctttgat    300

gccgatacga ttcgtatagc ccagccaaaa tcagctacag ctatttttga tactaccacg    360

cttaacccaa ctattgctgg agctggcgat gtg                                 393
```

<210> SEQ ID NO 151
<211> LENGTH: 56
<212> TYPE: PRT
<213> ORGANISM: Chlamydia trachomatis

<400> SEQUENCE: 151

```
Arg Ala Ser Phe Asp Ala Asp Thr Ile Arg Ile Ala Gln Pro Lys Ser
1               5                   10                  15

Ala Thr Ala Ile Phe Asp Thr Thr Thr Leu Asn Pro Thr Ile Ala Gly
            20                  25                  30

Ala Gly Asp Val Lys Thr Gly Ala Glu Gly Gln Leu Gly Asp Thr Met
        35                  40                  45

Gln Ile Val Ser Leu Gln Leu Asn
    50                  55
```

<210> SEQ ID NO 152
<211> LENGTH: 168
<212> TYPE: DNA
<213> ORGANISM: Chlamydia trachomatis

<400> SEQUENCE: 152

```
cgagcaagct ttgatgccga tacgattcgt atagcccagc caaaatcagc tacagctatt      60

tttgatacta ccacgcttaa cccaactatt gctggagctg gcgatgtgaa aactggcgca     120

gagggtcagc tcggagacac aatgcaaatc gtttccttgc aattgaac                  168
```

<210> SEQ ID NO 153
<211> LENGTH: 118
<212> TYPE: PRT
<213> ORGANISM: Chlamydia trachomatis

<400> SEQUENCE: 153

```
Thr Val Lys Ala Ile Val Glu Ser Thr Pro Glu Ala Pro Glu Glu Ile
1               5                   10                  15

Pro Pro Val Glu Gly Glu Glu Ser Thr Ala Thr Glu Asp Pro Asn Ser
            20                  25                  30

Asn Thr Glu Gly Ser Ser Ala Asn Thr Asn Leu Glu Gly Ser Gln Gly
        35                  40                  45

Asp Thr Ala Asp Thr Gly Thr Gly Asp Val Asn Asn Glu Ser Gln Asp
    50                  55                  60

Thr Ser Asp Thr Gly Asn Ala Glu Ser Glu Glu Gln Leu Gln Asp Ser
65                  70                  75                  80

Thr Gln Ser Asn Glu Glu Asn Thr Leu Pro Asn Ser Asn Ile Asp Gln
                85                  90                  95

Ser Asn Glu Asn Thr Asp Glu Ser Ser Asp Ser His Thr Glu Glu Ile
            100                 105                 110

Thr Asp Glu Ser Val Ser
        115
```

<210> SEQ ID NO 154
<211> LENGTH: 354
<212> TYPE: DNA
<213> ORGANISM: Chlamydia trachomatis

<400> SEQUENCE: 154

```
actgttaaag caatagtaga aagcactcct gaagctccag aagagattcc tccagtagaa      60

ggagaagagt ctacagcaac agaagatcca aattctaata cagaaggaag ttcggctaac     120
```

-continued

```
actaaccttg aaggatctca aggggatact gctgatacag ggactggtga tgttaacaat    180

gagtctcaag acacatcaga tactggaaac gctgaatctg aagaacaact acaagattct    240

acacaatcta atgaagaaaa tacccttccc aatagtaata ttgatcaatc taacgaaaac    300

acagacgaat catctgatag ccacactgag gaaataactg acgagagtgt ctcc          354


<210> SEQ ID NO 155
<211> LENGTH: 68
<212> TYPE: PRT
<213> ORGANISM: Chlamydia trachomatis

<400> SEQUENCE: 155

Pro Glu Val Val Ala Ser Ala Lys Ile Asn Arg Phe Phe Ala Ser Thr
1               5                   10                  15

Ala Lys Pro Ala Ala Pro Ser Leu Thr Glu Ala Glu Ser Asp Gln Thr
            20                  25                  30

Asp Gln Thr Glu Thr Ser Asp Thr Asn Ser Asp Ile Asp Val Ser Ile
        35                  40                  45

Glu Asn Ile Leu Asn Val Ala Ile Asn Gln Asn Thr Ser Ala Lys Lys
    50                  55                  60

Gly Gly Ala Ile
65


<210> SEQ ID NO 156
<211> LENGTH: 204
<212> TYPE: DNA
<213> ORGANISM: Chlamydia trachomatis

<400> SEQUENCE: 156

ccggaagtag ttgcttctgc taaaataaat cgattctttg cctctacggc aaaaccggca     60

gccccttctc taacagaggc tgagtctgat caaacggatc aaacagaaac ttctgatact    120

aatagcgata tagacgtgtc gattgagaac attttgaatg tcgctatcaa tcaaaacact    180

tctgcgaaaa aaggaggggc tatc                                           204


<210> SEQ ID NO 157
<211> LENGTH: 243
<212> TYPE: PRT
<213> ORGANISM: Chlamydia trachomatis

<400> SEQUENCE: 157

Val Gly Asn Gly Ala Glu Glu Ile Thr Leu Ser Asp Thr Asp Ser Gly
1               5                   10                  15

Ile Gly Asp Asp Val Ser Asp Thr Ala Ser Ser Ser Gly Asp Glu Ser
            20                  25                  30

Gly Gly Val Ser Ser Pro Ser Ser Glu Ser Asn Lys Asn Thr Ala Val
        35                  40                  45

Gly Asn Asp Gly Pro Ser Gly Leu Asp Ile Leu Ala Ala Val Arg Lys
    50                  55                  60

His Leu Asp Lys Val Tyr Pro Gly Asp Asn Gly Gly Ser Thr Glu Gly
65                  70                  75                  80

Pro Leu Gln Ala Asn Gln Thr Leu Gly Asp Ile Val Gln Asp Met Glu
                85                  90                  95

Thr Thr Gly Thr Ser Gln Glu Thr Val Val Ser Pro Trp Lys Gly Ser
            100                 105                 110

Thr Ser Ser Thr Glu Ser Ala Gly Gly Ser Gly Ser Val Gln Thr Leu
        115                 120                 125
```

-continued

```
Leu Pro Ser Pro Pro Pro Thr Pro Ser Thr Thr Thr Leu Arg Thr Gly
    130                 135                 140

Thr Gly Ala Thr Thr Thr Ser Leu Met Met Gly Gly Pro Ile Lys Ala
145                 150                 155                 160

Asp Ile Ile Thr Thr Gly Gly Gly Gly Arg Ile Pro Gly Gly Gly Thr
                165                 170                 175

Leu Glu Lys Leu Leu Pro Arg Ile Arg Ala His Leu Asp Ile Ser Phe
            180                 185                 190

Asp Ala Gln Gly Asp Leu Val Ser Thr Glu Glu Pro Gln Leu Gly Ser
        195                 200                 205

Ile Val Asn Lys Phe Arg Gln Glu Thr Gly Ser Arg Gly Ile Leu Ala
    210                 215                 220

Phe Val Glu Ser Ala Pro Gly Lys Pro Gly Ser Ala Gln Val Leu Thr
225                 230                 235                 240

Gly Thr Gly


<210> SEQ ID NO 158
<211> LENGTH: 729
<212> TYPE: DNA
<213> ORGANISM: Chlamydia trachomatis

<400> SEQUENCE: 158

gtaggtaatg gagcggaaga gatcactctt tccgacacag attctggtat cggagatgat      60

gtatccgata cagcgtcttc atctggggat gaatccggag gagtctcctc tccctcttca     120

gaatccaata aaaatactgc cgttggaaat gacggacctt ctggactaga tatcctcgct     180

gccgtacgta aacatttaga taaggtttac cctggcgaca atggtggttc tacagaaggg     240

cctctccaag ctaaccaaac tcttggagat atcgtccagg atatggaaac aacagggaca     300

tcccaagaaa ccgttgtatc ccatggaaa ggaagcactt cttcaacgga atcagcagga     360

ggaagtggta gcgtacaaac actactgcct tcaccacctc caaccccgtc aactacaaca     420

ttaagaacgg gcacaggagc taccaccaca tccttgatga tgggaggacc aatcaaagct     480

gacataataa caactggtgg cggaggacga attcctggag gaggaacgtt agaaaagctg     540

ctccctcgta tacgtgcgca cttagacata tcctttgatg cgcaaggcga tctcgtaagt     600

actgaagagc ctcagcttgg ctcgattgta aacaaattcc gccaagaaac tggttcaaga     660

ggaatcttag ctttcgttga gagtgctcca ggcaagccgg gatctgcaca ggtcttaacg     720

ggtacaggc                                                             729


<210> SEQ ID NO 159
<211> LENGTH: 93
<212> TYPE: PRT
<213> ORGANISM: Chlamydia trachomatis

<400> SEQUENCE: 159

Ser Asn Asn Tyr Asp Asp Val Gly Ser Asn Asn Gly Asp Ile Ser Ser
1               5                   10                  15

Asn Tyr Asp Asp Ala Ala Ala Asp Tyr Glu Pro Ile Arg Thr Thr Glu
            20                  25                  30

Asn Ile Tyr Glu Ser Ile Gly Gly Ser Arg Thr Ser Gly Pro Glu Asn
        35                  40                  45

Thr Ser Gly Gly Ala Ala Ala Ala Leu Asn Ser Leu Arg Gly Ser Ser
    50                  55                  60

Tyr Ser Asn Tyr Asp Asp Ala Ala Ala Asp Tyr Glu Pro Ile Arg Thr
65                  70                  75                  80
```

```
Thr Glu Asn Ile Tyr Glu Ser Ile Gly Gly Ser Arg Thr
                85                  90


<210> SEQ ID NO 160
<211> LENGTH: 279
<212> TYPE: DNA
<213> ORGANISM: Chlamydia trachomatis

<400> SEQUENCE: 160

agcaacaact acgatgacgt aggtagtaac aacggagata tcagtagcaa ttatgacgat      60

gctgctgctg attacgagcc gataagaact actgaaaata tttatgagag tattggtggc     120

tctagaacaa gtggcccaga aaatacaagt ggtggtgcag cagcagcact caattctcta     180

agaggctcct cctacagcaa ttatgacgat gctgctgctg attacgagcc gataagaact     240

actgaaaata tttatgagag tattggtggc tctagaaca                            279


<210> SEQ ID NO 161
<211> LENGTH: 79
<212> TYPE: PRT
<213> ORGANISM: Chlamydia trachomatis

<400> SEQUENCE: 161

Leu Asn Ser Leu Arg Gly Ser Ser Tyr Ser Asn Tyr Asp Asp Ala Ala
1               5                   10                  15

Ala Asp Tyr Glu Pro Ile Arg Thr Thr Glu Asn Ile Tyr Glu Ser Ile
            20                  25                  30

Gly Gly Ser Arg Thr Ser Gly Pro Glu Asn Thr Ser Asp Gly Ala Ala
        35                  40                  45

Ala Ala Ala Leu Asn Ser Leu Arg Gly Ser Ser Tyr Thr Thr Gly Pro
    50                  55                  60

Arg Asn Glu Gly Val Phe Gly Pro Gly Pro Glu Gly Leu Pro Asp
65                  70                  75


<210> SEQ ID NO 162
<211> LENGTH: 237
<212> TYPE: DNA
<213> ORGANISM: Chlamydia trachomatis

<400> SEQUENCE: 162

ctcaattctc taagaggctc ctcctacagc aattatgacg atgctgctgc tgattacgag      60

ccgataagaa ctactgaaaa tatttatgag agtattggtg gctctagaac aagtggccca     120

gaaaatacga gtgatggtgc agcagcagca gcactcaatt ctctaagagg ctcctcctac     180

acaacagggc ctcgtaacga gggtgtattc ggccctggac cggaaggact accagac        237


<210> SEQ ID NO 163
<211> LENGTH: 83
<212> TYPE: PRT
<213> ORGANISM: Chlamydia trachomatis

<400> SEQUENCE: 163

Ala Asp Tyr Glu Pro Ile Arg Thr Thr Glu Asn Ile Tyr Glu Ser Ile
1               5                   10                  15

Gly Gly Ser Arg Thr Ser Gly Pro Glu Asn Thr Ser Gly Gly Ala Ala
            20                  25                  30

Ala Ala Leu Asn Ser Leu Arg Gly Ser Ser Tyr Ser Asn Tyr Asp Asp
        35                  40                  45

Ala Ala Ala Asp Tyr Glu Pro Ile Arg Thr Thr Glu Asn Ile Tyr Glu
```

50 55 60

Ser Ile Gly Gly Ser Arg Thr Ser Gly Pro Glu Asn Thr Ser Asp Gly
65 70 75 80

Ala Ala Ala

<210> SEQ ID NO 164
<211> LENGTH: 249
<212> TYPE: DNA
<213> ORGANISM: Chlamydia trachomatis

<400> SEQUENCE: 164
gctgattacg agccgataag aactactgaa aatatttatg agagtattgg tggctctaga 60
acaagtggcc cagaaaatac gagtggtggt gcagcagcag cactcaattc tctaagaggc 120
tcctcctaca gcaattatga cgatgctgct gctgattacg agccgataag aactactgaa 180
aatatttatg agagtattgg tggctctaga acaagtggcc cagaaaatac gagtgatggt 240
gcagcagca 249

<210> SEQ ID NO 165
<211> LENGTH: 105
<212> TYPE: PRT
<213> ORGANISM: Chlamydia trachomatis

<400> SEQUENCE: 165

Gly Gly Ser Arg Thr Ser Gly Pro Glu Asn Thr Ser Gly Gly Ala Ala
1 5 10 15

Ala Ala Leu Asn Ser Leu Arg Gly Ser Ser Tyr Ser Asn Tyr Asp Asp
20 25 30

Ala Ala Ala Asp Tyr Glu Pro Ile Arg Thr Thr Glu Asn Ile Tyr Glu
35 40 45

Ser Ile Gly Gly Ser Arg Thr Ser Gly Pro Glu Asn Thr Ser Gly Gly
50 55 60

Ala Ala Ala Ala Leu Asn Ser Leu Arg Gly Ser Ser Tyr Ser Asn Tyr
65 70 75 80

Asp Asp Ala Ala Ala Asp Tyr Glu Pro Ile Arg Thr Thr Glu Asn Ile
85 90 95

Tyr Glu Ser Ile Gly Gly Ser Arg Thr
100 105

<210> SEQ ID NO 166
<211> LENGTH: 315
<212> TYPE: DNA
<213> ORGANISM: Chlamydia trachomatis

<400> SEQUENCE: 166
ggtggctcta gaacaagtgg cccagaaaat acaagtggtg gtgcagcagc agcactcaat 60
tctctaagag gctcctccta cagcaattat gacgatgctg ctgctgatta cgagccgata 120
agaactactg aaaatattta tgagagtatt ggtggctcta gaacaagtgg cccagaaaat 180
acgagtggtg gtgcagcagc agcactcaat tctctaagag gctcctccta cagcaattat 240
gacgatgctg ctgctgatta cgagccgata agaactactg aaaatattta tgagagtatt 300
ggtggctcta gaacc 315

<210> SEQ ID NO 167
<211> LENGTH: 164
<212> TYPE: PRT
<213> ORGANISM: Chlamydia trachomatis -continued

<400> SEQUENCE: 167

Asp Asp Ile Asn Thr Asn Asn Gln Thr Asp Asp Ile Asn Thr Thr Asp
1 5 10 15

Lys Asp Ser Asp Gly Ala Gly Gly Val Asn Gly Asp Ile Ser Glu Thr
20 25 30

Glu Ser Ser Ser Gly Asp Asp Ser Gly Ser Val Ser Ser Ser Glu Ser
35 40 45

Asp Lys Asn Ala Ser Val Gly Asn Asp Gly Pro Ala Met Lys Asp Ile
50 55 60

Leu Ser Ala Val Arg Lys His Leu Asp Val Val Tyr Pro Gly Glu Asn
65 70 75 80

Gly Gly Ser Thr Glu Gly Pro Leu Pro Ala Asn Gln Thr Leu Gly Asp
85 90 95

Val Ile Ser Asp Val Glu Asn Lys Gly Ser Ala Gln Asp Thr Lys Leu
100 105 110

Ser Gly Asn Thr Gly Ala Gly Asp Asp Asp Pro Thr Thr Thr Ala Ala
115 120 125

Val Gly Asn Gly Ala Glu Glu Ile Thr Leu Ser Asp Thr Asp Ser Gly
130 135 140

Ile Gly Asp Asp Val Ser Asp Thr Ala Ser Ser Ser Gly Asp Glu Ser
145 150 155 160

Gly Gly Val Ser

<210> SEQ ID NO 168
<211> LENGTH: 492
<212> TYPE: DNA
<213> ORGANISM: Chlamydia trachomatis

<400> SEQUENCE: 168
gatgacataa ataccaacaa ccaaactgat gatatcaata cgacagacaa agactctgac 60
ggagctggtg gagtcaatgg cgatatatcc gaaacagaat cctcttctgg agatgattca 120
ggaagtgtct cttcctcaga atcagacaag aatgcctctg tcggaaatga cggacctgct 180
atgaaagata tcctttctgc cgtgcgtaaa cacctagacg tcgtttaccc tggcgaaaat 240
ggcggttcta cagaagggcc tctcccagct aaccaaactc tcggagacgt aatctctgat 300
gtagagaata aaggctccgc tcaggataca aaattgtcag gaaatacagg agctggggat 360
gacgatccaa caaccacagc tgctgtaggt aatggagcgg aagagatcac tctttccgac 420
acagattctg gtatcggaga tgatgtatcc gatacagcgt cttcatctgg ggatgaatcc 480
ggaggagtct cc 492

<210> SEQ ID NO 169
<211> LENGTH: 110
<212> TYPE: PRT
<213> ORGANISM: Chlamydia trachomatis

<400> SEQUENCE: 169

Ala Ser Ala Pro Asn Val Thr Val Ser Thr Ser Ser Ser Ser Thr Gln
1 5 10 15

Ala Thr Ala Thr Ser Asn Lys Thr Ser Gln Ala Val Ala Gly Lys Ile
20 25 30

Thr Ser Pro Asp Thr Ser Glu Ser Ser Glu Thr Ser Ser Thr Ser Ser
35 40 45

Ser Asp His Ile Pro Ser Asp Tyr Asp Asp Val Gly Ser Asn Ser Gly

-continued

```
    50                  55                  60

Asp Ile Ser Asn Asn Tyr Asp Asp Val Gly Ser Asn Asn Gly Asp Ile
65                  70                  75                  80

Ser Ser Asn Tyr Asp Asp Ala Ala Ala Asp Tyr Glu Pro Ile Arg Thr
                85                  90                  95

Thr Glu Asn Ile Tyr Glu Ser Ile Gly Gly Ser Arg Thr Ser
            100                 105                 110


<210> SEQ ID NO 170
<211> LENGTH: 330
<212> TYPE: DNA
<213> ORGANISM: Chlamydia trachomatis

<400> SEQUENCE: 170

gcctccgccc ccaatgtaac tgtatcgacc tcctcttctt ccacacaagc cacagccact      60

tcgaataaaa cttcccaagc cgttgctgga aaaatcactt ctccagatac ttcagaaagc     120

tcagaaacta gctctacctc atcaagcgat catatcccta gcgattacga tgacgttggt     180

agcaatagtg gagatattag caacaactac gatgacgtag gtagtaacaa cggagatatc     240

agtagcaatt atgacgatgc tgctgctgat tacgagccga taagaactac tgaaaatatt     300

tatgagagta ttggtggctc tagaacaagt                                      330


<210> SEQ ID NO 171
<211> LENGTH: 90
<212> TYPE: PRT
<213> ORGANISM: Chlamydia trachomatis

<400> SEQUENCE: 171

Ala Ala Ala Leu Asn Ser Leu Arg Gly Ser Ser Tyr Ser Asn Tyr Asp
1               5                   10                  15

Asp Ala Ala Ala Asp Tyr Glu Pro Ile Arg Thr Thr Glu Asn Ile Tyr
            20                  25                  30

Glu Ser Ile Gly Gly Ser Arg Thr Ser Gly Pro Glu Asn Thr Ser Gly
        35                  40                  45

Gly Ala Ala Ala Ala Leu Asn Ser Leu Arg Gly Ser Ser Tyr Ser Asn
    50                  55                  60

Tyr Asp Asp Ala Ala Ala Asp Tyr Glu Pro Ile Arg Thr Thr Glu Asn
65                  70                  75                  80

Ile Tyr Glu Ser Ile Gly Gly Ser Arg Thr
                85                  90


<210> SEQ ID NO 172
<211> LENGTH: 270
<212> TYPE: DNA
<213> ORGANISM: Chlamydia trachomatis

<400> SEQUENCE: 172

gcagcagcac tcaattctct aagaggctcc tcctacagca attatgacga tgctgctgct      60

gattacgagc cgataagaac tactgaaaat atttatgaga gtattggtgg ctctagaaca     120

agtggcccag aaaatacgag tggtggtgca gcagcagcac tcaattctct aagaggctcc     180

tcctacagca attatgacga tgctgctgct gattacgagc cgataagaac tactgaaaat     240

atttatgaga gtattggtgg ctctagaacc                                      270


<210> SEQ ID NO 173
<211> LENGTH: 23
<212> TYPE: PRT
```

<213> ORGANISM: Chlamydia trachomatis

<400> SEQUENCE: 173

Lys Gly Gln Phe Ala Gly Leu Ser Lys Gly Ala Thr Phe Val Asp Phe
1 5 10 15

Gly Glu Phe Gly Met Gln Thr
20

<210> SEQ ID NO 174
<211> LENGTH: 69
<212> TYPE: DNA
<213> ORGANISM: Chlamydia trachomatis

<400> SEQUENCE: 174
aaaggtcagt ttgctggatt gagtaaggga gcaacgtttg ttgacttcgg cgaatttgga 60
atgcagact 69

<210> SEQ ID NO 175
<211> LENGTH: 23
<212> TYPE: PRT
<213> ORGANISM: Chlamydia trachomatis

<400> SEQUENCE: 175

Ala Ile Asn Arg Tyr Leu Lys Arg Lys Gly Lys Val Trp Ile Arg Val
1 5 10 15

Phe Pro Asp Lys Ser Val Thr
20

<210> SEQ ID NO 176
<211> LENGTH: 69
<212> TYPE: DNA
<213> ORGANISM: Chlamydia trachomatis

<400> SEQUENCE: 176
ggatggatta ccagccgcca aattgaggca tgcagggttg ctatcaacag atatttaaaa 60
cgtaaaggg 69

<210> SEQ ID NO 177
<211> LENGTH: 23
<212> TYPE: PRT
<213> ORGANISM: Chlamydia trachomatis

<400> SEQUENCE: 177

Ile Arg Val Phe Pro Asp Lys Ser Val Thr Lys Lys Pro Ala Glu Thr
1 5 10 15

Arg Met Gly Lys Gly Lys Gly
20

<210> SEQ ID NO 178
<211> LENGTH: 69
<212> TYPE: DNA
<213> ORGANISM: Chlamydia trachomatis

<400> SEQUENCE: 178
gctatcaaca gatatttaaa acgtaaaggg aaagtttgga ttcgagtttt cccagataag 60
agtgtaacg 69

<210> SEQ ID NO 179
<211> LENGTH: 23
<212> TYPE: PRT
<213> ORGANISM: Chlamydia trachomatis

<400> SEQUENCE: 179

```
Asp Ala Leu Arg Arg Ala Ala Ala Lys Leu Gly Ile Arg Thr Arg Phe
1               5                   10                  15

Val Lys Arg Val Glu Arg Val
            20
```

<210> SEQ ID NO 180
<211> LENGTH: 69
<212> TYPE: DNA
<213> ORGANISM: Chlamydia trachomatis

<400> SEQUENCE: 180

```
attcgagttt tcccagataa gagtgtaacg aaaaaacctg ctgaaactcg aatgggtaaa     60

ggtaaggga                                                             69
```

<210> SEQ ID NO 181
<211> LENGTH: 23
<212> TYPE: PRT
<213> ORGANISM: Chlamydia trachomatis

<400> SEQUENCE: 181

```
Asp Ala Leu Arg Arg Ala Ala Ala Lys Leu Gly Ile Arg Thr Arg Phe
1               5                   10                  15

Val Lys Arg Val Glu Arg Val
            20
```

<210> SEQ ID NO 182
<211> LENGTH: 69
<212> TYPE: DNA
<213> ORGANISM: Chlamydia trachomatis

<400> SEQUENCE: 182

```
gatgctttga gaagagctgc tgcaaagtta ggaattagaa cacgatttgt taagcgtgtg     60

gaaagggta                                                             69
```

<210> SEQ ID NO 183
<211> LENGTH: 28
<212> TYPE: PRT
<213> ORGANISM: Chlamydia trachomatis

<400> SEQUENCE: 183

```
Pro Ile Pro Val Asn Phe Pro Leu Ser Ser Gly Lys His Asn Pro Thr
1               5                   10                  15

Ala Leu Ala Ala Pro Val Glu Ala Gly Ile Ile Phe
            20                  25
```

<210> SEQ ID NO 184
<211> LENGTH: 84
<212> TYPE: DNA
<213> ORGANISM: Chlamydia trachomatis

<400> SEQUENCE: 184

```
cccattcctg ttaattttcc tttaagctca ggcaaacaca accctacagc tttagcagct     60

cctgtcgaag ccgggataat attc                                            84
```

<210> SEQ ID NO 185
<211> LENGTH: 106
<212> TYPE: PRT
<213> ORGANISM: Chlamydia trachomatis

<400> SEQUENCE: 185

Pro Cys Leu Gly Trp Lys Met Thr Glu Ser Tyr Val Asn Lys Glu Glu
1               5                   10                  15

Ile Ile Ser Leu Ala Lys Asn Ala Ala Leu Glu Leu Glu Asp Ala His
            20                  25                  30

Val Glu Glu Phe Val Thr Ser Met Asn Asp Val Ile Ala Leu Met Gln
        35                  40                  45

Glu Val Ile Ala Ile Asp Ile Ser Asp Ile Ile Leu Glu Ala Thr Val
    50                  55                  60

His His Phe Val Gly Pro Glu Asp Leu Arg Glu Asp Met Val Thr Ser
65                  70                  75                  80

Asp Phe Thr Gln Glu Glu Phe Leu Ser Asn Val Pro Val Ser Leu Gly
                85                  90                  95

Gly Leu Val Lys Val Pro Thr Val Ile Lys
            100                 105

<210> SEQ ID NO 186
<211> LENGTH: 321
<212> TYPE: DNA
<213> ORGANISM: Chlamydia trachomatis

<400> SEQUENCE: 186
ccatgtttag gatggaagat gacagagtca tatgtaaaca aagaagaaat catctcttta      60
gcaaagaatg ctgcattgga gttggaagat gcccacgtgg aagagttcgt aacatctatg     120
aatgacgtca ttgctttaat gcaggaagta atcgcgatag atatttcgga tatcattctt     180
gaagctacag tgcatcattt cgttggtcca gaggatctta gagaagacat ggtgacttcg     240
gattttactc aagaagaatt tttatctaac gttcccgtgt cgttgggagg attagtcaaa     300
gtccctacag ttatcaaata g                                               321

<210> SEQ ID NO 187
<211> LENGTH: 159
<212> TYPE: PRT
<213> ORGANISM: Chlamydia trachomatis

<400> SEQUENCE: 187

Arg Gln Pro Pro Phe Leu Phe Met Gly Arg Ala Asn Gln Gly Asn Tyr
1               5                   10                  15

Met Ser Glu His Val His Lys Glu Leu Leu His Leu Gly Glu Val Phe
            20                  25                  30

Arg Ser Gln Arg Glu Glu Arg Ala Leu Ser Leu Lys Asp Val Glu Ala
        35                  40                  45

Ala Thr Ser Ile Arg Leu Ser Ala Leu Glu Ala Ile Glu Ala Gly His
    50                  55                  60

Leu Gly Lys Leu Ile Ser Pro Val Tyr Ala Gln Gly Phe Met Lys Lys
65                  70                  75                  80

Tyr Ala Ala Phe Leu Asp Met Asp Gly Asp Arg Leu Leu Lys Glu His
                85                  90                  95

Pro Tyr Val Leu Lys Ile Phe Gln Glu Phe Ser Asp Gln Asn Met Asp
            100                 105                 110

Met Leu Leu Asp Leu Glu Ser Met Gly Gly Arg Asn Ser Pro Glu Lys
        115                 120                 125

Ala Ile Arg Ser Trp Leu Asn Leu Gly Trp Ala Gly Val Phe Val Val
    130                 135                 140

Gly Ala Ala Cys Ile Trp Trp Leu Gly Asn Leu Phe Asn Leu Phe

-continued 145 150 155

<210> SEQ ID NO 188
<211> LENGTH: 480
<212> TYPE: DNA
<213> ORGANISM: Chlamydia trachomatis

<400> SEQUENCE: 188
cgacagcctc ctttcctttt tatgggtaga gcaaaccagg ggaattacat gagcgaacat 60
gtccacaaag agttattaca tctaggggaa gtttttcgtt cgcaaagaga agaaagagcg 120
ctttctctaa aagatgtaga agctgccaca tctattcgtt tgtctgcatt agaggctata 180
gaagcaggac atctcgggaa attaatttct cctgtttatg cccaaggttt tatgaaaaaa 240
tacgcagctt ttttggatat ggatggggat agattgctga aagagcatcc ttatgtattg 300
aaaatttttc aggaattttc tgatcagaat atggacatgc tgcttgattt agaatccatg 360
ggaggaagaa attctcctga gaaagcgatc cgtagttggt taaatctagg ctgggctgga 420
gtcttcgtcg taggtgcagc ttgtatttgg tggctaggga atctattcaa ccttttctag 480

<210> SEQ ID NO 189
<211> LENGTH: 437
<212> TYPE: PRT
<213> ORGANISM: Chlamydia trachomatis

<400> SEQUENCE: 189

Glu Phe Val Met Lys Lys Thr Ser Val Ile Asp Thr Ser Val Leu Ile
1 5 10 15

Tyr Asp Pro Lys Ala Leu Ser Ser Phe Ser Asn Thr Arg Ile Ile Ile
20 25 30

Pro Phe Thr Val Ile Glu Glu Leu Glu Ser Cys Ala Lys Phe Arg Asp
35 40 45

Glu Ser Gly Lys Asn Ala Ser Arg Ala Leu Gly Asn Ile Arg Val Leu
50 55 60

Leu Glu Gln Ser Glu Arg Pro Ser Ser Gly Gln Ile Leu Leu Lys Asn
65 70 75 80

Gly Ser Glu Leu Cys Ile Glu Val Ser Pro Leu Val Asn Leu Ser Asn
85 90 95

His Lys Lys Gln Lys Lys His Leu Thr Leu Glu Leu Leu Gln Ile Ile
100 105 110

Ser Gln Arg Glu Ser Val Val Phe Val Thr Lys Ser Leu Gly Arg Arg
115 120 125

Val His Ala Glu Ala Leu Gly Ile Glu Ala Lys Asp Tyr Glu Asn Lys
130 135 140

Cys Val Ser Phe Gln Ser Leu Tyr Arg Gly His Arg Lys Leu Lys Val
145 150 155 160

Ala Asn Ser Thr Ile Glu Tyr Phe Tyr Lys Asp Gly Ser Ile Ala Phe
165 170 175

Pro Ser Asp Leu Ser Pro Leu Pro Ser Pro Asn Glu Tyr Phe Phe Leu
180 185 190

Ser Gly Asp Ser Asp Asn Tyr Ser Ala Val Gly Arg Tyr Ser Ser Lys
195 200 205

Asp Asn Lys Ile Leu Ser Leu Lys Pro Ala Pro Glu Lys Ile Trp Gly
210 215 220

Val Lys Pro Leu Asn Ile Glu Gln Arg Cys Ala Leu Asp Leu Leu Leu
225 230 235 240

```
Arg Asp Asp Ile Lys Leu Val Thr Leu Met Gly Gln Ala Gly Ser Gly
                245                 250                 255

Lys Thr Ile Leu Ala Leu Ala Ala Ala Met Tyr Gln Val Phe Glu Lys
            260                 265                 270

Pro Lys Tyr Asn Lys Leu Leu Val Ser Arg Pro Ile Ile Pro Met Gly
        275                 280                 285

Lys Asp Ile Gly Phe Leu Pro Gly Ile Lys Glu Ala Lys Leu Met His
    290                 295                 300

Trp Met Gln Pro Ile Tyr Asp Asn Met Glu Phe Leu Phe Asp Val Asn
305                 310                 315                 320

Asn Met Gly Asp Phe Ser Glu Thr Leu His Ser Leu Met Glu Thr Lys
                325                 330                 335

Lys Leu Glu Met Glu Ala Leu Thr Tyr Ile Arg Gly Arg Ser Leu Pro
            340                 345                 350

Lys Val Phe Met Ile Ile Asp Glu Ala Gln Asn Leu Thr Pro His Glu
        355                 360                 365

Ile Lys Thr Ile Ile Ser Arg Ala Gly Lys Gly Thr Lys Ile Val Leu
    370                 375                 380

Thr Gly Asp Pro Thr Gln Ile Asp Ser Leu Tyr Phe Asp Glu Asn Ser
385                 390                 395                 400

Asn Gly Leu Thr Tyr Leu Val Gly Lys Phe His His Leu Pro Leu Tyr
                405                 410                 415

Gly His Met Phe Met Thr Arg Thr Glu Arg Ser Glu Leu Ala Ala Ala
            420                 425                 430

Ala Ala Thr Ile Leu
        435
```

<210> SEQ ID NO 190
<211> LENGTH: 1314
<212> TYPE: DNA
<213> ORGANISM: Chlamydia trachomatis

<400> SEQUENCE: 190

```
ttaaagaata gttgcagcag ctgcagctag ttcggaacgt tccgttcggg tcataaacat      60

atgtccatac aaaggtaaat ggtgaaactt tcctactagg taggtgagac cattggaatt     120

ttcatcaaaa tatagactgt ctatttgggt aggatcgccg gttaacacaa tttttgttcc     180

tttcccggct cgagagatga ttgttttgat ttcatggggt gtgaggtttt gcgcctcgtc     240

gatgatcata aatactttag gtagagagcg tcctcggatg taagtaagcg cttccatttc     300

gagttttttt gtttccatta aactatgcaa agtttctgaa aagtcgccca tattattcac     360

atcgaataaa aattccatgt tgtcatagat cggttgcatc caatgcatga gcttcgcttc     420

ttttatacca ggaagaaatc caatgtcctt ccccatagga ataatgggtc tgctaactaa     480

gagtttgtta tatttaggtt tctcaaacac ttggtacatt gctgccgcta aggccagtat     540

tgtctttccg gatccagctt gtcccatcaa ggtcacaagt ttaatatcgt ctcttagtag     600

tagatctaga gcgcatcgtt gttctatgtt caaaggcttg acaccccaaa ttttttctgg     660

agcaggcttg agggatagga ttttgttatc tttagagcta tagcgaccaa cagcggaata     720

gttatcagag tcgccagaaa gaaaaaagta ttcgttagga gaaggtaaag gagatagatc     780

tgaagggaag gcgatagagc catccttata gaaatattca attgtgctat tcgctacctt     840

tagttttcta tgtccacggt aaagggattg gaaagatacg catttatttt catagtcttt     900

agcttcgatc cctagtgctt ccgcatggac tcgtctgcca agacttttgg ttacgaaaac     960
```

aacagactct cgttgagaaa tgatttggag tagctctagc gtgaggtgtt ttttctgttt 1020
cttgtggttt gaaagattga ctagaggaga gacttcaata cataactcgc tgccgttttt 1080
taataaaatt tgaccagaag agggtctttc cgactgctct agtaatacac gaatattgcc 1140
caatgctctg gaagcatttt tccctgattc atctcgaaac tttgcgcagg attccaattc 1200
ttcgattact gtaaaaggga taatgatgcg agtgttagaa aaagaggaaa gggccttagg 1260
atcgtaaatc aaaacgctgg tatcaataac agaggttttt ttcattacaa attc 1314

<210> SEQ ID NO 191
<211> LENGTH: 219
<212> TYPE: PRT
<213> ORGANISM: Chlamydia trachomatis

<400> SEQUENCE: 191

Lys Lys Phe Leu Ser Cys Glu Arg Glu Tyr Ser Arg Gly Ser Met Ser
1 5 10 15

Val Lys Val Ile Ser Pro Phe Ser Gln Asp Gly Val Gln Cys Phe Pro
20 25 30

Lys Leu Phe Ile Ile Ser Ala Pro Ala Gly Ala Gly Lys Thr Thr Leu
35 40 45

Thr His Met Leu Gln Arg Glu Phe Pro Asp Ala Phe Glu Lys Thr Val
50 55 60

Ser Ser Thr Thr Arg Ser Ala Arg Pro Gly Glu Val His Gly Val Asp
65 70 75 80

Tyr Leu Phe Val Ser Glu Asp Asp Phe Lys Gln Ser Leu Asp Arg Glu
85 90 95

Asp Phe Leu Glu Trp Val Phe Leu Phe Gly Thr Tyr Tyr Gly Thr Ser
100 105 110

Lys Ala Glu Ile Ser Arg Val Leu Gln Lys Gly Lys His Cys Ile Ala
115 120 125

Val Ile Asp Val Gln Gly Ala Leu Ala Leu Lys Lys Gln Met Pro Ala
130 135 140

Val Thr Ile Phe Ile Gln Ala Pro Ser Gln Glu Glu Leu Glu Arg Arg
145 150 155 160

Leu Asn Ala Arg Asp Ser Glu Lys Asp Phe Gln Lys Lys Glu Arg Leu
165 170 175

Glu His Ser Ala Val Glu Ile Ala Ala Ala Ser Glu Phe Asp Tyr Val
180 185 190

Val Val Asn Asp Asp Leu Ile Thr Ala Tyr Gln Val Leu Arg Ser Ile
195 200 205

Phe Ile Ala Glu Glu His Arg Met Ser His Gly
210 215

<210> SEQ ID NO 192
<211> LENGTH: 660
<212> TYPE: DNA
<213> ORGANISM: Chlamydia trachomatis

<400> SEQUENCE: 192
aaaaagtttc tctcctgtga aagagagtat tcaagaggga gtatgtcagt aaaggttatt 60
tccccctttt ctcaagacgg ggttcaatgc tttcccaagc tttttatcat tagcgctcct 120
gctggagcag ggaagacaac actcacccat atgctacaaa gagagtttcc tgatgcattt 180
gagaagacgg tgtcgtcaac gacacgttcg gctcgtccag gcgaagtgca tggcgtggat 240
tatttgtttg tatctgaaga tgactttaag caatctttag atagggaaga ttttttggaa 300

```
tgggtctttt tatttgggac ttattacgga acgagtaagg cggagatttc tagagttctg    360

caaaagggta agcactgtat agccgtgatt gatgtacaag gagctttggc tctgaagaag    420

caaatgccgg cagtcactat ttttattcaa gctccctctc aagaagaact tgagcgccgt    480

ttgaatgctc gggattcaga gaaagatttc cagaagaaag aaagattaga gcatagcgct    540

gtcgaaattg ctgccgctag cgaatttgat tatgttgtgg ttaatgatga tttgattaca    600

gcatatcaag ttttaagaag tatttttata gctgaagaac ataggatgag tcatggctag    660


<210> SEQ ID NO 193
<211> LENGTH: 242
<212> TYPE: PRT
<213> ORGANISM: Chlamydia trachomatis

<400> SEQUENCE: 193

Asn Thr Leu Val Ala Met Ala Leu Tyr Leu Leu Pro Asn Thr Leu Gly
1               5                   10                  15

Ser Lys Arg Ser Glu Asp Leu Pro Phe Ser Val Gly Glu Ile Val Arg
            20                  25                  30

Asn Lys Ile Gln Gly Leu Ile Val Glu Ser Asp Arg Gly Gly Arg Leu
        35                  40                  45

Phe Leu Ser Leu Trp Lys Val Glu Glu Pro His Arg Phe Pro Leu Ala
    50                  55                  60

Val Met Ser Lys Asn Asp Thr Ser Val Lys Ala Cys Asp Phe Tyr Leu
65                  70                  75                  80

Glu Pro Ile Leu Lys Lys Gln Glu Ser Trp Gly Val Ile Ser Asp Ala
                85                  90                  95

Gly Leu Pro Cys Ile Ala Asp Pro Gly Ala Lys Leu Val Arg Arg Ala
            100                 105                 110

Arg Thr Leu Gly Ile Pro Val His Ala Val Ser Gly Pro Cys Ser Ile
        115                 120                 125

Thr Gln Ala Leu Met Leu Ser Gly Leu Pro Gly Gln Asn Phe Thr Phe
    130                 135                 140

His Gly Tyr Leu Pro Gln Asn Pro Lys Glu Arg Ser Arg Tyr Leu Arg
145                 150                 155                 160

Ser Cys Ser Gly Lys Ser His Thr Gln Ile Cys Ile Glu Thr Pro Tyr
                165                 170                 175

Arg Asn Pro Tyr Thr Phe Asp Ala Leu Leu Asp Gln Leu Pro Asp His
            180                 185                 190

Gly Glu Leu Cys Val Ala Ile Asp Leu Met Gly Asp Gln Glu Tyr Val
        195                 200                 205

Ser Met Arg Ser Ile Ala Val Trp Asn Gln Ser Ser Asp Ile Glu Glu
    210                 215                 220

Val Cys Glu Arg Leu Lys Lys Val Pro Ala Ile Phe Leu Phe Ile Thr
225                 230                 235                 240

Ser Phe


<210> SEQ ID NO 194
<211> LENGTH: 729
<212> TYPE: DNA
<213> ORGANISM: Chlamydia trachomatis

<400> SEQUENCE: 194

aatacacttg tggctatggc gctgtatctt cttcccaata ctttaggtag taaaagatct     60

gaggaccttc ctttttcggt tggagagatt gttcggaata aaatccaggg attaatagta    120
```

```
gaaagtgatc gtggtgggcg gttattctta agtttatgga aagtagaaga gcctcatagg    180

tttcctcttg ccgtgatgag caagaatgac acttctgtta aggcttgtga cttttattta    240

gagcctattc tcaagaagca agagtcttgg ggcgtcattt ctgatgcagg gttgccttgt    300

attgctgatc ctggggctaa gttagtccga agagctcgga cattggggat tcccgtgcat    360

gctgtatctg gcccttgctc gattacgcaa gcgttgatgc tctctggact accagggcaa    420

aatttcacat ttcatggtta tttgccccaa aatcctaaag aaagatctcg ttatttgcga    480

agttgctccg ggaaatccca tacgcaaatc tgtatagaga ctccgtaccg taatccatat    540

acgtttgatg cgttattaga tcagcttccg gatcatggcg agctttgtgt tgcgattgat    600

ttaatgggag atcaagaata cgtttctatg cgaagcatag ccgtatggaa tcaatcttct    660

gatatcgaag aggtttgtga gcgtttgaaa aaagttccag ctatttttct atttattact    720

tctttttga                                                            729
```

```
<210> SEQ ID NO 195
<211> LENGTH: 260
<212> TYPE: PRT
<213> ORGANISM: Chlamydia trachomatis

<400> SEQUENCE: 195

Phe Val Lys Glu Ile Phe Phe Val Lys Thr His Asp Leu Ala Asp Thr
1               5                   10                  15

Trp Gln Leu Tyr Trp Ser Thr Lys Glu Ile His His Arg Asp Val Leu
            20                  25                  30

Ile Glu Ser Tyr Leu Pro Leu Val Lys Asn Val Ala His Arg Leu Ala
        35                  40                  45

Ser Gly Met Pro Ser His Val Lys Met Glu Asp Leu Tyr Ala Leu Gly
    50                  55                  60

Val Glu Gly Leu Ile Arg Ala Val Glu Arg Phe Asp Pro Glu Lys Ser
65                  70                  75                  80

Lys Arg Phe Glu Ser Tyr Ala Leu Phe Ile Ile Lys Ala Ala Ile Ile
                85                  90                  95

Asp Gly Leu Arg Lys Gln Asp Trp Val Pro Arg Ser Val Tyr Gln Arg
            100                 105                 110

Ala Asn Arg Leu Ala Asp Ala Met Asp Ser Leu Arg Gln Thr Leu Gly
        115                 120                 125

Lys Glu Pro Thr Asp Gly Glu Leu Cys Glu Tyr Leu Asn Ile Ser Gln
    130                 135                 140

Gln Glu Leu Ser His Trp Phe Ser Ser Ser Arg Pro Ala Leu Val Leu
145                 150                 155                 160

Ser Leu His Asp Asp Phe Ser Cys Gln Asp Asp Asp Glu Gly Leu Ala
                165                 170                 175

Leu Glu Glu Arg Ile Ala Asp Glu Arg Ala Glu Thr Gly Tyr Asp Val
            180                 185                 190

Ile Arg Lys Lys Glu Ala Ile Ser Ile Leu Thr Glu Ala Leu Leu Ala
        195                 200                 205

Leu Asp Glu Lys Glu Arg Gln Val Met Ala Leu Tyr Tyr Tyr Asp Asp
    210                 215                 220

Leu Val Leu Lys Glu Ile Gly Lys Ile Leu Gly Val Ser Glu Ser Arg
225                 230                 235                 240

Val Ser Gln Ile His Ser Lys Ala Leu Leu Lys Leu Arg Gly Thr Leu
                245                 250                 255
```

```
Ser Ser Leu Leu
            260


<210> SEQ ID NO 196
<211> LENGTH: 783
<212> TYPE: DNA
<213> ORGANISM: Chlamydia trachomatis

<400> SEQUENCE: 196

tttgtaaaag aaattttttt tgtgaagact cacgatctcg cagatacttg gcagctatat     60

tggtcgacaa aagaaatcca tcatagggat gttttgatcg aatcctacct tcctttagta    120

aagaatgtag cgcatcggct tgcttcagga atgccttctc atgtaaagat ggaagatctt    180

tatgctctgg gggttgaagg gttgattcgt gctgtcgaac gttttgatcc agaaaaaagc    240

aagcgattcg agagctatgc tctttttatc ataaaagctg cgattattga tggattgcgc    300

aaacaggatt gggtaccacg cagtgtttat caaagagcca atcgattagc tgatgcgatg    360

gattctttga gacagacttt aggtaaagaa cctactgatg gagaactttg tgagtatcta    420

aatatttcac aacaagagtt atcccattgg ttttcctcct ctagacctgc tctagttctt    480

tctttacatg atgatttctc ctgccaagat gacgatgagg ggcttgcttt agaagagcgc    540

atagcagatg agcgagcgga aaccggatac gatgtcatca gaaaaaaaga agctatttct    600

attttgacag aagctttgct ggctcttgat gaaaaagagc ggcaggttat ggctctttat    660

tactatgatg acttggtatt aaaagaaatt gggaagattt taggagtgag cgagtcccga    720

gtttctcaga tacactccaa agctttattg aagttacgag gtacattgtc cagtctgctt    780

tag                                                                  783


<210> SEQ ID NO 197
<211> LENGTH: 483
<212> TYPE: PRT
<213> ORGANISM: Chlamydia trachomatis

<400> SEQUENCE: 197

Glu Gly Ser Val Ala Pro Asn Thr Asp Ile Gly Leu Ile Gly Leu Ala
1               5                   10                  15

Val Met Gly Lys Asn Leu Val Leu Asn Met Val Asp His Gly Phe Ser
            20                  25                  30

Val Ser Val Tyr Asn Arg Ser Pro Ala Lys Thr Glu Glu Phe Leu Lys
        35                  40                  45

Asp His Gly Glu Ser Gly Ala Leu Gln Gly Phe Thr Thr Ile Gln Glu
    50                  55                  60

Phe Val Gln Ser Leu Lys Arg Pro Arg Lys Ile Met Ile Met Ile Lys
65                  70                  75                  80

Ala Gly Ala Pro Val Asp Glu Met Ile Ala Ser Leu Leu Pro Phe Leu
                85                  90                  95

Glu Glu Gly Asp Ile Leu Ile Asp Gly Gly Asn Ser Tyr Tyr Leu Asp
            100                 105                 110

Ser Glu Gln Arg Tyr Val Asp Leu Lys Lys Glu Gly Ile Leu Phe Val
        115                 120                 125

Gly Met Gly Val Ser Gly Gly Glu Glu Gly Ala Arg Lys Gly Pro Ser
    130                 135                 140

Ile Met Pro Gly Gly Asn Ile Asp Ala Trp Pro Ala Ile Ala Pro Ile
145                 150                 155                 160

Phe Gln Ser Ile Ala Ala Gln Val Asp Gly Arg Pro Cys Cys Ser Trp
                165                 170                 175
```

```
Ile Gly Thr Gly Gly Ala Gly His Phe Val Lys Ala Val His Asn Gly
            180                 185                 190

Ile Glu Tyr Gly Asp Ile Gln Leu Ile Cys Glu Thr Tyr Glu Ile Leu
        195                 200                 205

Lys Thr Arg Leu Asn Leu Ser Leu Glu Gln Ile Gly Asn Ile Phe Phe
    210                 215                 220

Glu Trp Asn Gln Thr Asp Leu Asn Ser Tyr Leu Ile Gly Ala Ala Ala
225                 230                 235                 240

Ala Val Leu Ile Ala Lys Asp Glu Asn Gly Asn Ala Ile Ala Ser Thr
                245                 250                 255

Ile Leu Asp Val Ala Gly Gln Lys Gly Thr Gly Arg Trp Val Ala Glu
            260                 265                 270

Asp Ala Ile Lys Ala Gly Val Pro Met Ser Leu Ile Ile Glu Ser Val
        275                 280                 285

Leu Ala Arg Tyr Leu Ser Thr Trp Lys Glu Val Arg Thr Lys Ala Ala
    290                 295                 300

Gln Glu Phe Pro Gly Ile Pro Leu Leu Cys Gln Pro Pro Gln Glu Ala
305                 310                 315                 320

Ser Ala Phe Ile Glu Asp Val Arg Glu Ala Leu Tyr Ala Ala Lys Ile
                325                 330                 335

Ile Ser Tyr Ala Gln Gly Phe Met Leu Leu Lys Gln Val Ser Gln Asp
            340                 345                 350

Lys Gly Trp Asp Leu Asn Leu Gly Glu Leu Ala Leu Ile Trp Arg Gly
        355                 360                 365

Gly Cys Ile Ile Gln Ser Ala Phe Leu Asp Lys Ile His Gln Gly Phe
    370                 375                 380

Glu Asn Ser Pro Glu Ala His Ser Leu Ile Leu Gln Asp Tyr Phe Lys
385                 390                 395                 400

Lys Val Leu Phe Asp Ser Glu Thr Gly Phe Arg Arg Ala Val Leu His
                405                 410                 415

Ala Ile Gly Ser Gly Val Ala Ile Pro Cys Leu Ser Ser Ala Leu Ser
            420                 425                 430

Phe Tyr Asp Gly Tyr Arg Thr Val Asp Ser Ser Leu Phe Leu Val Gln
        435                 440                 445

Gly Leu Arg Asp Tyr Phe Gly Ala His Gly Tyr Glu Arg Arg Asp Cys
    450                 455                 460

Pro Arg Gly Glu Phe Tyr His Thr Asp Trp Leu Glu Thr Lys Lys Thr
465                 470                 475                 480

Phe Arg Val


<210> SEQ ID NO 198
<211> LENGTH: 1452
<212> TYPE: DNA
<213> ORGANISM: Chlamydia trachomatis

<400> SEQUENCE: 198

gaggggtctg tggctccaaa tacagatatt gggttgattg gtttggccgt gatgggcaaa      60

aaccttgtat tgaacatggt ggatcatggt ttttctgttt ctgtctataa ccgaagtccg     120

gcgaaaacag aagagttctt gaaagatcat ggagagagtg gagctctgca aggatttact     180

acgattcaag agtttgttca atctttgaag cgtcctcgta agatcatgat catgattaaa     240

gcgggagctc ctgttgatga aatgattgcc tccctgcttc ctttcttgga agagggagat     300

attctcatcg atgggggaa tagctattat ttagattctg agcaacgcta tgtcgacctg     360
```

```
aaaaaagaag gaattctatt tgttgggatg ggagtctctg gaggggaaga gggggctaga    420

aaagggcctt ccattatgcc cggagggaat atagatgctt ggcctgcaat cgctcctatc    480

tttcaatcca tagctgctca ggtggatgga cgaccctgtt gctcttggat tggcacagga    540

ggtgcagggc attttgttaa ggctgttcac aatgggatcg aatacgggga tatccagtta    600

atttgtgaaa catatgagat tcttaagact cgtcttaatc tctctttaga gcagataggg    660

aatatctttt ttgaatggaa tcaaaccgat ctgaatagct acctcattgg agcagcagcg    720

gccgttttaa tagcaaaaga tgagaatggc aatgcgattg cttctacgat tcttgatgtt    780

gctggacaga aggggactgg gcgttgggtc gcagaggacg ctattaaggc aggcgttcct    840

atgtccctaa ttattgaatc ggtcttagct cgataccttt cgacttggaa agaagtgcgc    900

acaaaggcag ctcaagagtt tccagggatt cctcttctct gtcaacctcc acaagaagct    960

tctgccttca ttgaggatgt gcgagaggct ttgtatgcag ctaagattat cagttacgct   1020

caaggattta tgctgctgaa gcaggtctct caagataaag gatgggatct gaatttaggt   1080

gagttagctt tgatatggcg tggggggttgc attatacaaa gtgccttttt agataaaatt   1140

catcaaggtt ttgaaaatag tccagaagca cactctttga tattacaaga ttattttaaa   1200

aaggttctgt ttgattcaga aacaggtttc cggcgagctg ttttgcatgc tatcggatct   1260

ggtgtagcta ttccttgctt atcttctgca ctatcttttt atgatggata tcgtacggtg   1320

gattcatctt tattcttagt gcaaggatta agagattact ttggagctca tggttatgag   1380

cgtcgagact gtcctcgagg ggagttttat catacggatt ggctagaaac caagaaaact   1440

tttagagtat aa                                                       1452
```

<210> SEQ ID NO 199
<211> LENGTH: 307
<212> TYPE: PRT
<213> ORGANISM: Chlamydia trachomatis

<400> SEQUENCE: 199

```
Glu Arg Leu Phe Leu Ala Leu Arg Ala Asp Lys Arg Phe Val Ser Leu
1               5                   10                  15

Ser Leu Leu Tyr Ile Ala Ile Met Ser Val Ile Thr Ile Leu Ala Arg
            20                  25                  30

Ser Ser Thr Met Phe Ala Gln Leu Gln Lys Asn Trp Glu Gly Leu Phe
        35                  40                  45

Leu Asn Arg Asp Asn Ala Ile Ala Trp Ser Val Glu Asp Leu Cys Val
    50                  55                  60

Asn Tyr Asp His Ser Asp Val Leu Cys His Ile Thr Phe Ser Leu Pro
65                  70                  75                  80

Ala Gly Ala Met Ala Ala Ile Ile Gly Pro Asn Gly Ala Gly Lys Ser
                85                  90                  95

Thr Leu Leu Lys Ala Ser Leu Gly Leu Ile Arg Ala Ser Ser Gly Gln
            100                 105                 110

Ser Leu Phe Phe Gly Gln Arg Phe Ser Lys Val His His Arg Ile Ala
        115                 120                 125

Tyr Met Pro Gln Arg Ala Ser Val Asp Trp Asp Phe Pro Met Thr Val
    130                 135                 140

Leu Asp Leu Val Leu Met Gly Cys Tyr Gly Tyr Lys Gly Ile Trp Asn
145                 150                 155                 160

Arg Ile Ser Thr Asp Asp Arg Gln Glu Ala Met Arg Ile Leu Glu Arg
                165                 170                 175
```

```
Val Gly Leu Glu Ala Phe Ala Asn Arg Gln Ile Gly Lys Leu Ser Gly
            180                 185                 190

Gly Gln Gln Gln Arg Ala Phe Leu Ala Arg Ser Leu Met Gln Lys Ala
        195                 200                 205

Asp Leu Tyr Leu Met Asp Glu Leu Phe Ser Ala Ile Asp Met Ala Ser
    210                 215                 220

Tyr Gln Met Val Val Asp Val Leu Gln Glu Leu Lys Ser Glu Gly Lys
225                 230                 235                 240

Thr Ile Val Val Ile His His Asp Leu Ser Asn Val Arg Lys Leu Phe
                245                 250                 255

Asp His Val Ile Leu Leu Asn Lys His Leu Val Cys Ser Gly Ser Val
            260                 265                 270

Glu Glu Cys Leu Thr Lys Glu Ala Ile Phe Gln Ala Tyr Gly Cys Glu
        275                 280                 285

Leu Glu Leu Leu Asp Tyr Thr Leu Lys Leu Ser Arg Gly Lys Tyr Gln
    290                 295                 300

Gly Ser Cys
305
```

<210> SEQ ID NO 200
<211> LENGTH: 924
<212> TYPE: DNA
<213> ORGANISM: Chlamydia trachomatis

<400> SEQUENCE: 200

```
gaaagattgt ttcttgctct aagagcggac aaaagattcg tctcgctaag tctcctttat      60

atagcgataa tgtctgtgat aactatttta gcacgttcca gcacaatgtt cgcacaatta     120

cagaagaatt gggagggact gttcttgaat agagataatg caattgcttg gtccgtagag     180

gatctttgtg ttaattatga tcactcagac gtcttatgtc acattacttt ttctctgcct     240

gcaggggcaa tggctgctat tattgggccg aatggagctg gtaaaagtac tttgcttaag     300

gcttctttag gactgattcg tgcttcttct ggccaaagct tgttctttgg tcagagattt     360

tccaaggtac atcatagaat agcctatatg cctcaaagag cgagtgtgga ttgggatttc     420

ccaatgactg ttcttgatct cgtgttgatg ggtgttacg  gctataaagg aatatggaat     480

cgtatttcca ctgatgatcg tcaggaggct atgcgtattt tagagcgggt tggtttggaa     540

gcttttgcaa atcgtcaaat aggtaagctc tctggaggac aacaacagag agcttttta      600

gcgcggtcat taatgcaaaa agcagatttg tatctcatgg atgagctgtt ctctgcgatc     660

gatatggcct cttatcagat ggttgtagat gttttgcaag agcttaaaag cgaagggaag     720

actattgtgg tcattcatca tgatttgagt aatgtccgga agctttttga tcatgtgatt     780

ttattaaata agcatcttgt gtgctctgga agcgtagaag aatgcttgac taaagaagcc     840

atttttcagg cttatgggtg tgaacttgag cttttggatt acacactcaa attgtctaga     900

ggcaagtacc aaggatcgtg ctag                                            924
```

<210> SEQ ID NO 201
<211> LENGTH: 389
<212> TYPE: PRT
<213> ORGANISM: Chlamydia trachomatis

<400> SEQUENCE: 201

```
Val Arg Gln Cys Arg Glu Tyr Glu Val Leu Leu Lys His Leu Ala Leu
1               5                   10                  15
```

```
Ile Gly Ser Thr Gly Ser Ile Gly Arg Gln Val Leu Gln Val Val Arg
            20                  25                  30

Ser Ile Pro Asp Thr Phe Ile Ile Glu Thr Leu Ala Ala Tyr Gly Arg
        35                  40                  45

Asn Gln Glu Ala Leu Ile Ser Gln Ile Arg Glu Phe Asn Pro Arg Val
    50                  55                  60

Val Ala Val Arg Glu Glu Thr Thr Tyr Lys Glu Leu Arg Lys Leu Phe
65                  70                  75                  80

Pro His Ile Glu Ile Leu Leu Gly Glu Glu Gly Leu Val Ser Val Ala
                85                  90                  95

Thr Glu Pro Ser Val Thr Met Thr Ile Val Ala Ser Ser Gly Ile Asp
            100                 105                 110

Ala Leu Pro Ala Val Ile Ala Ala Ile Arg Gln Lys Lys Thr Ile Ala
        115                 120                 125

Leu Ala Asn Lys Glu Ser Leu Val Ala Ala Gly Glu Leu Val Thr Thr
    130                 135                 140

Leu Ala Arg Glu Asn Gly Val Gln Ile Leu Pro Ile Asp Ser Glu His
145                 150                 155                 160

Asn Ala Leu Phe Gln Cys Leu Glu Gly Arg Asp Ser Ser Thr Ile Lys
                165                 170                 175

Lys Leu Leu Leu Thr Ala Ser Gly Gly Pro Leu Arg Asn Lys Ser Lys
            180                 185                 190

Glu Glu Leu Gln Lys Val Ser Leu Gln Glu Val Leu Arg His Pro Val
        195                 200                 205

Trp Asn Met Gly Pro Lys Ile Thr Val Asp Ser Ser Thr Leu Val Asn
    210                 215                 220

Lys Gly Leu Glu Ile Ile Glu Ala Phe Trp Leu Phe Gly Leu Glu Ala
225                 230                 235                 240

Val Glu Ile Glu Ala Val Ile His Pro Gln Ser Leu Val His Gly Met
                245                 250                 255

Val Glu Phe Cys Asp Gly Thr Ile Leu Ser Val Met Asn Pro Pro Ser
            260                 265                 270

Met Leu Phe Pro Ile Gln His Val Leu Thr Phe Pro Glu Arg Ser Pro
        275                 280                 285

Ala Ile Gly Pro Gly Phe Asp Phe Leu Ser Asn Arg Thr Leu Glu Phe
    290                 295                 300

Phe Pro Ile Asp Glu Asp Arg Phe Pro Ser Val His Leu Ala Lys Arg
305                 310                 315                 320

Val Leu Leu Glu Lys Gly Ser Met Gly Cys Phe Phe Asn Gly Ala Asn
                325                 330                 335

Glu Ala Leu Val His Arg Phe Leu Ala Gly Glu Ile Ser Trp His Gln
            340                 345                 350

Ile Val Pro Lys Leu Gln Ala Leu Val Asp Gln His Arg Val Gln Ser
        355                 360                 365

Cys Leu Ser Leu Glu Glu Ile Leu Ser Val Asp Ala Glu Ala Arg Ala
    370                 375                 380

Arg Ala Gln Glu Cys
385
```

<210> SEQ ID NO 202
<211> LENGTH: 1170
<212> TYPE: DNA
<213> ORGANISM: Chlamydia trachomatis

<400> SEQUENCE: 202

```
gtaaggcaat gtagagaata cgaggttctt ttgaagcatt tagcactgat agggtcaaca     60

gggagtattg gtagacaggt tttacaagta gttcgttcta ttcccgatac ttttattata    120

gaaactcttg ctgcgtatgg acggaatcaa gaagcattga tttctcagat tagagagttt    180

aatcctcgcg tggtagccgt tcgtgaagaa acaacttaca aggagctccg taagttattc    240

cctcatattg agattctttt aggagaagag gggttagttt ctgttgctac agaaccttct    300

gtaacaatga ccattgtagc ttcgtctggt atagatgctt taccagcagt cattgcagct    360

atccgacaga aaaagacaat agctttggct aataaagagt cgttagtggc agctggagag    420

ttggttacca ctttggctag agagaatggt gtgcagattc ttcccatcga tagtgaacat    480

aacgcacttt tccagtgctt agaaggaaga gactcttcta ccattaaaaa attattgtta    540

acagcttctg gagggccgtt aaggaataaa tcaaaagaag aattacaaaa ggtctcttta    600

caagaggtct tgcgacaccc tgtttggaat atggggccca aaattacagt agattcttct    660

accttagtaa ataaaggctt agaaattata gaagctttct ggctatttgg gctggaagct    720

gtagagatag aggcggtgat ccatcctcaa agtcttgttc atggaatggt ggagttttgt    780

gatggaacga tcctttctgt gatgaatcct cccagtatgc tatttccaat acaacatgtt    840

ttgactttcc cagaacgtag ccctgcaata ggtccaggat tcgattttct ttcaaatcgc    900

actctagagt ttttcccgat agatgaagat agattcccta gtgttcatct agcaaagcga    960

gtgcttcttg aaaaggggtc tatggggtgt tttttcaatg gcgccaatga ggctttggtt   1020

catcgatttt tagcaggcga gatttcttgg catcaaatag ttcctaaatt acaagctctt   1080

gtggatcagc atcgcgtgca atcctgttta tccctggaag aaattctatc ggtagatgct   1140

gaggccagag ctcgtgctca agagtgttaa                                    1170
```

```
<210> SEQ ID NO 203
<211> LENGTH: 148
<212> TYPE: PRT
<213> ORGANISM: Chlamydia trachomatis

<400> SEQUENCE: 203

Ser Leu Ser Ile Val Arg Phe Met Thr Lys Val Tyr Ala Asn Ser Ile
1               5                   10                  15

Gln Gln Glu Arg Val Val Asp Arg Ile Ala Leu Leu Glu Arg Cys Leu
            20                  25                  30

Asp Pro Ser Asn Ser Leu Pro Thr Ala Lys Arg Leu Val Ala Val Ala
        35                  40                  45

Val Ala Thr Ile Leu Ala Val Ala Leu Leu Val Val Ala Gly Leu Leu
    50                  55                  60

Phe Ser Gly Val Leu Cys Ser Pro Val Ser Val Leu Ala Ala Ser Leu
65                  70                  75                  80

Phe Phe Gly Val Gly Ala Phe Leu Leu Gly Gly Ala Leu Val Gly Gly
                85                  90                  95

Val Leu Thr Thr Glu Ala Val Thr Arg Glu Arg Leu His Arg Ser Gln
            100                 105                 110

Thr Leu Met Trp Asn Asn Leu Cys Cys Lys Thr Ala Glu Val Glu Gln
        115                 120                 125

Lys Ile Ser Thr Ala Ser Ala Asn Ala Lys Ser Asn Asp Lys Thr Arg
    130                 135                 140

Lys Leu Gly Glu
145
```

<210> SEQ ID NO 204
<211> LENGTH: 447
<212> TYPE: DNA
<213> ORGANISM: Chlamydia trachomatis

<400> SEQUENCE: 204

```
agtctgtcga tagtgaggtt tatgactaag gtttatgcga atagcattca gcaagagaga     60

gttgtggata ggatagctct tttagagaga tgcttagacc cgagtaattc attgccgaca    120

gcgaaaagat tggtggcagt tgctgtggcc actatattgg ccgtcgctct tctagttgtt    180

gcgggcttgt tgttctctgg agtgctctgt agccctgttt ctgttttagc ggcatcttta    240

ttcttcgggg taggagcttt ccttttagga ggagctttgg ttggaggagt gctgactaca    300

gaagctgtga ctagagagcg gttgcatcga tcacaaactt tgatgtggaa caacttatgc    360

tgtaaaacag cagaggttga gcagaaaatc tcgacagcta gtgcaaatgc caaaagcaat    420

gataagactc gaaaactcgg tgagtaa                                        447
```

<210> SEQ ID NO 205
<211> LENGTH: 249
<212> TYPE: PRT
<213> ORGANISM: Chlamydia trachomatis

<400> SEQUENCE: 205

```
Pro Asn Gly Glu Met Met Lys Lys Arg Val Lys Arg Val Leu Phe Lys
1               5                   10                  15

Ile Ser Gly Glu Ala Leu Ser Asp Gly Asp Ser Ser Asn Arg Ile Ser
            20                  25                  30

Glu Glu Arg Leu Ser Arg Leu Ile Ala Glu Leu Lys Val Val Arg Asn
        35                  40                  45

Ala Asp Val Glu Val Ala Leu Val Ile Gly Gly Gly Asn Ile Leu Arg
    50                  55                  60

Gly Leu Ser Gln Ser Gln Ser Leu Gln Ile Asn Arg Val Ser Ala Asp
65                  70                  75                  80

Gln Met Gly Met Leu Ala Thr Leu Ile Asn Gly Met Ala Leu Ala Asp
                85                  90                  95

Ala Leu Lys Thr Glu Asp Val Pro Asn Leu Leu Thr Ser Thr Leu Ser
            100                 105                 110

Cys Pro Gln Leu Ala Glu Leu Tyr Asn Pro Gln Lys Ala Ser Asp Ala
        115                 120                 125

Leu Ser Gln Gly Lys Val Val Ile Cys Thr Met Gly Ala Gly Ala Pro
    130                 135                 140

Tyr Leu Thr Thr Asp Thr Gly Ala Ala Leu Arg Ala Cys Glu Leu Lys
145                 150                 155                 160

Val Asp Val Leu Leu Lys Ala Thr Met His Val Asp Gly Val Tyr Asp
                165                 170                 175

Gln Asp Pro Arg Glu Cys Ala Asp Ala Val Arg Tyr Asp His Ile Ser
            180                 185                 190

Tyr Arg Asp Phe Leu Ser Gln Gly Leu Gly Ala Ile Asp Pro Ala Ala
        195                 200                 205

Ile Ser Leu Cys Met Glu Ala Gly Ile Pro Ile Lys Met Phe Ser Phe
    210                 215                 220

Ala Arg His Ser Leu Glu Glu Ala Val Phe Asn Thr Val Gly Thr Val
225                 230                 235                 240

Ile Ser Ser Thr Glu Gly Gly Gln Leu
                245
```

<210> SEQ ID NO 206
<211> LENGTH: 750
<212> TYPE: DNA
<213> ORGANISM: Chlamydia trachomatis

<400> SEQUENCE: 206
tcataattgt cctccttccg tagaagatat cactgtacca acagtattaa agactgcctc 60
ctctaaagaa tgtctagcaa agctaaacat ctttatgggg attcctgctt ccatacacaa 120
agatatggct gccggatcga tcgctcccaa tccttgggag agaaagtctc tgtaagaaat 180
atgatcgtac cttactgcat cagcgcattc acgaggatct tggtcataca ccccatccac 240
gtgcatagtc gcttttagta aaacatcgac ctttaattca caggctcgca aagctgcacc 300
tgtgtccgtt gttagataag gagctcctgc tcccatggtg catatcacaa ctttaccctg 360
gcttagggcg tcagatgctt tttgcggatt gtataactct gctaactgtg ggcatgacaa 420
agtcgatgtc aataaattgg gcacatcctc agtcttcaaa gcatccgcta gcgccattcc 480
attaatcaat gtcgctaaca ttcccatctg atcagccgaa acccgattaa tctgcaggct 540
ctggctttgt gagaggccgc ggaggatatt gcccccaccg attaccagcg caacctcaac 600
atctgcattg cggacgactt ttaattccgc aattaatcgg gagagtcttt cttcactaat 660
tctattgcta gaatctccat cagaaagagc ctctccagag atcttgaata aaactcgttt 720
cactcgtttt ttcatcatct cgccatttgg 750

<210> SEQ ID NO 207
<211> LENGTH: 246
<212> TYPE: PRT
<213> ORGANISM: Chlamydia trachomatis

<400> SEQUENCE: 207

Ser Asn Glu Gln Arg Ser Glu Val Pro Cys Leu Leu Ala Leu Pro Lys
1 5 10 15

Asp Pro Tyr Leu Val Arg Arg Met Lys Phe Phe Ser Leu Ile Tyr Lys
20 25 30

Asp Gln Glu Val Val Pro Asn Lys Lys Val Leu Ser Pro Asp Ala Tyr
35 40 45

Thr Ala Val Leu Thr Ala Gln Glu Leu Leu Glu Lys Thr Gln Glu Asp
50 55 60

Cys Glu Ala Tyr Thr Gln Asn Thr His Glu Glu Cys Ala Lys Leu Arg
65 70 75 80

Glu Glu Ala Lys Asn Gln Gly Phe Gln Glu Gly Ser Lys Ala Trp Ser
85 90 95

Lys Gln Leu Ala Phe Leu Ile Thr Glu Thr Gln Ala Met Arg Glu Gln
100 105 110

Ile Lys Ala Ser Leu Val Pro Leu Ala Ile Ala Ser Ile Lys Lys Ile
115 120 125

Ile Gly Lys Glu Leu Glu Thr Lys Pro Glu Thr Val Val Ser Ile Ile
130 135 140

Ser Glu Ser Leu Lys Asp Leu Thr Gln Asn Lys Arg Ile Val Ile His
145 150 155 160

Ile Asn Pro Gln Asp Leu Ala Ile Val Glu Gln His Arg Pro Glu Leu
165 170 175

Lys Lys Leu Val Glu Tyr Ala Asp Val Leu Leu Leu Ser Pro Lys Ala
180 185 190

-continued

```
Ser Val Ser Pro Gly Gly Cys Ile Ile Glu Thr Glu Thr Gly Ile Val
        195                 200                 205

Asn Ala Gln Leu Asp Val Gln Leu Ala Ala Leu Glu Gln Ala Phe Ser
    210                 215                 220

Ala Ile Leu Lys His Lys Lys Pro Ala Asp Ala Ser Thr Ile Asp Gln
225                 230                 235                 240

Pro Gln Ser Lys Lys Asp
                245
```

<210> SEQ ID NO 208
<211> LENGTH: 741
<212> TYPE: DNA
<213> ORGANISM: Chlamydia trachomatis

<400> SEQUENCE: 208

```
agtaacgagc aaaggagcga ggttccctgc ctgttggctt tgccaaagga tccctacctc      60

gtcagaagga tgaaattttt cagtttaata tataaagacc aagaggtcgt ccctaataaa     120

aaagttctct ccccagacgc ctatactgcg gtgttaactg cccaagaact tctggagaaa     180

acacaagaag attgtgaagc ttatacacag aatactcatg aagaatgcgc aaagctaagg     240

gaagaggcta agaatcaagg cttccaggaa ggaagcaaag cttggagcaa acagctcgcc     300

tttcttatta cagaaacaca agcgatgcga gaacagatta aagcctccct cgtgccttta     360

gcgattgcta gcatcaaaaa gatcatcggc aaagaattag aaactaaacc agaaactgtg     420

gtttctatca tttcagagtc tttaaaagac ctcacgcaga ataaacggat tgtcatccac     480

atcaatcctc aggatctcgc cattgtcgaa caacatcgtc ctgagttaaa aaaactcgtg     540

gaatatgcag atgtgctttt actctctccc aaagccagtg tatcccctgg aggttgtatc     600

attgaaacag agaccggaat tgtaaatgct cagcttgatg tgcaactcgc tgccctggaa     660

caagctttct ctgccatcct aaaacataaa aaacctgcgg acgcctctac aatagatcag     720

cctcaaagca agaaagacta g                                               741
```

<210> SEQ ID NO 209
<211> LENGTH: 254
<212> TYPE: PRT
<213> ORGANISM: Chlamydia trachomatis

<400> SEQUENCE: 209

```
Lys Lys Asn Gln Phe Ala Ile Lys Gln Leu Lys Lys Val Arg Ile Ser
1               5                   10                  15

Met Asn Ile Ser Gly Ser Ile Lys Gln Lys Leu Leu Gln Phe Leu Lys
            20                  25                  30

Lys Gln Lys Ser Pro Glu Leu Leu Ala Thr Tyr Leu Phe Tyr Leu Glu
        35                  40                  45

Gln Ser Leu His Leu Ser Pro Val Val Phe Val Arg Asp Lys Ile Ile
    50                  55                  60

Phe Lys Ser Ala Glu Asp Ala Ile Gln Leu Leu Glu Ala Asp Lys Lys
65                  70                  75                  80

Ile Trp Arg Glu Thr Glu Ile Gln Ile Ser Ser Gly Lys Pro Glu Val
                85                  90                  95

Asn Glu Gln Thr Lys Arg Ile Tyr Ile Cys Pro Phe Thr Gly Lys Val
            100                 105                 110

Phe Ala Asp Asn Val Tyr Ala Asn Pro Gln Asp Ala Ile Tyr Asp Trp
        115                 120                 125

Leu Ser Ser Cys Pro Gln Asn Arg Glu Arg Gln Ser Gly Val Ala Val
```

```
    130                 135                 140

Lys Arg Phe Leu Val Ser Asp Asp Pro Glu Val Ile Arg Ala Tyr Ile
145                 150                 155                 160

Val Pro Pro Lys Glu Pro Ile Ile Lys Thr Val Tyr Ala Ser Ala Val
                165                 170                 175

Thr Gly Lys Leu Phe His Ser Leu Pro Thr Leu Leu Glu Asp Phe Lys
            180                 185                 190

Thr Ser Tyr Leu Arg Pro Met Thr Leu Glu Glu Val Gln Asn Gln Asn
        195                 200                 205

Lys Phe Gln Leu Glu Ser Ser Phe Leu Thr Leu Leu Gln Asp Ala Leu
    210                 215                 220

Glu Glu Glu Lys Ile Ala Glu Phe Val Glu Ser Leu Ala Asp Asp Thr
225                 230                 235                 240

Ala Phe His Lys Tyr Ile Ser Gln Trp Val Asp Thr Glu Glu
                245                 250
```

<210> SEQ ID NO 210
<211> LENGTH: 765
<212> TYPE: DNA
<213> ORGANISM: Chlamydia trachomatis

<400> SEQUENCE: 210

```
ttactcttct gtatctaccc attggctaat gtacttatga aacgctgtgt catccgcaag      60

gctttcgaca aactcagcga tcttttcctc ctctaaagca tcttgtaata gagtcaaaaa     120

tgagctttct aattggaact tattctgatt ttgtacttct tcgagagtca taggacgtaa     180

gtaagaagtt ttaaaatcct ccaagagagt tggtaaactg tggaacaact tccctgttac     240

tgcagaagca tagacagtct taatgattgg ttcctttggc ggaacaatgt aggctctgat     300

cacttcagga tcatcggata ctaaaaaacg tttgacagct acaccactct gacgctctct     360

attctgaggg caagaagaaa gccagtcata aatagcatcc tgagggtttg cgtagacgtt     420

atcagcaaaa accttcccag taaacggaca aatgtaaata cgctttgtct gctcattcac     480

ctctggttta ccagaagaaa tttgaatctc tgtttctctc cagatcttct tgtccgcctc     540

taacagctga atcgcatctt ctgcgctttt aaaaatgatt ttatcccgaa caaaaacaac     600

cggactcaag tgcaaagact gctctaaata aaacaagtac gttgctaaca attctgggga     660

tttttgcttt ttcaaaaact ggagaagttt ttgtttgata cttccagaaa tattcatact     720

tatccttact tttttcagtt gcttaatggc aaactgattc ttctt                     765
```

<210> SEQ ID NO 211
<211> LENGTH: 271
<212> TYPE: PRT
<213> ORGANISM: Chlamydia trachomatis

<400> SEQUENCE: 211

```
Lys Gly Ala Arg Leu Pro Pro Leu Gln Gly Leu His Leu Val Ile Asn
1               5                   10                  15

Met Lys Thr Ile Ala Val Asn Ser Phe Lys Gly Gly Thr Ala Lys Thr
            20                  25                  30

Ser Thr Thr Leu His Leu Gly Ala Ala Leu Ala Gln Tyr His Lys Ala
        35                  40                  45

Arg Val Leu Leu Ile Asp Phe Asp Ala Gln Ala Asn Leu Thr Ala Gly
    50                  55                  60

Leu Gly Leu Asp Pro Asp Cys Tyr Asp Ser Leu Ala Val Val Leu Gln
65                  70                  75                  80
```

```
Gly Glu Lys Asn Ile Glu Glu Val Ile Arg Pro Ile Asp Ser Ser Gly
                85                  90                  95

Leu Asp Leu Ile Pro Ala Asp Thr Trp Leu Glu Arg Val Glu Val Ser
            100                 105                 110

Gly Ser Leu Ala Ala Asp Arg Tyr Ser His Glu Arg Leu Lys Ile Ile
        115                 120                 125

Leu Ser Lys Ile Glu His Arg Tyr Asp Tyr Val Ile Ile Asp Thr Pro
    130                 135                 140

Pro Ser Leu Cys Trp Leu Thr Glu Ser Ala Leu Ile Ala Ala Gln His
145                 150                 155                 160

Ala Leu Ile Cys Ala Thr Pro Glu Phe Tyr Ser Val Lys Gly Leu Glu
                165                 170                 175

Arg Leu Ala Thr Phe Ile Gln Gly Ile Ser Ser Arg His Pro Leu Asn
            180                 185                 190

Ile Leu Gly Val Thr Leu Ser Phe Trp Asn Tyr Arg Gly Lys Asn Asn
        195                 200                 205

Ala Ala Phe Thr Glu Leu Ile Gln Lys Thr Phe Pro Gly Lys Leu Leu
    210                 215                 220

Asn Thr Arg Ile Arg Arg Asp Ile Thr Ile Ser Glu Ala Ala Ile His
225                 230                 235                 240

Gly Lys Pro Val Phe Ser Thr Ala Pro Ser Ala Arg Ala Ser Glu Asp
                245                 250                 255

Tyr Leu Lys Leu Thr Glu Glu Leu Leu Phe Leu Leu Arg Asn Ile
            260                 265                 270
```

<210> SEQ ID NO 212
<211> LENGTH: 816
<212> TYPE: DNA
<213> ORGANISM: Chlamydia trachomatis

<400> SEQUENCE: 212

```
aaaggagcga ggcttcctcc cctacaaggg cttcacctcg tgataaacat gaaaacaatc      60

gctgttaata gtttcaaagg cggcacagca aaaacctcta caaccctcca tttaggagcc     120

gcattagcgc aatatcataa agcacgcgtt ctactcatcg atttcgatgc acaagcgaat     180

cttacggcag gattaggcct agatcctgat tgttatgata gccttgctgt tgttctacaa     240

ggagaaaaaa acatagaaga ggtcatccgt cctattgatt cctcaggatt agatctcatc     300

cctgccgata cttggttgga acgtgtggaa gtctctggat ctttggctgc tgatcgttat     360

tctcatgaac gattaaagat tattctttct aagatagaac atcgatacga ctatgtcatt     420

atcgacacac ctccttcttt atgttggctc acagaatcag ctctaatcgc tgctcaacat     480

gcactcatct gcgctacacc agaattctat agtgttaaag gcttagaaag gcttgccacc     540

tttattcaag ggatctcatc gcgacaccct ctcaatattt taggagtcac gctatctttt     600

tggaattaca gagggaaaaa taacgcagcc ttcacagagc taattcaaaa aacgttccct     660

gggaaacttc ttaacacgcg catacgcaga gatattacta tctcagaagc cgctatccat     720

gggaaacctg ttttctccac agccccttca gcgcgagcct cggaagacta tctaaaatta     780

actgaagaac tgctattttt gttaaggaac atctaa                               816
```

<210> SEQ ID NO 213
<211> LENGTH: 601
<212> TYPE: PRT
<213> ORGANISM: Chlamydia trachomatis -continued

<400> SEQUENCE: 213

Val Phe Ile Leu Val Leu Gly Trp Phe Val Met Ser Ile Arg Gly Val
1               5                   10                  15

Gly Gly Asn Gly Asn Ser Arg Ile Pro Ser His Asn Gly Asp Gly Ser
            20                  25                  30

Asn Arg Arg Ser Gln Asn Thr Lys Gly Asn Asn Lys Val Glu Asp Arg
        35                  40                  45

Val Cys Ser Leu Tyr Ser Ser Arg Ser Asn Glu Asn Arg Glu Ser Pro
    50                  55                  60

Tyr Ala Val Val Asp Val Ser Ser Met Ile Glu Ser Thr Pro Thr Ser
65                  70                  75                  80

Gly Glu Thr Thr Arg Ala Ser Arg Gly Val Phe Ser Arg Phe Gln Arg
                85                  90                  95

Gly Leu Val Arg Val Ala Asp Lys Val Arg Arg Ala Val Gln Cys Ala
            100                 105                 110

Trp Ser Ser Val Ser Thr Arg Arg Ser Ser Ala Thr Arg Ala Ala Glu
        115                 120                 125

Ser Gly Ser Ser Ser Arg Thr Ala Arg Gly Ala Ser Ser Gly Tyr Arg
    130                 135                 140

Glu Tyr Ser Pro Ser Ala Ala Arg Gly Leu Arg Leu Met Phe Thr Asp
145                 150                 155                 160

Phe Trp Arg Thr Arg Val Leu Arg Gln Thr Ser Pro Met Ala Gly Val
                165                 170                 175

Phe Gly Asn Leu Asp Val Asn Glu Ala Arg Leu Met Ala Ala Tyr Thr
            180                 185                 190

Ser Glu Cys Ala Asp His Leu Glu Ala Asn Lys Leu Ala Gly Pro Asp
        195                 200                 205

Gly Val Ala Ala Ala Arg Glu Ile Ala Lys Arg Trp Glu Gln Arg Val
    210                 215                 220

Arg Asp Leu Gln Asp Lys Gly Ala Ala Arg Lys Leu Leu Asn Asp Pro
225                 230                 235                 240

Leu Gly Arg Arg Thr Pro Asn Tyr Gln Ser Lys Asn Pro Gly Glu Tyr
                245                 250                 255

Thr Val Gly Asn Ser Met Phe Tyr Asp Gly Pro Gln Val Ala Asn Leu
            260                 265                 270

Gln Asn Val Asp Thr Gly Phe Trp Leu Asp Met Ser Asn Leu Ser Asp
        275                 280                 285

Val Val Leu Ser Arg Glu Ile Gln Thr Gly Leu Arg Ala Arg Ala Thr
    290                 295                 300

Leu Glu Glu Ser Met Pro Met Leu Glu Asn Leu Glu Glu Arg Phe Arg
305                 310                 315                 320

Arg Leu Gln Glu Thr Cys Asp Ala Ala Arg Thr Glu Ile Glu Glu Ser
                325                 330                 335

Gly Trp Thr Arg Glu Ser Ala Ser Arg Met Glu Gly Asp Glu Ala Gln
            340                 345                 350

Gly Pro Ser Arg Ala Gln Gln Ala Phe Gln Ser Phe Val Asn Glu Cys
        355                 360                 365

Asn Ser Ile Glu Phe Ser Phe Gly Ser Phe Gly Glu His Val Arg Val
    370                 375                 380

Leu Cys Ala Arg Val Ser Arg Gly Leu Ala Ala Ala Gly Glu Ala Ile
385                 390                 395                 400

Arg Arg Cys Phe Ser Cys Cys Lys Gly Ser Thr His Arg Tyr Ala Pro
                405                 410                 415

-continued

Arg Asp Asp Leu Ser Pro Glu Gly Ala Ser Leu Ala Glu Thr Leu Ala
420 425 430

Arg Phe Ala Asp Asp Met Gly Ile Glu Arg Gly Ala Asp Gly Thr Tyr
435 440 445

Asp Ile Pro Leu Val Asp Asp Trp Arg Arg Gly Val Pro Ser Ile Glu
450 455 460

Gly Glu Gly Ser Asp Ser Ile Tyr Glu Ile Met Met Pro Ile Tyr Glu
465 470 475 480

Val Met Asp Met Asp Leu Glu Thr Arg Arg Ser Phe Ala Val Gln Gln
485 490 495

Gly His Tyr Gln Asp Pro Arg Ala Ser Asp Tyr Asp Leu Pro Arg Ala
500 505 510

Ser Asp Tyr Asp Leu Pro Arg Ser Pro Tyr Pro Thr Pro Pro Leu Pro
515 520 525

Pro Arg Tyr Gln Leu Gln Asn Met Asp Val Glu Ala Gly Phe Arg Glu
530 535 540

Ala Val Tyr Ala Ser Phe Val Ala Gly Met Tyr Asn Tyr Val Val Thr
545 550 555 560

Gln Pro Gln Glu Arg Ile Pro Asn Ser Gln Gln Val Glu Gly Ile Leu
565 570 575

Arg Asp Met Leu Thr Asn Gly Ser Gln Thr Phe Arg Asp Leu Met Arg
580 585 590

Arg Trp Asn Arg Glu Val Asp Arg Glu
595 600

<210> SEQ ID NO 214
<211> LENGTH: 1806
<212> TYPE: DNA
<213> ORGANISM: Chlamydia trachomatis

<400> SEQUENCE: 214
gtttttattt tagttttggg ttggtttgtt atgagcatca ggggagtagg aggcaacggg 60
aatagtcgaa tcccttctca taatggggat ggatcgaatc gcagaagtca aaatacgaag 120
ggtaataata aagttgaaga tcgagtttgt tctctatatt catctcgtag taacgaaaat 180
agagaatctc cttatgcagt agtagacgtc agctctatga tcgagagcac cccaacgagt 240
ggagagacga caagagcttc gcgtggagtg ttcagtcgtt tccaaagagg tttagtacga 300
gtagctgaca aagtaagacg agctgttcag tgtgcgtgga gttcagtctc tacaagaaga 360
tcgtctgcaa caagagccgc agaatccgga tcaagtagtc gtactgctcg tggtgcaagt 420
tctgggtata gggagtattc tccttcagca gctagagggc tgcgtcttat gttcacagat 480
ttctggagaa ctcgggtttt acgccagacc tctcctatgg ctggagtttt tgggaatctt 540
gatgtgaacg aggctcgttt gatggctgcg tacacaagtg agtgcgcgga tcatttagaa 600
gcgaacaagt tggctggccc tgacggggta gcggccgccc gggaaattgc taaaagatgg 660
gagcaaagag ttagagatct acaagataaa ggtgctgcac gaaaattatt aaatgatcct 720
ttaggccgac gaacacctaa ttatcagagc aaaaatccag gtgagtatac tgtagggaat 780
tccatgtttt acgatggtcc tcaggtagcg aatctccaga acgtcgacac tggtttttgg 840
ctggacatga gcaatctctc agacgttgta ttatccagag agattcaaac aggacttcga 900
gcacgagcta ctttggaaga atccatgccg atgttagaga atttagaaga gcgttttaga 960
cgtttgcaag aaacttgtga tgcggctcgt actgagatag aagaatcggg atggactcga 1020
gagtccgcat caagaatgga aggcgatgag gcgcaaggac cttctagagc acaacaagct 1080
tttcagagct ttgtaaatga atgtaacagc atcgagttct catttgggag ctttggagag 1140
catgtgcgag ttctctgcgc tagagtatca cgaggattag ctgccgcagg agaggcgatt 1200
cgccgttgct tctcttgttg taaaggatcg acgcatcgct acgctcctcg cgatgaccta 1260
tctcctgaag gtgcatcgtt agcagagact ttggctagat tcgcagatga tatgggaata 1320
gagcgaggtg ctgatggaac ctacgatatt cctttggtag atgattggag aagaggggtt 1380
cctagtattg aaggagaagg atctgactcg atctatgaaa tcatgatgcc tatctatgaa 1440
gttatggata tggatctaga aacacgaaga tcttttgcgg tacagcaagg gcactatcag 1500
gacccaagag cttcagatta tgacctccca cgtgctagcg actatgattt gcctagaagc 1560
ccatatccta ctccaccttt gcctcctaga tatcagctac agaatatgga tgtagaagca 1620
gggttccgtg aggcagttta tgcttctttt gtagcaggaa tgtacaatta tgtagtgaca 1680
cagccgcaag agcgtattcc caatagtcag caggtggaag ggattctgcg tgatatgctt 1740
accaacgggt cacagacatt tagagacctg atgaggcgtt ggaatagaga agtcgatagg 1800
gaataa 1806

<210> SEQ ID NO 215
<211> LENGTH: 416
<212> TYPE: PRT
<213> ORGANISM: Chlamydia trachomatis

<400> SEQUENCE: 215

Val Gln Phe Leu Phe Trp Ala Lys Asp Ile Gly Ser Lys Leu Ile Phe
1 5 10 15

Asn Leu Arg Ile Phe Glu Met Ser Lys Glu Thr Phe Gln Arg Asn Lys
20 25 30

Pro His Ile Asn Ile Gly Thr Ile Gly His Val Asp His Gly Lys Thr
35 40 45

Thr Leu Thr Ala Ala Ile Thr Arg Ala Leu Ser Gly Asp Gly Leu Ala
50 55 60

Asp Phe Arg Asp Tyr Ser Ser Ile Asp Asn Thr Pro Glu Glu Lys Ala
65 70 75 80

Arg Gly Ile Thr Ile Asn Ala Ser His Val Glu Tyr Glu Thr Ala Asn
85 90 95

Arg His Tyr Ala His Val Asp Cys Pro Gly His Ala Asp Tyr Val Lys
100 105 110

Asn Met Ile Thr Gly Ala Ala Gln Met Asp Gly Ala Ile Leu Val Val
115 120 125

Ser Ala Thr Asp Gly Ala Met Pro Gln Thr Lys Glu His Ile Leu Leu
130 135 140

Ala Arg Gln Val Gly Val Pro Tyr Ile Val Val Phe Leu Asn Lys Ile
145 150 155 160

Asp Met Ile Ser Glu Glu Asp Ala Glu Leu Val Asp Leu Val Glu Met
165 170 175

Glu Leu Val Glu Leu Leu Glu Glu Lys Gly Tyr Lys Gly Cys Pro Ile
180 185 190

Ile Arg Gly Ser Ala Leu Lys Ala Leu Glu Gly Asp Ala Ala Tyr Ile
195 200 205

Glu Lys Val Arg Glu Leu Met Gln Ala Val Asp Asp Asn Ile Pro Thr
210 215 220

Pro Glu Arg Glu Ile Asp Lys Pro Phe Leu Met Pro Ile Glu Asp Val

-continued 225 230 235 240

Phe Ser Ile Ser Gly Arg Gly Thr Val Val Thr Gly Arg Ile Glu Arg
245 250 255

Gly Ile Val Lys Val Ser Asp Lys Val Gln Leu Val Gly Leu Arg Asp
260 265 270

Thr Lys Glu Thr Ile Val Thr Gly Val Glu Met Phe Arg Lys Glu Leu
275 280 285

Pro Glu Gly Arg Ala Gly Glu Asn Val Gly Leu Leu Leu Arg Gly Ile
290 295 300

Gly Lys Asn Asp Val Glu Arg Gly Met Val Val Cys Leu Pro Asn Ser
305 310 315 320

Val Lys Pro His Thr Gln Phe Lys Cys Ala Val Tyr Val Leu Gln Lys
325 330 335

Glu Glu Gly Gly Arg His Lys Pro Phe Phe Thr Gly Tyr Arg Pro Gln
340 345 350

Phe Phe Phe Arg Thr Thr Asp Val Thr Gly Val Val Thr Leu Pro Glu
355 360 365

Gly Ile Glu Met Val Met Pro Gly Asp Asn Val Glu Phe Glu Val Gln
370 375 380

Leu Ile Ser Pro Val Ala Leu Glu Glu Gly Met Arg Phe Ala Ile Arg
385 390 395 400

Glu Gly Gly Arg Thr Ile Gly Ala Gly Thr Ile Ser Lys Ile Ile Ala
405 410 415

<210> SEQ ID NO 216
<211> LENGTH: 1251
<212> TYPE: DNA
<213> ORGANISM: Chlamydia trachomatis

<400> SEQUENCE: 216
ttatgcaatg atcttagaaa tagttccagc accgattgta cgaccacctt cacgaatcgc 60
aaatctcata ccttcttcta aagccacagg gctaatcaat tgcacttcaa actcaacgtt 120
atccccaggc atgaccatct caattccctc aggcagagtt accacacctg tgacgtctgt 180
tgtacggaag aagaattgag gtctatatcc tgtgaagaaa ggcttatgtc gtccaccttc 240
ttctttttgc aaaacgtaaa cagcacactt gaactgtgta tgaggtttaa cactgtttgg 300
caagcaaaca accattcctc tttccacatc gttcttacca atacctctga ggagcaatcc 360
aacgttctct cctgcacgac cttctgggag ttcttttctg aacatttcaa ccccagtaac 420
aatcgtttct ttagtatctc taagaccgac caactgaact ttatcggaaa ctttaacaat 480
tccacgctca atacgtccag ttactacagt tcctcgtccg gagatagaga atacgtcctc 540
aataggcatt aagaaaggct tgtcaatttc tctttctgga gtagggatgt tatcatcgac 600
ggcttgcatt agctctcgaa ctttctctat gtatgcagca tccccttcca aagctttcag 660
agcagaacct ctgatgattg gacacccttt gtatcctttc tcttcaagaa gctcaaccaa 720
ctccatctca actaagtcga ccaattcagc gtcttcttcg gaaatcatgt caattttatt 780
gagaaaaaca acgatgtaag gaaccccaac ttgtcttgcc aaaagaatat gctctttagt 840
ttgaggcata gctccgtctg ttgcagaaac tactagaata gccccgtcca tttgagctgc 900
accggtgatc atgtttttaa catagtcagc gtgaccaggg cagtccacgt gagcgtagtg 960
acgattagct gtttcgtact caacgtggga agcgttaatt gtaataccgc gagctttttc 1020
ttcaggagtg ttgtcaatag agctataatc acgaaaatca gccaacccat ctccagacaa 1080

-continued

```
cgcacgcgta atagcagctg tcaacgtagt cttaccatgg tcaacgtggc caatggtccc   1140

tatgttgata tgaggcttat tacgttgaaa agtttctttt gacatctcaa aaatcctcaa   1200

attaaaaatt agtttgctac caatatcttt tgcccagaat aggaattgaa c            1251
```

```
<210> SEQ ID NO 217
<211> LENGTH: 616
<212> TYPE: PRT
<213> ORGANISM: Chlamydia trachomatis

<400> SEQUENCE: 217

Thr Ala Ser Ser Lys Glu Arg Phe Met Thr Thr Ala Thr Thr Ser Gln
1               5                   10                  15

Thr Ala Leu Arg Ser Arg Lys Asp Val Pro Leu Ser Asp Cys Trp Asp
            20                  25                  30

Thr Lys Ser Leu Tyr Ala Ser Arg Glu Val Trp Gln Asp Glu Leu Lys
        35                  40                  45

Lys Val Gly Ala Glu Gly Ala Pro Phe Trp Pro His Leu Ser Glu Asn
    50                  55                  60

Asn Phe Asp Ile Lys Gln Pro Ser Ser Leu Arg Glu Leu Leu Thr Thr
65                  70                  75                  80

Val Phe Ser Ile Glu Arg Thr Leu Asp Lys Leu Tyr Val Tyr Ala His
                85                  90                  95

Leu Thr Tyr Asp Glu Asp Ile Ala Asn Gln Glu Ala Ala Ala Asp Leu
            100                 105                 110

Lys Ser Ile Thr Phe Leu Leu Thr Ser Phe Val Glu Glu Ile Ser Trp
        115                 120                 125

Ile Gln Pro Ala Leu Ile Ala Leu Pro Gln Gln Val Val Asn Met Leu
    130                 135                 140

Leu Ala Ser Pro Glu Leu Gln Glu Tyr His Phe Tyr Leu Lys Lys Leu
145                 150                 155                 160

Phe Arg Leu Ala Pro His Thr Gly Thr Ser Arg Glu Glu Lys Ile Leu
                165                 170                 175

Ala Ser Ser Phe Pro Ala Leu Glu Val Ala Tyr Lys Thr Phe Ser Ser
            180                 185                 190

Leu Thr Asp Ser Glu Ile Pro Phe Gly Glu Ala Val Asp Ser Glu Gly
        195                 200                 205

Lys Ser His Pro Leu Ser His Ala Leu Ala Ser Leu Tyr Met Gln Ser
    210                 215                 220

Thr Asp Arg Glu Leu Arg Lys Asn Thr Tyr Gln Lys Gln Cys Gln Arg
225                 230                 235                 240

His His Gly Tyr Arg Leu Ser Leu Ala Asn Leu Leu Asn Gly Lys Ile
                245                 250                 255

Gln Ala His Leu Phe Asn Ala Lys Ala Arg Asp Tyr Asp Ser Cys Leu
            260                 265                 270

Glu Ala Ala Leu Phe Gln Asn Asp Ile Ser Thr Ser Val Val Thr Thr
        275                 280                 285

Leu Ile Asp Thr Val Lys Gln His Thr His Leu Ile Thr Glu Tyr Phe
    290                 295                 300

Gln Leu Lys Gln Lys Ala Leu Gly Leu Ser Asp Phe His Phe Tyr Asp
305                 310                 315                 320

Val Tyr Ala Pro Leu Val Ala Ser Glu Ala Ser Arg His Tyr Ser Tyr
                325                 330                 335

Gln Glu Ala Val Thr Leu Ile Cys Asp Ser Leu Ser Leu Leu Gly Asn
            340                 345                 350
```

Asp Tyr Val Glu Thr Leu Arg Lys Gly Leu Thr Ser Asp Gly Trp Val
        355                 360                 365

Asp Lys Tyr Glu Asn Thr Asn Lys Arg Ser Gly Ala Tyr Ser Ser Gly
    370                 375                 380

Cys Tyr Asp Ser Lys Pro Tyr Ile Leu Leu Asn Tyr Thr Gly Thr Leu
385                 390                 395                 400

Tyr Asp Val Ser Val Val Ala His Glu Gly Gly His Ser Met His Ser
                405                 410                 415

Phe Leu Ser His Lys His Gln Ser Tyr His Glu Ala Gln Tyr Pro Ile
            420                 425                 430

Phe Leu Ala Glu Ile Ala Ser Thr Leu Asn Glu Thr Leu Leu Met Glu
        435                 440                 445

Phe Leu Leu Lys Gln Ala Pro Ser Lys Glu Glu Lys Ile Ala Ile Leu
    450                 455                 460

Ser Arg Ser Leu Asp Thr Val Phe Ala Thr Leu Phe Arg Gln Thr Leu
465                 470                 475                 480

Phe Ala Ala Phe Glu Leu Glu Met His Ser Ala Ala Glu Gln Gly Leu
                485                 490                 495

Pro Leu Thr Glu Glu Phe Phe Ser Gln Ser Tyr Glu Lys Leu Gln Arg
            500                 505                 510

Leu Phe Tyr Gly Asp Cys Ile Thr Phe Asp Glu His Ser Cys Ile Glu
        515                 520                 525

Trp Ala Arg Ile Pro His Phe Tyr Tyr Asn Phe Tyr Val Tyr Gln Tyr
    530                 535                 540

Ala Thr Gly Ile Ile Ala Ser Leu Cys Phe Ser Glu Arg Ile Leu Ser
545                 550                 555                 560

Gly Glu Glu Gly Ala Gln Glu Ala Tyr Leu Thr Phe Leu Arg Ser Gly
                565                 570                 575

Gly Ser Asp Phe Pro Ile Glu Ile Leu Lys Lys Ser Gly Leu Asp Met
            580                 585                 590

Thr Ser Ser Ala Pro Met Leu Lys Ala Phe Ser Tyr Ile Glu Arg Lys
        595                 600                 605

Leu Glu Glu Leu Ala Ser Leu Leu
    610                 615

<210> SEQ ID NO 218
<211> LENGTH: 1851
<212> TYPE: DNA
<213> ORGANISM: Chlamydia trachomatis

<400> SEQUENCE: 218
ttatagcaag ctagctagtt cttccagctt ccgttcgatg taggaaaagg ctttaagcat 60
aggagctgat gaggtcatat ccaatccaga ttttttcaaa atttcgatag ggaaatcgga 120
tccgccgcta cgcaaaaatg tgagatatgc ttcttgagca ccttcttctc cagaaagaat 180
tctttcagaa aaacacaacg atgcaatgat tcctgtggcg tattgataaa catagaagtt 240
gtagtagaaa tgaggaatgc gagcccattc gatacagcta tgttcatcaa aagttatgca 300
atcgccataa aataggcgct gcagtttctc gtaactttga gagaagaatt cttcagttaa 360
tgggagacct tgttcggctg cagaatgcat ttccagctca aaagcagcaa atagtgtttg 420
tcggaataaa gttgcaaaaa cagtgtctag agagcgagaa agaatagcaa tcttctcttc 480
tttagacgga gcttgtttta gcagaaattc catcaatagg gtttcattga gggttgaggc 540
gatttcagct agaaaaatcg gatactgagc ttcatgataa ctttgatgtt tatgactcaa 600

```
gaatgagtgc atactatgac caccttcgtg cgcaactacc gatacgtcgt ataacgttcc    660

tgtataattg agaagaatgt aaggtttgct gtcataacac ccagacgaat atgctcctga    720

gcgtttgtta gtattttcat atttatctac ccatccatcg gaagtgagac ctttgcgtag    780

agtctctaca taatcgttcc ctaaaaggga caagctatcg cagatcagag tgacagcttc    840

ttgataagaa taatggcgtg aagcttcgct agcgaccaac ggtgcataga catcatagaa    900

atggaaatcc gagagaccaa gagctttttg ttttaactga aaatactcag tgatcaggtg    960

tgtgtgttgt ttaacggtat caatgagcgt ggtaaccaca gaagtgctga tatcattctg   1020

aaatagtgct gcttctaaac aagaatcata atcgcgagct tttgcattga atagatgggc   1080

ttgaattttg ccattcagta gattcgcgag agataaacga tacccgtgat ggcgttgaca   1140

ttgtttctga taagtgtttt tgcgtagctc ccgatctgta gattgcatgt atagagaagc   1200

tagagcgtga gaaaggggat gagatttacc ttcggagtcg acagcttccc caaaaggaat   1260

ttcagaatct gttaagctag aaaaagtttt ataggctact tccaatgcag ggaaagaaga   1320

tgctaggatt ttttcttctc gagaagttcc tgtgtgcgga gctaaacgga atagtttttt   1380

caaatagaaa tggtattcct gaagttcggg agaggctaat agcatattaa ccacttgctg   1440

agggagggcg ataagggccg gttgaatcca agaaatttcc tctacaaatg atgtgagcaa   1500

gaaggtaata gatttcagat cagctgcggc ttcttgattc gcaatatcct catcataagt   1560

aagatgagcg tatacataaa gtttatccaa agttctttca atagaaaaga ctgtggttag   1620

cagctcacga agagaagaag gttgttttat atcaaaattg ttttcgctaa ggtgaggcca   1680

aaatggagct ccttcagcac ctactttttt taattcgtct tgccagactt cacgactcgc   1740

atacaaactt ttcgtatccc agcagtcaga aagaggaaca tcttttctag agcgtaaagc   1800

tgtttgtgaa gtagtagcag tggtcatgaa tctctcctta gaggaagctg t            1851
```

<210> SEQ ID NO 219
<211> LENGTH: 1258
<212> TYPE: PRT
<213> ORGANISM: Chlamydia trachomatis

<400> SEQUENCE: 219

```
Ser Leu Arg Arg Ala Arg Met Phe Lys Cys Pro Glu Arg Val Ser Ile
1               5                   10                  15

Lys Lys Lys Glu Asp Ile Leu Asp Leu Pro Asn Leu Val Glu Val Gln
            20                  25                  30

Ile Lys Ser Tyr Lys Gln Phe Leu Gln Ile Gly Lys Leu Ala Glu Glu
        35                  40                  45

Arg Glu Asn Ile Gly Leu Glu Glu Val Phe Arg Glu Ile Phe Pro Ile
    50                  55                  60

Lys Ser Tyr Asn Glu Ala Thr Ile Leu Glu Tyr Leu Ser Tyr Asn Leu
65                  70                  75                  80

Gly Val Pro Lys Tyr Ser Pro Glu Glu Cys Ile Arg Arg Gly Ile Thr
                85                  90                  95

Tyr Ser Val Thr Leu Lys Val Arg Phe Arg Leu Thr Asp Glu Thr Gly
            100                 105                 110

Ile Lys Glu Glu Glu Val Tyr Met Gly Thr Ile Pro Ile Met Thr Asp
        115                 120                 125

Lys Gly Thr Phe Ile Ile Asn Gly Ala Glu Arg Val Val Val Ser Gln
    130                 135                 140

Val His Arg Ser Pro Gly Ile Asn Phe Glu Gln Glu Lys His Ser Lys
```

-continued

```
145                 150                 155                 160

Gly Asn Val Leu Phe Ser Phe Arg Ile Ile Pro Tyr Arg Gly Ser Trp
                165                 170                 175

Leu Glu Ala Val Phe Asp Ile Asn Asp Leu Ile Tyr Ile His Ile Asp
            180                 185                 190

Arg Lys Lys Arg Arg Arg Lys Ile Leu Ala Met Thr Phe Ile Arg Ala
        195                 200                 205

Leu Gly Tyr Ser Thr Asp Ala Asp Ile Ile Glu Glu Phe Phe Ser Val
    210                 215                 220

Glu Glu Arg Ser Leu Arg Leu Glu Lys Asp Phe Val Ala Leu Val Gly
225                 230                 235                 240

Lys Val Leu Ala Asp Asn Val Val Asp Ala Asp Ser Ser Leu Val Tyr
                245                 250                 255

Gly Lys Ala Gly Glu Lys Leu Ser Thr Ala Met Leu Lys Arg Ile Leu
            260                 265                 270

Asp Ala Gly Val Gln Ser Leu Lys Ile Ala Val Gly Ala Asp Glu Asn
        275                 280                 285

His Pro Ile Ile Lys Met Leu Ala Lys Asp Pro Thr Asp Ser Tyr Glu
    290                 295                 300

Ala Ala Leu Lys Asp Phe Tyr Arg Arg Leu Arg Pro Gly Glu Pro Ala
305                 310                 315                 320

Thr Leu Val Asn Ala Arg Ser Thr Ile Met Arg Leu Phe Phe Asp Ala
                325                 330                 335

Lys Arg Tyr Asn Leu Gly Arg Val Gly Arg Tyr Lys Leu Asn Lys Lys
            340                 345                 350

Leu Gly Phe Pro Leu Asp Asp Glu Thr Leu Ser Gln Val Thr Leu Arg
        355                 360                 365

Lys Glu Asp Val Ile Gly Ala Leu Lys Tyr Leu Ile Arg Leu Arg Met
    370                 375                 380

Gly Asp Glu Lys Thr Ser Ile Asp Asp Ile Asp His Leu Ala Asn Arg
385                 390                 395                 400

Arg Val Arg Ser Val Gly Glu Leu Ile Gln Asn His Cys Arg Ser Gly
                405                 410                 415

Leu Ala Arg Met Glu Lys Ile Val Arg Glu Arg Met Asn Leu Phe Asp
            420                 425                 430

Phe Ser Ser Asp Thr Leu Thr Pro Gly Lys Ile Ile Ser Ala Lys Gly
        435                 440                 445

Leu Val Ser Val Leu Lys Asp Phe Phe Ser Arg Ser Gln Leu Ser Gln
    450                 455                 460

Phe Met Asp Gln Thr Asn Pro Val Ala Glu Leu Thr His Lys Arg Arg
465                 470                 475                 480

Leu Ser Ala Leu Gly Pro Gly Gly Leu Asn Arg Glu Arg Ala Gly Phe
                485                 490                 495

Glu Val Arg Asp Val His Ala Ser His Tyr Gly Arg Ile Cys Pro Ile
            500                 505                 510

Glu Thr Pro Glu Gly Pro Asn Ile Gly Leu Ile Thr Ser Leu Ser Ser
        515                 520                 525

Phe Ala Lys Ile Asn Glu Phe Gly Phe Ile Glu Thr Pro Tyr Arg Val
    530                 535                 540

Val Arg Asp Gly Ile Val Thr Asp Glu Ile Glu Tyr Met Thr Ala Asp
545                 550                 555                 560

Val Glu Glu Glu Cys Val Ile Ala Gln Ala Ser Ala Glu Leu Asp Glu
                565                 570                 575
```

-continued

```
Tyr Asp Met Phe Lys Thr Pro Val Cys Trp Ala Arg Tyr Lys Gly Glu
            580                 585                 590

Ala Phe Glu Ala Asp Thr Ser Thr Val Thr His Met Asp Val Ser Pro
        595                 600                 605

Lys Gln Leu Val Ser Val Val Thr Gly Leu Ile Pro Phe Leu Glu His
    610                 615                 620

Asp Asp Ala Asn Arg Ala Leu Met Gly Ser Asn Met Gln Arg Gln Ala
625                 630                 635                 640

Val Pro Leu Leu Lys Thr Glu Ala Ala Ile Val Gly Thr Gly Leu Glu
                645                 650                 655

Gly Arg Ala Ala Lys Asp Ser Gly Ala Ile Ile Val Ala Gln Glu Asp
            660                 665                 670

Gly Val Val Glu Tyr Val Asp Ser Tyr Glu Ile Val Val Ala Lys Lys
        675                 680                 685

Asn Asn Pro Thr Leu Lys Asp Arg Tyr Gln Leu Lys Lys Phe Leu Arg
    690                 695                 700

Ser Asn Ser Gly Thr Cys Ile Asn Gln Thr Pro Leu Cys Ser Val Gly
705                 710                 715                 720

Asp Val Val Thr His Gly Asp Val Leu Ala Asp Gly Pro Ala Thr Asp
                725                 730                 735

Lys Gly Glu Leu Ala Leu Gly Lys Asn Val Leu Val Ala Phe Met Pro
            740                 745                 750

Trp Tyr Gly Tyr Asn Phe Glu Asp Ala Ile Ile Ile Ser Glu Arg Leu
        755                 760                 765

Ile Lys Gln Asp Ala Tyr Thr Ser Ile Tyr Ile Glu Glu Phe Glu Leu
    770                 775                 780

Thr Ala Arg Asp Thr Lys Leu Gly Lys Glu Glu Ile Thr Arg Asp Ile
785                 790                 795                 800

Pro Asn Val Ser Glu Glu Val Leu Ala Asn Leu Gly Glu Asp Gly Val
                805                 810                 815

Val Arg Ile Gly Ala Glu Val Lys Pro Gly Asp Ile Leu Val Gly Lys
            820                 825                 830

Ile Thr Pro Lys Ser Glu Thr Glu Leu Ala Pro Glu Glu Arg Leu Leu
        835                 840                 845

Arg Ala Ile Phe Gly Glu Lys Ala Ala Asp Val Lys Asp Ala Ser Leu
    850                 855                 860

Thr Val Pro Pro Gly Thr Glu Gly Val Val Met Asp Val Lys Val Phe
865                 870                 875                 880

Ser Arg Lys Asp Arg Leu Ser Lys Ser Asp Asp Glu Leu Val Glu Glu
                885                 890                 895

Ala Val His Leu Lys Asp Leu Gln Lys Glu Tyr Lys Ser Gln Leu Ala
            900                 905                 910

Gln Leu Lys Val Glu His Arg Glu Lys Leu Gly Ala Leu Leu Leu Asn
        915                 920                 925

Glu Lys Ala Pro Ala Ala Ile Ile His Arg Arg Ser Ala Asp Ile Leu
    930                 935                 940

Val Gln Glu Gly Ala Ile Phe Asp Gln Glu Thr Ile Glu Leu Leu Glu
945                 950                 955                 960

Arg Glu Ser Leu Val Asp Leu Leu Met Ala Pro Cys Asp Met Tyr Asp
                965                 970                 975

Val Leu Lys Asp Ile Leu Ser Ser Tyr Glu Thr Ala Val Gln Arg Leu
            980                 985                 990
```

```
Glu Val Asn Tyr Lys Thr Glu Ala  Glu His Ile Lys Glu  Gly Asp Ala
        995                 1000                 1005

Asp Leu  Asp His Gly Val Ile  Arg Gln Val Lys Val  Tyr Val Ala
    1010                 1015                 1020

Ser Lys  Arg Lys Leu Gln Val  Gly Asp Lys Met Ala  Gly Arg His
    1025                 1030                 1035

Gly Asn  Lys Gly Val Val Ser  Lys Ile Val Pro Glu  Ala Asp Met
    1040                 1045                 1050

Pro Phe  Leu Ala Asn Gly Glu  Thr Val Gln Met Ile  Leu Asn Pro
    1055                 1060                 1065

Leu Gly  Val Pro Ser Arg Met  Asn Leu Gly Gln Val  Leu Glu Thr
    1070                 1075                 1080

His Leu  Gly Tyr Ala Ala Lys  Thr Ala Gly Ile Tyr  Val Lys Thr
    1085                 1090                 1095

Pro Val  Phe Glu Gly Phe Pro  Glu Ser Arg Ile Trp  Asp Met Met
    1100                 1105                 1110

Ile Glu  Gln Gly Leu Pro Glu  Asp Gly Lys Ser Tyr  Leu Phe Asp
    1115                 1120                 1125

Gly Lys  Thr Gly Glu Arg Phe  Asp Ser Lys Val Val  Val Gly Tyr
    1130                 1135                 1140

Ile Tyr  Met Leu Lys Leu Ser  His Leu Ile Ala Asp  Lys Ile His
    1145                 1150                 1155

Ala Arg  Ser Ile Gly Pro Tyr  Ser Leu Val Thr Gln  Gln Pro Leu
    1160                 1165                 1170

Gly Gly  Lys Ala Gln Met Gly  Gly Gln Arg Phe Gly  Glu Met Glu
    1175                 1180                 1185

Val Trp  Ala Leu Glu Ala Tyr  Gly Val Ala His Met  Leu Gln Glu
    1190                 1195                 1200

Ile Leu  Thr Val Lys Ser Asp  Asp Val Ser Gly Arg  Thr Arg Ile
    1205                 1210                 1215

Tyr Glu  Ser Ile Val Lys Gly  Glu Asn Leu Leu Arg  Ser Gly Thr
    1220                 1225                 1230

Pro Glu  Ser Phe Asn Val Leu  Ile Lys Glu Met Gln  Gly Leu Gly
    1235                 1240                 1245

Leu Asp  Val Arg Pro Met Val  Val Asp Ala
    1250                 1255
```

<210> SEQ ID NO 220
<211> LENGTH: 3777
<212> TYPE: DNA
<213> ORGANISM: Chlamydia trachomatis

<400> SEQUENCE: 220

```
ttaagcatct actaccatag ggcgaacatc aagccctaga ccttgcattt ctttaatcaa     60

aacgttgaac gactcaggcg ttccagaacg aagtaagttt tctcctttca cgattgattc    120

gtagatacga gttcttcccg aaacatcgtc ggacttaaca gtcagaatct cttgtaacat    180

atgagctacc ccatacgcct ctaaagccca tacctccatt tccccgaatc tctgtcctcc    240

catctgcgct ttacctccaa gaggttgctg cgtaacgaga gagtaaggtc ctatagaacg    300

agcgtggatc ttatcagcaa ttaagtgact caatttcaac atgtagatgt atccaacgac    360

cactttgcta tcgaaacgct ctccggtttt accatcaaat aggtaagact taccatcttc    420

gggcaatccc tgctctatca tcatatccca aatacgagac tctgggaacc cttcaaagac    480

cggagttttc acatagatac ctgcagtttt tgcagcatat cctaaatgtg tctctaaaac    540
```

ctgtccaagg ttcattcgag aaggcacccc taacgggttc aaaatcatct gtactgtttc 600
accgttagct aagaaaggca tgtctgcttc tggaacaatc ttggaaacca ctcccttgtt 660
tccgtgacgt ccagccattt tatccccaac ttgaagtttt cgcttggaag ccacgtaaac 720
tttaacttgt cggataactc catgatctaa gtcagcatca ccttctttta tgtgctcagc 780
ttcggtttta taattgactt ccaaacgctg aacagctgtt tcatagctag aaagaatatc 840
tttcaaaaca tcatacatgt cacaaggagc catcagcaaa tcaactagcg actctctttc 900
taagagttcg atagtctctt gatcaaaaat agcaccttct tgaaccaaaa tatctgccga 960
acgacggtgt ataatcgctg caggagcttt ttcattgagc aatagagccc ccagtttctc 1020
tctatgttct actttcaatt gagctaactg actcttatat tctttctgta gatccttaag 1080
atgcacagct tcttcaacca gttcatcatc gctcttggac aagcgatcct ttctgctgaa 1140
tactttgaca tccattacga ctccttctgt accaggagga accgttagag aggcatcttt 1200
tacgtccgcc gccttctctc caaaaatagc tcgcaacaaa cgctcttcag gagctagttc 1260
cgtctcagat ttcggagtga ttttaccgac aagaatatct cccggcttga cttcagcccc 1320
aatacggacg acaccatcct ctccgagatt tgccaaaacc tcttcagaaa cgttaggaat 1380
atctctagta atttcttctt taccgagttt tgtatctcga gctgttaact caaattcttc 1440
tatgtaaata gaagtgtacg catcttgttt aatcaacctc tcggagatga taatcgcatc 1500
ttcgaagtta tacccgtacc aaggcatgaa ggctactaat acgtttttac caagagccaa 1560
ttccccttta tcggttgctg ggccatccgc taaaacatct ccatgcgtaa ccacatctcc 1620
cacagaacac aaaggagttt ggttgatgca tgttccggag ttggatctta agaatttttt 1680
aagctgataa cgatccttaa gcgttggatt attcttcttc gctacgacaa tctcatagct 1740
atctacgtat tcgactaccc catcttcctg agccacaata atagctccag aatctttggc 1800
agcacgccct tctaatccag ttccaacaat agcagcttcc gttttcaata atggtacagc 1860
ctgccgttgc atgttcgatc ccataagagc tcggttagca tcgtcgtgtt ccaagaaagg 1920
aatcagcccc gtaaccacag ataccagctg ttttggagaa acgtccatat gcgtaaccgt 1980
acttgtgtcg gcttcaaaag cctctccttt gtatctagcc cagcatacgg gagttttaaa 2040
catatcatac tcatcgagct ccgcagaagc ctgagcaatg acacactctt cttcaacatc 2100
tgctgtcata tactcaattt catctgtcac gatgccatcg cgcacgacac gataaggagt 2160
ctctatgaat ccaaattcat tgatcttagc aaaggaagac agtgaagtaa tcaacccaat 2220
gtttggtcct tcaggagtct caattggaca aattctacca tagtggcttg cgtgaacgtc 2280
tcgaacttca aacccagctc tttctctatt caatccccca ggtcctaatg ctgacagacg 2340
acgcttgtgc gtcaattctg cgacagggtt tgtctgatcc ataaactgag ataattgaga 2400
acggctgaag aaatctttca ggacactgac taacccttta gcagaaataa tctttcctgg 2460
agttagggta tcagaagaga aatcaaagag attcattctt tctcgaacga tcttttccat 2520
tctagccaat ccagaacgac agtgattctg aattagttct ccaacagagc gaactcgtcg 2580
gtttgccaaa tggtcaatat catcgataga tgtcttctca tcgcccattc gcaaacgaat 2640
caaatatttc aacgcgccga taacatcttc ttttctcaaa gtcacttgag ataatgtttc 2700
gtcgtctaat gggaatccta attttttatt taatttataa cgtccaacgc ggcctaaatt 2760
atagcgttta gcatcgaaga ataagcgcat aattgtggat cgagcattaa ctaaagttgc 2820
aggctctcct ggtcgtaatc tgcgataaaa atctttaaga gcagcttcgt aagaatccgt 2880

-continued

```
aggatctttt gcgagcatct taataattgg gtgattttca tctgcgccaa cagcaatctt   2940

caaagattgg actcccgcat ctaagatgcg ttttagcata gcagtactta gcttctctcc   3000

agctttcccg taaactaatg aagaatccgc atcaactacg ttatcagcta aaactttacc   3060

aactaacgcg acaaaatcct tctctaaacg taaggaacgc tcctctacag aaaagaactc   3120

ttcaataata tctgcatctg ttgaatatcc taaagctcgg ataaacgtca tagctaaaat   3180

ctttctgcga cgttttttcc tatcaatatg gatatagata aggtcattaa tgtcgaagac   3240

agcttctaac caacttcctc gataaggaat aattctaaaa gaaaataaaa catttccttt   3300

agaatgtttt tcttgttcaa aattgattcc tggagaacgg tggacttgag aaacaacgac   3360

tctctctgcc ccattaataa taaaggttcc cttatcagtc atgatgggga tggttcccat   3420

atagacttct tcttctttaa tccccgtttc atcagttaaa cggaaacgaa cctttaaagt   3480

aacactatag gtgattcccc gacgaataca ctcttctggg gagtatttgg gcactcctaa   3540

gttataagag aggtactcta aaatcgtagc ttcattataa gacttgatag ggaaaatttc   3600

tctgaagact tcttctaaac caatgttttc tcgctcttca gcaagcttcc cgatttgaag   3660

aaactgctta tacgacttga tttgaacttc gacaagatta ggaagatcta aaatatcttc   3720

tttctttttg atgctgaccc gctccgggca cttgaacatg cgagctctcc taagact      3777
```

```
<210> SEQ ID NO 221
<211> LENGTH: 250
<212> TYPE: PRT
<213> ORGANISM: Chlamydia trachomatis

<400> SEQUENCE: 221

Asn Arg Gly Leu Ile Arg Thr Phe Phe Ala Ser Gly Tyr Val Glu Ser
1               5                   10                  15

Arg Lys Glu Met Met Glu Val Phe Met Asn Phe Leu Asp Gln Leu Asp
            20                  25                  30

Leu Ile Ile Gln Asn Lys His Met Leu Glu His Thr Phe Tyr Val Lys
        35                  40                  45

Trp Ser Lys Gly Glu Leu Thr Lys Glu Gln Leu Gln Ala Tyr Ala Lys
    50                  55                  60

Asp Tyr Tyr Leu His Ile Lys Ala Phe Pro Lys Tyr Leu Ser Ala Ile
65                  70                  75                  80

His Ser Arg Cys Asp Asp Leu Glu Ala Arg Lys Leu Leu Leu Asp Asn
                85                  90                  95

Leu Met Asp Glu Glu Asn Gly Tyr Pro Asn His Ile Asp Leu Trp Lys
            100                 105                 110

Gln Phe Val Phe Ala Leu Gly Val Thr Pro Glu Glu Leu Glu Ala His
        115                 120                 125

Glu Pro Ser Glu Ala Ala Lys Ala Lys Val Ala Thr Phe Met Arg Trp
    130                 135                 140

Cys Thr Gly Asp Ser Leu Ala Ala Gly Val Ala Ala Leu Tyr Ser Tyr
145                 150                 155                 160

Glu Ser Gln Ile Pro Arg Ile Ala Arg Glu Lys Ile Arg Gly Leu Thr
                165                 170                 175

Glu Tyr Phe Gly Phe Ser Asn Pro Glu Asp Tyr Ala Tyr Phe Thr Glu
            180                 185                 190

His Glu Glu Ala Asp Val Arg His Ala Arg Glu Glu Lys Ala Leu Ile
        195                 200                 205

Glu Met Leu Leu Lys Asp Asp Ala Asp Lys Val Leu Glu Ala Ser Gln
    210                 215                 220
```

Glu Val Thr Gln Ser Leu Tyr Gly Phe Leu Asp Ser Phe Leu Asp Pro
225 230 235 240

Gly Thr Cys Cys Ser Cys His Gln Ser Tyr
245 250

<210> SEQ ID NO 222
<211> LENGTH: 753
<212> TYPE: DNA
<213> ORGANISM: Chlamydia trachomatis

<400> SEQUENCE: 222
ttaataagat tgatgacaac tacaacaagt tcctggatcc aaaaaagaat ctaaaaagcc 60
atacaaagat tgcgttactt cttgcgatgc ctctaacact ttatcagcgt catctttgag 120
aagcatctca atgagcgctt tttcttctct agcatgccgc acatccgctt cttcatgttc 180
tgtgaaatat gcatagtctt caggattgga aaatccaaag tactcagtca atccacgaat 240
tttctctcta gcgatacgtg gaatttgact ctcataagaa tacaaagcag ccactcctgc 300
agctaaagaa tctcctgtac accaccgcat gaaagtagct actttcgctt ttgctgcttc 360
actaggctca tgagcctcta actcttctgg agtaactcct agagcaaaca caaactgctt 420
ccacaaatca atatgattag ggtaaccgtt ctcttcatcc atcaagttat ctaacaataa 480
cttacgcgcc tctaaatcat cgcaacgact atgaatcgca gataaatatt taggaaaggc 540
tttgatatgt aaataatagt ctttggcata cgcctgtaat tgctctttag taagctcccc 600
cttcgaccat ttcacataaa atgtgtgttc tagcatatgc ttattttgaa taattaaatc 660
taactgatct aaaaaattca taaacacctc catcatttct tttcttgact ccacgtaacc 720
gcttgcaaaa aaggtccgta taagtcctct gtt 753

<210> SEQ ID NO 223
<211> LENGTH: 1462
<212> TYPE: PRT
<213> ORGANISM: Chlamydia trachomatis

<400> SEQUENCE: 223

Gly Ile Ile Leu Pro Ser Lys Ile Val Phe Gln Glu Ser Met Ala Asn
1 5 10 15

Pro Ser Thr Pro Ser Phe Asn His Ser Asp Leu Ser Leu Gln Gly Arg
20 25 30

Leu Arg Ala Ser Ser Gln Gln Cys Thr Gln Ala Gly Gln Gly Asp Pro
35 40 45

Gln Pro Leu Ser Pro Glu Ser Arg Gly Leu Thr Ser Asn Phe Ser Thr
50 55 60

Arg Arg Asp Leu Ile Asp Val Val Glu Glu Ser Ile Glu Thr Ala Lys
65 70 75 80

Gly Ser Glu Leu Lys Lys Leu Arg Ile Tyr Glu Ile Ala Leu Lys Ile
85 90 95

Leu Thr Ile Ile Gly Ala Ala Ile Leu Phe Ala Val Pro Leu Cys Met
100 105 110

Leu Leu Gly Val Pro Leu Trp Ile Pro Ile Val Thr Cys Ile Gly Val
115 120 125

Gly Ile Ala Phe Ser Ile Ala Lys Gly Cys Leu Gln Lys Arg Cys Gln
130 135 140

Gln Ile Arg Glu Glu Tyr Arg Ala Leu His Leu Tyr His Arg Tyr Leu
145 150 155 160

-continued

```
Leu Ser Asn Lys Asp Ser Ile Asp Gly Thr Leu Leu Ser Arg Phe Asp
                165                 170                 175

Ile Arg Phe Arg Lys Ala Glu Glu Lys Leu His Gly Leu Asp Leu Asp
            180                 185                 190

Lys Arg Glu Ala Asn His Pro Leu Glu Ala Asp Lys Arg Tyr Asp Phe
        195                 200                 205

Ala Gly Leu Ala His Gln Arg Tyr Gln Val Asp Ala Ala Leu Gly Ile
    210                 215                 220

Ser Ser Ser Gln Asp Ala Phe Trp Arg Gly Val Ala Gln Gln Val Lys
225                 230                 235                 240

Ser Val Lys Asp Asp Val Val Leu Gly Asp Lys Ala Ser Thr Asp Leu
                245                 250                 255

Tyr Pro Ile Ala Gln Gln Ala Leu Gln Ala Ala Gly Val Gly Phe Ser
            260                 265                 270

Gly Ala Ala Gly Lys Glu Ser Leu Leu Asp Leu Ala Lys Ser Leu Ser
        275                 280                 285

Ser Leu Phe Ala Trp Gly Ser Gln Val Gly Lys Asp Ser His Glu Ala
    290                 295                 300

Leu Gln Gln Tyr Gln Met Arg Phe Leu Ser Ser Pro Ile Leu Ala Thr
305                 310                 315                 320

Trp Cys Gly Ala Gly Phe Ser Ala Ser Ala Gln Asp Phe Val Leu Lys
                325                 330                 335

Gly Glu Asn Ile Leu Asp Ile Ala Ser Glu Asn His Thr Lys Met Gln
            340                 345                 350

Asn Ala Ile Lys Arg Val Gln Leu Val Ser Val Leu Gly Lys Met Arg
        355                 360                 365

Asn Trp Lys Glu Lys Ile Asp Thr Leu Ile Gln Asn Lys Asn Leu Asp
    370                 375                 380

Gln Asp Ser Leu Arg Lys Leu Tyr Gln Asp Ile Glu Lys Ala Met His
385                 390                 395                 400

Lys Val Cys Ile Glu Asp Gly Val Ser Thr Ser Ile Gln Thr Gln Val
                405                 410                 415

Arg Lys Val Thr Gln Lys Tyr Leu Arg Gln Asp Leu Gln Glu Leu Leu
            420                 425                 430

Asn Lys Lys Ala Pro Leu Asn Glu Ser Asp Leu Ser Lys Met Gln Lys
        435                 440                 445

Gly Ile Ser Ser Cys Ala Asn Leu Val Val Thr Leu Leu Glu Ser Gln
    450                 455                 460

Leu Gly Thr Ser Gly Gln Thr Pro Ile Lys Glu Val Glu Glu Ser Ile
465                 470                 475                 480

Tyr Arg Asp Leu Ile Ala Thr Ile Leu Gln Met Gly Ser Ala Ala Gly
                485                 490                 495

Gly Val Thr Pro Leu Val Asp Gly Val His Lys Ala Ile Arg Glu Gly
            500                 505                 510

Lys Ala Leu Arg Ser Glu Leu Ser Arg Ala Met Ser Leu His Pro Arg
        515                 520                 525

Gln Ser Phe Leu Gly Val Gln Ser Ala Val Glu Lys Leu Gln Ala Phe
    530                 535                 540

Ile Arg Asp Pro Lys Trp Gly Ala Ser Ala Val His Thr Ser Ala Glu
545                 550                 555                 560

Glu Thr Leu Ala Gln Lys Gln Lys Phe Val Ser Asp Leu Thr Arg Ile
                565                 570                 575

Gln Thr Ser Leu Ala Asp Trp Arg Glu Arg Tyr Gly Leu Phe Glu Glu
```

```
            580                 585                 590

Thr Lys Leu Asn His Ile Val Ser Thr Asp Phe Val Ser Arg Thr Glu
        595                 600                 605

Ala Phe Leu Asp Thr Leu Lys Asn Val Ala Glu Ala Cys Ser Leu Glu
    610                 615                 620

Gln Ala Val Ala Glu Leu Lys Asp Cys Glu Asp Ala Met Lys Ala Asp
625                 630                 635                 640

Leu Thr His Val Glu Gln Lys Met Asn Pro Thr Glu Ile Glu Ser Ala
                645                 650                 655

Arg Glu Glu Phe Lys Arg Leu Met Glu Glu Leu Ala Gly Ile Gln Glu
            660                 665                 670

Gln Leu Glu Gln Ile Ala Gln Pro Ile Tyr Glu Glu Gly Val Ser Gly
        675                 680                 685

Glu Arg Leu Leu Leu Asn Thr Val Phe Phe His Pro Glu Val Leu Arg
    690                 695                 700

Lys Lys Val Gln Ala Lys Glu Ala Ser Leu Glu Ala Leu Thr Lys Gly
705                 710                 715                 720

Glu Gln Pro Ser Pro Thr Lys Lys Lys Thr Leu Lys Gln Leu Ser Glu
                725                 730                 735

Gly Cys Glu Tyr Phe Ser Ser Leu Val Ser Lys Ile Asn Ala Leu Lys
            740                 745                 750

Thr Ile Leu Glu Gly Ser Arg Gly Lys Lys Ile Ala Ser Gln Asp Ile
        755                 760                 765

Arg Gln Leu Ile Gly Leu Thr Asp Glu Leu Ala Leu Glu Leu Ser Ser
    770                 775                 780

Phe Gln Gln Asp Ser Leu Glu Ser Leu Leu Tyr Gly Leu Glu Gly Leu
785                 790                 795                 800

Ser Ile Pro Ala Ala Ser Ile Glu Gln Lys Lys Gly Ser Pro Lys Ser
                805                 810                 815

Ser Ser Ile Ala Glu Lys Val Val Tyr Ala Ser His Gln Arg Val His
            820                 825                 830

Asn Gly Val Lys Ala Lys Val Asn Arg Thr Leu Glu Ala Phe Ser Gln
        835                 840                 845

Leu Ile Lys Gly Leu Arg Gly Ser Leu Arg Asn Ala Met Ile Thr Lys
    850                 855                 860

Ala Val Val Ala Ala Val Leu Ser Val Ala Phe Ser Cys Leu Ala Ile
865                 870                 875                 880

Ala Leu Phe Ser Val Gln Leu Thr Trp Leu Pro Ile Met Leu Cys Val
                885                 890                 895

Leu Ala Leu Val Leu Glu Ala Ile Pro Ser Ala Leu Ser Ile Trp Val
            900                 905                 910

Glu Lys Arg Asn Trp Lys Tyr Glu Val Ala Ser Leu Ala Lys Gln Leu
        915                 920                 925

Val Ser Asp Gly Arg Lys Leu Pro Tyr Pro Asp Leu Gly Asp Gln Asn
    930                 935                 940

Ile Lys His Leu Glu Lys Ile Arg Asp Val Tyr Gly Leu Asp Gly Val
945                 950                 955                 960

Ala Glu Leu Arg Val Ala Glu Ala Ala Leu Leu Gly Val Gln Lys Leu
                965                 970                 975

Pro Glu Glu Gln Lys Gln Glu Ser Leu Lys Ser Ala Val Lys Ala Leu
            980                 985                 990

Arg Ala Asp Ala Lys Val Leu Asn  Lys Lys Phe Lys Lys  Leu Pro Glu
        995                 1000                1005
```

-continued

Ser Tyr Gln Pro Gln His Ser Glu Val Thr Gly Val Gln Gly Val
1010 1015 1020

Thr Glu Gln Glu Ser Arg Asp Asp Val Leu Val Ala Gln Asp Met
1025 1030 1035

Ala Ala Ile Glu Glu Leu Gln Asp Gln Tyr His Ala Ala Cys Leu
1040 1045 1050

Gln Phe Glu Ser Val Ser Thr Arg Phe Leu Ala Glu Gln Arg Lys
1055 1060 1065

Ala Lys Phe Leu Glu Glu Leu Leu Val Gln Lys Arg Arg Asp Val
1070 1075 1080

Ser His Leu Ser His Gln Glu Ala His Tyr Thr Gln Val Val Ser
1085 1090 1095

His Leu Lys Glu Leu Ile Ser Met Arg Lys Gly Ala Ser Thr Gln
1100 1105 1110

His Ala Ser Lys Glu Glu Ile Ser Thr Lys Met Arg Glu Leu Leu
1115 1120 1125

Ser Leu Asp Asp Gln Leu Leu Lys Ala His Thr Ala Gln Asp Val
1130 1135 1140

Asn Arg Asp Asn Ser Ile Asn Gly Gln Leu Gln Gln Gln Phe Lys
1145 1150 1155

Lys Leu Ser Glu Glu Gly Ser Leu Gln Lys Val Lys Ala Leu Leu
1160 1165 1170

Glu Leu Asn Met Cys Leu Gly Asn Ala Gly Gln Thr Leu Tyr His
1175 1180 1185

Ser Arg Leu Lys Arg Glu Val Phe Glu Ala Ser Leu Ser Gly Thr
1190 1195 1200

Ser Arg Gln Leu Leu Gln Tyr Gly Glu Asp Leu Phe Ala Ser Tyr
1205 1210 1215

Asp Gly Ser Asp Arg Ser Ala Leu Leu Arg Phe Val Leu Gly Ser
1220 1225 1230

Gly Tyr Glu Met Ile Ser Glu Ala Ser Ser Glu Leu Lys Ser Leu
1235 1240 1245

Arg Lys Arg Trp Lys Arg Ser Ala Ser Gln Ala Ala Ile Ala Pro
1250 1255 1260

Glu Asp Tyr Glu Lys Val Cys Arg Val Leu Glu Arg Phe Leu Lys
1265 1270 1275

Ala Arg Asp Ser Leu Arg Pro Lys Leu Gly Leu Pro Leu Gly Lys
1280 1285 1290

Ser Ser Asp Ala Thr Val Gly Leu Gln His Gln Ile Arg Asp Asn
1295 1300 1305

Gln Arg Val Lys Ala Arg Val Thr Ala Cys Tyr Gln Glu Ser Cys
1310 1315 1320

Arg Asn Val Leu Gln His Leu Glu Asp Trp Val Arg Lys Thr Arg
1325 1330 1335

Gln Glu Ser Ala Glu Cys Gln Lys Val Glu Thr Lys Ile Arg Glu
1340 1345 1350

Phe Cys Gln Lys Ala Gly Ser Lys Glu Asn Leu Ala Glu Ser Thr
1355 1360 1365

Glu Met Leu Phe Ser Ser Leu Glu Glu Asp Leu Asn Lys Ile Pro
1370 1375 1380

Leu Asp Val Leu Arg Ala Ile Leu Arg Ser Leu Ser Ser Lys Val
1385 1390 1395

```
Leu His  Ile Arg Asp Gln Lys  Leu Glu Leu Glu Lys  Leu Glu Glu
    1400                 1405                 1410

Gln Phe  Ala Lys Thr Asn Ala  Ile Val Lys Ala Lys  Glu Ala Glu
    1415                 1420                 1425

Phe Glu  Lys Asn Gly Glu Val  Trp His Asn Gln Tyr  Gln Met Leu
    1430                 1435                 1440

Lys Ser  Gln Met Glu Lys Leu  Glu Ser Gln Lys Arg  Arg Leu Thr
    1445                 1450                 1455

Asp Lys  Lys Glu
    1460


<210> SEQ ID NO 224
<211> LENGTH: 4389
<212> TYPE: DNA
<213> ORGANISM: Chlamydia trachomatis

<400> SEQUENCE: 224

ggtataatac ttccttcaaa aatagttttt caggaaagta tggcgaatcc gtctacaccc     60

tcattcaatc attccgacct ttctttacaa ggtcgtttaa gagcttcaag tcagcaatgt    120

acgcaggctg gacaagggga ccctcaacct ttgagtccag agtccagagg cttgacctca    180

aacttttcta ctcggcgaga tttaattgat gttgtagagg agtctataga gactgctaag    240

ggcagcgagc ttaaaaaact tcgaatatat gagattgctc taaagattct tacaattatt    300

ggagccgcga ttctcttcgc tgttcctctt tgtatgttgc tcggtgtacc tttatggatt    360

cctattgtaa cgtgtatcgg tgtaggaatt gcttttagta tcgccaaagg atgcttacag    420

aaaagatgtc agcagattcg agaagaatat cgtgctctac atctctatca tcgctatcta    480

ctttccaaca aagattccat tgatgggact cttttgagtc gcttcgatat ccgttttcga    540

aaagcggaag agaaattaca cggttagat cttgataaaa gagaggctaa tcatccacta     600

gaagcggaca agagatatga ttttgccggg ttggctcatc aacgctacca ggtggatgca    660

gctcttggaa tctctagtag ccaagacgct ttttggagag ggttgctca gcaggtaaaa     720

tctgttaagg acgatgttgt tttaggggat aaggcgagta cagatctgta cccgatagcg    780

caacaggctc tacaagcagc gggggtaggt ttctctggcg ctgcagggaa agagtctttg    840

ttggatctag caaaatcttt atccagtctg tttgcgtggg gttctcaagt cggcaaagac    900

tctcacgaag ctttacagca atatcaaatg cgctttttaa gtagtcccat cttagctacg    960

tggtgtgggg ctgggtttc cgcatctgct caggattttg ttcttaaagg tgagaatatc    1020

ttagatattg ctagtgaaaa tcatacgaag atgcagaatg ctatcaaacg tgtgcagcta   1080

gtttccgttt taggcaaaat gagaaattgg aaagagaaga ttgataccct aatccaaaac   1140

aaaaatcttg atcaagactc tctacgaaaa ctgtaccaag acattgaaaa agctatgcat   1200

aaggtttgta tcgaagatgg ggtttccact tctatacaga ctcaggtgcg taaggtcaca   1260

caaaaatatt tacgacaaga tttacaagag cttcttaata agaaagcacc attaaatgaa   1320

agcgatcttt ctaaaatgca aaaaggcatt agttcgtgtg ctaatcttgt tgtcacactc   1380

ttagaaagcc agttaggaac ttcggggcag actcctataa aagaagtcga agagagtatt   1440

taccgagact tgatcgctac tattttacaa atgggaagtg cggcaggagg agtgacacca   1500

ttagttgatg gtgtacataa agctattaga gaaggaaaag ctttacgtag cgaacttagc   1560

cgggctatgt ctttacatcc aagacaatct ttcctagggg tgcaatctgc tgtagagaag   1620

ttgcaagcat ttatccgaga tcctaagtgg ggagcatcgg cagtgcatac ctctgctgaa   1680
```

-continued gagactctag cgcaaaaaca gaagtttgtt tctgatctta cgcgcatcca aacgagccta 1740
gcagactgga gagaacgtta cgggctattt gaagagacaa aactgaatca tattgtgtct 1800
acggactttg tatcgagaac agaagctttt ctagataccc tgaaaaacgt tgctgaagca 1860
tgttctctgg agcaagctgt tgcagagctc aaagattgtg aggatgctat gaaagcagat 1920
ctcactcatg ttgagcaaaa aatgaatcct acagagatag agtctgcaag agaagagttt 1980
aagcggttga tggaagagct agctggtatt caagagcagc tagaacagat cgctcaacct 2040
atttatgaag aaggggtaag cggtgaacgt cttctactta atacagtctt ctttcatcca 2100
gaagtattac gtaagaaagt tcaagcaaaa gaagcctcgt tagaggcttt aacaaaaggc 2160
gaacagcctt ctccaacgaa gaagaaaacg ttgaagcagc tttctgaagg atgtgagtac 2220
ttctctagtc ttgtaagcaa gattaatgcg cttaagacaa tattagaagg ttctagaggc 2280
aagaaaattg cgtcccaaga tatacgacag ctgattggat tgactgatga gcttgctcta 2340
gagttgtcct ctttccaaca ggattcttta gagagtttgc tctatggatt agaggggtta 2400
agcattccag ctgcttctat agaacagaag aaaggatctc ctaagtcttc ttctatagca 2460
gagaaggtgg tgtatgcttc tcatcagcgt gtccataatg gggtaaaagc gaaagtgaat 2520
cgcacattag aagcattttc acagctgatc aaaggcttac gaggatcttt acgtaatgcg 2580
atgatcacta aagctgttgt agcggcggtt ctctctgtag ctttttcctg cctagcgatt 2640
gcgctcttct ctgtgcagct tacatggctt cctattatgc tctgcgtttt agctttggta 2700
ttggaagcta tcccttctgc tttatctatt tgggtggaga aaagaaactg gaaatatgag 2760
gttgcctctt tagcgaagca gttagtttcg gatggaagaa agcttcctta tccagatttg 2820
ggggatcaaa atatcaagca tctagagaag attcgagatg tttatgggct ggatggtgtt 2880
gcagaattac gggtagctga agcagcttta ttaggagttc agaaacttcc tgaagagcaa 2940
aaacaagaat ctttaaaaag tgctgttaaa gcattgcggg cggatgcgaa ggttcttaat 3000
aagaaattta agaagcttcc tgagtcatat cagcctcaac actctgaagt cacaggagtc 3060
caaggtgtaa cggaacaaga aagcagggat gacgttttgg tagcacaaga tatggctgcc 3120
atagaagaat tgcaagacca gtatcatgca gcttgcttgc aatttgagtc tgtgagtacg 3180
cgatttttag ccgaacagcg taaagctaag tttctggaag agctgttagt tcaaaaacgt 3240
cgagatgtgt cccatttatc tcatcaagaa gctcattata ctcaagtagt cagtcatttg 3300
aaagagctca tctcaatgag aaagggagca tctactcaac acgcttctaa agaagagatt 3360
tctacaaaaa tgagagagct gttgtcttta gatgatcaac ttctaaaagc tcatacagct 3420
caagatgtga accgggataa tagcataaac ggtcaactgc aacagcagtt taaaaagtta 3480
tctgaagaag gaagcctaca aaaagtaaaa gctctgctag aactaaatat gtgtttaggt 3540
aatgctgggc aaacccttta tcattcaagg ctaaagagag aggttttcga agcatctctc 3600
tctggaacct ctcggcaact tcttcaatac ggtgaagatc tgtttgcatc ttacgatgga 3660
agtgatcgat cggctcttct acggtttgtt ttaggatccg gatatgagat gatcagtgag 3720
gccagctctg agctgaagtc tctacgcaaa cgttggaaaa gaagcgcttc tcaagccgca 3780
attgctcctg aagattatga gaaagtctgc agagtgttag aacgttttct taaagcgcga 3840
gacagtctgc gtccgaagtt aggcttacct cttggtaaga gctcagatgc taccgttggt 3900
ttacaacatc aaatacgaga taatcaacga gttaaagctc gagtaaccgc ttgttaccaa 3960
gagagttgca gaaatgtttt acagcattta gaagattggg tgcggaaaac gcgacaggag 4020
tcggcagaat gtcaaaaagt agaaacaaaa atacgcgagt tctgccaaaa agccggatct 4080

```
aaggagaatc ttgctgaatc tacagagatg ctattttcta gcttagaaga agatttgaat   4140

aaaatacctc tagatgtttt gcgtgctatt ttacgatctt tgtcttctaa agttcttcat   4200

attagggatc aaaagttaga acttgaaaag ttagaagagc agtttgcgaa gacaaatgct   4260

attgtaaaag ccaaggaagc tgagttcgag aagaatgggg aagtgtggca taatcagtat   4320

cagatgctaa aaagtcagat ggagaagctg gagtctcaga aaagaagact gacagataag   4380

aaagaataa                                                           4389


<210> SEQ ID NO 225
<211> LENGTH: 200
<212> TYPE: PRT
<213> ORGANISM: Chlamydia trachomatis

<400> SEQUENCE: 225

Lys Cys Gly Lys Met Ser Thr Thr Ile Ser Gly Asp Ala Ser Ser Leu
1               5                   10                  15

Pro Leu Pro Thr Ala Ser Cys Val Glu Ile Lys Ser Thr Ser Ser Ser
            20                  25                  30

Thr Lys Gly Asn Thr Cys Ser Lys Ile Leu Asp Ile Ala Leu Ala Ile
        35                  40                  45

Val Gly Ala Leu Val Val Val Ala Gly Val Leu Ala Leu Val Leu Cys
    50                  55                  60

Ala Ser Asn Val Ile Phe Thr Ala Ile Gly Ile Ala Ala Leu Ile Ile
65                  70                  75                  80

Gly Ser Ala Cys Val Gly Ala Gly Ile Ser Arg Leu Met Cys Arg Ser
                85                  90                  95

Ser Tyr Ala Ser Leu Glu Ala Lys Asn Val Leu Ala Glu Gln Arg Leu
            100                 105                 110

Arg Asn Leu Ser Glu Glu Lys Asp Ala Leu Val Ser Val Ser Phe Ile
        115                 120                 125

Asn Lys Met Phe Leu Arg Gly Leu Thr Asp Asp Leu Gln Ala Leu Glu
    130                 135                 140

Ala Lys Ala Ile Glu Val Glu Ile Asp Cys Leu Asp Arg Leu Glu Lys
145                 150                 155                 160

Asn Glu Gln Ala Leu Leu Ser Asp Val Arg Leu Val Leu Ser Ser Tyr
                165                 170                 175

Thr Arg Trp Leu Asp Ser Ala Glu Lys Glu Lys Ala Ala Leu Lys Ala
            180                 185                 190

Ser Ile Asp Ala Asn Gln Ala Ser
        195                 200


<210> SEQ ID NO 226
<211> LENGTH: 603
<212> TYPE: DNA
<213> ORGANISM: Chlamydia trachomatis

<400> SEQUENCE: 226

ctaagaagct tggttagcgt ctatagatgc tttaagagca gctttttcct tttcagcact     60

atccaaccat cttgtgtagc tagataaaac taagcgcaca tcggacaata aagcttgctc    120

atttttctct aatctgtcca aacaatcaat ctcaacttct attgccttag cttccaaagc    180

ttggagatcg tccgtaagac ctcgcagaaa catcttatta atgaaagaga cggagaccaa    240

agcgtccttc tcttctgaaa gattacgcaa acgttgctca gccaaaacat tttttgcttc    300

taagctagca taagaggatc gacacataag acgagatatt cccgcaccca cacaagcaga    360
```

-continued

```
tccaataatt aatgcagcaa tacctattgc agtaaatatg acattgctag cgcacaaaac    420

caaagctaat accccagcga caacaactaa agcgcctacg atagctaaag ctatatccaa    480

aattttggaa caagtattcc cttttgttga agacgaagta gattttatct ctacgcagga    540

agctgttggc aatggtaaag aagaagcgtc tccgctaata gtagtactca tttttccaca    600

ttt                                                                  603


<210> SEQ ID NO 227
<211> LENGTH: 120
<212> TYPE: PRT
<213> ORGANISM: Chlamydia trachomatis

<400> SEQUENCE: 227

Phe Thr Glu Gly Asn Met Val His Ser Val Tyr Asn Ser Leu Ala Pro
1               5                   10                  15

Glu Gly Phe Ser Gln Val Ser Ile Gln Pro Ser Gln Ile Pro Thr Ser
            20                  25                  30

Lys Lys Val Met Ile Ala Ile Met Thr Leu Phe Ala Leu Thr Ala Ile
        35                  40                  45

Ala Ala Ile Val Leu Ser Ile Val Thr Val Cys Gly Gly Phe Pro Phe
    50                  55                  60

Leu Leu Ala Ala Leu Asn Thr Val Thr Ile Gly Ala Cys Val Ser Leu
65                  70                  75                  80

Pro Val Phe Thr Cys Ile Ala Thr Thr Leu Leu Leu Leu Cys Leu Arg
                85                  90                  95

Asn Ile Glu Leu Leu Ala Arg Pro Gln Val Phe Thr Leu Ser Thr Gln
            100                 105                 110

Phe Ser Pro Thr Lys Pro Gln Glu
        115                 120


<210> SEQ ID NO 228
<211> LENGTH: 363
<212> TYPE: DNA
<213> ORGANISM: Chlamydia trachomatis

<400> SEQUENCE: 228

ttcacagagg gaaatatggt tcattctgta tacaattcat tggctccaga aggttttagc     60

caagtctcta ttcaacccag tcagattcca accagcaaaa aagtaatgat tgcgataatg    120

actcttttg cactcacagc cattgcagca atagtccttt ccatcgttac agtttgtgga    180

gggtttcctt ttcttcttgc tgcacttaac accgtaacta ttggtgcatg cgtatccttg    240

ccggtattca cttgcatagc tacaacgtta ttacttcttt gtctccgtaa tatcgaactc    300

ctagccagac cgcaagtatt taccctctcc actcaattca gcccaacaaa acctcaagaa    360

tag                                                                  363


<210> SEQ ID NO 229
<211> LENGTH: 130
<212> TYPE: PRT
<213> ORGANISM: Chlamydia trachomatis

<400> SEQUENCE: 229

Ser Cys Cys Leu Gln Gly Val Leu Leu Tyr Arg Leu Asp Ile Ala Asp
1               5                   10                  15

Phe Arg Val Trp Val Ser Ile Gly Val Ser Glu Gln Glu Arg His Tyr
            20                  25                  30
```

Pro Gln Pro Val Leu Val Ser Leu Ser Leu Phe Phe Lys Glu Glu Pro
35 40 45

Lys Ala Cys Ser Thr Asp Lys Val Ser Asp Ser Val Cys Tyr Ala Glu
50 55 60

Leu Val Ser Leu Ile Glu Glu Val Ala Thr Asn Asn Pro Cys Ala Leu
65 70 75 80

Ile Glu Arg Leu Ala Lys Val Leu Leu Glu Lys Ile Glu Lys Ala Leu
85 90 95

Ala Gly Gln Val Ser Arg Ile Asp Leu Arg Val Ser Lys Glu Arg Pro
100 105 110

Pro Ile Pro Asp Leu Leu Ser Pro Val Ser Phe Ser Ile Ser Arg Glu
115 120 125

Val Pro
130

<210> SEQ ID NO 230
<211> LENGTH: 393
<212> TYPE: DNA
<213> ORGANISM: Chlamydia trachomatis

<400> SEQUENCE: 230
tcatggcacc tctctactta tgctgaaact tacaggactg agtagatctg ggatcggagg 60
acgctcttta cttactcgca agtcaatcct agaaacttgt ccagccaaag ccttttctat 120
tttttccagc aaaaccttag ctaaacgttc aattaaagca caaggattat tcgttgcaac 180
ttcttcaata agagaaacaa gctctgcata acacacgcta tcagagactt tgtccgtgga 240
acaagccttt ggctcttctt taaaaaaaag agataaagaa acaagaacgg gctgcggata 300
atgccgttct tgttctgaga ctcctataga tacccaaacg cgaaaatccg ctatatctaa 360
acgatacaac aacactcctt gtaggcagca aga 393

<210> SEQ ID NO 231
<211> LENGTH: 569
<212> TYPE: PRT
<213> ORGANISM: Chlamydia trachomatis

<400> SEQUENCE: 231

Met Pro Lys Gln Ala Asp Tyr Thr Trp Gly Ala Lys Lys Asn Leu Asp
1 5 10 15

Thr Ile Ala Cys Leu Pro Glu Asp Val Lys Gln Phe Lys Asp Leu Leu
20 25 30

Tyr Ala Met Tyr Gly Phe Thr Ala Thr Glu Glu Glu Pro Thr Ser Glu
35 40 45

Val His Pro Gly Ala Ile Leu Lys Gly Thr Val Val Asp Ile Ser Lys
50 55 60

Asp Phe Val Val Val Asp Val Gly Leu Lys Ser Glu Gly Val Ile Pro
65 70 75 80

Met Ser Glu Phe Ile Asp Ser Ser Glu Gly Leu Thr Val Gly Ala Glu
85 90 95

Val Glu Val Tyr Leu Asp Gln Thr Glu Asp Asp Glu Gly Lys Val Val
100 105 110

Leu Ser Arg Glu Lys Ala Thr Arg Gln Arg Gln Trp Glu Tyr Ile Leu
115 120 125

Ala His Cys Glu Glu Gly Ser Ile Val Lys Gly Gln Ile Thr Arg Lys
130 135 140

Val Lys Gly Gly Leu Ile Val Asp Ile Gly Met Glu Ala Phe Leu Pro

-continued

```
145                 150                 155                 160

Gly Ser Gln Ile Asp Asn Lys Lys Ile Lys Asn Leu Asp Asp Tyr Val
                165                 170                 175

Gly Lys Val Cys Glu Phe Lys Ile Leu Lys Ile Asn Val Asp Arg Arg
            180                 185                 190

Asn Val Val Val Ser Arg Arg Glu Leu Leu Glu Ala Glu Arg Ile Ser
        195                 200                 205

Lys Lys Ala Glu Leu Ile Glu Gln Ile Thr Ile Gly Glu Arg Arg Lys
    210                 215                 220

Gly Ile Val Lys Asn Ile Thr Asp Phe Gly Val Phe Leu Asp Leu Asp
225                 230                 235                 240

Gly Ile Asp Gly Leu Leu His Ile Thr Asp Met Thr Trp Lys Arg Ile
                245                 250                 255

Arg His Pro Ser Glu Met Val Glu Leu Asn Gln Glu Leu Glu Val Ile
            260                 265                 270

Ile Leu Ser Val Asp Lys Glu Lys Gly Arg Val Ala Leu Gly Leu Lys
        275                 280                 285

Gln Lys Glu His Asn Pro Trp Glu Asp Ile Glu Lys Lys Tyr Pro Pro
    290                 295                 300

Gly Lys Arg Val Arg Gly Lys Ile Val Lys Leu Leu Pro Tyr Gly Ala
305                 310                 315                 320

Phe Ile Glu Ile Glu Glu Gly Ile Glu Gly Leu Ile His Val Ser Glu
                325                 330                 335

Met Ser Trp Val Lys Asn Ile Val Asp Pro Asn Glu Val Val Asn Lys
            340                 345                 350

Gly Asp Glu Val Glu Val Val Val Leu Ser Ile Gln Lys Asp Glu Gly
        355                 360                 365

Lys Ile Ser Leu Gly Leu Lys Gln Thr Lys His Asn Pro Trp Asp Asn
    370                 375                 380

Ile Glu Glu Lys Tyr Pro Ile Gly Leu Arg Val Thr Ala Glu Ile Lys
385                 390                 395                 400

Asn Leu Thr Asn Tyr Gly Ala Phe Val Glu Leu Glu Pro Gly Ile Glu
                405                 410                 415

Gly Leu Ile His Ile Ser Asp Met Ser Trp Ile Lys Lys Val Ser His
            420                 425                 430

Pro Ser Glu Leu Phe Lys Lys Gly Asn Thr Val Glu Ala Val Ile Leu
        435                 440                 445

Ser Val Asp Lys Glu Ser Lys Lys Ile Thr Leu Gly Val Lys Gln Leu
    450                 455                 460

Thr Pro Asn Pro Trp Asp Glu Ile Glu Val Met Phe Pro Val Gly Ser
465                 470                 475                 480

Asp Ile Ser Gly Val Val Thr Lys Ile Thr Ala Phe Gly Ala Phe Val
                485                 490                 495

Glu Leu Gln Asn Gly Ile Glu Gly Leu Ile His Val Ser Glu Leu Ser
            500                 505                 510

Glu Lys Pro Phe Ala Lys Ile Glu Asp Val Leu Ser Ile Gly Asp Lys
        515                 520                 525

Val Ser Ala Lys Val Ile Lys Leu Asp Pro Asp His Lys Lys Val Ser
    530                 535                 540

Leu Ser Ile Lys Glu Phe Leu Val His Gly Gly Asp Ala Gly His Asp
545                 550                 555                 560

Ala Glu Glu Glu Ser Ser Asp Arg Asp
                565
```

<210> SEQ ID NO 232
<211> LENGTH: 1710
<212> TYPE: DNA
<213> ORGANISM: Chlamydia trachomatis

<400> SEQUENCE: 232
ctagtctctg tcagaagatt cttcttccgc atcgtgacca gcatctcccc catgaacaag 60
gaactcttta atagaaagag aaactttctt gtgatctggg tctagcttga taactttagc 120
agaaactttg tctccaatag agagaacatc ttcaatttta gcaaaaggtt tctctgaaag 180
ctcggataca tggatcagtc cttcgatacc attttgcaac tcaacgaaag ctccgaaagc 240
cgtaatttta gttactacgc cagagatatc acttccgaca gggaacataa cttcaatctc 300
atcccatgga ttaggagtta attgtttcac gcccaaagtg atttttttgc tttctttgtc 360
tacagacaga ataactgctt cgacggtatt accttttttg aagagctctg aaggatggga 420 aacttttta atccaactca tgtcagagat atggatcaaa ccttcgattc ctggctccaa 480
ctcaacgaaa gctccgtagt ttgtcagatt tttaatttct gctgttacgc ggaggccgat 540
aggatatttt tcttcaatgt tatcccaagg attgtgtttt gtttgtttga gaccgagaga 600
gatttttcct tcatcttttt ggatagaaag aacaactact tcgacttcat cacctttgtt 660
gaccacttca ttaggatcta caatgttctt aacccaagac atctctgaaa cgtgaataag 720
gccttcaatt ccttcttcga tttcaataaa tgctccataa ggaaggagtt taacaatttt 780
tccgcgaaca cgttttcctg gaggatattt cttctcaata tcttcccaag gattatgctc 840
tttttgtttg aggccaagag ctacgcgacc tttttcttta tcaacgctaa ggatgatgac 900
ttccaattct tggttgagtt caaccatttc ggatgggtga cgaatgcgtt tccatgtcat 960
gtctgtaatg tggagtaggc cgtcaatgcc atcaagatcc aagaatactc cgaaatctgt 1020
gatattctta acgatacctt tgcgacgctc accgatagtg atttgctcga tcaactctgc 1080
tttcttagaa atgcgttcag cttcgagaag ttctcttcta gatacaacaa cgttccgacg 1140
atctacgttg attttgagaa ttttgaactc acaaaccttg cctacgtaat catctaagtt 1200
cttgatcttc ttattgtcta tttgggatcc tggaaggaag gcttccatac caatatctac 1260
gatcaaacca cccttaactt ttcgggtaat ttgtccctta acaatagaac cttcctcgca 1320
gtgagcaaga atgtattccc attgtcgttg tcttgttgct ttttctctgg ataaaacaac 1380
ttttccttcg tcatcctcag tttggtctag gtaaacttcg acttcggctc cgacagttaa 1440
accttctgaa gagtcgataa actcagacat aggaataact ccctcagatt ttaagccgac 1500
atctacaaca acaaagtctt tgcttatgtc aacaactgta ccttttagga tcgcaccagg 1560
atgtacttcg ctagtgggtt cttcttctgt cgcggtgaag ccatacatcg cgtagagaag 1620
gtctttaaat tgtttaacgt cttctggtaa gcaagctatc gtatcgagat tctttttgc 1680 tccccaagta taatcagctt gttttggcat 1710

<210> SEQ ID NO 233
<211> LENGTH: 334
<212> TYPE: PRT
<213> ORGANISM: Chlamydia trachomatis

<400> SEQUENCE: 233

Leu Phe Phe Ile Arg Arg Glu Arg Ala Thr Val Glu Leu Leu Pro His
1 5 10 15

Glu Lys Gln Val Val Glu Tyr Glu Lys Thr Ile Ala Glu Phe Lys Glu

-continued

```
            20                  25                  30

Lys Asn Lys Glu Asn Ser Leu Leu Ser Ser Ser Glu Ile Gln Lys Leu
        35                  40                  45

Asp Lys Arg Leu Asp Arg Leu Lys Glu Lys Ile Tyr Ser Asp Leu Thr
    50                  55                  60

Pro Trp Glu Arg Val Gln Ile Cys Arg His Pro Ser Arg Pro Arg Thr
65                  70                  75                  80

Val Asn Tyr Ile Glu Gly Met Cys Glu Glu Phe Val Glu Leu Cys Gly
                85                  90                  95

Asp Arg Thr Phe Arg Asp Asp Pro Ala Val Val Gly Gly Phe Ala Lys
            100                 105                 110

Ile Gln Gly Gln Arg Phe Met Leu Ile Gly Gln Glu Lys Gly Cys Asp
        115                 120                 125

Thr Lys Ser Arg Met His Arg Asn Phe Gly Met Leu Cys Pro Glu Gly
    130                 135                 140

Phe Arg Lys Ala Leu Arg Leu Ala Lys Met Ala Glu Lys Phe Gly Leu
145                 150                 155                 160

Pro Ile Ile Phe Leu Val Asp Thr Pro Gly Ala Phe Pro Gly Leu Thr
                165                 170                 175

Ala Glu Glu Arg Gly Gln Gly Trp Ala Ile Ala Thr Asn Leu Phe Glu
            180                 185                 190

Leu Ala Arg Leu Ala Thr Pro Ile Ile Val Ile Val Ile Gly Glu Gly
        195                 200                 205

Cys Ser Gly Gly Ala Leu Gly Met Ala Ile Gly Asp Val Val Ala Met
    210                 215                 220

Leu Glu His Ser Tyr Tyr Ser Val Ile Ser Pro Glu Gly Cys Ala Ser
225                 230                 235                 240

Ile Leu Trp Lys Asp Pro Lys Lys Asn Ser Asp Ala Ala Ala Met Leu
                245                 250                 255

Lys Met His Gly Glu Asp Leu Lys Gly Phe Ala Ile Val Asp Ala Val
            260                 265                 270

Ile Lys Glu Pro Ile Gly Gly Ala His His Asn Pro Ala Ala Thr Tyr
        275                 280                 285

Arg Ser Val Gln Glu Tyr Val Leu Gln Glu Trp Leu Lys Leu Lys Asp
    290                 295                 300

Leu Pro Val Glu Glu Leu Leu Glu Lys Arg Tyr Gln Lys Phe Arg Thr
305                 310                 315                 320

Ile Gly Leu Tyr Glu Thr Ser Ser Glu Ser Asp Ser Glu Ala
                325                 330


<210> SEQ ID NO 234
<211> LENGTH: 1005
<212> TYPE: DNA
<213> ORGANISM: Chlamydia trachomatis

<400> SEQUENCE: 234

ttatgcctca gaatcgcttt cagaagaagt ttcatataga cctatcgttc ggaatttctg      60

atatcgtttt tctagcaact cttctaccgg taaatctttc aatttaagcc attcttgaag     120

gacatattct tgaacactac gatatgtggc cgcaggattg tgatgagccc cacctatggg     180

ttctttgatc actgcgtcca caatagcaaa tcccttaaga tcctctccat gcatttttaa     240

catggcagca gcatcgctgt tctttttagg atctttccat aaaatagaag cacacccttc     300

aggagaaatt acagaataat acgagtgttc tagcatcgct acaacatctc ctatagccat     360
```

-continued

```
tcctagagcg cctcctgaac atccttcacc aatcacaatt acaatgattg gggtagctaa    420

tctagctaac tcaaataagt ttgtcgcaat agcccaacct tgacctcttt cttcggctgt    480

taatccaggg aaagctccag gggtatcaac gagaaagata attggcaaac cgaatttctc    540

tgccatttta gctaagcgta gagcctttct aaagccttcg ggacaaagca tcccgaagtt    600

acgatgcatg cgagattttg tgtcgcaacc cttttcttgc cctataagca tgaaacgctg    660

cccttgaatc tttgcgaacc ctccgacaac tgcaggatca tctcggaacg ttcgatctcc    720

acaaagttct acaaactctt cgcacattcc ttcgatataa ttcactgttc taggtctcga    780

aggatgtcga caaatttgta ctctttccca aggggtgaga tcggaataaa tttttttcttt   840

taatctatct aaacgcttat ccaatttttg aatctctgaa gaagaaagca ggctgttttc    900

tttatttttt tctttaaact cggcgatcgt tttttcgtat tcgacaacct gtttttcatg    960

aggaagtagt tccaccgtag cacgctccct tcttataaaa aagag                   1005


<210> SEQ ID NO 235
<211> LENGTH: 355
<212> TYPE: PRT
<213> ORGANISM: Chlamydia trachomatis

<400> SEQUENCE: 235

Gly Ile Phe Met His Ile Ala Val Leu Gly Ala Gly Tyr Ala Gly Leu
1               5                   10                  15

Ser Val Thr Trp His Leu Leu Leu Tyr Thr Gln Gly Arg Ile Ser Val
            20                  25                  30

Asp Leu Phe Asp Pro Thr Pro Ile Gly Ser Gly Ala Ser Gly Leu Ser
        35                  40                  45

Ser Gly Leu Leu His Gly Phe Thr Gly Lys Lys Ala Ile Lys Pro Pro
    50                  55                  60

Leu Ala Asn Leu Gly Ile Thr Thr Thr His Ser Leu Ile Thr Lys Ala
65                  70                  75                  80

Ser Leu Ser Ile Gly Glu Pro Ile Val Thr Ser Asn Gly Ile Leu Arg
                85                  90                  95

Pro Ala Ala Ser Gln Glu Gln Ala Thr Ile Phe Met Gln Arg Ala Gln
            100                 105                 110

Glu Phe Pro Asp Glu Thr Glu Trp Trp Asp Lys Ala Arg Cys Glu Ile
        115                 120                 125

Thr Val Pro Gly Met Val Ile Ala Asp Gly Leu Gly Ala Leu Tyr Ile
    130                 135                 140

Lys His Gly Val Thr Ile Asp Asn Asp Lys Tyr Ile Ser Gly Leu Trp
145                 150                 155                 160

Asn Ala Cys Ala Ser Leu Gly Thr Gln Tyr Tyr Asp Glu Leu Ile Asp
                165                 170                 175

Asp Ile Ser Ala Ile Ala Glu Phe Tyr Asp His Ile Ile Val Thr Pro
            180                 185                 190

Gly Ala Asn Ala Asp Ile Leu Pro Glu Leu Lys His Leu Pro Leu Ser
        195                 200                 205

Lys Val Lys Gly Gln Leu Val Glu Ile Ala Trp Pro Ala Glu Ile Pro
    210                 215                 220

Met Pro Pro Phe Ser Ile Asn Gly Pro Lys Tyr Met Val Ala Asp Thr
225                 230                 235                 240

Thr Arg Asn Thr Cys Ile Leu Gly Ala Thr Phe Glu His Asn Gln Pro
                245                 250                 255

Asp Ala Thr Pro Asp Ala Gln Val Ala Tyr Gln Glu Ile Met Pro Pro
```

```
            260                 265                 270

Ile Leu Ala Leu Phe Pro Gly Leu Lys Asp Ala Gln Val Leu Asn Tyr
        275                 280                 285

Tyr Ala Gly Met Arg Ser Ser Ser Pro Thr His Leu Pro Met Ile Ser
    290                 295                 300

Arg Val Gln Glu Lys Leu Trp Tyr Leu Gly Gly Leu Gly Ser Lys Gly
305                 310                 315                 320

Leu Leu Tyr His Gly Leu Leu Gly Asp Met Leu Ala Gln Ala Leu Leu
                325                 330                 335

Arg Asp Ser Thr Ala Tyr Ile Ala Lys Glu Phe Leu Tyr Thr Pro Glu
            340                 345                 350

Gly Ala Ala
        355


<210> SEQ ID NO 236
<211> LENGTH: 1068
<212> TYPE: DNA
<213> ORGANISM: Chlamydia trachomatis

<400> SEQUENCE: 236

ggtattttta tgcacatagc ggttttggga gcgggatacg caggattatc tgtgacttgg      60

catcttctcc tttatacaca aggacgaatt agcgttgatc tctttgaccc aacccctatt     120

ggatctggag cctcaggcct atcttctggc cttcttcatg gctttacagg gaaaaaagct     180

atcaagcctc cgctagcaaa tctagggatc accacaaccc attctctcat taccaaagcg     240

agcctttcta taggggagcc catcgtgaca tccaatggga tcctccgtcc tgcagcctct     300

caggaacagg ccactatttt catgcaaaga gcacaggagt tccccgatga aacggagtgg     360

tgggataaag ctcggtgtga aattacagtt cctggaatgg tcattgccga tggactcgga     420

gccctttaca ttaaacatgg ggtaaccatt gataatgata aatatatcag cggtttatgg     480

aatgcctgtg ctagccttgg aacacaatat tacgatgagc tgatcgatga catttcagca     540

atcgctgagt tttatgatca cattattgta actcctggag cgaacgcaga tattctccct     600

gagcttaaac accttcccct atctaaagta aaaggtcagc tcgtagaaat tgcttggcca     660

gctgagatcc ctatgccacc attcagcatc aatggcccta aatatatggt tgctgataca     720

acaagaaata cttgtatatt gggagcaact ttcgagcaca accaaccaga tgccactcca     780

gatgctcaag ttgcctatca ggaaatcatg cctccgatcc tagctctttt ccctggactt     840

aaagacgctc aagtccttaa ttattacgct ggtatgcgct catcgagccc cactcattta     900

cccatgatca gtcgcgtaca agaaaaattg tggtatttag gaggtttggg atccaaaggt     960

cttctatacc atgggctttt aggagatatg ctcgcccagg ctctattacg ggattccacg    1020

gcatatatag ctaaggagtt tctctacact ccagagggag cagcctaa                 1068


<210> SEQ ID NO 237
<211> LENGTH: 490
<212> TYPE: PRT
<213> ORGANISM: Chlamydia trachomatis

<400> SEQUENCE: 237

Asn Asn Met Gly Ile Ala His Thr Glu Trp Glu Ser Val Ile Gly Leu
1               5                   10                  15

Glu Val His Val Glu Leu Asn Thr Glu Ser Lys Leu Phe Ser Pro Ala
            20                  25                  30

Arg Asn His Phe Gly Asp Glu Pro Asn Thr Asn Ile Ser Pro Val Cys
```

-continued

```
        35                  40                  45

Thr Gly Met Pro Gly Ser Leu Pro Val Leu Asn Lys Asp Ala Val Arg
    50                  55                  60

Lys Ala Val Leu Phe Gly Cys Ala Val Glu Gly Asp Val Ala Leu Phe
65                  70                  75                  80

Ser Arg Phe Asp Arg Lys Ser Tyr Phe Tyr Pro Asp Ser Pro Arg Asn
                85                  90                  95

Phe Gln Ile Thr Gln Tyr Glu His Pro Ile Val Arg Gly Gly Cys Ile
            100                 105                 110

Arg Ala Val Val Glu Gly Glu Glu Lys Thr Phe Glu Leu Ala Gln Thr
        115                 120                 125

His Leu Glu Asp Asp Ala Gly Met Leu Lys His Phe Gly Asp Phe Ala
    130                 135                 140

Gly Val Asp Tyr Asn Arg Ala Gly Val Pro Leu Ile Glu Ile Val Ser
145                 150                 155                 160

Lys Pro Cys Met Phe Ser Ala Glu Asp Ala Val Ala Tyr Ala Asn Ala
                165                 170                 175

Leu Val Ser Ile Leu Gly Tyr Ile Gly Ile Ser Asp Cys Asn Met Glu
            180                 185                 190

Glu Gly Ser Ile Arg Phe Asp Val Asn Ile Ser Val Arg Pro Arg Gly
        195                 200                 205

Ser Arg Glu Leu Arg Asn Lys Val Glu Ile Lys Asn Met Asn Ser Phe
    210                 215                 220

Thr Phe Met Ala Gln Ala Leu Glu Ala Glu Lys Arg Arg Gln Ile Glu
225                 230                 235                 240

Glu Tyr Leu Ser Tyr Pro Asn Glu Asp Pro Lys Lys Val Val Pro Ala
                245                 250                 255

Ala Thr Tyr Arg Trp Asp Pro Glu Lys Lys Lys Thr Val Leu Met Arg
            260                 265                 270

Leu Lys Glu Arg Ala Glu Asp Tyr Met Tyr Phe Val Glu Pro Asp Leu
        275                 280                 285

Pro Val Leu Gln Ile Thr Glu Thr Tyr Ile Asp Glu Val Arg Gln Thr
    290                 295                 300

Leu Pro Glu Leu Pro His Ser Lys Tyr Met Arg Tyr Ile Thr Asp Phe
305                 310                 315                 320

Asp Ile Ala Glu Asp Leu Ala Met Ile Leu Val Gly Asp Arg His Thr
                325                 330                 335

Ala His Phe Phe Glu Thr Ala Thr Met Ser Cys Lys Asn Tyr Arg Ala
            340                 345                 350

Leu Ser Asn Trp Ile Thr Val Glu Phe Ala Gly Arg Cys Lys Ala Arg
        355                 360                 365

Gly Lys Thr Leu Pro Phe Thr Gly Ile Leu Pro Glu Trp Val Ala Gln
    370                 375                 380

Leu Val Asn Phe Ile Asp Arg Gly Val Ile Thr Gly Lys Ile Ala Lys
385                 390                 395                 400

Glu Ile Ala Asp Arg Met Val Ser Ser Phe Gly Glu Ser Pro Glu Asp
                405                 410                 415

Ile Leu Arg Arg His Pro Ser Leu Leu Pro Met Thr Asp Asp His Ala
            420                 425                 430

Leu Arg Ala Ile Val Lys Glu Val Val Ala Gln Asn Thr Ala Ser Val
        435                 440                 445

Ala Asp Tyr Lys Asn Gly Lys Ala Lys Ala Leu Gly Phe Leu Val Gly
    450                 455                 460
```

Gln Ile Met Lys Arg Thr Glu Gly Lys Ala Pro Pro Lys Arg Val Asn
465 470 475 480

Glu Leu Leu Leu Ala Ala Met Arg Asp Met
485 490

<210> SEQ ID NO 238
<211> LENGTH: 1473
<212> TYPE: DNA
<213> ORGANISM: Chlamydia trachomatis

<400> SEQUENCE: 238
aataatatgg gcatagcaca tactgaatgg gagtctgtga tcggtctgga agttcacgtt 60
gaattgaata ccgaatccaa attatttagt cccgcacgta atcattttgg tgatgaaccc 120
aacacgaaca tttctcctgt atgcacaggg atgccaggat ctcttccggt cttgaataag 180
gatgctgtgc gtaaagctgt tttgttcggc tgcgctgtag agggggatgt cgctttattt 240
agccgttttg atagaaaatc ctatttttat cctgacagcc caagaaactt tcagatcacc 300
caatacgagc atcctatcgt aagaggtgga tgtattcgtg ctgtagtaga aggagaagag 360
aaaacctttg agctagcgca gacacatcta gaagatgatg cggggatgtt aaaacatttt 420 ggggatttg ctggtgtaga ctataacaga gcaggggttc cgttaattga gattgtttcc 480
aagccttgta tgtttagtgc agaggatgct gttgcatacg ccaatgcttt ggtatccatc 540
ctcggctaca taggtatttc cgattgtaat atggaagaag gttctatccg tttcgatgtg 600
aatatttctg ttcgccctcg aggaagtagg gagcttagaa ataaggtaga gatcaaaaac 660
atgaactcat ttacctttat ggcacaagct ttggaagctg aaaaacgtcg tcagattgaa 720
gagtatctta gctatcccaa tgaggatcca aaaaaagttg ttcctgcagc gacttatcgt 780
tgggatcctg aaaagaaaaa aacggttctg atgcgtctca aggaacgagc cgaagattat 840
atgtattttg tagagccgga tcttcctgtt ttgcagatca ccgagactta tattgatgag 900
gtgcgtcaaa cattaccaga gctacctcat agtaaatata tgcgttacat tacagacttt 960
gatatcgctg aagatttagc aatgattctt gttggtgatc gacatacggc tcatttcttt 1020
gaaacagcaa ctatgtcttg taagaactat cgtgctcttt cgaattggat cacagtcgaa 1080
tttgcgggcc gttgtaaagc tagagggaag acgctgccat tcacggggat tcttcctgaa 1140
tgggtagcgc aattggtgaa cttcatagat cgtggagtga tcacagggaa aatcgctaaa 1200
gaaattgcag atagaatggt ctcttctttt ggggaaagcc cagaagatat tttgcgtaga 1260
catccttcgt tgttacctat gacggacgac catgcgctac gcgctatcgt taaagaggtg 1320
gttgctcaaa ataccgcgtc tgtagcggat tacaagaacg ggaaagctaa agctttgggc 1380
tttttggttg gacagatcat gaagcgaaca gaagggaaag ctcctcctaa gcgagtaaac 1440
gaattgctat tagcagctat gcgagatatg taa 1473

<210> SEQ ID NO 239
<211> LENGTH: 121
<212> TYPE: PRT
<213> ORGANISM: Chlamydia trachomatis

<400> SEQUENCE: 239

Pro Tyr Val Ser Trp Met Ser Met Ala Ser Lys Lys Gln Thr Ser Trp
1 5 10 15

Phe Arg Tyr Met Glu Glu Cys Val Ile Arg Ser Trp Trp Leu Ile Leu
20 25 30

Cys Leu Leu Gly Gly Gly Phe Val Tyr Asp Arg Ala Ile Ser Gln Leu
35 40 45

Cys Thr Gln Glu Leu Arg Leu Gln Gln Arg Met Phe His Leu Lys Ser
50 55 60

His Leu Lys Glu Ala Leu Glu Lys Gln Gln Glu Leu Ser Thr His Leu
65 70 75 80

Ala Ser Trp Asp Asp Pro Lys Val Ile Glu Leu Ala Leu Ile His Lys
85 90 95

Leu Gly Leu Val Pro Lys Gly Tyr Glu Lys Ile Cys Phe Gln Asn Ser
100 105 110

Gln Lys Thr Lys Arg Asn His Arg Lys
115 120

<210> SEQ ID NO 240
<211> LENGTH: 366
<212> TYPE: DNA
<213> ORGANISM: Chlamydia trachomatis

<400> SEQUENCE: 240
ttattttcga tgatttcttt tcgtttttttg agagttctgg aagcagattt tttcataacc 60
tttaggcacc aaacctagtt tatgaataag tgctagctca ataactttcg gatcatccca 120
agaagctaga tgggtgctca actcttgctg tttctcgaga gcttctttta aatgggattt 180
taaatgaaac atgcgctgct gtaatcgcag ctcttgtgta catagttggg agatggctct 240
gtcatagaca aaaccacctc caagaagaca aagaataagc caccaagaac gaatgacaca 300
ttcttccata tacctgaacc aagaagtctg tttcttactt gccatactca tccaggaaac 360
ataggg 366

<210> SEQ ID NO 241
<211> LENGTH: 342
<212> TYPE: PRT
<213> ORGANISM: Chlamydia trachomatis

<400> SEQUENCE: 241

Ile Thr Thr Ile Ala Asn Thr Tyr Met Thr His Lys Ile Ser Val Leu
1 5 10 15

His Gln Asp Lys Lys Phe Asp Phe Ser Leu Arg Pro Lys Lys Leu Thr
20 25 30

Glu Phe Cys Gly Gln Lys Gln Leu Lys Glu Arg Leu Asp Leu Phe Leu
35 40 45

Arg Ala Ala Val Gln Arg Asn Glu Val Pro Gly His Cys Leu Phe Tyr
50 55 60

Gly Pro Pro Gly Leu Gly Lys Thr Ser Leu Ala His Ile Met Ala Asn
65 70 75 80

Thr Ile Gly Lys Gly Leu Val Ile Ala Ser Gly Pro Gln Leu Leu Lys
85 90 95

Pro Ser Asp Leu Ile Gly Leu Leu Thr Gly Leu Gln Glu Gly Asp Ile
100 105 110

Phe Phe Ile Asp Glu Ile His Arg Met Gly Lys Ala Ala Glu Glu Tyr
115 120 125

Leu Tyr Pro Ala Met Glu Asp Phe Lys Val Asp Ile Thr Leu Asp Ser
130 135 140

Gly Pro Gly Ala Arg Ser Val Arg Leu Asp Leu Ala Pro Phe Thr Leu
145 150 155 160

Val Gly Ala Thr Thr Arg Ala Gly Met Leu Ser Glu Pro Leu Arg Thr

-continued

```
                165                 170                 175

Arg Phe Ala Phe Thr Gly Arg Val Asp Tyr Tyr Thr Asp Glu Asp Leu
            180                 185                 190

Val Ser Ile Leu Ser Arg Ser Ser Gln Leu Leu Ala Ile Glu Ala Asn
        195                 200                 205

Gln Glu Thr Leu Leu Glu Ile Ala Arg Arg Ala Arg Gly Thr Pro Arg
    210                 215                 220

Leu Ala Asn Asn Leu Leu Arg Trp Val Arg Asp Phe Ala Gln Met Arg
225                 230                 235                 240

Glu Gly Asn Cys Ile Asn Ser Ala Val Ala Glu Lys Ala Leu Ala Met
                245                 250                 255

Leu Leu Ile Asp Asn Leu Gly Leu Asn Glu Ile Asp Ile Lys Leu Leu
            260                 265                 270

Ser Val Met Ile Asp Phe Tyr Gln Gly Gly Pro Val Gly Met Lys Thr
        275                 280                 285

Leu Ala Met Ala Val Gly Glu Asp Val Arg Thr Leu Glu Asp Met Tyr
    290                 295                 300

Glu Pro Phe Leu Ile Leu Lys Gly Leu Val Gln Arg Thr Ala Arg Gly
305                 310                 315                 320

Arg Val Ala Thr Pro Leu Ala Tyr Glu His Leu Asn Arg Asn Pro Lys
325                 330                 335

Asp Arg Trp Gly Glu Glu
                340
```

<210> SEQ ID NO 242
<211> LENGTH: 1029
<212> TYPE: DNA
<213> ORGANISM: Chlamydia trachomatis

<400> SEQUENCE: 242

```
ataactacta ttgcgaatac ttatatgact cataaaattt ctgttttaca tcaggataaa     60

aagtttgatt tttctttaag gccaaagaaa ctaacagagt tttgtgggca aaaacaattg    120

aaagaacgat tggatttatt tcttcgagct gctgtccagc ggaatgaagt ccccggacat    180

tgtttatttt atggtccccc aggtttgggt aagacttcgc tagcacatat tatggctaac    240

acgataggaa aaggcttggt aattgcttcc gggccgcagt tgttaaagcc ttccgatctc    300

ataggactat tgaccggtct acaagaggga gatatttttt tcatcgatga aatccatcgc    360

atggggaaag ctgctgaaga gtatctctat cctgccatgg aagattttaa agtagatatt    420

accttggatt caggtcccgg agctcgctca gtgcgtctcg atttagctcc atttactttg    480

gtaggtgcga ccactcgcgc tggaatgtta agcgagcctt tgcgtacgcg ttttgctttt    540

actgggcgtg tagattacta tactgatgaa gatcttgttt ccattctttc tcgttcctct    600

cagttgctcg ccatagaagc caatcaggaa actctattag agattgctag aagggctcga    660

gggacaccac gtttggctaa taatttactt cgatgggtgc gtgattttgc tcaaatgcga    720

gagggaaatt gtattaatag cgccgtagca gaaaaagctt tagctatgtt attaatagat    780

aacttagggt taaacgagat tgacattaag cttctctccg tgatgattga tttttatcaa    840

ggaggccccg ttggaatgaa aacgctcgca atggcggtag gggaagatgt cagaactctg    900

gaagatatgt acgagccctt tttgattttg aagggtttgg ttcagcgaac cgcaagagga    960

cgggttgcaa ccccctttggc atatgaacat cttaacagga accctaagga caggtgggga   1020

gaagaataa                                                            1029
```

```
<210> SEQ ID NO 243
<211> LENGTH: 382
<212> TYPE: PRT
<213> ORGANISM: Chlamydia trachomatis

<400> SEQUENCE: 243

Ile Leu Thr Arg Met Asn Gly Lys Thr Pro Leu Ala Leu Tyr Ile His
1               5                   10                  15

Ile Pro Phe Cys Ser Lys Lys Cys His Tyr Cys Ser Phe Tyr Thr Ile
            20                  25                  30

Pro Tyr Lys Glu Glu Leu Met Arg Ser Tyr Cys Glu Ala Val Ile Lys
        35                  40                  45

Glu Gly Leu Lys Lys Leu Ala Pro Leu Arg Cys Ser His Tyr Ile Asp
    50                  55                  60

Thr Val Phe Phe Gly Gly Gly Thr Pro Ser Leu Val Pro Pro Ala Leu
65                  70                  75                  80

Ile Gln Asp Ile Leu Val Ala Leu Glu Ala Gln His Ala Thr Glu Ile
                85                  90                  95

Thr Leu Glu Ala Asn Pro Glu Asn Leu Ser Leu Glu Tyr Ile Gln Ala
            100                 105                 110

Leu Ala Leu Thr Ser Ile Asn Arg Ile Ser Ile Gly Val Gln Thr Phe
        115                 120                 125

Asn Asp Pro Leu Leu Lys Leu Leu Gly Arg Thr His Ser Ser Ser Lys
    130                 135                 140

Ala Ile Glu Ala Phe Met Leu Cys Ser Gln Tyr Gly Phe Ser Asn Val
145                 150                 155                 160

Ser Ala Asp Leu Ile Tyr Gly Leu Pro Thr Gln Ser Ile Ser Asp Phe
                165                 170                 175

Ile Val Asp Leu His Gln Ala Ile Ser Leu Pro Ile Gln His Ile Ser
            180                 185                 190

Ile Tyr Asn Leu Thr Ile Asp Pro His Thr Ser Phe Tyr Lys His Arg
        195                 200                 205

Lys Arg Ile Leu Pro Ser Ile Ala Asp Asp Asp Ser Leu Ala Glu Met
    210                 215                 220

Ala Leu Ala Ala Glu Glu Leu Leu Glu Asn Gln Gly Phe Thr Arg Tyr
225                 230                 235                 240

Glu Leu Ala Ser Tyr Ala Lys Asn Gln Ala Ala Ser Lys His Asn Thr
                245                 250                 255

Tyr Tyr Trp Thr Ala Lys Pro Phe Leu Gly Leu Gly Val Ser Ala Ser
            260                 265                 270

Gln Tyr Leu His Gly Ile Arg Ser Lys Asn Leu Ser Arg Ile Ser His
        275                 280                 285

Tyr Leu Arg Ala Ala His Gln His Leu Pro Thr Leu Glu Ser Met Glu
    290                 295                 300

Glu Leu Pro Pro Asn Glu Arg Ile Lys Glu Thr Leu Ala Leu Arg Leu
305                 310                 315                 320

Arg Leu Cys Asp Pro Ile Pro Phe Gly Val Phe Pro Gln Glu Leu Ile
                325                 330                 335

Asp Glu Ile Leu Met His Pro Ser Ile Gly Ser Leu Phe Thr Lys Asp
            340                 345                 350

Asp Lys Ala Phe Ser Leu Asn Lys Lys Gly Arg Leu Phe His Asp Ser
        355                 360                 365

Ile Ala Glu Glu Ile Met Ala Ser Ser Phe Ser Phe Ser Lys
    370                 375                 380
```

<210> SEQ ID NO 244
<211> LENGTH: 1149
<212> TYPE: DNA
<213> ORGANISM: Chlamydia trachomatis

<400> SEQUENCE: 244
ttattttgaa aatgaaaaag aagaagccat gatttcttct gctatagaat catgaaaaag 60
acgccctttt ttatttaatg aaaaagcttt gtcatcctta gtaaatagag aacctataga 120
cgggtgcatt aatatttcgt ctatgagttc ctgagggaaa actccaaagg ggatggggtc 180
gcagagacgg aggcgcaaag ctagagtctc tttaatgcgt tcgtttggag ggagctcttc 240
catagactct aaagtcggta gatgttgatg cgcagctcgt aagtaatgcg agatcctaga 300
aaggtttttg gatcgaatgc catggagata ttgtgaggca gaaactccta atcctaagaa 360
aggcttagct gtccagtagt aggtattgtg tttagaagcc gcttggtttt ttgcatagga 420
agcaagttca tagcgagtaa atccttgatt ctctagtagc tcttcggctg ctagtgccat 480
ctcagctagg gagtcgtcat ctgctatgga tggaagaata cgtttacggt gtttgtaaaa 540
ggaggtgtga gggtctatag ttagattata aatagagatg tgttggattg ggagagaaat 600
agcttggtga agatcaacaa taaaatcact aatcgactgt gtagggaggc cataaataag 660
gtctgcagac acattagaaa atccgtattg ggagcagagc ataaaggctt caatcgcttt 720
agatgaagag tgtgtgcgtc ctagtagctt aagtagggga tcattgaatg tttgtacgcc 780
aatgctaatg cgattgatcg aggtcaaggc gagagcctgg atatactcca gagaaagatt 840
ttcagggttt gcttcaagag tgatttctgt ggcatgctga gcttctagag ctacgagaat 900
atcttgaatc aaagcagggg gaactaaaga aggagtccct cctccaaaga atactgtatc 960
aatatagtga gaacaacgta gaggggctag ttttttttagc cctctttaa tgacagcttc 1020 acaataagag cgcattaact cttctttata cgggatcgta tagaaactac aataatgaca 1080
tttcttcgag cagaaaggga tatgtatgta aagagctaag ggagtcttac cattcattcg 1140
cgtcaggat 1149

<210> SEQ ID NO 245
<211> LENGTH: 169
<212> TYPE: PRT
<213> ORGANISM: Chlamydia trachomatis

<400> SEQUENCE: 245

Glu Ala Ser Lys Leu Ala Leu Arg Gly Phe Pro Val Ser Ile Ile Glu
1 5 10 15

Gln Asp Tyr Leu Arg Met Lys Ser Glu Arg Leu Lys Lys Leu Glu Ser
20 25 30

Glu Leu His Asp Leu Thr Gln Trp Met Gln Leu Gly Leu Val Pro Lys
35 40 45

Lys Glu Ile Glu Arg His Gln Glu Glu Ile Arg Leu Leu Glu Ser Lys
50 55 60

Ile Leu Glu Glu Lys Glu Arg Leu Gln Leu Leu Lys Glu Ser Gly Glu
65 70 75 80

Ile Lys Glu Tyr Val Thr Pro Arg Arg Thr Pro Ala Lys Thr Ile Tyr
85 90 95

Pro Asp Gly Pro Ser Val Ser Asp Val Glu Phe Val Glu Ser Ser Asp
100 105 110

Thr Glu Val Asp Leu Asp Ala Gly Asp Thr Ile Glu Ile Asp Leu Gly

```
        115                 120                 125

Asp Glu Ala Arg Glu Glu Ser Gly Asn Glu Leu Asp Tyr Ser Ser Glu
    130                 135                 140

Asp Asp Glu Asp Pro Phe Ser Asp Arg Asn Arg Trp Arg Arg Gly Gly
145                 150                 155                 160

Ile Ile Asp Pro Asp Ala Asn Glu Trp
                165


<210> SEQ ID NO 246
<211> LENGTH: 510
<212> TYPE: DNA
<213> ORGANISM: Chlamydia trachomatis

<400> SEQUENCE: 246

ttaccattca ttcgcgtcag gatctatgat gcctcctcgg cgccaacgat tgcgatcact     60

gaaaggatcc tcatcgtctt cactagagta gtcgagttcg tttccgcttt cttctcttgc    120

ctcatcacct aggtcaatct caattgtgtc accggcatcg agatccactt ctgtatccga    180

ggattctaca aactcaacgt ctgaaacgct ggggccatct gggtaaatgg ttttagctgg    240

agttcttcga ggggttacgt actctttgat ctcaccgctt tctttgagaa gttgtagacg    300

ttctttctct tcaaggattt tgctttctag cagacggatt tcttcctggt gtctctcgat    360

ttctttttta ggaacaaggc caagttgcat ccactgggta agatcatgaa gctctgattc    420

taattttttt aaacgctcac ttttcattcg taaatagtcc tgttctatga ttgaaaccgg    480

aaaccccctg agagccaatt tacttgcttc                                      510


<210> SEQ ID NO 247
<211> LENGTH: 277
<212> TYPE: PRT
<213> ORGANISM: Chlamydia trachomatis

<400> SEQUENCE: 247

Leu Ser Glu Asp Leu Leu Lys Ile Asp Asn Leu Val Val Ser Val Lys
1               5                   10                  15

Asp Ser Asn Gln Arg Leu Val Asn His Leu Ser Leu Thr Ile Lys Arg
            20                  25                  30

Cys Gln Ser Met Ala Leu Val Gly Glu Asn Gly Ser Gly Lys Thr Thr
        35                  40                  45

Val Ser Lys Ala Val Leu Gly Phe Leu Pro Asp Asn Cys Tyr Ile Gln
    50                  55                  60

Ser Gly Arg Ile Leu Tyr Ser Ser Thr Asp Ile Thr Arg Leu Ser Arg
65                  70                  75                  80

Arg Gln Leu Gln Thr Ile Arg Gly Lys Lys Ile Ala Thr Ile Phe Gln
                85                  90                  95

Asn Ala Met Gly Thr Leu Thr Pro Ser Met Arg Val Gly Ala Gln Ile
            100                 105                 110

Val Glu Thr Leu Arg His His Phe Asp Met Ser Lys Glu Glu Ala Phe
        115                 120                 125

Ser Lys Ala Arg Glu Leu Leu Glu Ser Val His Ile Glu Ser Pro Asp
    130                 135                 140

Arg Cys Leu Gln Leu Tyr Pro Phe Glu Leu Ser Gly Gly Met Cys Gln
145                 150                 155                 160

Arg Val Ser Ile Ala Ile Ala Leu Ala Thr Asn Pro Glu Leu Ile Ile
                165                 170                 175

Ala Asp Glu Pro Ser Thr Ala Leu Asp Ser Ile Ser Gln Ala Gln Val
```

```
            180                 185                 190

Leu Arg Val Leu Thr Gln Ile His Gln Asn His Ser Thr Ala Leu Leu
        195                 200                 205

Leu Ile Thr His Asn Leu Ala Leu Val Ser Glu Leu Cys Glu Glu Met
    210                 215                 220

Ala Ile Ile Arg Tyr Gly Glu Ile Val Glu Gln Gly Pro Val Gln Glu
225                 230                 235                 240

Leu Leu His Ser Pro Ser His Pro Tyr Thr Gln Gln Leu Ile Arg Ala
                245                 250                 255

Ile Pro Lys Ile Pro Ser Pro Ser Tyr Leu Ser Pro Lys Glu Pro Leu
            260                 265                 270

Ala Thr Thr Ala Tyr
        275


<210> SEQ ID NO 248
<211> LENGTH: 831
<212> TYPE: DNA
<213> ORGANISM: Chlamydia trachomatis

<400> SEQUENCE: 248

ttgtctgaag atttattaaa aattgataat ctagtcgtct ccgtaaaaga ttccaatcaa      60

cgattagtca atcacttgtc gctcactatc aagcgatgcc aaagtatggc acttgtagga     120

gaaaatggtt cggggaaaac aaccgtttct aaagcagttt tggggtttct ccccgataat     180

tgttacatcc aatctggaag aatcctttac tccagcacag atattacacg cttatctcgt     240

agacaacttc aaacaatccg cgggaagaaa atcgcaacta ttttccaaaa tgccatggga     300

accctgactc cttctatgcg tgtaggagct caaattgtag aaaccctaag acatcatttc     360

gatatgtcta aagaagaagc tttctctaaa gcaagagaac tgcttgagag tgtacacatc     420

gaatctcctg atcgatgcct acaattatat ccctttgagc ttagcggtgg catgtgtcaa     480

cgagttagca ttgctattgc tctggcaacc aatccggaac tcattattgc agatgaacct     540

tcaacagcgc tagattctat atcccaggct caggtattgc gtgtactgac acaaattcac     600

caaaaccatt ctacagctct actactcatc actcataatt tagctttagt atctgaactg     660

tgtgaagaaa tggccattat acgctatggg gagatcgttg agcaaggtcc tgtgcaagag     720

ctactgcact ctccgtctca tccttatacc cagcaactga tccgcgctat tcctaaaatt     780

cctagtccta gctatctttc acctaaagaa cctcttgcaa caaccgcgta t              831


<210> SEQ ID NO 249
<211> LENGTH: 340
<212> TYPE: PRT
<213> ORGANISM: Chlamydia trachomatis

<400> SEQUENCE: 249

Met His Pro Leu Thr Leu Asn Ile Ala Ser Glu Glu Thr Thr Glu Ala
1               5                   10                  15

Arg Val Phe His Val Ile Glu Asn Phe Gly Asn Ser Phe Cys Ile Asp
            20                  25                  30

Leu Leu Lys Lys Met Leu Leu Ile Arg Glu Phe Glu Ile Arg Gly Glu
        35                  40                  45

Glu Ala Tyr Leu Glu Gly Leu Val Gly Gly Phe Tyr His Ser Tyr Ile
    50                  55                  60

Gly Gln Glu Ala Val Ala Thr Ala Ala Ile Ala Cys Thr Gly Lys Asp
65                  70                  75                  80
```

-continued

```
His Trp Phe Phe Ser Ser Tyr Arg Cys His Gly Val Ala Leu Leu Leu
                85                  90                  95

Asp Ile Pro Leu Arg Gln Leu Ala Ala Glu Leu Leu Gly Lys Glu Thr
            100                 105                 110

Gly Cys Ala Leu Gly Arg Gly Gly Ser Met His Met Cys Gly Asp Arg
        115                 120                 125

Leu Pro Gly Gly Phe Gly Ile Val Gly Gly Gln Ile Pro Leu Ala Ala
    130                 135                 140

Gly Ala Ala Phe Ser Met Lys Tyr Gln Asn Ser Ser Ser Ile Ser Met
145                 150                 155                 160

Cys Phe Ile Gly Asp Gly Ala Val Ala Gln Gly Val Phe His Glu Thr
                165                 170                 175

Leu Asn Phe Val Ala Leu His Ser Leu Pro Leu Met Leu Ile Ile Glu
            180                 185                 190

Asn Asn Gly Trp Ser Met Gly Thr Ala Leu His Arg Ala Ile Ala Lys
        195                 200                 205

Gln Pro Ile Ala Glu Ser Gln Ala Ile Ser Tyr Gly Leu Ser Ser Ile
    210                 215                 220

Thr Leu Asn Gly Phe Asp Leu Phe Asn Ser Leu Ile Gly Phe Arg Glu
225                 230                 235                 240

Ala Tyr His His Met Gln Gln Thr Gly Ser Pro Ile Ile Val Glu Ala
                245                 250                 255

Leu Cys Ser Arg Phe Arg Gly His Ser Ile Ser Asp Pro Asn Leu Tyr
            260                 265                 270

Arg Ser Lys Glu Glu Met Gln Cys Leu Leu Lys Arg Asp Pro Ile Leu
        275                 280                 285

Phe Ala Lys Glu Trp Leu Ile Arg Ala Asn Val Leu Ser Glu Asp Asp
    290                 295                 300

Phe Lys Asp Leu Arg Gln Thr Ser Lys Thr Ala Val Leu Glu Ala Val
305                 310                 315                 320

Ala Gln Ala Arg Leu Asp Pro Glu Pro Ala Val Ala Thr Leu Glu Glu
                325                 330                 335

Gly Val Tyr Ala
            340
```

<210> SEQ ID NO 250
<211> LENGTH: 1020
<212> TYPE: DNA
<213> ORGANISM: Chlamydia trachomatis

<400> SEQUENCE: 250

```
atgcatcctc tgactctcaa catagcttct gaggaaacta cagaagcccg agtttttcat     60

gttattgaaa acttcggaaa ttctttctgc attgaccttt tgaaaaaaat gctactcatt    120

cgcgaatttg agattcgcgg agaagaggcc tatttagaag gccttgttgg aggattttat    180

cactcttata tcggtcaaga agctgttgct acagcagcta ttgcttgcac agggaaagac    240

cactggtttt tttcctctta tcgttgtcac ggagtagctc tgctgctgga tatcccttta    300

cgacaactgg cagcagaact tctagggaaa gaaacagggt gtgctttagg acgaggcgga    360

tctatgcata tgtgtggtga tcgtcttcct ggaggttttg gtatcgttgg tggacaaatt    420

cctctggctg caggtgcagc atttctatg aagtaccaaa actcatcttc tatatctatg    480

tgttttattg gagatggagc tgtagctcaa ggagtctttc atgaaacatt aaattttgta    540

gcgcttcact cccttccctt aatgctcatt attgaaaaca atggatggag tatgggaaca    600
```

-continued

```
gccttacata gagccattgc taaacagcct atagcagaat cccaagcgat ttcttatggt    660

ctttcttcga tcactttgaa tggattcgat ttatttaatt cgcttatagg atttagagaa    720

gcttatcacc acatgcaaca aacaggttct cctattatcg tagaggcgct atgttctcga    780

tttagaggac actctatttc cgatcctaat ttatatcgct ctaaagagga aatgcaatgt    840

cttctcaaaa gagatcctat cctttttgca aaagaatggc tcattcgtgc gaatgtccta    900

tccgaagatg attttaaaga tttgcgtcaa acaagcaaaa cagctgtcct agaagcagtc    960

gctcaagctc gtcttgatcc agaaccagct gtagctactt tagaagaggg ggtctatgcc   1020
```

<210> SEQ ID NO 251
<211> LENGTH: 328
<212> TYPE: PRT
<213> ORGANISM: Chlamydia trachomatis

<400> SEQUENCE: 251

```
Met Pro Asn Phe Val Thr Leu Glu Ile Arg Glu Ala Ile Arg Gln Ala
1               5                   10                  15

Ile Asp Glu Glu Met Thr Arg Asp Pro Asn Val Cys Ile Leu Gly Glu
            20                  25                  30

Glu Val Ala Glu Tyr Asn Gly Ala Tyr Lys Val Thr Lys Asn Leu Leu
        35                  40                  45

Asp Lys Trp Gly Pro Thr Arg Val Ile Asp Thr Pro Ile Ser Glu Ala
    50                  55                  60

Ala Phe Ser Gly Ile Gly Ile Gly Ala Ala Leu Thr Gly Leu Arg Pro
65                  70                  75                  80

Ile Ile Glu Phe Met Ser Trp Asn Phe Ser Leu Val Ala Ala Asp Gln
                85                  90                  95

Ile Ile Ser His Ala Ala Lys Met Tyr Tyr Met Thr Gly Gly Lys Phe
            100                 105                 110

Ala Val Pro Ile Val Phe Arg Gly Ala Asn Gly Ala Ala Ala Gln Val
        115                 120                 125

Ser Cys Gln His Ser His Cys Ile Glu Ala Leu Tyr Ala Asn Ile Pro
    130                 135                 140

Gly Leu Ile Val Ile Ala Pro Ser Thr Pro Ala Asp Ala Lys Gly Leu
145                 150                 155                 160

Leu Lys Ser Ala Ile Arg Asp Asn Asn Pro Val Leu Phe Leu Glu Asn
                165                 170                 175

Glu Leu Asp Tyr Asn Leu Lys Gly Glu Val Pro Ser Glu Glu Tyr Leu
            180                 185                 190

Ile Pro Ile Gly Lys Ala Arg Ile Val Gln Glu Gly Lys Asp Leu Thr
        195                 200                 205

Ile Ile Ser His Ser Arg Met Val Ser Ile Val Glu Gln Ala Ala Lys
    210                 215                 220

Thr Ala Lys Gln Arg Trp Gly Leu Ser Ile Glu Thr Ile Asp Leu Arg
225                 230                 235                 240

Thr Ile Lys Pro Leu Asp Val Ala Thr Leu Leu Thr Ser Val Lys Lys
                245                 250                 255

Thr Gly Asn Cys Leu Val Val Glu Glu Gly His Tyr Phe Cys Gly Ile
            260                 265                 270

Ser Ser Glu Val Ile Thr Thr Ile Thr Glu His Ile Phe Asp Tyr Leu
        275                 280                 285

Asp His Pro Pro Leu Arg Val Cys Gln Lys Glu Thr Pro Met Pro Tyr
    290                 295                 300
```

Asn Lys Thr Leu Glu Met Ala Thr Leu Pro Asn Ile Asn Arg Ile Leu
305 310 315 320

Asp Ala Ile Glu Lys Ile Met Arg
325

<210> SEQ ID NO 252
<211> LENGTH: 984
<212> TYPE: DNA
<213> ORGANISM: Chlamydia trachomatis

<400> SEQUENCE: 252
atgcctaatt ttgttacact cgaaatccga gaggctatta gacaagctat tgatgaagaa 60
atgaccagag atcctaacgt ctgtatccta ggagaggagg tcgctgaata taatggtgct 120
tataaagtta ctaaaaacct cttagataaa tggggaccca ctcgagttat tgatacaccc 180
attagcgaag ctgctttctc tggaattgga atcggagcag cgctaactgg acttcgccca 240
attattgaat ttatgagctg gaacttctct ctagttgctg ctgatcaaat catttctcat 300
gcagcaaaaa tgtattatat gactggaggg aaatttgctg ttcctatcgt tttagaggc 360 gctaatggag ctgctgcgca agtctcttgc caacattctc attgtattga agctctttat 420
gccaatattc ctggcttaat tgtcattgct ccatcaactc cagccgatgc aaagggactt 480
cttaaatctg ctattcggga taacaacccc gttctattct tagaaaatga attagactac 540
aatcttaagg gagaggtccc ttcagaagaa tacctgatcc ccattgggaa agctcgtatc 600
gttcaagaag gaaaagattt aacaatcatt tcgcatagcc gcatggtttc tatcgttgag 660
caagctgcta aaacagcaaa acaacgatgg ggactctcta ttgaaaccat tgacttacga 720
acgatcaaac ctttggatgt tgccactctc ctcacttctg tcaaaaaaac agggaattgt 780
cttgtcgttg aagaagggca ttatttttgt ggtatatctt cggaagtgat tacgacgatt 840
acagaacata tttttgacta cctagatcat cctcctctac gagtctgtca aaaagaaacg 900
cctatgccat ataataaaac tctagagatg gcgactctcc caaatattaa ccgcatcctg 960
gatgccattg aaaaaattat gagg 984

<210> SEQ ID NO 253
<211> LENGTH: 199
<212> TYPE: PRT
<213> ORGANISM: Chlamydia trachomatis

<400> SEQUENCE: 253

Met Phe Ser Gly Ile Ile Gln Glu Val Ala Arg Val Asp Leu Ile His
1 5 10 15

His Leu Arg Asp Ser Met Glu Ile Gly Val Phe Ala Arg Lys Leu Ile
20 25 30

Asp Val Val Pro Gly Ser Ser Phe Ser Val Asp Gly Ile Cys Leu Thr
35 40 45

Leu Val Lys Arg Gln Tyr Glu Leu Leu Phe Phe Asp Val Thr Glu Glu
50 55 60

Thr Met Ala Trp Thr Thr Ile Lys Asp Tyr Thr Val Gly Thr Met Val
65 70 75 80

Asn Leu Glu Arg Ser Val Arg Leu Gly Asp Glu Ile Gly Gly His Phe
85 90 95

Val Ser Gly His Val Cys Gly Ile Gly Thr Ile Ile Ala Ile Glu Lys
100 105 110

Ser Tyr Met Phe Phe Lys Ala Pro Ala Asn Leu Val Pro Tyr Ile Leu
115 120 125

Glu Lys Gly Phe Ile Ala Ile Asp Gly Ile Ser Leu Thr Ile Ala Arg
130 135 140

Val Lys Gly Asp Ile Phe Ser Val Ser Leu Ile Pro Glu Thr Arg Ala
145 150 155 160

Arg Thr Ser Leu Gly Tyr Lys Gln Val Gly Ala His Val Asn Met Glu
165 170 175

Pro Asp Met Met Thr Lys Met Gln Val Asp Thr Ile Met Arg Phe His
180 185 190

Ala Glu Lys Glu Ile Ser Lys
195

<210> SEQ ID NO 254
<211> LENGTH: 597
<212> TYPE: DNA
<213> ORGANISM: Chlamydia trachomatis

<400> SEQUENCE: 254
atgttttcag gcattattca agaagtcgca cgggtagatc ttattcacca tctcagggat 60
tccatggaga ttggagtttt tgctcgcaag ttgatcgatg tggttccggg gagtagcttc 120
tctgtcgatg gcatatgttt gactctggtc aaacgacagt acgaattact ctttttgat 180 gtgactgaag aaaccatggc ttggactacc atcaaagatt atacggtggg aaccatggta 240
aatttagaac gctcggttcg attaggagat gaaataggag gacattttgt ctctgggcat 300
gtctgtggga taggcactat tattgctata gagaaatcct atatgttttt taaggctcca 360
gctaatttag tgccttatat tttagagaaa ggcttcattg ctattgatgg catcagtttg 420
acaattgcac gagttaaagg ggacatcttt tcagttagtt tgattccgga gactcgagcg 480
cgcacctcat tgggttataa acaggtgggt gctcacgtga atatggagcc tgatatgatg 540
acaaaaatgc aggtggacac aattatgcgt ttccatgccg aaaaagagat cagcaaa 597

<210> SEQ ID NO 255
<211> LENGTH: 107
<212> TYPE: PRT
<213> ORGANISM: Chlamydia trachomatis

<400> SEQUENCE: 255

Met Glu Pro Tyr Ala Val Ile Gln Thr Gly Asn Lys Gln Tyr Gln Val
1 5 10 15

Arg Lys Gly Asp Val Ile Asp Val Glu Leu Leu Asp Gly Ile Ser Glu
20 25 30

Glu Asn Lys Glu Val Leu Phe Gln Asp Val Leu Phe Thr Phe Asp Gly
35 40 45

Glu Lys Ala Ser Val Gly Ala Pro Thr Val Gly Asn Ala Val Val Lys
50 55 60

Gly Glu Leu Val Ser Phe Val Arg Gly Glu Lys Val Val Ala Tyr Lys
65 70 75 80

Tyr Lys Lys Arg Lys Asn Tyr His Lys Lys Ile Gly His Arg Gln Asn
85 90 95

Tyr Leu Arg Val Lys Ile Ser Asp Leu Val Met
100 105

<210> SEQ ID NO 256
<211> LENGTH: 321
<212> TYPE: DNA
<213> ORGANISM: Chlamydia trachomatis

<400> SEQUENCE: 256
atggagcctt acgctgtaat tcagactgga aataagcaat accaggttcg caaaggtgac 60
gttatagacg tcgaactgtt ggatgggatt tctgaagaga acaaagaagt cctttttcaa 120
gatgtattat ttacttttga cggagaaaaa gcttccgttg gtgctccaac agttggcaac 180
gctgtagtga aaggagaatt agtttctttc gttcgcggag aaaaggttgt ggcttacaag 240
tacaaaaaac gtaagaatta tcacaagaaa atcggccatc gtcaaaatta ccttcgggtg 300
aagattagcg atttggttat g 321

<210> SEQ ID NO 257
<211> LENGTH: 369
<212> TYPE: PRT
<213> ORGANISM: Chlamydia trachomatis

<400> SEQUENCE: 257

Met Thr Thr Leu Pro Ala Arg Ile Leu Pro Lys Ser Ala Cys Leu Lys
1 5 10 15

Thr Leu Phe Asp Asp Tyr Leu Ser Gly Ala Arg Leu Ser Glu Glu Gln
20 25 30

Ala Leu Gln Leu Leu Leu Val Asp Ala Glu Asp Gln Gln Ala Leu Trp
35 40 45

Ser Phe Ala Asp Leu Ile Arg Ala Asn Arg Val Gly Asp Thr Val Phe
50 55 60

Tyr Ser Ser Thr Leu Tyr Leu Tyr Pro Thr Asn Phe Cys Gln Phe Asn
65 70 75 80

Cys Thr Phe Cys Ser Phe Tyr Ala Lys Pro Gly Asn Pro Thr Gly Trp
85 90 95

Phe Phe Thr Pro Asp Gln Leu Val Gln Ser Ile Lys Glu Asn Pro Ser
100 105 110

Pro Ile Thr Glu Thr His Ile Val Ala Gly Cys Tyr Pro Ser Cys Asn
115 120 125

Leu Ala Tyr Tyr Glu Glu Leu Phe Ser Lys Ile Lys Gln Asn Phe Pro
130 135 140

Asp Leu His Ile Lys Ala Leu Ser Ala Ile Glu Tyr Asp Tyr Leu Ser
145 150 155 160

Lys Leu Asp Asn Leu Pro Val Lys Glu Val Met Gln Arg Leu Arg Ile
165 170 175

Ala Gly Leu Asp Ser Ile Pro Gly Gly Gly Ala Glu Ile Leu Val Asp
180 185 190

Glu Val Arg Glu Thr Leu Ser Arg Gly Arg Leu Ser Ser Gln Gly Phe
195 200 205

Leu Glu Ile His Glu Thr Ala His Ser Leu Gly Ile Pro Ser Asn Ala
210 215 220

Thr Met Leu Cys Tyr His Arg Glu Thr Pro Ala Asp Ile Met Thr His
225 230 235 240

Met Ser Lys Leu Arg Ala Leu Gln Asp Lys Thr Ser Gly Phe Lys Asn
245 250 255

Phe Ile Leu Leu Lys Phe Ala Ser Glu Asn Asn Ala Leu Gly Lys Arg
260 265 270

Leu His Lys Met Thr Ser Arg His Ser Ile Pro Pro Ala Thr Ile Ile
275 280 285

Ala Val Ala Arg Leu Phe Leu Asp Asn Ile Pro Asn Ile Lys Ala Leu
290 295 300

-continued

Trp Asn Tyr Leu Gly Leu Asp Val Ala Leu His Leu Leu Ser Cys Gly
305 310 315 320

Ala Asn Asp Leu Ser Ser Thr His Gln Gly Glu Lys Val Phe Arg Met
325 330 335

Ala Ser Ser Gln Glu Pro Ile Arg Met Asp Ile Glu Gly Met Ser His
340 345 350

Leu Ile Ile Gln His Gly Arg Ile Pro Cys Leu Val Asn Ser Lys Thr
355 360 365

Val

<210> SEQ ID NO 258
<211> LENGTH: 1107
<212> TYPE: DNA
<213> ORGANISM: Chlamydia trachomatis

<400> SEQUENCE: 258
atgacgactc ttccagctcg aatcctacct aaaagcgcat gtcttaaaac tttatttgat 60
gactatttat ctggagcgcg tctttctgaa gaacaagctt tacaattact tctcgttgat 120
gctgaggatc aacaagcttt atggagcttt gctgatctta ttcgtgccaa tcgtgttggt 180
gacacagttt tctactcgtc gaccctttat ttatacccta caaacttctg tcagtttaac 240
tgtacgtttt gttctttcta tgccaaacca gggaacccta caggatggtt ctttactcca 300
gatcaactcg tacaatctat aaaagaaaac ccttctccca ttacagaaac gcatattgta 360
gcaggatgct acccctcttg taatcttgct tactatgaag agctcttctc caaaattaag 420
caaaatttcc cagatctaca tattaaagcg ctctcagcta tcgagtatga ttatctgtca 480
aaattagaca atctcccagt taaagaagtc atgcaacgct tgcgtatcgc tggccttgat 540
tctattcctg gtgggggtgc tgagatctta gtcgatgaag tccgagagac cctctcgcga 600
ggcagattat cttcccaagg attcttagag atccatgaaa cagcgcattc cttaggaatc 660
cctagcaatg ctaccatgct gtgctaccat cgagagactc ctgcagatat aatgacacat 720
atgagtaaac tgcgcgctct tcaagacaaa acttctggct ttaagaattt tatcctcctc 780
aaatttgcgt cagagaataa tgctttagga aagcgtctac acaaaatgac ttcaagacac 840
tcgattcctc ctgcaactat tattgcagtt gctcgactat tcctagacaa catccctaat 900
attaaagctc tatggaatta tttaggtctc gacgttgctc tacacttgtt atcatgcgga 960
gccaatgatt tgtcttccac tcaccaagga gaaaaggtat ttcgaatggc ctcttcccaa 1020
gagcctattc gtatggatat tgaagggatg tcccatctca taatacaaca tggtcgtatc 1080
ccatgcttag tcaattccaa gaccgtt 1107

<210> SEQ ID NO 259
<211> LENGTH: 377
<212> TYPE: PRT
<213> ORGANISM: Chlamydia trachomatis

<400> SEQUENCE: 259

Met Ser Asp Ser Ser His Asn Leu Leu Tyr Asn Lys Phe Glu Leu Pro
1 5 10 15

Glu Ser Val Lys Met Ser Pro Val Glu Gly Ala Val Gly Gly Ile Asp
20 25 30

Lys Val Ala Arg Phe Val Ala Asp Pro Leu Glu Lys Gly Met Gly His
35 40 45

Thr Leu Gly Ser Ala Leu Arg Arg Ala Leu Leu Ile Gly Leu Glu Ala
50 55 60

```
Pro Ala Ile Val Ser Phe Ser Met Thr Gly Val Leu His Glu Tyr Met
65                  70                  75                  80

Ala Val Glu Gly Ile Ile Glu Asp Val Thr Asn Ile Val Leu Asn Leu
                85                  90                  95

Lys Gly Ser Leu Leu Lys Lys Tyr Pro Leu Gln Asp Cys Glu Gly Gly
            100                 105                 110

Arg Cys Ser Gln Lys Leu Arg Ala Thr Ile Ser Ile Asp Ala Ser Asp
        115                 120                 125

Leu Ala Ala Ala Gly Gly Gln Lys Glu Val Thr Leu Gly Asp Leu Leu
    130                 135                 140

Gln Glu Gly Thr Phe Glu Ala Val Asn Pro Glu His Val Ile Phe Thr
145                 150                 155                 160

Val Thr Arg Pro Met Gln Leu Glu Val Met Leu Arg Val Ala Phe Gly
                165                 170                 175

Arg Gly Tyr Ser Pro Ser Glu Arg Ile Val Leu Glu Glu Arg Gly Met
            180                 185                 190

Asn Glu Ile Val Leu Asp Ala Ala Phe Ser Pro Val Val Leu Val Asn
        195                 200                 205

Tyr Phe Val Glu Asp Thr Arg Val Gly Gln Asp Thr Asp Phe Asp Arg
    210                 215                 220

Leu Val Leu Gln Val Glu Thr Asp Gly Arg Val Ala Pro Lys Glu Ala
225                 230                 235                 240

Val Ala Phe Ala Thr Gln Ile Leu Ser Lys His Phe Ser Val Phe Glu
                245                 250                 255

Lys Met Asp Glu Lys Arg Ile Val Phe Glu Glu Ala Ile Ser Val Glu
            260                 265                 270

Lys Glu Asn Lys Asp Asp Ile Leu His Lys Leu Val Leu Gly Ile Asn
        275                 280                 285

Glu Ile Glu Leu Ser Val Arg Ser Thr Asn Cys Leu Ser Asn Ala Asn
    290                 295                 300

Ile Glu Thr Ile Gly Glu Leu Val Ile Met Pro Glu Pro Arg Leu Leu
305                 310                 315                 320

Gln Phe Arg Asn Phe Gly Lys Lys Ser Leu Cys Glu Ile Lys Asn Lys
                325                 330                 335

Leu Lys Glu Met Lys Leu Glu Leu Gly Met Asp Leu Ser Gln Phe Gly
            340                 345                 350

Val Gly Leu Asp Asn Val Lys Glu Lys Met Lys Trp Tyr Ala Glu Lys
        355                 360                 365

Ile Arg Ser Ser Lys Asn Thr Lys Gly
    370                 375
```

<210> SEQ ID NO 260
<211> LENGTH: 1131
<212> TYPE: DNA
<213> ORGANISM: Chlamydia trachomatis

<400> SEQUENCE: 260

```
atgtcggata gttcacacaa tttactttat aacaaatttg agttgcctga atcggtgaag      60

atgtctcctg tggaaggggc tgttggcggc attgataaag tagctcgatt tgttgcagat     120

cccttggaaa aagggatggg gcacaccttg ggaagcgcct tgcgacgtgc tctgttaatc     180

ggcttggaag ctcctgctat tgtctctttc tctatgacag gagttttgca cgaatatatg     240

gcggtagagg ggatcattga agatgttacc aatatcgttt tgaatttgaa aggttcgttg     300
```

-continued

```
cttaaaaagt atcctctaca agattgtgaa ggtggaagat gctctcaaaa gttacgagct    360

acgatttcta ttgatgcatc cgatttagct gccgctggtg ggcagaagga agttacttta    420

ggagatttgc tacaagaagg aacttttgaa gcggtcaatc ctgagcacgt aatttttacg    480

gtcacgcgtc caatgcaact tgaggttatg ttgcgagttg cttttggtag aggatactct    540

ccttctgaaa gaatcgttct tgaagaaaga ggcatgaatg agatcgtttt agatgcggca    600

ttctctcctg ttgttctggt taactatttt gttgaagaca cccgcgttgg acaagataca    660

gatttcgatc gtttagtgtt gcaagtggaa accgatggtc gtgtggctcc taaagaagct    720

gtagcttttg ctacacagat tttgagtaag catttttctg ttttcgaaaa aatggacgag    780

aagagaatcg tttttgagga agcaatctct gtagagaaag aaaacaaaga cgatattctt    840

cataaattgg ttttaggcat taatgagata gaactttctg tacgatctac aaattgttta    900

tctaatgcca atatcgaaac gataggggaa ttggtaatta tgccagagcc tcgtctgtta    960

caatttagaa atttcgggaa gaagtctctc tgcgagatta agaataaact gaaagaaatg   1020

aaattagagt taggcatgga cctcagccag tttggtgttg gtctggataa cgttaaagaa   1080

aaaatgaagt ggtatgccga gaaaattcgg tcgagtaaaa ataccaaggg a            1131
```

<210> SEQ ID NO 261
<211> LENGTH: 165
<212> TYPE: PRT
<213> ORGANISM: Chlamydia trachomatis

<400> SEQUENCE: 261

```
Met Thr Leu Ser Arg Asn Ser His Lys Glu Asp Gln Leu Glu Glu Lys
1               5                   10                  15

Val Leu Val Val Asn Arg Cys Cys Lys Val Val Lys Gly Gly Arg Lys
            20                  25                  30

Phe Ser Phe Ser Ala Leu Ile Leu Val Gly Asp Arg Lys Gly Arg Leu
        35                  40                  45

Gly Phe Gly Phe Ala Lys Ala Asn Glu Leu Thr Asp Ala Ile Arg Lys
    50                  55                  60

Gly Gly Asp Ala Ala Arg Lys Asn Leu Val Ser Ile Asn Ser Leu Glu
65                  70                  75                  80

Gly Gly Ser Ile Pro His Glu Val Leu Val Asn His Asp Gly Ala Glu
                85                  90                  95

Leu Leu Leu Lys Pro Ala Lys Pro Gly Thr Gly Ile Val Ala Gly Ser
            100                 105                 110

Arg Ile Arg Leu Ile Leu Glu Met Ala Gly Val Lys Asp Ile Val Ala
        115                 120                 125

Lys Ser Leu Gly Ser Asn Asn Pro Met Asn Gln Val Lys Ala Ala Phe
    130                 135                 140

Lys Ala Leu Leu Thr Leu Ser Cys Lys Asp Asp Ile Met Lys Arg Arg
145                 150                 155                 160

Ala Val Ile Asn Asp
                165
```

<210> SEQ ID NO 262
<211> LENGTH: 495
<212> TYPE: DNA
<213> ORGANISM: Chlamydia trachomatis

<400> SEQUENCE: 262

```
atgacgctat caagaaattc tcataaggaa gatcagctgg aagagaaggt tctcgtcgtc     60
```

aaccgttgtt gtaaggttgt taaaggaggc cgtaagttta gtttttctgc gcttatttta 120
gttggcgata gaaaagggcg tttaggcttc ggatttgcga aagctaacga gctaactgat 180
gccatccgta aaggtggaga tgctgctcga aaaaatcttg tctctatcaa ttctcttgag 240
ggaggatcta ttcctcatga ggttcttgtc aatcatgatg gagcagagct tctgttaaaa 300
cctgctaagc caggaaccgg aatcgttgca ggatctcgta ttcggttgat tttagagatg 360
gccggggtaa aggacatcgt agcaaagagt ttaggatcca ataatcctat gaatcaggtt 420
aaagcggctt ttaaagccct cctgacactc tcttgtaaag atgatattat gaaaaggaga 480
gccgttatca atgat 495

<210> SEQ ID NO 263
<211> LENGTH: 123
<212> TYPE: PRT
<213> ORGANISM: Chlamydia trachomatis

<400> SEQUENCE: 263

Met Glu Ser Ser Leu Tyr Lys Lys Thr Ser Gly Lys Ala Arg Arg Ala
1 5 10 15

Leu Arg Val Arg Lys Ala Leu Lys Gly Cys Ser Leu Lys Pro Arg Leu
20 25 30

Ser Val Val Lys Thr Asn Lys His Val Tyr Val Gln Leu Ile Asp Asp
35 40 45

Val Glu Gly Lys Thr Leu Ala Ser Ile Ser Thr Leu Ala Lys Val Ala
50 55 60

Lys Thr Ser Gly Leu Thr Arg Lys Asn Gln Asp Asn Ala Lys Ala Leu
65 70 75 80

Gly Ile Lys Ile Ala Glu Leu Gly Lys Gly Leu Gln Val Asp Arg Val
85 90 95

Val Phe Asp Arg Gly Ala His Lys Tyr His Gly Val Val Ala Met Val
100 105 110

Ala Asp Gly Ala Arg Glu Gly Gly Leu Gln Phe
115 120

<210> SEQ ID NO 264
<211> LENGTH: 369
<212> TYPE: DNA
<213> ORGANISM: Chlamydia trachomatis

<400> SEQUENCE: 264
atggaaagct ctttatataa gaaaacttcg gggaaagctc gtagagcttt aagagtgcgg 60
aaagccttaa agggatgttc tttaaagccc agattatccg ttgtaaagac aaataagcat 120
gtttatgtgc agctgattga tgatgttgaa gggaaaactt tagcatctat ttcaactttg 180
gctaaggttg caaaaacttc tggattaact agaaaaaatc aggataatgc caaagctttg 240
ggaataaaaa ttgctgaatt agggaaaggc cttcaagtag atcgagttgt tttcgatcga 300
ggagctcata agtatcatgg tgtagtagct atggttgctg atggagccag agagggtgga 360
ttacagttt 369

<210> SEQ ID NO 265
<211> LENGTH: 183
<212> TYPE: PRT
<213> ORGANISM: Chlamydia trachomatis

<400> SEQUENCE: 265

Met Ser Arg Lys Ala Arg Asp Pro Ile Val Leu Pro Gln Gly Val Glu

-continued

```
1               5                   10                  15

Val Ser Ile Gln Asn Asp Glu Ile Ser Val Lys Gly Pro Lys Gly Ser
            20                  25                  30

Leu Thr Gln Val Leu Ala Lys Glu Val Glu Ile Ala Val Lys Gly Asn
        35                  40                  45

Glu Val Phe Val Thr Pro Ala Ala His Val Val Asp Arg Pro Gly Arg
    50                  55                  60

Ile Gln Gly Leu Tyr Trp Ala Leu Ile Ala Asn Met Val Lys Gly Val
65                  70                  75                  80

His Thr Gly Phe Glu Lys Arg Leu Glu Met Ile Gly Val Gly Phe Arg
                85                  90                  95

Ala Ala Val Gln Gly Ser Leu Leu Asp Leu Ser Ile Gly Val Ser His
            100                 105                 110

Pro Thr Lys Met Pro Ile Pro Thr Gly Leu Glu Val Ser Val Glu Lys
        115                 120                 125

Asn Thr Leu Ile Ser Ile Lys Gly Ile Asn Lys Gln Leu Val Gly Glu
    130                 135                 140

Phe Ala Ala Cys Val Arg Ala Lys Arg Pro Pro Glu Pro Tyr Lys Gly
145                 150                 155                 160

Lys Gly Ile Arg Tyr Glu Asn Glu Tyr Val Arg Arg Lys Ala Gly Lys
                165                 170                 175

Ala Ala Lys Thr Gly Lys Lys
            180
```

<210> SEQ ID NO 266
<211> LENGTH: 549
<212> TYPE: DNA
<213> ORGANISM: Chlamydia trachomatis

<400> SEQUENCE: 266

```
atgtctcgta aagctcgaga ccctattgtg cttcctcaag gcgtagaggt ctctattcaa     60

aatgatgaaa tctcagtgaa aggtcctaaa gggtctttga cgcaggtatt ggctaaagaa    120

gttgagattg ccgttaaagg taatgaggtg tttgttactc ctgcggctca cgttgtagat    180

agacctggtc gtatacaagg gctttattgg gccttaatag caaatatggt caaaggtgtc    240

catactggat ttgagaagcg tttagaaatg atcggagtcg gcttcagagc tgcagtacaa    300

gggtccttgt tagatctgtc aataggggtt tctcacccta caaaaatgcc tattcctacg    360

ggattagaag tctctgttga gaaaaacaca ttgatctcca ttaaaggtat caataagcag    420

ttagttggag aatttgcggc ttgtgttcgt gcaaaacgcc ctccagaacc atacaaaggt    480

aaaggaattc gttacgaaaa cgaatatgtt cgtcgtaagg ctgggaaagc agcgaaaact    540

ggtaaaaaa                                                            549
```

<210> SEQ ID NO 267
<211> LENGTH: 180
<212> TYPE: PRT
<213> ORGANISM: Chlamydia trachomatis

<400> SEQUENCE: 267

```
Met Ser Arg Leu Lys Lys Leu Tyr Thr Glu Glu Ile Arg Lys Thr Leu
1               5                   10                  15

Gln Asp Lys Phe Gln Tyr Glu Asn Val Met Gln Ile Pro Val Leu Lys
            20                  25                  30

Lys Ile Val Ile Ser Met Gly Leu Ala Glu Ala Ala Lys Asp Lys Asn
        35                  40                  45
```

```
Leu Phe Gln Ala His Leu Glu Glu Leu Ala Val Ile Ser Ser Gln Lys
    50                  55                  60

Pro Leu Val Thr Arg Ala Arg Asn Ser Ile Ala Gly Phe Lys Leu Arg
65                  70                  75                  80

Glu Gly Gln Gly Ile Gly Ala Lys Val Thr Leu Arg Gly Ile Arg Met
                85                  90                  95

Tyr Asp Phe Met Asp Arg Phe Cys Asn Ile Val Ser Pro Arg Ile Arg
            100                 105                 110

Asp Phe Arg Gly Phe Ser Cys Lys Gly Asp Gly Arg Gly Cys Tyr Ser
        115                 120                 125

Phe Gly Leu Asp Asp Gln Gln Ile Phe Pro Glu Val Asp Leu Asp Arg
    130                 135                 140

Val Lys Arg Ser Gln Gly Met Asn Ile Thr Trp Val Thr Thr Ala Gln
145                 150                 155                 160

Thr Asp Ala Glu Cys Leu Thr Leu Leu Glu Cys Met Gly Leu Arg Phe
                165                 170                 175

Lys Lys Ala Gln
            180
```

<210> SEQ ID NO 268
<211> LENGTH: 540
<212> TYPE: DNA
<213> ORGANISM: Chlamydia trachomatis

<400> SEQUENCE: 268

```
atgagcaggt taaaaaaact atatactgaa gagataagaa agactcttca agataagttt     60

cagtatgaaa atgtaatgca aatccctgtt cttaagaaga tcgtaataag catggggctt    120

gcagaggctg caaaggataa aaaccttttc caggctcatt tagaggaatt ggcggttatc    180

tctagtcaaa aacctttggt aacaagagct agaaactcta tcgcaggctt caagttacga    240

gagggtcagg gcatcggagc aaaagtcact ctacgtggaa tccgtatgta tgactttatg    300

gaccgttttt gcaatattgt ctccccaaga attcgagact ttagaggatt ctcttgtaaa    360

ggagatggac gaggatgtta ttcctttggt ttagatgatc agcaaatctt tcctgaagtt    420

gatttagatc gtgttaaacg atctcaggga atgaatatta cttgggtaac tacagcacaa    480

accgatgcgg agtgccttac cttgttagag tgtatgggct tgcgtttcaa gaaggctcaa    540
```

<210> SEQ ID NO 269
<211> LENGTH: 130
<212> TYPE: PRT
<213> ORGANISM: Chlamydia trachomatis

<400> SEQUENCE: 269

```
Val Thr Thr Glu Ser Leu Glu Thr Leu Val Glu Gln Leu Ser Gly Leu
1               5                   10                  15

Thr Val Leu Glu Leu Ser Gln Leu Lys Lys Leu Leu Glu Glu Lys Trp
            20                  25                  30

Asp Val Thr Ala Ala Ala Pro Val Val Ala Val Ala Gly Ala Ala Ala
        35                  40                  45

Ala Gly Asp Ala Pro Ala Ser Ala Glu Pro Thr Glu Phe Ala Val Ile
    50                  55                  60

Leu Glu Asp Val Pro Ser Asp Lys Lys Ile Gly Val Leu Lys Val Val
65                  70                  75                  80

Arg Glu Val Thr Gly Leu Ala Leu Lys Glu Ala Lys Glu Met Thr Glu
                85                  90                  95
```

```
Gly Leu Pro Lys Thr Val Lys Glu Lys Thr Ser Lys Ser Asp Ala Glu
            100                 105                 110

Asp Thr Val Lys Lys Leu Gln Glu Ala Gly Ala Lys Ala Val Ala Lys
        115                 120                 125

Gly Leu
    130


<210> SEQ ID NO 270
<211> LENGTH: 390
<212> TYPE: DNA
<213> ORGANISM: Chlamydia trachomatis

<400> SEQUENCE: 270

gtgacaacag aaagtttgga aactttagta gaacagttga gcggcttgac ggtgcttgaa      60

ttgtctcagc ttaaaaaatt attggaagaa aagtgggacg ttactgctgc cgctcctgta     120

gtagctgttg ctggtgctgc tgccgctggt gatgctcctg cttctgcaga gcctacagag     180

tttgctgtaa ttctggaaga cgttccttct gataagaaaa tcggggttct gaaagttgtt     240

agagaagtta ctggattagc tttgaaagaa gctaaagaaa tgactgaagg attacctaag     300

acggttaaag aaaaaacttc taaaagtgat gcagaagaca ctgttaagaa gttacaagaa     360

gccggtgcta aggctgttgc taaagggctg                                      390


<210> SEQ ID NO 271
<211> LENGTH: 123
<212> TYPE: PRT
<213> ORGANISM: Chlamydia trachomatis

<400> SEQUENCE: 271

Met Pro Thr Ile Asn Gln Leu Ile Arg Lys Lys Arg Gln Ser Gly Ala
1               5                   10                  15

Thr Arg Lys Lys Ser Pro Ala Leu Gln Lys Ser Pro Gln Lys Arg Gly
            20                  25                  30

Val Cys Leu Gln Val Lys Thr Lys Thr Pro Lys Lys Pro Asn Ser Ala
        35                  40                  45

Leu Arg Lys Val Ala Trp Val Arg Leu Ser Asn Gly Gln Glu Val Ile
    50                  55                  60

Ala Tyr Ile Gly Gly Glu Gly His Asn Leu Gln Glu His Ser Ile Val
65                  70                  75                  80

Leu Val Gln Gly Gly Arg Val Lys Asp Leu Pro Gly Val Arg Tyr His
                85                  90                  95

Ile Val Arg Gly Ala Leu Asp Cys Ala Ala Val Lys Asn Arg Lys Gln
            100                 105                 110

Ser Arg Ser Arg Tyr Gly Ala Lys Arg Pro Lys
        115                 120


<210> SEQ ID NO 272
<211> LENGTH: 369
<212> TYPE: DNA
<213> ORGANISM: Chlamydia trachomatis

<400> SEQUENCE: 272

atgccgacga ttaatcagtt aatacgtaag aagcgtcagt ctggcgcaac tagaaagaaa      60

tctccagctt tacaaaagtc tcctcagaaa agaggggtct gtcttcaggt aaaaactaaa     120

actccgaaga aacctaactc agctttgcgt aaggttgctt gggttcgttt gtctaatgga     180

caagaggtaa ttgcctacat cggtggagag ggtcataatt tgcaggagca cagcatcgtt     240
```

```
ttagtccaag gcggaagagt taaggatttg ccaggggtgc gttatcacat cgtccgaggt    300

gctttagatt gtgctgccgt aaaaaataga aaacagagcc gttctcgcta cggcgcaaag    360

cgtcctaag                                                            369


<210> SEQ ID NO 273
<211> LENGTH: 202
<212> TYPE: PRT
<213> ORGANISM: Chlamydia trachomatis

<400> SEQUENCE: 273

Met Leu Asp Leu Leu Lys Ile Ser Val Thr Gly Asp Pro Ser Ser Gly
1               5                   10                  15

Lys Thr Glu Ala Cys Gln Val Phe Glu Asp Leu Gly Ala Tyr Val Ile
            20                  25                  30

Ser Ala Asp Lys Val Ser His Ser Phe Leu Val Pro Tyr Thr Ser Val
        35                  40                  45

Gly Gln Arg Ile Ile Asp Leu Leu Gly Pro Glu Ile Ile Ile Glu Asn
    50                  55                  60

Thr Leu Ser Arg Lys Ala Ile Ala Glu Lys Val Phe Gly Asn Arg Asp
65                  70                  75                  80

Leu Leu Leu Ser Leu Glu Glu Ile Leu His Pro Glu Val Cys Arg Phe
                85                  90                  95

Val Glu Glu Lys Tyr Ala His Val Val Gln Glu Gln Lys Tyr Pro Leu
            100                 105                 110

Phe Ile Ala Glu Phe Pro Leu Leu Tyr Glu Ile Gln Tyr Ala Asp Trp
        115                 120                 125

Phe Asp Gln Val Ile Leu Ile Ser Ala Asp Thr Gly Ile Arg Lys Glu
    130                 135                 140

Arg Phe Leu Lys Lys Thr Gly Gly Ser Asp Thr Ser Phe Asp Leu Arg
145                 150                 155                 160

Cys Ala Arg Phe Ser Ser Leu Glu Glu Lys Ile Leu Arg Ala Asp Val
                165                 170                 175

Val Ile Glu Asn Asn Gly Thr Lys Glu Glu Phe Arg Arg Lys Val Lys
            180                 185                 190

Gln Cys Phe Lys Ala Leu Lys Gly Thr Ile
        195                 200


<210> SEQ ID NO 274
<211> LENGTH: 606
<212> TYPE: DNA
<213> ORGANISM: Chlamydia trachomatis

<400> SEQUENCE: 274

atgctagatt tattgaagat ttctgttaca ggagatccct cttcagggaa aactgaggcg     60

tgtcaggttt ttgaagattt gggagcttat gtaattagtg ctgataaagt ttctcatagt    120

ttccttgttc cttatacctc agtgggtcaa cgtataattg atcttttggg tccagagata    180

atcatagaga atactcttag tagaaaggcc attgctgaaa aagtttttgg taaccgggat    240

ttattgctgt ctttagaaga gattttgcat ccggaagtgt gtcgttttgt tgaggaaaaa    300

tatgcgcacg tggttcagga acaaaagtat cctctgttta ttgcggaatt tcctctgttg    360

tatgagattc agtatgcgga ttggtttgat caggttattt taatttctgc agatacaggt    420

atacgcaaag agcgttttct taaaaaaact ggaggttcgg acaccagttt cgatcttcgg    480

tgtgcacgct tttcttcttt agaagaaaaa atcctgcgag cggatgtggt catagagaat    540
```

aatggaacga aagaagaatt tcgtcgcaaa gtaaaacaat gttttaaggc tttaaaggga 600
acaata 606

<210> SEQ ID NO 275
<211> LENGTH: 72
<212> TYPE: PRT
<213> ORGANISM: Chlamydia trachomatis

<400> SEQUENCE: 275

Met Gly Ala Lys Lys Asn Leu Leu Ala Glu Leu Arg Glu Lys Ser Ser
1 5 10 15

Glu Glu Leu Asp Glu Phe Ile Arg Asp Asn Lys Lys Ala Leu Phe Ala
20 25 30

Leu Arg Ala Glu Ala Ala Leu Gln Asn Lys Val Val Lys Thr His Gln
35 40 45

Phe Ser Leu Tyr Lys Lys Ser Ile Ala Arg Ala Leu Thr Ile Lys Gln
50 55 60

Glu Lys Lys Asp Arg Val His Gly
65 70

<210> SEQ ID NO 276
<211> LENGTH: 216
<212> TYPE: DNA
<213> ORGANISM: Chlamydia trachomatis

<400> SEQUENCE: 276
atgggagcaa aaaagaattt attagcggag cttagagaga agagctctga agagttggat 60
gagtttattc gtgataataa aaaagctctc ttcgctttgc gtgcggaagc tgctttacag 120
aataaagttg tgaaaactca tcagttttct ctgtataaga aaagcattgc tcgtgctcta 180
acaataaaac aagaaaaaaa ggatagagtc catggc 216

<210> SEQ ID NO 277
<211> LENGTH: 111
<212> TYPE: PRT
<213> ORGANISM: Chlamydia trachomatis

<400> SEQUENCE: 277

Met Phe Lys Ala Thr Ala Arg Tyr Ile Arg Val Gln Pro Arg Lys Ala
1 5 10 15

Arg Leu Ala Ala Gly Leu Met Arg Asn Arg Ser Val Val Glu Ala Gln
20 25 30

Gln Gln Leu Ser Phe Ser Gln Met Lys Ala Gly Arg Cys Leu Lys Lys
35 40 45

Val Leu Asp Gly Ala Ile Ala Asn Ala Glu Ser Asn Glu Asn Ile Lys
50 55 60

Arg Glu Asn Leu Cys Val Leu Glu Val Arg Val Asp Val Gly Pro Met
65 70 75 80

Phe Lys Arg Met Lys Ser Lys Ser Arg Gly Gly Arg Ala Pro Ile Leu
85 90 95

Lys Arg Thr Ser His Leu Thr Val Ile Val Gly Glu Arg Gly Gln
100 105 110

<210> SEQ ID NO 278
<211> LENGTH: 333
<212> TYPE: DNA
<213> ORGANISM: Chlamydia trachomatis

<400> SEQUENCE: 278
atgtttaaag cgacagcccg atacatacgg gttcagccaa gaaaggctcg tttagctgca 60
ggattgatga gaaaccgtag tgttgttgaa gctcaacagc aactcagctt ttctcagatg 120
aaggctggaa gatgccttaa aaaagtgttg gatggcgcta ttgcaaatgc agagtccaat 180
gaaaatataa aacgtgaaaa tctttgcgtt ctagaagttc gggttgatgt cggcccaatg 240
ttcaaaagaa tgaagtctaa gagtcgtggg ggaagagccc cgattttgaa gcgcacgagt 300
catctaactg tgattgttgg cgagagaggg cag 333

<210> SEQ ID NO 279
<211> LENGTH: 111
<212> TYPE: PRT
<213> ORGANISM: Chlamydia trachomatis

<400> SEQUENCE: 279

Met Lys Asp Pro Tyr Asp Val Val Lys Arg His Tyr Val Thr Glu Lys
1 5 10 15

Ala Lys Met Leu Glu Gly Leu Ser Leu Gly Asp Gly Glu Gly Lys Lys
20 25 30

Lys Gly Ser Phe Cys Lys Asp Pro Lys Tyr Ile Phe Ile Val Ala Gly
35 40 45

Asp Ala Thr Lys Pro Met Ile Ala Glu Ala Ile Glu Ala Ile Tyr Ser
50 55 60

Ala Lys Gly Val Lys Val Lys Lys Val Asn Thr Met Cys Val Lys Pro
65 70 75 80

Gln Pro Thr Arg Ile Phe Arg Gly Arg Arg Lys Gly Arg Thr Ala Gly
85 90 95

Phe Lys Lys Ala Ile Val Thr Phe Val Asp Gly His Ser Ile Gly
100 105 110

<210> SEQ ID NO 280
<211> LENGTH: 333
<212> TYPE: DNA
<213> ORGANISM: Chlamydia trachomatis

<400> SEQUENCE: 280
atgaaagatc cttatgatgt tgtcaaaaga cattatgtga ccgagaaggc aaagatgttg 60
gaaggtttga gtctcggaga cggagaaggt aaaaagaaag gcagtttctg caaagatcct 120
aagtacatat ttattgttgc tggggacgcc acgaagccta tgattgctga agccatagaa 180
gcaatttatt ctgctaaagg tgtgaaggtt aaaaaagtaa acaccatgtg tgttaaacct 240
caacctacaa gaatattccg aggccgaaga aaaggaagaa ccgcagggtt taagaaggct 300
attgtgactt ttgttgatgg tcactctatt ggt 333

<210> SEQ ID NO 281
<211> LENGTH: 243
<212> TYPE: PRT
<213> ORGANISM: Chlamydia trachomatis

<400> SEQUENCE: 281

Met Lys Ile Thr Pro Ile Lys Thr Arg Lys Val Phe Ala His Asp Ser
1 5 10 15

Leu Gln Glu Ile Leu Gln Glu Ala Leu Pro Pro Leu Gln Glu Arg Ser
20 25 30

Val Val Val Val Ser Ser Lys Ile Val Ser Leu Cys Glu Gly Ala Val
35 40 45

```
Ala Asp Ala Arg Met Cys Lys Ala Glu Leu Ile Lys Lys Glu Ala Asp
    50                  55                  60

Ala Tyr Leu Phe Cys Glu Lys Ser Gly Ile Tyr Leu Thr Lys Lys Glu
65                  70                  75                  80

Gly Ile Leu Ile Pro Ser Ala Gly Ile Asp Glu Ser Asn Thr Asp Gln
                85                  90                  95

Pro Phe Val Leu Tyr Pro Lys Asp Ile Leu Gly Ser Cys Asn Arg Ile
            100                 105                 110

Gly Glu Trp Leu Arg Asn Tyr Phe Arg Val Lys Glu Leu Gly Val Ile
        115                 120                 125

Ile Thr Asp Ser His Thr Thr Pro Met Arg Arg Gly Val Leu Gly Ile
    130                 135                 140

Gly Leu Cys Trp Tyr Gly Phe Ser Pro Leu His Asn Tyr Ile Gly Ser
145                 150                 155                 160

Leu Asp Cys Phe Gly Arg Pro Leu Gln Met Thr Gln Ser Asn Leu Val
                165                 170                 175

Asp Ala Leu Ala Val Ala Ala Val Val Cys Met Gly Glu Gly Asn Glu
            180                 185                 190

Gln Thr Pro Leu Ala Val Ile Glu Gln Ala Pro Asn Met Val Tyr His
        195                 200                 205

Ser His Pro Thr Ser Arg Glu Glu Tyr Cys Ser Leu Arg Ile Asp Glu
    210                 215                 220

Thr Glu Asp Leu Tyr Gly Pro Phe Leu Gln Ala Val Thr Trp Ser Gln
225                 230                 235                 240

Glu Lys Lys
```

<210> SEQ ID NO 282
<211> LENGTH: 729
<212> TYPE: DNA
<213> ORGANISM: Chlamydia trachomatis

<400> SEQUENCE: 282

```
atgaaaataa ctccgatcaa aacacgtaaa gtatttgcac atgattcgct tcaagagatc      60

ttgcaagagg ctttgccgcc tctgcaagaa cggagtgtgg tagttgtctc ttcaaagatt     120

gtgagtttat gtgaaggcgc tgtcgctgat gcaagaatgt gcaaagcaga gctgataaaa     180

aaagaagcgg atgcttattt gttttgtgag aaaagcggga tatatctaac gaaaaaagaa     240

ggtattttga ttccttctgc agggattgat gaatcgaata cggaccagcc ttttgtttta     300

tatcctaaag atattttggg atcgtgtaat cgcatcggag aatggttaag aaattatttt     360

cgagtgaaag agctaggcgt aatcattaca gatagccata ctactccaat gcggcgtgga     420

gtactgggta tcgggctgtg ttggtatgga ttttctccat tacacaacta tataggatcg     480

ctagattgtt tcggtcgtcc cttacagatg acgcaaagta atcttgtaga tgccttagca     540

gttgcggctg ttgtttgtat gggagagggg aatgagcaaa caccgttagc ggtgatagag     600

caggcaccta atatggtcta ccattcacat cctacttctc gagaagagta ttgttctttg     660

cgcatagatg aaacagagga cttatacgga ccttttttgc aagcggttac gtggagtcaa     720

gaaaagaaa                                                             729
```

<210> SEQ ID NO 283
<211> LENGTH: 450
<212> TYPE: PRT
<213> ORGANISM: Chlamydia trachomatis

<400> SEQUENCE: 283

Met Thr Ser Trp Asn Phe Val Cys Leu Ser Leu Gly Ser Asn Leu Gly
1 5 10 15

Asn Arg His Glu His Ile Arg Arg Ala Tyr Ala Ser Leu Lys Lys Ala
20 25 30

Gly Ile Arg Asn Leu Lys Ser Ser Val Ile Leu Glu Thr Lys Ala Leu
35 40 45

Leu Leu Glu Gly Ala Pro Lys Glu Trp Asp Leu Pro Tyr Phe Asn Ser
50 55 60

Val Val Ile Gly Glu Thr Gln Leu Ser Pro Asp Glu Leu Ile Glu Glu
65 70 75 80

Ile Lys Met Ile Glu Ser Arg Phe Gly Gln Asp Ala Ser Leu Lys Trp
85 90 95

Gly Pro Arg Pro Ile Asp Ile Asp Val Leu Phe Tyr Gly Asp Glu Ala
100 105 110

Phe Ser Tyr His Ser Asp Lys Cys Thr Ile Pro His Pro Lys Val Leu
115 120 125

Glu Arg Pro Phe Leu Leu Ser Met Ile Ala Ser Leu Cys Pro Tyr Arg
130 135 140

Arg Phe Arg Leu Glu Gly Ser Ser Cys Asn Gly Lys Thr Phe Ala Glu
145 150 155 160

Leu Ala Ala Ile Tyr Pro Leu Thr Glu Glu Asp Ala Leu Gly Ser Phe
165 170 175

Gly Ser Ala Thr Gln Ile Met Gly Ile Val Asn Ile Thr Asp Asn Ser
180 185 190

Ile Ser Asp Thr Gly Leu Phe Leu Glu Ala Arg Arg Ala Ala Ala His
195 200 205

Ala Glu Arg Leu Phe Ala Glu Gly Ala Ser Ile Ile Asp Leu Gly Ala
210 215 220

Gln Ala Thr Asn Pro Arg Val Lys Asp Leu Gly Ser Val Glu Gln Glu
225 230 235 240

Trp Glu Arg Leu Glu Pro Val Leu Arg Leu Leu Ala Glu Arg Trp Gly
245 250 255

Ala Ala Gln Gln Cys Pro Asp Val Ser Ile Asp Thr Phe Arg Pro Glu
260 265 270

Ile Ile Arg Arg Ala Val Glu Val Phe Pro Ile Arg Trp Ile Asn Asp
275 280 285

Val Ser Gly Gly Ser Leu Glu Met Ala His Leu Ala Lys Glu Phe Gly
290 295 300

Leu Arg Leu Leu Ile Asn His Ser Cys Ser Leu Pro Pro Arg Pro Asp
305 310 315 320

Cys Val Leu Ser Tyr Glu Glu Ser Pro Ile Glu Gln Met Leu Arg Trp
325 330 335

Gly Glu Ser Gln Leu Glu Gln Phe Ala Gln Val Gly Leu Asp Thr Ser
340 345 350

Trp Gln Val Val Phe Asp Pro Gly Ile Gly Phe Gly Lys Thr Pro Val
355 360 365

Gln Ser Met Leu Leu Met Asp Gly Val Lys Gln Phe Lys Arg Val Leu
370 375 380

Glu Cys Pro Val Leu Ile Gly His Ser Arg Lys Ser Cys Leu Ser Met
385 390 395 400

Leu Gly Arg Phe Asn Ser Asn Asp Arg Asp Trp Glu Thr Ile Gly Cys
405 410 415

```
Ser Val Ser Leu His Asp Arg Gly Val Asp Tyr Leu Arg Val His Gln
            420                 425                 430

Val Glu Gly Asn Arg Arg Ala Leu Ala Ala Ala Ala Trp Ala Gly Met
        435                 440                 445

Phe Val
    450


<210> SEQ ID NO 284
<211> LENGTH: 1350
<212> TYPE: DNA
<213> ORGANISM: Chlamydia trachomatis

<400> SEQUENCE: 284

atgactagtt ggaattttgt ttgtttaagt ttgggttcca atttaggtaa ccggcatgag      60

catataagac gcgcttatgc aagtttaaag aaggctggga tccgaaattt aaaaagttct     120

gtgattttag agacgaaggc tttgttgtta gaaggggctc cgaaagaatg ggatcttcct     180

tattttaact ctgtggttat tggggaaacg cagctatctc cagacgagtt gattgaagaa     240

atcaagatga tagaaagtcg ttttggacaa gatgcttctt tgaaatgggg gcctcgaccg     300

attgatattg atgtgctttt ctatggagac gaagcttttt cttatcatag tgacaaatgt     360

acaatcccac atcctaaggt attagaaaga ccttttcttc tttctatgat agcttcttta     420

tgtccgtatc gtcgtttccg tttggaagga tcttcttgta atgggaaaac gtttgcagag     480

cttgctgcta tttatccatt gacggaggag gatgcgttag gcagtttcgg ttctgctacc     540

caaattatgg gtattgttaa tattacggat aactcgatct ccgatacagg attgtttctg     600

gaggcgagaa gagccgcagc ccatgctgag agactctttg cagaaggagc ttctattatt     660

gatttagggg cgcaagcaac caatcctcgt gtaaaagatt taggaagcgt agaacaagag     720

tgggagcgtc tagaacctgt tttgcgttta ttagcggagc ggtgggggc tgctcaacaa     780

tgccctgatg tatctatcga tacatttcgt ccagagatta ttcgacgagc tgttgaagta     840

tttccgattc gttggatcaa tgatgtttct ggaggctctt tggaaatggc tcatttggcg     900

aaggagtttg ggctacggct attaataaat cattcgtgtt cgctgcctcc aagaccagat     960

tgtgtacttt cttatgaaga atctcctatt gagcaaatgt tgcgttgggg agagtctcag    1020

ttagaacaat ttgctcaagt aggtttagat acaagttggc aagttgtttt cgatccagga    1080

ataggatttg ggaagactcc cgttcagtcg atgttattga tggatggagt aaagcagttt    1140

aaacgtgttt tagagtgtcc tgtattaata ggccattcta gaaaatcgtg tttgagtatg    1200

ttgggccgat ttaatagtaa cgatcgtgat tgggaaacga tcggctgttc tgtatctctt    1260

catgatcgag gagttgatta tctacgcgtg catcaggttg aaggtaacag acgtgcctta    1320

gccgctgctg cttgggctgg tatgtttgta                                     1350


<210> SEQ ID NO 285
<211> LENGTH: 209
<212> TYPE: PRT
<213> ORGANISM: Chlamydia trachomatis

<400> SEQUENCE: 285

Met Ala Arg Tyr Cys Gly Pro Lys Asn Arg Ile Ala Arg Arg Phe Gly
1               5                   10                  15

Ala Asn Ile Phe Gly Arg Gly Arg Asn Pro Leu Leu Arg Lys Pro Asn
            20                  25                  30

Pro Pro Gly Gln His Gly Met Gln Arg Lys Lys Lys Ser Asp Tyr Gly
```

```
        35                  40                  45

Leu Gln Leu Glu Glu Lys Gln Lys Leu Lys Ala Cys Tyr Gly Met Ile
    50                  55                  60

Leu Glu Lys Gln Leu Val Lys Ala Tyr Lys Glu Val Val Asn Lys Gln
65                  70                  75                  80

Gly Asn Val Ala Gln Met Phe Leu Glu Lys Phe Glu Cys Arg Leu Asp
                85                  90                  95

Asn Ile Val Tyr Arg Leu Gly Phe Ala Lys Thr Ile Phe Ala Ala Gln
            100                 105                 110

Gln Leu Val Ser His Gly His Val Leu Val Asn Gly Lys Lys Val Asp
        115                 120                 125

Arg Arg Ser Phe Phe Val Arg Pro Gly Met Gln Ile Ser Leu Lys Glu
    130                 135                 140

Lys Ser Lys Arg Leu Ala Ile Val Thr Glu Ser Leu Glu Asn Lys Asp
145                 150                 155                 160

Gln Ser Ser Leu Pro Ala Tyr Leu Ser Leu Asp Lys Ala Ala Phe Lys
                165                 170                 175

Gly Glu Leu Val Val Ala Pro Glu Leu Asp Gln Ile Ala Ser Gln Leu
            180                 185                 190

Pro Leu Pro Val Asn Val Ser Val Ile Cys Glu Phe Leu Ser His Arg
        195                 200                 205

Thr


<210> SEQ ID NO 286
<211> LENGTH: 627
<212> TYPE: DNA
<213> ORGANISM: Chlamydia trachomatis

<400> SEQUENCE: 286

atggcgagat attgtggccc taaaaacaga atagcgagac gttttggagc taacatcttt      60

gggagaggtc gaaacccttt gctgagaaag cccaatcctc cgggtcagca cggcatgcaa     120

agaaaaaaga aatctgacta cggcttacag ttagaagaaa agcaaaaatt aaaagcttgc     180

tacggaatga tcttagagaa gcaattggtt aaagcttaca aagaggttgt aaataagcaa     240

ggaaacgttg cgcaaatgtt cctagagaaa tttgagtgcc gtttggacaa tatcgtctat     300

agactaggat tcgcaaaaac gatctttgct gctcaacaat tggtttctca tgggcacgta     360

ttggtgaacg ggaaaaaggt agatagacgc tcgttcttcg ttcgtcctgg aatgcagatc     420

tctttgaaag aaaaatcaaa aagattagct atcgttacag aatctttaga gaacaaagat     480

caaagctctc ttcctgccta tctatctttg gataaagcag cttttaaagg agagttggtt     540

gttgctccag aactggatca aatcgcttct caacttcctt taccagtaaa cgtttctgtt     600

atttgtgagt ttctatccca cagaaca                                         627


<210> SEQ ID NO 287
<211> LENGTH: 227
<212> TYPE: PRT
<213> ORGANISM: Chlamydia trachomatis

<400> SEQUENCE: 287

Met Ala Gly Pro Lys His Val Leu Leu Val Ser Glu Asn Trp Asp Leu
1               5                   10                  15

Phe Phe Gln Thr Lys Glu Leu Leu Asn Pro Glu Glu Tyr Arg Cys Thr
            20                  25                  30

Ile Gly Gln Gln Tyr Lys Gln Glu Leu Ser Ala Asp Leu Val Val Cys
```

```
        35                  40                  45

Glu Tyr Ser Leu Leu Pro Arg Glu Val Arg Ser Pro Lys Ser Leu Lys
    50                  55                  60

Gly Ser Phe Val Leu Val Leu Leu Asp Phe Phe Asp Glu Glu Thr Ser
65                  70                  75                  80

Val Asp Leu Leu Asp Arg Gly Phe Trp Tyr Leu Ile Gln Pro Ile Thr
                85                  90                  95

Pro Arg Ile Leu Lys Ser Ala Ile Ser Leu Phe Leu Ser Gln His Ser
            100                 105                 110

Leu His Ser Val Pro Glu Ser Ile Arg Phe Gly Pro Asn Val Phe His
        115                 120                 125

Val Leu Lys Leu Thr Val Glu Thr Pro Glu Gly Ser Val His Leu Thr
    130                 135                 140

Pro Ser Glu Ser Gly Ile Leu Lys Arg Leu Leu Ile Asn Lys Gly Gln
145                 150                 155                 160

Leu Cys Leu Arg Lys His Leu Leu Glu Glu Ile Lys Asn His Ala Lys
                165                 170                 175

Ala Ile Val Ala Arg Asn Val Asp Val His Ile Ala Ser Leu Arg Lys
            180                 185                 190

Lys Leu Gly Ala Tyr Gly Ser Arg Ile Val Thr Leu Arg Gly Val Gly
        195                 200                 205

Tyr Leu Phe Ser Asp Asp Gly Asp Lys Lys Phe Ser Gln Gln Asp Thr
    210                 215                 220

Lys Leu Ser
225
```

<210> SEQ ID NO 288
<211> LENGTH: 681
<212> TYPE: DNA
<213> ORGANISM: Chlamydia trachomatis

<400> SEQUENCE: 288

```
atggcagggc ctaaacatgt gttactagta agtgaaaatt gggatttatt ttttcaaaca     60

aaagaattgc ttaatcctga agagtatcgg tgcactattg ggcagcaata taaacaagaa    120

ctgtccgcag acttggttgt ctgcgaatat tcattgcttc caagagaggt tcgttctcca    180

aaatctttaa aaggtagttt tgttttagtt cttttagatt tttttgatga agaaactagt    240

gttgatcttt tggatcgtgg tttttggtat ttaattcagc ctattactcc tagaatttta    300

aaatccgcaa tcagcttgtt tctttctcag cattcgctac attctgttcc ggaaagtatt    360

cgttttgggc ctaatgtatt tcatgtattg aagctcacag tagaaactcc agaagggagt    420

gttcatttaa caccatcgga gtctggtatt ttgaaacgac ttcttattaa caaaggacaa    480

ctttgtttac gaaaacatct tcttgaagaa attaagaatc atgccaaagc gattgtagca    540

aggaatgtag acgtacacat agcttcttta aggaaaaagt taggagctta tggaagtaga    600

attgtcacct tacgaggtgt tgggtatcta ttttcagatg atggagataa aaaattctct    660

caacaagata caaagctttc t                                              681
```

<210> SEQ ID NO 289
<211> LENGTH: 192
<212> TYPE: PRT
<213> ORGANISM: Chlamydia trachomatis

<400> SEQUENCE: 289

```
Met Arg Arg Leu Gly Val Trp Val Leu Leu Leu Leu Ala Ser Gly Ala
```

-continued

```
1               5                   10                  15

Ala Ser Leu Pro Ala Ile Gly Ala Trp Cys Trp Arg Gln Arg Thr Ala
            20                  25                  30

Glu Ala Trp Glu Asn Leu Leu Ile Asp Met Arg Asp Phe Gln Ser Lys
        35                  40                  45

Arg Glu Arg Ser Ser Gln Val Ala Ile Lys Asn Ala Arg Leu Lys Ala
    50                  55                  60

Ala His Lys Gln Ala Ser Phe Pro Asn Trp Ile Ala Gln Gly Glu Asn
65                  70                  75                  80

Leu Val Phe Leu Asn Lys Glu Arg Asp Ala Leu Ala Lys Leu Pro Ala
                85                  90                  95

Thr Ala Trp Val Val Arg Ser Arg Ala Val Lys Asp Arg Lys Ala Phe
            100                 105                 110

Leu Glu Asp Asn Arg Leu Ser Trp Gln Glu Gln Thr Leu Gly Glu Lys
        115                 120                 125

Ser Thr Leu Phe Ser Phe Gln Lys Glu Leu Gln Ile Asp Asp Glu Asp
    130                 135                 140

Ile Pro Val Leu Leu Gly Leu Phe Asp Pro Lys Tyr Thr Gln Ile Pro
145                 150                 155                 160

Ile Val Phe Leu Ser Tyr Trp Glu Met Thr Lys Gln Val Ser Ser Leu
                165                 170                 175

Gly Asn Glu Val Trp Val Val His Ala Glu Ala Trp Gly Arg Cys Val
            180                 185                 190
```

<210> SEQ ID NO 290
<211> LENGTH: 576
<212> TYPE: DNA
<213> ORGANISM: Chlamydia trachomatis

<400> SEQUENCE: 290

```
atgcgacgct taggagtatg ggtgctgtta ctattagcga gtggggctgc ttctcttcct     60

gcaataggag catggtgttg gcgtcagcgt acagcagagg cttgggaaaa tttactcatc    120

gatatgagag attttcagtc taaacgagag cgatcttctc aggtagcaat caagaatgcg    180

cggctgaaag cagcgcataa acaagcgagt ttccccaatt ggattgccca aggagagaat    240

ctcgttttct tgaataagga gcgagatgct ctagctaaac ttcctgcaac agcctgggtg    300

gtgagaagtc gtgcagtcaa ggatcggaag gctttcttag aagataaccg cttgtcatgg    360

caggagcaga ctttaggaga gaaaagcacg ctgttttctt tccaaaaaga gctccaaata    420

gatgacgagg acattcctgt attattagga ttgtttgatc ctaagtatac ccaaataccc    480

attgtttttc tttcttactg ggaaatgacg aagcaggtgt catcattagg aaatgaggtg    540

tgggtcgttc acgcggaggc ttggggacga tgtgtg                              576
```

<210> SEQ ID NO 291
<211> LENGTH: 178
<212> TYPE: PRT
<213> ORGANISM: Chlamydia trachomatis

<400> SEQUENCE: 291

```
Met Lys Asn Ile Val Glu Gln Lys Arg Cys Leu Arg Arg Glu Gly Leu
1               5                   10                  15

Ala Lys Arg Glu Gln Leu Ser Val Gln Arg Arg Asp Glu Ala Ala Arg
            20                  25                  30

Glu Leu Met His Phe Val Met Gln Thr Ile Pro Gln Gly Phe Val Leu
        35                  40                  45
```

Ser Tyr Ile Pro Phe Arg Ser Glu Leu Asp Val Arg Gly Ile Asn Ala
50 55 60

Trp Leu Ala Gln Glu Asn Arg Leu Leu Leu Pro Lys Met Gln Gly Met
65 70 75 80

Asp Ile Val Pro Ile Ala Leu Pro Phe Thr Lys Ile Glu Ser Leu Tyr
85 90 95

Ser Pro Lys Asp Leu Asn Arg Ile Glu Gly Glu Glu Ile Glu Ala Gln
100 105 110

Gln Ile Ala Ala Ala Leu Ile Pro Ala Ile Val Phe Asp Gln Asn Lys
115 120 125

Phe Arg Leu Gly Tyr Gly Gly Gly Tyr Tyr Asp Arg Phe Leu Ser Lys
130 135 140

Tyr Pro Tyr Ile Trp Thr Ile Gly Val Gly Phe Lys Glu Gln Leu Leu
145 150 155 160

Ala Tyr Leu Pro Arg Glu Glu Tyr Asp Val Pro Leu Asp Gln Leu Tyr
165 170 175

Leu Thr

<210> SEQ ID NO 292
<211> LENGTH: 534
<212> TYPE: DNA
<213> ORGANISM: Chlamydia trachomatis

<400> SEQUENCE: 292
atgaaaaaca ttgtagagca gaaacgttgt ttgcgacgag aagggttagc gaagcgcgag 60
cagctttctg tccagcgcag agatgaagca gctcgtgagc tgatgcattt tgttatgcag 120
acaattccgc aaggctttgt gttatcctat attccttttc gctcagagtt ggatgttcga 180
gggatcaatg catggttagc gcaagagaac cgactcctcc tacctaaaat gcaagggatg 240
gatatcgttc cgatagctct tccttttacc aagatagaga gtctgtattc tcctaaagat 300
ttgaatcgga tagaaggaga agagatcgag gcacaacaga ttgcagcggc cttgattcct 360
gcgatagtct ttgatcagaa caagtttcgt ttaggatatg gcggaggcta ctatgatcgt 420
tttttgtcta agtatccgta tatttggaca ataggcgtgg gatttaaaga gcagctgttg 480
gcgtatcttc caagggaaga gtatgatgtt cccttagatc agttatatct cact 534

<210> SEQ ID NO 293
<211> LENGTH: 184
<212> TYPE: PRT
<213> ORGANISM: Chlamydia trachomatis

<400> SEQUENCE: 293

Met Lys Glu Ile Tyr Tyr Glu Ile Ala Arg Thr Glu Ser Thr Asn Thr
1 5 10 15

Thr Ala Lys Glu Gly Leu Ser Leu Trp Asp Pro Tyr Ala Leu Thr Val
20 25 30

Ile Thr Thr Arg Glu Gln Thr Ala Gly Arg Gly Lys Phe Gly Arg Val
35 40 45

Trp His Ser Thr Asp Gln Asp Leu Leu Ala Ser Phe Cys Phe Phe Leu
50 55 60

Ser Val Asn Asn Val Asp Ser Ala Leu Leu Phe Arg Ile Gly Thr Glu
65 70 75 80

Ala Val Met Arg Leu Gly Glu Ser Leu Gly Ile Gln Glu Ala Val Met
85 90 95

```
Lys Trp Pro Asn Asp Val Leu Val Gln Gly Lys Lys Leu Ser Gly Val
            100                 105                 110

Leu Cys Glu Thr Ile Pro Val Lys Thr Gly Thr Cys Val Ile Ile Gly
        115                 120                 125

Ile Gly Val Asn Gly Asn Val Gly Ala Asp Glu Leu Leu Gly Ile Asp
    130                 135                 140

Gln Pro Ala Thr Ser Leu Gln Glu Leu Ile Gly Arg Pro Val Asp Met
145                 150                 155                 160

Glu Glu Gln Leu Lys Arg Leu Thr Lys Glu Ile Lys His Leu Ile Gln
                165                 170                 175

Thr Leu Pro Leu Trp Gly Arg Glu
            180


<210> SEQ ID NO 294
<211> LENGTH: 552
<212> TYPE: DNA
<213> ORGANISM: Chlamydia trachomatis

<400> SEQUENCE: 294

atgaaagaaa tctattatga aatagcacgt acggaatcaa cgaatacgac agcaaaagag     60

gggctttctt tgtgggatcc ctatgctctc acagtgatca cgaccagaga acaaacggcg    120

ggaagaggga aatttggaag ggtctggcac tccacagatc aagatctttt ggcttcgttt    180

tgtttctttt taagtgtgaa taatgtggac agtgctttgt tatttcgtat agggacagaa    240

gccgtgatgc gtctcgggga atcgttaggc attcaagaag ctgtcatgaa atggcctaac    300

gacgtgttag ttcaggggaa aaaactttca ggagtgttgt gtgagaccat ccctgttaag    360

actggaacgt gtgtcattat tggtatcggt gtgaatggta atgtgggtgc tgatgaattg    420

ctaggtattg atcagcctgc aacgtctctc caggaattga tagggaggcc tgtagatatg    480

gaagaacagc ttaagcggct cacgaaagaa atcaagcatc ttatccagac gctaccgtta    540

tgggggcgag aa                                                        552


<210> SEQ ID NO 295
<211> LENGTH: 221
<212> TYPE: PRT
<213> ORGANISM: Chlamydia trachomatis

<400> SEQUENCE: 295

Met Lys Lys Phe Ile Tyr Lys Tyr Ser Phe Gly Ala Leu Leu Leu Leu
1               5                   10                  15

Ser Gly Leu Ser Gly Leu Ser Ser Cys Cys Ala Asn Ser Tyr Gly Ser
            20                  25                  30

Thr Leu Ala Lys Asn Thr Ala Glu Ile Lys Glu Glu Ser Val Thr Leu
        35                  40                  45

Arg Glu Lys Pro Asp Ala Gly Cys Lys Lys Lys Ser Ser Cys Tyr Leu
    50                  55                  60

Arg Lys Phe Phe Ser Arg Lys Lys Pro Lys Glu Lys Thr Glu Pro Val
65                  70                  75                  80

Leu Pro Asn Phe Lys Ser Tyr Ala Asp Pro Met Thr Asp Ser Glu Arg
                85                  90                  95

Lys Asp Leu Ser Phe Val Val Ser Ala Ala Ala Asp Lys Ser Ser Ile
            100                 105                 110

Ala Leu Ala Met Ala Gln Gly Glu Ile Lys Gly Ala Leu Ser Arg Ile
        115                 120                 125

Arg Glu Ile His Pro Leu Ala Leu Leu Gln Ala Leu Ala Glu Asp Pro
```

```
    130                 135                 140

Ala Leu Ile Ala Gly Met Lys Lys Met Gln Gly Arg Asp Trp Val Trp
145                 150                 155                 160

Asn Ile Phe Ile Thr Glu Leu Ser Lys Val Phe Ser Gln Ala Ala Ser
                165                 170                 175

Leu Gly Ala Phe Ser Val Ala Asp Val Ala Ala Phe Ala Ser Thr Leu
            180                 185                 190

Gly Leu Asp Ser Gly Thr Val Thr Ser Ile Val Asp Gly Glu Arg Trp
        195                 200                 205

Ala Glu Leu Ile Asp Val Val Ile Gln Asn Pro Ala Ile
    210                 215                 220


<210> SEQ ID NO 296
<211> LENGTH: 663
<212> TYPE: DNA
<213> ORGANISM: Chlamydia trachomatis

<400> SEQUENCE: 296

atgaaaaagt ttatctataa gtatagcttt ggagctctct tgttgctctc cgggctctcc      60

ggattgagca gctgttgcgc caactcttat ggatcgactc ttgcaaaaaa tacagccgag     120

ataaaagaag aatctgttac acttcgcgag aagccggatg ccggctgtaa aaagaaatct     180

tcttgttact tgagaaaatt tttctcgcgc aagaaaccta aagagaagac agagcctgtg     240

ttgccgaact ttaagtctta cgcagatcca atgacagatt ccgaaagaaa agacctttct     300

ttcgtagtat ctgctgctgc tgataagtct tctattgctt tggctatggc tcagggggaa     360

attaaaggcg cattatcgcg tattagagag atccatcctc ttgcattgtt acaagctctt     420

gcagaagatc ctgctttaat tgctggaatg aaaaagatgc aaggacggga ttgggtctgg     480

aatatcttta tcacagaatt aagcaaagtt ttttctcaag cagcatcttt aggggctttc     540

agcgttgcag acgttgccgc gttcgcgtcg accttaggat tagactcggg gaccgttacc     600

tcaattgttg atggggaaag gtgggctgag ctgatcgatg tcgtgattca gaaccctgct     660

ata                                                                   663


<210> SEQ ID NO 297
<211> LENGTH: 229
<212> TYPE: PRT
<213> ORGANISM: Chlamydia trachomatis

<400> SEQUENCE: 297

Met His Ser Leu Ala Val Phe Gln Glu Ile Phe Asn Arg Tyr Thr Glu
1               5                   10                  15

Lys Pro Tyr Pro Ala Thr Ser Thr Leu Val Pro Leu Tyr Phe Pro Glu
            20                  25                  30

Glu Pro Leu Thr Phe Ser Glu Asp Leu Ser Pro Ser Thr Ala Pro Ile
        35                  40                  45

Leu Asn Pro Pro Gly Leu Glu Pro Gln Ala Leu Pro Val Glu Thr Pro
    50                  55                  60

Lys Asp Pro Val Thr Thr Ser Ile Pro Pro Pro Ser His Pro Lys Glu
65                  70                  75                  80

Ser Lys His Ser Trp Ala Cys Val Pro Ile Tyr Pro Gly Leu Ser His
                85                  90                  95

Glu Glu Leu Leu Lys Glu Asn Tyr Pro Ala Leu Lys Arg Tyr Ile Gln
            100                 105                 110

Arg Pro Ala Arg Ala Ser Cys Gly Ile Phe Val His Glu Ser Gln Glu
```

-continued

```
        115                 120                 125

Tyr Glu Ile Leu Phe Phe Asn Arg Leu Ala Lys Ile Leu Ser Gln Lys
    130                 135                 140

Ile Phe Pro Thr Arg Leu Val Leu Phe His Gln Lys Thr Leu Ser Asp
145                 150                 155                 160

Phe Ser His Ser Pro His Pro Phe Cys Leu Ala Pro Leu Pro Thr Ile
                165                 170                 175

Arg Tyr Lys Asn Ser Gln Val Asn Tyr His Tyr Pro Val Leu His Asp
            180                 185                 190

Lys Val Thr Cys Ile Pro Ile Tyr Ser Ser Ser Gln Tyr Glu Lys Asp
        195                 200                 205

Ser Ala Leu Lys Arg Asp Leu Trp Thr Leu Leu Thr Ser Leu Ser Ala
    210                 215                 220

Ser Met Gln Lys Ser
225


<210> SEQ ID NO 298
<211> LENGTH: 687
<212> TYPE: DNA
<213> ORGANISM: Chlamydia trachomatis

<400> SEQUENCE: 298

atgcattcac ttgctgtttt tcaagaaatt tttaatcgct acacagaaaa gccctacccc     60

gccacgtcta cactggtccc actatatttt ccagaagaac ctcttacctt ttccgaggac    120

ttatctccat ccacggctcc tattcttaat cccccaggct tagaaccgca agctcttccg    180

gtagaaactc ccaaagaccc tgttacaact tctattcccc caccttccca tcctaaagaa    240

tccaaacact cctgggcctg tgttcctatt taccctggac tctctcatga agaactactg    300

aaagaaaatt atcctgcttt aaaacgttat attcaacgac ctgcaagggc ctcatgtggc    360

atttttgtcc atgaatctca ggaatatgag attcttttct ttaatcgctt agctaaaatt    420

ctttcacaga aaatttttcc tactcgcctc gttctttttc accaaaaaac tttgtctgat    480

tttagtcatt cccctcatcc tttttgtttg gcgcccttac caacaatcag gtataaaaat    540

tcgcaagtga actatcacta tcctgttttg cacgataaag taacctgcat acccatttat    600

tcctcttccc aatatgaaaa agattcagca ttaaaaagag atttatggac cctactcacc    660

agcctttccg cctctatgca gaagtca                                         687


<210> SEQ ID NO 299
<211> LENGTH: 112
<212> TYPE: PRT
<213> ORGANISM: Chlamydia trachomatis

<400> SEQUENCE: 299

Met Lys Lys Lys Thr Gly Gln Leu Tyr Glu Gly Ala Tyr Val Phe Ser
1               5                   10                  15

Val Thr Leu Ser Glu Asp Ala Arg Arg Lys Ala Leu Glu Lys Val Thr
            20                  25                  30

Ser Gly Ile Thr Asn Tyr Gly Gly Glu Val Leu Lys Ile His Asp Gln
        35                  40                  45

Gly Arg Lys Lys Leu Ala Tyr Thr Ile Arg Gly Ala Arg Glu Gly Tyr
    50                  55                  60

Tyr Tyr Phe Ile Tyr Phe Thr Val Ala Pro Glu Ala Ile Ala Glu Leu
65                  70                  75                  80

Trp Arg Glu Tyr His Leu Asn Glu Asp Leu Leu Arg Phe Met Thr Leu
```

```
                85                  90                  95

Lys Ala Ser Ala Val Lys Glu Val Leu Glu Phe Ala Thr Leu Pro Glu
            100                 105                 110
```

<210> SEQ ID NO 300
<211> LENGTH: 336
<212> TYPE: DNA
<213> ORGANISM: Chlamydia trachomatis

<400> SEQUENCE: 300

```
atgaaaaaaa aaacaggcca actttatgag ggagcctatg tttttagcgt gacgttaagt      60

gaagacgcta gacgtaaggc tttagaaaaa gttacttctg ggatcaccaa ttatggtggc     120

gaagttctga aaattcatga tcaggggcgc aaaaagttag cttacacaat tcgtggtgct     180

agagaaggct attactactt tatttatttc acagtagccc cagaagctat cgcagagttg     240

tggagagagt atcatttaaa cgaagatctt cttcgattca tgactcttaa agcaagcgct     300

gtgaaagaag ttttagaatt cgctacattg ccagaa                               336
```

<210> SEQ ID NO 301
<211> LENGTH: 193
<212> TYPE: PRT
<213> ORGANISM: Chlamydia trachomatis

<400> SEQUENCE: 301

```
Leu Trp Phe Phe Leu Gly Ser Pro Ser Ala Ile Thr Asn Phe Ser Arg
1               5                   10                  15

Val Asp Val Ala Leu Asn Leu Arg Ile Asn Arg Gln Ile Arg Ala Pro
            20                  25                  30

Arg Val Arg Val Ile Gly Ser Ala Gly Glu Gln Leu Gly Ile Leu Ser
        35                  40                  45

Ile Lys Glu Ala Leu Asp Leu Ala Lys Glu Ala Asn Leu Asp Leu Val
    50                  55                  60

Glu Val Ala Ser Asn Ser Glu Pro Pro Val Cys Lys Ile Met Asp Tyr
65                  70                  75                  80

Gly Lys Tyr Arg Tyr Asp Val Thr Lys Lys Glu Lys Asp Ser Lys Lys
                85                  90                  95

Ala Gln His Gln Val Arg Ile Lys Glu Val Lys Leu Lys Pro Asn Ile
            100                 105                 110

Asp Asp Asn Asp Phe Leu Thr Lys Ala Lys Gln Ala Arg Ala Phe Ile
        115                 120                 125

Glu Lys Gly Asn Lys Val Lys Val Ser Cys Met Phe Arg Gly Arg Glu
    130                 135                 140

Leu Ala Tyr Pro Glu His Gly Tyr Lys Val Ile Gln Arg Met Cys Gln
145                 150                 155                 160

Gly Leu Glu Asp Ile Gly Phe Val Glu Ser Glu Pro Lys Leu Asn Gly
                165                 170                 175

Arg Ser Leu Ile Cys Val Ile Ala Pro Gly Thr Leu Lys Thr Lys Lys
            180                 185                 190

Lys
```

<210> SEQ ID NO 302
<211> LENGTH: 579
<212> TYPE: DNA
<213> ORGANISM: Chlamydia trachomatis

<400> SEQUENCE: 302

```
ttgtggtttt ttttaggctc tccgtcagcg attactaatt ttagcagggt agatgtggct     60

ttaaacctaa gaataaatag gcagatacga gctcctaggg tacgtgtaat aggttccgca    120

ggagagcagc taggcatatt gagtataaaa gaggccctag atttagccaa ggaagctaat    180

ttagaccttg ttgaggttgc ttcaaactca gagcctcccg tgtgcaaaat catggactat    240

gggaagtatc gttacgacgt aactaaaaaa gaaaaagata gtaagaaagc acagcaccaa    300

gtacgtatca aagaggttaa gcttaagcct aatatcgatg ataacgactt tcttacgaaa    360

gcaaagcaag ctagagcctt tattgagaaa ggaaataaag taaaggtttc ttgtatgttt    420

cgggggcgag agttggctta tcccgaacac gggtataagg ttattcaaag aatgtgtcag    480

ggcttagagg acataggttt tgttgagtca gagcctaaac tgaatggccg ttctttgatc    540

tgtgttattg ctccgggaac actaaaaact aagaaaaaa                           579
```

<210> SEQ ID NO 303
<211> LENGTH: 123
<212> TYPE: PRT
<213> ORGANISM: Chlamydia trachomatis

<400> SEQUENCE: 303

```
Met Val Arg Ala Thr Gly Ser Val Ala Ser Arg Ser Arg Arg Lys Arg
1               5                   10                  15

Val Leu Lys Gln Ala Lys Gly Phe Trp Gly Asp Arg Lys Gly His Phe
            20                  25                  30

Arg Gln Ser Arg Ser Ser Val Met Arg Ala Met Ala Phe Asn Tyr Met
        35                  40                  45

His Arg Lys Asp Arg Lys Gly Asp Phe Arg Ser Leu Trp Ile Thr Arg
    50                  55                  60

Leu Ser Val Ala Ser Arg Ile His Gly Leu Ser Tyr Ser Arg Leu Ile
65                  70                  75                  80

Asn Gly Leu Lys Gln Ala Gly Ile His Leu Asn Arg Lys Met Leu Ser
                85                  90                  95

Glu Met Ala Ile His Asp Pro Gln Gly Phe Ala Val Val Ala Thr Gln
            100                 105                 110

Ala Lys Leu Ala Leu Glu Ala Ala Val Gln Gly
        115                 120
```

<210> SEQ ID NO 304
<211> LENGTH: 369
<212> TYPE: DNA
<213> ORGANISM: Chlamydia trachomatis

<400> SEQUENCE: 304

```
atggtaagag caactggttc agtagcttct agatcgcgtc gtaaacgcgt tttaaaacaa     60

gcaaaaggat tctggggaga tagaaaggga cactttcgtc aaagtcggtc ctctgttatg    120

cgggctatgg cttttaacta catgcaccga aaagatcgta aaggtgattt tcgaagcctt    180

tggatcactc gtttgagtgt ggcttccaga attcatggat tgtcttacag ccgtttgatc    240

aatggtctca aacaagctgg tattcattta aatagaaaaa tgttgtctga gatggctatt    300

catgaccctc aagggtttgc tgtagtagct acccaagcta aactcgcttt ggaagcagct    360

gttcaggga                                                            369
```

<210> SEQ ID NO 305
<211> LENGTH: 342
<212> TYPE: PRT
<213> ORGANISM: Chlamydia trachomatis

<400> SEQUENCE: 305

Met Thr Ile Gln Glu Glu Leu Glu Ala Val Lys Gln Gln Phe Ser Cys
1               5                   10                  15

Asp Val Ser Leu Ala His Ser Ser Lys Asp Leu Phe Asp Val Lys Val
            20                  25                  30

Lys Tyr Leu Gly Lys Lys Gly Ile Phe Arg Gly Phe Ala Asp Gln Leu
        35                  40                  45

Arg Lys Tyr Pro Ile Glu Gln Lys Ala Thr Val Gly Ala Ser Ile Asn
    50                  55                  60

Ala Cys Lys Gln Tyr Val Glu Glu Val Leu Leu Glu Arg Gly Lys Ala
65                  70                  75                  80

Val Leu Ala Lys Glu Glu Ala Glu Glu Phe Leu Lys Glu Lys Ile Asp
                85                  90                  95

Ile Ser Leu Pro Gly Ser Glu Glu Ala Ala Leu Gly Gly Lys His Val
            100                 105                 110

Ile Lys Lys Val Leu Asp Asp Val Val Asp Ile Phe Val Arg Phe Gly
        115                 120                 125

Phe Cys Val Arg Glu Ala Pro Asn Ile Glu Ser Glu Lys Asn Asn Phe
    130                 135                 140

Ser Leu Leu Asn Phe Glu Glu Asp His Pro Ala Arg Gln Met Gln Asp
145                 150                 155                 160

Thr Phe Tyr Leu Asp Pro Thr Thr Val Leu Arg Thr His Thr Ser Asn
                165                 170                 175

Val Gln Ser Arg Glu Leu Ala Arg Asn Lys Pro Pro Val Arg Ile Val
            180                 185                 190

Ala Pro Gly Glu Cys Phe Arg Asn Glu Asp Val Ser Ala Arg Ser His
        195                 200                 205

Val Ile Phe His Gln Val Glu Ala Phe Cys Val Asp Lys Asp Ile Ser
    210                 215                 220

Phe Ser Asp Leu Thr Ser Met Leu Ala Gly Phe Tyr His Ile Phe Phe
225                 230                 235                 240

Gly Arg Lys Val Glu Leu Arg Phe Arg His Ser Tyr Phe Pro Phe Val
                245                 250                 255

Glu Pro Gly Ile Glu Val Asp Ile Ser Cys Glu Cys His Gly Ala Gly
            260                 265                 270

Cys Ser Leu Cys Lys His Ala Gly Trp Leu Glu Val Ala Gly Ala Gly
        275                 280                 285

Met Ile His Pro Asn Val Leu Arg Lys Ala Ser Ile Asp Pro Glu Glu
    290                 295                 300

Tyr Ser Gly Tyr Ala Leu Gly Met Gly Ile Glu Arg Leu Ala Met Leu
305                 310                 315                 320

Lys Tyr Gly Ile Ser Asp Ile Arg Leu Phe Ser Glu Asn Asp Leu Arg
                325                 330                 335

Phe Leu Arg Gln Phe Ser
            340

<210> SEQ ID NO 306
<211> LENGTH: 1026
<212> TYPE: DNA
<213> ORGANISM: Chlamydia trachomatis

<400> SEQUENCE: 306
atgacaattc aagaggaact tgaggctgtt aaacagcagt ttagttgtga tgtaagcctt      60

-continued

```
gcgcattctt ctaaagatct tttcgatgtg aaagtaaaat acctgggaaa gaagggaatc    120

tttcgaggtt ttgctgatca gttgaggaag taccctatag agcagaaagc gactgttggc    180

gcttccatta acgcttgtaa gcaatacgtg gaggaagttt tactcgagag aggcaaggcc    240

gttttggcta aagaagaagc agaagagttc cttaaggaga agatagatat cagtttacct    300

ggtagcgaag aagctgctct tggtggtaag catgttatca agaaagtcct tgatgatgtt    360

gtagatatct ttgttcgctt tggattttgt gttcgggaag ctcctaatat cgaaagtgaa    420

aaaaacaatt tttctcttct taatttcgaa gaagatcatc ctgctcgaca gatgcaggat    480

actttctatt tggatcccac cacggtcttg cgtacgcaca cgtcgaatgt gcagtctcgg    540

gagttagcga gaaacaaacc tcctgttaga attgtcgctc caggagagtg tttccgtaat    600

gaagacgttt ctgcgcgttc gcatgtgatt tttcaccaag tagaggcttt ctgcgtagat    660

aaagatattt ctttttcaga cttgacatcg atgttggcag ggttttacca tatcttcttt    720

ggacgcaaag tggagttgcg gtttagacac agctatttcc cttttgtcga gccagggatc    780

gaggtagaca tttcttgtga atgtcatgga gccggatgtt ctttgtgtaa gcatgctggt    840

tggttggaag ttgctggagc aggaatgatt catccgaatg tcttgcgtaa ggcaagcatt    900

gatccagaag agtattctgg gtatgccttg ggatgggta tagagcgtct cgcgatgctc    960

aagtacggta tttccgatat tcgattgttt agtgagaacg atttgcggtt tttacggcaa   1020

ttttct                                                              1026
```

<210> SEQ ID NO 307
<211> LENGTH: 92
<212> TYPE: PRT
<213> ORGANISM: Chlamydia trachomatis

<400> SEQUENCE: 307

```
Met Lys Glu Glu Ile Leu Ala Leu Leu Asp His Leu Tyr Thr Glu Gln
1               5                   10                  15

Glu Arg Arg Leu Met Ser Leu Gly Thr Thr Ile Val Pro Gly Leu Thr
            20                  25                  30

Lys Glu Asp Leu Leu Gln Pro Met Asp Tyr Asp Glu Leu Glu Glu Asn
        35                  40                  45

Pro Ser Phe Arg Phe Glu Glu Gly Val Leu Asn Gly Ile Gly Glu Thr
    50                  55                  60

Arg Ala Ala Leu Tyr Ser Phe Phe Ser Asp Leu Glu Asp Ser Phe Cys
65                  70                  75                  80

Val Glu Ser Ser Ser Asp Thr Ser Leu Cys Lys Asp
                85                  90
```

<210> SEQ ID NO 308
<211> LENGTH: 276
<212> TYPE: DNA
<213> ORGANISM: Chlamydia trachomatis

<400> SEQUENCE: 308

```
atgaaggaag aaattctcgc gctacttgat catttatata cggagcagga aagacgatta     60

atgtcgctag ggacgacgat tgttcctgga ttgacgaaag aggatctttt acagcctatg    120

gattatgatg aacttgagga gaacccttct tttagatttg aagaaggagt tttgaatgga    180

ataggagaga ctcgagccgc attatattct ttttttctg atctagaaga ctccttttgc    240

gtggagtctt ctagcgatac gagcctctgt aaggat                              276
```